US007642278B2

(12) United States Patent
Jansen et al.

(10) Patent No.: US 7,642,278 B2
(45) Date of Patent: Jan. 5, 2010

(54) INDAZOLE BENZIMIDAZOLE COMPOUNDS

(75) Inventors: Johanna M. Jansen, San Francisco, CA (US); Christopher McBride, Oakland, CA (US); Paul A. Renhowe, Danville, CA (US); Cynthia Shafer, Moraga, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 505 days.

(21) Appl. No.: 11/261,995

(22) Filed: Oct. 27, 2005

(65) Prior Publication Data

US 2006/0079564 A1   Apr. 13, 2006

Related U.S. Application Data

(63) Continuation-in-part of application No. 10/187,967, filed on Jul. 2, 2002, now Pat. No. 7,064,215.

(60) Provisional application No. 60/302,791, filed on Jul. 3, 2001.

(51) Int. Cl.
*A01N 43/52* (2006.01)
*C07D 235/00* (2006.01)

(52) U.S. Cl. .................... 514/394; 514/405; 548/304.4; 548/361.1

(58) Field of Classification Search ................ 514/394, 514/405; 548/304.4, 361.1
See application file for complete search history.

(56) References Cited

U.S. PATENT DOCUMENTS

| 4,940,710 | A  | 7/1990 | Sum et al. |
|---|---|---|---|
| 6,605,617 | B2 | 8/2003 | Renhowe et al. |
| 6,756,383 | B2 | 6/2004 | Renhowe et al. |
| 7,064,215 | B2 | 6/2006 | Renhowe et al. |
| 2002/0103230 | A1 | 8/2002 | Renhowe et al. |
| 2003/0028018 | A1 | 2/2003 | Renhowe et al. |

FOREIGN PATENT DOCUMENTS

| DE | 19752990 | 11/1997 |
|---|---|---|
| WO | WO 92/18483 | 10/1992 |
| WO | WO 97/48694 | 12/1997 |
| WO | WO 97/49699 | 12/1997 |
| WO | WO 00/68206 | 11/2000 |
| WO | WO 01/02369 | 1/2001 |
| WO | WO 01/28993 | 4/2001 |
| WO | WO 01/29025 | 4/2001 |
| WO | WO 01/53268 | 7/2001 |

OTHER PUBLICATIONS

Druker, B.J.; "Inhibition of the Bcr-Abl tyrosine kinase as a therapeutic strategy for CML," *Oncogene*, vol. 21, pp. 8541-8546, 2002.
Inokuchi, K., "Chronic Myelogenous Leukemia: From Molecular Biology to Clinical Aspects and Novel Targeted Therapies," *J. Nippo Med. Sch.*, vol. 73, No. 4, pp. 178-192, 2006.
Jentsch-Ullrich, et al., "Complete molecular remission in a patient with Philadelphia-chromosome positive acute myeloid leukemia after conventional therapy Imatinib," *Haematologica*, vol. 89, pp. 49-51, 2004.
Kurzrock, R et al., "Expression of c-abl in Philadelphia-Positive Acute Myelogenous Leukemia," *Blood*, vol. 70, No. 5, pp. 1584-1588, 1987.
Kurzrock, R., et al., "Philadelphia Chromosome-Postive Leukemias: From Basic Mechanisms to Molecular Therapeutics," *Ann. Intern. Med.* vol. 138, pp. 819-830, 2003.
Mauro, et al., "STI571: Targeting BCR-ABL as Therapy for CML," *Oncologist*, vol. 6, pp. 233-238, 2001.
The Merck Manual of Diagnosis and Therapy, Seventeenth Ed. 1999, p. 952.
Anderson, W.K. et al., "Design, synthesis, and study of 9-substituted ellipticine and 2-methylellipticinium analogues as potential CNS-selective antitumor agents," *Journal of Medicinal Chemistry*, vol. 37, No. 13, pp. 1955-1963, 1994.
Angiogenesis Foundation, "New Study Shows That Acute Myeloid Leukemia is Angiogenesis-Dependent," Jan. 4, 2000; www.angio.org/newsandviews/archive2000/jan_4_2000.html.
Aprelikova, O., et al., "FLT4, a novel Class III Receptor Tyrosine Kinase in chromosome 5q33-qter1," *Cancer Res.*, vol. 52, pp. 746-748, Feb. 1, 1992, published by The American Association for Cancer Research, Stanford University Libraries' High Wire Press, California, United States of America.
Beals, C. R. et al., "Nuclear Export of NF-ATc Enhanced by Glycogen Synthase Kinase-3," *Science*, vol. 275, pp. 1930-1933, Mar. 28, 1997.

(Continued)

*Primary Examiner*—James O. Wilson
*Assistant Examiner*—Paul V. Ward
(74) *Attorney, Agent, or Firm*—Vinit Kathardekar; Joseph Meara

(57) ABSTRACT

Organic compounds having the structure I are provided where the variables have the values described herein.

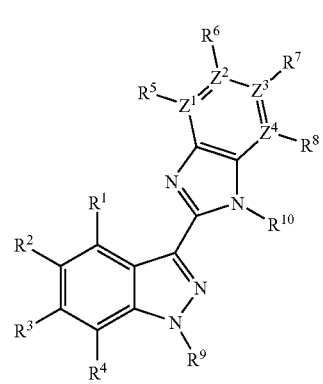

A method of inhibiting c-ABL in a patient includes administering an effective amount of a compound of structure I, a tautomer of the compound, a pharmaceutically acceptable salt of the compound, or a pharmaceutically acceptable salt of the tautomer to the patient.

12 Claims, No Drawings

OTHER PUBLICATIONS

Brownlees, J. et al., "Tau phosphorylation in transgenic mice expressing glycogen synthase kinase-3β transgenes," *NeuroReport*, vol. 8, No. 15, pp. 3251-3255, Oct. 20, 1997; published by Rapid Science Publishers.

Buchi, G. et al., "Direct Acting, Highly Mutagenic, α-Hydroxy N-Nitrosamines from 4-Chloroindoles," *J. Am. Chem. Soc.*, vol. 108, pp. 4115-4119, 1986.

Carmeliet, P. et al., "Angiogenesis in Cancer and Other Diseases," *Nature*, vol. 407, pp. 249-257, 2000.

Chan, T. A. et al., "14-3-3σ is required to prevent mitotic catastrophe after DNA damage," *Nature*, vol. 401, pp. 616-620, Oct. 7, 1999; published by Macmillan Magazines Ltd.

Chen, G. et al., "The Mood-Stabilizing Agent Valproate Inhibits the Activity of Glycogen Synthase Kinase-3," *J. Neurochem.*, vol. 72, No. 3, 1999, pp. 1327-1330; published by Lippincott Williams & Wilkins, Inc., Philadelphia.

Connolly, D., et al., "Human Vascular Permeability Factor," *J. Biol. Chem.*, vol. 264, pp. 20017-20024, 1989, published by The American Society For Biochemistry and Molecular Biology, Inc., Stanford University Libraries' High Wire Press, California, United States of America.

Connolly, D., et al., "Tumor Vascular Permeability Factor Stimulates Endothelial Cell Growth and Angiogenesis," *J. Clin. Invest.*, vol. 84, pp. 1470-1478, Nov. 1989, published by The American Society for Clinical Investigation, Inc., Stanford University Libraries' High Wire Press, California, United States of America.

Cross, A. E. et al., "The inhibition of glycogen synthase kinase-3 by insulin or insulin-like growth factor 1 in the rat skeletal muscle cell line L6 blocked by wortmannin, but not by rapamycin: evidence that wortmannin blocks activation of the mitogen-activated protein kinase pathway in L6 cells between Ras and Raf," *Biochem J.*, vol. 303, pp. 21-26, 1994; (printed in Great Britain).

Curran, W.V. et al., "Selective Borane Reduction of a Trifluoroacetamide Substituent in the Presence of a Carbamate," *J. Org. Chem.*, vol. 31, pp. 3867-3868, 1966.

Dankbar, B. et al., "Vascular endothelial growth factor and interleukin-6 in paracrine tumor-stromal cell interactions in multiple myeloma," *Blood*, 2000, vol. 5(8), pp. 2630-2636.

Dermer, G. B., "Another Anniversary for the War on Cancer," *Biotechnology*, 1994, vol. 12, p. 320.

Devries, C., et al., "The fms-Like Tyrosine Kinase, a Receptor for Vascular Endothelial Growth Factor," *Science*, vol. 255, pp. 989-991, Feb. 21, 1992, published by The American Society for the Advancement of Science, Stanford University Libraries' High Wire Press, California, United States of America.

Doukas, M. A. et al., "Effect of Lithium on Stem Cell and Stromal Cell Proliferation in vitro," *Exp. Hematol.*, vol. 14, pp. 215-221, 1986; published by International Society for Experimental Hematology.

Examination Report for EP 02752132.7 dated Mar. 10, 2006.

Examination Report for EP 02752132.7 dated Mar. 7, 2008.

Examination Report for EP 02752132.7 dated Sep. 15, 2008.

Ferrara, N., et al., "The Biology of Vascular Endothelial Growth Factor," *Endocrinol. Rev.*, vol. 18, No. 1, pp. 4-25, 1997, published by The Endocrine Society, Stanford University Libraries' High Wire Press, California, United States of America.

Flückiger-Isler, R. E. et al., "Stimulation of rat liver glycogen synthesis by the adenosine kinase inhibitor 5-iodotubercidin," *Biochem. J.*, vol. 292, pp. 85-91, 1993; (printed in Great Britain).

Folkman, J., "Fighting Cancer by Attacking Its Blood Supply," *Scientific American*, vol. 275, pp. 150-154, Sep. 1996, published by Scientific American, Inc., New York, New York, United States of America.

Freshney, R. I., *Culture of Animal Cells—A Manual of Basic Technique*, 1983, pp. 1-4; published by Alan R. Liss, Inc.

Gruber, G. et al., "Basic Fibroblast Growth Factor is Expressed in CD19/CD11c-Positive Cells in Hairy Cell Leukemia," *Blood*, 1999, vol. 94(3), pp. 1077-1085.

Gura, T., "Systems for Identifying New Drugs Are Often Faulty," *Science*, 1997, vol. 278, pp. 1041-1042.

Hammond, W. P. et al., "Lithium Therapy of Canine Cyclic Hematopoiesis," *Blood*, vol. 55, No. 1, pp. 26-28, Jan. 1980.

Hirao, A. et al., "DNA Damage-Induced Activation of p53 by the Checkpoint Kinase CHk2," *Science*, vol. 287, pp. 1824-1827, Mar. 10, 2000.

Hussong, J. W. et al., "Evidence of increased angiogenesis in acute myeloid leukemia," *Blood*, 2000, vol. 95(1), pp. 309-313; The American Society of Hematology.

International Preliminary Examination Report for PCT/US02/20844 dated Dec. 12, 2003.

International Search Report for PCT/US02/20844 dated Nov. 21, 2002.

Kerbel, R. S., "Tumor Angiogenesis: Past, Present and Near Future," *Carcinogenesis*, 2000, vol. 21(3), pp. 505-515; Oxford University Press.

Klein, P. S. et al., "A molecular mechanism for the effect of lithium on development," *Proc. Natl. Acad. Sci. USA*, vol. 93, pp. 8455-8459, Aug. 1996.

Lee, J. et al., "Positive Regulation of Wee1 by Chk1 and 14-3-3 Proteins," *Molecular Biology of the Cell*, vol. 12, pp. 551-563, Mar. 2001; published by The American Society for Cell Biology.

Leung, D., et al., "Vascular Endothelial Growth Factor Is a Secreted Angiogenic Mitogen," *Science*, vol. 246, pp. 1306-1309, Dec. 8, 1989, published by The American Society for the Advancement of Science, Stanford University Libraries' High Wire Press, California, United States of America.

Liu, Q. et al., "Chk1 is an essential kinase that is regulated by Atr and required for the $G_2$/M DNA damage checkpoint," *Genes & Development*, vol. 14, 2000, pp. 1448-1459; published by Cold Springs Harbor Laboratory Press.

Lopez-Girona, A. et al., "Nuclear localization of Cdc25 is regulated by DNA damage and a 14-3-3 protein," *Nature*, vol. 397, pp. 172-175, Jan. 14, 1999; published by Macmillan Magazines Ltd.

Lovestone, S. et al., "Alzheimer's disease-like phosphorylation of the microtubule-associated protein tau by glycogen synthase kinase-3 in transfected mammalian cells," *Current Biology*, vol. 4, pp. 1077-1086, Dec. 1, 1994; published by Elsevier Science Ltd.

Lundberg, L. G. et al., "Bone Marrow in Polycythemia Vera, Chronic Myelocytic Leukemia and Myelofibrosis Has an Increased Vascularity," *American Journal of Pathology*, 2000, vol. 157(1), pp. 15-19.

Lymboussaki, A., "Vascular endothelial growth factors and their receptors in embryos, adults, and in tumors," Academic Dissertation, University of Helsinki, Molecular/Cancer Biology Laboratory and Department of Pathology, Haartman Institute, 1999.

Massillon, D. et al., "Identification of the glycogenic compound 5-iodotubercidin as a general protein kinase inhibitor," *Biochem. J.*, vol. 299, pp. 123-128, 1994; printed in Great Britain.

McMahon, G., "VEGF Receptor Signaling in Tumor Angiogenesis," *The Oncologist 2000*, vol. 5 (suppl. 1), pp. 3-10 (2000).

Menzel, T. et al., "Elevated Intracellular Level of Basic Fibroblast Growth Factor Correlates with Stage of Chronic Lymphocytic Leukemia and is Associated With Resistance to Fludarabine," *Blood*, 1996, vol. 87(3), pp. 1056-1063.

Millauer, B. et al., "Glioblastoma growth inhibited in vivo by a dominant-negative Flk-1 mutant," *Nature*, vol. 367, pp. 576-579 (1994); published by Nature Publishing Group.

MSNBC News Services, "Mixed results on new cancer drug," Nov. 9, 2000.

Mustonen, T., et al., "Endothelial Receptor Tyrosine Kinases Involved in Angiogenesis," *J. Cell Biology*, vol. 129, No. 4, pp. 895-898, May 1995, published by The Rockefeller University Press, New York, New York, United States of America.

Nonaka, S. et al., "Chronic lithium treatment robustly protects neurons in the central nervous system against excitotoxicity by inhibiting N-methyl-D-aspartate receptor-mediated calcium influx," *Proc. Natl. Acad. Sci. USA*, vol. 95, pp. 2642-2647, Mar. 1998.

Parker, L. L. et al., "Inactivation of the p34cdc2-Cyclin B Complex by the Human WEE1 Tyrosine Kinase," *Science*, vol. 257, pp. 1955-1957, Sep. 25, 1992.

Pei, J.-J. et al., "Distribution, Levels, and Activity of Glycogen Synthase Kinase-3 in the Alzheimer Disease Brain," *Journal of*

*Neuropathology and Experimental Neurology*, vol. 56, No. 1, pp. 70-78, Jan. 1997; published by the American Association of Neuropathologists.

Peng, C.-Y. et al., "Mitotic and $G_2$ Checkpoint Control: Regulation of 14-3-3 Protein Binding by Phosphorylation of Cdc25C on Serine-216," *Science*, vol. 277, pp. 1501-1505, Sep. 5, 1997.

Pinedo, H. M. et al., "Translational Research: The Role of VEGF in Tumor Angiogenesis," *The Oncologist 2000*, vol. 5 (suppl. 1), pp. 1-2 (2000).

Plouet, J., et al., "Isolation and characterization of a newly identified endothelial cell mitogen produced by AtT-20 cells," *EMBO J.*, vol. 8, No. 12, pp. 3801-3806, 1989, published by IRL Press.

Quinn, T., et al., "Fetal liver kinase 1 is a receptor for vascular endothelial growth factor and is selectively expressed in vascular endothelium," *Proc. Natl. Acad. Sci. USA*, vol. 90, pp. 7533-7537, Aug. 1993.

Rosen, T. et al., "Design, synthesis, and properties of (4S)-7-(4-amino-2-substituted-pyrrolidin-1-yl)quinolone-3-carboxylic acids," *J. Med. Chem.*, vol. 31, No. 8, pp. 1598-1611, 1988.

Saito, Y. et al., "The mechanism by which epidermal growth factor inhibits glycogen synthase kinase 3 in A431 cells," *Biochem. J.*, vol. 303, pp. 27-31, 1994; printed in Great Britain.

Salmon, S. E. et al., *Basic & Clinical Pharmacology*, Seventh Edition, edited by B. Katzung, Appleton & Lange, pp. 29, 881-884 (1998).

Sanchez, Y. et al., "Conservation of the Chk1 Checkpoint Pathway in Mammals: Linkage of DNA Damage to Cdk Regulation Through Cdc25," *Science*, vol. 277, pp. 1497-1501, Sep. 5, 1997.

Shibuya, M., et al., "Nucleotide sequence and expression of a novel human receptor-type tyrosine kinase gene (flt) closely related to the fms family," *Oncogene*, vol. 5, pp. 519-524, 1990, published by Macmillan Press Ltd., Stockton Press Company, Great Britain.

Soos et al., "Novel Thermal Rearrangement of Fused Diaryl-v-Triazolium Salts to Neutral Indazole Derivatives," *Journal of Organic Chemistry*, vol. 62, No. 4, pp. 1136-1138, 1997.

Soussi, T., "The p53 Tumor Suppressor Gene: From Molecular Biology to Clinical Investigation," *Ann. N.Y. Acad. Sci.*, vol. 910, pp. 121-139, 2000.

Stambolic, V. et al., "Lithium inhibits glycogen synthase kinase-3 activity and mimics Wingless signaling in intact cells," *Current Biology*, vol. 6, No. 12, pp. 1664-1668, 1996; published by Current Biology Ltd. ISSN 0960-9822.

Takashima, A. et al., "Presenilin 1 associates with glycogen synthase kinase-3β and its substrate tau," *Proc. Natl. Acad. Sci. USA*, vol. 95, pp. 9637-9641, Aug. 1998; published by The National Academy of Sciences.

Takashima, A. et al., "tau protein kinase I is essential for amyloid β-protein-induced neurotoxicity," *Proc. Natl. Acad. Sci. USA*, vol. 90, pp. 7789-7793, Aug. 1993.

Terman, B., et al., "Identification of a new endothelial cell growth factor receptor tyrosine kinase," *Oncogene*, vol. 6, pp. 1677-1683, 1991, published by Macmillan Press Ltd., Stockton Press Company, Great Britain.

Thomas, M.D., R. J. et al., "Progress in Geriatrics: Excitatory Amino Acids in Health and Disease," *J. of the American Geriatrics Society*, vol. 43, No. 11, pp. 1279-1289, Nov. 1995; published by American Geriatrics Society.

Ullrich, A., et al., "Signal Transduction by Receptors with Tyrosine Kinase Activity," *Cell*, vol. 61, pp. 203-212, Apr. 20, 1990, published by Cell Press, Cambridge, Massachusetts, United States of America.

Van Der Geer, P., et al., "Receptor Protein-Tyrosine Kinases and Their Signal Transduction Pathways," *Annu. Rev. Cell Biol.*, vol. 10, pp. 251-337, 1994, published by Annual Reviews, Inc., Palo Alto, California, United States of America.

Vogelstein, B. et al., "Surfing the p53 network," *Nature*, vol. 408, pp. 307-310, Nov. 16, 2000; published by Macmillan Magazines Ltd.

Wedge, S. R. et al., "ZD6474 Inhibits Vascular Endothelial Growth Factor Signaling Angiogenesis, and Tumor Growth following Oral Administration," *Cancer Research*, vol. 62, pp. 4645-4655, Aug. 15, 2002.

Welsh, G. I. et al., "Glycogen synthase kinase-3 is rapidly inactivated in response to insulin and phosphorylates eukaryotic initiation factor elF-2B," *Biochem. J.*, vol. 294, pp. 625-629, 1993; printed in Great Britain.

Woodgett, "A Common Denominator Linking Glycogen Metabolism, Nuclear Oncogenes and Development," *Trends Biochem. Sci.*, vol. 16, pp. 177-181, 1991.

Zetter, B. R., "Angiogenesis and Tumor Metastasis," *Annu. Rev. Med.*, 1998, vol. 49, pp. 407-424; published by Annual Review Inc.

Zhang, Z. et al., "Destabilization of β-catenin by mutations in presenilin-1 potentiates neuronal apoptosis," *Nature*, vol. 395, pp. 698-702, Oct. 15, 1998; published by Macmillan Publishers Ltd.

Zhao, H. et al., "ATR-Mediated Checkpoint Pathways Regulate Phosphorylation and Activation of Human Chk1," *Molecular and Cellular Biology*, vol. 21, No. 13, pp. 4129-4139, Jul. 2001; published by American Society for Microbiology.

INDAZOLE BENZIMIDAZOLE COMPOUNDS

CROSS REFERENCES TO RELATED APPLICATIONS

This application is a continuation in part of, and claims priority to, U.S. patent application Ser. No. 10/187,967, filed on Jul. 2, 2002, now U.S. Pat. No. 7,064,215, which claims priority to U.S. Provisional Application No. 60/302,791, filed on Jul. 3, 2001, the entire disclosures of which are hereby incorporated by reference in their entireties and for all purposes as if fully set forth herein.

FIELD OF THE INVENTION

This invention pertains generally to methods and compositions for treating a variety of patients and cell subjects. More particularly, the present invention provides novel compositions of matter and methods for angiogenesis inhibition, treating cancer, treating diabetes, stimulating insulin-dependent processes, treating Alzheimer's disease, treating central nervous system disorders, prolonging immune responses, reducing the splitting of centrosomes, blocking DNA repair, modulating cell cycle arrest, and inhibiting enzymes such as serine/threonine kinases and tyrosine kinases. The present invention thus has application in the areas of oncology, diabetes, immunology, and medicinal chemistry.

BACKGROUND OF THE INVENTION

Capillaries reach into almost all tissues of the human body and supply tissues with oxygen and nutrients as well as removing harmful waste products. Under typical conditions, the endothelial cells lining capillaries do not divide, and capillaries, therefore, do not normally increase in number or size in a human adult. Under certain normal conditions, however, such as when a tissue is damaged, or during certain parts of the menstrual cycle, capillaries begin to proliferate rapidly. This process of forming new capillaries from pre-existing blood vessels is known as angiogenesis or neovascularization. See Folkman, J. Scientific American 275, 150-154 (1996). Angiogenesis during wound healing is an example of pathophysiological neovascularization during adult life. During wound healing, the additional capillaries provide a supply of oxygen and nutrients, promote granulation tissue, and aid in waste removal. After termination of the healing process, the capillaries normally regress. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999).

Angiogenesis also plays an important role in the growth of cancer cells. It is known that once a nest of cancer cells reaches a certain size, roughly 1 to 2 mm in diameter, the cancer cells must develop a blood supply in order for the tumor to grow larger as diffusion will not be sufficient to supply the cancer cells with enough oxygen and nutrients. A compound that inhibits angiogenesis will thus act to retard or halt the growth of cancer cells.

Receptor tyrosine kinases (RTKs) are polypeptides that regulate developmental cell growth and differentiation and remodeling and regeneration of adult tissues. Mustonen, T. et al., J. Cell Biology 129, 895-898 (1995); van der Geer, P. et al. Ann Rev. Cell Biol. 10, 251-337 (1994). Polypeptide ligands known as growth factors or cytokines, are known to activate RTKs. Signaling involves ligand binding and a shift in conformation in the external domain of the receptor resulting in its dimerization. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999); Ullrich, A. et al., Cell 61, 203-212 (1990). Binding of the ligand to the RTK results in receptor trans-phosphorylation at specific tyrosine residues and activation of the catalytic domains for the phosphorylation of cytoplasmic substrates. Id.

Two subfamilies of RTKs are specific to the vascular endothelium. These include the VEGF subfamily and the Tie receptor subfamily. Class III RTKs include VEGFR-1, VEGFR-2, and VEGFR-3. Shibuya, M. et al., Oncogene 5, 519-525 (1990); Terman, B. et al., Oncogene 6, 1677-1683 (1991); Aprelikova, O. et al., Cancer Res. 52, 746-748 (1992).

A number of substances have been identified that promote angiogenesis. These include angiopoietin-1, basic fibroblast growth factor (bFGF) and vascular endothelial growth factor (VEGF). VEGF was first described as a protein able to induce vascular permeability and endothelial cell proliferation and was identified as a major inducer of angiogenesis and vasculogenesis. Ferrara, N. et al., Endocrinol. Rev. 18, 4-25 (1997). VEGF is known to specifically bind to RTKs including VEGFR-1 and VEGFR-2. DeVries, C. et al., Science 255, 989-991 (1992); Quinn, T. et al., Proc. Natl. Acad. Sci. 90, 7533-7537 (1993). It is now known that VEGF stimulates the migration and proliferation of endothelial cells and induces angiogenesis both in vitro and in vivo. Connolly, D. et al., J. Biol. Chem. 264, 20017-20024 (1989); Connolly, D. et al., J. Clin. Invest. 84, 1470-1478 (1989); Ferrara, N. et al., Endocrino. Rew. 18, 4-25 (1997); Leung, D. et al., Science 246, 1306-1309 (1989); Plouet, J. et al., EMBO J 8, 3801-3806 (1989).

Because angiogenesis is known to be critical to the growth of cancer and to be controlled by VEGF and VEGF-RTK, substantial efforts have been undertaken to develop compounds which inhibit or retard angiogenesis and inhibit VEGF-RTK.

Platelet derived growth factor receptor kinase (PDGFRK) is another type of RTK. PDGF expression has been shown in a number of different solid tumors, from glioblastomas to prostate carcinomas. In these various tumor types, the biologicical role of PDGF signaling can vary from autocrine stimulation of cancer cell growth to more subtle paracrine interactions involving adjacent stroma and angiogenesis. Therefore, inhibiting the PDGFR kinase activity with small molecules may interfere with tumor growth and angiogenesis.

Tie-2 is a membrane RTK. Upon binding to its ligand, Tie-2 is activated and phosphorylates its downstream signal proteins. Tie-2 kinase activity may then trigger a pathway of cellular response that leads to stabilization of vascular vessels in cancer. Therefore, blocking kinase activity of Tie-2, in synergy with blockage of activity of other angiogenic kinases such as VEGF and bFGF receptor kinases, may be effective in cutting off the blood supply to cancer cells and in treating the disease.

c-ABL is a tyrosine kinase that was originally identified as an oncogene product from the genome of the Abelson murine leukemia virus. About 90% of chronic myelogenous leukemia (CML), 20-30% of acute lymphoblastic leukemia (ALL) and about 1% of acute myeloblastic leukemia (AML) have a reciprocal translocation between chromsome 9 and 22. The translocation results in the 'Philadelphia' chromosome and is the reason for the expression of a chimeric BCR/ABL transcript.

Glycogen synthase kinase 3 (GSK-3) is a serine/threonine kinase for which two isoforms, α and β, have been identified. Woodgett, *Trends Biochem. Sci.*, 16:177-81 (1991). Both GSK-3 isoforms are constitutively active in resting cells. GSK-3 was originally identified as a kinase that inhibits glycogen synthase by direct phosphorylation. Upon insulin activation, GSK-3 is inactivated, thereby allowing the activation of glycogen synthase and possibly other insulin-dependent events, such glucose transport. Subsequently, it has been shown that GSK-3 activity is also inactivated by other growth factors that, like insulin, signal through receptor tyrosine kinases (RTKs). Examples of such signaling molecules include IGF-1 and EGF. Saito et al., *Biochem. J.*, 303:27-31 (1994); Welsh et al., *Biochem. J.* 294:625-29 (1993); and Cross et al., *Biochem. J.*, 303:21-26 (1994).

Agents that inhibit GSK-3 activity are useful in the treatment of disorders that are mediated by GSK-3 activity. In addition, inhibition of GSK-3 mimics the activation of growth factor signaling pathways and consequently GSK-3 inhibitors are useful in the treatment of diseases in which such pathways are insufficiently active. Examples of diseases that can be treated with GSK-3 inhibitors are described below.

Type 2 diabetes is an increasingly prevalent disease of aging. It is initially characterized by decreased sensitivity to insulin and a compensatory elevation in circulating insulin concentrations, the latter of which is required to maintain normal blood glucose levels. Increased insulin levels are caused by increased secretion from the pancreatic beta cells, and the resulting hyperinsulinemia is associated with cardiovascular complications of diabetes. As insulin resistance worsens, the demand on the pancreatic beta cells steadily increases until the pancreas can no longer provide adequate levels of insulin, resulting in elevated levels of glucose in the blood. Ultimately, overt hyperglycemia and hyperlipidemia occur, leading to the devastating long-term complications associated with diabetes, including cardiovascular disease, renal failure and blindness. The exact mechanism(s) causing type 2 diabetes are unknown, but result in impaired glucose transport into skeletal muscle and increased hepatic glucose production, in addition to inadequate insulin response. Dietary modifications are often ineffective, therefore the majority of patients ultimately require pharmaceutical intervention in an effort to prevent and/or slow the progression of the complications of the disease. Many patients can be treated with one or more of the many oral anti-diabetic agents available, including sulfonylureas, to increase insulin secretion. Examples of sulfonylurea drugs include metformin for suppression of hepatic glucose production, and troglitazone, an insulin-sensitizing medication. Despite the utility of these agents, 30-40% of diabetics are not adequately controlled using these medications and require subcutaneous insulin injections. Additionally, each of these therapies has associated side effects. For example, sulfonylureas can cause hypoglycemia and troglitazone can cause severe hepatoxicity. Presently, there is a need for new and improved drugs for the treatment of prediabetic and diabetic patients.

As described above, GSK-3 inhibition stimulates insulin-dependent processes and is consequently useful in the treatment of type 2 diabetes. Recent data obtained using lithium salts provides evidence for this notion. The lithium ion has recently been reported to inhibit GSK-3 activity. Klein et al., *PNAS* 93:8455-9 (1996). Since 1924, lithium has been reported to have antidiabetic effects including the ability to reduce plasma glucose levels, increase glycogen uptake, potentiate insulin, up-regulate glucose synthase activity and to stimulate glycogen synthesis in skin, muscle and fat cells. However, lithium has not been widely accepted for use in the inhibition of GSK-3 activity, possibly because of its documented effects on molecular targets other than GSK-3. The purine analog 5-iodotubercidin, also a GSK-3 inhibitor, likewise stimulates glycogen synthesis and antagonizes inactivation of glycogen synthase by glucagon and vasopressin in rat liver cells. Fluckiger-Isler et al., *Biochem. J.* 292:85-91 (1993); and Massillon et al., *Biochem. J.* 299:123-8 (1994). However, this compound has also been shown to inhibit other serine/threonine and tyrosine kinases. Massillon et al., *Biochem J.* 299:123-8 (1994).

GSK-3 is also involved in biological pathways relating to Alzheimer's disease (AD). The characteristic pathological features of AD are extracellular plaques of an abnormally processed form of the amyloid precursor protein (APP), so called β-amyloid peptide (β-AP) and the development of intracellular neurofibrillary tangles containing paired helical filaments (PHF) that consist largely of hyperphosphorylated tau protein. GSK-3 is one of a number of kinases that have been found to phosphorylate tau protein in vitro on the abnormal sites characteristic of PHF tau, and is the only kinase also demonstrated to do this in living cells and in animals. Lovestone et al., *Current Biology* 4:1077-86 (1994); and Brownlees et al., *Neuroreport* 8: 3251-3255 (1997). Furthermore, the GSK-3 kinase inhibitor, LiCl, blocks tau hyperphosphorylation in cells. Stambolic et al., *Current Biology* 6:1664-8 (1996). Thus GSK-3 activity may contribute to the generation of neurofibrillary tangles and consequently to disease progression. Recently it has been shown that GSK-3β associates with another key protein in AD pathogenesis, presenillin 1 (PS1). Takashima et., *PNAS* 95:9637-9641 (1998). Mutations in the PS1 gene lead to increased production of β-AP, but the authors also demonstrate that the mutant PSI proteins bind more tightly to GSK-3β and potentiate the phosphorylation of tau, which is bound to the same region of PS1.

It has also been shown that another GSK-3 substrate, β-catenin, binds to PS1. Zhong et al., *Nature* 395:698-702 (1998). Cytosolic β-catenin is targeted for degradation upon phosphorylation by GSK-3 and reduced β-catenin activity is associated with increased sensitivity of neuronal cells to β-AP induced neuronal apoptosis. Consequently, increased association of GSK-3β with mutant PS1 may account for the reduced levels of β-catenin that have been observed in the brains of PS1-mutant AD patients and to the disease related increase in neuronal cell-death. Consistent with these observations, it has been shown that injection of GSK-3 antisense but not sense, blocks the pathological effects of β-AP on neurons in vitro, resulting in a 24 hour delay in the onset of cell death and increased cell survival at 1 hr from 12 to 35%. Takashima et al., *PNAS* 90:7789-93. (1993). In these latter studies, the effects on cell-death are preceded (within 3-6 hours of β-AP administration) by a doubling of intracellular GSK-3 activity, suggesting that in addition to genetic mechanisms that increase the proximity of GSK-3 to its substrates, β-AP may actually increase GSK-3 activity. Further evidence for a role for GSK-3 in AD is provided by the observation that the protein expression level (but, in this case, not specific activity) of GSK-3 is increased by 50% in postsynaptosomal supernatants of AD vs. normal brain tissue. Pei et al., *J. Neuropathol Exp.*, 56:70-78 (1997). Thus, specific inhibitors of GSK-3 should slow the progression of Alzheimer's Disease.

In addition to the effects of lithium described above, there is a long history of the use of lithium to treat bipolar disorder (manic depressive syndrome). This clinical response to lithium may reflect an involvement of GSK-3 activity in the etiology of bipolar disorder, in which case GSK-3 inhibitors could be relevant to that indication. In support of this notion it was recently shown that valproate, another drug commonly used in the treatment of bipolar disorder, is also a GSK-3 inhibitor. Chen et al., *J. Neurochemistry*, 72:1327-1330 (1999). One mechanism by which lithium and other GSK-3 inhibitors may act to treat bipolar disorder is to increase the survival of neurons subjected to aberrantly high levels of excitation induced by the neurotransmitter, glutamate. Nonaka et al., *PNAS* 95: 2642-2647 (1998). Glutamate-induced neuronal excitotoxicity is also believed to be a major cause of neurodegeneration associated with acute damage, such as in cerebral ischemia, traumatic brain injury and bacterial infection. Furthermore it is believed that excessive glutamate signaling is a factor in the chronic neuronal damage seen in diseases such as Alzheimer's, Huntingdon's, Parkinson's, AIDS associated dementia, amyotrophic lateral sclerosis (AML) and multiple sclerosis (MS). Thomas, *J. Am. Geriatr. Soc.* 43: 1279-89 (1995). Consequently, GSK-3 inhibitors should provide a useful treatment in these and other neurodegenerative disorders.

GSK-3 phosphorylates transcription factor NF-AT and promotes its export from the nucleus, in opposition to the effect of calcineurin. Beals et al., *Science* 275:1930-33 (1997). Thus, GSK-3 blocks early immune response gene activation via NF-AT, and GSK-3 inhibitors may tend to permit or prolong activation of immune responses. Thus, GSK-3 inhibitors are believed to prolong and potentiate the immunostimulatory effects of certain cytokines, and such an effect may enhance the potential of those cytokines for tumor immunotherapy or indeed for immunotherapy in general.

Lithium has other biological effects. It is a potent stimulator of hematopoiesis, both in vitro and in vivo. Hammond et al., *Blood* 55: 26-28 (1980). In dogs, lithium carbonate eliminated recurrent neutropenia and normalized other blood cell counts. Doukas et al. *Exp. Hematol.* 14: 215-221 (1986). If these effects of lithium are mediated through the inhibition of GSK-3, GSK-3 inhibitors may have even broader applications. Since inhibitors of GSK-3 are useful in the treatment of many diseases, the identification of new inhibitors of GSK-3 would be highly desirable.

NEK-2 is a mammalian serine threonine kinase, which is structurally related to the NimA kinase from the fungus *Aspergillus nidulans*. Mutations in NimA result in G2 phase arrest of cells and overexpression of wt NimA results in premature chromatin condensation, even when ectopically expressed in mammalian cells. Both protein and kinase levels peak in S/G2 phase of the cell cycle. NimA also appears to be required for the localization of cdk1/cyclinB complex to the nucleus and spindle pole body. Histone H3 has been shown to be an in vitro substrate for the kinase, and if this is also the case in vivo, it may explain the role of the kinase in chromosome condensation. Six NimA kinases have been identified to date in mammals, and of these, NEK-2 appears to be the most closely related to NimA. It's activity is also cell cycle regulated, peaking in S/G2 phase. Overexpression of NEK-2, however, does not affect chromatin condensation but instead results in a pronounced splitting of centrosomes, possibly due to the loss of centriole/centriole adhesion. There is evidence that NEK-2 is regulated by phosphorylation and can interact with protein phosphatase PP1. NEK-2 is ubiquitously expressed and appears to be most abundant in testis. Hyseq cluster 374113, containing only NEK-2 sequences shows dramatic overexpression of NEK-2 in lymph node metastasis (13.3×) and in primary tumor (6.5×). Inhibition of NEK-2 by antisense oligonucleotides inhibited cell proliferation and reduced the capability of cells to grow in soft agar. In addition, increased cell death was observed in these cells both in the presence and absence of cisplatin.

Ultraviolet light, ionizing radiation, environmental agents and cytotoxic drugs can result in damage to cellular DNA integrity. When such damage occurs during DNA replication or cell division it is potentially catastrophic and may result in cell death. The cellular response is to arrest the cell cycle at one of two checkpoints (G1/S or G2/M) to either permit DNA repair or initiate apoptosis.

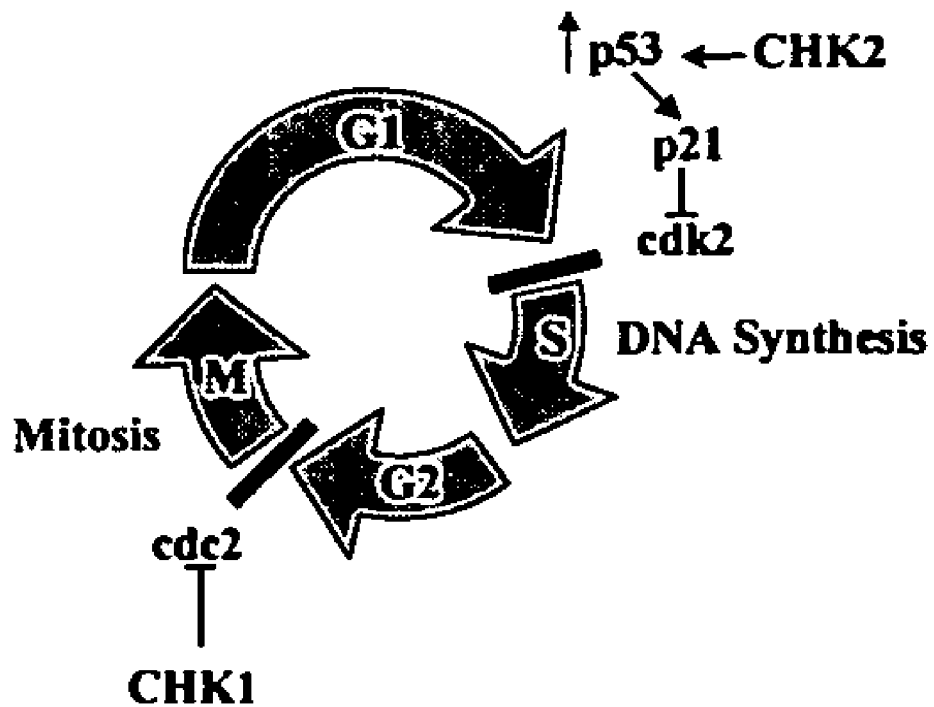

The G1/S checkpoint is regulated by the p53 transcriptional activator protein and the absence of this critical protein is often an important step in tumorigenesis, thus defining p53 as a tumor suppressor. In fact, nearly 50% of all cancers are p53 defective due to mutation. T. Soussi, *Ann. N.Y. Acad Sci.,* 910, 121 (2001). In response to DNA damage, checkpoint kinase 2 (CHK-2) phosphorylates p53 and this results in stabilization of the protein and an elevation in p53 levels. A. Hirao et al., *Science,* 287, 1824 (2000). Consequently, negative cell cycle regulators, such as p21Waf1/Cip1, are activated and halt the cell cycle at the G1/S checkpoint. B. Vogelstein et al., *Nature,* 408, 307 (2000).

The G2/M checkpoint is monitored by the serine/threonine checkpoint kinase 1 (CHK-1). Upon DNA damage, the protein kinase ATR (ataxia-telangiectasia mutated-rad53 related kinase) is activated. H. Zhao et al., *Mol. Cell Biol.,* 21, 4129 (2001); Q. Liu et al., *Genes Dev.,* 14, 1448 (2000). SATR-dependent phosphorylation of CHK-1 promotes its phosphorylation of cdc25 and Wee1 and ultimately inactivation of cdc 2. Thus, CHK-1 phosphorylation of cdc25c targets it for nuclear export to the cytoplasm and as a result the cdc25c phosphatase is rendered unavailable to activate cdc 2 by dephosphorylation. Y. Sanchez et al., *Science,* 277, 1497 (1997); C. Y. Peng et al., *Science,* 277, 1501 (1997); T. A. Chen et al., *Nature,* 401, 616 (1999); and A. Lopez-Girona et al., *Nature,* 397, 172 (1999). In addition, CHK-1 activates the protein kinase Wee1, which phosphorylates and inactivates cdc 2. J. Lee et al. *Mol. Biol. Cell,* 12, 551 (2001); L. L. Parker et al., *Science,* 257, 1955 (1992). These dual pathways thus converge to result in cell cycle arrest. Because cell cycle arrest is a potential mechanism by which tumor cells can overcome the damage induced by cytotoxic agents, abrogation of these checkpoints with novel therapeutic agents should increase the sensitivity of tumors to chemotherapy. The presence of two checkpoints, coupled with the tumor specific abrogation of one of these by p53 mutations in 50% of cancers, can be exploited to design tumor-selective agents. Thus, in p53 minus tumors, therapeutic inhibition of G2/M arrest leaves cancerous cells no options for DNA damage repair and results in apoptosis. Normal cells have wild type p53 and retain an intact G1/S checkpoint. Thus these cells have an opportunity to correct DNA damage and survive. One approach to the design of chemosensitizers that abrogate the G2/M checkpoint is to identify inhibitors of the key G2/M regulatory kinase, CHK-1.

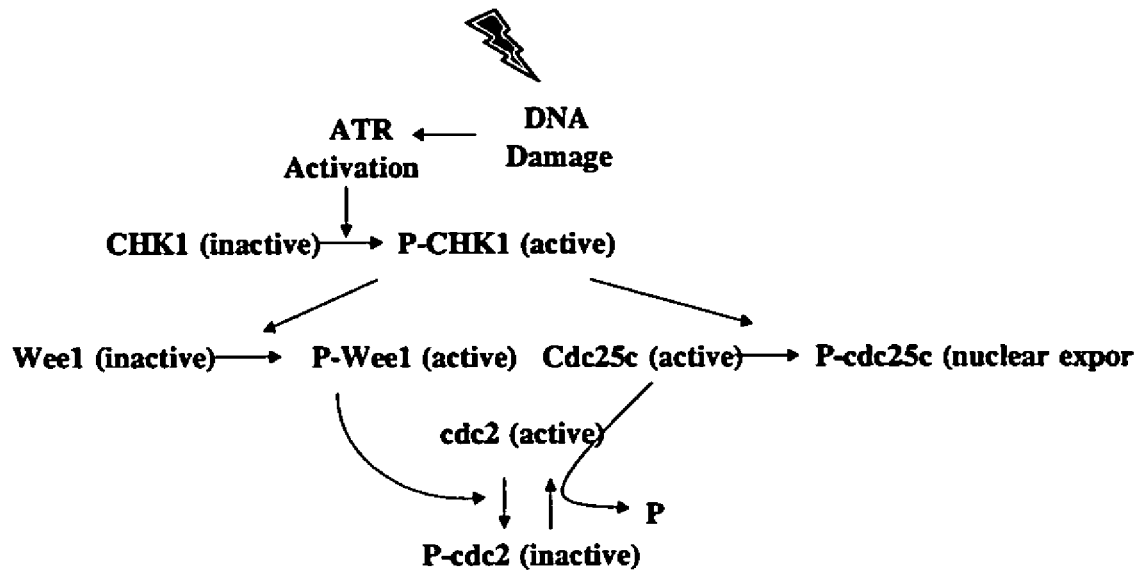

The synthesis of various quinoline derivatives is disclosed in WO 97/48694. These compounds are disclosed as capable of binding to nuclear hormone receptors and being useful for stimulating osteoblast proliferation and bone growth. The compounds are also disclosed as being useful in the treatment or prevention of diseases associated with nuclear hormone receptor families.

Various quinoline derivatives in which the benzene ring of the quinolone is substituted with a sulfur group are disclosed in WO 92/18483. These compounds are disclosed as being useful in pharmaceutical formulations and as medicaments.

Various indolyl substituted compounds have recently been disclosed in WO 01/29025, and various benzimidazolyl substituted compounds have recently been disclosed in WO 01/28993. Such compounds are reportedly capable of inhibiting, modulating and/or regulating signal transduction of both receptor-type and non-receptor type tyrosine kinases. Neither of the PCT publications discloses benzimidazole-substituted indazoles.

Various indazole compounds and pharmaceutical formulations containing them are disclosed in WO 01/02369 and recently published WO 01/53268. Such compositions are purportedly useful for mediating tyrosine kinase signal transduction and thereby modulating and/or inhibiting cell proliferation. Some of the disclosed compounds include the benzimidazole group. Various benzimidazoles substituted with —C(═O)—NH$_2$ are disclosed in WO 00/68206 as useful as inhibitors of the enzyme poly(ADP-ribose)polymerase and for use in producing medicaments.

A continuing need exists for compounds that inhibit the proliferation of capillaries, inhibit the growth of tumors, treat cancer, treat diabetes, stimulate insulin-dependent processes, treat Alzheimer's disease, treat central nervous system disorders, prolong immune responses, reduce the splitting of centrosomes, block DNA repair, modulate cell cycle arrest, and/or inhibit enzymes such as flt-1 (VEGFR2), flt-3, KDR (VEGFR2), Flk-1, bFGFR, GSK-3, NEK-2, CHK-1, Tie-2, PDGF, and cdc 2, and pharmaceutical formulations and medicaments that contain such compounds. A need also exists for methods for administering such compounds, pharmaceutical formulations, and medicaments to patients or subjects in need thereof.

SUMMARY OF THE INVENTION

The present invention provides compounds, pharmaceutical formulations and medicaments that include the compounds, methods of preparing the pharmaceutical formulations, medicaments, and compounds, and methods of inhibiting enzymes such as c-ABL in patients using the pharmaceutical formulations and compounds.

In one aspect, the present invention provides a method for inhibiting c-ABL in a patient. The method includes administering an effective amount of a compound having the structure I, a tautomer of the compound, a pharmaceutically acceptable salt of the compound, or a pharmaceutically acceptable salt of the tautomer to a patient. The IC$_{50}$ value of the compound, the tautomer, the pharmaceutically acceptable salt of the compound, or the pharmaceutically acceptable salt of the tautomer is less than 10 micromolar with respect to c-ABL and the compound having the structure I has the following structure:

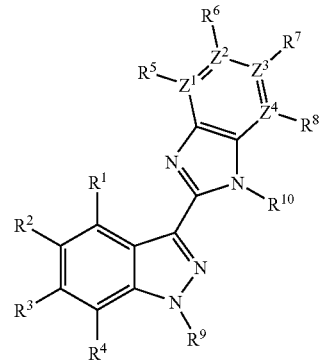

where:

$Z^1$, $Z^2$, $Z^3$, and $Z^4$ are selected independently from C or N;

$R^1$ is selected from the group consisting of —H, —F, —Cl, —Br, —NO$_2$, —C≡N, —C(═O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(═O)-aryl groups, substituted and unsubstituted —N(H)—C(═O)-alkyl groups, substituted and unsubstituted —N(H)C(═O)N(H)-alkyl groups, substituted and unsubstituted —N(H)C(═O)N(H)-aryl groups, substituted and unsubstituted —N(H)C(═O)N(H)-heterocyclyl groups, substituted and unsubstituted —N(H)—SO$_2$-alkyl groups, substituted and unsubstituted —N(H)—SO$_2$-aryl groups, —N(H)—SO$_2$-CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(═O)—N(H)-alkyl groups, substituted and unsubstituted —C(═O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl) aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(═O)-alkyl groups, substituted and unsubstituted -alkyl-N(alkyl)-C(═O)-aryl groups, substituted and unsubstituted -alkyl-N(alkyl)-C(═O)-heterocyclyl groups, substituted and unsubstituted -alkyl-N(alkyl)-C(═O)-alkyl-aryl groups, and unsubstituted -alkyl-N(alkyl)-C(═O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(═O)-alkyl groups, substituted and unsubstituted -alkyl-N(H)—C(═O)-aryl groups, substituted and unsubstituted -alkyl-N(H)—C(═O)-heterocyclyl groups, substituted and unsubstituted -alkyl-N(H)—C(═O)-alkyl-aryl groups, and substituted and unsubstituted -alkyl-N(H)—C(═O)-alkyl-heterocyclyl groups;

$R^2$ is selected from the group consisting of —H, —F, —Cl, —Br, —C≡N, —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclylalkylamino groups, substituted and unsubstituted arylalkylamino groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups; or $R^2$ and $R^3$ are a group of formula —OCH$_2$O— such that $R^2$ and $R^3$ define a fused 5-membered ring that includes 2 oxygen atoms;

$R^3$ is selected from the group consisting of —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocyclyl groups, substituted and unsubstituted —N(H)—C(=O)-alkyl groups, substituted and unsubstituted —N(H)—C(=O)-aryl groups, substituted and unsubstituted —N(H)—(SO2)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^4$ is selected from the group consisting of —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF3 groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^5$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;

$R^8$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is selected from the group consisting of —H, and substituted and unsubstituted alkyl groups.

In another aspect, the present invention provides compounds having the structure I. The invention also provides tautomers of the compounds, pharmaceutically acceptable salts of the compounds, and pharmaceutically acceptable salts of the tautomers. Structure I has the following formula:

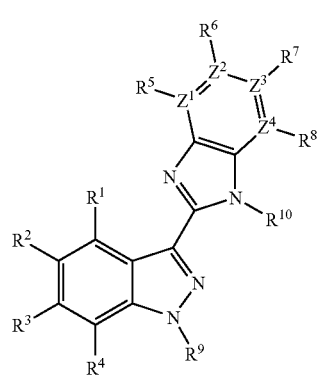

where, in one group of compounds:

$Z^1, Z^2, Z^3$, and $Z^4$ are selected independently from C or N;

$R^1$ is selected from the group consisting of —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl) aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^2$ is selected from the group consisting of substituted or unsubstituted arylalkoxy groups, substituted and unsubstituted aryloxy groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted heterocyclylalkylamino groups, substituted and unsubstituted arylalkylamino groups; substituted and unsubstituted —N(H)-heterocyclyl groups, substituted and unsubstituted alkoxy groups, and substituted and unsubstituted heterocyclyloxy groups;

$R^3$ is selected from the group consisting of —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups and substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^4$ is selected from the group consisting of —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^5$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;

$R^8$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is selected from the group consisting of —H, and substituted and unsubstituted alkyl groups.

The present invention also provides another group of compounds having the structure I. The invention also provides tautomers of the compounds, pharmaceutically acceptable salts of the compounds, and pharmaceutically acceptable salts of the tautomers. Structure I has the following formula:

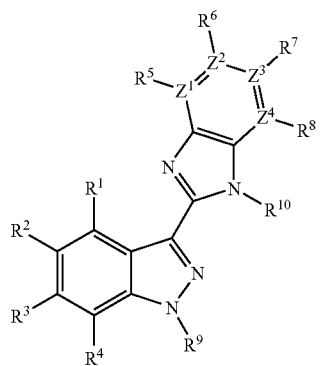

where:

$Z^1, Z^2, Z^3$, and $Z^4$ are selected independently from C or N;

$R^1$ is selected from the group consisting of —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)C(=O)-alkyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^2$ is selected from the group consisting of —H, —F, —Cl, —Br, —C≡N, —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclylalkylamino groups, substituted and unsubstituted arylalkylamino groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups; or $R^2$ and $R^3$ are a group of formula —OCH$_2$O— such that $R^2$ and $R^3$ define a fused 5-membered ring that includes 2 oxygen atoms;

$R^3$ is selected from the group consisting of —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^4$ is selected from the group consisting of —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^5$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from the group consisting of —H, —F, —Cl, —Br, —$CF_3$, —$CO_2H$, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;

$R^8$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H;

$R^{10}$ is selected from the group consisting of —H, and substituted and unsubstituted alkyl groups; and at least one of $Z^2$ or $Z^3$ is C and at least one of $R^6$ and $R^7$ is selected from the group consisting of substituted and unsubstituted piperidinyl groups; substituted and unsubstituted morpholinyl compounds, substituted and unsubstituted heterocyclylheterocyclyl groups, substituted and unsubstituted azabicyclic amine groups, and substituted and unsubstituted heterocyclylalkyl groups.

Pharmaceutical formulations according to the present invention are provided which include any of the compounds described above in combination with a pharmaceutically acceptable carrier.

The invention further provides methods for synthesizing the compounds of formula I.

A method of treating a patient is also provided which includes administering an effective amount of the pharmaceutical formulation according to the present invention to a patient in need thereof.

A method for inhibiting tumor growth in a patient is provided and includes administering an effective amount of a compound according to the invention to a patient having a tumor.

A method for inhibiting the proliferation of capillaries in a patient in need is still further provided and includes administering an effective amount of a compound according to the present invention to a patient in need.

Various other methods for inhibiting enzymes and treating patients and cells using the compounds and pharmaceutical formulations of the invention are further disclosed in the following detailed description.

Further objects, features and advantages of the invention will be apparent from the following detailed description.

DETAILED DESCRIPTION OF THE INVENTION

The present invention relates to a novel class of compounds which act as inhibitors of receptor tyrosine kinases, including inhibitors of bFGF, VEGF-RTK, KDR, Flk-1, GSK-3, NEK-2, CHK-1, Tie-2, PDGF, c-ABL, CDC7, CSF1R, c-KIT and cdc 2. These compounds can be formulated into pharmaceutical formulations that are useful in treating patients with a need for such inhibitors (e.g., those suffering from cancer). The compounds described herein are also useful for reducing capillary proliferation and in the treatment of cancer and other medical or cellular conditions in human and cell subjects.

The following abbreviations and definitions are used throughout this application:

"VEGF" is an abbreviation that stands for vascular endothelial growth factor.

"RTK" is an abbreviation that stands for receptor tyrosine kinase.

"VEGF-RTK" is an abbreviation that stands for vascular endothelial growth factor receptor tyrosine kinase.

"Flt-1" is an abbreviation that stands for fms-like tyrosine kinase-1, also known as vascular endothelial growth factor receptor-1 or VEGFR1.

"Flt-3" is an abbreviation that stands for fms-like tyrosine kinase-3.

"KDR" is an abbreviation that stands for kinase-insert domain tyrosine kinase, also known as vascular endothelial growth factor receptor-2 or VEGFR2.

"bFGF" is an abbreviation that stands for basic fibroblast growth factor.

"bFGFR" is an abbreviation that stands for basic fibroblast growth factor receptor.

"GSK-3" is an abbreviation that stands for glycogen synthase kinase 3.

"NEK-2" is an abbreviation that stands for NIM-A related kinase.

"NIM-A" is an abbreviation that stands for never in mitosis.

"CHK 1" is an abbreviation that stands for checkpoint kinase 1.

"Cdc 2" is an abbreviation that stands for cell division cycle 2.

"Cdc 7" is an abbreviation that stands for cell division cycle 7.

"CSF1R" is an abbreviation that stands for colony stimulating factor 1 receptor.

"Tie-2" is an abbreviation that stands for tyrosine kinase with Ig and EGF homology domains.

"c-ABL" is an abbreviation for a tyrosine kinase that stands for an oncogene product originally isolated from the Abelson leukemia virus.

"PDGF" is an abbreviation that stands for platelet derived growth factor.

"Flk-1" is an abbreviation that stands for fetal liver tyrosine kinase 1.

"AD" is an abbreviation that stands for Alzheimer Disease.

"APP" is an abbreviation that stands for amyloid precursor protein.

"PHF" is an abbreviation that stands for paired helical filaments.

"PS 1" is an abbreviation that stands for presenellin 1.

"MS" is an abbreviation that stands for multiple sclerosis.

"AML" is an abbreviation that stands for amyotropic lateral sclerosis.

Generally, reference to a certain element such as hydrogen or H is meant to include all isotopes of that element. For example, if an R group is defined to include hydrogen or H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. Thus the phrase unsubstituted alkyl groups includes primary alkyl groups, secondary alkyl groups, and tertiary alkyl groups. Unsubstituted alkyl groups may be bonded to one or more carbon atom(s), oxygen atom(s), and/or nitrogen atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 8, from 1 to 6 or from 1 to 4 carbon atoms. Other preferred unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heterocyclyl group, or cycloalkyl group. Preferred substituted alkyl groups include, among others, alkyl groups in which one or more bonds to a carbon or hydrogen atom is/are replaced by one or more bonds to fluorine atoms. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Still other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group.

The phrase "unsubstituted aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members as aryl groups such as tolyl are substituted aryl groups. A preferred unsubstituted aryl group is phenyl. Unsubstituted aryl groups may be bonded to one or more carbon atom(s), oxygen atom(s), and/or nitrogen atom(s) in the parent compound.

The phrase "substituted aryl group" has the same meaning with respect to unsubstituted aryl groups that substituted alkyl groups had with respect to unsubstituted alkyl groups. A substituted aryl group includes aryl groups in which one of the aromatic carbons is bonded to a non-carbon or non-hydrogen atom and also includes aryl groups in which one or more aromatic carbons of the aryl group is bonded to a substituted and/or unsubstituted alkyl group. Thus, the phrase "substituted aryl" includes, but is not limited to tolyl, and hydroxyphenyl among others.

The phrase "unsubstituted arylalkyl" refers to unsubstituted alkyl groups as defined above in which a hydrogen or carbon bond of the unsubstituted alkyl group is replaced with a bond to an aryl group as defined above. For example, methyl (—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted arylalkyl group. Thus the phrase includes, but is not limited to, groups such as benzyl, diphenylmethyl, —CH(C$_6$H$_5$)(CH$_3$), and —CH$_2$CH$_2$(C$_6$H$_5$) among others.

The phrase "substituted arylalkyl" has the same meaning with respect to unsubstituted arylalkyl groups that substituted aryl groups had with respect to unsubstituted aryl groups. However, a substituted arylalkyl group also includes groups in which a carbon or hydrogen bond of the alkyl part of the group is replaced by a bond to a non-carbon or a non-hydrogen atom. Examples of substituted arylalkyl groups include, but are not limited to, —CH$_2$C(=O)(C$_6$H$_5$), and —CH$_2$(2-methylphenyl) among others.

The phrase "unsubstituted heterocyclyl" refers to both aromatic and nonaromatic ring compounds containing 3 or more ring members of which one or more is a heteroatom such as, but not limited to, N, O, and S. Although the phrase "unsubstituted heterocyclyl" includes condensed heterocyclic rings such as benzimidazolyl and indazolyl, it does not include heterocyclyl groups that have other groups such as alkyl or halo groups bonded to one of the ring members because compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H-tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furanyl (the furan group); unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, pyridine, 2,5-diazabicyclo [2.2.1]heptane, 1-4-diazacycloheptane, imidazole, pyrazole, 1,2,3-triazole, 1,2,4-triazole, tetrazole, thiomorpholine, pyrrole, homopiperazine, oxazolidin-2-one, pyrrolidin-2-one, oxazole, thiazole, isoxazole, furan, and tetrahydrofuran.

The phrase "substituted heterocyclyl" refers to an unsubstituted heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, 1-ethylpiperazinyl, 1-isopropylpiperazinyl, 4-(piperidinyl)piperidinyl, 2,6-dimethylpiperazinyl, 3,5-dimethylpiperazinyl, 2,6-dimethylmorpholinyl, dimethyl[(5-methylmorpholin-2-yl)methyl]amine, dimethyl(morpholin-2-ylmethyl)amine, 5-methyl-2-(dimethylaminomethyl)-1-oxa-4-azacycloheptyl, 1-methyl-1,4-diazabicycloheptane, hydroxyalkylpiperazinyl, dialkylaminopyrrolidinyl, alkylpyrrolidinyl, and 2-chloropyridyl among others.

The phrase "unsubstituted heteroaryl" refers to an unsubstituted heterocyclyl group as defined above which is aromatic. Pyridine is just one example of such a group.

The phrase "substituted heteroaryl" refers to an unsubstituted heteroaryl group as defined above in which a ring member of the heteroaryl group is bonded to a non-hydrogen atom.

The phrase "unsubstituted arylheterocyclyl" refers to heterocyclyl groups as defined above in which a ring member of a heterocyclyl group is bonded to an otherwise unsubstituted aryl group as defined above. For example, piperazine is a heterocyclyl group. If a nitrogen or carbon atom of the piperazinyl group is bonded to an unsubstituted aryl group, then the compound is an unsubstituted arylheterocyclyl group if the heterocyclyl group is also unsubstituted save for its point of attachment to the parent compound.

The phrase "substituted arylheterocyclyl" refers to heterocyclyl groups as defined above in which a ring member of a heterocyclyl group is bonded to an aryl group as defined above. For example, piperazine is a heterocyclyl group. If a nitrogen or carbon atom of the piperazinyl group is bonded to an aryl group, then the compound is a substituted arylheterocyclyl group if the aryl group is otherwise substituted and/or the heterocyclyl group is also substituted in addition to its point of attachment to the parent compound.

The phrase "unsubstituted cycloalkylheterocyclyl" refers to heterocyclyl groups as defined above in which a ring member of a heterocyclyl group is bonded to an otherwise unsubstituted cycloalkyl group. For example, piperazine is a heterocyclyl group. If a nitrogen or carbon atom of the piperazinyl group is bonded to an unsubstituted cycloalkyl group, then the compound is an unsubstituted cycloalkylheterocyclyl group if the heterocyclyl group is also unsubstituted save for its point of attachment to the parent compound. Unsubstituted cycloalkylheterocyclyl groups include, but are not limited to N-cyclohexylpiperazinyl groups, 4-(cyclohexyl)piperidinyl groups, 4-cyclopentylpiperidinyl groups, and the like.

The phrase "substituted cycloalkylheterocyclyl" refers to heterocyclyl groups as defined above in which a ring member of a heterocyclyl group is bonded to a cycloalkyl group as defined above. For example, piperazine is a heterocyclyl group. If a nitrogen or carbon atom of the piperazinyl group is bonded to a cycloalkyl group, then the compound is a substituted cycloalkylheterocyclyl group if the cycloalkyl group is otherwise substituted and/or the heterocyclyl group is also substituted in addition to its point of attachment to the parent compound.

The phrase "unsubstituted heterocyclylheterocyclyl" refers to heterocyclyl groups as defined above in which a ring member of a first heterocyclyl group is bonded to a second otherwise unsubstituted heterocyclyl group as defined above. For example, piperazine is a heterocyclyl group. If a nitrogen or carbon atom of the piperazinyl group is bonded to a second unsubstituted heterocyclyl group, then the compound is an unsubstituted heterocyclylheterocyclyl group if the first heterocyclyl group is otherwise unsubstituted save for its point of attachment to the parent compound. Unsubstituted heterocyclylheterocyclyl groups include, among others piperidinylpiperidinyl groups and the like such as, but not limited to, 4-(piperidinyl)piperidinyl.

The phrase "substituted heterocyclylheterocyclyl" refers to heterocyclyl groups as defined above in which a ring member of a first heterocyclyl group is bonded to a second heterocyclyl group as defined above. For example, piperazine is a heterocyclyl group. If a nitrogen or carbon atom of the piperazinyl group is bonded to a second heterocyclyl group, then the compound is a substituted heterocyclylheterocyclyl group if the second heterocyclyl group is otherwise substituted and/ or the first heterocyclyl group is also substituted in addition to its point of attachment to the parent compound.

The phrase "unsubstituted heterocyclylalkyl" refers to unsubstituted alkyl groups as defined above in which a hydrogen or carbon bond of the unsubstituted alkyl group is replaced with a bond to a an otherwise unsubstituted heterocyclyl group as defined above. For example, methyl (—CH$_3$) is an unsubstituted alkyl group. If a hydrogen atom of the methyl group is replaced by a bond to an unsubstituted heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted arylalkyl groups had with respect to unsubstituted arylalkyl groups. However, a substituted heterocyclylalkyl group also includes groups in which a nonhydrogen atom is bonded to a heteroatom in the heterocyclyl group of the heterocyclylalkyl group such as, but not limited to, a nitrogen atom in the piperidine ring of a piperidinylalkyl group.

The phrase "unsubstituted alkoxy" refers to an —O-alkyl group where the alkyl group is otherwise unsubstituted. Examples of unsubstituted alkoxy groups include, but are not limited to methoxy, ethoxy, n-propoxy, i-propoxy, and n-butoxy groups.

The phrase "substituted alkoxy" refers to an —O-alkyl group where the alkyl group is otherwise substituted.

The phrase "unsubstituted aryloxy" refers to an —O-aryl group where the aryl group is otherwise unsubstituted. Examples of unsubstituted aryloxy groups include, but are not limited to, phenyloxy, and naphthyloxy groups.

The phrase "substituted aryloxy" refers to an —O-aryl group where the aryl group is otherwise substituted. Examples of such groups include 4-chlorophenyloxy and 2-methylphenyloxy groups.

The phrase "unsubstituted heterocyclyloxy" refers to an —O-heterocyclyl group where the heterocyclyl group is otherwise unsubstituted.

The phrase "substituted heterocyclyloxy" refers to an —O-heterocyclyl group where the heterocyclyl group is otherwise substituted.

The phrase "unsubstituted arylalkoxy" refers to an arylalkyl-O— group where the alkyl group of the arylalkyl group is bonded to the O atom and the arylalkyl group is otherwise unsubstituted.

The phrase "substituted arylalkoxy" refers to an arylalkyl-O— group where the alkyl group of the arylalkyl group is bonded to the O atom and the arylalkyl group is otherwise substituted.

The phrase "unsubstituted heterocyclylalkoxy" refers to a heterocyclylalkyl-O— group where the alkyl group of the heterocycyalkyl group is bonded to the O atom and the heterocyclylalkyl group is otherwise unsubstituted.

The phrase "substituted heterocyclylalkoxy" refers to an heterocyclylalkyl-O— group where the alkyl group of the heterocycyalkyl group is bonded to the O atom and the heterocyclylalkyl group is otherwise substituted.

The phrase "unsubstituted alkoxyalkoxy" refers to an —O-alkyl-O-alkyl group where both of the alkyl groups are otherwise unsubstituted.

The phrase "substituted alkoxyalkoxy" refers to an —O-alkyl-O-alkyl group where one or both of the alkyl groups are otherwise substituted.

The phrase "unsubstituted amino" refers to —NH$_2$.

The phrase "substituted amino" refers to an amino group in which one or more bonds to the hydrogen atoms of the amino group are replaced by bonds to non-hydrogen atom. Examples of substituted amino groups include, but are not limited to, substituted and unsubstituted alkylamino groups, heterocyclylamino groups, arylamino groups, dialkylamino groups, diheterocyclylamino groups, diarylamino groups, (alkyl)(heterocycyl)amino groups, (alkyl)(aryl)amino groups, and (heterocyclyl)(aryl) groups.

The phrase "unsubstituted alkylamino" refers to an amino group in which one of the bonds to one of the hydrogen atoms in the amino group is replaced with a bond to an otherwise unsubstituted alkyl group as defined above. Examples of unsubstituted alkylamino groups include, but are not limited to, methylamino, ethylamino, i-propylamino, n-propylamino, butylamino, and cyclohexylamino groups.

The phrase "substituted alkylamino" refers to an amino group in which one of the bonds to one of the hydrogen atoms in the amino group is replaced with a bond to an otherwise substituted alkyl group as defined above.

The phrase "unsubstituted heterocyclylamino" refers to an amino group in which one of the bonds to one of the hydrogen atoms in the amino group is replaced with a bond to an otherwise unsubstituted heterocyclyl group as defined above.

The phrase "substituted heterocyclylamino" refers to an amino group in which one of the bonds to one of the hydrogen atoms in the amino group is replaced with a bond to an otherwise substituted heterocyclyl group as defined above.

The phrase "unsubstituted dialkylamino" refers to an amino group in which the bonds to the two hydrogen atoms in the amino group are replaced with bonds to two alkyl groups which may be the same or different and which are otherwise unsubstituted alkyl groups as defined above. Examples of unsubstituted dialkylamino groups include, but are not limited to, dimethylamino groups, (methyl)(ethyl)amino groups, and (methyl)(cyclohexyl)amino groups where the parentheses in groups such as (methyl)(cyclohexyl)amino group indicate that the methyl group is bonded to the nitrogen atom of the amino group and the cyclohexyl group is bonded to the nitrogen atom of the amino group.

The phrase "substituted dialkylamino" refers to an amino group in which the bonds to the two hydrogen atoms in the amino group are replaced with bonds to two alkyl groups which may be the same or different. Furthermore, in substituted dialkylamino groups, at least one of two alkyl groups is an otherwise substituted alkyl group as defined above.

The phrase "unsubstituted (alkyl)(heterocyclyl)amino" refers to an amino group in which one of the bonds to one of the hydrogen atoms of the amino group is replaced by a bond to an otherwise unsubstituted alkyl group as defined above and the bond to the other hydrogen atom of the amino group is replaced by a bond to an otherwise unsubstituted heterocyclyl group. Examples of unsubstituted (alkyl)(heterocyclyl)amino groups include, but are not limited to, (methyl)(pyridyl)amino groups, (methyl)(morpholinyl)amino groups, and (methyl)(piperidinyl)amino groups.

The phrase "substituted (alkyl)(heterocyclyl)amino" refers to an amino group in which one of the bonds to one of the hydrogen atoms of the amino group is replaced by a bond to an otherwise substituted or unsubstituted alkyl group as defined above and the bond to the other hydrogen atom of the amino group is replaced by a bond to an otherwise substituted or unsubstituted heterocyclyl group. However, if the bond to one of the hydrogen atoms in the amino group is replaced by a bond to an otherwise unsubstituted alkyl group, then the bond to the other hydrogen atom of the amino group is replaced by a bond to an otherwise substituted heterocyclyl group. The reverse is also true so that the alkyl group and/or the heterocyclyl group is substituted in a substituted (alkyl)(heterocyclyl)amino group.

The phrase "unsubstituted heterocyclylalkylamino" refers to an amino group in which a bond to one of the hydrogen atoms in the amino group is replaced with a bond to the alkyl group of an otherwise unsubstituted heterocyclylalkyl group. Examples of unsubstituted heterocyclylalkylamino groups include, but are not limited to, 3-pyridylmethylamino, 1-piperidinylmethylamino, and 4-morpholinylmethylamino groups.

The phrase "substituted heterocyclylalkylamino" refers to an amino group in which a bond to one of the hydrogen atoms in the amino group is replaced with a bond to the alkyl group of an otherwise substituted heterocyclylalkyl group.

The phrase "unsubstituted arylalkylamino" refers to an amino group in which a bond to one of the hydrogen atoms in the amino group is replaced with a bond to the alkyl group of an otherwise unsubstituted arylalkyl group. Examples of unsubstituted arylalkylamino groups include, but are not limited to, phenylmethylamino, and naphthylethylamino groups.

The phrase "substituted arylalkylamino" refers to an amino group in which a bond to one of the hydrogen atoms in the amino group is replaced with a bond to the alkyl group of an otherwise substituted arylalkyl group.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W., John Wiley & Sons, New York, N.Y., (1st Edition, 1981) which can be added or removed using the procedures set forth therein. Examples of protected hydroxyl groups include, but are not limited to, silyl ethers such as those obtained by reaction of a hydroxyl group with a reagent such as, but not limited to, t-butyldimethylchlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

The present invention provides compounds, pharmaceutical formulations including the compounds, methods of preparing the pharmaceutical formulations, and methods of treating patients with the pharmaceutical formulations and compounds.

The present invention provides compounds having the structure I. The invention also provides tautomers of the compounds, pharmaceutically acceptable salts of the compounds, and pharmaceutically acceptable salts of the tautomers. Structure I has the following formula:

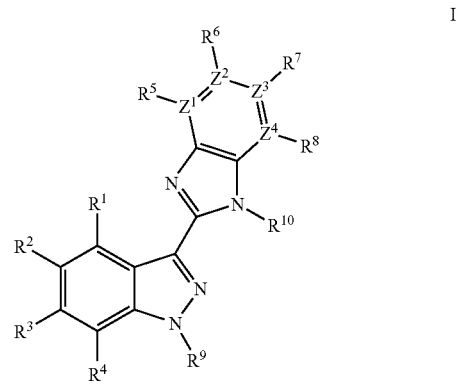

where, in the first group of compounds:

$Z^1$, $Z^2$, $Z^3$, and $Z^4$ are selected independently from C or N;

$R^1$-$R^8$ are selected independently from the group consisting of —H, —F, —Cl, —Br, —C≡N, —NO$_2$, —CF$_3$, —CO$_2$H, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted alkoxy groups, substituted and unsubstituted aryloxy groups, substituted and unsubstituted arylalkoxy groups, substituted and unsubstituted heterocyclyloxy groups, substituted and unsubstituted heterocyclylalkoxy groups, substituted and unsubstituted alkylheterocyclyl groups, substituted and unsubstituted —C(=O)N(H)-alkyl groups, substituted and unsubstituted —C(=O)N(H)-aryl groups, substituted and unsubstituted —C(=O)N(H)-heteroaryl groups, substituted and unsubstituted —C(=O)—N(H)-heterocyclyl groups, substituted and unsubstituted —C(=O)—N(H)-alkyl-heterocyclyl groups, substituted and unsubstituted —C(=O)—N(alkyl)(heterocyclyl) groups, substituted and unsubstituted —C(=O)-heterocyclyl groups, substituted and unsubstituted —N(H)C(=O)-alkyl groups, substituted and unsubstituted —N(H)C(=O)-aryl groups, substituted and unsubstituted —N(H)C(=O)-heteroaryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, substituted and unsubstituted —N(H)—(SO$_2$)-alkyl groups, substituted and unsubstituted aryl groups, substituted and unsubstituted heteroaryl groups, and substituted and unsubstituted heterocyclyl groups;

$R^9$ is —H, —C(=O)-alkyl, or —C(=O)-aryl; and $R^{10}$ is —H, —C(=O)-alkyl, or —C(=O)-aryl.

More particular embodiments of the compounds of the invention having the general structure shown in I above are provided. The second group of compounds are those for which:

$Z^1$, $Z^2$, $Z^3$, and $Z^4$ are independently selected from C or N;

$R^1$ is selected from —H, —F, —Cl, and —Br;

$R^2$ is selected from —H, —F, —Cl, —Br, —C≡N, —NO$_2$, —CO$_2$H, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, substituted and unsubstituted alkoxy groups, substituted and unsubstituted arylalkoxy groups, substituted and unsubstituted aryloxy groups, substituted and unsubstituted heterocyclyloxy groups, and substituted and unsubstituted heterocyclylalkoxy groups;

or $R^2$ is selected from —H, —F, —Cl, —Br, —C≡N, —NO$_2$, —CO$_2$H, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, and substituted and unsubstituted alkoxy groups;

$R^3$ is selected from —H, —F, —Cl, —Br, and substituted and unsubstituted alkoxy groups;

$R^4$ is —H;

$R^5$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, and substituted and unsubstituted —C(=O)N(H)-heterocyclyl groups; or $R^6$ is absent if $Z^2$ is N;

$R^7$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, and substituted and unsubstituted —C(=O)N(H)-heterocyclyl groups; or $R^7$ is absent if $Z^3$ is N;

$R^8$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is —H. In some embodiments of the second group of compounds, at least one of $R^1$, $R^2$, $R^3$, $R^5$, $R^6$, $R^7$ or $R^8$ is not —H. In other such embodiments, at least two of $R^1$, $R^2$, $R^3$, $R^5$, $R^6$, $R^7$ or $R^8$ are not —H.

In one embodiment of the second group of compounds, each of $Z^1$, $Z^2$, $Z^3$, and $Z^4$ are C.

In another embodiment of the second group of compounds, $Z^1$ is N and each of $Z^2$, $Z^3$, and $Z^4$ are C.

In another embodiment of the second group of compounds, $Z^1$ and $Z^3$ are both N and $Z^2$ and $Z^4$ are both C.

In another embodiment of the second group of compounds, $Z^3$ is N and each of $Z^1$, $Z^2$, and $Z^4$ are C.

In another embodiment of the second group of compounds, $Z^1$-$Z^4$ have any of the values in previous embodiments, and $R^1$ is selected from —H, —F, —Cl, and —Br.

In another embodiment of the second group of compounds, $Z^1$-$Z^4$ and $R^1$ have any of the values in previous embodiments, and $R^2$ is selected from —H, —F, —Cl, —CO$_2$H, substituted and unsubstituted alkyl groups, substituted and unsubstituted —C(=O)O-alkyl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, substituted and unsubstituted alkoxy groups, substituted and unsubstituted arylalkoxy groups, substituted and unsubstituted aryloxy groups and substituted and unsubstituted heterocyclylalkoxy groups.

In another embodiment thereof, $R^2$ is selected from —H, —F, —Cl, —CO$_2$H, substituted and unsubstituted alkyl groups, substituted and unsubstituted —C(=O)O-alkyl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, substituted and unsubstituted alkoxy groups.

In another embodiment of the second group of compounds, $Z_1$-$Z^4$ and $R^1$ have any of the values in previous embodiments, and $R^2$ is an unsubstituted alkoxy group having from 1 to 4 carbon atoms.

In another embodiment of the second group of compounds, $Z^1$-$Z^4$ and $R^1$ have any of the values in previous embodiments, and $R^2$ is —OMe.

In another embodiment of the second group of compounds, $Z^1$-$Z^4$ and $R^1$ have any of the values in previous embodiments, and $R^2$ is —O-i-Pr.

In another embodiment of the second group of compounds, $Z^1$-$Z^4$ and $R^1$ have any of the values in previous embodiments, and $R^2$ is a substituted or unsubstituted arylalkoxy group.

In another embodiment of the second group of compounds, $Z^1$-$Z^4$ and $R^1$ have any of the values in previous embodiments, and $R^2$ is a benzyloxy group.

In another embodiment of the second group of compounds, $Z^1$-$Z^4$ and $R^1$ have any of the values in previous embodiments, and $R^2$ is a substituted or unsubstituted aryloxy group.

In another embodiment of the second group of compounds, $Z^1$-$Z^4$ and $R^1$ have any of the values in previous embodiments, and $R^2$ is a phenyloxy group.

In another embodiment of the second group of compounds, $Z^1$-$Z^4$ and $R^1$ have any of the values in previous embodiments, and $R^2$ is an unsubstituted alkyl group having from 1 to 4 carbon atoms.

In another embodiment of the second group of compounds, $Z^1$-$Z^4$ and $R^1$ have any of the values in previous embodiments, and $R^2$ is a methyl group.

In another embodiment of the second group of compounds, $Z^1$-$Z^4$, $R^1$, and $R^2$ have any of the values in previous embodiments, and $R^3$ is selected from —H, —F, —Cl, and —OMe.

In another embodiment of the second group of compounds, $Z^1$-$Z^4$, $R^1$, and $R^2$ have any of the values in previous embodiments, and $R^3$ is selected from —F, —Cl, —Br, and substituted and unsubstituted alkoxy groups.

In another embodiment of the second group of compounds, $Z^1$-$Z^4$, $R^1$, and $R^2$ have any of the values in previous embodiments, and $R^3$ is —H.

In another embodiment of the second group of compounds, $Z^1$-$Z^4$, $R^1$, and $R^2$ have any of the values in previous embodiments, and $R^3$ is —F.

In another embodiment of the second group of compounds, $Z^1$-$Z^4$, $R^1$, and $R^2$ have any of the values in previous embodiments, and $R^3$ is —Cl.

In another embodiment of the second group of compounds, $Z^1$-$Z^4$, $R^1$, and $R^2$ have any of the values in previous embodiments, and $R^3$ is —OMe.

In another embodiment of the second group of compounds, $Z^2$-$Z^4$, $R^1$, $R^2$, and $R^3$ have any of the values in previous embodiments, $Z^1$ is C, and $R^5$ is H.

In another embodiment of the second group of compounds, $Z^2$-$Z^4$, $R^1$, $R^2$, and $R^3$ have any of the values in previous embodiments, $Z^1$ is C, and $R^5$ is —CH$_3$.

In another embodiment of the second group of compounds, $Z^2$-$Z^4$, $R^1$, $R^2$, and $R^3$ have any of the values in previous embodiments, $Z^1$ is C, and $R^5$ is morpholine.

In another embodiment of the second group of compounds, $Z^1$-$Z^3$, $R^1$, $R^2$, and $R^3$ have any of the values in previous embodiments, $Z^4$ is C, and $R^8$ is H.

In another embodiment of the second group of compounds, $Z^1$-$Z^3$, $R^1$, $R^2$, and $R^3$ have any of the values in previous embodiments, $Z^4$ is C, and $R^8$ is —CH$_3$.

In another embodiment of the second group of compounds, $Z^1$-$Z^3$, $R^1$, $R^2$, and $R^3$ have any of the values in previous embodiments, $Z^4$ is C, and $R^8$ is morpholine.

In another embodiment of the second group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from —Br, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted heterocyclyl groups including substituted and unsubstituted heterocyclylheterocyclyl groups, substituted and unsubstituted arylheterocyclyl groups, and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other such embodiments, $R^6$ has the values described in the preceding sentence and $R^7$ is —H.

In another embodiment of the second group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkoxy group having from 1-6 carbon atoms. In still other such embodiments, $R^6$ is a methoxy group. In still other such embodiments where $R^6$ is an alkoxy group having from 1-6 carbon atoms such as a methoxy group, $R^7$ is —H.

In another embodiment of the second group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkyl group having from 1-6 carbon atoms. In still other such embodiments, $R^6$ is a methyl group. In still other such embodiments where $R^6$ is an alkyl group having from 1-6 carbon atoms such as a methyl group, $R^7$ is —H.

In another embodiment of the second group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted alkoxy group having the formula —OCH$_2$(CH$_2$)$_m$R$^{11}$ where m is an integer selected from 0, 1, or 2 and $R^{11}$ is selected from substituted and unsubstituted alkoxy groups, substituted and unsubstituted aryl groups, and substituted and unsubstituted heterocyclyl groups. In still other such embodiments, $R^{11}$ is selected from substituted alkoxy groups. In still other such embodiments, $R^{11}$ is selected from substituted and unsubstituted heterocyclyl groups selected from pyrrolidinyl groups, pyridyl groups, morpholinyl groups, piperazinyl groups, and piperidinyl groups. In still other such embodiments where $R^6$ is a substituted alkoxy group having the formula —OCH$_2$(CH$_2$)$_m$R$^{11}$, $R^7$ is —H.

In another embodiment of the second group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula —N(R$^{12}$)CH$_2$(CH$_2$)$_m$R$^{13}$ where m is an integer selected from 0, 1, or 2, $R^{13}$ is selected from substituted and unsubstituted alkoxy groups, substituted and unsubstituted aryl groups, and substituted and unsubstituted heterocyclyl groups, and $R^{12}$ is —H or a substituted or unsubstituted alkyl group. In some such embodiments $R^{12}$ is H. In other embodiments $R^{12}$ is a —CH$_3$ group. In still other such embodiments, $R^{13}$ is selected from substituted alkoxy groups. In still other such embodiments, $R^{13}$ is selected from substituted and unsubstituted heterocyclyl groups selected from pyrrolidinyl groups, pyridyl groups, morpholinyl groups, piperazinyl groups, and piperidinyl groups.

In still other embodiments of the second group of compounds where $R^6$ is a substituted amino group having the formula —N(R$^{12}$)CH$_2$(CH$_2$)$_m$R$^{13}$, $R^7$ is —H.

In another embodiment of the second group of compounds, $Z^1$, $Z^3$, $Z^4$, $R^1$, $R^2$, $R^3$, $R^5$, and $R^8$ have any of the values defined in the previous embodiments, $Z^2$ is C, and $R^6$ is a substituted or unsubstituted heterocyclyl group. In some embodiments of the second group of compounds where $R^6$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted 2,5-diazabicyclo[2.2.1]heptane groups, and substituted and unsubstituted 1,4-diazabicyclo[2.2.2]octane groups. In other embodiments of the second group of compounds where $R^6$ is a heterocyclyl group, the heterocyclyl group is an unsubstituted morpholine group, a dialkyl substituted morpholinyl group, an unsubstituted piperazine group, a dialkyl substituted piperazinyl group, a monoalkyl substituted piperazinyl group, an aryl substituted piperazinyl group, a —CH$_2$C(=O)O-alkyl substituted piperazinyl group, a —C(=O)-alkyl substituted piperazinyl group, a —C(=O)O-alkyl substituted piperazinyl group, a cycloalkyl substituted piperazinyl group, an unsubstituted piperidine group, an aryl substituted piperidinyl group, a cycloalkyl substituted piperidinyl group, a piperidinyl substituted piperidinyl group, a dialkylamino substituted pyrrolidinyl group, an unsubstituted 2,5-diazabicyclo[2.2.1]heptane group, and an alkyl substituted 2,5-diazabicyclo[2.2.1]heptane group. In still other embodiments of the second group of compounds where $R^6$ is a substituted or unsubstituted heterocyclyl group, $R^7$ is —H.

In another embodiment of the second group of compounds, $Z^1$, $Z^2$, $Z^4$, $R^1$, $R^2$, $R^3$, $R^5$, and $R^8$ have any of the values in previous embodiments, $Z^3$ is C, and $R^7$ is selected from substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted heterocyclyl groups including substituted and unsubstituted heterocyclylheterocyclyl groups, substituted and unsubstituted arylheterocyclyl groups, and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other such embodiments, $R^7$ has the values described in the preceding sentence and $R^6$ is —H.

In another embodiment of the second group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkoxy group having from 1-6 carbon atoms. In still other such embodiments, $R^7$ is a methoxy group. In still other embodiments of the second group of compounds where $R^7$ is an alkoxy group having from 1-6 carbon atoms such as a methoxy group, $R^6$ is —H.

In another embodiment of the second group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkyl group having from 1-6 carbon atoms. In still other such embodiments, $R^7$ is a methyl group. In still other embodiments of the second group of compounds where $R^7$ is an alkyl group having from 1-6 carbon atoms such as a methyl group, $R^6$ is —H.

In another embodiment of the second group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted alkoxy group having the formula —OCH$_2$(CH$_2$)$_n$R$^{14}$ where n is an integer selected from 0, 1, or 2 and $R^{14}$ is selected from substituted and unsubstituted alkoxy groups, substituted and unsubstituted aryl groups, and substituted and unsubstituted heterocyclyl groups. In still other such embodiments, $R^{14}$ is selected from substituted alkoxy groups. In still other such embodiments, $R^{14}$ is selected from substituted and unsubstituted heterocyclyl groups selected from pyrrolidinyl groups, pyridyl groups, morpholinyl groups, piperazinyl groups, and piperidinyl groups. In still other embodiments of the second group of compounds where $R^7$ is a substituted alkoxy group having the formula —OCH$_2$(CH$_2$)$_n$R$^{14}$, $R^6$ is —H.

In another embodiment of the second group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted amino group having the formula —N(R$^{15}$)CH$_2$(CH$_2$)$_n$R$^{16}$ where n is an integer selected from 0, 1, or 2, $R^{16}$ is selected from substituted and unsubstituted alkoxy groups, substituted and unsubstituted aryl groups, and substituted and unsubstituted heterocyclyl groups, and $R^{15}$ is selected from —H and alkyl groups. In some such embodiments, $R^{15}$ is a —H group. In other such embodiments, $R^{15}$ is a —CH$_3$ group. In still other such embodiments, $R^{16}$ is selected from substituted alkoxy groups. In still other such embodiments, $R^{16}$ is selected from substituted and unsubstituted heterocyclyl groups selected from pyrrolidinyl groups, pyridyl groups, morpholinyl groups, piperazinyl groups, and piperidinyl groups.

In still other embodiments of the second group of compounds where $R^7$ is a substituted amino group having the formula —N($R_{15}$)CH$_2$(CH$_2$)$_n$R$^{16}$, $R^6$ is —H.

In another embodiment of the second group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted or unsubstituted heterocyclyl group. In some such embodiments where $R^7$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted 2,5-diazabicyclo[2.2.1]heptane groups, and substituted and unsubstituted 1,4-diazabicyclo[2.2.2]octane groups. In still other embodiments of the second group of compounds where $R^7$ is a heterocyclyl group, the heterocyclyl group is an unsubstituted morpholine group, a dialkyl substituted morpholinyl group, an unsubstituted piperazine group, a dialkyl substituted piperazinyl group, a monoalkyl substituted piperazinyl group, an aryl substituted piperazinyl group, a —CH$_2$C(=O)O-alkyl substituted piperazinyl group, a —C(=O)-alkyl substituted piperazinyl group, a —C(=O)O-alkyl substituted piperazinyl group, a cycloalkyl substituted piperazinyl group, an unsubstituted piperidine group, an aryl substituted piperidinyl group, a cycloalkyl substituted piperidinyl group, a piperidinyl substituted piperidinyl group, a dialkylamino substituted pyrrolidinyl group, an unsubstituted 2,5-diazabicyclo[2.2.1]heptane group, and an alkyl substituted 2,5-diazabicyclo[2.2.1]heptane group. In still other embodiments of the second group of compounds where $R^7$ is a substituted or unsubstituted heterocyclyl group, $R^6$ is —H.

Other more particular embodiments of the compounds of the invention having the general structure shown in I above are provided. Such compounds form a third group of compounds for which:

$Z^1$, $Z^2$, $Z^3$, and $Z^4$ are independently selected from C or N;

$R^1$ is selected from —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, and substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)-C(=O)-alkyl-aryl groups, and substituted and unsubstituted -alkyl-N(H)-C(=O)-alkyl-heterocyclyl groups;

$R^2$ is selected from —H, —F, —Cl, —Br, —C≡N, —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)-C(=O)-alkyl-aryl groups, and substituted and unsubstituted -alkyl-N(H)-C(=O)-alkyl-heterocyclyl groups; or $R^2$ and $R^3$ are a group of formula —OCH$_2$O— such that $R^2$ and $R^3$ define a fused 5-membered ring that includes 2 oxygen atoms;

$R^3$ is selected from —H, —F, —Cl, —Br, —CF$_3$, —C≡N, substituted and unsubstituted alkyl groups, substituted and unsubstituted amino groups, substituted and unsubstituted alkoxy groups, substituted and unsubstituted —C(=O)—O-alkyl groups, substituted and unsubstituted arylalkoxy groups, substituted and unsubstituted saturated heterocyclyloxy groups, substituted and unsubstituted alkoxyalkyl groups, substituted and unsubstituted arylalkoxyalkyl groups, substituted and unsubstituted saturated heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, and substituted and unsubstituted -alkyl-N(alkyl)-C(=O)-alkyl-heterocyclyl groups;

$R^4$ is —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)-C(=O)-alkyl-aryl groups, and substituted and unsubstituted -alkyl-N(H)—C(=O)-alkyl-heterocyclyl groups;

$R^5$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;

$R^8$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is selected from the group consisting of —H, and substituted and unsubstituted alkyl groups. In some such embodiments of the third group of compounds, at least one of $R^1$, $R^2$, $R^3$, $R^4$, $R^5$, $R^6$, $R^7$ or $R^8$ is not —H. In other such embodiments, at least two of $R^1$, $R^2$, $R^3$, $R^4$, $R^5$, $R^6$, $R^7$ or $R^8$ are not —H. In some embodiments, $R^{10}$ is —H. In other embodiments, $R^{10}$ is an unsubstituted alkyl group having from 1 to 6 carbon atoms such as a methyl, ethyl, propyl, i-propyl group, or the like. In some such embodiments, $R^{10}$ is a —CH$_3$ group.

In one embodiment of the third group of compounds, each of $Z^1$, $Z^2$, $Z^3$, and $Z^4$ are C.

In another embodiment of the third group of compounds, $Z^1$ is N and each of $Z^2$, $Z^3$, and $Z^4$ are C.

In another embodiment of the third group of compounds, $Z^1$ and $Z^3$ are both N and $Z^2$ and $Z^4$ are both C.

In another embodiment of the third group of compounds, $Z^3$ is N and each of $Z^1$, $Z^2$, and $Z^4$ are C.

In another embodiment of the third group of compounds, $Z^1$-$Z^4$ have any of the values in previous embodiments, and $R^1$ is selected from —H, —F, —Cl, and —Br.

In another embodiment of the third group of compounds, $Z^1$-$Z^4$ have any of the values in previous embodiments, and $R^1$ is a substituted and unsubstituted heterocyclylamino group. In some such embodiments, $R^1$ is a substituted and unsubstituted heteroarylamino groups. In some embodiments, $R^1$ is a substituted and unsubstituted heterocyclylamino group such as, but not limited to, substituted and unsubstituted pyrroldinylalkylamino groups and the like, such as, but not limited to, substituted and unsubstituted pyrrolidinylmethylamino groups and the like.

In another embodiment of the third group of compounds, $Z^1$-$Z^4$ and $R^1$ have any of the values in previous embodiments, and $R^2$ is selected from —H, —F, —Cl, —CO$_2$H, substituted and unsubstituted alkyl groups, substituted and unsubstituted —C(=O)O-alkyl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, substituted and unsubstituted heterocyclyl groups, substituted and unsubstituted alkoxy groups, substituted and unsubstituted arylalkoxy groups, substituted and unsubstituted aryloxy groups, substituted and unsubstituted heterocyclyloxy, and substituted and unsubstituted heterocyclylalkoxy groups; or $R^2$ and $R^3$ are a group of formula —OCH$_2$O— such that $R^2$ and $R^3$ define a fused 5-membered ring that includes 2 oxygen atoms.

In another embodiment of the third group of compounds, $Z^1$-$Z^4$ and $R^1$ have any of the values in previous embodiments, and $R^2$ is —H.

In another embodiment of the third group of compounds, $Z^1$-$Z^4$ and $R^1$ have any of the values in previous embodiments, and $R^2$ is an unsubstituted alkoxy group having from 1 to 4 carbon atoms.

In another embodiment of the third group of compounds, $Z^1$-$Z^4$ and $R^1$ have any of the values in previous embodiments, and $R^2$ is a —OMe, —OEt, —O-i-Pr, or —OCH$_2$CH(CH$_3$)$_2$ group.

In another embodiment of the third group of compounds, $Z^1$-$Z^4$ and $R^1$ have any of the values in previous embodiments, and $R^2$ is a substituted or unsubstituted arylalkoxy, a substituted or unsubstituted aryloxy group, or a substituted or unsubstituted heterocyclyoxy group.

In another embodiment of the third group of compounds, $Z^1$-$Z^4$ and $R^1$ have any of the values in previous embodiments, and $R^2$ is a substituted or unsubstituted benzyloxy group, a substituted or unsubstituted phenoxy group, or a substituted or unsubstituted pyridyloxy group.

In another embodiment of the third group of compounds, $Z^1$-$Z^4$ and $R^1$ have any of the values in previous embodiments, and $R^2$ is an unsubstituted alkyl group having from 1 to 4 carbon atoms.

In another embodiment of the third group of compounds, $Z^1$-$Z^4$ and $R^1$ have any of the values in previous embodiments, and $R^2$ is a methyl group.

In another embodiment of the third group of compounds, $Z^1$-$Z^4$ and $R^1$ have any of the values in previous embodiments, and $R^2$ is a substituted or unsubstituted —N(H)C(=O)—N(H)-alkyl-aryl group.

In another embodiment of the third group of compounds, $Z^1$-$Z^4$ and $R^1$ have any of the values in previous embodiments, and $R^2$ is a substituted or unsubstituted amino group selected from the group consisting of substituted and unsubstituted alkylamino groups, dialkylamino groups, cycloalkylamino groups, heterocyclylamino groups, heterocyclylalkylamino groups, arylalkylamino groups, arylalkoxyarylmethylamino groups, and aryloxyarylalkylamino groups. In some embodiments, the substituted and unsubstituted alkylamino groups are substituted and unsubstituted aminoalkylamino groups such as, but not limited to, dialkylaminoalkylamino and the like. In some such embodiments the substituted and unsubstituted heterocyclylalkylamino groups are substituted and unsubstituted heteroarylalkylamino groups. In some embodiments, the heterocyclylalkylamino groups include, but are not limited to, substituted and unsubstituted pyrrolidinylalkylamino groups such as, but not limited to, substituted and unsubstituted pyrrolidinylmethylalkylamino groups and the like; substituted and unsubstituted thiazolylalkylamino groups such as, but not limited to substituted and unsubstituted thiazolylmethylamino groups and the like; substituted and unsubstituted imidazolylalkylamino groups such as, but not limited to, imidazolylmethylamino groups and the like; substituted and unsubstituted furanylalkylamino groups such as, but not limited to, substituted and unsubstituted furanylmethylamino groups, and the like; and the like. In other such embodiments, the heterocyclylamino groups are substituted and unsubstituted heteroarylamino groups. In other such embodiments, the substituted and unsubstituted heterocyclylamino groups are substituted and unsubstituted arylalkylheterocyclylamino groups.

In another embodiment of the third group of compounds, $Z^1$-$Z^4$ and $R^1$ have any of the values in previous embodiments, and $R^2$ is a substituted or unsubstituted amino group selected from the group consisting of isopropylamino groups, 3-(N, N-dimethylamino)propylamino groups, pyrrolidinylmethylamino groups, arylmethylamino groups, arylalkoxyarylmethylamino groups, aryloxyarylmethylamino groups, and pyridylmethylamino groups, and pyridylamino groups.

In another embodiment of the third group of compounds, $Z^1$-$Z^4$ and $R^1$ have any of the values in previous embodiments, and $R^2$ is a substituted or unsubstituted heterocyclyl groups. In some such embodiments $R^2$ is a substituted or unsubstituted benzimidazolyl group or is a substituted or unsubstituted pyrazolyl group.

In another embodiment of the third group of compounds, $Z^1$-$Z^4$ and $R^1$ have any of the values in previous embodiments, and $R^2$ and $R^3$ are a group of formula —OCH$_2$O— such that $R^2$ and $R^3$ define a fused 5-membered ring that includes 2 oxygen atoms.

In another embodiment of the third group of compounds, $Z^1$-$Z^4$, $R^1$, and $R^2$ have any of the values in previous embodiments, and $R^3$ is selected from —H, —F, —Cl, and —OMe.

In another embodiment of the third group of compounds, $Z^1$-$Z^4$, $R^1$, and $R^2$ have any of the values in previous embodiments, and $R^3$ is —H.

In another embodiment of the third group of compounds, $Z^1$-$Z^4$, $R^1$, and $R^2$ have any of the values in previous embodiments, and $R^3$ is selected from the group consisting of —F, —Cl, —Br, —CF$_3$, —C≡N, substituted and unsubstituted alkyl groups, substituted and unsubstituted alkoxy groups, substituted and unsubstituted arylalkoxy groups, substituted and unsubstituted heterocyclyloxy groups, substituted and unsubstituted —N(H)C(=O)N(H)-alkyl groups, and substituted and unsubstituted —N(H)C(=O)N(H)-aryl groups; or $R^2$ and $R^3$ are a group of formula —OCH$_2$O— such that $R^2$ and $R^3$ define a fused 5-membered ring that includes 2 oxygen atoms.

In another embodiment of the third group of compounds, $Z^1$-$Z^4$, $R^1$, and $R^2$ have any of the values in previous embodiments, and $R^3$ is selected from the group consisting of substituted and unsubstituted —N(H)C(=O)N(H)-alkyl groups, and substituted and unsubstituted —N(H)C(=O)N(H)-aryl groups. In some such embodiments, $R^3$ is a substituted or unsubstituted —N(H)C(=O)N(H)CH$_2$CH$_3$ group, a substituted or unsubstituted —N(H)C(=O)N(H)CH(CH$_3$)$_2$ group, a substituted or unsubstituted —N(H)C(=O)N(H)C(CH$_3$)$_3$ group, or a substituted or unsubstituted —N(H)C(=O)N(H)-aryl group or the like. In some such embodiments, $R^3$ is a substituted or unsubstituted —N(H)C(=O)N(H)-aryl group such as, but not limited to, a —N(H)C(=O)N(H)-(2-methoxyphenyl) group, a-N(H)C(=O)N(H)-(3-trifluoromethylphenyl) group, or the like.

In another embodiment of the third group of compounds, $Z^1$-$Z^4$, $R^1$, and $R^2$ have any of the values in previous embodiments, and $R^3$ is —F.

In another embodiment of the third group of compounds, $Z^1$-$Z^4$, $R^1$, and $R^2$ have any of the values in previous embodiments, and $R^3$ is —Cl.

In another embodiment of the third group of compounds, $Z^1$-$Z^4$, $R^1$, and $R^2$ have any of the values in previous embodiments, and $R^3$ is —OMe.

In some embodiments of the third group of compounds, $Z^1$-$Z^4$, $R^1$, and $R^2$ have any of the values in previous embodiments, and if $R^3$ is H, at least one of $R^6$ or $R^7$ is selected from the group consisting of —CO$_2$H, substituted and unsubstituted heterocyclylalkoxy groups, substituted and unsubstituted arylalkoxy groups, substituted and unsubstituted alkoxyalkoxy groups, substituted and unsubstituted heterocyclylheterocyclyl groups, substituted and unsubstituted arylheterocyclyl groups, substituted and unsubstituted cycloalkylheterocyclyl groups, substituted and unsubstituted saturated heterocyclyloxy groups, substituted and unsubstituted —N(H)-alkyl groups, substituted and unsubstituted —N(H)-alkyl-heterocyclyl groups, substituted and unsubstituted —N(H)-alkyl-aryl groups, substituted and unsubstituted —N(H)-heterocyclyl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, and substituted and unsubstituted —C(=O)-heterocyclyl groups. In some such embodiments, if $R^3$ is H, at least one of $R^6$ or $R^7$ is selected from the group consisting of —CO$_2$H, substituted and unsubstituted saturated heterocyclyloxy groups, substituted and unsubstituted —C(=O)N(H)-alkyl groups, substituted and unsubstituted —C(=O)N(H)-aryl groups, substituted and unsubstituted —C(=O)N(H)-heterocyclyl groups, and substituted and unsubstituted —C(=O)-heterocyclyl groups.

In another embodiment of the third group of compounds, $Z^2$-$Z^4$, $R^1$, $R^2$, and $R^3$ have any of the values in previous embodiments, $Z^1$ is C, and $R^5$ is H. In some such embodiments, $R^8$ is also H.

In another embodiment of the third group of compounds, $Z^2$-$Z^4$, $R^1$, $R^2$, and $R^3$ have any of the values in previous embodiments, $Z^1$ is C, and $R^5$ is —CH$_3$.

In another embodiment of the third group of compounds, $Z^2$-$Z^4$, $R^1$, $R^2$, and $R^3$ have any of the values in previous embodiments, $Z^1$ is C, and $R^5$ is morpholine.

In another embodiment of the third group of compounds, $Z^1$-$Z^3$, $R^1$, $R^2$, and $R^3$ have any of the values in previous embodiments, $Z^4$ is C, and $R^8$ is H.

In another embodiment of the third group of compounds, $Z^1$-$Z^3$, $R^1$, $R^2$, and $R^3$ have any of the values in previous embodiments, $Z^4$ is C, and $R^8$ is —CH$_3$.

In another embodiment of the third group of compounds, $Z^1$-$Z^3$, $R^1$, $R^2$, and $R^3$ have any of the values in previous embodiments, $Z^4$ is C, and $R^8$ is morpholine.

In another embodiment of the third group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from a first group of compounds; or $Z^1$, $Z^2$, $Z^4$, $R^1$, $R^2$, $R^3$, $R^5$, and $R^8$ have any of the values in previous embodiments, $Z^3$ is C, and $R^7$ is selected from the first group of compounds, the first group of compounds comprising members selected from the group consisting of —CO$_2$H, substituted and unsubstituted heterocyclylalkoxy groups, substituted and unsubstituted arylalkoxy groups, substituted and unsubstituted alkoxyalkoxy groups, substituted and unsubstituted heterocyclylheterocyclyl groups, substituted and unsubstituted arylheterocyclyl groups, substituted and unsubstituted cycloalkylheterocyclyl groups, substituted and unsubstituted saturated heterocyclyloxy groups, substituted and unsubstituted (alkyl)(heterocyclyl)amino groups, substituted and unsubstituted heterocyclylalkylamino groups, substituted and unsubstituted arylalkylamino groups, substituted and unsubstituted heterocyclylamino groups, substituted and unsubstituted —C(=O)N(H)-aryl groups, —C(=O)N(H)-heteroaryl groups, substituted and unsubstituted —C(=O)N(alkyl)(heterocyclyl) groups, and substituted and unsubstituted —C(=O)-heterocyclyl groups.

In another embodiment of the third group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from —Br, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, substituted and unsubstituted —C(=O)-heterocyclyl groups, substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, and substituted and unsubstituted arylalkylamino groups, and substituted and unsubstituted heterocyclylamino groups. In still other embodiments, $R^6$ has the values described in the preceding sentence and $R^7$ is —H.

In another embodiment of the third group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkoxy group having from 1-6 carbon atoms. In still other such embodiments, $R^6$ is a methoxy group. In still other embodiments of the third group of compounds where $R^6$ is an alkoxy group having from 1-6 carbon atoms such as a methoxy group, $R^7$ is —H.

In another embodiment of the third group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkyl group having from 1-6 carbon atoms. In still other such embodiments, $R^6$ is a methyl group. In still other embodiments of the third group of compounds where $R^6$ is an alkyl group having from 1-6 carbon atoms such as a methyl group, $R^7$ is —H.

In another embodiment of the third group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted alkoxy group having the formula —OCH$_2$(CH$_2$)$_m$R$^{11}$ where m is an integer selected from 0, 1, or 2 and $R^{11}$ is selected from substituted and unsubstituted alkoxy groups, substituted and unsubstituted aryl groups, and substituted and unsubstituted heterocyclyl groups. In still other such embodiments, $R^{11}$ is selected from substituted alkoxy groups such as, but not limited to methoxy groups, ethoxy groups, propoxy groups, and the like. In still other such embodiments, $R^{11}$ is selected from substituted and unsubstituted heterocyclyl groups selected from pyrrolidinyl groups, pyridyl groups, morpholinyl groups, piperazinyl groups, and piperidinyl groups. In still other embodiments where $R^6$ is a substituted alkoxy group having the formula —OCH$_2$(CH$_2$)$_m$R$^{11}$, $R^7$ is —H. In still other embodiments, $R^6$ is a pyrrolidinylalkoxy groups, such as but not limited to, a pyrrolidinylpropoxy group or the like; an alkoxyethoxy group such as, but not limited to, a methoxyethoxy group or the like; or a substituted or unsubstituted pyridinylalkoxy group such as, but not limited to, (3-pyridinyl)methoxy groups, or the like.

In another embodiment of the third group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula —N(R$^{12}$)(CH$_2$)$_p$R$^{13}$ where p is an integer selected from 0, 1, 2, or 3, $R^{13}$ is selected from substituted and unsubstituted alkoxy groups, substituted and unsubstituted amino groups, substituted and unsubstituted aryl groups, and substituted and unsubstituted heterocyclyl groups, and $R^{12}$ is selected from —H or substituted and unsubstituted alkyl groups such as, but not limited to, methyl, ethyl, propyl, and isopropyl. In some such embodiments, $R^{13}$ is selected from substituted amino groups such as alkylamino groups and dialkylamino groups, such as, but not limited to, dimethylamino, diethylamino, dipropylamino, (methyl)(ethyl)amino, (ethyl)(propyl)amino, (methyl)(propyl)amino groups, and the like. In some such embodiments, $R^{12}$ is a CH$_3$ group. In still other embodiments, $R^{13}$ is selected from substituted alkoxy groups. In still other embodiments, $R^{13}$ is selected from substituted and unsubstituted heterocyclyl groups such as those selected from pyrrolidinyl groups, pyrazolyl groups, pyridyl groups, morpholinyl groups, piperazinyl groups, piperidinyl groups, and the like. In some embodiments, $R^6$ is selected from —N(H)(3-piperidinyl) groups, —N(H)(4-piperidinyl) groups, —N(H)(4-(2-methoxymethylpyrrolidinyl)) groups, —N(CH$_3$)(4-(1-methylpiperidinyl)) groups, —N(H)CH$_2$(2-pyridyl) groups, —N(H)CH$_2$(3-pyridyl) groups, —N(H)CH$_2$(4-pyridyl) groups, —N(H)CH$_2$CH$_2$(2-pyridyl) groups, —N(H)CH$_2$CH$_2$(3-pyridyl) groups, —N(H)CH$_2$CH$_2$(4-pyridyl) groups, —N(CH$_3$)CH$_2$CH$_2$(2-pyridyl) groups —N(H)CH$_2$CH$_2$(4-piperidinyl) groups, —N(H)CH$_2$CH$_2$(4-morpholinyl) groups, —N(H)CH$_2$CH$_2$CH$_2$(1-imidazolyl) groups, —N(H)CH$_2$CH$_2$CH$_2$(1-(4-methylpiperazinyl)) groups, —N(H)CH$_2$CH$_2$CH$_2$(4-morpholinyl) groups, —N(H)CH$_2$CH$_2$CH$_2$(1-imidazolyl) groups, —N(H)CH$_2$CH$_2$CH$_2$(1-pyrrolidinyl) groups, —N(CH$_3$)CH$_2$CH$_2$CH$_2$(diethylamino) groups, and the like.

In still other embodiments of the third group of compounds where $R^6$ is a substituted amino group having the formula —N(R$^{12}$)(CH$_2$)$_p$R$^{13}$, $R^7$ is —H.

In another embodiment of the third group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula —N(R$^{12}$)(CH$_2$)$_p$R$^{13}$ or the formula —N(R$^{12}$)C(H)(alkyl)((CH$_2$)$_p$R$^{13}$) where p is an integer selected from 0, 1, 2, or 3, $R^{13}$ is selected from a methyl group, substituted and unsubstituted alkoxy groups, substituted and unsubstituted amino groups such as —N(H)(alkyl) groups, —N(alkyl)$_2$ groups and the like, substituted and unsubstituted aryl groups, and substituted and unsubstituted heterocyclyl groups, and $R^{12}$ is selected from —H; substituted and unsubstituted alkyl groups such as, but not limited to, methyl, ethyl, propyl, and isopropyl groups; —C(=O)-alkyl groups such as —C(=O)—CH$_3$ groups and the like; —C(=O)-alkyl-N(H)(alkyl) groups such as —C(=O)—CH$_2$—N(H)(alkyl) groups and the like; —C(=O)-alkyl-N(alkyl)$_2$ groups such as —C(=O)—CH$_2$-N(alkyl)$_2$ groups and the like; —C(=O)-alkyl-N(R$^{12a'}$)(R$^{12b'}$) groups such as —C(=O)—CH$_2$—N(alkyl)$_2$ groups and the like —C(=O)-alkyl-heterocyclyl groups such as —C(=O)—CH$_2$-heterocyclyl groups and the like such as —C(=O)—CH$_2$-(1-piperazinyl) groups and the like; —C(=O)-heterocyclyl groups; —C(=O)-aryl groups; —C(=O)-alkyl-O-alkyl groups such as —C(=O)—CH$_2$-O-alkyl groups; —C(=O)-alkyl-S-alkyl groups such as —C(=O)—CH$_2$—S-alkyl groups and the like; and the like where $R^{12a'}$ is selected from —H, and substituted and unsubstituted alkyl groups, and $R^{12b'}$ is selected from —H, —SO$_2$-alkyl, —SO$_2$-aryl, —C(=O)-alkyl, —C(=O)-aryl, heterocyclyl groups such as 2-pyridyl groups and the like, heterocyclylalkyl groups, arylalkyl groups, alkyl groups, and —C(=O)-alkyl-halogen groups.

In another embodiment of the third group of compounds, $Z^1$, $Z^3$, $Z^4$, $R^1$, $R^2$, $R^3$, $R^5$, and $R^8$ have any of the values defined in the previous embodiments, $Z^2$ is C, and $R^6$ is a substituted or unsubstituted heterocyclyl group. In some embodiments of the third group of compounds where $R^6$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted pyrazolyl groups, substituted and unsubstituted pyrrolyl groups, substituted and unsubstituted imidazolyl groups, substituted and unsubstituted 1-aza-4-oxacycloheptane groups, substituted and unsubstituted 1,4-diazacycloheptane groups, substituted and unsubstituted 2,5-diazabicyclo[2.2.1]heptane groups, substituted and unsubstituted 1,4-diazabicyclo[2.2.2]octane groups, substituted or unsubstituted 1,4-diazabicyclo[4.3.0]nonane group, and substituted or unsubstituted 1,4-diazacycloheptane groups. In still other embodiments of the third group of compounds where $R^6$ is a heterocyclyl group, the heterocyclyl group is an unsubstituted morpholine group; a dialkyl substituted morpholinyl group such as, but not limited to, a dimethyl substituted morpholinyl group, and the like, such as, but not limited to, a 3,5-dimethyl substituted morpholinyl group; a hydroxy substituted morpholinyl group; a hydroxyalkyl substituted morpholinyl group; an aryl substituted morpholinyl group; an aminoalkyl substituted morpholinyl group including dialkylaminoalkyl substituted morpholinyl groups such as, but not limited to, dimethylaminomethyl substituted morpholinyl groups and the like such as, but not limited to, a morpholinyl group that is substituted on a ring carbon bonded to the ring O atom with a dimethylaminomethyl group and is substituted with a methyl group on the carbon bonded to the ring N atom which carbon is not bonded to the carbon bearing the dimethylaminomethyl group and the like; a heterocyclyl substituted morpholinyl group; an unsubstituted piperazine group; a dialkyl substituted piperazinyl group such as, but not limited to, a dimethyl substituted piperazinyl group, and the like such as a 3,5-dimethyl substituted piperazinyl group and the like; a monoalkyl substituted piperazinyl group such as a 3-alkyl substituted piperazinyl group, an N-alkyl substituted piperazinyl group, and the like such as, but not limited to, a 3-methyl substituted piperazinyl group, a N-alkyl substituted piperazinyl group, such as, but not limited to, N-methyl, N-ethyl, N-isopropyl substituted piperazinyl groups and the like; a hydroxyalkyl substituted piperazinyl group such as, but not limited to, hydroxyethyl and hydroxymethyl substituted piperazinyl groups and the like such as, but not limited to, N-hydroxyethyl substituted piperazinyl groups and the like; an aryl substituted piperazinyl group; a heterocyclyl substituted piperazinyl group such as, but not limited to, 2-, 3-, and 4-(2-, 3-, and 4-piperidinyl) substituted piperazinyl groups and 2-, 3-, and 4-(2-, 3-, and 4-pyridyl) substituted piperazinyl groups and the like; a —CH$_2$C(=O)-alkyl substituted piperazinyl group; a —C(=O)-alkyl substituted piperazinyl group such as, but not limited to, a —C(=O)-ethyl or a —C(=O)-methyl substituted piperazinyl group, and the like such as a piperazinyl group where the —C(=O)-ethyl or the —C(=O)-methyl substitution is on one of the piperazinyl N atoms and the other N atom is bonded to $Z^2$, and the like; a —C(=O)O-alkyl substituted piperazinyl group such as, but not limited to, a —C(=O)—O-ethyl or a —C(=O)—O-methyl substituted piperazinyl group, and the like such as a piperazinyl group where the —C(=O)—O-ethyl or the —C(=O)—O-methyl substitution is on one of the piperazinyl N atoms and the other N atom is bonded to $Z^2$, and the like; a cycloalkyl substituted piperazinyl group such as, but not limited to, a cyclohexyl and cyclopentyl substituted piperazinyl group and the like such as, but not limited to, a N-cyclohexyl substituted piperazinyl group and the like; an unsubstituted piperidine group; an alkyl substituted piperidinyl group such as, but not limited to, 2-, 3-, and 4-alkyl substituted piperidinyl groups, and the like such as, but not limited to, 2-, 3-, and 4-hydroxyalkyl substituted piperidinyl groups and the like such as, but not limited to, 2-, 3-, and 4-hydroxymethyl substituted piperidinyl groups and the like; a hydroxy substituted piperidinyl group such as 2-, 3-, and 4-hydroxy substituted piperidinyl groups; a hydroxyalkyl substituted piperidinyl group; an aryl substituted piperidinyl group such as, but not limited to, a 4-aryl substituted piperidinyl group and the like such as, but not limited to, a piperidinyl group that is substituted in the 4 position with both an aryl group and a hydroxy group and the like such as, but not limited to, a piperidinyl group that is substituted in the 4 position with both a hydroxy group and a phenyl group; a cycloalkyl substituted piperidinyl group; a heterocyclyl substituted piperidinyl group such as, but not limited to, a piperidinyl substituted piperidinyl group and the like such as, but not limited to, 4-piperidinyl substituted piperidinyl groups, 4-(2(3H)-benzimidazolone) substituted piperidinyl group, and the like; an unsubstituted pyrrolidinyl group; an alkyl substituted pyrrolidinyl group such as, but not limited to, a methyl substituted pyrrolidinyl group, a heterocyclylalkyl substituted pyrrolidinyl group, and the like such as, but not limited to, a 2-methyl substituted pyrrolidinyl group, a 2-pyrrolidinylmethyl substituted pyrrolidinyl group, and the like; an amino substituted pyrrolidinyl group such as, but not limited to, a dialkylamino substituted pyrrolidinyl group such as, but not limited to, 2- and 3-dialkylamino substituted pyrrolidinyl groups and the like such as, but not limited to, 2- and 3-substituted N,N-dimethylamino substituted pyrrolidinyl groups and the like such as, but not limited to, a pyrrolidinyl group that is substituted with both an alkyl group and an N,N-dimethylamino group and the like such as, but not limited to, a pyrrolidinyl group that is substituted with a methyl group in the 2 position and with a N,N-dimethylamino group in the 4 position; a hydroxy substituted pyrrolidinyl group such as, but not limited to, 2- and 3-hydroxy substituted pyrrolidinyl groups; a heterocyclylalkyl substituted pyrrolidinyl group; substituted and unsubstituted pyrrolyl groups; substituted and unsubstituted 2,5-diazabicyclo[2.2.1]heptane groups; an alkyl substituted 2,5-diazabicyclo[2.2.1]heptane group such as, but not limited to, a N-methyl substituted 2,5-diazabicyclo[2.2.1]heptane group and the like; a substituted or unsubstituted 1,4-diazabicyclo[4.3.0]nonane group; and a substituted or unsubstituted 1,4-diazacycloheptane group such as, but not limited to, an alkyl substituted 1,4-diazacycloheptane group and the like, such as, but not limited to, an N-alkyl substituted 1,4-diazacycloheptane substituted group and the like such as, but not limited to, a N-methyl substituted 1,4-diazacycloheptane group and the like. In still other embodiments of the third group of compounds where $R^6$ is a substituted or unsubstituted heterocyclyl group, $R^7$ is —H.

In another embodiment of the third group of compounds, $Z^1$, $Z^2$, $Z^4$, $R^1$, $R^2$, $R^3$, $R^5$, and $R^8$ have any of the values in previous embodiments, $Z^3$ is C, and $R^7$ is selected from substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, substituted and unsubstituted —C(=O)-heterocyclyl groups, substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other such embodiments, $R^7$ has the values described in the preceding sentence and $R^6$ is —H.

In another embodiment of the third group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkoxy group having from 1-6 carbon atoms. In still other such embodiments, $R^7$ is a methoxy group. In still other embodiments of the third group of compounds where $R^7$ is an alkoxy group having from 1-6 carbon atoms such as a methoxy group, $R^6$ is —H.

In another embodiment of the third group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkyl group having from 1-6 carbon atoms. In still other such embodiments, $R^7$ is a methyl group. In still other embodiments of the third group of compounds where $R^7$ is an alkyl group having from 1-6 carbon atoms such as a methyl group, $R^6$ is —H.

In another embodiment of the third group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted alkoxy group having the formula —OCH$_2$(CH$_2$)$_n$R$^{14}$ where n is an integer selected from 0, 1, or 2 and $R^{14}$ is selected from substituted and unsubstituted alkoxy groups, substituted and unsubstituted aryl groups, and substituted and unsubstituted heterocyclyl groups. In some embodiments, $R^{14}$ is selected from substituted alkoxy groups such as, but not limited to, methoxy groups, ethoxy groups, propoxy groups, and the like. In still other such embodiments, $R^{14}$ is selected from substituted and unsubstituted heterocyclyl groups selected from pyrrolidinyl groups, pyridyl groups, morpholinyl groups, piperazinyl groups, and piperidinyl groups. In still other embodiments of the third group of compounds where $R^7$ is a substituted alkoxy group having the formula —OCH$_2$(CH$_2$)$_n$R$^{14}$, $R^6$ is —H. In still other embodiments, $R^7$ is a pyrrolidinylalkoxy groups, such as but not limited to, a pyrrolidinylpropoxy group or the like; an alkoxyethoxy group such as, but not limited to, a methoxyethoxy group or the like; or a substituted or unsubstituted pyridinylalkoxy group such as, but not limited to, (3-pyridinyl)methoxy groups, or the like.

In another embodiment of the third group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted amino group having the formula —N(R$^{15}$)(CH$_2$)$_q$R$^{16}$ where q is an integer selected from 0, 1, 2, or 3 and R$^{16}$ is selected from substituted and unsubstituted alkoxy groups, substituted and unsubstituted amino groups, substituted and unsubstituted aryl groups, and substituted and unsubstituted heterocyclyl groups, and R$^{15}$ is —H or a substituted or unsubstituted alkyl groups, such as, but not limited to, methyl, ethyl, propyl, and isopropyl groups. In some such embodiments, R$^{16}$ is selected from substituted amino groups such as alkylamino groups and dialkylamino groups, such as, but not limited to, dimethylamino, diethylamino, dipropylamino, (methyl)(ethyl)amino, (ethyl)(propyl)amino, (methyl)(propyl)amino groups, and the like. In some such embodiments, R$^{15}$ is a CH$_3$ group. In still other such embodiments, R$^{16}$ is selected from substituted alkoxy groups. In still other such embodiments, R$^{16}$ is selected from substituted and unsubstituted heterocyclyl groups such as those selected from pyrrolidinyl groups, pyrazolyl groups, pyridyl groups, morpholinyl groups, piperazinyl groups, piperidinyl groups, and the like. In some embodiments, $R^7$ is selected from —N(H)(3-piperidinyl) groups, —N(H)(4-piperidinyl) groups, —N(H)(4-(2-methoxymethylpyrrolidinyl)) groups, —N(CH$_3$)(4-(1-methylpiperidinyl)) groups, —N(H)CH$_2$(2-pyridyl) groups, —N(H)CH$_2$(3-pyridyl) groups, —N(H)CH$_2$(4-pyridyl) groups, —N(H)CH$_2$CH$_2$(2-pyridyl) groups, —N(H)CH$_2$CH$_2$(3-pyridyl) groups, —N(H)CH$_2$CH$_2$(4-pyridyl) groups, —N(CH$_3$) CH$_2$CH$_2$(2-pyridyl) groups —N(H)CH$_2$CH$_2$(4-piperidinyl) groups, —N(H)CH$_2$CH$_2$(4-morpholinyl) groups, —N(H) CH$_2$CH$_2$CH$_2$(1-imidazolyl) groups, —N(H)CH$_2$CH$_2$CH$_2$(1-(4-methylpiperazinyl)) groups, —N(H)CH$_2$CH$_2$CH$_2$(4-morpholinyl) groups, —N(H)CH$_2$CH$_2$CH$_2$(1-imidazolyl) groups, —N(H)CH$_2$CH$_2$CH$_2$(1-pyrrolidinyl) groups, —N(CH$_3$)CH$_2$CH$_2$CH$_2$(diethylamino) groups, and the like.

In still other embodiments of the third group of compounds where $R^7$ is a substituted amino group having the formula —N(R$^{15}$)(CH$_2$)$_q$R$^{16}$, $R^6$ is —H.

In another embodiment of the third group of compounds, $Z^1$, $Z^3$, $Z^4$, $R^1$, $R^2$, $R^3$, $R^5$, and $R^8$ have any of the values in previous embodiments, $Z^3$ is C, and $R^7$ is a substituted amino group having the formula —N(R$^{15}$)(CH$_2$)$_q$R$^{16}$ or the formula —N(R$^{15}$)C(H)(alkyl)((CH$_2$)$_q$R$^{16}$) where q is an integer selected from 0, 1, 2, or 3, R$^{16}$ is selected from a methyl group, substituted and unsubstituted alkoxy groups, substituted and unsubstituted amino groups such as —N(H)(alkyl) groups, —N(alkyl)$_2$ groups and the like, substituted and unsubstituted aryl groups, and substituted and unsubstituted heterocyclyl groups, and R$^{15}$ is selected from —H; substituted and unsubstituted alkyl groups such as, but not limited to, methyl, ethyl, propyl, and isopropyl groups; —C(=O)-alkyl groups such as —C(=O)—CH$_3$ groups and the like; —C(=O)-alkyl-N(H)(alkyl) amino groups such as —C(=O)—CH$_2$—N(H) (alkyl) groups and the like; —C(=O)-alkyl-N(alkyl)$_2$ groups such as —C(=O)—CH$_2$-N(alkyl)$_2$ groups and the like; —C(=O)-alkyl-N(R$^{15a'}$)(R$^{15b'}$b) groups such as —C(=O)—CH$_2$—N(alkyl)$_2$ groups and the like —C(=O)-alkyl-heterocyclyl groups such as —C(=O)—CH$_2$-heterocyclyl groups and the like such as —C(=O)—CH$_2$-(1-piperazinyl) groups and the like; —C(=O)-heterocyclyl groups; —C(=O)-aryl groups; —C(=O)-alkyl-O-alkyl groups such as —C(=O)—CH$_2$-O-alkyl groups; —C(=O)-alkyl-S-alkyl groups such as —C(=O)—CH$_2$-S-alkyl groups and the like; and the like where R$^{15a'}$ is selected from —H, and substituted and unsubstituted alkyl groups, and R$^{15b'}$ is selected from —H, —SO$_2$-alkyl, —SO$_2$-aryl, —C(=O)-alkyl, —C(=O)-aryl, heterocyclyl groups such as 2-pyridyl groups and the like, heterocyclylalkyl groups, arylalkyl groups, alkyl groups, and —C(=O)-alkyl-halogen groups.

In another embodiment of the third group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted or unsubstituted heterocyclyl group. In some embodiments of the third group of compounds where $R^7$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted pyrazolyl groups, substituted and unsubstituted pyrrolyl groups, substituted and unsubstituted imidazolyl groups, substituted and unsubstituted 1-aza-4-oxacycloheptane groups, substituted and unsubstituted 1,4-diazacycloheptane groups, substituted and unsubstituted 2,5-diazabicyclo[2.2.1]heptane groups, substituted and unsubstituted 1,4-diazabicyclo[2.2.2]octane groups, substituted or unsubstituted 1,4-diazabicyclo[4.3.0]nonane group, and substituted or unsubstituted 1,4-diazacycloheptane groups. In still other embodiments of the third group of compounds where $R^7$ is a heterocyclyl group, the heterocyclyl group is an unsubstituted morpholine group; a dialkyl substituted morpholinyl group such as, but not limited to, a dimethyl substituted morpholinyl group, and the like, such as, but not limited to, a 3,5-dimethyl substituted morpholinyl group; a hydroxy substituted morpholinyl group; a hydroxyalkyl substituted morpholinyl group; an aryl substituted morpholinyl group; an aminoalkyl substituted morpholinyl group including dialkylaminoalkyl substituted morpholinyl groups such as, but not limited to, dimethylaminomethyl substituted morpholinyl groups and the like such as, but not limited to, a morpholinyl group that is substituted on a ring carbon bonded to the ring O atom with a dimethylaminomethyl group and is substituted with a methyl group on the carbon bonded to the ring N atom which carbon is not bonded to the carbon bearing the dimethylaminomethyl group and the like; a heterocyclyl substituted morpholinyl group; an unsubstituted piperazine group; a dialkyl substituted piperazinyl group such as, but not limited to, a dimethyl substituted piperazinyl group, and the like such as a 3,5-dimethyl substituted piperazinyl group and the like; a monoalkyl substituted piperazinyl group such as a 3-alkyl substituted piperazinyl group, an N-alkyl substituted piperazinyl group, and the like such as, but not limited to, a 3-methyl substituted piperazinyl group, a N-alkyl substituted piperazinyl group, such as, but not limited to, N-methyl, N-ethyl, N-isopropyl substituted piperazinyl groups and the like; a hydroxyalkyl substituted piperazinyl group such as, but not limited to, hydroxyethyl and hydroxymethyl substituted piperazinyl groups and the like such as, but not limited to, N-hydroxyethyl substituted piperazinyl groups and the like; an aryl substituted piperazinyl group; a heterocyclyl substituted piperazinyl group such as, but not limited to, 2-, 3-, and 4-(2-, 3-, and 4-piperidinyl) substituted piperazinyl groups and 2-, 3-, and 4-(2-, 3-, and 4-pyridyl) substituted piperazinyl groups and the like; a —CH$_2$C(=O)O-alkyl substituted piperazinyl group; a —C(=O)-alkyl substituted piperazinyl group such as, but not limited to, a —C(=O)-ethyl or a —C(=O)-methyl substituted piperazinyl group, and the like such as a piperazinyl group where the —C(=O)-ethyl or the —C(=O)-methyl substitution is on one of the piperazinyl N atoms and the other N atom is bonded to $Z^3$, and the like; a —C(=O)O-alkyl substituted piperazinyl group such as, but not limited to, a —C(=O)—O-ethyl or a —C(=O)—O-methyl substituted piperazinyl group, and the like such as a piperazinyl group where the —C(=O)—O-ethyl or the —C(=O)—O-methyl substitution is on one of the piperazinyl N atoms and the other N atom is bonded to $Z^3$, and the like; a cycloalkyl substituted piperazinyl group such as, but not limited to, a cyclohexyl and cyclopentyl substituted piperazinyl group and the like such as, but not limited to, a N-cyclohexyl substituted piperazinyl group and the like; an unsubstituted piperidine group; an alkyl substituted piperidinyl group such as, but not limited to, 2-, 3-, and 4-alkyl substituted piperidinyl groups, and the like such as, but not limited to, 2-, 3-, and 4-hydroxyalkyl substituted piperidinyl groups and the like such as, but not limited to, 2-, 3-, and 4-hydroxymethyl substituted piperidinyl groups and the like; a hydroxy substituted piperidinyl group such as 2-, 3-, and 4-hydroxy substituted piperidinyl groups; a hydroxyalkyl substituted piperidinyl group; an aryl substituted piperidinyl group such as, but not limited to, a 4-aryl substituted piperidinyl group and the like such as, but not limited to, a piperidinyl group that is substituted in the 4 position with both an aryl group and a hydroxy group and the like such as, but not limited to, a piperidinyl group that is substituted in the 4 position with both a hydroxy group and a phenyl group; a cycloalkyl substituted piperidinyl group; a heterocyclyl substituted piperidinyl group such as, but not limited to, a piperidinyl substituted piperidinyl group and the like such as, but not limited to, 4-piperidinyl substituted piperidinyl groups, 4-(2(3H)-benzimidazolone) substituted piperidinyl group, and the like; an unsubstituted pyrrolidinyl group; an alkyl substituted pyrrolidinyl group such as, but not limited to, a methyl substituted pyrrolidinyl group, a heterocyclylalkyl substituted pyrrolidinyl group, and the like such as, but not limited to, a 2-methyl substituted pyrrolidinyl group, a 2-pyrrolidinylmethyl substituted pyrrolidinyl group, and the like; an amino substituted pyrrolidinyl group such as, but not limited to, a dialkylamino substituted pyrrolidinyl group such as, but not limited to, 2- and 3-dialkylamino substituted pyrrolidinyl groups and the like such as, but not limited to, 2- and 3-substituted N,N-dimethylamino substituted pyrrolidinyl groups and the like such as, but not limited to, a pyrrolidinyl group that is substituted with both an alkyl group and an N,N-dimethylamino group and the like such as, but not limited to, a pyrrolidinyl group that is substituted with a methyl group in the 2 position and with a N,N-dimethylamino group in the 4 position; a hydroxy substituted pyrrolidinyl group such as, but not limited to, 2- and 3-hydroxy substituted pyrrolidinyl groups; a heterocyclylalkyl substituted pyrrolidinyl group; substituted and unsubstituted pyrrolyl groups; substituted and unsubstituted 2,5-diazabicyclo[2.2.1]heptane groups; an alkyl substituted 2,5-diazabicyclo[2.2.1]heptane group such as, but not limited to, a N-methyl substituted 2,5-diazabicyclo[2.2.1] heptane group and the like; a substituted or unsubstituted 1,4-diazabicyclo[4.3.0]nonane group; and a substituted or unsubstituted 1,4-diazacycloheptane group such as, but not limited to, an alkyl substituted 1,4-diazacycloheptane group and the like, such as, but not limited to, an N-alkyl substituted 1,4-diazacycloheptane substituted group and the like such as, but not limited to, a N-methyl substituted 1,4-diazacycloheptane group and the like. In still other embodiments of the third group of compounds where $R^7$ is a substituted or unsubstituted heterocyclyl group, $R^6$ is —H.

In another embodiment of the third group of compounds, $Z^1$-$Z^4$, $R^1$, $R^2$, and $R^3$ have any of the values in previous embodiments, and one of $R^6$ or $R^7$ is a substituted or unsubstituted pyridyloxy group. In some such embodiments, one of $R^6$ or $R^7$ is substituted or unsubstituted 2-pyridyloxy group, a 3-pyridyloxy group, or a 4-pyridyloxy group. In other such embodiments, one of $R^6$ or $R^7$ is a (2-N-alkylamido-4-pyridyl)oxy group such as a (2-N-methylamido-4-pyridyl)oxy group or the like; or a (5-N-alkylamido-3-pyridyl)oxy group such as a (5-N-methylamido-3-pyridyl)oxy group, or the like.

Other more particular embodiments of the compounds of the invention having the general structure shown in I above are provided. Such compounds form a fourth group of compounds for which:

$Z^1$, $Z^2$, $Z^3$, and $Z^4$ are independently selected from C or N; $R^1$ is selected from —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)-C(=O)-alkyl-aryl groups, and substituted and unsubstituted -alkyl-N(H)-C(=O)-alkyl-heterocyclyl groups;

$R^2$ is selected from —H, —F, —Cl, —Br, —C≡N, —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups; or $R^2$ and $R^3$ are a group of formula —OCH$_2$O— such that $R^2$ and $R^3$ define a fused 5-membered ring that includes 2 oxygen atoms;

$R^3$ is selected from —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, and substituted and unsubstituted -alkyl-N(alkyl)-C(=O)-alkyl-heterocyclyl groups;

$R^4$ is —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, and substituted and unsubstituted -alkyl-N (alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)-C(=O)-alkyl-aryl groups, and substituted and unsubstituted -alkyl-N(H)-C(=O)-alkyl-heterocyclyl groups;

$R^5$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;

$R^8$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is selected from the group consisting of —H, and substituted and unsubstituted alkyl groups. In some such embodiments of the fourth group of compounds, at least one of $R^1$, $R^2$, $R^3$, $R^4$, $R^5$, $R^6$, $R^7$ or $R^8$ is not —H. In other such embodiments, at least two of $R^1$, $R^2$, $R^3$, $R^4$, $R^5$, $R^6$, $R^7$ or $R^8$ are not —H. In some embodiments, $R^{10}$ is —H. In other embodiments, $R^{10}$ is an unsubstituted alkyl group having from 1 to 6 carbon atoms such as a methyl, ethyl, propyl, i-propyl group, or the like. In some such embodiments, $R^{10}$ is a —CH$_3$ group In one embodiment of the fourth group of compounds, each of $Z^1$, $Z^2$, $Z^3$, and $Z^4$ are C.

In another embodiment of the fourth group of compounds, $Z^1$ is N and each of $Z^2$, $Z^3$, and $Z^4$ are C.

In another embodiment of the fourth group of compounds, $Z^1$ and $Z^3$ are both N and $Z^2$ and $Z^4$ are both C.

In another embodiment of the fourth group of compounds, $Z^3$ is N and each of $Z^1$, $Z^2$, and $Z^4$ are C.

In another embodiment of the fourth group of compounds, $Z^1$-$Z^4$ have any of the values in previous embodiments, and $R^1$ is selected from —H, —F, —Cl, and —Br.

In another embodiment of the fourth group of compounds, $Z^1$-$Z^4$ have any of the values in previous embodiments, and $R^1$ is a substituted and unsubstituted heterocyclylamino group. In some such embodiments, $R^1$ is a substituted and unsubstituted heteroarylamino groups. In some embodiments, $R^1$ is an unsubstituted —NH$_2$ group or is a substituted or unsubstituted heterocyclylamino group such as, but not limited to, substituted and unsubstituted pyrroldinylalkylamino groups and the like, such as, but not limited to, substituted and unsubstituted pyrrolidinylmethylamino groups and the like such as, but not limited to, —N(H)—CH$_2$-(2-pyrrolidinyl) groups and the like.

In another embodiment of the fourth group of compounds, $Z^1$-$Z^4$ and $R^1$ have any of the values in previous embodiments, and $R^2$ is selected from —H, —F, —Cl, —CO$_2$H, substituted and unsubstituted alkyl groups, substituted and unsubstituted —C(=O)O-alkyl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, substituted and unsubstituted heterocyclyl groups, substituted and unsubstituted alkoxy groups, substituted and unsubstituted arylalkoxy groups, substituted and unsubstituted aryloxy groups, substituted and unsubstituted heterocyclyloxy, and substituted and unsubstituted heterocyclylalkoxy groups; or $R^2$ and $R^3$ are a group of formula —OCH$_2$O— such that $R^2$ and $R^3$ define a fused 5-membered ring that includes 2 oxygen atoms. In another embodiment of the fourth group of compounds, $R^2$ is selected from the group consisting of substituted and unsubstituted thiazolylalkylamino groups, substituted and unsubstituted pyrrolidinylalkylamino groups, and substituted and unsubstituted aminoalkylamino groups. In other such embodiments, $R^2$ is selected from the group consisting of —N(H)—CH$_2$-(2-thiazolyl) groups, —N(H)—CH$_2$-(2-pyrroldinyl groups), —N(H)—CH$_2$CH$_2$CH$_2$—N(H)(alkyl) groups, and —NH—CH$_2$CH$_2$CH$_2$—N(alkyl)$_2$ groups. In still other such embodiments, $R^2$ is selected from the group consisting of —N(H)—CH$_2$-(2-thiazolyl) groups, —N(H)—CH$_2$-(2-pyrroldinyl groups), —N(H)—CH$_2$CH$_2$CH$_2$—N(H)(CH$_3$) groups, and —NH—CH$_2$CH$_2$CH$_2$—N(CH$_3$)$_2$ groups.

In another embodiment of the fourth group of compounds, $Z^1$-$Z^4$ and $R^1$ have any of the values in previous embodiments, and $R^2$ is —H.

In another embodiment of the fourth group of compounds, $Z^1$-$Z^4$ and $R^1$ have any of the values in previous embodiments, and $R^2$ is an unsubstituted alkoxy group having from 1 to 4 carbon atoms.

In another embodiment of the fourth group of compounds, $Z^1$-$Z^4$ and $R^1$ have any of the values in previous embodiments, and $R^2$ is a —OMe, —OEt, —O-i-Pr, or —OCH$_2$CH(CH$_3$)$_2$ group.

In another embodiment of the fourth group of compounds, $Z^1$-$Z^4$ and $R^1$ have any of the values in previous embodiments, and $R^2$ is a substituted or unsubstituted arylalkoxy, a substituted or unsubstituted aryloxy group, or a substituted or unsubstituted heterocyclyoxy group.

In another embodiment of the fourth group of compounds, $Z^1$-$Z^4$ and $R^1$ have any of the values in previous embodiments, and $R^2$ is a substituted or unsubstituted benzyloxy group, a substituted or unsubstituted phenoxy group, or a substituted or unsubstituted pyridyloxy group.

In another embodiment of the fourth group of compounds, $Z^1$-$Z^4$ and $R^1$ have any of the values in previous embodiments, and $R^2$ is an unsubstituted alkyl group having from 1 to 4 carbon atoms.

In another embodiment of the fourth group of compounds, $Z^1$-$Z^4$ and $R^1$ have any of the values in previous embodiments, and $R^2$ is a methyl group.

In another embodiment of the fourth group of compounds, $Z^1$-$Z^4$ and $R^1$ have any of the values in previous embodiments, and $R^2$ is a substituted or unsubstituted —N(H)C(=O)—N(H)-alkyl-aryl group.

In another embodiment of the fourth group of compounds, $Z^1$-$Z^4$ and $R^1$ have any of the values in previous embodiments, and $R^2$ is a substituted or unsubstituted amino group selected from the group consisting of substituted and unsubstituted alkylamino groups, dialkylamino groups, cycloalkylamino groups, heterocyclylamino groups, heterocyclylalkylamino groups, arylalkylamino groups, arylalkoxyarylmethylamino groups, and aryloxyarylalkylamino groups. In some embodiments, the substituted and unsubstituted alkylamino groups are substituted and unsubstituted aminoalkylamino groups such as, but not limited to, dialkylaminoalkylamino and the like. In some such embodiments the substituted and unsubstituted heterocyclylalkylamino groups are substituted and unsubstituted heteroarylalkylamino groups. In some embodiments, the heterocyclylalkylamino groups include, but are not limited to, substituted and unsubstituted pyrrolidinylalkylamino groups such as, but not limited to, substituted and unsubstituted pyrrolidinylmethylalkylamino groups and the like; substituted and unsubstituted thiazolylalkylamino groups such as, but not limited to substituted and unsubstituted thiazolylmethylamino groups and the like; substituted and unsubstituted imidazolylalkylamino groups such as, but not limited to, imidazolylmethylamino groups and the like;

substituted and unsubstituted furanylalkylamino groups such as, but not limited to, substituted and unsubstituted furanylmethylamino groups, and the like; and the like. In other such embodiments, the heterocyclylamino groups are substituted and unsubstituted heteroarylamino groups. In other such embodiments, the substituted and unsubstituted heterocyclylamino groups are substituted and unsubstituted arylalkylheterocyclylamino groups.

In another embodiment of the fourth group of compounds, $Z^1$-$Z^4$ and $R^1$ have any of the values in previous embodiments, and $R^2$ is a substituted or unsubstituted amino group selected from the group consisting of isopropylamino groups, 3-(N,N-dimethylamino)propylamino groups, pyrrolidinylmethylamino groups, arylmethylamino groups, arylalkoxyarylmethylamino groups, aryloxyarylmethylamino groups, and pyridylmethylamino groups, and pyridylamino groups.

In another embodiment of the fourth group of compounds, $Z^1$-$Z^4$ and $R^1$ have any of the values in previous embodiments, and $R^2$ is a substituted or unsubstituted heterocyclyl groups. In some such embodiments $R^2$ is a substituted or unsubstituted benzimidazolyl group or is a substituted or unsubstituted pyrazolyl group.

In another embodiment of the fourth group of compounds, $Z^1$-$Z^4$ and $R^1$ have any of the values in previous embodiments, and $R^2$ and $R^3$ are a group of formula —OCH$_2$O— such that $R^2$ and $R^3$ define a fused 5-membered ring that includes 2 oxygen atoms.

In another embodiment of the fourth group of compounds, $Z^1$-$Z^4$, $R^1$, and $R^2$ have any of the values in previous embodiments, and $R^3$ is selected from —H, —F, —Cl, and —OMe.

In another embodiment of the fourth group of compounds, $Z^1$-$Z^4$, $R^1$, and $R^2$ have any of the values in previous embodiments, and $R^3$ is —H.

In another embodiment of the fourth group of compounds, $Z^1$-$Z^4$, $R^1$, and $R^2$ have any of the values in previous embodiments, and $R^3$ is selected from the group consisting of —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —N(H)C(=O)N(H)-alkyl groups, substituted and unsubstituted —N(H)C(=O)N(H)-aryl groups and substituted and unsubstituted —C(=O)N(H)-alkyl-heterocyclyl groups; or $R^2$ and $R^3$ are a group of formula —OCH$_2$O— such that $R^2$ and $R^3$ define a fused 5-membered ring that includes 2 oxygen atoms.

In another embodiment of the fourth group of compounds, $Z^1$-$Z^4$, $R^1$, and $R^2$ have any of the values in previous embodiments, and $R^3$ is selected from the group consisting of substituted and unsubstituted —N(H)C(=O)N(H)-alkyl groups, and substituted and unsubstituted —N(H)C(=O)N(H)-aryl groups. In some such embodiments, $R^3$ is a substituted or unsubstituted —N(H)C(=O)N(H)CH$_2$CH$_3$ group, a substituted or unsubstituted —N(H)C(=O)N(H)CH(CH$_3$)$_2$ group, a substituted or unsubstituted —N(H)C(=O)N(H)C(CH$_3$)$_3$ group, or a substituted or unsubstituted —N(H)C(=O)N(H)-aryl group or the like. In some such embodiments, $R^3$ is a substituted or unsubstituted —N(H)C(=O)N(H)-aryl group such as, but not limited to, a —N(H)C(=O)N(H)-(2-methoxyphenyl) group, a-N(H)C(=O)N(H)-(3-trifluoromethylphenyl) group, or the like.

In another embodiment of the fourth group of compounds, $Z^1$-$Z^4$, $R^1$, and $R^2$ have any of the values in previous embodiments, and $R^3$ is a substituted amino group selected from substituted or unsubstituted arylalkylamino groups such as, but not limited to, phenylalkylamino groups, (halo)(alkoxy)arylalkylamino groups, such as, but not limited to 2-fluoro-5-methoxyphenylmethylamino groups, monoalkoxyarylalkylamino groups, dialkoxyarylalkylamino groups, and the like, such as, but not limited to, 2,5-dialkoxyarylalkylamino groups and the like such as, but not limited to 2,5-dialkoxyarylmethylamino groups, substituted and unsubstituted arylalkoxyarylalkylamino groups such as, but not limited to substituted and unsubstituted arylalkoxyarylmethylamino groups and the like, such as, but not limited to, substituted and unsubstituted arylmethoxyarylmethylamino groups and the like, such as, but not limited to substituted and unsubstituted fluoroarylmethoxyarylmethylamino groups and the like, such as, but not limited to, substituted and unsubstituted 4-fluorophenylmethoxyphenyl-methylamino groups and the like; substituted and unsubstituted heterocyclylalkylamino groups including heteroarylalkylamino groups such as, but not limited to substituted and unsubstituted thiazolylalkylamino groups, benzimidazolylalkylamino groups such as, but not limited to N-methylbenzimidazolylalkylamino groups and the like, imidazolylalkylamino groups such as, but not limited to phenylimidazolylalkylamino groups, ethylmethylimidazolylalkylamino groups, and the like, substituted and unsubstituted quinolinylalkylamino groups, such as, but not limited to substituted and unsubstituted quinolinylmethylamino groups and the like, such as, but not limited to alkoxyquinolinylmethylamino groups and the like, such as, but not limited to substituted and unsubstituted 4-alkoxy-2-quinolinylmethylamino groups and the like, and furanylalkylamino groups, and the like. In other embodiments of the fourth group of compounds, $R^3$ is selected from the group consisting of substituted and unsubstituted thiazolylalkylamino groups, substituted and unsubstituted benzimidazolylalkylamino groups, substituted and unsubstituted imidazolylalkylamino groups, substituted and unsubstituted furanylalkylamino groups, and substituted and unsubstituted arylalkylamino groups. In some such embodiments, $R^3$ is selected from the group consisting of (2-thiazolyl)alkylamino groups, 1-(3-methylbenzimidazolyl)alkylamino groups, 4-(2-phenylimidazolyl)alkylamino groups, 4-(2-ethyl-5-methylimidazolyl)alkylamino groups, (2-furanyl)alkylamino groups, phenylalkylamino groups, and 1-(2-fluoro-5-alkoxyphenyl) alkylamino groups. In still other such embodiments, $R^3$ is selected from the group consisting of —N(H)—CH$_2$-(2-thiazolyl) groups, —N(H)—CH$_2$-(1-(3-methylbenzimidazolyl)) groups, —N(H)—CH$_2$-(4-(2-phenylimidazolyl)) groups, —N(H)—CH$_2$-(4-(2-ethyl-5-methylimidazolyl)) groups, —N(H)—CH$_2$-(2-furanyl) groups, —N(H)—CH$_2$-phenyl groups, and —N(H)—CH$_2$-(1-(2-fluoro-5-alkoxyphenyl)) groups. In still another embodiment, $R^1$ is selected from the group consisting of unsubstituted —NH$_2$ groups, and substituted and unsubstituted pyrrolidinylalkylamino groups; $R^2$ is selected from the group consisting of substituted and unsubstituted thiazolylalkylamino groups, substituted and unsubstituted pyrrolidinylalkylamino groups, and substituted and unsubstituted aminoalkylamino groups; and/or $R^3$ is selected from the group consisting of substituted and unsubstituted thiazolylalkylamino groups, substituted and unsubstituted benzimidazolylalkylamino groups, substituted and unsubstituted imidazolylalkylamino groups, substituted and unsubstituted furanylalkylamino groups, and substituted and unsubstituted arylalkylamino groups. In such compounds, $Z^1$-$Z^4$, $R^4$, $R^5$, $R^6$, $R^7$, $R^8$, $R^9$, and $R^{10}$ can have any of the other values described in any of the other embodiments of any of the groups of compounds.

In another embodiment of the fourth group of compounds, $Z^1$-$Z^4$, $R^1$, and $R^2$ have any of the values in previous embodiments, and $R^3$ is —F.

In another embodiment of the fourth group of compounds, $Z^1$-$Z^4$, $R^1$, and $R^2$ have any of the values in previous embodiments, and $R^3$ is —Cl.

In another embodiment of the fourth group of compounds, $Z^1$-$Z^4$, $R^1$, and $R^2$ have any of the values in previous embodiments, and $R^3$ is —OMe.

In another embodiment of the fourth group of compounds, $Z^1$-$Z^4$, $R^1$, and $R^2$ have any of the values in previous embodiments, and $R^3$ is a substituted and unsubstituted —C(=O)N(H)-alkyl-heterocyclyl groups where the heterocyclyl group of the —C(=O)N(H)-alkyl-heterocyclyl groups is selected from the group consisting of morpholinyl, piperazinyl, and piperidinyl groups.

In another embodiment of the fourth group of compounds, $Z^2$-$Z^4$, $R^1$, $R^2$, and $R^3$ have any of the values in previous embodiments, $Z^1$ is C, and $R^5$ is H. In some such embodiments, $R^8$ is also H.

In another embodiment of the fourth group of compounds, $Z^2$-$Z^4$, $R^1$, $R^2$, and $R^3$ have any of the values in previous embodiments, $Z^1$ is C, and $R^5$ is —CH$_3$.

In another embodiment of the fourth group of compounds, $Z^2$-$Z^4$, $R^1$, $R^2$, and $R^3$ have any of the values in previous embodiments, $Z^1$ is C, and $R^5$ is morpholine.

In another embodiment of the fourth group of compounds, $Z^1$-$Z^3$, $R^1$, $R^2$, and $R^3$ have any of the values in previous embodiments, $Z^4$ is C, and $R^8$ is H.

In another embodiment of the fourth group of compounds, $Z^1$-$Z^3$, $R^1$, $R^2$, and $R^3$ have any of the values in previous embodiments, $Z^4$ is C, and $R^8$ is —CH$_3$.

In another embodiment of the fourth group of compounds, $Z^1$-$Z^3$, $R^1$, $R^2$, and $R^3$ have any of the values in previous embodiments, $Z^4$ is C, and $R^8$ is morpholine.

In another embodiment of the fourth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from a first group; or $Z^1$, $Z^2$, $Z^4$, $R^1$, $R^2$, $R^3$, $R^5$, and $R^8$ have any of the values in previous embodiments, $Z^3$ is C, and $R^7$ is selected from the first group, the first group comprising members selected from the group consisting of —Br, —CO$_2$H, substituted and unsubstituted heterocyclylalkoxy groups, substituted and unsubstituted arylalkoxy groups, substituted and unsubstituted alkoxyalkoxy groups, substituted and unsubstituted heterocyclylheterocyclyl groups, substituted and unsubstituted arylheterocyclyl groups, substituted and unsubstituted cycloalkylheterocyclyl groups, substituted and unsubstituted heterocyclyloxy groups, substituted and unsubstituted aryloxy groups, substituted and unsubstituted (alkyl)(heterocyclyl)amino groups, substituted and unsubstituted heterocyclylalkylamino groups, substituted and unsubstituted arylalkylamino groups, substituted and unsubstituted heterocyclylamino groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups. In some such embodiments, $R^3$ is selected from the group consisting of —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, and substituted and unsubstituted —C(=O)N(H)-alkyl-heterocyclyl groups; or $R^2$ and $R^3$ are a group of formula —OCH$_2$O— such that $R^2$ and $R^3$ define a fused 5-membered ring that includes 2 oxygen atoms.

In another embodiment of the fourth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from —Br, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, substituted and unsubstituted —C(=O)-heterocyclyl groups, substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other embodiments, $R^6$ has the values described in the preceding sentence and $R^7$ is —H.

In another embodiment of the fourth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkoxy group having from 1-6 carbon atoms. In still other such embodiments, $R^6$ is a methoxy group. In still other embodiments of the fourth group of compounds where $R^6$ is an alkoxy group having from 1-6 carbon atoms such as a methoxy group, $R^7$ is —H.

In another embodiment of the fourth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkyl group having from 1-6 carbon atoms. In still other such embodiments, $R^6$ is a methyl group. In still other embodiments of the fourth group of compounds where $R^6$ is an alkyl group having from 1-6 carbon atoms such as a methyl group, $R^7$ is —H.

In another embodiment of the fourth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted alkoxy group having the formula —OCH$_2$(CH$_2$)$_m$R$^{11}$ where m is an integer selected from 0, 1, or 2 and $R^{11}$ is selected from substituted and unsubstituted alkoxy groups, substituted and unsubstituted aryl groups, and substituted and unsubstituted heterocyclyl groups. In still other such embodiments, $R^{11}$ is selected from substituted alkoxy groups such as, but not limited to methoxy groups, ethoxy groups, propoxy groups, and the like. In still other embodiments, $R^{11}$ is selected from substituted and unsubstituted heterocyclyl groups selected from pyrrolidinyl groups, pyridyl groups, morpholinyl groups, piperazinyl groups, and piperidinyl groups. In still other embodiments where $R^6$ is a substituted alkoxy group having the formula —OCH$_2$(CH$_2$)$_m$R$^{11}$, $R^7$ is —H. In still other embodiments, $R^6$ is a pyrrolidinylalkoxy groups, such as but not limited to, a pyrrolidinylpropoxy group or the like; an alkoxyethoxy group such as, but not limited to, a methoxyethoxy group or the like; or a substituted or unsubstituted pyridinylalkoxy group such as, but not limited to, (3-pyridinyl)methoxy groups, or the like.

In another embodiment of the fourth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula —N(R$^{12}$)(CH$_2$)$_p$R$^{13}$ where p is an integer selected from 0, 1, 2, or 3, $R^{13}$ is selected from substituted and unsubstituted alkoxy groups, substituted and unsubstituted amino groups, substituted and unsubstituted aryl groups, and substituted and unsubstituted heterocyclyl groups, and $R^{12}$ is selected from —H or substituted and unsubstituted alkyl groups such as, but not limited to, methyl, ethyl, propyl, and isopropyl. In some such embodiments, $R^{13}$ is selected from substituted amino groups such as alkylamino groups and dialkylamino groups, such as, but not limited to, dimethylamino, diethylamino, dipropylamino, (methyl)(ethyl)amino, (ethyl)(propyl)amino, (methyl)(propyl)amino groups, and the like. In some such embodiments, $R^{12}$ is a CH$_3$ group. In still other such embodiments, $R^{13}$ is selected from substituted alkoxy groups. In still other such embodiments, $R^{13}$ is selected from substituted and unsubstituted heterocyclyl groups such as those selected from pyrrolidinyl groups, pyrazolyl groups, pyridyl groups, morpholinyl groups, piperazinyl groups, piperidinyl groups, and the like. In some embodiments, $R^6$ is selected from —N(H)(3-piperidinyl) groups, —N(H)(4-piperidinyl) groups, —N(H)(4-(2-methoxymethylpyrrolidinyl)) groups, —N(CH$_3$)(4-(1-methylpiperidinyl)) groups, —N(H)CH$_2$(2-pyridyl) groups, —N(H)CH$_2$(3-pyridyl) groups, —N(H)CH$_2$(4-pyridyl) groups, —N(H)CH$_2$CH$_2$(2-pyridyl) groups, —N(H)CH$_2$CH$_2$(3-pyridyl) groups, —N(H)CH$_2$CH$_2$(4-pyridyl) groups, —N(CH$_3$)CH$_2$CH$_2$(2-pyridyl) groups —N(H)CH$_2$CH$_2$(4-piperidinyl) groups, —N(H)CH$_2$CH$_2$(4-morpholinyl) groups, —N(H)CH$_2$CH$_2$CH$_2$(1-imidazolyl) groups, —N(H)CH$_2$CH$_2$CH$_2$(1-(4-methylpiperazinyl)) groups, —N(H)CH$_2$CH$_2$CH$_2$(4-morpholinyl) groups, —N(H)CH$_2$CH$_2$CH$_2$(1-imidazolyl) groups, —N(H)CH$_2$CH$_2$CH$_2$(1-pyrrolidinyl) groups, —N(CH$_3$)CH$_2$CH$_2$CH$_2$(diethylamino) groups, and the like.

In still other embodiments of the fourth group of compounds where $R^6$ is a substituted amino group having the formula —N(R$^{12}$)(CH$_2$)$_p$R$^{13}$, $R^7$ is —H.

In another embodiment of the fourth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula —N(R$^{12}$)(CH$_2$)$_p$R$^{13}$ or the formula —N(R$^{12}$)C(H)(alkyl)((CH$_2$)$_p$R$^{13}$) where p is an integer selected from 0, 1, 2, or 3, $R^{13}$ is selected from a methyl group, substituted and unsubstituted alkoxy groups, substituted and unsubstituted amino groups such as —N(H)(alkyl) groups, —N(alkyl)$_2$ groups and the like, substituted and unsubstituted aryl groups, and substituted and unsubstituted heterocyclyl groups, and $R^{12}$ is selected from —H; substituted and unsubstituted alkyl groups such as, but not limited to, methyl, ethyl, propyl, and isopropyl groups; —C(=O)-alkyl groups such as —C(=O)—CH$_3$ groups and the like; —C(=O)-alkyl-N(H)(alkyl) groups such as —C(=O)—CH$_2$—N(H)(alkyl) groups and the like; —C(=O)-alkyl-N(alkyl)$_2$ groups such as —C(=O)—CH$_2$—N(alkyl)$_2$ groups and the like; —C(=O)-alkyl-N(R$^{12a'}$)(R$^{12b'}$) groups such as —C(=O)—CH$_2$—N(alkyl)$_2$ groups and the like —C(=O)-alkyl-heterocyclyl groups such as —C(=O)—CH$_2$-heterocyclyl groups and the like such as —C(=O)—CH$_2$-(1-piperazinyl) groups and the like; —C(=O)-heterocyclyl groups; —C(=O)-aryl groups; —C(=O)-alkyl-O-alkyl groups such as —C(=O)—CH$_2$—O-alkyl groups; —C(=O)-alkyl-S-alkyl groups such as —C(=O)—CH$_2$—S-alkyl groups and the like; and the like where $R^{12a'}$ is selected from —H, and substituted and unsubstituted alkyl groups, and $R^{12b'}$ is selected from —H, —SO$_2$-alkyl, —SO$_2$-aryl, —C(=O)-alkyl, —C(=O)-aryl, heterocyclyl groups such as 2-pyridyl groups and the like, heterocyclylalkyl groups, arylalkyl groups, alkyl groups, and —C(=O)-alkyl-halogen groups.

In another embodiment of the fourth group of compounds, $Z^1$, $Z^3$, $Z^4$, $R^1$, $R^2$, $R^3$, $R^5$, and $R^8$ have any of the values defined in the previous embodiments, $Z^2$ is C, and $R^6$ is a substituted or unsubstituted heterocyclyl group. In some embodiments of the fourth group of compounds where $R^6$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted pyrazolyl groups, substituted and unsubstituted pyrrolyl groups, substituted and unsubstituted imidazolyl groups, substituted and unsubstituted 1-aza-4-oxacycloheptane groups, substituted and unsubstituted 1,4-diazacycloheptane groups, substituted and unsubstituted 2,5-diazabicyclo[2.2.1]heptane groups, substituted and unsubstituted 1,4-diazabicyclo[2.2.2]octane groups, substituted or unsubstituted 1,4-diazabicyclo[4.3.0] nonane group, and substituted or unsubstituted 1,4-diazacycloheptane groups. In still other embodiments of the fourth group of compounds where $R^6$ is a heterocyclyl group, the heterocyclyl group is an unsubstituted morpholine group; a dialkyl substituted morpholinyl group such as, but not limited to, a dimethyl substituted morpholinyl group, and the like, such as, but not limited to, a 3,5-dimethyl substituted morpholinyl group; a hydroxy substituted morpholinyl group; a hydroxyalkyl substituted morpholinyl group; an aryl substituted morpholinyl group; an aminoalkyl substituted morpholinyl group including dialkylaminoalkyl substituted morpholinyl groups such as, but not limited to, dimethylaminomethyl substituted morpholinyl groups and the like such as, but not limited to, a morpholinyl group that is substituted on a ring carbon bonded to the ring O atom with a dimethylaminomethyl group and is substituted with a methyl group on the carbon bonded to the ring N atom which carbon is not bonded to the carbon bearing the dimethylaminomethyl group and the like; a heterocyclyl substituted morpholinyl group; an unsubstituted piperazine group; a dialkyl substituted piperazinyl group such as, but not limited to, a dimethyl substituted piperazinyl group, and the like such as a 3,5-dimethyl substituted piperazinyl group and the like; a monoalkyl substituted piperazinyl group such as a 3-alkyl substituted piperazinyl group, an N-alkyl substituted piperazinyl group, and the like such as, but not limited to, a 3-methyl substituted piperazinyl group, a N-alkyl substituted piperazinyl group, such as, but not limited to, N-methyl, N-ethyl, N-isopropyl substituted piperazinyl groups and the like; a hydroxyalkyl substituted piperazinyl group such as, but not limited to, hydroxyethyl and hydroxymethyl substituted piperazinyl groups and the like such as, but not limited to, N-hydroxyethyl substituted piperazinyl groups and the like; an aryl substituted piperazinyl group; a heterocyclyl substituted piperazinyl group such as, but not limited to, 2-, 3-, and 4-(2-, 3-, and 4-piperidinyl) substituted piperazinyl groups and 2-, 3-, and 4-(2-, 3-, and 4-pyridyl) substituted piperazinyl groups and the like; a —CH$_2$C(=O)O-alkyl substituted piperazinyl group; a —C(=O)-alkyl substituted piperazinyl group such as, but not limited to, a —C(=O)-ethyl or a —C(=O)-methyl substituted piperazinyl group, and the like such as a piperazinyl group where the —C(=O)-ethyl or the —C(=O)-methyl substitution is on one of the piperazinyl N atoms and the other N atom is bonded to $Z^2$, and the like; a —C(=O)O-alkyl substituted piperazinyl group such as, but not limited to, a —C(=O)—O-ethyl or a —C(=O)—O-methyl substituted piperazinyl group, and the like such as a piperazinyl group where the —C(=O)—O-ethyl or the —C(=O)—O-methyl substitution is on one of the piperazinyl N atoms and the other N atom is bonded to $Z^2$, and the like; a cycloalkyl substituted piperazinyl group such as, but not limited to, a cyclohexyl and cyclopentyl substituted piperazinyl group and the like such as, but not limited to, a N-cyclohexyl substituted piperazinyl group and the like; an unsubstituted piperidine group; an alkyl substituted piperidinyl group such as, but not limited to, 2-, 3-, and 4-alkyl substituted piperidinyl groups, and the like such as, but not limited to, 2-, 3-, and 4-hydroxyalkyl substituted piperidinyl groups and the like such as, but not limited to, 2-, 3-, and 4-hydroxymethyl substituted piperidinyl groups and the like; a hydroxy substituted piperidinyl group such as 2-, 3-, and 4-hydroxy substituted piperidinyl groups; a hydroxyalkyl substituted piperidinyl group; an aryl substituted piperidinyl group such as, but not limited to, a 4-aryl substituted piperidinyl group and the like such as, but not limited to, a piperidinyl group that is substituted in the 4 position with both an aryl group and a hydroxy group and the like such as, but not limited to, a piperidinyl group that is substituted in the 4 position with both a hydroxy group and a phenyl group; a cycloalkyl substituted piperidinyl group; a heterocyclyl substituted piperidinyl group such as, but not limited to, a piperidinyl substituted piperidinyl group and the like such as, but not limited to, 4-piperidinyl substituted piperidinyl groups, 4-(2(3H)-benzimidazolone) substituted piperidinyl group, and the like; an unsubstituted pyrrolidinyl group; an alkyl substituted pyrrolidinyl group such as, but not limited to, a methyl substituted pyrrolidinyl group, a heterocyclylalkyl substituted pyrrolidinyl group, and the like such as, but not limited to, a 2-methyl substituted pyrrolidinyl group, a 2-pyrrolidinylmethyl substituted pyrrolidinyl group, and the like; an amino substituted pyrrolidinyl group such as, but not limited to, a dialkylamino substituted pyrrolidinyl group such as, but not limited to, 2- and 3-dialkylamino substituted pyrrolidinyl groups and the like such as, but not limited to, 2- and 3-substituted N,N-dimethylamino substituted pyrrolidinyl groups and the like such as, but not limited to, a pyrrolidinyl group that is substituted with both an alkyl group and an N,N-dimethylamino group and the like such as, but not limited to, a pyrrolidinyl group that is substituted with a methyl group in the 2 position and with a N,N-dimethylamino group in the 4 position; a hydroxy substituted pyrrolidinyl group such as, but not limited to, 2- and 3-hydroxy substituted pyrrolidinyl groups; a heterocyclylalkyl substituted pyrrolidinyl group; substituted and unsubstituted pyrrolyl groups; substituted and unsubstituted 2,5-diazabicyclo[2.2.1]heptane groups; an alkyl substituted 2,5-diazabicyclo[2.2.1]heptane group such as, but not limited to, a N-methyl substituted 2,5-diazabicyclo[2.2.1]heptane group and the like; a substituted or unsubstituted 1,4-diazabicyclo[4.3.0]nonane group; and a substituted or unsubstituted 1,4-diazacycloheptane group such as, but not limited to, an alkyl substituted 1,4-diazacycloheptane group and the like, such as, but not limited to, an N-alkyl substituted 1,4-diazacycloheptane substituted group and the like such as, but not limited to, a N-methyl substituted 1,4-diazacycloheptane group and the like. In still other embodiments of the fourth group of compounds where $R^6$ is a substituted or unsubstituted heterocyclyl group, $R^7$ is —H.

In another embodiment of the fourth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is selected from substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, substituted and unsubstituted —C(═O)-heterocyclyl groups, substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other such embodiments, $R^7$ has the values described in the preceding sentence and $R^6$ is —H.

In another embodiment of the fourth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkoxy group having from 1-6 carbon atoms. In still other such embodiments, $R^7$ is a methoxy group. In still other embodiments of the fourth group of compounds where $R^7$ is an alkoxy group having from 1-6 carbon atoms such as a methoxy group, $R^6$ is —H.

In another embodiment of the fourth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkyl group having from 1-6 carbon atoms. In still other such embodiments, $R^7$ is a methyl group. In still other embodiments of the fourth group of compounds where $R^7$ is an alkyl group having from 1-6 carbon atoms such as a methyl group, $R^6$ is —H.

In another embodiment of the fourth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted alkoxy group having the formula $OCH_2(CH_2)_nR^4$ where n is an integer selected from 0, 1, or 2 and $R^{14}$ is selected from substituted and unsubstituted alkoxy groups, substituted and unsubstituted aryl groups, and substituted and unsubstituted heterocyclyl groups. In some embodiments, $R^{14}$ is selected from substituted alkoxy groups such as, but not limited to, methoxy groups, ethoxy groups, propoxy groups, and the like. In still other such embodiments, $R^{14}$ is selected from substituted and unsubstituted heterocyclyl groups selected from pyrrolidinyl groups, pyridyl groups, morpholinyl groups, piperazinyl groups, and piperidinyl groups. In still other embodiments of the fourth group of compounds where $R^7$ is a substituted alkoxy group having the formula $OCH_2(CH_2)_nR^4$, $R^6$ is —H. In still other embodiments, $R^7$ is a pyrrolidinylalkoxy groups, such as but not limited to, a pyrrolidinylpropoxy group or the like; an alkoxyethoxy group such as, but not limited to, a methoxyethoxy group or the like; or a substituted or unsubstituted pyridinylalkoxy group such as, but not limited to, (3-pyridinyl)methoxy groups, or the like.

In another embodiment of the fourth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted amino group having the formula $—N(R^{15})(CH_2)_qR^{16}$ where q is an integer selected from 0, 1, 2, or 3 and $R^{16}$ is selected from substituted and unsubstituted alkoxy groups, substituted and unsubstituted amino groups, substituted and unsubstituted aryl groups, and substituted and unsubstituted heterocyclyl groups, and $R^{15}$ is —H or a substituted or unsubstituted alkyl groups, such as, but not limited to, methyl, ethyl, propyl, and isopropyl groups. In some such embodiments, $R^{16}$ is selected from substituted amino groups such as alkylamino groups and dialkylamino groups, such as, but not limited to, dimethylamino, diethylamino, dipropylamino, (methyl)(ethyl)amino, (ethyl)(propyl)amino, (methyl)(propyl)amino groups, and the like. In some such embodiments, $R^{15}$ is a $CH_3$ group. In still other such embodiments, $R^{16}$ is selected from substituted alkoxy groups. In still other such embodiments, $R^{16}$ is selected from substituted and unsubstituted heterocyclyl groups such as those selected from pyrrolidinyl groups, pyrazolyl groups, pyridyl groups, morpholinyl groups, piperazinyl groups, piperidinyl groups, and the like. In some embodiments, $R^7$ is selected from —N(H)(3-piperidinyl) groups, —N(H)(4-piperidinyl) groups, —N(H)(4-(2-methoxymethylpyrrolidinyl)) groups, —N(CH$_3$)(4-(1-methylpiperidinyl)) groups, —N(H)CH$_2$(2-pyridyl) groups, —N(H)CH$_2$(3-pyridyl) groups, —N(H)CH$_2$(4-pyridyl) groups, —N(H)CH$_2$CH$_2$(2-pyridyl) groups, —N(H)CH$_2$CH$_2$(3-pyridyl) groups, —N(H)CH$_2$CH$_2$(4-pyridyl) groups, —N(CH$_3$)CH$_2$CH$_2$(2-pyridyl) groups —N(H)CH$_2$CH$_2$(4-piperidinyl) groups, —N(H)CH$_2$CH$_2$(4-morpholinyl) groups, —N(H)CH$_2$CH$_2$CH$_2$(1-imidazolyl) groups, —N(H)CH$_2$CH$_2$CH$_2$(1-(4-methylpiperazinyl)) groups, —N(H)CH$_2$CH$_2$CH$_2$(4-morpholinyl) groups, —N(H)CH$_2$CH$_2$CH$_2$(1-imidazolyl) groups, —N(H)CH$_2$CH$_2$CH$_2$(1-pyrrolidinyl) groups, —N(CH$_3$)CH$_2$CH$_2$CH$_2$(diethylamino) groups, and the like.

In still other embodiments of the fourth group of compounds where $R^7$ is a substituted amino group having the formula $—N(R^{15})(CH_2)_qR^{16}$, $R^6$ is —H.

In another embodiment of the fourth group of compounds, $Z^1$, $Z^3$, $Z^4$, $R^1$, $R^2$, $R^3$, $R^5$, and $R^8$ have any of the values in previous embodiments, $Z^3$ is C, and $R^7$ is a substituted amino group having the formula $—N(R^{15})(CH_2)_qR^{16}$ or the formula $—N(R^{15})C(H)(alkyl)((CH_2)_qR^{16})$ where q is an integer selected from 0, 1, 2, or 3, $R^{16}$ is selected from a methyl group, substituted and unsubstituted alkoxy groups, substituted and unsubstituted amino groups such as —N(H)(alkyl) groups, —N(alkyl)$_2$ groups and the like, substituted and unsubstituted aryl groups, and substituted and unsubstituted heterocyclyl groups, and $R^{15}$ is selected from —H; substituted and unsubstituted alkyl groups such as, but not limited to, methyl, ethyl, propyl, and isopropyl groups; —C(═O)-alkyl groups such as —C(═O)—CH$_3$ groups and the like; —C(═O)-alkyl-N(H)(alkyl) groups such as —C(═O)—CH$_2$—N(H)(alkyl) groups and the like; —C(═O)-alkyl-N(alkyl)$_2$ groups such as —C(═O)—CH$_2$—N(alkyl)$_2$ groups and the like; —C(═O)-alkyl-N(R$^{15a'}$)(R$^{15b'}$) groups such as —C(═O)—CH$_2$—N(alkyl)$_2$ groups and the like —C(═O)-alkyl-heterocyclyl groups such as —C(═O)—CH$_2$-heterocyclyl groups and the like such as —C(═O)—CH$_2$-(1-piperazinyl) groups and the like; —C(═O)-heterocyclyl groups; —C(═O)-aryl groups; —C(═O)-alkyl-O-alkyl groups such as —C(═O)—CH$_2$—O-alkyl groups; —C(═O)-alkyl-S-alkyl groups such as —C(═O)—CH$_2$—S-alkyl groups and the like; and the like where R$^{15a'}$ is selected from —H, and substituted and unsubstituted alkyl groups, and R$^{15b'}$ is selected from —H, —SO$_2$-alkyl, —SO$_2$-aryl, —C(═O)-alkyl, —C(═O)-aryl, heterocyclyl groups such as 2-pyridyl groups and the like, heterocyclylalkyl groups, arylalkyl groups, alkyl groups, and —C(═O)-alkyl-halogen groups.

In another embodiment of the fourth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted or unsubstituted heterocyclyl group. In some embodiments of the fourth group of compounds where $R^7$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted pyrazolyl groups, substituted and unsubstituted pyrrolyl groups, substituted and unsubstituted imidazolyl groups, substituted and unsubstituted 1-aza-4-oxacycloheptane groups, substituted and unsubstituted 1,4-diazacycloheptane groups, substituted and unsubstituted 2,5-diazabicyclo[2.2.1]heptane groups, substituted and unsubstituted 1,4-diazabicyclo[2.2.2]octane groups, substituted or unsubstituted 1,4-diazabicyclo[4.3.0]nonane group, and substituted or unsubstituted 1,4-diazacycloheptane groups. In still other embodiments of the fourth group of compounds where $R^7$ is a heterocyclyl group, the heterocyclyl group is an unsubstituted morpholine group; a dialkyl substituted morpholinyl group such as, but not limited to, a dimethyl substituted morpholinyl group, and the like, such as, but not limited to, a 3,5-dimethyl substituted morpholinyl group; a hydroxy substituted morpholinyl group; a hydroxyalkyl substituted morpholinyl group; an aryl substituted morpholinyl group; an aminoalkyl substituted morpholinyl group including dialkylaminoalkyl substituted morpholinyl groups such as, but not limited to, dimethylaminomethyl substituted morpholinyl groups and the like such as, but not limited to, a morpholinyl group that is substituted on a ring carbon bonded to the ring O atom with a dimethylaminomethyl group and is substituted with a methyl group on the carbon bonded to the ring N atom which carbon is not bonded to the carbon bearing the dimethylaminomethyl group and the like; a heterocyclyl substituted morpholinyl group; an unsubstituted piperazine group; a dialkyl substituted piperazinyl group such as, but not limited to, a dimethyl substituted piperazinyl group, and the like such as a 3,5-dimethyl substituted piperazinyl group and the like; a monoalkyl substituted piperazinyl group such as a 3-alkyl substituted piperazinyl group, an N-alkyl substituted piperazinyl group, and the like such as, but not limited to, a 3-methyl substituted piperazinyl group, a N-alkyl substituted piperazinyl group, such as, but not limited to, N-methyl, N-ethyl, N-isopropyl substituted piperazinyl groups and the like; a hydroxyalkyl substituted piperazinyl group such as, but not limited to, hydroxyethyl and hydroxymethyl substituted piperazinyl groups and the like such as, but not limited to, N-hydroxyethyl substituted piperazinyl groups and the like; an aryl substituted piperazinyl group; a heterocyclyl substituted piperazinyl group such as, but not limited to, 2-, 3-, and 4-(2-, 3-, and 4-piperidinyl) substituted piperazinyl groups and 2-, 3-, and 4-(2-, 3-, and 4-pyridyl) substituted piperazinyl groups and the like; a —CH$_2$C(═O)O-alkyl substituted piperazinyl group; a —C(═O)-alkyl substituted piperazinyl group such as, but not limited to, a —C(═O)-ethyl or a —C(═O)-methyl substituted piperazinyl group, and the like such as a piperazinyl group where the —C(═O)-ethyl or the —C(═O)-methyl substitution is on one of the piperazinyl N atoms and the other N atom is bonded to $Z^3$, and the like; a —C(═O)O-alkyl substituted piperazinyl group such as, but not limited to, a —C(═O)—O-ethyl or a —C(═O)—O-methyl substituted piperazinyl group, and the like such as a piperazinyl group where the —C(═O)—O-ethyl or the —C(═O)—O-methyl substitution is on one of the piperazinyl N atoms and the other N atom is bonded to $Z^3$, and the like; a cycloalkyl substituted piperazinyl group such as, but not limited to, a cyclohexyl and cyclopentyl substituted piperazinyl group and the like such as, but not limited to, a N-cyclohexyl substituted piperazinyl group and the like; an unsubstituted piperidine group; an alkyl substituted piperidinyl group such as, but not limited to, 2-, 3-, and 4-alkyl substituted piperidinyl groups, and the like such as, but not limited to, 2-, 3-, and 4-hydroxyalkyl substituted piperidinyl groups and the like such as, but not limited to, 2-, 3-, and 4-hydroxymethyl substituted piperidinyl groups and the like; a hydroxy substituted piperidinyl group such as 2-, 3-, and 4-hydroxy substituted piperidinyl groups; a hydroxyalkyl substituted piperidinyl group; an aryl substituted piperidinyl group such as, but not limited to, a 4-aryl substituted piperidinyl group and the like such as, but not limited to, a piperidinyl group that is substituted in the 4 position with both an aryl group and a hydroxy group and the like such as, but not limited to, a piperidinyl group that is substituted in the 4 position with both a hydroxy group and a phenyl group; a cycloalkyl substituted piperidinyl group; a heterocyclyl substituted piperidinyl group such as, but not limited to, a piperidinyl substituted piperidinyl group and the like such as, but not limited to, 4-piperidinyl substituted piperidinyl groups, 4-(2(3H)-benzimidazolone) substituted piperidinyl group, and the like; an unsubstituted pyrrolidinyl group; an alkyl substituted pyrrolidinyl group such as, but not limited to, a methyl substituted pyrrolidinyl group, a heterocyclylalkyl substituted pyrrolidinyl group, and the like such as, but not limited to, a 2-methyl substituted pyrrolidinyl group, a 2-pyrrolidinylmethyl substituted pyrrolidinyl group, and the like; an amino substituted pyrrolidinyl group such as, but not limited to, a dialkylamino substituted pyrrolidinyl group such as, but not limited to, 2- and 3-dialkylamino substituted pyrrolidinyl groups and the like such as, but not limited to, 2- and 3-substituted N,N-dimethylamino substituted pyrrolidinyl groups and the like such as, but not limited to, a pyrrolidinyl group that is substituted with both an alkyl group and an N,N-dimethylamino group and the like such as, but not limited to, a pyrrolidinyl group that is substituted with a methyl group in the 2 position and with a N,N-dimethylamino group in the 4 position; a hydroxy substituted pyrrolidinyl group such as, but not limited to, 2- and 3-hydroxy substituted pyrrolidinyl groups; a heterocyclylalkyl substituted pyrrolidinyl group; substituted and unsubstituted pyrrolyl groups; substituted and unsubstituted 2,5-diazabicyclo[2.2.1]heptane groups; an alkyl substituted 2,5-diazabicyclo[2.2.1]heptane group such as, but not limited to, a N-methyl substituted 2,5-diazabicyclo[2.2.1]heptane group and the like; a substituted or unsubstituted 1,4-diazabicyclo[4.3.0]nonane group; and a substituted or unsubstituted 1,4-diazacycloheptane group such as, but not limited to, an alkyl substituted 1,4-diazacycloheptane group and the like, such as, but not limited to, an N-alkyl substituted 1,4-diazacycloheptane substituted group and the like such as, but not limited to, a N-methyl substituted 1,4-diazacycloheptane group and the like. In still other embodiments of the fourth group of compounds where $R^7$ is a substituted or unsubstituted heterocyclyl group, $R^6$ is —H.

In another embodiment of the fourth group of compounds, $Z^1$-$Z^4$, $R^1$, $R^2$, and $R^3$ have any of the values in previous embodiments, and one of $R^6$ or $R^7$ is a substituted or unsubstituted pyridyloxy group. In some such embodiments, one of $R^6$ or $R^7$ is substituted or unsubstituted 2-pyridyloxy group, a 3-pyridyloxy group, or a 4-pyridyloxy group. In other such embodiments, one of $R^6$ or $R^7$ is a (2-N-alkylamido-4-pyridyl)oxy group such as a (2-N-methylamido-4-pyridyl)oxy group or the like; or a (5-N-alkylamido-3-pyridyl)oxy group such as a (5-N-methylamido-3-pyridyl)oxy group, or the like.

Other more particular embodiments of the compounds of the invention having the general structure shown in I above are provided. Such compounds form a fifth group of compounds for which:

$Z^1$, $Z^2$, $Z^3$, and $Z^4$ are independently selected from C or N;
$R^1$ is selected from —H, —F, —Cl, —Br, —NO$_2$, —C≡N, —C(═O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

R$^2$ is selected from —H, —F, —Cl, —Br, —C≡N, —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups; or R$^2$ and R$^3$ are a group of formula OCH$_2$O— such that R$^2$ and R$^3$ define a fused 5-membered ring that includes 2 oxygen atoms;

R$^3$ is selected from —F, —Cl, —Br, —CF$_3$, —C≡N, substituted and unsubstituted alkyl groups, substituted and unsubstituted alkoxy groups, substituted and unsubstituted arylalkoxy groups, substituted and unsubstituted saturated heterocyclyloxy groups, substituted and unsubstituted alkoxyalkyl groups, substituted and unsubstituted arylalkoxyalkyl groups, substituted and unsubstituted saturated heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, and substituted and unsubstituted —N(H)C(=O)N(H)-aryl groups;

R$^4$ is —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^5$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, and substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, and substituted and unsubstituted —C(=O)N(alkyl)(heterocyclyl) groups, and substituted and unsubstituted —C(=O)-heterocyclyl groups; or $R^7$ is absent if $Z^3$ is N;

$R^8$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is selected from the group consisting of —H, and substituted and unsubstituted alkyl groups.

In some embodiments, $R^{10}$ is —H. In other embodiments, $R^{10}$ is an unsubstituted alkyl group having from 1 to 6 carbon atoms such as a methyl, ethyl, propyl, i-propyl group, or the like. In some such embodiments, $R^{10}$ is a —CH$_3$ group.

In one embodiment of the fifth group of compounds, each of $Z^1$, $Z^2$, $Z^3$, and $Z^4$ are C.

In another embodiment of the fifth group of compounds, $Z^1$ is N and each of $Z^2$, $Z^3$, and $Z^4$ are C.

In another embodiment of the fifth group of compounds, $Z^1$ and $Z^3$ are both N and $Z^2$ and $Z^4$ are both C.

In another embodiment of the fifth group of compounds, $Z^3$ is N and each of $Z^1$, $Z^2$, and $Z^4$ are C.

In another embodiment of the fifth group of compounds, $Z^1$-$Z^4$ have any of the values in previous embodiments, and $R^1$ is selected from —H, —F, —Cl, and —Br.

In another embodiment of the fifth group of compounds, $Z^1$-$Z^4$ have any of the values in previous embodiments, and $R^1$ is a substituted and unsubstituted heterocyclylamino group. In some such embodiments, $R^1$ is a substituted and unsubstituted heteroarylamino groups. In some embodiments, $R^1$ is a substituted and unsubstituted heterocyclylamino group such as, but not limited to, substituted and unsubstituted pyrrolidinylalkylamino groups and the like, such as, but not limited to, substituted and unsubstituted pyrrolidinylmethylamino groups and the like.

In another embodiment of the fifth group of compounds, $Z^1$-$Z^4$ and $R^1$ have any of the values in previous embodiments, and $R^2$ is selected from —H, —F, —Cl, —CO$_2$H, substituted and unsubstituted alkyl groups, substituted and unsubstituted —C(=O)O-alkyl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, substituted and unsubstituted heterocyclyl groups, substituted and unsubstituted alkoxy groups, substituted and unsubstituted arylalkoxy groups, substituted and unsubstituted aryloxy groups, substituted and unsubstituted heterocyclyloxy, and substituted and unsubstituted heterocyclylalkoxy groups; or $R^2$ and $R^3$ are a group of formula —OCH$_2$O— such that $R^2$ and $R^3$ define a fused 5-membered ring that includes 2 oxygen atoms.

In another embodiment of the fifth group of compounds, $Z^1$-$Z^4$ and $R^1$ have any of the values in previous embodiments, and $R^2$ is —H.

In another embodiment of the fifth group of compounds, $Z^1$-$Z^4$ and $R^1$ have any of the values in previous embodiments, and $R^2$ is an unsubstituted alkoxy group having from 1 to 4 carbon atoms.

In another embodiment of the fifth group of compounds, $Z^1$-$Z^4$ and $R^1$ have any of the values in previous embodiments, and $R^2$ is a —OMe, —OEt, —O-i-Pr, or —OCH$_2$CH(CH$_3$)$_2$ group.

In another embodiment of the fifth group of compounds, $Z^1$-$Z^4$ and $R^1$ have any of the values in previous embodiments, and $R^2$ is a substituted or unsubstituted arylalkoxy, a substituted or unsubstituted aryloxy group, or a substituted or unsubstituted heterocyclyoxy group.

In another embodiment of the fifth group of compounds, $Z^1$-$Z^4$ and $R^1$ have any of the values in previous embodiments, and $R^2$ is a substituted or unsubstituted benzyloxy group, a substituted or unsubstituted phenoxy group, or a substituted or unsubstituted pyridyloxy group.

In another embodiment of the fifth group of compounds, $Z^1$-$Z^4$ and $R^1$ have any of the values in previous embodiments, and $R^2$ is an unsubstituted alkyl group having from 1 to 4 carbon atoms.

In another embodiment of the fifth group of compounds, $Z^1$-$Z^4$ and $R^1$ have any of the values in previous embodiments, and $R^2$ is a methyl group.

In another embodiment of the fifth group of compounds, $Z^1$-$Z^4$ and $R^1$ have any of the values in previous embodiments, and $R^2$ is a substituted or unsubstituted —N(H)C(=O)—N(H)-alkyl-aryl group.

In another embodiment of the fifth group of compounds, $Z^1$-$Z^4$ and $R^1$ have any of the values in previous embodiments, and $R^2$ is a substituted or unsubstituted amino group selected from the group consisting of substituted and unsubstituted alkylamino groups, dialkylamino groups, cycloalkylamino groups, heterocyclylamino groups, heterocyclylalkylamino groups, arylalkylamino groups, arylalkoxyarylmethylamino groups, and aryloxyarylalkylamino groups. In some embodiments, the substituted and unsubstituted alkylamino groups are substituted and unsubstituted aminoalkylamino groups such as, but not limited to, dialkylaminoalkylamino and the like. In some such embodiments the substituted and unsubstituted heterocyclylalkylamino groups are substituted and unsubstituted heteroarylalkylamino groups. In some embodiments, the heterocyclylalkylamino groups include, but are not limited to, substituted and unsubstituted pyrrolidinylalkylamino groups such as, but not limited to, substituted and unsubstituted pyrrolidinylmethylalkylamino groups and the like; substituted and unsubstituted thiazolylalkylamino groups such as, but not limited to substituted and unsubstituted thiazolylmethylamino groups and the like; substituted and unsubstituted imidazolylalkylamino groups such as, but not limited to, imidazolylmethylamino groups and the like; substituted and unsubstituted furanylalkylamino groups such as, but not limited to, substituted and unsubstituted furanylmethylamino groups, and the like; and the like. In other such embodiments, the heterocyclylamino groups are substituted and unsubstituted heteroarylamino groups. In other such embodiments, the substituted and unsubstituted heterocyclylamino groups are substituted and unsubstituted arylalkylheterocyclylamino groups.

In another embodiment of the fifth group of compounds, $Z^1$-$Z^4$ and $R^1$ have any of the values in previous embodiments, and $R^2$ is a substituted or unsubstituted amino group selected from the group consisting of isopropylamino groups, 3-(N,N-dimethylamino)propylamino groups, pyrrolidinylmethylamino groups, arylmethylamino groups, arylalkoxyarylmethylamino groups, aryloxyarylmethylamino groups, and pyridylmethylamino groups, and pyridylamino groups.

In another embodiment of the fifth group of compounds, $Z^1$-$Z^4$ and $R^1$ have any of the values in previous embodiments, and $R^2$ is a substituted or unsubstituted heterocyclyl groups.

In some such embodiments $R^2$ is a substituted or unsubstituted benzimidazolyl group or is a substituted or unsubstituted pyrazolyl group.

In another embodiment of the fifth group of compounds, $Z^1$-$Z^4$ and $R^1$ have any of the values in previous embodiments, and $R^2$ and $R^3$ are a group of formula —OCH$_2$O— such that $R^2$ and $R^3$ define a fused 5-membered ring that includes 2 oxygen atoms.

In another embodiment of the fifth group of compounds, $Z^1$-$Z^4$, $R^1$, and $R^2$ have any of the values in previous embodiments, and $R^3$ is selected from —F, —Cl, and —OMe.

In another embodiment of the fifth group of compounds, $Z^1$-$Z^4$, $R^1$, and $R^2$ have any of the values in previous embodiments, and $R^3$ is selected from the group consisting of substituted and unsubstituted —N(H)C(=O)N(H)-alkyl groups, and substituted and unsubstituted —N(H)C(=O)N(H)-aryl groups. In some such embodiments, $R^3$ is a substituted or unsubstituted —N(H)C(=O)N(H)CH$_2$CH$_3$ group, a substituted or unsubstituted —N(H)C(=O)N(H)CH(CH$_3$)$_2$ group, a substituted or unsubstituted —N(H)C(=O)N(H)C(CH$_3$)$_3$ group, or a substituted or unsubstituted —N(H)C(=O)N(H)-aryl group or the like. In some such embodiments, $R^3$ is a substituted or unsubstituted —N(H)C(=O)N(H)-aryl group such as, but not limited to, a —N(H)C(=O)N(H)-(2-methoxyphenyl) group, a-N(H)C(=O)N(H)-(3-trifluoromethylphenyl) group, or the like.

In another embodiment of the fifth group of compounds, $Z^1$-$Z^4$, $R^1$, and $R^2$ have any of the values in previous embodiments, and $R^3$ is —F.

In another embodiment of the fifth group of compounds, $Z^1$-$Z^4$, $R^1$, and $R^2$ have any of the values in previous embodiments, and $R^3$ is —Cl.

In another embodiment of the fifth group of compounds, $Z^1$-$Z^4$, $R^1$, and $R^2$ have any of the values in previous embodiments, and $R^3$ is —OMe. In another embodiment thereof, $R^3$ is aryloxy or heterocyclyloxy, specifically benzyloxy, phenyloxy, or pyridyloxy.

In some embodiments of the fifth group of compounds, $Z^1$-$Z^4$, $R^1$, and $R^2$ have any of the values in previous embodiments, and at least one of $R^6$ or $R^7$ is selected from the group consisting of —CO$_2$H, substituted and unsubstituted heterocyclylalkoxy groups, substituted and unsubstituted arylalkoxy groups, substituted and unsubstituted alkoxyalkoxy groups, substituted and unsubstituted heterocyclylheterocyclyl groups, substituted and unsubstituted arylheterocyclyl groups, substituted and unsubstituted cycloalkylheterocyclyl groups, substituted and unsubstituted saturated heterocyclyloxy groups, substituted and unsubstituted —N(H) alkyl groups, substituted and unsubstituted —N(H)alkyl-heterocyclyl groups, substituted and unsubstituted —N(H)-alkyl-aryl groups, substituted and unsubstituted —N(H)-heterocyclyl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, and substituted and unsubstituted —C(=O)-heterocyclyl groups. In some such embodiments, at least one of $R^6$ or $R^7$ is selected from the group consisting of —CO$_2$H, substituted and unsubstituted saturated heterocyclyloxy groups, substituted and unsubstituted —C(=O)N(H)-alkyl groups, substituted and unsubstituted —C(=O)N(H)-aryl groups, substituted and unsubstituted —C(=O)N(H)-heterocyclyl groups, and substituted and unsubstituted —C(=O)-heterocyclyl groups. In another embodiments of the fifth group of compounds, at least one of $R^6$ or $R^7$ is selected from the group consisting of substituted and unsubstituted piperidinyl substituted heterocyclyl groups, substituted and unsubstituted heterocyclyl substituted piperidinyl groups, substituted and unsubstituted hydroxymethyl substituted piperidinyl groups, dimethylaminoalkyl substituted pyrrolidinyl groups, substituted and unsubstituted 3-alkyl substituted piperazinyl groups, substituted and unsubstituted 3,5-dialkyl substituted piperazinyl groups, substituted and unsubstituted N-hydroxyalkyl substituted piperazinyl groups, substituted and unsubstituted N-alkyl substituted 1,4-diazacycloheptyl groups, substituted and unsubstituted N-ethylpiperazinyl groups, substituted and unsubstituted N-isopropylpiperazinyl groups, substituted and unsubstituted N-sec-butylpiperazinyl groups, unsubstituted piperazinyl groups, substituted and unsubstituted N-2-pyridyl substituted piperazinyl groups, substituted and unsubstituted N-3-pyridyl substituted piperazinyl groups, substituted and unsubstituted N-4-pyridyl substituted piperazinyl groups, substituted and unsubstituted N(H)—$CH_2$-pyridyl groups, substituted and unsubstituted imidazolyl groups, substituted and unsubstituted morpholinyl groups, substituted and unsubstituted 3-alkyl substituted morpholinyl groups, substituted and unsubstituted 3,5-dialkyl substituted morpholinyl groups, dialkylamino substituted pyrrolidinyl groups, pyrrolidinyl groups substituted with both dialkylamino and alkyl groups, substituted and unsubstituted 4-hydroxy substituted piperidinyl groups, substituted and unsubstituted 4-aryl substituted piperidinyl groups, substituted and unsubstituted 4-hydroxy4-phenyl substituted piperidinyl groups, substituted and unsubstituted cyclohexylpiperazinyl groups, substituted and unsubstituted cyclopentylpiperazinyl groups, substituted and unsubstituted N-alkyl substituted diazabicycloalkane groups, substituted and unsubstituted —$N(CH_3)$(N-alkyl(4-piperidinyl)) groups, substituted and unsubstituted piperazinyl groups further substituted with a —C(=O)-alkyl group on one of the N atoms of the piperazinyl group, substituted and unsubstituted —N(H)$CH_2CH_2CH_2$-imidazolyl groups, substituted and unsubstituted —N(H)$CH_2CH_2CH_2$-pyrrolidinyl groups, substituted and unsubstituted —N(H)$CH_2CH_2CH_2$-morpholinyl groups, substituted and unsubstituted —N(H)$CH_2CH_2CH_2$-piperazinyl groups, substituted and unsubstituted —N(H)$CH_2CH_2CH_2$-piperidinyl groups, substituted and unsubstituted —N(H)$CH_2CH_2CH_2$-pyridyl groups, substituted and unsubstituted —N(H)$CH_2CH_2$-imidazolyl groups, substituted and unsubstituted —N(H)$CH_2CH_2$-pyrrolidinyl groups, substituted and unsubstituted —N(H)$CH_2CH_2$-morpholinyl groups, substituted and unsubstituted —N(H)$CH_2CH_2$-piperazinyl groups, substituted and unsubstituted —N(H)$CH_2CH_2$-piperidinyl groups, substituted and unsubstituted —N(H)$CH_2CH_2$-pyridyl groups, substituted and unsubstituted 1-aza-4-oxacycloheptane groups, and substituted and unsubstituted 1,4-diazacycloheptane groups. In other embodiments, at least one of $R^6$ or $R^7$ is selected from the group consisting of piperidinyl substituted piperidinyl groups such as 4-piperidinylpiperidinyl groups or the like, 4-hydroxymethylpiperidinyl groups, 3-dimethylaminomethylpyrrolidinyl groups, 3-alkyl substituted piperazinyl groups, 3,5-dialkyl substituted piperazinyl groups, N-hydroxyethylpiperazinyl groups, N-hydroxymethylpiperazinyl groups, N-hydroxypropylpiperazinyl groups, N-methyl substituted 1,4-diazacycloheptyl groups, N-ethylpiperazinyl groups, N-isopropylpiperazinyl groups, N-sec-butylpiperazinyl groups, unsubstituted piperazinyl groups, N-(2-pyridyl)piperazinyl groups, N-(3-pyridyl)piperazinyl groups, N-(4-pyridyl)piperazinyl groups, N(H)—$CH_2$-pyridyl groups, imidazolyl groups, unsubstituted morpholinyl groups, 3-alkylmorpholinyl groups, 3,5-dialkylmorpholinyl groups, 2-dimethylaminopyrrolidinyl groups, 2-methyl-4-dialkylaminopyrroldinyl groups, 4-hydroxypiperidinyl groups, 4-arylpiperidinyl groups, 4-hydroxy-4-phenylpiperidinyl groups, cyclohexylpiperazinyl groups, cyclopentylpiperazinyl groups, N-methyl substituted diazabicycloalkane groups, —$N(CH_3)$(N-alkyl(4-piperidinyl)) groups, piperazinyl groups further substituted with a —C(=O)-methyl group on one of the N atoms of the piperazinyl group, —N(H)$CH_2CH_2CH_2$-imidazolyl groups, —N(H)$CH_2CH_2CH_2$-pyrrolidinyl groups, —N(H)$CH_2CH_2CH_2$-morpholinyl groups, —N(H)$CH_2CH_2CH_2$-piperazinyl groups, —N(H)$CH_2CH_2CH_2$-piperidinyl groups, and —N(H)$CH_2CH_2CH_2$-pyridyl groups. In some such embodiments, at least one of $R^6$ or $R^7$ is selected from the group consisting of 4-piperidinylpiperidinyl groups, 4-hydroxymethylpiperidinyl groups, 3-dimethylaminomethylpyrrolidinyl groups, 3,5-dimethyl substituted piperazinyl groups, N-methyl substituted 1,4-diazacycloheptyl groups, N-(2-pyridyl)piperazinyl groups, N(H)—$CH_2$-(4-pyridyl) groups, imidazolyl groups, unsubstituted morpholinyl groups, 3-methylmorpholinyl groups, 3,5-dimethylmorpholinyl groups, 2-dimethylaminopyrrolidinyl groups, 2-methyl-4-dimethylaminopyrroldinyl groups, 4-hydroxy-4-phenylpiperidinyl groups, cyclohexylpiperazinyl groups, N-methyl substituted diazabicycloalkane groups, —$N(CH_3)$(N-methyl(4-piperidinyl)) groups, piperazinyl groups further substituted with a —C(=O)-methyl group on one of the N atoms of the piperazinyl group, —N(H)$CH_2CH_2CH_2$-imidazolyl groups, —N(H)$CH_2CH_2CH_2$-pyrrolidinyl groups, —N(H)$CH_2CH_2CH_2$-morpholinyl groups, —N(H)$CH_2CH_2CH_2$-piperazinyl groups, —N(H)$CH_2CH_2CH_2$-piperidinyl groups, and —N(H)$CH_2CH_2CH_2$-pyridyl groups.

In another embodiment of the fifth group of compounds, $Z^2$-$Z^4$, $R^1$, $R^2$, and $R^3$ have any of the values in previous embodiments, $Z^1$ is C, and $R^5$ is H. In some such embodiments, $R^8$ is also H.

In another embodiment of the fifth group of compounds, $Z^2$-$Z^4$, $R^1$, $R^2$, and $R^3$ have any of the values in previous embodiments, $Z^1$ is C, and $R^5$ is —$CH_3$.

In another embodiment of the fifth group of compounds, $Z^2$-$Z^4$, $R^1$, $R^2$, and $R^3$ have any of the values in previous embodiments, $Z^1$ is C, and $R^5$ is morpholine.

In another embodiment of the fifth group of compounds, $Z^1$-$Z^3$, $R^1$, $R^2$, and $R^3$ have any of the values in previous embodiments, $Z^4$ is C, and $R^8$ is H.

In another embodiment of the fifth group of compounds, $Z^1$-$Z^3$, $R^1$, $R^2$, and $R^3$ have any of the values in previous embodiments, $Z^4$ is C, and $R^8$ is —$CH_3$.

In another embodiment of the fifth group of compounds, $Z_1$-$Z^3$, $R^1$, $R^2$, and $R^3$ have any of the values in previous embodiments, $Z^4$ is C, and $R^8$ is morpholine.

In another embodiment of the fifth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from a first group of compounds; or $Z^1$, $Z^2$, $Z^4$, $R^1$, $R^2$, $R^3$, $R^5$, and $R^8$ have any of the values in previous embodiments, $Z^3$ is C, and $R^7$ is selected from the first group of compounds, the first group of compounds comprising members selected from the group consisting of —$CO_2H$, substituted and unsubstituted heterocyclylalkoxy groups, substituted and unsubstituted arylalkoxy groups, substituted and unsubstituted alkoxyalkoxy groups, substituted and unsubstituted heterocyclylheterocyclyl groups, substituted and unsubstituted arylheterocyclyl groups, substituted and unsubstituted cycloalkylheterocyclyl groups, substituted and unsubstituted saturated heterocyclyloxy groups, substituted and unsubstituted (alkyl)(heterocyclyl)amino groups, substituted and unsubstituted heterocyclylalkylamino groups, substituted and unsubstituted arylalkylamino groups, substituted and unsubstituted heterocyclylamino groups, substituted and unsubstituted —C(=O)N(H)-aryl groups, —C(=O)N(H)-heteroaryl groups, substituted and unsubstituted —C(=O)N(alkyl)(heterocyclyl) groups, and substituted and unsubstituted —C(=O)-heterocyclyl groups.

In another embodiment of the fifth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from —Br, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, substituted and unsubstituted —C(=O)-heterocyclyl groups, substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other embodiments, $R^6$ has the values described in the preceding sentence and $R^7$ is —H.

In another embodiment of the fifth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkoxy group having from 1-6 carbon atoms. In still other such embodiments, $R^6$ is a methoxy group. In still other embodiments of the fifth group of compounds where $R^6$ is an alkoxy group having from 1-6 carbon atoms such as a methoxy group, $R^7$ is —H.

In another embodiment of the fifth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkyl group having from 1-6 carbon atoms. In still other such embodiments, $R^6$ is a methyl group. In still other embodiments of the fifth group of compounds where $R^6$ is an alkyl group having from 1-6 carbon atoms such as a methyl group, $R^7$ is —H.

In another embodiment of the fifth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted alkoxy group having the formula $OCH_2(CH_2)_m R^{11}$ where m is an integer selected from 0, 1, or 2 and $R^{11}$ is selected from substituted and unsubstituted alkoxy groups, substituted and unsubstituted aryl groups, and substituted and unsubstituted heterocyclyl groups. In still other such embodiments, $R^{11}$ is selected from substituted alkoxy groups such as, but not limited to methoxy groups, ethoxy groups, propoxy groups, and the like. In still other embodiments, $R^{11}$ is selected from substituted and unsubstituted heterocyclyl groups selected from pyrrolidinyl groups, pyridyl groups, morpholinyl groups, piperazinyl groups, and piperidinyl groups. In still other embodiments where $R^6$ is a substituted alkoxy group having the formula —$OCH_2(CH_2)_m R^{11}$, $R^7$ is —H. In still other embodiments, $R^6$ is a pyrrolidinylalkoxy groups, such as but not limited to, a pyrrolidinylpropoxy group or the like; an alkoxyethoxy group such as, but not limited to, a methoxyethoxy group or the like; or a substituted or unsubstituted pyridinylalkoxy group such as, but not limited to, (3-pyridinyl)methoxy groups, or the like.

In another embodiment of the fifth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula —$N(R^{12})(CH_2)_p R^{13}$ where p is an integer selected from 0, 1, 2, or 3, $R^{13}$ is selected from substituted and unsubstituted alkoxy groups, substituted and unsubstituted amino groups, substituted and unsubstituted aryl groups, and substituted and unsubstituted heterocyclyl groups, and $R^{12}$ is selected from —H or substituted and unsubstituted alkyl groups such as, but not limited to, methyl, ethyl, propyl, and isopropyl. In some such embodiments, $R^{13}$ is selected from substituted amino groups such as alkylamino groups and dialkylamino groups, such as, but not limited to, dimethylamino, diethylamino, dipropylamino, (methyl)(ethyl)amino, (ethyl)(propyl)amino, (methyl)(propyl)amino groups, and the like. In some such embodiments, $R^{12}$ is a $CH_3$ group. In still other such embodiments, $R^{13}$ is selected from substituted alkoxy groups. In still other such embodiments, $R^{13}$ is selected from substituted and unsubstituted heterocyclyl groups such as those selected from pyrrolidinyl groups, pyrazolyl groups, pyridyl groups, morpholinyl groups, piperazinyl groups, piperidinyl groups, and the like. In some embodiments, $R^6$ is selected from —N(H)(3-piperidinyl) groups, —N(H)(4-piperidinyl) groups, —N(H)(4-(2-methoxymethylpyrrolidinyl)) groups, —N($CH_3$)(4-(1-methylpiperidinyl)) groups, —N(H)$CH_2$(2-pyridyl) groups, —N(H)$CH_2$(3-pyridyl) groups, —N(H)$CH_2$(4-pyridyl) groups, —N(H)$CH_2CH_2$(2-pyridyl) groups, —N(H)$CH_2CH_2$(3-pyridyl) groups, —N(H)$CH_2CH_2$(4-pyridyl) groups, —N($CH_3$)$CH_2CH_2$(2-pyridyl) groups —N(H)$CH_2CH_2$(4-piperidinyl) groups, —N(H)$CH_2CH_2$(4-morpholinyl) groups, —N(H)$CH_2CH_2CH_2$(1-imidazolyl) groups, —N(H)$CH_2CH_2CH_2$(1-(4-methylpiperazinyl)) groups, —N(H)$CH_2CH_2CH_2$(4-morpholinyl) groups, —N(H)$CH_2CH_2CH_2$(1-imidazolyl) groups, —N(H)$CH_2CH_2CH_2$(1-pyrrolidinyl) groups, —N($CH_3$)$CH_2CH_2CH_2$(diethylamino) groups, and the like.

In still other embodiments of the fifth group of compounds where $R^6$ is a substituted amino group having the formula —$N(R^{12})(CH_2)_p R^{13}$, $R^7$ is —H.

In another embodiment of the fifth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula —$N(R^{12})(CH_2)_p R^{13}$ or the formula —$N(R^{12})C(H)(alkyl)((CH_2)_p R^{13})$ where p is an integer selected from 0, 1, 2, or 3, $R^{13}$ is selected from a methyl group, substituted and unsubstituted alkoxy groups, substituted and unsubstituted amino groups such as —N(H)(alkyl) groups, —N(alkyl)$_2$ groups and the like, substituted and unsubstituted aryl groups, and substituted and unsubstituted heterocyclyl groups, and $R^{12}$ is selected from —H; substituted and unsubstituted alkyl groups such as, but not limited to, methyl, ethyl, propyl, and isopropyl groups; —C(=O)-alkyl groups such as —C(=O)—$CH_3$ groups and the like; —C(=O)-alkyl-N(H)(alkyl) groups such as —C(=O)—$CH_2$—N(H)(alkyl) groups and the like; —C(=O)-alkyl-N(alkyl)$_2$ groups such as —C(=O)—$CH_2$—N(alkyl)$_2$ groups and the like; —C(=O)-alkyl-N($R^{12a'}$)($R^{12'}$) groups such as —C(=O)—$CH_2$—N(alkyl)$_2$ groups and the like —C(=O)-alkyl-heterocyclyl groups such as —C(=O)—$CH_2$-heterocyclyl groups and the like such as —C(=O)—$CH_2$-(1-piperazinyl) groups and the like; —C(=O)-heterocyclyl groups; —C(=O)-aryl groups; —C(=O)-alkyl-O-alkyl groups such as —C(=O)—$CH_2$—O-alkyl groups; —C(=O)-alkyl-S-alkyl groups such as —C(=O)—$CH_2$—S-alkyl groups and the like; and the like where $R^{12b'}$ is selected from —H, and substituted and unsubstituted alkyl groups, and $R^{12b'}$ is selected from —H, —SO$_2$-alkyl, —SO$_2$-aryl, —C(=O)-alkyl, —C(=O)-aryl, heterocyclyl groups such as 2-pyridyl groups and the like, heterocyclylalkyl groups, arylalkyl groups, alkyl groups, and —C(=O)-alkyl-halogen groups.

In another embodiment of the fifth group of compounds, $Z^1$, $Z^3$, $Z^4$, $R^1$, $R^2$, $R^3$, $R^5$, and $R^8$ have any of the values defined in the previous embodiments, $Z^2$ is C, and $R^6$ is a substituted or unsubstituted heterocyclyl group. In some embodiments of the fifth group of compounds where $R^6$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted pyrazolyl groups, substituted and unsubstituted pyrrolyl groups, substituted and unsubstituted imidazolyl groups, substituted and unsubstituted 1,4-diazacycloheptane groups, substituted and unsubstituted 2,5-diazabicyclo[2.2.1]heptane groups, substituted and unsubstituted 1,4-diazabicyclo[2.2.2]octane groups, substituted or unsubstituted 1,4-diazabicyclo[4.3.0]nonane group, and substituted or unsubstituted 1,4-diazacycloheptane groups. In still other embodiments of the fifth group of compounds where $R^6$ is a heterocyclyl group, the heterocyclyl group is an unsubstituted morpholine group; a dialkyl substituted morpholinyl group such as, but not limited to, a dimethyl substituted morpholinyl group, and the like, such as, but not limited to, a 3,5-dimethyl substituted morpholinyl group; a hydroxy substituted morpholinyl group; a hydroxyalkyl substituted morpholinyl group; an aryl substituted morpholinyl group; an aminoalkyl substituted morpholinyl group including dialkylaminoalkyl substituted morpholinyl groups such as, but not limited to, dimethylaminomethyl substituted morpholinyl groups and the like such as, but not limited to, a morpholinyl group that is substituted on a ring carbon bonded to the ring O atom with a dimethylaminomethyl group and is substituted with a methyl group on the carbon bonded to the ring N atom which carbon is not bonded to the carbon bearing the dimethylaminomethyl group and the like; a heterocyclyl substituted morpholinyl group; an unsubstituted piperazine group; a dialkyl substituted piperazinyl group such as, but not limited to, a dimethyl substituted piperazinyl group, and the like such as a 3,5-dimethyl substituted piperazinyl group and the like; a monoalkyl substituted piperazinyl group such as a 3-alkyl substituted piperazinyl group, an N-alkyl substituted piperazinyl group, and the like such as, but not limited to, a 3-methyl substituted piperazinyl group, a N-alkyl substituted piperazinyl group, such as, but not limited to, N-methyl, N-ethyl, N-isopropyl substituted piperazinyl groups and the like; a hydroxyalkyl substituted piperazinyl group such as, but not limited to, hydroxyethyl and hydroxymethyl substituted piperazinyl groups and the like such as, but not limited to, N-hydroxyethyl substituted piperazinyl groups and the like; an aryl substituted piperazinyl group; a heterocyclyl substituted piperazinyl group such as, but not limited to, 2-, 3-, and 4-(2-, 3-, and 4-piperidinyl) substituted piperazinyl groups and 2-, 3-, and 4-(2-, 3-, and 4-pyridyl) substituted piperazinyl groups and the like; a —CH$_2$C(=O)O-alkyl substituted piperazinyl group; a —C(=O)-alkyl substituted piperazinyl group such as, but not limited to, a —C(=O)-ethyl or a —C(=O)-methyl substituted piperazinyl group, and the like such as a piperazinyl group where the —C(=O)-ethyl or the —C(=O)-methyl substitution is on one of the piperazinyl N atoms and the other N atom is bonded to $Z^2$, and the like; a —C(=O)O-alkyl substituted piperazinyl group such as, but not limited to, a —C(=O)—O-ethyl or a —C(=O)—O-methyl substituted piperazinyl group, and the like such as a piperazinyl group where the —C(=O)—O-ethyl or the —C(=O)—O-methyl substitution is on one of the piperazinyl N atoms and the other N atom is bonded to $Z^2$, and the like; a cycloalkyl substituted piperazinyl group such as, but not limited to, a cyclohexyl and cyclopentyl substituted piperazinyl group and the like such as, but not limited to, a N-cyclohexyl substituted piperazinyl group and the like; an unsubstituted piperidine group; an alkyl substituted piperidinyl group such as, but not limited to, 2-, 3-, and 4-alkyl substituted piperidinyl groups, and the like such as, but not limited to, 2-, 3-, and 4-hydroxyalkyl substituted piperidinyl groups and the like such as, but not limited to, 2-, 3-, and 4-hydroxymethyl substituted piperidinyl groups and the like; a hydroxy substituted piperidinyl group such as 2-, 3-, and 4-hydroxy substituted piperidinyl groups; a hydroxyalkyl substituted piperidinyl group; an aryl substituted piperidinyl group such as, but not limited to, a 4-aryl substituted piperidinyl group and the like such as, but not limited to, a piperidinyl group that is substituted in the 4 position with both an aryl group and a hydroxy group and the like such as, but not limited to, a piperidinyl group that is substituted in the 4 position with both a hydroxy group and a phenyl group; a cycloalkyl substituted piperidinyl group; a heterocyclyl substituted piperidinyl group such as, but not limited to, a piperidinyl substituted piperidinyl group and the like such as, but not limited to, 4-piperidinyl substituted piperidinyl groups, 4-(2(3H)-benzimidazolone) substituted piperidinyl group, and the like; an unsubstituted pyrrolidinyl group; an alkyl substituted pyrrolidinyl group such as, but not limited to, a methyl substituted pyrrolidinyl group, a heterocyclylalkyl substituted pyrrolidinyl group, and the like such as, but not limited to, a 2-methyl substituted pyrrolidinyl group, a 2-pyrrolidinylmethyl substituted pyrrolidinyl group, and the like; an amino substituted pyrrolidinyl group such as, but not limited to, a dialkylamino substituted pyrrolidinyl group such as, but not limited to, 2- and 3-dialkylamino substituted pyrrolidinyl groups and the like such as, but not limited to, 2- and 3-substituted N,N-dimethylamino substituted pyrrolidinyl groups and the like such as, but not limited to, a pyrrolidinyl group that is substituted with both an alkyl group and an N,N-dimethylamino group and the like such as, but not limited to, a pyrrolidinyl group that is substituted with a methyl group in the 2 position and with a N,N-dimethylamino group in the 4 position; a hydroxy substituted pyrrolidinyl group such as, but not limited to, 2- and 3-hydroxy substituted pyrrolidinyl groups; a heterocyclylalkyl substituted pyrrolidinyl group; substituted and unsubstituted pyrrolyl groups; substituted and unsubstituted 2,5-diazabicyclo[2.2.1]heptane groups; an alkyl substituted 2,5-diazabicyclo[2.2.1]heptane group such as, but not limited to, a N-methyl substituted 2,5-diazabicyclo[2.2.1]heptane group and the like; a substituted or unsubstituted 1,4-diazabicyclo[4.3.0]nonane group; and a substituted or unsubstituted 1,4-diazacycloheptane group such as, but not limited to, an alkyl substituted 1,4-diazacycloheptane group and the like, such as, but not limited to, an N-alkyl substituted 1,4-diazacycloheptane substituted group and the like such as, but not limited to, a N-methyl substituted 1,4-diazacycloheptane group and the like. In still other embodiments of the fifth group of compounds where $R^6$ is a substituted or unsubstituted heterocyclyl group, $R^7$ is —H.

In another embodiment of the fifth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is selected from substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, substituted and unsubstituted —C(=O)-heterocyclyl groups, substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other such embodiments, $R^7$ has the values described in the preceding sentence and $R^6$ is —H.

In another embodiment of the fifth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkoxy group having from 1-6 carbon atoms. In still other such embodiments, $R^7$ is a methoxy group. In still other embodiments of the fifth group of compounds where $R^7$ is an alkoxy group having from 1-6 carbon atoms such as a methoxy group, $R^6$ is —H.

In another embodiment of the fifth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkyl group having from 1-6 carbon atoms. In still other such embodiments, $R^7$ is a methyl group. In still other embodiments of the fifth group of compounds where $R^7$ is an alkyl group having from 1-6 carbon atoms such as a methyl group, $R^6$ is —H.

In another embodiment of the fifth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted alkoxy group having the formula —OCH$_2$(CH$_2$)$_n$R$^{14}$ where n is an integer selected from 0, 1, or 2 and $R^{14}$ is selected from substituted and unsubstituted alkoxy groups, substituted and unsubstituted aryl groups, and substituted and unsubstituted heterocyclyl groups. In some embodiments, $R^{14}$ is selected from substituted alkoxy groups such as, but not limited to methoxy groups, ethoxy groups, propoxy groups, and the like. In still other such embodiments, $R^{14}$ is selected from substituted and unsubstituted heterocyclyl groups selected from pyrrolidinyl groups, pyridyl groups, morpholinyl groups, piperazinyl groups, and piperidinyl groups. In still other embodiments of the fifth group of compounds where $R^7$ is a substituted alkoxy group having the formula OCH$_2$(CH$_2$)$_n$ R$^{14}$, $R^6$ is —H. In still other embodiments, $R^7$ is a pyrrolidinylalkoxy groups, such as but not limited to, a pyrrolidinylpropoxy group or the like; an alkoxyethoxy group such as, but not limited to, a methoxyethoxy group or the like; or a substituted or unsubstituted pyridinylalkoxy group such as, but not limited to, (3-pyridinyl)methoxy groups, or the like.

In another embodiment of the fifth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted amino group having the formula —N(R$^{15}$)(CH$_2$)$_q$R$^{16}$ where q is an integer selected from 0, 1, 2 ,or 3 and $R^{16}$ is selected from substituted and unsubstituted alkoxy groups, substituted and unsubstituted amino groups, substituted and unsubstituted aryl groups, and substituted and unsubstituted heterocyclyl groups, and $R^{15}$ is —H or a substituted or unsubstituted alkyl groups, such as, but not limited to, methyl, ethyl, propyl, and isopropyl groups. In some such embodiments, $R^{16}$ is selected from substituted amino groups such as alkylamino groups and dialkylamino groups, such as, but not limited to, dimethylamino, diethylamino, dipropylamino, (methyl)(ethyl)amino, (ethyl)(propyl)amino, (methyl)(propyl)amino groups, and the like. In some such embodiments, $R^{15}$ is a CH$_3$ group. In still other such embodiments, $R^{16}$ is selected from substituted alkoxy groups. In still other such embodiments, $R^{16}$ is selected from substituted and unsubstituted heterocyclyl groups such as those selected from pyrrolidinyl groups, pyrazolyl groups, pyridyl groups, morpholinyl groups, piperazinyl groups, piperidinyl groups, and the like. In some embodiments, $R^7$ is selected from —N(H)(3-piperidinyl) groups, —N(H)(4-piperidinyl) groups, —N(H)(4-(2-methoxymethylpyrrolidinyl)) groups, —N(CH$_3$)(4-(1-methylpiperidinyl)) groups, —N(H)CH$_2$(2-pyridyl) groups, —N(H)CH$_2$(3-pyridyl) groups, —N(H)CH$_2$(4-pyridyl) groups, —N(H)CH$_2$CH$_2$(2-pyridyl) groups, —N(H)CH$_2$CH$_2$(3-pyridyl) groups, —N(H)CH$_2$CH$_2$(4-pyridyl) groups, —N(CH$_3$)CH$_2$CH$_2$(2-pyridyl) groups —N(H)CH$_2$CH$_2$(4-piperidinyl) groups, —N(H)CH$_2$CH$_2$(4-morpholinyl) groups, —N(H)CH$_2$CH$_2$CH$_2$(1-imidazolyl) groups, —N(H)CH$_2$CH$_2$CH$_2$(1-(4-methylpiperazinyl)) groups, —N(H)CH$_2$CH$_2$CH$_2$(4-morpholinyl) groups, —N(H)CH$_2$CH$_2$CH$_2$(1-imidazolyl) groups, —N(H)CH$_2$CH$_2$CH$_2$(1-pyrrolidinyl) groups, —N(CH$_3$)CH$_2$CH$_2$CH$_2$(diethylamino) groups, and the like.

In still other embodiments of the fifth group of compounds where $R^7$ is a substituted amino group having the formula —N(R$^{15}$)(CH$_2$)$_q$R$^{16}$, $R^6$ is —H.

In another embodiment of the fifth group of compounds, $Z^1$, $Z^3$, $Z^4$, $R^1$, $R^2$, $R^3$, $R^5$, and $R^8$ have any of the values in previous embodiments, $Z^3$ is C, and $R^7$ is a substituted amino group having the formula —N(R$^{15}$)(CH$_2$)$_q$R$^{16}$ or the formula —N(R$^{15}$)C(H)(alkyl)((CH$_2$)$_q$R$^{16}$) where q is an integer selected from 0, 1, 2, or 3, $R^{16}$ is selected from a methyl group, substituted and unsubstituted alkoxy groups, substituted and unsubstituted amino groups such as —N(H)(alkyl) groups, —N(alkyl)$_2$ groups and the like, substituted and unsubstituted aryl groups, and substituted and unsubstituted heterocyclyl groups, and $R^{15}$ is selected from —H; substituted and unsubstituted alkyl groups such as, but not limited to, methyl, ethyl, propyl, and isopropyl groups; —C(=O)-alkyl groups such as —C(=O)—CH$_3$ groups and the like; —C(=O)-alkyl-N(H)(alkyl) groups such as —C(=O)—CH$_2$—N(H)(alkyl) groups and the like; —C(=O)-alkyl-N(alkyl)$_2$ groups such as —C(=O)—CH$_2$—N(alkyl)$_2$ groups and the like; —C(=O)-alkyl-N(R$^{15a}$)(R$^{15b'}$) groups such as —C(=O)—CH$_2$—N(alkyl)$_2$ groups and the like —C(=O)-alkyl-heterocyclyl groups such as —C(=O)—CH$_2$-heterocyclyl groups and the like such as —C(=O)—CH$_2$-(1-piperazinyl) groups and the like; —C(=O)-heterocyclyl groups; —C(=O)-aryl groups; —C(=O)-alkyl-O-alkyl groups such as —C(=O)—CH$_2$—O-alkyl groups; —C(=O)-alkyl-S-alkyl groups such as —C(=O)—CH$_2$—S-alkyl groups and the like; and the like where $R^{15a'}$ is selected from —H, and substituted and unsubstituted alkyl groups, and $R^{15b'}$ is selected from —H, —SO$_2$-alkyl, —SO$_2$-aryl, —C(=O)-alkyl, —C(=O)-aryl, heterocyclyl groups such as 2-pyridyl groups and the like, heterocyclylalkyl groups, arylalkyl groups, alkyl groups, and —C(=O)-alkyl-halogen groups.

In another embodiment of the fifth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted or unsubstituted heterocyclyl group. In some embodiments of the fifth group of compounds where $R^7$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted pyrazolyl groups, substituted and unsubstituted pyrrolyl groups, substituted, and unsubstituted imidazolyl groups, and substituted and unsubstituted 1-aza-4-oxacycloheptane groups, substituted and unsubstituted 1,4-diazacycloheptane groups, substituted and unsubstituted 2,5-diazabicyclo[2.2.1]heptane groups, substituted and unsubstituted 1,4-diazabicyclo[2.2.2]octane groups, substituted or unsubstituted 1,4-diazabicyclo[4.3.0]nonane group, and substituted or unsubstituted 1,4-diazacycloheptane groups. In still other embodiments of the fifth group of compounds where $R^7$ is a heterocyclyl group, the heterocyclyl group is an unsubstituted morpholine group; a dialkyl substituted morpholinyl group such as, but not limited to, a dimethyl substituted morpholinyl group, and the like, such as, but not limited to, a 3,5-dimethyl substituted morpholinyl group; a hydroxy substituted morpholinyl group; a hydroxyalkyl substituted morpholinyl group; an aryl substituted morpholinyl group; an aminoalkyl substituted morpholinyl group including dialkylaminoalkyl substituted morpholinyl groups such as, but not limited to, dimethylaminomethyl substituted morpholinyl groups and the like such as, but not limited to, a morpholinyl group that is substituted on a ring carbon bonded to the ring O atom with a dimethylaminomethyl group and is substituted with a methyl group on the carbon bonded to the ring N atom which carbon is not bonded to the carbon bearing the dimethylaminomethyl group and the like; a heterocyclyl substituted morpholinyl group; an unsubstituted piperazine group; a dialkyl substituted piperazinyl group such as, but not limited to, a dimethyl substituted piperazinyl group, and the like such as a 3,5-dimethyl substituted piperazinyl group and the like; a monoalkyl substituted piperazinyl group such as a 3-alkyl substituted piperazinyl group, an N-alkyl substituted piperazinyl group, and the like such as, but not limited to, a 3-methyl substituted piperazinyl group, a N-alkyl substituted piperazinyl group, such as, but not limited to, N-methyl, N-ethyl, N-isopropyl substituted piperazinyl groups and the like; a hydroxyalkyl substituted piperazinyl group such as, but not limited to, hydroxyethyl and hydroxymethyl substituted piperazinyl groups and the like such as, but not limited to, N-hydroxyethyl substituted piperazinyl groups and the like; an aryl substituted piperazinyl group; a heterocyclyl substituted piperazinyl group such as, but not limited to, 2-, 3-, and 4-(2-, 3-, and 4-piperidinyl) substituted piperazinyl groups and 2-, 3-, and 4-(2-, 3-, and 4-pyridyl) substituted piperazinyl groups and the like; a —CH$_2$C(═O)O-alkyl substituted piperazinyl group; a —C(═O)-alkyl substituted piperazinyl group such as, but not limited to, a —C(═O)-ethyl or a —C(═O)-methyl substituted piperazinyl group, and the like such as a piperazinyl group where the —C(═O)-ethyl or the —C(═O)-methyl substitution is on one of the piperazinyl N atoms and the other N atom is bonded to $Z^3$, and the like; a —C(═O)O-alkyl substituted piperazinyl group such as, but not limited to, a —C(═O)—O-ethyl or a —C(═O)—O-methyl substituted piperazinyl group, and the like such as a piperazinyl group where the —C(═O)—O-ethyl or the —C(═O)—O-methyl substitution is on one of the piperazinyl N atoms and the other N atom is bonded to $Z^3$, and the like; a cycloalkyl substituted piperazinyl group such as, but not limited to, a cyclohexyl and cyclopentyl substituted piperazinyl group and the like such as, but not limited to, a N-cyclohexyl substituted piperazinyl group and the like; an unsubstituted piperidine group; an alkyl substituted piperidinyl group such as, but not limited to, 2-, 3-, and 4-alkyl substituted piperidinyl groups, and the like such as, but not limited to, 2-, 3-, and 4-hydroxyalkyl substituted piperidinyl groups and the like such as, but not limited to, 2-, 3-, and 4-hydroxymethyl substituted piperidinyl groups and the like; a hydroxy substituted piperidinyl group such as 2-, 3-, and 4-hydroxy substituted piperidinyl groups; a hydroxyalkyl substituted piperidinyl group; an aryl substituted piperidinyl group such as, but not limited to, a 4-aryl substituted piperidinyl group and the like such as, but not limited to, a piperidinyl group that is substituted in the 4 position with both an aryl group and a hydroxy group and the like such as, but not limited to, a piperidinyl group that is substituted in the 4 position with both a hydroxy group and a phenyl group; a cycloalkyl substituted piperidinyl group; a heterocyclyl substituted piperidinyl group such as, but not limited to, a piperidinyl substituted piperidinyl group and the like such as, but not limited to, 4-piperidinyl substituted piperidinyl groups, 4-(2(3H)-benzimidazolone) substituted piperidinyl group, and the like; an unsubstituted pyrrolidinyl group; an alkyl substituted pyrrolidinyl group such as, but not limited to, a methyl substituted pyrrolidinyl group, a heterocyclylalkyl substituted pyrrolidinyl group, and the like such as, but not limited to, a 2-methyl substituted pyrrolidinyl group, a 2-pyrrolidinylmethyl substituted pyrrolidinyl group, and the like; an amino substituted pyrrolidinyl group such as, but not limited to, a dialkylamino substituted pyrrolidinyl group such as, but not limited to, 2- and 3-dialkylamino substituted pyrrolidinyl groups and the like such as, but not limited to, 2- and 3-substituted N,N-dimethylamino substituted pyrrolidinyl groups and the like such as, but not limited to, a pyrrolidinyl group that is substituted with both an alkyl group and an N,N-methylamino group and the like such as, but not limited to, a pyrrolidinyl group that is substituted with a methyl group in the 2 position and with a N,N-dimethylamino group in the 4 position; a hydroxy substituted pyrrolidinyl group such as, but not limited to, 2- and 3-hydroxy substituted pyrrolidinyl groups; a heterocyclylalkyl substituted pyrrolidinyl group; substituted and unsubstituted pyrrolyl groups; substituted and unsubstituted 2,5-diazabicyclo[2.2.1]heptane groups; an alkyl substituted 2,5-diazabicyclo[2.2.1]heptane group such as, but not limited to, a N-methyl substituted 2,5-diazabicyclo[2.2.1]heptane group and the like; a substituted or unsubstituted 1,4-diazabicyclo[4.3.0]nonane group; and a substituted or unsubstituted 1,4-diazacycloheptane group such as, but not limited to, an alkyl substituted 1,4-diazacycloheptane group and the like, such as, but not limited to, an N-alkyl substituted 1,4-diazacycloheptane substituted group and the like such as, but not limited to, a N-methyl substituted 1,4-diazacycloheptane group and the like. In still other embodiments of the fifth group of compounds where $R^7$ is a substituted or unsubstituted heterocyclyl group, $R^6$ is —H.

In another embodiment of the fifth group of compounds, $Z^1$-$Z^4$, $R^1$, $R^2$, and $R^3$ have any of the values in previous embodiments, and one of $R^6$ or $R^7$ is a substituted or unsubstituted pyridyloxy group. In some such embodiments, one of $R^6$ or $R^7$ is substituted or unsubstituted 2-pyridyloxy group, a 3-pyridyloxy group, or a 4-pyridyloxy group. In other such embodiments, one of $R^6$ or $R^7$ is a (2—N-alkylamido-4-pyridyl)oxy group such as a (2—N-methylamido-4-pyridyl)oxy group or the like; or a (5—N-alkylamido-3-pyridyl)oxy group such as a (5—N-methylamido-3-pyridyl)oxy group, or the like.

Other more particular embodiments of the compounds of the invention having the general structure shown in I above are provided. Such compounds form a sixth group of compounds for which:

$Z^1$, $Z^2$, $Z^3$, and $Z^4$ are independently selected from C or N; $R^1$ is selected from —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^2$ is selected from —F, —Cl, —Br, —C≡N, —CO$_2$H, —OH, substituted and unsubstituted guanidinyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted arylalkoxy groups, substituted and unsubstituted aryloxy groups, substituted and unsubstituted heterocyclyloxy, and substituted and unsubstituted heterocyclylalkoxy groups; or $R^2$ and $R^3$ are a group of formula —OCH$_2$O— such that $R^2$ and $R^3$ define a fused 5-membered ring that includes 2 oxygen atoms;

$R^3$ is selected from —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)N(H)-alkyl-heterocyclyl groups, substituted and unsubstituted (alkyl)(alkyl)aminoalkyl groups, substituted and unsubstituted (alkyl)(aryl) aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^4$ is —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)

aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^5$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;

$R^9$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is selected from the group consisting of —H, and substituted and unsubstituted alkyl groups.

In some embodiments, $R^{10}$ is —H. In other embodiments, $R^{10}$ is an unsubstituted alkyl group having from 1 to 6 carbon atoms such as a methyl, ethyl, propyl, i-propyl group, or the like. In some such embodiments, $R^{10}$ is a —CH$_3$ group.

In one embodiment of the sixth group of compounds, each of $Z^1$, $Z^2$, $Z^3$, and $Z^4$ are C.

In another embodiment of the sixth group of compounds, $Z^1$ is N and each of $Z^2$, $Z^3$, and $Z^4$ are C.

In another embodiment of the sixth group of compounds, $Z^1$ and $Z^3$ are both N and $Z^2$ and $Z^4$ are both C.

In another embodiment of the sixth group of compounds, $Z^3$ is N and each of $Z^1$, $Z^2$, and $Z^4$ are C.

In another embodiment of the sixth group of compounds, $Z^1$-$Z^4$ have any of the values in previous embodiments, and $R^1$ is selected from —H, —F, —Cl, and —Br.

In another embodiment of the sixth group of compounds, $Z^1$-$Z^4$ have any of the values in previous embodiments, and $R^1$ is a substituted and unsubstituted heterocyclylamino group. In some such embodiments, $R^1$ is a substituted and unsubstituted heteroarylamino groups. In some embodiments, $R^1$ is a substituted and unsubstituted heterocyclylamino group such as, but not limited to, substituted and unsubstituted pyrroldinylalkylamino groups and the like, such as, but not limited to, substituted and unsubstituted pyrrolidinylmethylamino groups and the like.

In another embodiment of the sixth group of compounds, $Z^1$-$Z^4$ and $R^1$ have any of the values in previous embodiments, and $R^2$ is an unsubstituted alkoxy group having from 1 to 4 carbon atoms.

In another embodiment of the sixth group of compounds, $Z^1$-$Z^4$ and $R^1$ have any of the values in previous embodiments, and $R^2$ is a —OMe, —OEt, —O-i-Pr, or —OCH$_2$CH(CH$_3$)$_2$ group.

In another embodiment of the sixth group of compounds, $Z^1$-$Z^4$ and $R^1$ have any of the values in previous embodiments, and $R^2$ is a substituted or unsubstituted arylalkoxy, a substituted or unsubstituted aryloxy group, or a substituted or unsubstituted heterocyclyloxy group.

In another embodiment of the sixth group of compounds, $Z^1$-$Z^4$ and $R^1$ have any of the values in previous embodiments, and $R^2$ is a substituted or unsubstituted benzyloxy group, a substituted or unsubstituted phenoxy group, or a substituted or unsubstituted pyridyloxy group.

In another embodiment of the sixth group of compounds, $Z^1$-$Z^4$ and $R^1$ have any of the values in previous embodiments, and $R^2$ is a substituted or unsubstituted —N(H)C(=O)—N(H)-alkyl-aryl group such as, but not limited to, a —N(H)C (═O)—N(H)—CH$_2$-aryl group, a —N(H)C(═O)—N(H)—CH$_2$CH$_2$-aryl group, or the like such as a —N(H)C(═O)—N(H)—CH$_2$-phenyl group, or a —N(H)C(═O)—N(H)—CH$_2$CH$_2$-phenyl group, or the like.

In another embodiment of the sixth group of compounds, $Z^1$-$Z^4$ and $R^1$ have any of the values in previous embodiments, and $R^2$ and $R^3$ are a group of formula —OCH$_2$O— such that $R^2$ and $R^3$ define a fused 5-membered ring that includes 2 oxygen atoms.

In another embodiment of the sixth group of compounds, $Z^1$-$Z^4$, $R^1$, and $R^2$ have any of the values in previous embodiments, and $R^3$ is selected from —H, —F, —Cl, and —OMe.

In another embodiment of the sixth group of compounds, $Z^1$-$Z^4$, $R^1$, and $R^2$ have any of the values in previous embodiments, and $R^3$ is —H.

In another embodiment of the sixth group of compounds, $Z^1$-$Z^4$, $R^1$, and $R^2$ have any of the values in previous embodiments, and $R^3$ is selected from the group consisting of —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —N(H)C(═O)N(H)-alkyl groups, substituted and unsubstituted —N(H)C(═O)N(H)-aryl groups and substituted and unsubstituted —C(═O)N(H)-alkyl-heterocyclyl groups; or $R^2$ and $R^3$ are a group of formula —OCH$_2$O— such that $R^2$ and $R^3$ define a fused 5-membered ring that includes 2 oxygen atoms.

In another embodiment of the sixth group of compounds, $Z^1$-$Z^4$, $R^1$, and $R^2$ have any of the values in previous embodiments, and $R^3$ is selected from the group consisting of substituted and unsubstituted —N(H)C(═O)N(H)-alkyl groups, and substituted and unsubstituted —N(H)C(═O)N(H)-aryl groups. In some such embodiments, $R^3$ is a substituted or unsubstituted —N(H)C(═O)N(H)CH$_2$CH$_3$ group, a substituted or unsubstituted —N(H)C(═O)N(H)CH(CH$_3$)$_2$ group, a substituted or unsubstituted —N(H)C(═O)N(H)C(CH$_3$)$_3$ group, or a substituted or unsubstituted —N(H)C(═O)N(H)-aryl group or the like. In some such embodiments, $R^3$ is a substituted or unsubstituted —N(H)C(═O)N(H)-aryl group such as, but not limited to, a —N(H)C(═O)N(H)-(2-methoxyphenyl) group, a-N(H)C(═O)N(H)-(3-trifluoromethylphenyl) group, or the like.

In another embodiment of the sixth group of compounds, $Z^1$-$Z^4$, $R^1$, and $R^2$ have any of the values in previous embodiments, and $R^3$ is a substituted amino group selected from substituted or unsubstituted arylalkylamino groups such as, but not limited to, phenylalkylamino groups, (halo)(alkoxy) arylalkylamino groups, such as, but not limited to 2-fluoro-5-methoxyphenylmethylamino groups, monoalkoxyarylalkylamino groups, dialkoxyarylalkylamino groups, and the like, such as, but not limited to, 2,5-dialkoxyarylalkylamino groups and the like such as, but not limited to 2,5-dialkoxyarylmethylamino groups, substituted and unsubstituted arylalkoxyarylalkylamino groups such as, but not limited to substituted and unsubstituted arylalkoxyarylmethylamino groups and the like, such as, but not limited to, substituted and unsubstituted arylmethoxyarylmethylamino groups and the like, such as, but not limited to substituted and unsubstituted fluoroarylmethoxyarylmethylamino groups and the like, such as, but not limited to, substituted and unsubstituted 4-fluorophenylmethoxyphenyl-methylamino groups and the like; substituted and unsubstituted heterocyclylalkylamino groups including heteroarylalkylamino groups such as, but not limited to substituted and unsubstituted thiazolylalkylamino groups, benzimidazolylalkylamino groups such as, but not limited to N-methylbenzimidazolylalkylamino groups and the like, imidazolylalkylamino groups such as, but not limited to phenylimidazolylalkylamino groups, ethylmethylimidazolylalkylamino groups, and the like, substituted and unsubstituted quinolinylalkylamino groups, such as, but not limited to substituted and unsubstituted quinolinylmethylamino groups and the like, such as, but not limited to alkoxyquinolinylmethylamino groups and the like, such as, but not limited to substituted and unsubstituted 4-alkoxy-2-quinolinylmethylamino groups and the like, and furanylalkylamino groups, and the like.

In another embodiment of the sixth group of compounds, $Z^1$-$Z^4$, $R^1$, and $R^2$ have any of the values in previous embodiments, and $R^3$ is —F.

In another embodiment of the sixth group of compounds, $Z^1$-$Z^4$, $R^1$, and $R^2$ have any of the values in previous embodiments, and $R^3$ is —Cl.

In another embodiment of the sixth group of compounds, $Z^1$-$Z^4$, $R^1$, and $R^2$ have any of the values in previous embodiments, and $R^3$ is —OMe.

In another embodiment of the sixth group of compounds, $Z^1$-$Z^4$, $R^1$, and $R^2$ have any of the values in previous embodiments, and $R^3$ is a substituted and unsubstituted —C(═O)N(H)-alkyl-heterocyclyl groups where the heterocyclyl group of the —C(═O)N(H)-alkyl-heterocyclyl groups is selected from the group consisting of morpholinyl, piperazinyl, and piperidinyl groups.

In another embodiment of the sixth group of compounds, $Z^2$-$Z^4$, $R^1$, $R^2$, and $R^3$ have any of the values in previous embodiments, $Z^1$ is C, and $R^5$ is H. In some such embodiments, $R^8$ is also H.

In another embodiment of the sixth group of compounds, $Z^2$-$Z^4$, $R^1$, $R^2$, and $R^3$ have any of the values in previous embodiments, $Z^1$ is C, and $R^5$ is —CH$_3$.

In another embodiment of the sixth group of compounds, $Z^2$-$Z^4$, $R^1$, $R^2$, and $R^3$ have any of the values in previous embodiments, $Z^1$ is C, and $R^5$ is morpholine.

In another embodiment of the sixth group of compounds, $Z^1$-$Z^3$, $R^1$, $R^2$, and $R^3$ have any of the values in previous embodiments, $Z^4$ is C, and $R^8$ is H.

In another embodiment of the sixth group of compounds, $Z^1$-$Z^3$, $R^1$, $R^2$, and $R^3$ have any of the values in previous embodiments, $Z^4$ is C, and $^8$ is —CH$_3$.

In another embodiment of the sixth group of compounds, $Z^1$-$Z^3$, $R^1$, $R^2$, and $R^3$ have any of the values in previous embodiments, $Z^4$ is C, and $R^8$ is morpholine.

In another embodiment of the sixth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from a first group; or $Z^1$, $Z^2$, $Z^4$, $R^1$, $R^2$, $R^3$, $R^5$, and $R^8$ have any of the values in previous embodiments, $Z^3$ is C, and $R^7$ is selected from the first group, the first group comprising members selected from the group consisting of —Br, —CO$_2$H, substituted and unsubstituted heterocyclylalkoxy groups, substituted and unsubstituted arylalkoxy groups, substituted and unsubstituted alkoxyalkoxy groups, substituted and unsubstituted heterocyclylheterocyclyl groups, substituted and unsubstituted arylheterocyclyl groups, substituted and unsubstituted cycloalkylheterocyclyl groups, substituted and unsubstituted heterocyclyloxy groups, substituted and unsubstituted aryloxy groups, substituted and unsubstituted (alkyl)(heterocyclyl)amino groups, substituted and unsubstituted heterocyclylalkylamino groups, substituted and unsubstituted arylalkylamino groups, substituted and unsubstituted heterocyclylamino groups, substituted and unsubstituted —C(═O)N(H)-aryl groups, substituted and unsubstituted —C(═O)N(H)-heterocyclyl groups, substituted and unsubstituted —C(═O)N(alkyl)(heterocyclyl) groups, and substituted and unsubstituted —C(=O)-heterocyclyl groups. In some such embodiments, $R^3$ is selected from the group consisting of —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, and substituted and unsubstituted —C(=O)N(H)-alkyl-heterocyclyl groups; or $R^2$ and $R^3$ are a group of formula —OCH$_2$O— such that $R^2$ and $R^3$ define a fused 5-membered ring that includes 2 oxygen atoms. In another embodiments of the sixth group of compounds, at least one of $Z^2$ or $Z^3$ is C and at least one of $R^6$ or $R^7$ is selected from the group consisting of substituted and unsubstituted piperidinyl substituted heterocyclyl groups, substituted and unsubstituted heterocyclyl substituted piperidinyl groups, substituted and unsubstituted hydroxymethyl substituted piperidinyl groups, dimethylaminoalkyl substituted pyrrolidinyl groups, substituted and unsubstituted 3-alkyl substituted piperazinyl groups, substituted and unsubstituted 3,5-dialkyl substituted piperazinyl groups, substituted and unsubstituted N-hydroxyalkyl substituted piperazinyl groups, substituted and unsubstituted N-alkyl substituted 1,4-diazacycloheptyl groups, substituted and unsubstituted N-ethylpiperazinyl groups, substituted and unsubstituted N-isopropylpiperazinyl groups, substituted and unsubstituted N-sec-butylpiperazinyl groups, unsubstituted piperazinyl groups, substituted and unsubstituted N-2-pyridyl substituted piperazinyl groups, substituted and unsubstituted N-3-pyridyl substituted piperazinyl groups, substituted and unsubstituted N-4-pyridyl substituted piperazinyl groups, substituted and unsubstituted N(H)—CH$_2$-pyridyl groups, substituted and unsubstituted imidazolyl groups, substituted and unsubstituted morpholinyl groups, substituted and unsubstituted 3-alkyl substituted morpholinyl groups, substituted and unsubstituted 3,5-dialkyl substituted morpholinyl groups, dialkylamino substituted pyrrolidinyl groups, pyrrolidinyl groups substituted with both dialkylamino and alkyl groups, substituted and unsubstituted 4-hydroxy substituted piperidinyl groups, substituted and unsubstituted 4-aryl substituted piperidinyl groups, substituted and unsubstituted 4-hydroxy-4-phenyl substituted piperidinyl groups, substituted and unsubstituted cyclohexylpiperazinyl groups, substituted and unsubstituted cyclopentylpiperazinyl groups, substituted and unsubstituted N-alkyl substituted diazabicycloalkane groups, substituted and unsubstituted —N(CH$_3$)(N-alkyl(4-piperidinyl)) groups, substituted and unsubstituted piperazinyl groups further substituted with a —C(=O)-alkyl group on one of the N atoms of the piperazinyl group, substituted and unsubstituted —N(H)CH$_2$CH$_2$CH$_2$-imidazolyl groups, substituted and unsubstituted —N(H)CH$_2$CH$_2$CH$_2$-pyrrolidinyl groups, substituted and unsubstituted —N(H)CH$_2$CH$_2$CH$_2$-morpholinyl groups, substituted and unsubstituted —N(H)CH$_2$CH$_2$CH$_2$-piperazinyl groups, substituted and unsubstituted —N(H)CH$_2$CH$_2$CH$_2$-piperidinyl groups, substituted and unsubstituted —N(H)CH$_2$CH$_2$CH$_2$-pyridyl groups, substituted and unsubstituted —N(H)CH$_2$CH$_2$-imidazolyl groups, substituted and unsubstituted —N(H)CH$_2$CH$_2$-pyrrolidinyl groups, substituted and unsubstituted —N(H)CH$_2$CH$_2$-morpholinyl groups, substituted and unsubstituted —N(H)CH$_2$CH$_2$-piperazinyl groups, substituted and unsubstituted —N(H)CH$_2$CH$_2$-piperidinyl groups, substituted and unsubstituted —N(H)CH$_2$CH$_2$-pyridyl groups, substituted and unsubstituted 1-aza4-oxacycloheptane groups, and substituted and unsubstituted 1,4-diazacycloheptane groups. In other embodiments, at least one of $R^6$ or $R^7$ is selected from the group consisting of piperidinyl substituted piperidinyl groups such as 4-piperidinylpiperidinyl groups or the like, 4-hydroxymethylpiperidinyl groups, 3-dimethylaminomethylpyrrolidinyl groups, 3-alkyl substituted piperazinyl groups, 3,5-dialkyl substituted piperazinyl groups, N-hydroxyethylpiperazinyl groups, N-hydroxymethylpiperazinyl groups, N-hydroxypropylpiperazinyl groups, N-methyl substituted 1,4-diazacycloheptyl groups, N-ethylpiperazinyl groups, N-isopropylpiperazinyl groups, N-sec-butylpiperazinyl groups, unsubstituted piperazinyl groups, N-(2-pyridyl)piperazinyl groups, N-(3-pyridyl)piperazinyl groups, N-(4-pyridyl)piperazinyl groups, N(H)—CH$_2$-pyridyl groups, imidazolyl groups, unsubstituted morpholinyl groups, 3-alkylmorpholinyl groups, 3,5-dialkylmorpholinyl groups, 2-dimethylaminopyrrolidinyl groups, 2-methyl-4-dialkylaminopyrroldinyl groups, 4-hydroxypiperidinyl groups, 4-arylpiperidinyl groups, 4-hydroxy-4-phenylpiperidinyl groups, cyclohexylpiperazinyl groups, cyclopentylpiperazinyl groups, N-methyl substituted diazabicycloalkane groups, —N(CH$_3$)(N-alkyl(4-piperidinyl)) groups, piperazinyl groups further substituted with a —C(=O)-methyl group on one of the N atoms of the piperazinyl group, —N(H)CH$_2$CH$_2$CH$_2$-imidazolyl groups, —N(H)CH$_2$CH$_2$CH$_2$-pyrrolidinyl groups, —N(H)CH$_2$CH$_2$CH$_2$-morpholinyl groups, —N(H)CH$_2$CH$_2$CH$_2$-piperazinyl groups, —N(H)CH$_2$CH$_2$CH$_2$-piperidinyl groups, and —N(H)CH$_2$CH$_2$CH$_2$-pyridyl groups. In some such embodiments, at least one of $R^6$ or $R^7$ is selected from the group consisting of 4-piperidinylpiperidinyl groups, 4-hydroxymethylpiperidinyl groups, 3-dimethylaminomethylpyrrolidinyl groups, 3,5-dimethyl substituted piperazinyl groups, N-methyl substituted 1,4-diazacycloheptyl groups, N-(2-pyridyl)piperazinyl groups, N(H)—CH$_2$-(4-pyridyl) groups, imidazolyl groups, unsubstituted morpholinyl groups, 3-methylmorpholinyl groups, 3,5-dimethylmorpholinyl groups, 2-dimethylaminopyrrolidinyl groups, 2-methyl-4-dimethylaminopyrroldinyl groups, 4-hydroxy4-phenylpiperidinyl groups, cyclohexylpiperazinyl groups, N-methyl substituted diazabicycloalkane groups, —N(CH$_3$)(N-methyl(4-piperidinyl)) groups, piperazinyl groups further substituted with a —C(=O)-methyl group on one of the N atoms of the piperazinyl group, —N(H)CH$_2$CH$_2$CH$_2$-imidazolyl groups, —N(H)CH$_2$CH$_2$CH$_2$-pyrrolidinyl groups, —N(H)CH$_2$CH$_2$CH$_2$-morpholinyl groups, —N(H)CH$_2$CH$_2$CH$_2$-piperazinyl groups, —N(H)CH$_2$CH$_2$CH$_2$-piperidinyl groups, and —N(H)CH$_2$CH$_2$CH$_2$-pyridyl groups.

In another embodiment of the sixth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is selected from —Br, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, substituted and unsubstituted —C(=O)-heterocyclyl groups, substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other embodiments, $R^6$ has the values described in the preceding sentence and $R^7$ is —H.

In another embodiment of the sixth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkoxy group having from 1-6 carbon atoms. In still other such embodiments, $R^6$ is a methoxy group. In still other embodiments of the sixth group of compounds where $R^6$ is an alkoxy group having from 1-6 carbon atoms such as a methoxy group, $R^7$ is —H.

In another embodiment of the sixth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is an alkyl group having from 1-6 carbon atoms. In still other such embodiments, $R^6$ is a methyl group. In still other embodiments of the sixth group of compounds where $R^6$ is an alkyl group having from 1-6 carbon atoms such as a methyl group, $R^7$ is —H.

In another embodiment of the sixth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted alkoxy group having the formula $OCH_2(CH_2)_mR^{11}$ where m is an integer selected from 0, 1, or 2 and $R^{11}$ is selected from substituted and unsubstituted alkoxy groups, substituted and unsubstituted aryl groups, and substituted and unsubstituted heterocyclyl groups. In still other such embodiments, $R^{11}$ is selected from substituted alkoxy groups such as, but not limited to methoxy groups, ethoxy groups, propoxy groups, and the like. In still other such embodiments, $R^{11}$ is selected from substituted and unsubstituted heterocyclyl groups selected from pyrrolidinyl groups, pyridyl groups, morpholinyl groups, piperazinyl groups, and piperidinyl groups. In still other embodiments where $R^6$ is a substituted alkoxy group having the formula $—OCH_2(CH_2)_mR^{11}$, $R^7$ is —H. In still other embodiments, $R^6$ is a pyrrolidinylalkoxy groups, such as but not limited to, a pyrrolidinylpropoxy group or the like; an alkoxyethoxy group such as, but not limited to, a methoxyethoxy group or the like; or a substituted or unsubstituted pyridinylalkoxy group such as, but not limited to, (3-pyridinyl)methoxy groups, or the like.

In another embodiment of the sixth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula $—N(R^{12})(CH_2)_pR^{13}$ where p is an integer selected from 0, 1, 2, or 3, $R^{13}$ is selected from substituted and unsubstituted alkoxy groups, substituted and unsubstituted amino groups, substituted and unsubstituted aryl groups, and substituted and unsubstituted heterocyclyl groups, and $R^{12}$ is selected from —H or substituted and unsubstituted alkyl groups such as, but not limited to, methyl, ethyl, propyl, and isopropyl. In some such embodiments, $R^{13}$ is selected from substituted amino groups such as alkylamino groups and dialkylamino groups, such as, but not limited to, dimethylamino, diethylamino, dipropylamino, (methyl)(ethyl)amino, (ethyl)(propyl)amino, (methyl)(propyl)amino groups, and the like. In some such embodiments, $R^{12}$ is a $CH_3$ group. In still other such embodiments, $R^{13}$ is selected from substituted alkoxy groups. In still other such embodiments, $R^{13}$ is selected from substituted and unsubstituted heterocyclyl groups such as those selected from pyrrolidinyl groups, pyrazolyl groups, pyridyl groups, morpholinyl groups, piperazinyl groups, piperidinyl groups, and the like. In some embodiments, $R^6$ is selected from —N(H)(3-piperidinyl) groups, —N(H)(4-piperidinyl) groups, —N(H)(4-(2-methoxymethylpyrrolidinyl)) groups, —N(CH₃)(4-(1-methylpiperidinyl)) groups, —N(H)CH₂(2-pyridyl) groups, —N(H)CH₂(3-pyridyl) groups, —N(H)CH₂(4-pyridyl) groups, —N(H)CH₂CH₂(2-pyridyl) groups, —N(H)CH₂CH₂(3-pyridyl) groups, —N(H)CH₂CH₂(4-pyridyl) groups, —N(CH₃)CH₂CH₂(2-pyridyl) groups —N(H)CH₂CH₂(4-piperidinyl) groups, —N(H)CH₂CH₂(4-morpholinyl) groups, —N(H)CH₂CH₂CH₂(1-imidazolyl) groups, —N(H)CH₂CH₂CH₂(1-(4-methylpiperazinyl)) groups, —N(H)CH₂CH₂CH₂(4-morpholinyl) groups, —N(H)CH₂CH₂CH₂(1-imidazolyl) groups, —N(H)CH₂CH₂CH₂(1-pyrrolidinyl) groups, —N(CH₃)CH₂CH₂CH₂(diethylamino) groups, and the like.

In still other embodiments of the sixth group of compounds where $R^6$ is a substituted amino group having the formula $—N(R^{12})(CH_2)_pR^{13}$, $R^7$ is —H.

In another embodiment of the sixth group of compounds, $Z^1$, $Z^3$, $Z^4$, $R^1$, $R^2$, $R^3$, $R^5$, and $R^8$ have any of the values in previous embodiments, $Z^2$ is C, and $R^6$ is a substituted amino group having the formula $—N(R^{12})(CH_2)_pR^{13}$ or the formula $—N(R^{12})C(H)(alkyl)((CH_2)_pR^{13})$ where p is an integer selected from 0, 1, 2, or 3, $R^{13}$ is selected from a methyl group, substituted and unsubstituted alkoxy groups, substituted and unsubstituted amino groups such as —N(H)(alkyl) groups, —N(alkyl)₂ groups and the like, substituted and unsubstituted aryl groups, and substituted and unsubstituted heterocyclyl groups, and $R^{12}$ is selected from —H; substituted and unsubstituted alkyl groups such as, but not limited to, methyl, ethyl, propyl, and isopropyl groups; —C(=O)-alkyl groups such as —C(=O)—CH₃ groups and the like; —C(=O)-alkyl-N(H)(alkyl) groups such as —C(=O)—CH₂—N(H)(alkyl) groups and the like; —C(=O)-alkyl-N(alkyl)₂ groups such as —C(=O)—CH₂—N(alkyl)₂ groups and the like; —C(=O)-alkyl-N($R^{12a'}$)($R^{12b'}$) groups such as —C(=O)—CH₂—N(alkyl)₂ groups and the like —C(=O)-alkyl-heterocyclyl groups such as —C(=O)—CH₂-heterocyclyl groups and the like such as —C(=O)—CH₂-(1-piperazinyl) groups and the like; —C(=O)-heterocyclyl groups; —C(=O)-aryl groups; —C(=O)-alkyl-O-alkyl groups such as —C(=O)—CH₂—O-alkyl groups; —C(=O)-alkyl-S-alkyl groups such as —C(=O)—CH₂—S-alkyl groups and the like; and the like where $R^{12a'}$ is selected from —H, and substituted and unsubstituted alkyl groups, and $R^{12b'}$ is selected from —H, —SO₂-alkyl, —SO₂-aryl, —C(=O)-alkyl, —C(=O)-aryl, heterocyclyl groups such as 2-pyridyl groups and the like, heterocyclylalkyl groups, arylalkyl groups, alkyl groups, and —C(=O)-alkyl-halogen groups.

In another embodiment of the sixth group of compounds, $Z^1$, $Z^3$, $Z^4$, $R^1$, $R^2$, $R^3$, $R^5$, and $R^8$ have any of the values defined in the previous embodiments, $Z^2$ is C, and $R^6$ is a substituted or unsubstituted heterocyclyl group. In some embodiments of the sixth group of compounds where $R^6$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted pyrazolyl groups, substituted and unsubstituted pyrrolyl groups, substituted and unsubstituted imidazolyl groups, substituted and unsubstituted 1-aza4-oxacycloheptane groups, substituted and unsubstituted 1,4-diazacycloheptane groups, substituted and unsubstituted 2,5-diazabicyclo[2.2.1]heptane groups, substituted and unsubstituted 1,4-diazabicyclo[2.2.2]octane groups, substituted or unsubstituted 1,4-diazabicyclo[4.3.0]nonane group, and substituted or unsubstituted 1,4-diazacycloheptane groups. In still other embodiments of the sixth group of compounds where $R^6$ is a heterocyclyl group, the heterocyclyl group is an unsubstituted morpholine group; a dialkyl substituted morpholinyl group such as, but not limited to, a dimethyl substituted morpholinyl group, and the like, such as, but not limited to, a 3,5-dimethyl substituted morpholinyl group; a hydroxy substituted morpholinyl group; a hydroxyalkyl substituted morpholinyl group; an aryl substituted morpholinyl group; an aminoalkyl substituted morpholinyl group including dialkylaminoalkyl substituted morpholinyl groups such as, but not limited to, dimethylaminomethyl substituted morpholinyl groups and the like such as, but not limited to, a morpholinyl group that is substituted on a ring carbon bonded to the ring O atom with a dimethylaminomethyl group and is substituted with a methyl group on the carbon bonded to the ring N atom which carbon is not bonded to the carbon bearing the dimethylaminomethyl group and the like; a heterocyclyl substituted morpholinyl group; an unsubstituted piperazine group; a dialkyl substituted piperazinyl group such as, but not limited to, a dimethyl substituted piperazinyl group, and the like such as a 3,5-dimethyl substituted piperazinyl group and the like; a monoalkyl substituted piperazinyl group such as a 3-alkyl substituted piperazinyl group, an N-alkyl substituted piperazinyl group, and the like such as, but not limited to, a 3-methyl substituted piperazinyl group, a N-alkyl substituted piperazinyl group, such as, but not limited to, N-methyl, N-ethyl, N-isopropyl substituted piperazinyl groups and the like; a hydroxyalkyl substituted piperazinyl group such as, but not limited to, hydroxyethyl and hydroxymethyl substituted piperazinyl groups and the like such as, but not limited to, N-hydroxyethyl substituted piperazinyl groups and the like; an aryl substituted piperazinyl group; a heterocyclyl substituted piperazinyl group such as, but not limited to, 2-, 3-, and 4-(2-, 3-, and 4-piperidinyl) substituted piperazinyl groups and 2-, 3-, and 4-(2-, 3-, and 4-pyridyl) substituted piperazinyl groups and the like; a —CH$_2$C(=O)O-alkyl substituted piperazinyl group; a —C(=O)-alkyl substituted piperazinyl group such as, but not limited to, a —C(=O)-ethyl or a —C(=O)-methyl substituted piperazinyl group, and the like such as a piperazinyl group where the —C(=O)-ethyl or the —C(=O)-methyl substitution is on one of the piperazinyl N atoms and the other N atom is bonded to $Z^2$, and the like; a —C(=O)O-alkyl substituted piperazinyl group such as, but not limited to, a —C(=O)—O-ethyl or a —C(=O)—O-methyl substituted piperazinyl group, and the like such as a piperazinyl group where the —C(=O)—O-ethyl or the —C(=O)—O-methyl substitution is on one of the piperazinyl N atoms and the other N atom is bonded to $Z^2$, and the like; a cycloalkyl substituted piperazinyl group such as, but not limited to, a cyclohexyl and cyclopentyl substituted piperazinyl group and the like such as, but not limited to, a N-cyclohexyl substituted piperazinyl group and the like; an unsubstituted piperidine group; an alkyl substituted piperidinyl group such as, but not limited to, 2-, 3-, and 4-alkyl substituted piperidinyl groups, and the like such as, but not limited to, 2-, 3-, and 4-hydroxyalkyl substituted piperidinyl groups and the like such as, but not limited to, 2-, 3-, and 4-hydroxymethyl substituted piperidinyl groups and the like; a hydroxy substituted piperidinyl group such as 2-, 3-, and 4-hydroxy substituted piperidinyl groups; a hydroxyalkyl substituted piperidinyl group; an aryl substituted piperidinyl group such as, but not limited to, a 4-aryl substituted piperidinyl group and the like such as, but not limited to, a piperidinyl group that is substituted in the 4 position with both an aryl group and a hydroxy group and the like such as, but not limited to, a piperidinyl group that is substituted in the 4 position with both a hydroxy group and a phenyl group; a cycloalkyl substituted piperidinyl group; a heterocyclyl substituted piperidinyl group such as, but not limited to, a piperidinyl substituted piperidinyl group and the like such as, but not limited to, 4-piperidinyl substituted piperidinyl groups, 4-(2(3H)-benzimidazolone) substituted piperidinyl group, and the like; an unsubstituted pyrrolidinyl group; an alkyl substituted pyrrolidinyl group such as, but not limited to, a methyl substituted pyrrolidinyl group, a heterocyclylalkyl substituted pyrrolidinyl group, and the like such as, but not limited to, a 2-methyl substituted pyrrolidinyl group, a 2-pyrrolidinylmethyl substituted pyrrolidinyl group, and the like; an amino substituted pyrrolidinyl group such as, but not limited to, a dialkylamino substituted pyrrolidinyl group such as, but not limited to, 2- and 3-dialkylamino substituted pyrrolidinyl groups and the like such as, but not limited to, 2- and 3-substituted N,N-dimethylamino substituted pyrrolidinyl groups and the like such as, but not limited to, a pyrrolidinyl group that is substituted with both an alkyl group and an N,N-dimethylamino group and the like such as, but not limited to, a pyrrolidinyl group that is substituted with a methyl group in the 2 position and with a N,N-dimethylamino group in the 4 position; a hydroxy substituted pyrrolidinyl group such as, but not limited to, 2- and 3-hydroxy substituted pyrrolidinyl groups; a heterocyclylalkyl substituted pyrrolidinyl group; substituted and unsubstituted pyrrolyl groups; substituted and unsubstituted 2,5-diazabicyclo[2.2.1]heptane groups; an alkyl substituted 2,5-diazabicyclo[2.2.1]heptane group such as, but not limited to, a N-methyl substituted 2,5-diazabicyclo[2.2.1]heptane group and the like; a substituted or unsubstituted 1,4-diazabicyclo[4.3.0]nonane group; and a substituted or unsubstituted 1,4-diazacycloheptane group such as, but not limited to, an alkyl substituted 1,4-diazacycloheptane group and the like, such as, but not limited to, an N-alkyl substituted 1,4-diazacycloheptane substituted group and the like such as, but not limited to, a N-methyl substituted 1,4-diazacycloheptane group and the like. In still other embodiments of the sixth group of compounds where $R^6$ is a substituted or unsubstituted heterocyclyl group, $R^7$ is —H.

In another embodiment of the sixth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is selected from substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, substituted and unsubstituted —C(=O)-heterocyclyl groups, substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups and substituted and unsubstituted cycloalkylheterocyclyl groups; substituted and unsubstituted heterocyclyloxy groups, substituted and unsubstituted aryloxy groups, and substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups. In still other such embodiments, $R^7$ has the values described in the preceding sentence and $R^6$ is —H.

In another embodiment of the sixth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkoxy group having from 1-6 carbon atoms. In still other such embodiments, $R^7$ is a methoxy group. In still other embodiments of the sixth group of compounds where $R^7$ is an alkoxy group having from 1-6 carbon atoms such as a methoxy group, $R^6$ is —H.

In another embodiment of the sixth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is an alkyl group having from 1-6 carbon atoms. In still other such embodiments, $R^7$ is a methyl group. In still other embodiments of the sixth group of compounds where $R^7$ is an alkyl group having from 1-6 carbon atoms such as a methyl group, $R^6$ is —H.

In another embodiment of the sixth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted alkoxy group having the formula —OCH$_2$(CH$_2$)$_n$R$^{14}$ where n is an integer selected from 0, 1, or 2 and $R^{14}$ is selected from substituted and unsubstituted alkoxy groups, substituted and unsubstituted aryl groups, and substituted and unsubstituted heterocyclyl groups. In some embodiments, $R^{14}$ is selected from substituted alkoxy groups such as, but not limited to, methoxy groups, ethoxy groups, propoxy groups, and the like. In still other such embodiments, $R^{14}$ is selected from substituted and unsubstituted heterocyclyl groups selected from pyrrolidinyl groups, pyridyl groups, morpholinyl groups, piperazinyl groups, and piperidinyl groups. In still other embodiments of the sixth group of compounds where $R^7$ is a substituted alkoxy group having the formula OCH$_2$(CH$_2$)$_n$R$^{14}$, $R^6$ is —H. In still other embodiments, $R^7$ is a pyrrolidinylalkoxy groups, such as but not limited to, a pyrrolidinylpropoxy group or the like; an alkoxyethoxy group such as, but not limited to, a methoxyethoxy group or the like; or a substituted or unsubstituted pyridinylalkoxy group such as, but not limited to, (3-pyridinyl)methoxy groups, or the like.

In another embodiment of the sixth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted amino group having the formula —N(R$^{15}$)(CH$_2$)$_q$R$^{16}$ where q is an integer selected from 0, 1, 2, or 3 and $R^{16}$ is selected from substituted and unsubstituted alkoxy groups, substituted and unsubstituted amino groups, substituted and unsubstituted aryl groups, and substituted and unsubstituted heterocyclyl groups, and $R^{15}$ is —H or a substituted or unsubstituted alkyl groups, such as, but not limited to, methyl, ethyl, propyl, and isopropyl groups. In some such embodiments, $R^{16}$ is selected from substituted amino groups such as alkylamino groups and dialkylamino groups, such as, but not limited to, dimethylamino, diethylamino, dipropylamino, (methyl)(ethyl)amino, (ethyl)(propyl)amino, (methyl)(propyl)amino groups, and the like. In some such embodiments, $R^{15}$ is a CH$_3$ group. In still other such embodiments, $R^{16}$ is selected from substituted alkoxy groups. In still other such embodiments, $R^{16}$ is selected from substituted and unsubstituted heterocyclyl groups such as those selected from pyrrolidinyl groups, pyrazolyl groups, pyridyl groups, morpholinyl groups, piperazinyl groups, piperidinyl groups, and the like. In some embodiments, $R^7$ is selected from —N(H)(3-piperidinyl) groups, —N(H)(4-piperidinyl) groups, —N(H)(4-(2-methoxymethylpyrrolidinyl)) groups, —N(CH$_3$)(4-(1-methylpiperidinyl)) groups, —N(H)CH$_2$(2-pyridyl) groups, —N(H)CH$_2$(3-pyridyl) groups, —N(H)CH$_2$(4-pyridyl) groups, —N(H) CH$_2$CH$_2$(2-pyridyl) groups, —N(H)CH$_2$CH$_2$(3-pyridyl) groups, —N(H)CH$_2$CH$_2$(4-pyridyl) groups, —N(CH$_3$) CH$_2$CH$_2$(2-pyridyl) groups —N(H)CH$_2$CH$_2$(4-piperidinyl) groups, —N(H)CH$_2$CH$_2$(4-morpholinyl) groups, —N(H) CH$_2$CH$_2$CH$_2$(1-imidazolyl) groups, —N(H)CH$_2$CH$_2$CH$_2$(1-(4-methylpiperazinyl)) groups, —N(H)CH$_2$CH$_2$CH$_2$(4-morpholinyl) groups, —N(H)CH$_2$CH$_2$CH$_2$(1-imidazolyl) groups, —N(H)CH$_2$CH$_2$CH$_2$(1-pyrrolidinyl) groups, —N(CH$_3$)CH$_2$CH$_2$CH$_2$(diethylamino) groups, and the like.

In still other embodiments of the sixth group of compounds where $R^7$ is a substituted amino group having the formula —N(R$^{15}$)(CH$_2$)$_q$R$^{16}$, $R^6$ is —H.

In another embodiment of the sixth group of compounds, $Z^1$, $Z^3$, $Z^4$, $R^1$, $R^2$, $R^3$, $R^5$, and $R^8$ have any of the values in previous embodiments, $Z^3$ is C, and $R^7$ is a substituted amino group having the formula —N(R$^{15}$)(CH$_2$)$_q$R$^{16}$ or the formula —N(R$^{15}$)C(H)(alkyl)((CH$_2$)$_q$R$^{16}$) where q is an integer selected from 0, 1, 2, or 3, $R^{16}$ is selected from a methyl group, substituted and unsubstituted alkoxy groups, substituted and unsubstituted amino groups such as —N(H)(alkyl) groups, —N(alkyl)$_2$ groups and the like, substituted and unsubstituted aryl groups, and substituted and unsubstituted heterocyclyl groups, and $R^{15}$ is selected from —H; substituted and unsubstituted alkyl groups such as, but not limited to, methyl, ethyl, propyl, and isopropyl groups; —C(=O)-alkyl groups such as —C(=O)—CH$_3$ groups and the like; —C(=O)-alkyl-N(H)(alkyl) groups such as —C(=O)—CH$_2$—N(H) (alkyl) groups and the like; —C(=O)-alkyl-N(alkyl)$_2$ groups such as —C(=O)—CH$_2$—N(alkyl)$_2$ groups and the like; —C(=O)-alkyl-N(R$^{15a'}$)(R$^{15b'}$) groups such as —C(=O)— CH$_2$—N(alkyl)$_2$ groups and the like —C(=O)-alkyl-heterocyclyl groups such as —C(=O)—CH$_2$-heterocyclyl groups and the like such as —C(=O)—CH$_2$-(1-piperazinyl) groups and the like; —C(=O)-heterocyclyl groups; —C(=O)-aryl groups; —C(=O)-alkyl-O-alkyl groups such as —C(=O)— CH$_2$—O-alkyl groups; —C(=O)-alkyl-S-alkyl groups such as —C(=O)—CH$_2$—S-alkyl groups and the like; and the like where $R^{15a'}$ is selected from —H, and substituted and unsubstituted alkyl groups, and $R^{15b'}$ is selected from —H, —SO$_2$-alkyl, —SO$_2$-aryl, —C(=O)-alkyl, —C(=O)-aryl, heterocyclyl groups such as 2-pyridyl groups and the like, heterocyclylalkyl groups, arylalkyl groups, alkyl groups, and —C(=O)-alkyl-halogen groups.

In another embodiment of the sixth group of compounds, $Z^1$, $Z^2$, $Z^4$, $R^1$, $R^2$, $R^3$, $R^5$, and $R^8$ have any of the values in previous embodiments, $Z^3$ is C, and $R^7$ is a substituted or unsubstituted heterocyclyl group. In some embodiments of the sixth group of compounds where $R^7$ is a heterocyclyl group, the heterocyclyl group is selected from substituted or unsubstituted pyrrolidinyl groups, substituted and unsubstituted pyridyl groups, substituted and unsubstituted morpholinyl groups, substituted and unsubstituted piperazinyl groups, substituted and unsubstituted piperidinyl groups, substituted and unsubstituted pyrazolyl groups, substituted and unsubstituted imidazolyl groups, substituted and unsubstituted 1-aza4-oxacycloheptane groups, substituted and unsubstituted pyrrolyl groups, substituted and unsubstituted 1,4-diazacycloheptane groups, substituted and unsubstituted 2,5-diazabicyclo[2.2.1]heptane groups, substituted and unsubstituted 1,4-diazabicyclo[2.2.2]octane groups, substituted or unsubstituted 1,4-diazabicyclo[4.3.0]nonane group, and substituted or unsubstituted 1,4-diazacycloheptane groups. In still other embodiments of the sixth group of compounds where $R^7$ is a heterocyclyl group, the heterocyclyl group is an unsubstituted morpholine group; a dialkyl substituted morpholinyl group such as, but not limited to, a dimethyl substituted morpholinyl group, and the like, such as, but not limited to, a 3,5-dimethyl substituted morpholinyl group; a hydroxy substituted morpholinyl group; a hydroxyalkyl substituted morpholinyl group; an aryl substituted morpholinyl group; an aminoalkyl substituted morpholinyl group including dialkylaminoalkyl substituted morpholinyl groups such as, but not limited to, dimethylaminomethyl substituted morpholinyl groups and the like such as, but not limited to, a morpholinyl group that is substituted on a ring carbon bonded to the ring O atom with a dimethylaminomethyl group and is substituted with a methyl group on the carbon bonded to the ring N atom which carbon is not bonded to the carbon bearing the dimethylaminomethyl group and the like; a heterocyclyl substituted morpholinyl group; an unsubstituted piperazine group; a dialkyl substituted piperazinyl group such as, but not limited to, a dimethyl substituted piperazinyl group, and the like such as a 3,5-dimethyl substituted piperazinyl group and the like; a monoalkyl substituted piperazinyl group such as a 3-alkyl substituted piperazinyl group, an N-alkyl substituted piperazinyl group, and the like such as, but not limited to, a 3-methyl substituted piperazinyl group, a N-alkyl substituted piperazinyl group, such as, but not limited to, N-methyl, N-ethyl, N-isopropyl substituted piperazinyl groups and the like; a hydroxyalkyl substituted piperazinyl group such as, but not limited to, hydroxyethyl and hydroxymethyl substituted piperazinyl groups and the like such as, but not limited to, N-hydroxyethyl substituted piperazinyl groups and the like; an aryl substituted piperazinyl group; a heterocyclyl substituted piperazinyl group such as, but not limited to, 2-, 3-, and 4-(2-, 3-, and 4-piperidinyl) substituted piperazinyl groups and 2-, 3-, and 4-(2-, 3-, and 4-pyridyl) substituted piperazinyl groups and the like; a —CH$_2$C(=O)O-alkyl substituted piperazinyl group; a —C(=O)-alkyl substituted piperazinyl group such as, but not limited to, a —C(=O)-ethyl or a —C(=O)-methyl substituted piperazinyl group, and the like such as a piperazinyl group where the —C(=O)-ethyl or the —C(=O)-methyl substitution is on one of the piperazinyl N atoms and the other N atom is bonded to $Z^3$, and the like; a —C(=O)O-alkyl substituted piperazinyl group such as, but not limited to, a —C(=O)—O-ethyl or a —C(=O)—O-methyl substituted piperazinyl group, and the like such as a piperazinyl group where the —C(=O)—O-ethyl or the —C(=O)—O-methyl substitution is on one of the piperazinyl N atoms and the other N atom is bonded to $Z^3$, and the like; a cycloalkyl substituted piperazinyl group such as, but not limited to, a cyclohexyl and cyclopentyl substituted piperazinyl group and the like such as, but not limited to, a N-cyclohexyl substituted piperazinyl group and the like; an unsubstituted piperidine group; an alkyl substituted piperidinyl group such as, but not limited to, 2-, 3-, and 4-alkyl substituted piperidinyl groups, and the like such as, but not limited to, 2-, 3-, and 4-hydroxyalkyl substituted piperidinyl groups and the like such as, but not limited to, 2-, 3-, and 4-hydroxymethyl substituted piperidinyl groups and the like; a hydroxy substituted piperidinyl group such as 2-, 3-, and 4-hydroxy substituted piperidinyl groups; a hydroxyalkyl substituted piperidinyl group; an aryl substituted piperidinyl group such as, but not limited to, a 4-aryl substituted piperidinyl group and the like such as, but not limited to, a piperidinyl group that is substituted in the 4 position with both an aryl group and a hydroxy group and the like such as, but not limited to, a piperidinyl group that is substituted in the 4 position with both a hydroxy group and a phenyl group; a cycloalkyl substituted piperidinyl group; a heterocyclyl substituted piperidinyl group such as, but not limited to, a piperidinyl substituted piperidinyl group and the like such as, but not limited to, 4-piperidinyl substituted piperidinyl groups, 4-(2(3H)-benzimidazolone) substituted piperidinyl group, and the like; an unsubstituted pyrrolidinyl group; an alkyl substituted pyrrolidinyl group such as, but not limited to, a methyl substituted pyrrolidinyl group, a heterocyclylalkyl substituted pyrrolidinyl group, and the like such as, but not limited to, a 2-methyl substituted pyrrolidinyl group, a 2-pyrrolidinylmethyl substituted pyrrolidinyl group, and the like; an amino substituted pyrrolidinyl group such as, but not limited to, a dialkylamino substituted pyrrolidinyl group such as, but not limited to, 2- and 3-dialkylamino substituted pyrrolidinyl groups and the like such as, but not limited to, 2- and 3-substituted N,N-dimethylamino substituted pyrrolidinyl groups and the like such as, but not limited to, a pyrrolidinyl group that is substituted with both an alkyl group and an N,N-dimethylamino group and the like such as, but not limited to, a pyrrolidinyl group that is substituted with a methyl group in the 2 position and with a N,N-dimethylamino group in the 4 position; a hydroxy substituted pyrrolidinyl group such as, but not limited to, 2- and 3-hydroxy substituted pyrrolidinyl groups; a heterocyclylalkyl substituted pyrrolidinyl group; substituted and unsubstituted pyrrolyl groups; substituted and unsubstituted 2,5-diazabicyclo[2.2.1]heptane groups; an alkyl substituted 2,5diazabicyclo[2.2.1]heptane group such as, but not limited to, a N-methyl substituted 2,5-diazabicyclo[2.2.1]heptane group and the like; a substituted or unsubstituted 1,4-diazabicyclo[4.3.0]nonane group; and a substituted or unsubstituted 1,4-diazacycloheptane group such as, but not limited to, an alkyl substituted 1,4-diazacycloheptane group and the like, such as, but not limited to, an N-alkyl substituted 1,4-diazacycloheptane substituted group and the like such as, but not limited to, a N-methyl substituted 1,4-diazacycloheptane group and the like. In still other embodiments of the sixth group of compounds where $R^7$ is a substituted or unsubstituted heterocyclyl group, $R^6$ is —H.

In another embodiment of the sixth group of compounds, $Z^1$-$Z^4$, $R^1$, $R^2$, and $R^3$ have any of the values in previous embodiments, and one of $R^6$ or $R^7$ is a substituted or unsubstituted pyridyloxy group. In some such embodiments, one of $R^6$ or $R^7$ is substituted or unsubstituted 2-pyridyloxy group, a 3-pyridyloxy group, or a 4-pyridyloxy group. In other such embodiments, one of $R^6$ or $R^7$ is a (2-N-alkylamido-4-pyridyl)oxy group such as a (2-N-methylamido-4-pyridyl)oxy group or the like; or a (5-N-alkylamido-3-pyridyl)oxy group such as a (5-N-methylamido-3-pyridyl)oxy group, or the like.

Other more particular embodiments of the compounds of the invention having the general structure shown in I above are provided. Such compounds form a seventh group of compounds for which:

$Z^1$, $Z^2$, $Z^3$, and $Z^4$ are independently selected from C or N; $R^1$ is selected from —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N (alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^2$ is selected from —H, —F, —Cl, —Br, —C≡N, —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups; or $R^2$ and $R^3$ are a group of formula —OCH$_2$O— such that $R^2$ and $R^3$ define a fused 5-membered ring that includes 2 oxygen atoms;

$R^3$ is selected from —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^4$ is —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)

aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^5$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;

$R^8$ is selected from —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H;

$R^{10}$ is selected from the group consisting of —H, and substituted and unsubstituted alkyl groups; and at least one of $Z^2$ or $Z^3$ is C and at least one of $R^6$ or $R^7$ is selected from the group consisting of substituted and unsubstituted piperidinyl substituted heterocyclyl groups, substituted and unsubstituted heterocyclyl substituted piperidinyl groups, substituted and unsubstituted hydroxymethyl substituted piperidinyl groups, dimethylaminoalkyl substituted pyrrolidinyl groups, substituted and unsubstituted 3-alkyl substituted piperazinyl groups, substituted and unsubstituted 3,5-dialkyl substituted piperazinyl groups, substituted and unsubstituted N-hydroxyalkyl substituted piperazinyl groups, substituted and unsubstituted 1,4-diazacycloheptyl groups, substituted and unsubstituted 1-aza-4-oxacycloheptyl groups, substituted and unsubstituted N-ethylpiperazinyl groups, substituted and unsubstituted N-isopropylpiperazinyl groups, substituted and unsubstituted N-sec-butylpiperazinyl groups, substituted and unsubstituted N-2-pyridyl substituted piperazinyl groups, substituted and unsubstituted N-3-pyridyl substituted piperazinyl groups, substituted and unsubstituted N-4-pyridyl substituted piperazinyl groups, substituted and unsubstituted N(H)—CH$_2$-pyridyl groups, substituted and unsubstituted imidazolyl groups, substituted and unsubstituted 3-alkyl substituted morpholinyl groups, substituted and unsubstituted 3,5-dialkyl substituted morpholinyl groups, dialkylamino substituted pyrrolidinyl groups, pyrrolidinyl groups substituted with both dialkylamino and alkyl groups, substituted and unsubstituted 4-hydroxy substituted piperidinyl groups, substituted and unsubstituted 4-aryl substituted piperidinyl groups, substituted and unsubstituted 4-hydroxy-4-phenyl substituted piperidinyl groups, substituted and unsubstituted cyclohexylpiperazinyl groups, substituted and unsubstituted cyclopentylpiperazinyl groups, substituted and unsubstituted N-alkyl substituted diazabicycloalkane groups, substituted and unsubstituted —N(CH$_3$)(N-alkyl(4-piperidinyl)) groups, substituted and unsubstituted piperazinyl groups further substituted with a —C(=O)-alkyl group on one of the N atoms of the piperazinyl group, substituted and unsubstituted —N(H)CH$_2$CH$_2$CH$_2$-imidazolyl groups, substituted and unsubstituted —N(H)CH$_2$CH$_2$CH$_2$-pyrrolidinyl groups, substituted and unsubstituted —N(H)CH$_2$CH$_2$CH$_2$-morpholinyl groups, substituted and unsubstituted —N(H)CH$_2$CH$_2$CH$_2$-piperazinyl groups, substituted and unsubstituted —N(H)CH$_2$CH$_2$CH$_2$-piperidinyl groups, substituted and unsubstituted —N(H)CH$_2$CH$_2$CH$_2$-pyridyl groups, substituted and unsubstituted —N(H)CH$_2$CH$_2$-imidazolyl groups, substituted and unsubstituted —N(H)CH$_2$CH$_2$-pyrrolidinyl groups, substituted and unsubstituted —N(H)CH$_2$CH$_2$-morpholinyl groups, substituted and unsubstituted —N(H)CH$_2$CH$_2$-piperazinyl groups, substituted and unsubstituted —N(H)CH$_2$CH$_2$-piperidinyl groups, substituted and unsubstituted —N(H)CH$_2$CH$_2$-pyridyl groups, substituted and unsubstituted cyclobutylpiperazinyl groups, substituted and unsubstituted —OCH$_2$-pyrrolidinyl groups, substituted and unsubstituted —OCH$_2$CH$_2$-pyrrolidinyl groups, substituted and unsubstituted —OCH$_2$CH$_2$CH$_2$-pyrrolidinyl groups, substituted and unsubstituted piperazinyl groups further substituted with a —CH$_2$C(=O)—O-alkyl group bonded to one of the N atoms of the piperazinyl group, substituted and unsubstituted piperazinyl groups further substituted with a —C(=O)—O-alkyl group bonded to one of the N atoms of the piperazinyl group, substituted and unsubstituted hydroxypyrrolidinyl groups, substituted and unsubstituted hydroxypiperidinyl groups, substituted and unsubstituted —OCH$_2$-pyridyl groups, substituted and unsubstituted piperidinylamino groups, substituted and unsubstituted pyridyloxy groups with a —C(=O)—N(H)(alkyl) group bonded to a carbon atom of the pyridine ring of the pyridyloxy group, and substituted and unsubstituted pyridyloxy groups with a —C(=O)—N(alkyl)$_2$ group bonded to a carbon atom of the pyridine ring of the pyridyloxy group.

In some embodiments, R$^{10}$ is —H. In other embodiments, R$^{10}$ is an unsubstituted alkyl group having from 1 to 6 carbon atoms such as a methyl, ethyl, propyl, i-propyl group, or the like. In some such embodiments, R$^{10}$ is a —CH$_3$ group.

In one embodiment of the seventh group of compounds, each of Z$^1$, Z$^2$, Z$^3$, and Z$^4$ are C.

In another embodiment of the seventh group of compounds, Z$^1$ is N and each of Z$^2$, Z$^3$, and Z$^4$ are C.

In another embodiment of the seventh group of compounds, Z$^1$ and Z$^3$ are both N and Z$^2$ and Z$^4$ are both C.

In another embodiment of the seventh group of compounds, Z$^3$ is N and each of Z$^1$, Z$^2$, and Z$^4$ are C.

In another embodiment of the seventh group of compounds, Z$^1$-Z$^4$ have any of the values in previous embodiments, and R$^1$ is selected from —H, —F, —Cl, and —Br.

In another embodiment of the seventh group of compounds, Z$^1$-Z$^4$ have any of the values in previous embodiments, and R$^1$ is a substituted and unsubstituted heterocyclylamino group. In some such embodiments, R$^1$ is a substituted and unsubstituted heteroarylamino groups. In some embodiments, R$^1$ is a substituted and unsubstituted heterocyclylamino group such as, but not limited to, substituted and unsubstituted pyrroldinylalkylamino groups and the like, such as, but not limited to, substituted and unsubstituted pyrrolidinylmethylamino groups and the like.

In another embodiment of the seventh group of compounds, Z$^1$-Z$^4$ and R$^1$ have any of the values in previous embodiments, and R$^2$ is selected from —H, —F, —Cl, —CO$_2$H, substituted and unsubstituted alkyl groups, substituted and unsubstituted —C(=O)O-alkyl groups, substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)-heterocyclyl groups, substituted and unsubstituted heterocyclyl groups, substituted and unsubstituted alkoxy groups, substituted and unsubstituted arylalkoxy groups, substituted and unsubstituted aryloxy groups, substituted and unsubstituted heterocyclyloxy, and substituted and unsubstituted heterocyclylalkoxy groups; or R$^2$ and R$^3$ are a group of formula —OCH$_2$O— such that R$^2$ and R$^3$ define a fused 5-membered ring that includes 2 oxygen atoms.

In another embodiment of the seventh group of compounds, Z$^1$-Z$^4$ and R$^1$ have any of the values in previous embodiments, and R$^2$ is —H.

In another embodiment of the seventh group of compounds, Z$^1$-Z$^4$ and R$^1$ have any of the values in previous embodiments, and R$^2$ is an unsubstituted alkoxy group having from 1 to 4 carbon atoms.

In another embodiment of the seventh group of compounds, Z$^1$-Z$^4$ and R$^1$ have any of the values in previous embodiments, and R$^2$ is a —OMe, —OEt, —O-i-Pr, or —OCH$_2$CH(CH$_3$)$_2$ group.

In another embodiment of the seventh group of compounds, Z$^1$-Z$^4$ and R$^1$ have any of the values in previous embodiments, and R$^2$ is a substituted or unsubstituted arylalkoxy, a substituted or unsubstituted aryloxy group, or a substituted or unsubstituted heterocyclyoxy group.

In another embodiment of the seventh group of compounds, Z$^1$-Z$^4$ and R$^1$ have any of the values in previous embodiments, and R$^2$ is a substituted or unsubstituted benzyloxy group, a substituted or unsubstituted phenoxy group, or a substituted or unsubstituted pyridyloxy group.

In another embodiment of the seventh group of compounds, Z$^1$-Z$^4$ and R$^1$ have any of the values in previous embodiments, and R$^2$ is an unsubstituted alkyl group having from 1 to 4 carbon atoms.

In another embodiment of the seventh group of compounds, Z$^1$-Z$^4$ and R$^1$ have any of the values in previous embodiments, and R$^2$ is a methyl group.

In another embodiment of the seventh group of compounds, Z$^1$-Z$^4$ and R$^1$ have any of the values in previous embodiments, and R$^2$ is a substituted or unsubstituted —N(H)C(=O)—N(H)-alkyl-aryl group.

In another embodiment of the seventh group of compounds, Z$^1$-Z$^4$ and R$^1$ have any of the values in previous embodiments, and R$^2$ is a substituted or unsubstituted amino group selected from the group consisting of substituted and unsubstituted alkylamino groups, dialkylamino groups, cycloalkylamino groups, heterocyclylamino groups, heterocyclylalkylamino groups, arylalkylamino groups, arylalkoxyarylmethylamino groups, and aryloxyarylalkylamino groups. In some embodiments, the substituted and unsubstituted alkylamino groups are substituted and unsubstituted aminoalkylamino groups such as, but not limited to, dialkylaminoalkylamino and the like. In some such embodiments the substituted and unsubstituted heterocyclylalkylamino groups are substituted and unsubstituted heteroarylalkylamino groups. In some embodiments, the heterocyclylalkylamino groups include, but are not limited to, substituted and unsubstituted pyrrolidinylalkylamino groups such as, but not limited to, substituted and unsubstituted pyrrolidinylmethylalkylamino groups and the like; substituted and unsubstituted thiazolylalkylamino groups such as, but not limited to substituted and unsubstituted thiazolylmethylamino groups and the like; substituted and unsubstituted imidazolylalkylamino groups such as, but not limited to, imidazolylmethylamino groups and the like; substituted and unsubstituted furanylalkylamino groups such as, but not limited to, substituted and unsubstituted furanylmethylamino groups, and the like; and the like. In other such embodiments, the heterocyclylamino groups are substituted and unsubstituted heteroarylamino groups. In other such embodiments, the substituted and unsubstituted heterocyclylamino groups are substituted and unsubstituted arylalkylheterocyclylamino groups.

In another embodiment of the seventh group of compounds, $Z^1$-$Z^4$ and $R^1$ have any of the values in previous embodiments, and $R^2$ is a substituted or unsubstituted amino group selected from the group consisting of isopropylamino groups, 3-(N,N-dimethylamino)propylamino groups, pyrrolidinylmethylamino groups, arylmethylamino groups, arylalkoxyarylmethylamino groups, aryloxyarylmethylamino groups, and pyridylmethylamino groups, and pyridylamino groups.

In another embodiment of the seventh group of compounds, $Z^1$-$Z^4$ and $R^1$ have any of the values in previous embodiments, and $R^2$ is a substituted or unsubstituted heterocyclyl groups. In some such embodiments $R^2$ is a substituted or unsubstituted benzimidazolyl group or is a substituted or unsubstituted pyrazolyl group.

In another embodiment of the seventh group of compounds, $Z^1$-$Z^4$ and $R^1$ have any of the values in previous embodiments, and $R^2$ and $R^3$ are a group of formula —OCH$_2$O— such that $R^2$ and $R^3$ define a fused 5-membered ring that includes 2 oxygen atoms.

In another embodiment of the seventh group of compounds, $Z^1$-$Z^4$, $R^1$, and $R^2$ have any of the values in previous embodiments, and $R^3$ is selected from —H, —F, —Cl, and —OMe.

In another embodiment of the seventh group of compounds, $Z^1$-$Z^4$, $R^1$, and $R^2$ have any of the values in previous embodiments, and $R^3$ is —H.

In another embodiment of the seventh group of compounds, $Z^1$-$Z^4$, $R^1$, and $R^2$ have any of the values in previous embodiments, and $R^3$ is selected from the group consisting of —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —N(H)C(=O)N(H)-alkyl groups, substituted and unsubstituted —N(H)C(=O)N(H)-aryl groups and substituted and unsubstituted —C(=O)N(H)-alkyl-heterocyclyl groups; or $R^2$ and $R^3$ are a group of formula —OCH$_2$O— such that $R^2$ and $R^3$ define a fused 5-membered ring that includes 2 oxygen atoms.

In another embodiment of the seventh group of compounds, $Z^1$-$Z^4$, $R^1$, and $R^2$ have any of the values in previous embodiments, and $R^3$ is selected from the group consisting of substituted and unsubstituted —N(H)C(=O)N(H)-alkyl groups, and substituted and unsubstituted —N(H)C(=O)N(H)-aryl groups. In some such embodiments, $R^3$ is a substituted or unsubstituted —N(H)C(=O)N(H)CH$_2$CH$_3$ group, a substituted or unsubstituted —N(H)C(=O)N(H)CH(CH$_3$)$_2$ group, a substituted or unsubstituted —N(H)C(=O)N(H)C(CH$_3$)$_3$ group, or a substituted or unsubstituted —N(H)C(=O)N(H)-aryl group or the like. In some such embodiments, $R^3$ is a substituted or unsubstituted —N(H)C(=O)N(H)-aryl group such as, but not limited to, a —N(H)C(=O)N(H)-(2-methoxyphenyl) group, a-N(H)C(=O)N(H)-(3-trifluoromethylphenyl) group, or the like.

In another embodiment of the seventh group of compounds, $Z^1$-$Z^4$, $R^1$, and $R^2$ have any of the values in previous embodiments, and $R^3$ is a substituted ammo group selected from substituted or unsubstituted arylalkylamino groups such as, but not limited to, phenylalkylamino groups, (halo)(alkoxy)arylalkylamino groups, such as, but not limited to 2-fluoro-5-methoxyphenylmethylamino groups, monoalkoxyarylalkylamino groups, dialkoxyarylalkylamino groups, and the like, such as, but not limited to, 2,5-dialkoxyarylalkylamino groups and the like such as, but not limited to 2,5-dialkoxyarylmethylamino groups, substituted and unsubstituted arylalkoxyarylalkylamino groups such as, but not limited to substituted and unsubstituted arylalkoxyarylmethylamino groups and the like, such as, but not limited to, substituted and unsubstituted arylmethoxyarylmethylamino groups and the like, such as, but not limited to substituted and unsubstituted fluoroarylmethoxyarylmethylamino groups and the like, such as, but not limited to, substituted and unsubstituted 4-fluorophenylmethoxyphenylmethylamino groups and the like; substituted and unsubstituted heterocyclylalkylamino groups including heteroarylalkylamino groups such as, but not limited to substituted and unsubstituted thiazolylalkylamino groups, benzimidazolylalkylamino groups such as, but not limited to N-methylbenzimidazolylalkylamino groups and the like, imidazolylalkylamino groups such as, but not limited to phenylimidazolylalkylamino groups, ethylmethylimidazolylalkylamino groups, and the like, substituted and unsubstituted quinolinylalkylamino groups, such as, but not limited to substituted and unsubstituted quinolinylmethylamino groups and the like, such as, but not limited to alkoxyquinolinylmethylamino groups and the like, such as, but not limited to substituted and unsubstituted 4-alkoxy-2-quinolinylmethylamino groups and the like, and furanylalkylamino groups, and the like.

In another embodiment of the seventh group of compounds, $Z^1$-$Z^4$, $R^1$, and $R^2$ have any of the values in previous embodiments, and $R^3$ is —F.

In another embodiment of the seventh group of compounds, $Z^1$-$Z^4$, $R^1$, and $R^2$ have any of the values in previous embodiments, and $R^3$ is —Cl.

In another embodiment of the seventh group of compounds, $Z^1$-$Z^4$, $R^1$, and $R^2$ have any of the values in previous embodiments, and $R^3$ is —OMe.

In another embodiment of the seventh group of compounds, $Z^1$-$Z^4$, $R^1$, and $R^2$ have any of the values in previous embodiments, and $R^3$ is a substituted and unsubstituted —C(=O)N(H)-alkyl-heterocyclyl groups where the heterocyclyl group of the —C(=O)N(H)-alkyl-heterocyclyl groups is selected from the group consisting of morpholinyl, piperazinyl, and piperidinyl groups.

In another embodiment of the seventh group of compounds, $Z^2$-$Z^4$, $R^1$, $R^2$, and $R^3$ have any of the values in previous embodiments, $Z^1$ is C, and $R^5$ is H. In some such embodiments, $R^8$ is also H.

In another embodiment of the seventh group of compounds, $Z^2$-$Z^4$, $R^1$, $R^2$, and $R^3$ have any of the values in previous embodiments, $Z^1$ is C, and $R^8$ is —CH$_3$.

In another embodiment of the seventh group of compounds, $Z^2$-$Z^4$, $R^1$, $R^2$, and $R^3$ have any of the values in previous embodiments, $Z^1$ is C, and $R^5$ is morpholine.

In another embodiment of the seventh group of compounds, $Z^1$-$Z^3$, $R^1$, $R^2$, and $R^3$ have any of the values in previous embodiments, $Z^4$ is C, and $R^8$ is H.

In another embodiment of the seventh group of compounds, $Z^1$-$Z^3$, $R^1$, $R^2$, and $R^3$ have any of the values in previous embodiments, $Z^4$ is C, and $R^8$ is —CH$_3$.

In another embodiment of the seventh group of compounds, $Z^1$-$Z^3$, $R^1$, $R^2$, and $R^3$ have any of the values in previous embodiments, $Z^4$ is C, and $R^8$ is morpholine.

In another embodiment of the seventh group of compounds, at least one of $R^6$ or $R^7$ is selected from the group consisting of piperidinyl substituted piperidinyl groups such as 4-piperidinylpiperidinyl groups or the like, 4-hydroxymethylpiperidinyl groups, 3-dimethylaminomethylpyrrolidinyl groups, 3-alkyl substituted piperazinyl groups, 3,5-dialkyl substituted piperazinyl groups, N-hydroxyethylpiperazinyl groups, N-hydroxymethylpiperazinyl groups, N-hydroxypropylpiperazinyl groups, N-methyl substituted 1,4-diazacycloheptyl groups, N-ethylpiperazinyl groups, N-isopropylpiperazinyl groups, N-sec-butylpiperazinyl groups, unsubstituted piperazinyl groups, N-(2-pyridyl)piperazinyl groups, N-(3-pyridyl)piperazinyl groups, N-(4-pyridyl)piperazinyl groups, N(H)—CH$_2$-pyridyl groups, imidazolyl groups, unsubstituted morpholinyl groups, 3-alkylmorpholinyl groups, 3,5-dialkylmorpholinyl groups, 2-dimethylaminopyrrolidinyl groups, 2-methyl4-dialkylaminopyrroldinyl groups, 4-hydroxypiperidinyl groups, 4-arylpiperidinyl groups, 4-hydroxy4-phenylpiperidinyl groups, cyclohexylpiperazinyl groups, cyclopentylpiperazinyl groups, N-methyl substituted diazabicycloalkane groups, —N(CH$_3$)(N-alkyl(4-piperidinyl)) groups, piperazinyl groups further substituted with a —C(=O)-methyl group on one of the N atoms of the piperazinyl group, —N(H)CH$_2$CH$_2$CH$_2$-imidazolyl groups, —N(H)CH$_2$CH$_2$CH$_2$-pyrrolidinyl groups, —N(H)CH$_2$CH$_2$CH$_2$-morpholinyl groups, —N(H)CH$_2$CH$_2$CH$_2$-piperazinyl groups, —N(H)CH$_2$CH$_2$CH$_2$-piperidinyl groups, and —N(H)CH$_2$CH$_2$CH$_2$-pyridyl groups. In some such embodiments, at least one of R$^6$ or R$^7$ is selected from the group consisting of 4-piperidinylpiperidinyl groups, 4-hydroxymethylpiperidinyl groups, 3-dimethylaminomethylpyrrolidinyl groups, 3,5-dimethyl substituted piperazinyl groups, N-methyl substituted 1,4-diazacycloheptyl groups, N-(2-pyridyl)piperazinyl groups, N(H)—CH$_2$-(4-pyridyl) groups, imidazolyl groups, unsubstituted morpholinyl groups, 3-methylmorpholinyl groups, 3,5-dimethylmorpholinyl groups, 2-dimethylaminopyrrolidinyl groups, 2-methyl-4-dimethylaminopyrroldinyl groups, 4-hydroxy-4-phenylpiperidinyl groups, cyclohexylpiperazinyl groups, N-methyl substituted diazabicycloalkane groups, —N(CH$_3$)(N-methyl(4-piperidinyl)) groups, piperazinyl groups further substituted with a —C(=O)-methyl group on one of the N atoms of the piperazinyl group, —N(H)CH$_2$CH$_2$CH$_2$-imidazolyl groups, —N(H)CH$_2$CH$_2$CH$_2$-pyrrolidinyl groups, —N(H)CH$_2$CH$_2$CH$_2$-morpholinyl groups, —N(H)CH$_2$CH$_2$CH$_2$-piperazinyl groups, —N(H)CH$_2$CH$_2$CH$_2$-piperidinyl groups, and —N(H)CH$_2$CH$_2$CH$_2$-pyridyl groups.

Other more particular embodiments of the compounds of the invention having the general structure shown in I above are provided. Such compounds form an eighth group of compounds for which:

$Z^1$, $Z^2$, $Z^3$, and $Z^4$ are selected independently from C or N;

$R^1$ is selected from the group consisting of —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^2$ is selected from the group consisting of substituted or unsubstituted arylalkoxy groups, substituted and unsubstituted aryloxy groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted heterocyclylalkylamino groups, substituted and unsubstituted arylalkylamino groups; substituted and unsubstituted —N(H)-heterocyclyl groups, substituted and unsubstituted alkoxy groups, and substituted and unsubstituted heterocyclyloxy groups;

$R^3$ is selected from the group consisting of —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(═O)-alkyl groups, substituted and unsubstituted -alkyl-N(H)—C(═O)-aryl groups, substituted and unsubstituted -alkyl-N(H)—C(═O)-heterocyclyl groups, substituted and unsubstituted -alkyl-N(H)—C(═O)-alkyl-aryl groups, and substituted and unsubstituted -alkyl-N(H)—C(═O)-alkyl-heterocyclyl groups;

$R^4$ is selected from the group consisting of —H, —F, —Br, —Cl, —NO$_2$, —C≡N, —C(═O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(═O)-aryl groups, substituted and unsubstituted —N(H)—C(═O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(═O)—N(H)-alkyl groups, substituted and unsubstituted —C(═O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(═O)-alkyl groups, substituted and unsubstituted -alkyl-N(alkyl)-C(═O)-aryl groups, substituted and unsubstituted -alkyl-N(alkyl)-C(═O)-heterocyclyl groups, substituted and unsubstituted -alkyl-N(alkyl)-C(═O)-alkyl-aryl groups, substituted and unsubstituted -alkyl-N(alkyl)-C(═O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(═O)-alkyl groups, substituted and unsubstituted -alkyl-N(H)—C(═O)-aryl groups, substituted and unsubstituted -alkyl-N(H)—C(═O)-heterocyclyl groups, substituted and unsubstituted -alkyl-N(H)—C(═O)-alkyl-aryl groups, and substituted and unsubstituted -alkyl-N(H)—C(═O)-alkyl-heterocyclyl groups;

$R^5$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N.

$R^6$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(═O)N(H)-alkyl groups, substituted and unsubstituted —C(═O)N(H)-aryl groups, substituted and unsubstituted —C(═O)N(H)-heterocyclyl groups, substituted and unsubstituted —C(═O)N(alkyl)(heterocyclyl) groups, and substituted and unsubstituted —C(═O)-heterocyclyl groups; or $R^6$ is absent if $Z^2$ is N;

$R^7$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(═O)N(H)-alkyl groups, substituted and unsubstituted —C(═O)N(H)-aryl groups, substituted and unsubstituted —C(═O)N(H)-heterocyclyl groups, substituted and unsubstituted —C(═O)N(alkyl)(heterocyclyl) groups, and substituted and unsubstituted —C(═O)-heterocyclyl groups; or $R^7$ is absent if $Z^3$ is N;

$R^8$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is selected from the group consisting of —H, and substituted and unsubstituted alkyl groups.

In some embodiments of the eighth group of compounds, $R^2$ is selected from the group consisting of

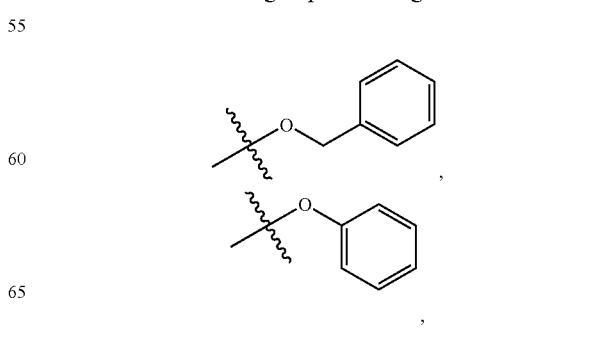

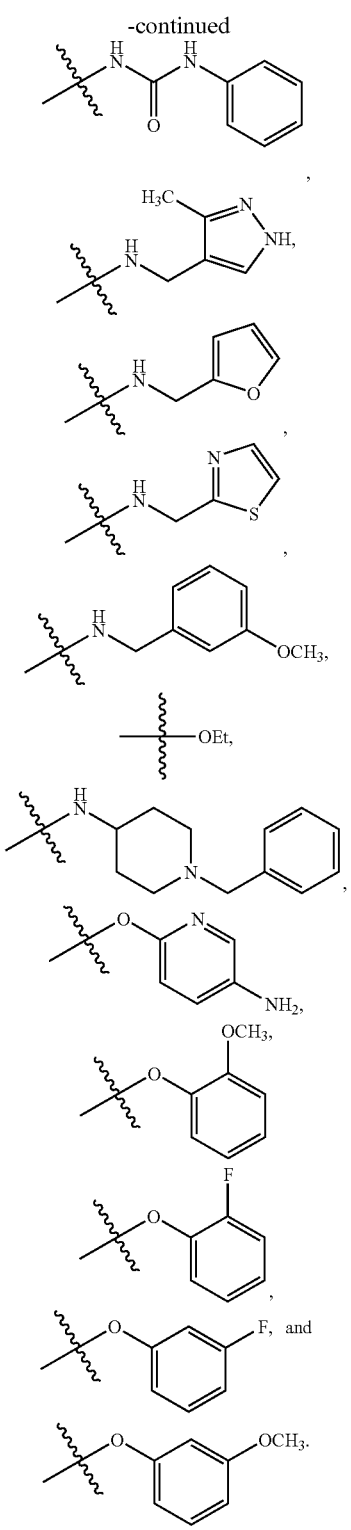

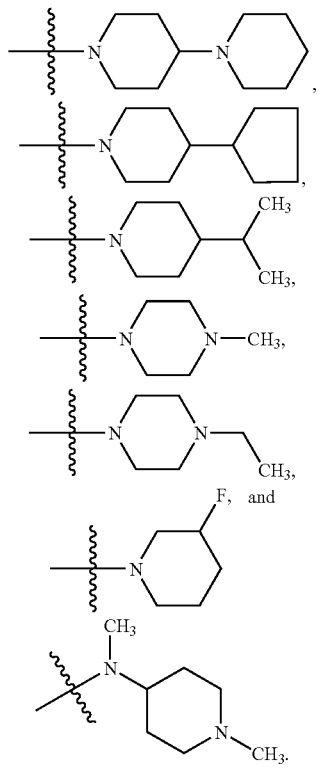

In some embodiments of the eighth group of compounds, each of $Z^1$, $Z^2$, $Z^3$, and $Z^4$ is C.

In some embodiments of the eighth group of compounds, $R^{10}$ is H.

In some embodiments of the eighth group of compounds, at least one of $R^6$ or $R^7$ is selected from the group consisting of substituted and unsubstituted heterocyclyl groups, substituted and unsubstituted heterocyclylalkyl groups, and substituted and unsubstituted amino groups.

In some embodiments of the eighth group of compounds, at least one of $R^6$ or $R^7$ is selected from the group consisting of substituted and unsubstituted heterocyclylheterocyclyl groups, substituted and unsubstituted alkylheterocyclyl groups, substituted and unsubstituted (alkyl)(heterocyclyl) amino groups, and substituted and unsubstituted heterocyclylalkyl groups.

In some embodiments of the eighth group of compounds, at least one of $R^6$ or $R^7$ is selected from the group consisting of:

In some embodiments of the eighth group of compounds, at least one of $R^6$ or $R^7$ is selected from the group consisting of substituted and unsubstituted heterocyclyl groups, substituted and unsubstituted heterocyclylalkyl groups, and substituted and unsubstituted amino groups, and further wherein the other of $R^6$ or $R^7$ is selected from H or F.

In some embodiments of the eighth group of compounds, $R^1$, $R^4$, $R^5$, and $R^8$ are all H.

In some embodiments of the eighth group of compounds, $R^3$ is selected from H or a substituted or unsubstituted alkoxy group.

Other more particular embodiments of the compounds of the invention having the general structure shown in I above are provided. Such compounds form an ninth group of compounds for which:

$Z^1$, $Z^2$, $Z^3$, and $Z^4$ are selected independently from C or N;
$R^1$ is selected from the group consisting of —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C (=O)-aryl groups, substituted and unsubstituted —N(H)—C(=O)-alkyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^2$ is selected from the group consisting of —H, —F, —Cl, —Br, —C≡N, —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclylalkylamino groups, substituted and unsubstituted arylalkylamino groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups; or $R^2$ and $R^3$ are a group of formula —OCH$_2$O— such that $R^2$ and $R^3$ define a fused 5-membered ring that includes 2 oxygen atoms;

$R^3$ is selected from the group consisting of —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^4$ is selected from the group consisting of —H, —F, —Br, —Cl, —$NO_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—$SO_2$-alkyl groups, substituted and unsubstituted —N(H)—$SO_2$-aryl groups, —N(H)—$SO_2$—$CF_3$ groups, substituted and unsubstituted —N(H)—$SO_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^5$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;

$R^6$ is selected from the group consisting of —H, —F, —Cl, —Br, —$CF_3$, —$CO_2H$, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from the group consisting of —H, —F, —Cl, —Br, —$CF_3$, —$CO_2H$, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;

$R^8$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H;

$R^{10}$ is selected from the group consisting of —H, and substituted and unsubstituted alkyl groups; and at least one of $Z^2$ or $Z^3$ is C and at least one of $R^6$ and $R^7$ is selected from the group consisting of substituted and unsubstituted piperidinyl groups; substituted and unsubstituted morpholinyl compounds, substituted and unsubstituted heterocyclylheterocyclyl groups, substituted and unsubstituted azabicyclic amine groups, and substituted and unsubstituted heterocyclylalkyl groups.

In some embodiments of the ninth group of compounds, at least one of $R^6$ and $R^7$ is selected from the group consisting of

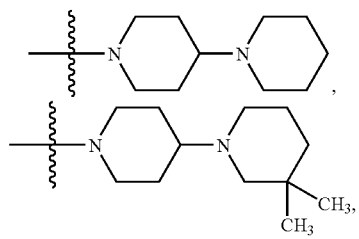

-continued
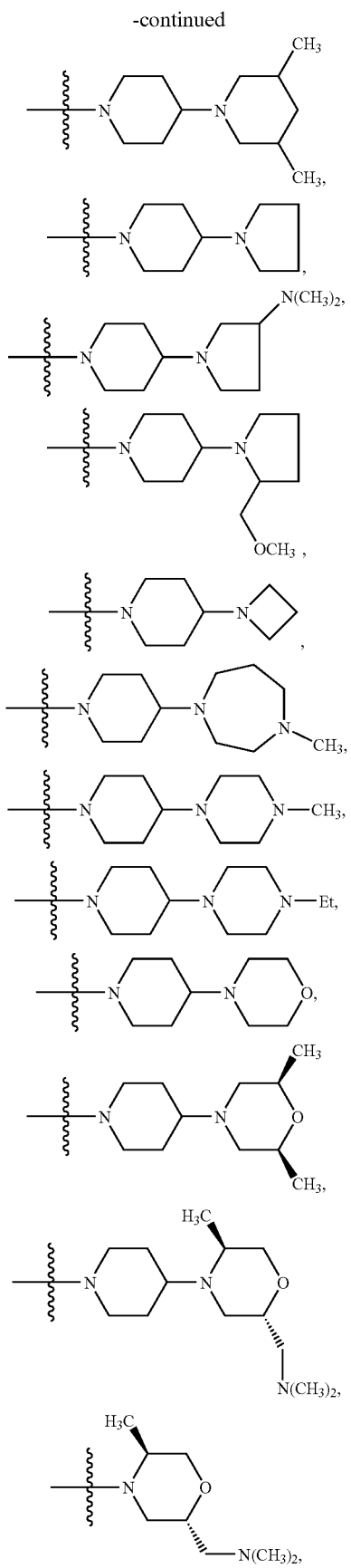
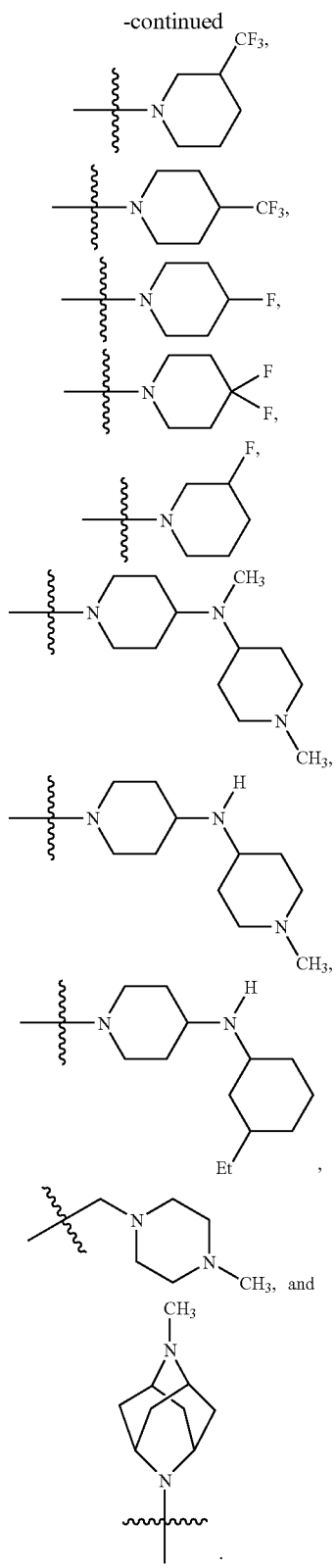
In some embodiments of the ninth group of compounds, at least one of $R^6$ and $R^7$ is selected from the group consisting of substituted and unsubstituted piperidinyl substituted piperidinyl groups, substituted and unsubstituted pyrrolidinyl substituted piperidinyl groups, substituted and unsubstituted azetidinyl substituted piperidinyl groups, substituted and unsubstituted diazepanyl substituted piperidinyl groups, substituted and unsubstituted piperazinyl substituted piperidinyl groups, substituted and unsubstituted morpholinyl substituted piperidinyl groups, substituted and unsubstituted morpholinyl groups, trifluoromethyl substituted piperidinyl groups, fluoro substituted piperidinyl groups, difluoro substituted piperidinyl groups, substituted and unsubstituted heterocyclylamino substituted piperidinyl groups, substituted an unsubstituted piperazinylalkyl groups, and substituted and unsubstituted azabicyclo amine groups.

In some embodiments of the ninth group of compounds, each of $Z^1$, $Z^2$, $Z^3$, and $Z^4$ is C.

In some embodiments of the ninth group of compounds, $R^{10}$ is H.

In some embodiments of the ninth group of compounds, $R^1$, $R^4$, $R^5$, and $R^8$ are all H.

In some embodiments of the ninth group of compounds, $R^3$ is selected from H or a substituted or unsubstituted alkoxy group.

In one aspect, the invention provides a method for inhibiting c-ABL in a patient. The method includes administering an effective amount of a compound having the structure I, a tautomer of the compound, a pharmaceutically acceptable salt of the compound, or a pharmaceutically acceptable salt of the tautomer to a patient. In some embodiments, the $IC_{50}$ value of the compound, the tautomer, the pharmaceutically acceptable salt of the compound, or the pharmaceutically acceptable salt of the tautomer is less than 10 micromolar with respect to c-ABL and in other embodiments is less than 1 micromolar. The compound having the structure I has the following structure:

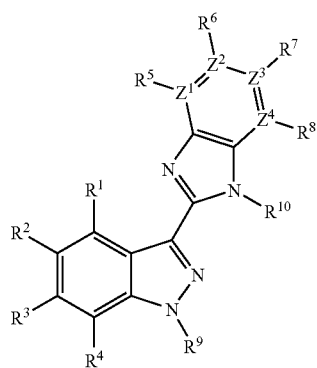

I where:
$Z^1$, $Z^2$, $Z^3$, and $Z^4$ are selected independently from C or N;
$R^1$ is selected from the group consisting of —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl) aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^2$ is selected from the group consisting of —H, —F, —Cl, —Br, —C≡N, —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclylalkylamino groups, substituted and unsubstituted arylalkylamino groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups; or $R^2$ and $R^3$ are a group of formula —OCH$_2$O— such that $R^2$ and $R^3$ define a fused 5-membered ring that includes 2 oxygen atoms;

$R^3$ is selected from the group consisting of —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)—alkyl groups, substituted and unsubstituted —N(H)C(=O)N(H)-aryl groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^4$ is selected from the group consisting of —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^5$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^5$ is absent if $Z^1$ is N;.

$R^6$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^6$ is absent if $Z^2$ is N;

$R^7$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl) amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups; or $R^7$ is absent if $Z^3$ is N;.

$R^8$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups, or $R^8$ is absent if $Z^4$ is N;

$R^9$ is —H; and $R^{10}$ is selected from the group consisting of —H, and substituted and unsubstituted alkyl groups.

In some embodiments of the method of inhibiting c-ABL, each of $Z^1$, $Z^2$, $Z^3$, and $Z^4$ is C.

In some embodiments of the method of inhibiting c-ABL, $R^{10}$ is H.

In some embodiments of the method of inhibiting c-ABL, $R^2$ is selected from the group consisting of H, F, Cl, Br, unsubstituted alkyl groups, substituted and unsubstituted arylalkoxy groups, substituted and unsubstituted aryloxy groups, substituted and unsubstituted heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted heterocyclylalkylamino groups, substituted and unsubstituted arylalkylamino groups; substituted and unsubstituted —N(H)-heterocyclyl groups, substituted and unsubstituted alkoxy groups, and substituted and unsubstituted heterocyclyloxy groups.

In some embodiments of the method of inhibiting c-ABL, $R^2$ is selected from the group consisting of substituted and unsubstituted arylalkoxy groups, substituted and unsubstituted aryloxy groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted heterocyclylalkylamino groups, substituted and unsubstituted arylalkylamino groups; substituted and unsubstituted —N(H)-heterocyclyl groups, substituted and unsubstituted alkoxy groups, and substituted and unsubstituted heterocyclyloxy groups.

In some embodiments of the method of inhibiting c-ABL, $R^2$ is selected from the group consisting of

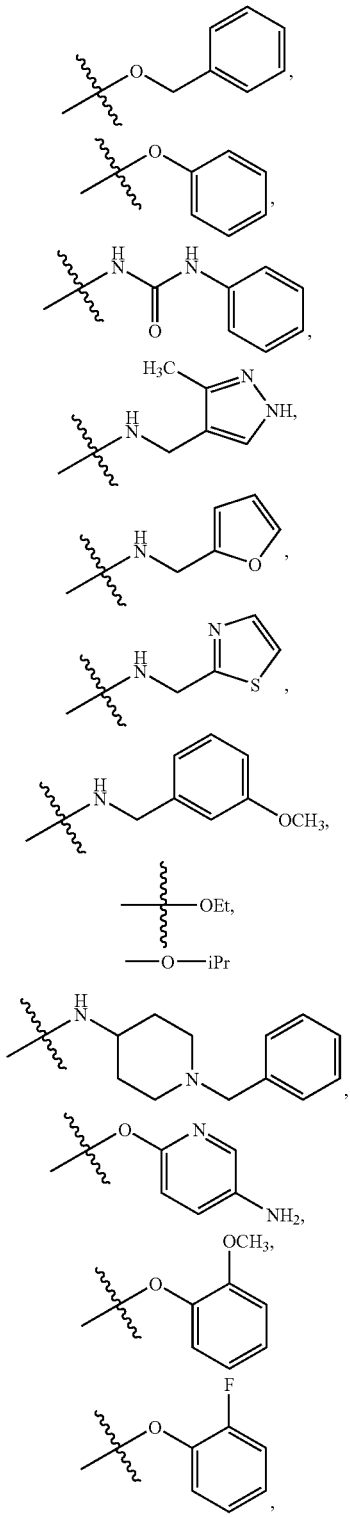

-continued

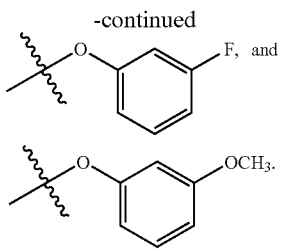

In some embodiments of the method of inhibiting c-ABL, at least one of $R^6$ and $R^7$ is selected from the group consisting of H, F, substituted and unsubstituted heterocyclyl groups including substituted and unsubstituetd heterocyclylheterocyclyl groups, substituted and unsubstituted heterocyclylalkyl groups, substituted and unsubstituted heterocyclyloxy groups, and substituted and unsubstituted amino groups.

In some embodiments of the method of inhibiting c-ABL, at least one of $R^6$ or $R^7$ is selected from the group consisting of substituted and unsubstituted heterocyclyl groups, substituted and unsubstituted heterocyclylalkyl groups, and substituted and unsubstituted amino groups.

In some embodiments of the method of inhibiting c-ABL, at least one of $R^6$ or $R^7$ is selected from the group consisting of substituted and unsubstituted heterocyclylheterocyclyl groups, substituted and unsubstituted alkylheterocyclyl groups, substituted and unsubstituted (alkyl)(heterocyclyl) amino groups, and substituted and unsubstituted heterocyclylalkyl groups.

In some embodiments of the method of inhibiting c-ABL, at least one of $R^6$ or $R^7$ is selected from the group consisting of substituted and unsubstituted heterocyclyl groups, substituted and unsubstituted heterocyclylalkyl groups, and substituted and unsubstituted amino groups, and further wherein the other of $R^6$ or $R^7$ is selected from H or F.

In some embodiments of the method of inhibiting c-ABL, at least one of $R^6$ or $R^7$ is selected from the group consisting of

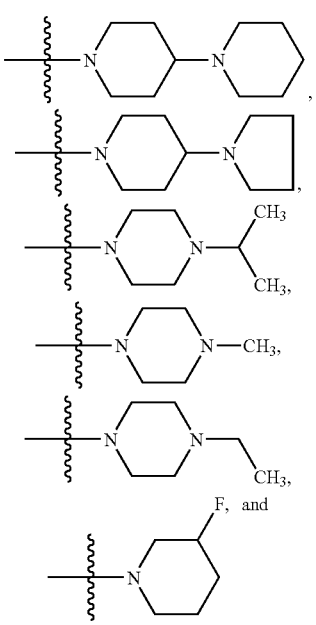

-continued

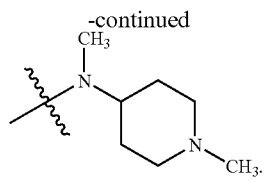

In some embodiments of the method of inhibiting c-ABL, $R^1$, $R^4$, $R^5$, and $R^8$ are all H.

In some embodiments of the method of inhibiting c-ABL, $R^3$ is selected from H or a substituted or unsubstituted alkoxy group.

In some embodiments of the method of inhibiting c-ABL, $R^3$ is selected from the group consisting of H, F, Cl, $NO_2$, substituted and unsubstituted heterocyclylalkylamino groups, substituted and unsubstituted alkoxy groups, substituted and unsubstituted arylalkoxy groups, substituted and unsubstituted arylalkylamino groups, substituted and unsubstituted (arylalkyl)(alkyl)amino groups, and substituted and unsubstituted —N(H)C(=O)N(H)-aryl groups.

In some embodiments of the method of inhibiting c-ABL, $R^1$ is selected from the group consisting of H, substituted and unsubstituted heterocyclylalkylamino groups, and substituted and unsubstituted heterocyclylamino groups.

In some embodiments of the method of inhibiting c-ABL, $R^4$ is selected from the group consisting of H and Cl.

In some embodiments of the method of inhibiting c-ABL, $R^5$ is selected from the group consisting of H and F.

In some embodiments of the method of inhibiting c-ABL, $R^8$ is selected from the group consisting of H and F.

The heterocyclic groups of the present invention may be attached in various ways. For example, where $R^6$ is a heterocyclyl group such as morpholine, the morpholine may be attached to $Z^2$ as shown below in Structures II, III, and IV.

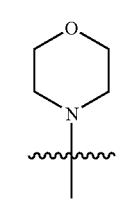

II

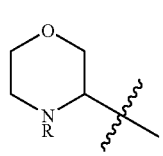

III

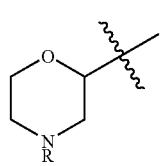

IV

As a further example, where $R^6$ is a piperazine group, the piperazine may be attached to $Z^2$ as shown below in Structures V, VI, VII, and VIII.

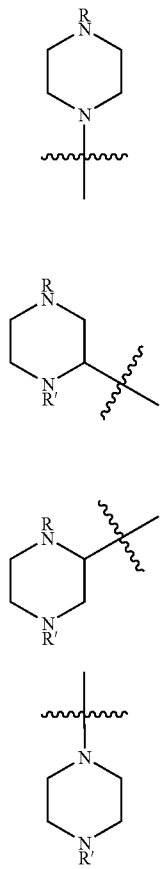

As a further example, where R⁶ is a pyrrolidinyl group, then the pyrrolidinyl group may be attached to Z² as shown below in structures IX, X, and XI.

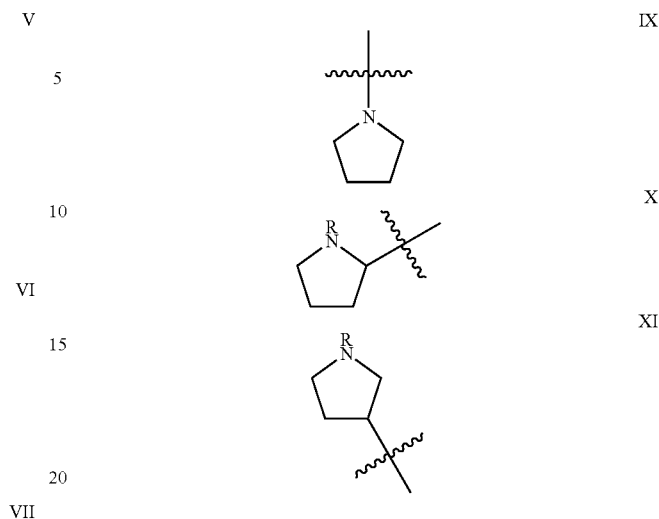

The indazole benzimidazoles of the present invention may generally be assembled by coupling a suitably substituted indazole fragment with a suitably substituted 2-amino aniline or 2-nitro aniline compound. In one method, shown in Scheme 1, an indazole-3-carboxylic acid is reacted with POCl₃ to form a dimer. The resulting dione is then heated in the presence of a suitably substituted diamine to form the desired indazole benzimidazole adduct. If a nitro aniline is used in place of the diamine, an additional reduction and cyclodehydration step is required to effect the ring closure. Alternatively a diamine having one protected amine group may be reacted in place of the diamine. Formation of the indazole benzimidazole by this procedure will include a deprotection and cyclodehydration to afford the desired indazole benzimidazole compound. These reactions may be conducted in aromatic solvents such as toluene and non-nucleophilic bases such as trialkylamines such as triethylamine may be employed.

Scheme 1

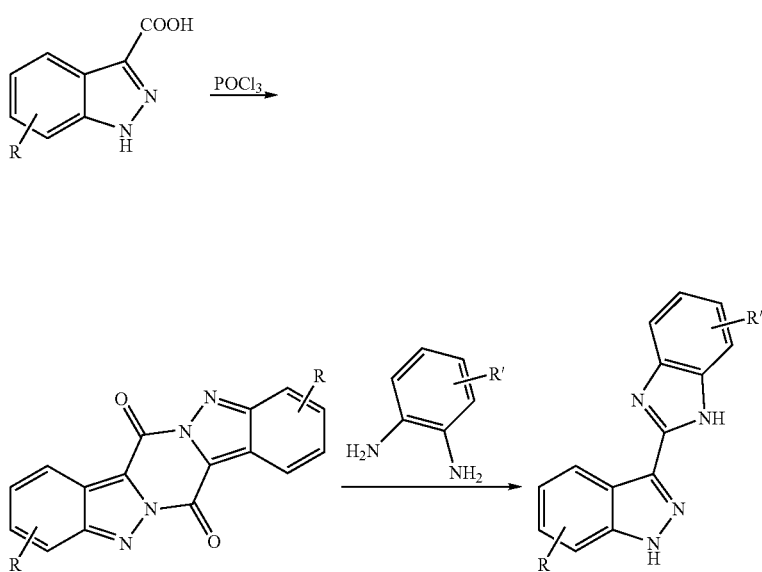

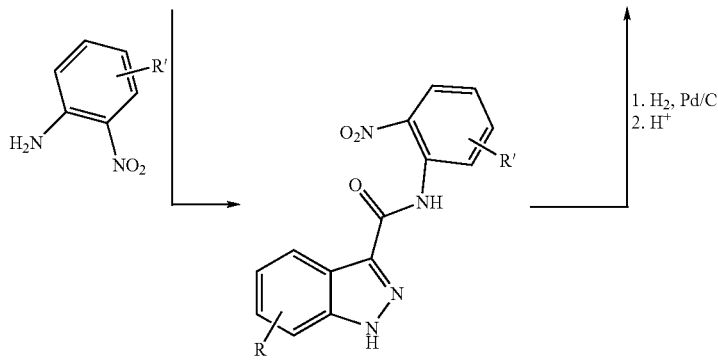

Therefore, according to one embodiment, the invention provides a method for synthesizing a substituted or unsubstituted indazole benzimidazole. The method includes: (a) reacting a dimer formed from two molecules of an indazole-3-carboxylic acid, wherein the six membered benzene ring of the indazole-3-carboxylic acid may be substituted or unsubstituted, with an amino compound selected from the group consisting of:

(i) a diaminobenzene derivative comprising a benzene ring and at least two amine groups bonded to adjacent carbon atoms in the benzene ring, wherein the benzene ring may be further substituted or may comprise 1,2-diaminobenzene, and further wherein the substituted or unsubstituted indazole benzimidazole is formed by reaction with the dimer;

(ii) a nitroaminobenzene derivative comprising a benzene ring, at least one nitro group, and at least one amine group, wherein the at least one amine group is bonded to a carbon atom in the benzene ring that is adjacent to another carbon atom in the benzene ring to which the at least one nitro group is bonded, further wherein the benzene ring may be further substituted or may comprise 1-amino-2-nitrobenzene, and further wherein an amide comprising a nitro group is formed by reaction with the dimer;

(iii) a first (protected amino)(amino)benzene derivative comprising a benzene ring, at least one protected amine group, and at least one —$NH_2$ group, wherein the at least one protected amine group is bonded to a first carbon atom in the benzene ring that is adjacent to a second carbon atom in the benzene ring to which the at least one —$NH_2$ group is bonded, further wherein the benzene ring may be further substituted or may only include H atoms bonded to the four other carbon atoms of the benzene ring, and further wherein an amide comprising at least one protected amine group is formed by reaction with the dimer; and (iv) a second (protected amino)(amino)benzene derivative comprising a benzene ring, at least one protected amine group, and at least one —$NH_2$ group, wherein the at least one protected amine group is bonded to a first carbon atom in the benzene ring that is adjacent to a second carbon atom in the benzene ring to which the at least one —$NH_2$ group is bonded, further wherein the benzene ring may be further substituted or may only include H atoms bonded to the four other carbon atoms of the benzene ring, further wherein the protected amine group comprises a protecting group that is removed during the reaction with the dimer such that the substituted or unsubstituted indazole benzimidazole is formed by the reaction with the dimer, wherein, if the dimer is reacted with the nitroaminobenzene derivative, the method further comprises (b):

(b) reducing the nitro group of the amide comprising the nitro group and cyclodehydrating to form the substituted or unsubstituted indazole benzimidazole;

and further wherein, if the dimer is reacted with the first (protected amino)(amino)benzene derivative, then the method further comprises (c):

(c) removing the protecting group from the amide comprising the at least one protected amine group and cyclodehydrating to form the substituted or unsubstituted benzimidazole.

In some embodiments, the dimer is reacted with the diaminobenzene derivative, the nitroaminobenzene derivative, the first (protected amino)(amino)benzene derivative, or the second (protected amino)(amino)benzene derivative in a toluene solution which may be a refluxing toluene solution in some embodiments. In some embodiments, the dimer is reacted with the diaminobenzene derivative, the nitroaminobenzene derivative, the first (protected amino)(amino)benzene derivative, or the second (protected amino)(amino)benzene derivative at a temperature of greater than 85° C. whereas in other embodiments, the temperature ranges from about 95° C. to about 111° C., from about 95° C. to about 105° C., or from about 98° C. to about 110° C.

In some embodiments, the method includes reacting the dimer with a salt such as hydrochloride, hydrobromide, dihydrochloride, dihydrobromide, or the like salt of the diaminobenzene derivative, the nitroaminobenzene derivative, the first (protected amino)(amino)benzene derivative, or the second (protected amino)(anino)benzene derivative. In other embodiments, the diaminobenzene derivative, the nitroaminobenzene derivative, the first (protected amino)(amino)benzene derivative, or the second (protected amino)(amino)benzene derivative is reacted with the dimer in the presence of a base such as, but not limited to, triethylamine, tripropylamine, tributylamine, ethyldipropylamine, propyldiethylamine, or the like.

In some embodiments, the method includes reacting the indazole-3-carboxylic acid with a reagent affecting the conversion of the acid to an acid halide or anhydride such as, but not limited to, cyanuric fluoride, tetramethylfluoroformamidinium hexafluorophosphate, cyanuric chloride, $SOCl_2$, $PCl_3$, $PCl_5$, $PBr_3$, $PBr_5$, $POCl_3$, carbonyl diimidazole/HCl, Oxalyl chloride, and carbodiimides, followed by in situ dimerization.

In some embodiments in which the nitroaminobenzene derivative is reacted with the dimer, the method includes reducing the nitro group of the amide with hydrogen using a hydrogenation catalyst such as, but not limited to, Pd on carbon, Pt on carbon, or the like. In some such embodiments, the catalyst is Pd on carbon. In some such embodiments, the reduced product is cyclodehydrated by treating the reduced product with an acid such as, but not limited to, acetic acid. In some cases the reduced product is cyclodehydrated by treating the reduced product with sodium acetate and acetic acid and heating such as at a reflux temperature. In some embodiments in which the first (protected amino)(amino)benzene derivative is reacted with the dimer, cyclodehydrating includes reacting the amine formed by removal of the protecting group with an acid such as, but not limited to, acetic acid. In some cases the amine formed by removal of the protecting group is cyclodehydrated by treating the reduced product with sodium acetate and acetic acid and heating such as at a reflux temperature. In some cases, the amide comprising the protected amine group formed by reaction of the first (protected amino)(amino)benzene derivative with the dimer is removed and the product is cyclodehydrated, in one procedure, using an acid. Most commonly used protective groups for amines are stable to the reaction with the dimer. Boc may come off during the reaction with the dimer, but only if the temperature is maintained at from 130-150° C. or higher. Examples of protective groups for the amines that are stable upon reaction with the dimer include, but are not limited to, carbamates such as, but not limited to, methyl ethyl, t-butyl, benzyl, and 9-fluorenylmethyl carbamates and the like; amides such as, but not limited to, acetamide, chloroacetamide, trifluoroacetamide, benzamide and the like; sulfonamides such as, but not limited to, benzenesulfonamide, p-toluenesulfonamide, trifluoromethanesulfonamide, and the like; and groups such as, but not limited to, N-allyl, N-benzyl, N-o-nitrobenzyl, N-p-methoxybenzyl, N-2,4-dimethoxybenzyl, N-triphenylmethyl, SEM, and the like. Groups which are sensitive to acids such as, but not limited to, N-2,4-dimethoxybenzyl, N-triphenylmethyl, may come off during cyclodehydration when it is performed in refluxing AcOH. If the cyclodehydration is performed in the presence of a non nucleophilic base such as triethylamine, some carbamates such as, but not limited to, 9-fluorenylmethyl carbamate and 2,4-dichlorobenzyl carbamate may be cleaved.

In some embodiments, the indazole-3-carboxylic acid used to form the dimer has the formula XII where $R^1$, $R^2$, $R^3$, $R^4$, and $R^9$ have any of the values set forth above with respect to the first, second, third, fourth, fifth, sixth, and seventh group of compounds having the formula I. Compound XII has the following structure.

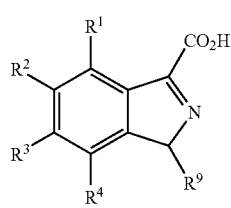

XII

In some embodiments, the dimer is a compound having the formula XIII where $R^1$, $R^2$, $R^3$, and $R^4$ have any of the values set forth above with respect to the first, second, third, fourth, fifth, sixth, and seventh group of compounds having the formula I. With respect to the indazole-3-carboxylic acid of formula XII and the dimer of formula XIII, one skilled in the art will recognize that certain nucleophilic $R^1$ through $R^4$ groups may need to be protected with suitable protecting groups prior to formation of the dimer or prior to reaction with the diaminobenzene derivative, the nitroaminobenzene derivative, the first (protected amino)(amino)benzene derivative, or the second (protected amino)(amino)benzene derivative. Compound of formula XIII have the following structure.

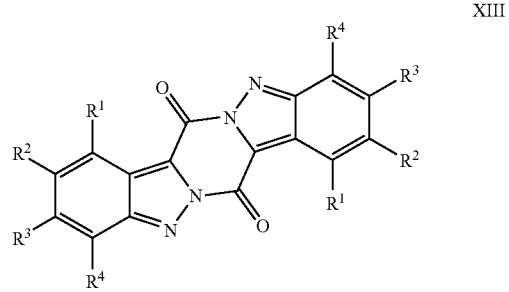

XIII

In some embodiments in which the diaminobenzene derivative is reacted with the dimer, the diaminobenzene derivative is a compound having the formula XIV where $R^5$, $R^6$, $R^7$, and $R^8$ have any of the values set forth above with respect to the first, second, third, fourth, fifth, sixth, and seventh group of compounds having the formula I. One skilled in the art will recognize that certain nucleophilic $R^5$ through $R^8$ groups may need to be protected with suitable protecting groups for reaction with the dimer. Compounds of formula XIV has the following structure.

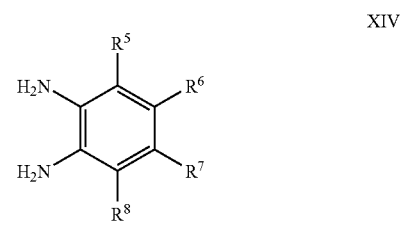

XIV

In some embodiments in which the nitroaminobenzene derivative is reacted with the dimer, the diaminobenzene derivative is a compound having the formula XVA or XVB where $R^5$, $R^6$, $R^7$, and $R^8$ have any of the values set forth above with respect to the first, second, third, fourth, fifth, sixth, and seventh group of compounds having the formula I. One skilled in the art will recognize that certain nucleophilic $R^5$ through $R^8$ groups may need to be protected with suitable protecting groups for reaction with the dimer. Compounds of formula XVA and XVB have the following structures.

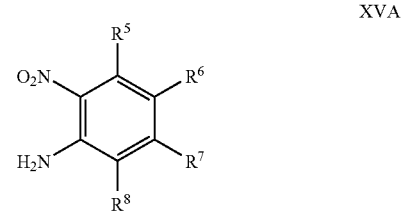

XVA

XVB

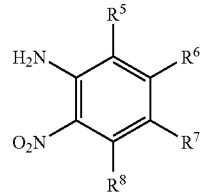

The indazole fragment may also be constructed from suitably substituted indoles via a nitrosation reaction to form a suitably substituted indazole-3-carbaldehyde as the key coupling precursor (Scheme 2). This strategy affords considerable flexibility in the synthesis of functionalized indazole benzimidazoles. By using appropriately substituted indole, 1,2-diaminobenzene, or 1,2-diaminoheteroaryl starting materials, many of which are commercially available or may be easily made by one of skill in the art, a wide variety of desired indazole benzimidazole compounds may be synthesized. Without being bound to hypothesis, it is believed that a hemiaminal intermediate compound is initially obtained which is then cyclooxidized to provide the substituted and unsubstituted indazole benzimidazole compounds of the invention. The suitably substituted indazole-3-carbaldehyde may alternatively be reacted with a suitably substituted monoprotected substituted or unsubstituted 1,2-diaminobenzene to form an imine that includes the protecting group. The intermediate imine product may then be deprotected and oxidatively cyclized to produce the desired indazole benzimidazole product. The suitably substituted indazole-3-carbaldehyde may also be reacted with a suitably substituted benzene bearing at least two amine groups one of which is protected with a suitable protecting group that provides a protected benzimidazole indazole product. Removal of the protecting group in such embodiments affords the indazole benzimidazole product. In another embodiment, the indazole-3-carbaldehyde may be reacted with a monoprotected substituted or unsubstituted 1,2-diaminobenzene derivative in a reaction in which the protecting group is lost and the indazole benzimidazole is formed. Generally, the $O_2$ for the oxidative cyclization step comes from that dissolved in the solvent in the reaction vessel. In one alternative embodiment, $O_2$ may be bubbled through the reaction mixture. In other embodiments, compounds which provide a source for $O_2$ such as nitrobenzene may be used in the oxidative cyclization to form the indazole benzimidazole product.

Scheme 2

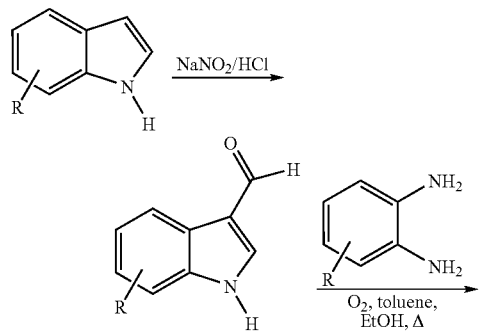

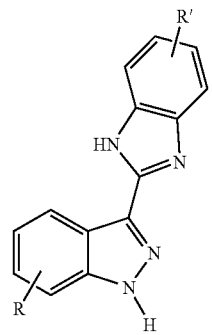

In one embodiment, the invention provides a first alternative method for synthesizing a substituted or unsubstituted indazole benzimidazole. The method includes reacting a substituted or unsubstituted indazole-3-carbaldehyde with an amino compound selected from the group consisting of:

(i) a diaminobenzene derivative comprising a benzene ring and at least two amine groups bonded to adjacent carbon atoms in the benzene ring, wherein the benzene ring may be further substituted or may comprise 1,2-diaminobenzene, and further wherein the substituted or unsubstituted indazole benzimidazole is formed by reaction with the substituted or unsubstituted indazole-3-carbaldehyde;

(ii) a first (protected amino)(amino)benzene derivative comprising a benzene ring, at least one protected amine group, and at least one —$NH_2$ group, wherein the at least one protected amine group is bonded to a first carbon atom in the benzene ring that is adjacent to a second carbon atom in the benzene ring to which the at least one —$NH_2$ group is bonded, further wherein the benzene ring may be further substituted or may only include H atoms bonded to the four other carbon atoms of the benzene ring, and further wherein a N-protected substituted or unsubstituted indazole benzimidazole is formed by reaction with the substituted or unsubstituted indazole-3-carbaldehyde;

(iii) a second (protected amino)(amino)benzene derivative comprising a benzene ring, at least one protected amine group, and at least one —$NH_2$ group, wherein the at least one protected amine group is bonded to a first carbon atom in the benzene ring that is adjacent to a second carbon atom in the benzene ring to which the at least one —$NH_2$ group is bonded, further wherein the benzene ring may be further substituted or may only include H atoms bonded to the four other carbon atoms of the benzene ring, and further wherein an imine comprising at least one protected amine group is formed by reaction with the substituted or unsubstituted indazole-3-carbaldehyde; and (iv) a third (protected amino)(amino)benzene derivative comprising a benzene ring, at least one protected amine group, and at least one —$NH_2$ group, wherein the at least one protected amine group is bonded to a first carbon atom in the benzene ring that is adjacent to a second carbon atom in the benzene ring to which the at least one —$NH_2$ group is bonded, further wherein the benzene ring may be further substituted or may only include H atoms bonded to the four other carbon atoms of the benzene ring, further wherein the protected amine group comprises a protecting group that is removed during the reaction with the substituted or unsubstituted indazole- 3-carbaldehyde such that the substituted or unsubstituted indazole benzimidazole is formed by the reaction with the substituted or unsubstituted indazole-3-carbaldehyde, wherein, if the substituted or unsubstituted indazole-3-carbaldehyde is reacted with the first (protected amino)(amino)benzene derivative, the method further comprises (b):

(b) removing the protecting group from the N-protected substituted or unsubstituted indazole benzimidazole to form the substituted or unsubstituted indazole benzimidazole;

and further wherein, if the substituted or unsubstituted indazole-3-carbaldehyde is reacted with the second (protected amino)(amino)benzene derivative, then the method further comprises (c):

(c) removing the protecting group from the imine comprising the at least one protected amine group and oxidatively cyclizing to form the substituted or unsubstituted benzimidazole.

In other embodiments, the diaminobenzene derivative, the first (protected amino)(amino)benzene derivative, the second (protected amino)(amino)benzene derivative, or the third (protected amino)(amino)benzene derivative is reacted with the indazole-3-carbaldehyde in the presence of a base such as, but not limited to, triethylamine, tripropylamine, tributylamine, ethyldipropylamine, propyldiethylamine, or the like.

In some embodiments of the first alternative methods, the method includes reacting the indazole-3-carbaldehyde with the diaminobenzene derivative, the first (protected amino)(amino)benzene derivative, the second (protected amino)(amino)benzene derivative, or the third (protected amino)(amino)benzene derivative in an aromatic solvent such as toluene, an alcohol solvent such as ethanol, or a combination of these such as a 3:1 toluene ethanol mixture. In other embodiments, the diaminobenzene derivative, the first (protected amino)(amino)benzene derivative, the second (protected amino)(amino)benzene derivative, or the third (protected amino)(amino)benzene derivative is reacted with the indazole-3-carbaldehyde at a temperature of greater than 85° C. whereas in other embodiments, the temperature ranges from about 95° C. to about 111° C., from about 95° C. to about 105° C., or from about 98° C. to about 110° C.

In some embodiments in which the first (protected amino)(amino)benzene derivative is reacted with the indazole-3-carbaldehyde to produce the N-protected indazole benzimidazole, the protected amino group is protected with a protecting group such as Bn, SEM, and the like. In some embodiments in which the second (protected amino)(amino)benzene derivative is reacted with the indazole-3-carbaldehyde to produce the imine, the protected amino group is protected with a protecting group such as Fmoc, Boc, and the like. In some embodiments in which the third (protected amino)(amino)benzene derivative is reacted with the indazole-3-carbaldehyde to produce the indazole benzimidazole, the protected amino group is protected with a protecting group such as TMS, TES, and the like.

In some embodiments, the indazole-3-carbaldehyde used to form the indazole benzimidazole is a compound having the formula XVI where $R^1$, $R^2$, $R^3$, and $R^4$ have any of the values set forth above with respect to the first, second, third, fourth, fifth, sixth, and seventh group of compounds having the formula I. Compound XVI has the following structure.

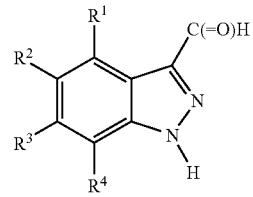

XVI

In some embodiments in which the diaminobenzene derivative is reacted with the indazole-3-carbaldehyde, the diaminobenzene derivative is a compound having the formula XIV as set forth above where $R^5$, $R^6$, $R^7$, and $R^8$ have any of the values set forth above with respect to the first, second, third, fourth, fifth, sixth, and seventh group of compounds having the formula I. One skilled in the art will recognize that certain nucleophilic $R^5$ through $R^8$ groups may need to be protected with suitable protecting groups for reaction with the indazole-3-carbaldehyde. In addition, certain $R^1$-$R^4$ groups such as —OH may require protection during reaction of the substituted indole with $NaNO_2$/HCl and during reaction with the diamine in toluene. Groups such as —OH may be protected with a suitable protecting groups such as Cbz which may then be removed after the indazole-3-carbaldehyde has been reacted with the diamine. Such transformation are well within the realm of those skilled in the art.

In some embodiments of the first alternative method of forming a substituted or unsubstituted indazole benzimidazole, the indazole-3-carbaldehyde, such as compounds of formula XVI, are formed by reacting a suitably substituted indole with $NaNO_2$. In such procedures, the reaction is generally conducted in the dark. The reaction may be protected from light by, for example, covering the reaction vessel with an opaque material such as aluminum foil or the like. In such procedures, a substituted or unsubstituted indole is generally added to a reaction vessel that includes an aqueous solution of $NaNO_2$ at an acidic pH such as at a pH ranging from at or about 2 to a pH of at or about 3. In one embodiment, the pH is at or about 2.5. The $NaNO_2$ solution is generally made acidic by adding an acid such as HCl or HBr although other acids may be employed for this purpose An organic solvent such as dioxane or tetrahydrofuran may be added to the aqueous NaNO solution along with the indole or prior to adding the indole. Generally, the indole is added slowly to the reaction vessel that contains the $NaNO_2$ solution. Suitable indoles for use in the synthesis of the indazole-3-carbaldehydes typically are compounds having the formula XVII where $R^1$ through $R^4$ have any of the values set forth above with respect to the first, second, third, fourth, fifth, sixth, and seventh groups of compound of formula I. Compounds of formula XVII have the following structure.

XVII

A wide variety of indoles are commercially available for use in preparing the indazole-3-carbaldydes of formula XVI. Examples of R¹ groups in commercially available indoles include, but are not limited to, —H, —F, —Cl, —CH₃, —CF₃, —OMe, —CO₂Me, —CO₂Et, —OBn, —C≡N, and the like. Examples of R² groups of commercially available indoles include, but are not limited to, —H, —F, —Cl, —Br, —OMe, —CF₃, and the like. Examples of R³ groups of commercially available indoles include, but are not limited to, —H, —F, —Cl, —OMe, —OBn, —CF₃, —C≡N, and the like. Examples of R⁴ groups of commercially available indoles include, but are not limited to, —H, —F, —Cl, —Br, -Et, —OMe, —CO₂Me, —CO₂Et, —OBn, —NO₂, and the like.

Scheme 3 illustrates just a few of the methods that may be used to produce a variety of 1,2-diamino benzenes. Halo (X=halogen) nitroanilines may be reacted with a wide variety of nucleophiles (Nu⁻) such as alcohols and amines to produce functionalized nitroanilines which may subsequently be reduced to diamines. The alcohol moiety of a nitroamino phenol may be modified using known methods to introduce a broad range of substituents into a diamine for subsequent inclusion in an indazole benzimidazole compound.

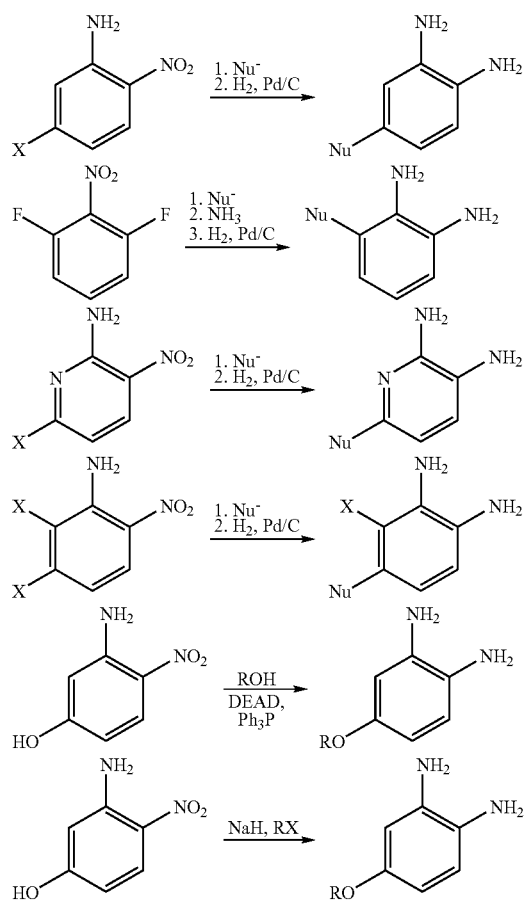

Scheme 3

In addition to the above schemes, it should be noted that various groups, including, but not limited to, hydroxyl groups and amine groups may be introduced into the indazole benzimidazole compounds of the present invention as protected groups using traditional protecting group chemistry. The use of standard protecting groups and the removal of such groups is well known in the art and various such groups may be used to prepare compounds in accordance with the present invention.

The instant invention also provides for compositions which may be prepared by mixing one or more compounds of the instant invention, or pharmaceutically acceptable salts or tautomers thereof, with pharmaceutically acceptable carriers, excipients, binders, diluents or the like to treat or ameliorate a variety of disorders related to the activity of VEGF-RTK, more particularly angiogenesis associated with cancer or related to the activity of KDR, Flt-1, Flt-3, Flk-1, bFGFR, GSK-3, NEK-2, CHK-1, cdc 2, Tie-2, c-ABL, CDC7, CSF1R, c-KIT and PDGF. The compositoins of the inventions may be used to create formulations and to inhibit tyrosine kinases and serine/threonine kinases. Such compositions can be in the form of, for example, granules, powders, tablets, capsules, syrup, suppositories, injections, emulsions, elixirs, suspensions or solutions. The instant compositions can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and (optionally other compounds such as, but not limited to, stabilizers, antimicrobial agents, anti-oxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

"Treating" within the context of the instant invention, means an alleviation of symptoms associated with a disorder or disease, or halt of further progression or worsening of those symptoms, or prevention or prophylaxis of the disease or disorder. For example, within the context of treating patients in need of an inhibitor of VEGF-RTK, successful treatment may include a reduction in the proliferation of capillaries feeding a tumor or diseased tissue, an alleviation of symptoms related to a cancerous growth or tumor, proliferation of capillaries, or diseased tissue, a halting in capillary proliferation, or a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anti-cancer drugs including those used in antisense and gene therapy. Appropriate combinations can be determined by those of skill in the oncology and medicine arts.

Pharmaceutical formulations and medicaments according to the invention include any of the compounds described above in combination with a pharmaceutically acceptable carrier. Thus, the compounds of the invention may be used to prepare medicaments and pharmaceutical formulations. In some such embodiments, the medicaments and pharmaceutical formulations comprise any of the compounds of any of the embodiments of the first, second, third, fourth, fifth, sixth, seventh, eighth, and/or ninth group of compounds of formula I or pharmaceutically acceptable salts thereof. The invention also provides for the use of any of the compounds of any of the embodiments of the first, second, third, fourth, fifth, sixth, seventh, eighth and/or ninth group of compounds of formula I or pharmaceutically acceptable salts thereof for the inhibition of an enzyme such as flt-1 (VEGFR1), Flt-3, KDR (VEGFR2), Flk-1, bFGFR, GSK-3, CHK-1, NEK-2, c-ABL, cdc 2, or for the treatment of a disease or condition associated with any of these enzymes as described in greater detail below. The invention also provides the use of any of the compounds of any of the embodiments of the first, second, third, fourth, fifth, sixth, seventh, eighth, and/or ninth group of compounds of formula I or pharmaceutically acceptable salts thereof for the manufacture of enzyme inhibition agent such as a tyrosine kinase inhibitor or a serine/threonine kinase inhibitor, a pharmaceutical formulation, or a medicament that inhibits enzymes such as flt-1 (VEGFR1), Flt-3, KDR (VEGFR2), Flk-1, bFGFR, GSK-3, CHK-1, NEK-2, cdc 2, PDGF, c-ABL, CDC7, CSF1R, c-KIT and Tie-2 or treats a disease or condition associated with any of these enzymes as described in greater detail below.

A method of treating a patient in need of an inhibitor of vascular endothelial growth factor receptor tyrosine kinase includes administering an effective amount of a pharmaceutical formulation, a medicament according to the invention or any of the compounds of any of the embodiments of the first, second, third, fourth, fifth, sixth, seventh, eighth, and/or ninth group of compounds of formula I to a patient in need thereof.

A method for inhibiting tumor growth in a patient includes administering an effective amount of the compound, a pharmaceutically acceptable salt thereof of any of the of the first, second, third, fourth, fifth, sixth, seventh, eighth, and/or ninth groups of compounds of formula I, or a medicament to a patient having a tumor.

A method for inhibiting angiogenesis and tumor growth in a patient includes administering an effective amount of the compound or a pharmaceutically acceptable salt thereof according to a patient in need.

The invention provides a method of treating a subject with various tumor types. The method includes administering to the subject, such as a human subject, a compound according to any of the embodiments of the first, second, third, fourth, fifth, sixth, seventh, eighth, and/or ninth group of compounds or a pharmaceutically acceptable salt thereof of formula I to the subject. In some such embodiments, the method includes a method of treating a cancer patient.

In one embodiment, the invention provides a method of inhibiting c-ABL. The method includes administering an effective amount of a compound, or a pharmaceutically acceptable salt thereof, of any of the embodiments of compounds set forth herein to a subject, such as a human, in need thereof. In some embodiments, the invention provides a method of treating a cancer such as chronic myelogeneous leukemia, acute lymphoblastic leukemia, or acute myeloblastic leukemia. In such methods, an effective amount of a compound according to any of the embodiments described herein is administered to a subject, such as a human cancer patient. In some embodiments the patient has a reciprocal translocation between chromosome 9 and 22.

The invention provides a method of inhibiting an enzyme such as a serine/threonine kinase. The method includes administering to a subject, such as a human subject, a mammalian subject, or a cell subject, a compound according to any of the embodiments of the first, second, third, fourth, fifth, sixth, seventh, eighth, and/or ninth group of compounds or a pharmaceutically acceptable salt thereof of formula I to the subject. In some such embodiments, the serine/threonine kinase is GSK-3. In other such embodiments, the serine/threonine kinase is CHK-1. In other such embodiments, the serine/threonine kinase is NEK-2.

The invention provides a method of inhibiting an enzyme such as a tyrosine kinase. The method includes administering to a subject, such as a human subject, a mammalian subject, or a cell subject, a compound according to any of the embodiments of the first, second, third, fourth, fifth, sixth, seventh, eighth, and/or ninth group of compounds or a pharmaceutically acceptable salt thereof of formula I to the subject. In some such embodiments, the tyrosine kinase is VEGF.

The invention provides a method of treating a subject with type II diabetes. The method includes administering to the subject, such as a human subject, a compound according to any of the embodiments of the first, second, third, fourth, fifth, sixth, seventh, eighth, and/or ninth group of compounds or a pharmaceutically acceptable salt thereof of formula I to the subject. In some such embodiments, the method includes a method of treating a prediabetic or diabetic patient.

The invention provides a method of stimulating insulin-dependent processes in a patient. The method includes administering to the patient, such as a human patient, a compound according to any of the embodiments of the first, second, third, fourth, fifth, sixth, seventh, eighth, and/or ninth group of compounds of formula I, or a pharmaceutically acceptable salt thereof, to the subject. In some such embodiments, the method includes a method of reducing plasma glucose levels, increasing glycogen uptake, potentiating insulin, upregulating glucose synthase activity, and stimulating glycogen synthesis such as in skin, muscle, and fat cells.

The invention provides a method of treating a subject with Alzheimer's disease. The method includes administering to the subject, such as a human subject, a compound according to any of the embodiments of the first, second, third, fourth, fifth, sixth, seventh, eighth, and/or ninth group of compounds of formula I, or a pharmaceutically acceptable salt thereof, to the subject. In some such embodiments, the method includes reducing tau hyperphosphorylation, reducing the generation of neurofibrillary tangles, and slowing the progression of Alzheimer's disease.

The invention provides a method of treating a subject with a central nervous system disorder. The method includes administering to the subject, such as a human subject, a compound according to any of the embodiments of the first, second, third, fourth, fifth, sixth, seventh, eighth, and/or ninth group of compounds of formula I, or a pharmaceutically acceptable salt thereof, to the subject. In some such embodiments, the method includes a method of treating bipolar disorder; increasing the survival of neurons subjected to aberrantly high levels of excitation induced by glutamate; reducing neurodegeneration asscociated with acute damage such as in cerebral ischemia, traumatic brain injury, and bacterial injury; and reducing chronic neuronal damage associated with Alzheimer's disease, Huntington's disease, Parkinson's disease, AIDS associated dementia, amyotrophic lateral sclerosis (AML) and multiple sclerosis.

The invention provides a method of prolonging an immune response in a subject. The method includes administering to the subject, such as a human subject, a compound according to any of the embodiments of the first, second, third, fourth, fifth, sixth, seventh, eighth, and/or ninth group of compounds of formula I, or a pharmaceutically acceptable salt thereof, to the subject. In some such embodiments, the method includes prolonging and/or potentiating immunostimulatory effects of cytokines, and enhancing the potential of cytokines for immunotherapy such as tumor immunotherapy.

The invention provides a method of reducing the splitting of centrosomes in the cells of a subject. The method includes administering to the subject, such as a human subject, a compound according to any of the embodiments of the first, second, third, fourth, fifth, sixth, seventh, eighth, and/or ninth group of compounds of formula I, or a pharmaceutically acceptable salt thereof, to the subject. In some such embodiments, the subject is a cancer patient.

The invention provides a method of blocking DNA repair in a cancer cell of a cancer patient. The method includes administering to the patient, such as a human patient, a compound according to any of the embodiments of the first, second, third, fourth, fifth, sixth, seventh, eighth, and/or ninth group of compounds of formula I, or a pharmaceutically acceptable salt thereof, to the patient.

The invention provides a method of promoting phosphorylation of cyc25 and Wee1 in a patient. The method includes administering to the patient, such as a human patient, a compound according to any of the embodiments of the first, second, third, fourth, fifth, sixth, seventh, eighth, and/or ninth group of compounds of formula I, or a pharmaceutically acceptable salt thereof, to the patient.

The invention provides a method of modulating and/or preventing cell cycle arrest in a cell. The method includes contacting the cell with a compound according to any of the embodiments of the first, second, third, fourth, fifth, sixth, seventh, eighth, and/or ninth group of compounds of formula I, or a pharmaceutically acceptable salt thereof. In one method, the cells are defective in the p53 gene and/or have p53 mutations and/or are deficient in p53. In some embodiments, the cells are cancer cells such as those deficient in p53. In some embodiments, arrest at the G2/M checkpoint is prevented or inhibited. In some embodiments, the method includes treating a patient, such as a human patient with any of the compounds of the invention, and in some such further embodiments; the method further includes treating the patient with another therapeutic agent such as a chemotherapeutic agent or with radiation or heat.

A method of preparing pharmaceutical formulations and medicaments includes mixing any of the above-described compounds with a pharmaceutically acceptable carrier.

The present invention, thus generally described, will be understood more readily by reference to the following examples, which are provided by way of illustration and are not intended to be limiting of the present invention.

EXAMPLES

Nomenclature for the Example compounds was provided using ACD Name version 5.07 software (Nov. 14, 2001) available from Advanced Chemistry Development, Inc., ChemInnovation NamExpert+Nomenclator™ brand software available from ChemInnovation Software, Inc., and AutoNom version 2.2 available in the ChemOffice® Ultra software package version 7.0 available from CambridgeSoft Corporation (Cambridge, Mass.). Some of the compounds and starting materials were named using standard IUPAC nomenclature.

The following abbreviations are used throughout the application with respect to chemical terminology:

AcOH: Acetic acid
ATP: Adenosine triphosphate
BINAP: 2,2'-Bis(diphenylphosphino)-1,1'-binaphthyl
Boc: N-tert-Butoxycarbonyl
Bn: Benzyl
BSA: Bovine Serum Albumin
Cbz: Carbobenzyloxy
DEAD: Diethyl azodicarboxylate
DIEA: Diisopropylethylamine
DMA: N,N-Dimethylacetamide
DMAP: 4-Dimethylaminopyridine
DMF: N,N-Dimethylformamide
DMSO: Dimethylsulfoxide
dppf: 1,1'(diphenylphosphino)ferrocene
DTT: DL-Dithiothreitol
$ED_{50}$: Dose therapeutically effective in 50% of the population
EDC or EDCI: 1-(3-Dimethylaminopropyl)-3-ethylcarbodiimide hydrochloride
EDTA: Ethylene diamine tetraacetic acid
EtOAc: Ethyl acetate
EtOH: Ethanol
Fmoc: 9-fluorenylmethyl
HBTU: O-Benzotriazol-1-yl-N,N,N', N'-tetramethyluronium hexafluorophosphate
HPLC: High Pressure Liquid Chromatography
$IC_{50}$ value: The concentration of an inhibitor that causes a 50% reduction in a measured activity.
KHMDS: Potassium bis(trimethylsilyl)amide
LC/MS: Liquid Chromatography/Mass Chromatography
LiHMDS: Lithium bis(trimethylsilyl)amide
MeOH: Methanol
NMP: N-methylpyrrolidone
Pd(dba)2: Bis(dibenzylideneacetone)Palladium
PPTS: Pyridinium p-toluenesulfonate
Pyr: Pyridine
SEMCl: 2-(Trimethylsilyl)ethoxymethyl chloride
TBAF: Tetrabutylammonium fluoride
TEA: Triethylamine
TES: Triethylsilyl
TFAA: Trifluoroacetic anhydride
THF: Tetrahydrofuran
TMS: Trimethylsilyl Purification and Characterization of Compounds Compounds of the present invention were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburg, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; Solvent system: 5-95% acetonitrile in water with 0.05% TFA; Flow rate 0.8 mL/min; Molecular weight range 150-850; Cone Voltage 20 V; Column temperature 40° C.) or a Hewlett Packard System (Series 1100 HPLC; Column: Eclipse XDB-C18, 2.1×50 mm; Solvent system: 1-95% acetonitrile in water with 0.05 % TFA; Flow rate 0.4 mL/min; Molecular weight range 150-850; Cone Voltage 50 V; Column temperature 30° C.). All masses are reported as those of the protonated parent ions.

GCMS analysis was performed on a Hewlet Packard instrument (HP6890 Series gas chromatograph with a Mass Selective Detector 5973; Injector volume: 1 µL; Initial column temperature: 50° C.; Final column temperature: 250° C.; Ramp time: 20 minutes; Gas flow rate: 1 mL/min; Column: 5% Phenyl Methyl Siloxane, Model #HP 190915-443, Dimensions: 30.0 m×25 µm×0.25 µm).

Preparative separations were carried out using either a Flash 40 chromatography system and KP-Sil, 60A (Biotage, Charlottesville, Va.), or by HPLC using a C-18 reversed phase column. Typical solvents employed for the Flash 40 Biotage system were dichloromethane, methanol, ethyl acetate, hexane and triethyl amine. Typical solvents employed for the reverse phase HPLC were varying concentrations of acetonitrile and water with 0.1% trifluoroacetic acid.

Various functionalized aryl diamines were obtained from commercial sources, prepared by methods know to those of skilled in the art, or were prepared by the following general methods:

METHOD 1

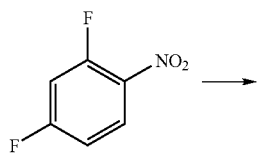

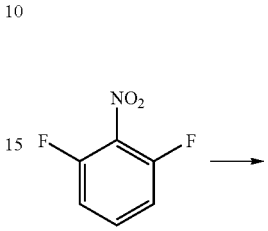

2,4-Difluoronitrobenzene (1.0 equivalent) was placed in a dry round-bottomed flask equipped with a dry ice condenser charged with acetone and dry ice. Ammonia was condensed into the flask and the resulting solution was stirred at reflux for 7 hours. A yellow precipitate formed within 1 hour. After 7 hours, the condenser was removed and the liquid ammonia was allowed to evaporate over several hours. The crude product was purified by flash chromatography on silica gel (85:15 hexanes:ethyl acetate, product at $R_f$=0.32, contaminant at $R_f$=0.51); GC/MS (m/z) 156.1 (M+), $R_t$ 11.16 minutes.

The resulting 5-fluoro-2-nitrophenylamine (1.0 equivalent) and an amine (1.1 equivalents) e.g. N-methyl piperazine, were dissolved in N-methylpyrrolidinone and triethylamine (2.0 equivalents) was added. The reaction mixture was heated at 100° C. for 3 hours. The solution was then cooled to room temperature and diluted with water. The resulting precipitate was filtered and dried under vacuum to provide the 2-amino-4-dialkylamino nitrobenzene or 4-dialkylamino nitroaniline. Alternatively, the same product may be obtained by the reaction of commercially available 5-chloro-2-nitrophenylamine (1.0 equivalent) and an amine (5 equivalents; neat). The two are heated at 130° C. for 1-2 days and the product is isolated in an identical manner. LC/MS (m/z) 237.1 (MH+), $R_t$ 1.304 minutes.

The nitroamine (1.0 equivalent) and 10% Pd/C (0.1 equivalents) were suspended in anhydrous ethanol at room temperature. The reaction flask was evacuated and subsequently filled with $H_2$. The resulting mixture was then stirred under a hydrogen atmosphere overnight. The resulting solution was filtered through Celite and concentrated under vacuum to provide the crude product which was used without further purification.

METHOD 2

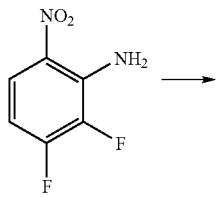

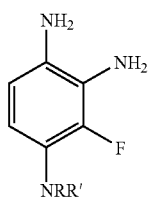

A round bottom flask was charged with 2,3-difluoro-6-nitrophenylamine (1 equivalent) and enough NMP to make a viscous slurry. An amine (5 equivalents), e.g. N-methyl piperazine, was added and the solution was heated at 100° C. After 2 hours, the solution was cooled and poured into water. A bright yellow solid formed which was filtered and dried. The nitroamine was reduced as in Method 1 to provide the crude product which was used without further purification. LC/MS (m/z) 225.1 (MH+), $R_t$ 0.335 minutes.

METHOD 3

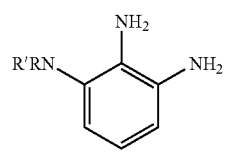

To a 0.1 M DMF solution of 1,3-difluoro-2-nitrobenzene was added $Et_3N$ (2 equivalents) followed by an amine (1 equivalent), e.g. morpholine. The mixture was stirred for 18 hours and then diluted with water and extracted with ethyl acetate. The combined organic layers were dried over $MgSO_4$, filtered, and concentrated. LC/MS (m/z): 227.2 (MH+), $R_t$ 2.522 minutes Ammonia was condensed into a bomb containing the crude product. The bomb was sealed and heated to 100° C. (over 400 psi). After 72 hours the bomb was allowed to cool and the ammonia was evaporated to provide a reddish solid. The nitroamine was reduced as in Method 1 to provide the crude product which was used without further purification. LC/MS (m/z) 194.1 (MH+), $R_t$ 1.199 minutes.

METHOD 4

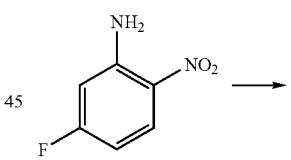

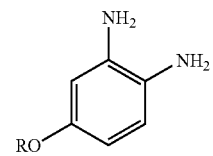

To a stirred N-methylpyrrolidinone solution containing NaH (1.3 equivalents) was added an alcohol (1.0 equivalent), e.g. 2-methoxyethanol. The resulting mixture was then stirred for 30 minutes. A slurry of 5-fluoro-2-nitrophenylamine in N-methylpyrrolidinone was then added slowly. The mixture was then heated to 100° C. After 2 hours, the reaction mixture was cooled and water was added. The mixture was then filtered and the solid was washed with water and purified by silica gel chromatography (1:1 ethyl acetate:hexane). LC/MS (m/z) 213.2 (MH+), $R_t$ 2.24 minutes. The nitroamine was reduced as in Method 1 to provide the crude product which was used without further purification. LC/MS (m/z) 183.1 (MH+), $R_t$ 0.984 minutes.

METHOD 5

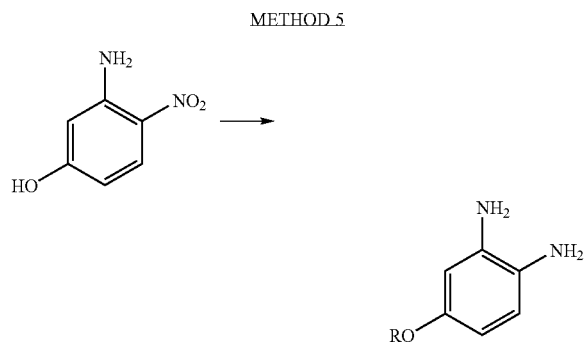

Diisopropyl azodicarboxylate (1.1 equivalents) was added dropwise to a stirred solution of 4-amino-3-nitrophenol (1.0 equivalent), triphenylphosphine (1.1 equivalents), and an alcohol, e.g. N-(2-hydroxyethyl)morpholine (1.0 equivalent), in tetrahydrofuran at 0° C. The mixture was allowed to warm to room temperature and stirred for 18 hours. The solvent was evaporated, and the product was purified by silica gel chromatography (98:2 $CH_2Cl_2$:methanol) to yield 4-(2-morpholin-4-ylethoxy)-2-nitrophenylamine as a dark reddish-brown oil. LC/MS (m/z) 268.0 (MH+), $R_t$ 1.01 minutes. The nitroamine was reduced as in Method 1 to give the crude product which was used without further purification. LC/MS (m/z) 238.3 (MH+), $R_t$ 0.295 minutes.

METHOD 6

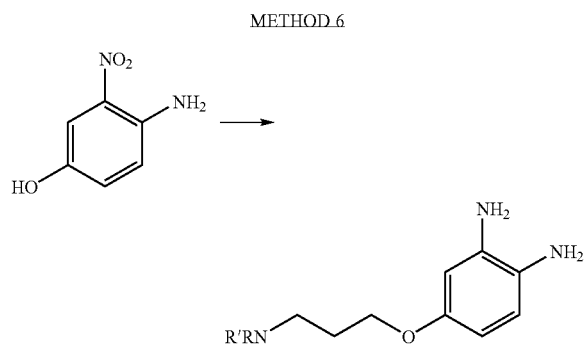

To a flask charged with 4-amino-3-nitrophenol (1 equivalent), $K_2CO_3$ (2 equivalents), and 2-butanone was added an alkyl dibromide, e.g. 1,3-dibromopropane (1.5 equivalents). The resulting mixture was then heated at 80° C. for 18 hours. After cooling, the mixture was filtered, concentrated, and diluted with water. The solution was then extracted with $CH_2Cl_2$ (3×) and the combined organic layers were concentrated to give a solid that was then washed with pentane. LC/MS (m/z) 275.1 (MH+), $R_t$ 2.74 minutes.

An acetonitrile solution of the bromide prepared above, an amine, e.g. pyrrolidine (5 equivalents), $Cs_2CO_3$ (2 equivalents) and $Bu_4NI$ (0.1 equivalents) was heated at 70° C. for 48 hours. The reaction mixture was cooled, filtered, and concentrated. The residue was dissolved in $CH_2Cl_2$, washed with water, and concentrated to give the desired nitroamine, e.g. 2-nitro-4-(3-pyrrolidin-1-ylpropoxy)phenylamine. LC/MS (m/z) 266.2 (MH+), $R_t$ 1.51 minutes. The nitroamine was reduced as in Method 1 to provide the crude product which was used without further purification.

METHOD 7

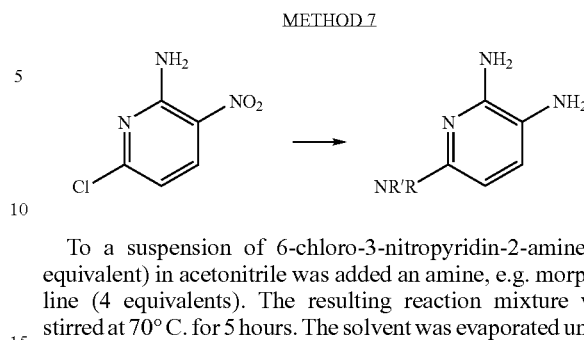

To a suspension of 6-chloro-3-nitropyridin-2-amine (1 equivalent) in acetonitrile was added an amine, e.g. morpholine (4 equivalents). The resulting reaction mixture was stirred at 70° C. for 5 hours. The solvent was evaporated under reduced pressure, and the residue triturated with ether to provide the desired compound as a bright yellow powder. LC/MS (m/z) 225.0 (MH+), $R_t$ 1.79 minutes. The nitroamine was reduced as in Method 1 to provide the crude product which was used without further purification.

Method 8

Synthesis of {[(5S,2R)-4-(3-Amino-4-nitrophenyl)-5-methylmorpholin-2-yl]methyl}dimethylamine and {[(5S,2R)-4-(3,4-diaminophenyl)-5-methyhnorpholin-2-yl]methyl}dimethylamine Step 1. Synthesis of (2S)-[benzylamino]propan-1-ol

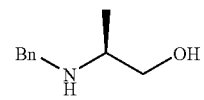

A mixture of (2S)-2-amino propanol (1.2 equivalents), benzaldehyde (1 equivalent), $NaHCO_3$ (1.5 equivalents) and MeOH, was heated at reflux for 4 hours and then cooled to 0° C. Sodium borohydride (5.0 equivalents) was then added over 1 hour while the reaction was vigorously stirred. The reaction mixture was stirred at room temperature for 4 hours and then filtered over Celite. The filtrate was concentrated, and the residue was dissolved in $CH_2C_2$. The solution was washed successively with water (×2) and brine (×1). The organic extracts were collected and dried over $Na_2SO_4$. The solvent was evaporated to give the desired product as a white solid. GC/MS: 134 (100%, M+-$CH_2OH$), $R_t$=11.57 minutes.

Step 2. Synthesis of (2S,5S)-2-(chloromethyl)-5-methyl-4-benzylmorpholine

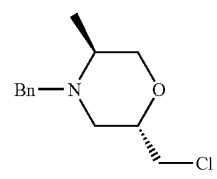

A mixture of (2S)-2-[benzylamino]propan-1-ol (1 equivalent) and epichlorohydrin (1 equivalent) was stirred at room temperature overnight. The mixture was cooled down to 0° C. and cold trifluoromethanesulfonic acid (4 equivalents) was added. The flask was equipped with a reflux condenser and the mixture was stirred at 160° C. overnight. The reaction mixture was cooled to room temperature, diluted with CH₂Cl₂ and quenched with ice water. The mixture was then made basic (pH=12) with a 30% NaOH solution. The two phases were separated, and the aqueous phase was extracted with CH₂Cl₂. The organic layer was washed with water, brine, dried over Na₂SO₄ and concentrated to afford a dark brown oil. The crude product contained an equimolar mixture of (2R,5S)-2-(chloromethyl)-5-methyl-4-benzylmorpholine (cis diastereoisomer) and (2S,5S)-2-(chloromethyl)-5-methyl-4-benzylmorpholine(trans diastereoisomer), which were separated by chromatography on silica gel (ethyl acetate/hexanes 1:20 to 1:8). (2S,5S)-2-(chloromethyl)-5-methyl-4-benzyl morpholine was obtained as the isomer with the lower $R_f$. GC/MS: 239 (15%, M+), $R_t$=15.08 minutes; LC/MS (m/z): 240.0 (MH+), $R_t$ 1.56 minutes.

Step 3. Synthesis of {[(5S,2R)-5-methyl-4benzyl-morpholin-2-yl]methyl}dimethylamine

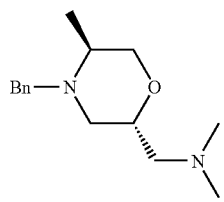

A mixture of (2S,5S)-2-(chloromethyl)-5-methyl-4-benzylmorpholine (1 equivalent) and dimethylamine (5 equivalents) in ethanol, was heated at 150° C. for 36 hours in a sealed high pressure vessel. The reaction mixture was cooled to room temperature and concentrated under reduced pressure. The residue was taken up in 1 N HCl, and the solution was washed with CH₂Cl₂. The water phase was made basic with a 30% aq. NaOH solution (pH=12) and extracted with CH₂Cl₂. The organic extracts were collected and dried over Na₂SO₄. Evaporation of the solvent under reduced pressure afforded (2S,5S)-2-[dimethylamino(methyl)]-5-methyl-4-benzylmorpholine as a yellow oil. GC/MS: 247 (2%, M-H), 204 (55%, M-NMe₂), $R_t$=15.5 min; LC/MS (m/z): 249.2 (MH+), $R_t$ 0.72 minutes.

Step 4. Synthesis of [((2S,5S)-5-methylmorpholin-2-yl)methyl]dimethylamine

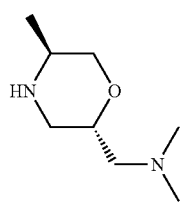

{[(5S,2R)-5-methyl-4-benzylmorpholin-2-yl]methyl}dimethylamine (1 equivalent), was dissolved in EtOH and the solution was transferred to a stainless steel high pressure vessel equipped with a pressure gauge. 10% Pd/C was added (10 wt. %), and the vessel charged with H₂. The reaction mixture was stirred at 130° C. and 200 psi of H₂ overnight. The reaction mixture was cooled to room temperature, filtered over a pad of Celite, and then evaporated. The desired amine was obtained in quantitative yield as a pale yellow oil. GC/MS: 128 (10%, M+−2×CH₃), 58 (100%, NHCH₂CHO), $R_t$=8.16 minutes.

Step 5. Synthesis of {[(5S,2R)-4(3-amino-4-nitro-phenyl)-5-methylmorpholin-2-yl]methyl}dimethylamine

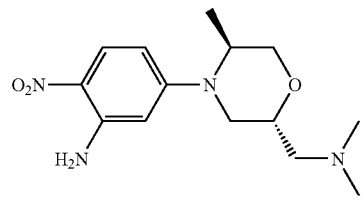

A mixture of 5-fluoro-2-nitroaniline (1.1 equivalents), [((2S,5S)-5-methylmorpholin-2-yl)methyl]dimethylamine (1 equivalent), triethylamine (3 equivalents), and N-methylpyrrolidinone was heated at 140° C. for 48 hours in a sealed high pressure vessel. The reaction mixture was then cooled to 25° C. and dissolved in CH₂Cl₂. The solution was washed with water (×2) and dried over Na₂SO₄. Purification via chromatography on silica gel (10% MeOH in dichloromethane) afforded the desired product as a dark yellow foam. LC/MS (m/z) 295.2 (MH+) $R_t$ 1.55 minutes.

Step 6. Synthesis of {[(5S,2R)-4(3,4-Diaminophenyl)-5-methylmorpholin-2-yl]methyl}dimethylamine

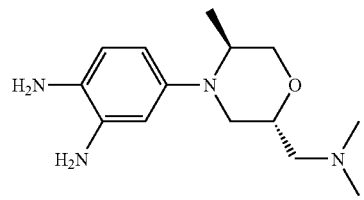

The nitroaniline produced in Step 5 was reduced using the method set forth in Method 1 to provide the crude title compound which was used without further purification.

Method 9

Synthesis of 1,2-diamino-3-methyl-4-fluorobenzene

Step 1. Synthesis of N-(3-fluoro-2-methylphenyl)acetamide

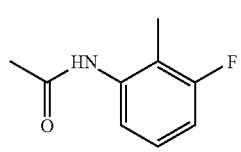

1-amino-3-fluoro-2-methylbenzene (1 equivalent) was dissolved in CH₂C₂ and acetic anhydride (2.0 equivalents) was added slowly. The solution was stirred at room temperature for 4 hours. The reaction mixture was then quenched with water, and the aqueous layer was extracted with ethyl acetate.

The organic layer was washed with H₂O, a 10% HCl solution, H₂O, and brine. It was then dried over Na₂SO₄ and concentrated in vacuo, to yield N-(3-fluoro-2-methylphenyl)acetamide as a pink solid. LC/MS (m/z) 168.2 (MH+), $R_t$ 1.91 minutes.

Step 2. Synthesis of
1-amino-3-fluoro-2-methyl-4-nitrobenzene

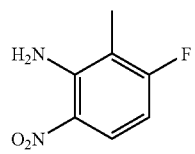

A mixture of HNO₃/H₂SO₄ (1:1, 60% HNO₃:conc. H₂SO₄) cooled to 0° C. was added dropwise to N-(3-fluoro-2-methylphenyl)acetamide to form a 0.16 M solution. The solution was stirred at 0° C. for 10 minutes and then at room temperature for 30 minutes. The solution was then diluted with water and made basic (pH=10) by addition of 6 N NaOH. The mixture was then extracted CH₂Cl₂ (3×), dried over Na₂SO₄, and concentrated in vacuo to yield 1-amino-3-fluoro-2-methyl-6-nitrobenzene (the acetyl group was removed during basic work up). LC/MS (m/z) 171.1 (MH+), $R_t$ 1.87 minutes.

Step 3. Synthesis of
1,2-diamino-4-fluoro-3-methylbenzene

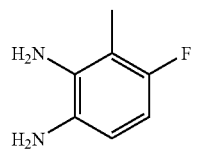

Reduction of the nitro group on 1-amino-3-fluoro-2-methyl-6-nitrobenzene was carried out as described in Method 1 to yield the title compound. LC/MS (m/z) 141.1 (MH+), $R_t$ 0.43 minutes.

Method 10

Synthesis of 4-(4-dimethylamino-2-methylpyrrolidin-1-yl)-1,2-diaminobenzene

Step 1. Synthesis of
(2S,4S)-4-dimethylamino-2-methylpyrrolidin

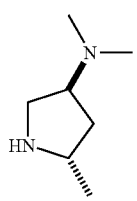

(2S,4S)-4-dimethylamino-2-methylpyrrolidine was synthesized from the Boc-protected cis-4-hydroxy-D-proline methyl ester (available from Bachem) as described in T. Rosen, D. T. W. Chu, I. M. Lico, P. B. Gernandes, K. Marsh, L. Shen, V. G. Cepa, A. G. Pernet, *J. Med. Chem.*, 1988, 31(8), 1598-1611.

Step 2. Synthesis of 3-[(2S,4S)-4-dimethylamino-2-methylpyrrolidin-1-yl]-1-amino-6-nitrobenzene

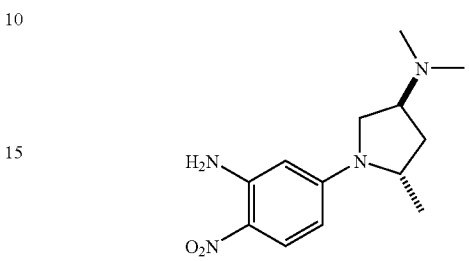

(2S,4S)-4-dimethylamino-2-methylpyrrolidine (1.0 equivalent) and 1-amino-3-fluoro-6-nitrobenzene (1.2 equivalents) were dissolved in N-methylpyrrolidinone, and Et₃N (5.0 equivalents) was added. The solution was heated for 5 hours at 100° C. The solution was then cooled and diluted with water. The aqueous layer was extracted with ethyl acetate. The organic layer was then washed twice with H₂O, once with brine, dried over Na₂SO₄, filtered, and concentrated. The crude material was purified by column chromatography (1:1 ethyl acetate:hexane to 1:20 MeOH:ethyl acetate to 1:1 MeOH:ethyl acetate to give the title compound as a yellow gum. LC/MS (m/z) 265.2 (MH⁺), $R_t$ 1.65 minutes.

Step 3. Synthesis of 4-[(2S,4S)-4-dimethylamino-2-methylpyrrolidin-1-yl]-1,2-diaminobenzene

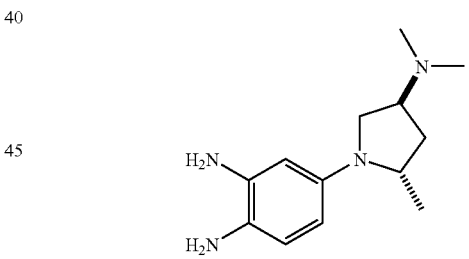

3-[(2S,4S)-4-Dimethylamino-2-methylpyrrolidin-1-yl]-1-amino-6-nitrobenzene was reduced as in Method 1 to afford the title compound. LC/MS (m/z) 235.4 (MH⁺), $R_t$ 0.37 minutes.

Example 1

3-(1H-Benzimidazol-2-yl)-1H-indazole

Synthesis of 11a,5a-Dihydro-1H-indazolo[2',3'-2,1]piperazino[4,5-b]1H-indazole-6,12-dione Indazole-3-carboxylic acid (1.0 equivalents) was dissolved in phosphorus oxychloride (0.05 equivalents) and refluxed. After 4 hours, the mixture was cooled and concentrated in vacuo. The resulting dione was washed three times with benzene, dried, and isolated as a red solid. LC/MS (m/z) 289.1 (MH$^+$), $R_t$ 2.90 minutes.

Synthesis of 3-(1H-Benzimidazol-2-yl)-1H-indazole

A toluene solution containing 11a,5a-dihydro-1H-indazolo[2',3'-2,1]piperazino[4,5-b]1H-indazole-6,12dione (1.0 equivalent) and phenylenediamine (1.5 equivalents), was heated to 100° C. After 18 hours, the solvent was evaporated and the residue was washed repeatedly with water, followed by methanol, and then filtered. Purification by reverse phase preparatory HPLC gave the title compound as a yellow solid. LC/MS (m/z) 235.3 (MH$^+$), $R_t$ 1.90 minutes.

Example 2

3-(6-Methoxy-1H-benzimidazol-2-yl)-1H-indazole

Procedure 1
A solution of 11a,5a-dihydro-1H-indazolo[2',3'-2,1]piperazino[4,5-b]1H-indazole-6,12-dione (1.0 equivalent) from Example 1 and 4-methoxy-o-phenylenediamine dihydrochloride (1.5 equivalents) in toluene was heated to 100° C. After 36 hours, the solvent was evaporated and the residue was washed repeatedly with water. The filtrate lyophilized, and the recovered material was purified by reverse phase HPLC yielding the title compound as a grey solid. LC/MS (m/z) 265.3 (MH$^+$), $R_t$ 2.04 minutes.
Procedure 2
A solution containing of 11a,5a-dihydro-1H-indazolo[2',3'-2,1]piperazino[4,5-b]1H-indazole-6,12-dione (1.0 equivalent) from Example 1, and 4-methoxy-o-phenylenediamine dihydrochloride (1.5 equivalents) in toluene was heated at reflux. After two days, the solvent was evaporated and the residue was washed repeatedly with water. The filtrate was frozen and lyophilized, and the recovered material was purified by reverse phase HPLC yielding the title compound as a grey solid. LC/MS (m/z) 265.3 (MH$^+$), $R_t$ 2.04 minutes.

Example 3

3-{6-[(2R,6S)-2,6-Dimethylmorpholin-4-yl]-1H-benzimidazol-2-yl}-1H-indazole

Synthesis of 1H-Indazol-3-yl-N-[5-((6S,2R)-2,6-dimethylmorpholin-4-yl)-2-nitrophenyl]carboxamide A toluene solution containing 5-[cis-(6S,2R)-2,6-dimethylmorpholin-4-yl)]-2-nitroaniline (2.0 equivalents; synthesized following the procedure described in Method 1 starting from 2,6-cis-dimethylmorpholine and omitting the reduction step), 11a,5a-dihydro-1H-indazolo[2',3'-2,1]piperazino[4,5-b]1H-indazole-6,12-dione from Example 1 (1.0 equivalent), and Et$_3$N (2.1 equivalents) was heated at reflux for two days. The resulting mixture was then cooled and filtered. The crude material was washed with methanol to provide a brown solid LC/MS (m/z) 396.1 (MH$^+$), $R_t$ 3.44 minutes.

Synthesis of 1H-Indazol-3-yl-N-[5-((6S,2R)-2,6-dimethylmorpholin-4-yl)-2-aminophenyl]carboxamide To a solution of 1H-indazol-3-yl-N-[5-((6S,2R)-2,6-dimethyl-morpholin-4-yl)-2-nitrophenyl]carboxamide (1.0 equivalent) in ethanol was added 10% Pd/C (0.5 equivalents). The reaction vessel was repeatedly purged with nitrogen, and then the reaction was stirred under a hydrogen atmosphere (1 atm) for 18 hours. The product was filtered through Celite with ethanol. The solvent was removed to provide a brown solid which was used without purification. LC/MS (m/z) 366.2 (MH$^+$), $R_t$ 2.19 minutes.

Synthesis of 3-{6-[(2R,6S)-2,6-Dimethylmorpholin-4-yl]-1H-benzimidazol-2-yl}-1H-indazole 1H-Indazol-3-yl-N-[5-((6S,2R)-2,6-dimethyl-morpholin-4-yl)-2-aminophenyl]carboxamide (1.0 equivalent) was dissolved in acetic acid, and sodium acetate (1.1 equivalents) was added. The solution was heated at reflux for 1 hour and then cooled. The acetic acid was removed, and the residue was triturated with ethyl acetate and filtered. The filtrate was concentrated to provide a green foam which was purified by reverse phase HPLC. LC/MS (m/z) 348.1 (MH$^+$), $R_t$ 2.23 minutes.

Example 4

5-Chloro-3-(5-methyl-1H-benzimidazol-2-yl)-1H-indazole

Procedure 1
A 0.25 M aqueous solution of NaNO$_2$ (1.0 equivalent) was brought to a pH of 2.5 by the addition of dilute HCl. Dioxane was added to the solution (10% by volume). The flask was protected from light with aluminum foil and 5-chloroindole (1.0 equivalent) was added slowly. The solution was stirred vigorously for 2 hours. The solution was then extracted with three portions of ethyl acetate. The organic layers were combined, washed with water, dried over MgSO$_4$, filtered, and concentrated. The product was purified by flash chromatography (ethyl acetate:hexane, 1:1, v/v) yielding 5-chloro-1H-indazole-3-carbaldehyde as a purple solid. LC/MS (m/z) 181.3 (MH+), $R_t$ 2.7 minutes.
A flask was charged with 5-chloro-1H-indazole-3-carbaldehyde (1.0 equivalent) and 3,4-diaminotoluene (1.0 equivalent) in toluene and ethanol (approximately 3:1). The flask was heated to 100° C. for 18 hours. The solvent was evaporated, and the residue purified by reverse phase HPLC to provide the desired product as a white solid. LC/MS (m/z) 283.1 (MH$^+$), $R_t$ 2.5 minutes.
Procedure 2
A 0.05 M solution of NaNO$_2$ (1.0 equivalent) was brought to a pH of 2.5 with the addition of dilute HCl. The flask was protected from light with foil and 5-chloroindole (1.0 equivalent) was added slowly. The solution was left to stir vigorously for 2 hours. The solution was then filtered and extracted with three portions of ethyl acetate. The organic layers were combined, dried over MgSO$_4$, filtered, and concentrated. The product was purified by flash chromatography (ethyl acetate: hexane, 1:1, v/v) yielding a purple solid. LC/MS (m/z) 181.3 (MH+), $R_t$ 2.7 minutes.
A flask was charged with 5-chloro-1H-indazole-3-carbaldehyde (1.0 equivalent) and 3,4-diaminotoluene (1.0 equivalent) in toluene and EtOH. The reaction mixture was heated to 100° C. for 18 hours. The solvent was then evaporated, and the residue was purified by reverse phase HPLC yielding a white solid. LC/MS (m/z) 283.1 (MH+), $R_t$ 2.5 minutes.

Examples 5-670

Examples 5-670 were synthesized following the indole modification and coupling procedure of Example 4. The aryl diamine and the indole precursors are readily recognizable by one skilled in the art and are commercially available from Aldrich (Milwaukee, Wis.) or Acros Organics (Pittsburgh, Pa.). 5-Fluoro-6-chloroindole, 6-(trifluoromethyl)indole, 6-nitroindole, and 5-carbethoxyindole may be obtained from Biosynth International (Naperville, Ill.). 5,6-Difluoroindole and 4,6-difluoroindole may be obtained from Asymchem International, Inc. (Durham, N.C.). 5,6-Methylenedioxyindole may be obtained from Maybridge Chemical Company Ltd. (Cornwall, UK). N-(4-Morpholinoethyl)indole-6-carboxamide may be obtained from Peakdale Molecular (High Peak, UK). The preparation for some of the compounds employed is described in the various methods disclosed herein.

| Example | Name | LC/MS (m/z) (MH+) |
|---|---|---|
| 5 | 3-(5-morpholin-4-yl-1H-benzimidazol-2-yl)-1H-indazole | 320.1 |
| 6 | 5-chloro-3-{5-[(2R,6S)-2,6-dimethylmorpholin-4-yl]-1H-benzimidazol-2-yl}-1H-indazole | 382.1 |
| 7 | 3-{5-[(2R,6S)-2,6-dimethylmorpholin-4-yl]-1H-benzimidazol-2-yl}-5-fluoro-1H-indazole | 366.2 |
| 8 | 3-{5-[(3R,5S)-3,5-dimethylpiperazin-1-yl]-1H-benzimidazol-2-yl}-1H-indazole | 347.2 |
| 9 | 3-{5-[(3R,5S)-3,5-dimethylpiperazin-1-yl]-1H-benzimidazol-2-yl}-5-fluoro-1H-indazole | 365.2 |
| 10 | 3-[5-(3-pyrrolidin-1-ylpropoxy)-1H-benzimidazol-2-yl]-1H-indazole | 362.3 |
| 11 | 5-fluoro-3-[5-(3-pyrrolidin-1-ylpropoxy)-1H-benzimidazol-2-yl]-1H-indazole | 380.1 |
| 12 | 6-fluoro-3-[5-(3-pyrrolidin-1-ylpropoxy)-1H-benzimidazol-2-yl]-1H-indazole | 380.1 |
| 13 | 6-chloro-3-[5-(3-pyrrolidin-1-ylpropoxy)-1H-benzimidazol-2-yl]-1H-indazole | 396.1 |
| 14 | 3-[5-(3-pyrrolidin-1-ylpropoxy)-1H-benzimidazol-2-yl]-1H-indazole-5-carbonitrile | 387.2 |
| 15 | 3-[5-(2-methoxyethoxy)-1H-benzimidazol-2-yl]-1H-indazole | 309.2 |
| 16 | 5-fluoro-3-[5-(2-methoxyethoxy)-1H-benzimidazol-2-yl]-1H-indazole | 327.2 |
| 17 | 6-fluoro-3-[5-(2-methoxyethoxy)-1H-benzimidazol-2-yl]-1H-indazole | 327.2 |
| 18 | 3-{5-[(2R,6S)-2,6-dimethylmorpholin-4-yl]-1H-benzimidazol-2-yl}-6-fluoro-1H-indazole | 366.3 |
| 19 | 6-chloro-3-{5-[(2R,6S)-2,6-dimethylmorpholin-4-yl]-1H-benzimidazol-2-yl}-1H-indazole | 382.3 |
| 20 | ethyl {4-[2-(1H-indazol-3-yl)-1H-benzimidazol-5-yl]piperazin-1-yl}acetate | 405.3 |
| 21 | (3S)-1-[2-(1H-indazol-3-yl)-1H-benzimidazol-5-yl]-N,N-dimethylpyrrolidin-3-amine | 347.1 |
| 22 | 2-(1H-indazol-3-yl)-5-morpholin-4-yl-1H-imidazo[4,5-b]pyridine | 321.3 |
| 23 | 2-(6-fluoro-1H-indazol-3-yl)-5-morpholin-4-yl-1H-imidazo[4,5-b]pyridine | 339.1 |
| 24 | 2-(5-methoxy-1H-indazol-3-yl)-5-morpholin-4-yl-1H-imidazo[4,5-b]pyridine | 351.3 |
| 25 | 3-(5-morpholin-4-yl-1H-imidazo[4,5-b]pyridin-2-yl)-1H-indazole-5-carbonitrile | 346.3 |
| 26 | 5-[(3R,5S)-3,5-dimethylpiperazin-1-yl]-2-(1H-indazol-3-yl)-1H-imidazo[4,5-b]pyridine | 348.2 |
| 27 | 5-[(3R,5S)-3,5-dimethylpiperazin-1-yl]-2-(6-fluoro-1H-indazol-3-yl)-1H-imidazo[4,5-b]pyridine | 366.2 |
| 28 | 5-[(3R,5S)-3,5-dimethylpiperazin-1-yl]-2-(5-methoxy-1H-indazol-3-yl)-1H-imidazo[4,5-b]pyridine | 378.3 |
| 29 | 3-[6-(pyridin-3-ylmethoxy)-1H-benzimidazol-2-yl]-1H-indazole | 342.2 |
| 30 | 6-fluoro-3-[6-(pyridin-3-ylmethoxy)-1H-benzimidazol-2-yl]-1H-indazole | 359.8 |
| 31 | 6-chloro-5-fluoro-3-[6-(pyridin-3-ylmethoxy)-1H-benzimidazol-2-yl]-1H-indazole | 393.8 |
| 32 | 4,6-difluoro-3-[6-(pyridin-3-ylmethoxy)-1H-benzimidazol-2-yl]-1H-indazole | 377.9 |
| 33 | 3-[6-(pyridin-3-ylmethoxy)-1H-benzimidazol-2-yl]-1H-indazole-5-carbonitrile | 367.1 |
| 34 | 6-fluoro-3-[6-(pyridin-4-ylmethoxy)-1H-benzimidazol-2-yl]-1H-indazole | 360.2 |
| 35 | 4,6-difluoro-3-[6-(pyridin-4-ylmethoxy)-1H-benzimidazol-2-yl]-1H-indazole | 377.2 |
| 36 | 1'-[2-(1H-indazol-3-yl)-1H-benimidazol-6-yl]-1,4'-bipiperidine | 401.3 |
| 37 | 1'-[2-(6-fluoro-1H-indazol-3-yl)-1H-benzimidazol-6-yl]-1,4'-bipiperidine | 419.3 |

-continued

| Example | Name | LC/MS (m/z) (MH+) |
|---|---|---|
| 38 | 1'-[2-(6-chloro-5-fluoro-1H-indazol-3-yl)-1H-benzimidazol-6-yl]-1,4'-bipiperidine | 453.3 |
| 39 | 1'-[2-(4,6-difluoro-1H-indazol-3-yl)-1H-benzimidazol-6-yl]-1,4'-bipiperidine | 437.2 |
| 40 | 3-[6-(4-cyclohexylpiperazin-1-yl)-1H-benzimidazol-2-yl]-1H-indazole | 401.3 |
| 41 | 3-[6-(4-cyclohexylpiperazin-1-yl)-1H-benzimidazol-2-yl]-6-fluoro-1H-indazole | 419.3 |
| 42 | 6-chloro-3-[6-(4-cyclohexylpiperazin-1-yl)-1H-benzimidazol-2-yl]-5-fluoro-1H-indazole | 453.3 |
| 43 | 3-[6-(4-cyclohexylpiperazin-1-yl)-1H-benzimidazol-2-yl]-4,6-difluoro-1H-indazole | 437.2 |
| 44 | 3-[6-(4-acetylpiperazin-1-yl)-1H-benzimidazol-2-yl]-1H-indazole | 361.2 |
| 45 | 3-[6-(4-acetylpiperazin-1-yl)-1H-benzimidazol-2-yl]-6-fluoro-1H-indazole | 379.2 |
| 46 | 3-[5-(4-acetylpiperazin-1-yl)-1H-benzimidazol-2-yl]-4,6-difluoro-1H-indazole | 397.2 |
| 47 | 3-[6-(4-acetylpiperazin-1-yl)-1H-benzimidazol-2-yl]-6-chloro-5-fluoro-1H-indazole | 413.1 |
| 48 | 2-(1H-indazol-3-yl)-N-methyl-N-(1-methylpiperidin-4-yl)-1H-benzimidazol-6-amine | 362.2 |
| 49 | 2-(6-fluoro-1H-indazol-3-yl)-N-methyl-N-(1-methylpiperidin-4-yl)-1H-benzimidazol-6-amine | 379.2 |
| 50 | 2-(4,6-difluoro-1H-indazol-3-yl)-N-methyl-N-(1-methylpiperidin-4-yl)-1H-benzimidazol-6-amine | 397.2 |
| 51 | 2-(6-chloro-5-fluoro-1H-indazol-3-yl)-N-methyl-N-(1-methylpiperidin-4-yl)-1H-benzimidazol-6-amine | 413.2 |
| 52 | 2-(5-fluoro-1H-indazol-3-yl)-N-methyl-N-(1-methylpiperidin-4-yl)-1H-benzimidazol-6-amine | 379.2 |
| 53 | 2-(4-chloro-1H-indazol-3-yl)-N-methyl-N-(1-methylpiperidin-4-yl)-1H-benzimidazol-6-amine | 395.2 |
| 54 | 2-(4-fluoro-1H-indazol-3-yl)-N-methyl-N-(1-methylpiperidin-4-yl)-1H-benzimidazol-6-anine | 379.3 |
| 55 | 3-[6-(5-methyl-2,5-diazabicyclo[2.2.1]hept-2-yl)-1H-benzimidazol-2-yl]-1H-indazole | 345.2 |
| 56 | 6-fluoro-3-[6-(5-methyl-2,5-diazabicyclo[2.2.1]hept-2-yl)-1H-benzimidazol-2-yl]-1H-indazole | 363.2 |
| 57 | 4,6-difluoro-3-[6-(5-methyl-2,5-diazabicyclo[2.2.1]hept-2-yl)-1H-benzimidazol-2-yl]-1H-indazole | 381.2 |
| 58 | 6-chloro-5-fluoro-3-[6-(5-methyl-2,5-diazabicyclol[2.2.1]hept-2-yl)-1H-benimidazol-2-yl]-1H-indazole | 397.2 |
| 59 | 5-fluoro-3-[6-(5-methyl-2,5-diazabicyclo[2.2.1]hept-2-yl)-1H-benzimidazol-2-yl]-1H-indazole | 363.2 |
| 60 | 4-chloro-3-[6-(5-methyl-2,5-diazabicyclo[2.2.1]hept-2-yl)-1H-benzimidazol-2-yl]-1H-indazole | 379.2 |
| 61 | 4-fluoro-3-[6-(5-methyl-2,5-diazabicyclo[2.2.1]hept-2-y1)-1H-benzimidazol-2-yl]-1H-indazole | 363.2 |
| 62 | 3-[6-(4-isopropylpiperazin-1-yl)-1H-benzimidazol-2-yl]-1H-indazole | 361.3 |
| 63 | 6-fluoro-3-[6-(4-isopropylpiperazin-1-yl)-1H-benzimidazol-2-yl]-1H-indazole | 379.3 |
| 64 | 6-chloro-5-fluoro-3-[6-(4-isopropylpiperazin-1-yl)-1H-benzimidazol-2-yl]-1H-indazole | 413.2 |
| 65 | 5-fluoro-3-[6-(4-isopropylpiperazin-1-yl)-1H-benzimidazol-2-yl]-1H-indazole | 379.3 |
| 66 | 4-fluoro-3-[6-(4-isopropylpiperazin-1-yl)-1H-benzimidazol-2-yl]-1H-indazole | 395.2 |
| 67 | 4-fluoro-3-[6-(4-isopropylpiperazin-1-yl)-1H-benzimidazol-2-yl]-1H-indazole | 379.3 |
| 68 | 5,6-difluoro-3-[6-(4-isopropylpiperazin-1-yl)-1H-benzimidazol-2-yl]-1H-indazole | 397.2 |
| 69 | 4-{[2-(1H-indazol-3-yl)-1H-benzimidazol-6-yl]oxy}-N-methylpyridine-2-carboxamide | 385.1 |
| 70 | 4-{[2-(5-methoxy-1H-indazol-3-yl)-1H-benzimidazol-6-yl]oxy}-N-methylpyridine-2-carboxamide | 415.2 |
| 71 | 4-{[2-(6-chloro-5-fluoro-1H-indazol-3-yl)-1H-benzimidazol-6-yl]oxy}-N-methylpyridine-2-carboxamide | 437.1 |
| 72 | 4-{[2-(5-fluoro-1H-indazol-3-yl)-1H-benzimidazol-6-yl]oxy}-N-methylpyridine-2-carboxamide | 403.1 |
| 73 | 4-{[2-(4-fluoro-1H-indazol-3-yl)-1H-benzimidazol-6-yl]oxy}-N-methylpyridine-2-carboxamide | 403.1 |
| 74 | 4-{[2-(6-chloro-1H-indazol-3-yl)-1H-benzimidazol-6-yl]oxy}-N-methylpyridine-2-carboxamide | 419.1 |

-continued

| Example | Name | LC/MS (m/z) (MH+) |
|---|---|---|
| 75 | 6-methoxy-3-[5-(4-methylpiperazin-1-yl)-1H-benzimidazol-2-yl]-1H-indazole | 363.1 |
| 76 | 3-[5-(4-methylpiperazin-1-yl)-1H-benzimidazol-2-yl]-1H-indazole | 333.1 |
| 77 | 5-chloro-3-[5-(4-methylpiperazin-1-yl)-1H-benzimidazol-2-yl]-1H-indazole | 367.1 |
| 78 | 5-fluoro-3-[5-(4-methylpiperazin-1-yl)-1H-benzimidazol-2-yl]-1H-indazole | 351.1 |
| 79 | 5-methoxy-3-[5-(4-methylpiperazin-1-yl)-1H-benzimidazol-2-yl]-1H-indazole | 363.1 |
| 80 | 2-(1H-indazol-3-yl)-3H-imidazo[4,5-b]pyridine | 236.1 |
| 81 | 3-[4-chloro-6-(trifluoromethyl)-1H-benzimidazol-2-yl]-1H-indazole | 337.1 |
| 82 | 2-(1H-indazol-3-yl)-1H-benzimidazole-6-carboxylic acid | 279.1 |
| 83 | 3-[6-(4-methylpiperazin-1-yl)-1H-benzimidazol-2-yl]-5-nitro-1H-indazole | 378.2 |
| 84 | methyl 3-[6-(4-methylpiperazin-1-yl)-1H-benzimidazol-2-yl]-1H-indazole-5-carboxylate | 391.1 |
| 85 | 3-(5-fluoro-6-morpholin-4-yl-1H-benzimidazol-2-yl)-1H-indazole | 338.2 |
| 86 | 3-[5-(4-methylpiperazin-1-yl)-1H-benzimidazol-2-yl]-1H-indazole-5-carbonitrile | 358.4 |
| 87 | 4,6-difluoro-3-[5-(4-methylpiperazin-1-yl)-1H-benzimidazol-2-yl]-1H-indazole | 369.1 |
| 88 | 6-fluoro-3-[5-(4-methylpiperazin-1-yl)-1H-benzimidazol-2-yl]-1H-indazole | 351.1 |
| 89 | 6-chloro-5-fluoro-3-[5-(4-methylpiperazin-1-yl)-1H-benzimidazol-2-yl]-1H-indazole | 385.1 |
| 90 | 5-chloro-3-[5-(2-methoxyethoxy)-1H-benzimidazol-2-yl]-1H-indazole | 343.2 |
| 91 | 4,6-difluoro-3-[5-(2-methoxyethoxy)-1H-benzimidazol-2-yl]-1H-indazole | 345.2 |
| 92 | 6-chloro-5-fluoro-3-[5-(2-methoxyethoxy)-1H-benzimidazol-2-yl]-1H-indazole | 361.1 |
| 93 | 3-[5-(2-methoxyethoxy)-1H-benzimidazol-2-yl]-1H-indazole-5-carbonitrile | 334.1 |
| 94 | 1-[2-(6-chloro-5-fluoro-1H-indazol-3-yl)-4-methyl-1H-benzimidazol-5-yl]-N,N-dimethylpyrrolidin-3-amine | 353.2 |
| 95 | 1-[2-(5-methoxy-1H-indazol-3-yl)-4-methyl-1H-benzimidazol-5-yl]-N,N-dimethylpyrrolidin-3-amine | 391.3 |
| 96 | 1-[2-(1H-indazol-3-yl)-4-methyl-1H-benzimidazol-5-yl]-N,N-dimethylpyrrolidin-3-amine | 361.3 |
| 97 | 1-[2-(6-chloro-5-fluoro-1H-indazol-3-yl)-4-methyl-1H-benzimidazol-5-yl]-N,N-dimethylpyrrolidin-3-amine | 413.2 |
| 98 | 3-(5-morpholin-4-yl-1H-imidazo[4,5-b]pyridin-2-yl)-1H-indazole-5-carboxylic acid | 365.2 |
| 99 | 2-(4,6-difluoro-1H-indazol-3-yl)-5-morpholin-4-yl-1H-imidazo[4,5-b]pyridine | 357.2 |
| 100 | 2-(6-chloro-5-fluoro-1H-indazol-3-yl)-5-morpholin-4-yl-1H-imidazo[4,5-b]pyridine | 373.2 |
| 101 | ethyl 4-[2-(5,6-difluoro-1H-indazol-3-yl)-1H-benzimidazol-5-yl]piperazine-1-carboxylate | 427.2 |
| 102 | ethyl 4-[2-(6-fluoro-1H-indazol-3-yl)-1H-benimidazol-5-yl]piperazine-1-carboxylate | 409.2 |
| 103 | ethyl 4-[2-(1H-indazol-3-yl)-1H-benzimidazol-5-yl]piperazine-1-carboxylate | 391.2 |
| 104 | ethyl 4-[2-(4-fluoro-1H-indazol-3-yl)-1H-benzimidazol-5-yl]piperazine-1-carboxylate | 409.2 |
| 105 | 1'-{2-[5-(benzyloxy)-1H-indazol-3-yl]-1H-benzimidazol-5-yl}-1,4'-bipiperidine | 507.4 |
| 106 | 1'-[2-(4-bromo-1H-indazol-3-yl)-1H-benzimidazol-6-yl]-1,4'-bipiperidine | 479.0 |
| 107 | 1'-[2-(5-methyl-1H-indazol-3-yl)-1H-benzimidazol-5-yl]-1,4'-bipiperidine | 415.0 |
| 108 | 1'-[2-(4-fluoro-1H-indazol-3-yl)-1H-benzimidazol-5-yl]-1,4'-bipiperidine | 419.0 |
| 109 | 1'-[2-(4-chloro-1H-indazol-3-yl)-1H-benzimidazol-5-yl]-1,4'-bipiperidine | 435.0 |
| 110 | 1'-[2-(5-nitro-1H-indazol-3-yl)-1H-benzimidazol-5-yl]-1,4'-bipiperidine | 446.0 |
| 111 | 3-[4-fluoro-5-(4-methylpiperazin-1-yl)-1H-benzimidazol-2-yl]-1H-indazole | 351.0 |
| 112 | 4-fluoro-3-[4-fluoro-5-(4-methylpiperazin-1-yl)-1H-benzimidazol-2-yl]-1H-indazole | 369.0 |

-continued

| Example | Name | LC/MS (m/z) (MH+) |
|---|---|---|
| 113 | 4-chloro-3-[4-fluoro-5-(4-methylpiperazin-1-yl)-1H-benzimidazol-2-yl]-1H-indazole | 385.0 |
| 114 | 5-fluoro-3-[4-fluoro-5-(4-methylpiperazin-1-yl)-1H-benzimidazol-2-yl]-1H-indazole | 369.0 |
| 115 | 6-fluoro-3-[4-fluoro-5-(4-methylpiperazin-1-yl)-1H-benzimidazol-2-yl]-1H-indazole | 369.0 |
| 116 | 3-[4-fluoro-5-(4-methylpiperazin-1-yl)-1H-benzimidazol-2-yl]-5-(methyloxy)-1H-indazole | 381.0 |
| 117 | 6-chloro-5-fluoro-3-[4-fluoro-5-(4-methylpiperazin-1-yl)-1H-benzimidazol-2-yl]-1H-indazole | 403.0 |
| 118 | 5,6-difluoro-3-[4-fluoro-5-(4-methylpiperazin-1-yl)-1H-benzimidazol-2-yl]-1H-indazole | 387.0 |
| 119 | 4-{[2-(4-bromo-1H-indazol-3-yl)-1H-benzimidazol-6-yl]oxy}-N-methylpyridine-2-carboxamide | 464.3 |
| 120 | 3-(7-morpholin-4-yl-1H-benzimidazol-2-yl)-1H-indazole | 320.4 |
| 121 | 4-fluoro-3-(7-morpholin-4-yl-1H-benzimidazol-2-yl)-1H-indazole | 338.4 |
| 122 | 5-methyl-3-(7-morpholin-4-yl-1H-benzimidazol-2-yl)-1H-indazole | 334.4 |
| 123 | 5-fluoro-3-(7-morpholin-4-yl-1H-benzimidazol-2-yl)-1H-indazole | 338.4 |
| 124 | 6-chloro-3-(7-morpholin-4-yl-1H-benzimidazol-2-yl)-1H-indazole | 354.8 |
| 125 | 5-methoxy-3-(7-morpholin-4-yl-1H-benzimidazol-2-yl)-1H-indazole | 350.4 |
| 126 | 5,6-difluoro-3-(4-morpholin-4-yl-1H-benzimidazol-2-yl)-1H-indazole | 356.3 |
| 127 | 6-chloro-5-fluoro-3-(4-morpholin-4-yl-1H-benzimidazol-2-yl)-1H-indazole | 372.8 |
| 128 | 2-(1H-indazol-3-yl)-N-(pyridin-4-ylmethyl)-1H-benzimidazol-6-amine | 341.4 |
| 129 | 2-(5-methoxy-1H-indazol-3-yl)-N-(pyridin-4-ylmethyl)-1H-benzimidazol-6-amine | 371.4 |
| 130 | 2-(6-chloro-5-fluoro-1H-indazol-3-yl)-N-(pyridin-4-ylmethyl)-1H-benzimidazol-6-amine | 393.8 |
| 131 | 2-(5-fluoro-1H-indazol-3-yl)-N-(pyridin-4-ylmethyl)-1H-benzimidazol-6-amine | 359.4 |
| 132 | 2-(4-bromo-1H-indazol-3-yl)-N-(pyridin-4-ylmethyl)-1H-benzimidazol-6-amine | 420.3 |
| 133 | 2-(4-fluoro-1H-indazol-3-yl)-N-(pyridin-4-ylmethyl)-1H-benzimidazol-6-amine | 359.4 |
| 134 | 2-(6-chloro-1H-indazol-3-yl)-N-(pyridin-4-ylmethyl)-1H-benzimidazol-6-amine | 375.8 |
| 135 | 2-(1H-indazol-3-yl)-N-(2-pyridin-2-ylethyl)-1H-benzimidazol-6-amine | 355.4 |
| 136 | 2-(5-methoxy-1H-indazol-3-yl)-N-(2-pyridin-2-ylethyl)-1H-benzimidazol-6-amine | 385.4 |
| 137 | 2-(6-chloro-5-fluoro-1H-indazol-3-yl)-N-(2-pyridin-2-ylethyl)-1H-benzimidazol-6-amine | 407.9 |
| 138 | 2-(5-fluoro-1H-indazol-3-yl)-N-(2-pyridin-2-ylethyl)-1H-benzimidazol-6-amine | 373.4 |
| 139 | 2-(4-fluoro-1H-indazol-3-yl)-N-(2-pyridin-2-ylethyl)-1H-benzimidazol-6-amine | 373.4 |
| 140 | 2-(6-chloro-1H-indazol-3-yl)-N-(2-pyridin-2-ylethyl)-1H-benzimidazol-6-amine | 389.9 |
| 141 | 2-(1H-indazol-3-yl)-N-(pyridin-3-ylmethyl)-1H-benzimidazol-6-amine | 341.4 |
| 142 | 2-(5-methoxy-1H-indazol-3-yl)-N-(pyridin-3-ylmethyl)-1H-benzimidazol-6-amine | 371.4 |
| 143 | 2-(6-chloro-5-fluoro-1H-indazol-3-yl)-N-(pyridin-3-ylmethyl)-1H-benzimidazol-6-amine | 393.8 |
| 144 | 2-(5-fluoro-1H-indazol-3-yl)-N-(pyridin-3-ylmethyl)-1H-benzimidazol-6-amine | 359.4 |
| 145 | 2-(1H-indazol-3-yl)-3H-imidazo[4,5-c]pyridine | 236.2 |
| 146 | 2-(6-chloro-5-fluoro-1H-indazol-3-yl)-3H-imidazo[4,5-c]pyridine | 288.7 |
| 147 | 2-(5-fluoro-1H-indazol-3-yl)-3H-imidazo[4,5-c]pyridine | 254.2 |
| 148 | 2-(6-chloro-1H-indazol-3-yl)-3H-imidazo[4,5-c]pyridine | 270.7 |
| 149 | 2-(6-fluoro-1H-indazol-3-yl)-3H-imidazo[4,5-c]pyridine | 254.2 |
| 150 | 2-(5-chloro-1H-indazol-3-yl)-3H-imidazo[4,5-c]pyridine | 270.7 |
| 151 | 4-fluoro-3-[6-(3-pyrrolidin-1-ylpropoxy)-1H-benzimidazol-2-yl]-1H-indazole | 380.4 |
| 152 | 5-isopropoxy-3-[6-(3-pyrrolidin-1-ylpropoxy)-1H-benzimidazol-2-yl]-1H-indazole | 420.5 |

-continued

| Example | Name | LC/MS (m/z) (MH+) |
|---|---|---|
| 153 | 5-methoxy-3-[6-(3-pyrrolidin-1-ylpropoxy)-1H-benzimidazol-2-yl]-1H-indazole | 392.5 |
| 154 | 5-chloro-3-[6-(3-pyrrolidin-1-ylpropoxy)-1H-benzimidazol-2-yl]-1H-indazole | 396.9 |
| 155 | 4,6-difluoro-3-[6-(3-pyrrolidin-1-ylpropoxy)-1H-benzimidazol-2-yl]-1H-indazole | 398.4 |
| 156 | 6-chloro-5-fluoro-3-[6-(3-pyrrolidin-1-ylpropoxy)-1H-benzimidazol-2-yl]-1H-indazole | 414.9 |
| 157 | 3-[6-(1,4'-bipiperidin-1'-yl)-1H-benimidazol-2-yl]-N-(2-morpholin-4-ylethyl)-1H-indazole-6-carboxamide | 557.7 |
| 158 | 1'-[2-(6-nitro-1H-indazol-3-yl)-1H-benzimidazol-6-yl]-1,4'-bipiperidine | 446.5 |
| 159 | 3-[6-(1,4'-bipiperidin-1'-yl)-1H-benzimidazol-2-yl]-1H-indazole-5-carbonitrile | 426.5 |
| 160 | methyl 3-[6-(1,4'-bipiperidin-1'-yl)-1H-benzimidazol-2-yl]-1H-indazole-5-carboxylate | 459.6 |
| 161 | 1'-[2-(5-phenoxy-1H-indazol-3-yl)-1H-benzimidazol-6-yl]-1,4'-bipiperidine | 493.6 |
| 162 | 2-(4-fluoro-1H-indazol-3-yl)-N-(pyridin-3-ylmethyl)-1H-benzimidazol-6-amine | 359.4 |
| 163 | 2-(6-chloro-1H-indazol-3-yl)-N-(pyridin-3-ylmethyl)-1H-benzimidazol-6-amine | 375.8 |
| 164 | 2-(5-isopropoxy-1H-indazol-3-yl)-N-(pyridin-3-ylmethyl)-1H-benzimidazol-6-amine | 399.5 |
| 165 | 8-(5-fluoro-1H-indazol-3-yl)-9H-purine | 255.2 |
| 166 | 8-(6-fluoro-1H-indazol-3-yl)-9H-purine | 255.2 |
| 167 | 6-bromo-2-(5-methoxy-1H-indazol-3-yl)-3H-imidazo[4,5-b]pyridine | 345.2 |
| 168 | 6-bromo-2-(5-fluoro-1H-indazol-3-yl)-3H-imidazo[4,5-b]pyridine | 333.1 |
| 169 | 6-bromo-2-(4-bromo-1H-indazol-3-yl)-3H-imidazo[4,5-b]pyridine | 394.0 |
| 170 | 8-(6-chloro-1H-indazol-3-yl)-6-methyl-9H-purine | 285.7 |
| 171 | 8-(5-isopropoxy-1H-indazol-3-yl)-6-methyl-9H-purine | 309.3 |
| 172 | N-{3-[6-(1,4'-bipiperidin-1'-yl)-1H-benzimidazol-2-yl]-1H-indazol-5-yl}-N'-ethylurea | 487.6 |
| 173 | 1'-[2-(1H-indazol-3-yl)-3H-imidazo[4,5-b]pyridin-5-yl]-1,4'-bipiperidine | 402.5 |
| 174 | 1'-[2-(4-bromo-1H-indazol-3-yl)-3H-imidazo[4,5-b]pyridin-5-yl]-1,4'-bipiperidine | 481.4 |
| 175 | 1'-[2-(5-chloro-1H-indazol-3-yl)-3H-imidazo[4,5-b]pyridin-5-yl]-1,4'-bipiperidine | 437.0 |
| 176 | 1'-[2-(5-nitro-1H-indazol-3-yl)-3H-imidazo[4,5-b]pyridin-5-yl]-1,4'-bipiperidine | 447.5 |
| 177 | 1'-[2-(5-isopropoxy-1H-indazol-3-yl)-3H-imidazo[4,5-b]pyridin-5-yl]-1,4'-bipiperidine | 460.6 |
| 178 | 8-(1H-indazol-3-yl)-6-methyl-9H-purine | 251.3 |
| 179 | 8-(5-methoxy-1H-indazol-3-yl)-6-methyl-9H-purine | 281.3 |
| 180 | 8-(5-fluoro-1H-indazol-3-yl)-6-methyl-9H-purine | 269.3 |
| 181 | 3-(5-fluoro-4-methyl-1H-benzimidazol-2-yl)-1H-indazole | 267.3 |
| 182 | 3-(5-fluoro-4-methyl-1H-benzimidazol-2-yl)-5-methoxy-1H-indazole | 297.3 |
| 183 | 3-(5-fluoro-4-methyl-1H-benzimidazol-2-yl)-N-(2-morpholin-4-ylethyl)-1H-indazole-6-carboxamide | 423.5 |
| 184 | 3-[6-(1,4'-bipiperidin-1'-yl)-1H-benzimidazol-2-yl]-N-(5-nitropyridin-2-yl)-1H-indazol-5-amine | 538.6 |
| 185 | 1-{1-[2-(1H-indazol-3-yl)-1H-benzimidazol-5-yl]piperidin-4-yl}-1,3-dihydro-2H-benzimidazol-2-one | 450.5 |
| 186 | 1-{1-[2-(4-bromo-1H-indazol-3-yl)-1H-benzimidazol-5-yl]piperidin-4-yl}-1,3-dihydro-2H-benzimidazol-2-one | 529.4 |
| 187 | 1-{1-[2-(5-fluoro-1H-indazol-3-yl)-1H-benzimidazol-5-yl]piperidin-4-yl}-1,3-dihydro-2H-benzimidazol-2-one | 468.5 |
| 188 | 1-{1-[2-(5-methoxy-1H-indazol-3-yl)-1H-benzimidazol-5-yl]piperidin-4-yl}-1,3-dihydro-2H-benzimidazol-2-one | 480.5 |
| 189 | 1-{1-[2-(5-nitro-1H-indazol-3-yl)-1H-benzimidazol-5-yl]piperidin-4-yl}-1,3-dihydro-2H-benzimidazol-2-one | 495.5 |
| 190 | 2-{4-[2-(5-fluoro-1H-indazol-3-yl)-1H-benzimidazol-6-yl]piperazin-1-yl}ethanol | 381.4 |
| 191 | 2-{4-[2-(5-methoxy-1H-indazol-3-yl)-1H-benzimidazol-6-yl]piperazin-1-yl}ethanol | 393.5 |
| 192 | 2-{4-[2-(5-chloro-1H-indazol-3-yl)-1H-benzimidazol-6-yl]piperazin-1-yl}ethanol | 397.9 |
| 193 | 2-{4-[2-(5-nitro-1H-indazol-3-yl)-1H-benimidazol-6-yl]piperazin-1-yl}ethanol | 408.4 |

-continued

| Example | Name | LC/MS (m/z) (MH+) |
|---|---|---|
| 194 | methyl 3-{6-[4-(2-hydroxyethyl)piperazin-1-yl]-1H-benzimidazol-2-yl}-1H-indazole-5-carboxylate | 421.5 |
| 195 | 2-{4-[2-(5-isopropoxy-1H-indazol-3-yl)-1H-benzimidazol-6-yl]piperazin-1-yl}ethanol | 421.5 |
| 196 | 2-{4-[2-(6-chloro-1H-indazol-3-yl)-1H-benzimidazol-6-yl]piperazin-1-yl}ethanol | 397.9 |
| 197 | 2-{4-[2-(5-ethoxy-1H-indazol-3-yl)-1H-benzimidazol-6-yl]piperazin-1-yl}ethanol | 407.5 |
| 198 | 2-{4-[2-(5-phenoxy-1H-indazol-3-yl)-1H-benzimidazol-6-yl]piperazin-1-yl}ethanol | 455.5 |
| 199 | 2-{4-[2-(6-nitro-1H-indazol-3-yl)-1H-benzimidazol-6-yl]piperazin-1-yl}ethanol | 408.4 |
| 200 | 3-{6-[4-(2-hydroxyethyl)piperazin-1-yl]-1H-benzimidazol-2-yl}-N-(2-morpholin-4-ylethyl)-1H-indazole-6-carboxamide | 519.6 |
| 201 | 2-(6-chloro-1H-indazol-3-yl)-N-piperidin-3-yl-1H-benzimidazol-6-amine | 367.9 |
| 202 | 2-(6-chloro-1H-indazol-3-yl)-N-[(5R)-5-(methoxymethyl)pyrrolidin-3-yl]-1H-benzimidazol-6-amine | 397.9 |
| 203 | 6-chloro-3-{5-[(2S)-2-(pyrrolidin-1-ylmethyl)pyrrolidin-1-yl]-1H-benzimidazol-2-yl}-1H-indazole | 421.9 |
| 204 | 6-fluoro-3-{5-[(2S)-2-(pyrrolidin-1-ylmethyl)pyrrolidin-1-yl]-1H-benzimidazol-2-yl}-1H-indazole | 405.5 |
| 205 | 5-(benzyloxy)-3-{5-[(2S)-2-(pyrrolidin-1-ylmethyl)pyrrolidin-1-yl]-1H-benzimidazol-2-yl}-1H-indazole | 493.6 |
| 206 | 5-methoxy-3-{5-[(2S)-2-(pyrrolidin-1-ylmethyl)pyrrolidin-1-yl]-1H-benzimidazol-2-yl}-1H-indazole | 417.5 |
| 207 | 2-(1H-indazol-3-yl)-N-(2-pyridin-3-ylethyl)-1H-benzimidazol-5-amine | 355.4 |
| 208 | 2-(5-fluoro-1H-indazol-3-yl)-N-(2-pyridin-3-ylethyl)-1H-benzimidazol-5-amine | 373.4 |
| 209 | 2-(5-methoxy-1H-indazol-3-yl)-N-(2-pyridin-3-ylethyl)-1H-benzimidazol-5-amine | 385.4 |
| 210 | 2-(5-chloro-1H-indazol-3-yl)-N-(2-pyridin-3-ylethyl)-1H-benzimidazol-6-amine | 389.9 |
| 211 | 2-(5-nitro-1H-indazol-3-yl)-N-(2-pyridin-3-ylethyl)-1H-benzimidazol-6-amine | 400.4 |
| 212 | methyl 3-{6-[(2-pyridin-3-ylethyl)amino]-1H-benzimidazol-2-yl}-1H-indazole-5-carboxylate | 413.5 |
| 213 | 2-(5-isopropoxy-1H-indazol-3-yl)-N-(2-pyridin-3-ylethyl)-1H-benzimidazol-6-amine | 413.5 |
| 214 | 2-(6-fluoro-1H-indazol-3-yl)-N-(2-pyridin-3-ylethyl)-1H-benzimidazol-6-amine | 373.4 |
| 215 | 2-(6-chloro-1H-indazol-3-yl)-N-(2-pyridin-3-ylethyl)-1H-benzimidazol-6-amine | 389.9 |
| 216 | 2-(6-methoxy-1H-indazol-3-yl)-N-(2-pyridin-3-ylethyl)-1H-benzimidazol-6-amine | 385.4 |
| 217 | 2-(5-ethoxy-1H-indazol-3-yl)-N-(2-pyridin-3-ylethyl)-1H-benzimidazol-6-amine | 399.5 |
| 218 | 2-(5-phenoxy-1H-indazol-3-yl)-N-(2-pyridin-3-ylethyl)-1H-benzimidazol-6-amine | 447.5 |
| 219 | 2-(6-nitro-1H-indazol-3-yl)-N-(2-pyridin-3-ylethyl)-1H-benzimidazol-6-amine | 400.4 |
| 220 | 2-(5-chloro-1H-indazol-3-yl)-N-[3-(1H-indazol-1-yl)propyl]-1H-benzimidazol-6-amine | 392.9 |
| 221 | N-[3-(1H-imidazol-1-yl)propyl]-2-(5-methoxy-1H-indazol-3-yl)-1H-benzimidazol-6-amine | 388.4 |
| 222 | N-[3-(1H-indazol-1-yl)propyl]-2-(5-nitro-1H-indazol-3-yl)-1H-benzimidazol-6-amine | 403.4 |
| 223 | methyl 3-(6-{[3-(1H-imidazol-1-yl)propyl]amino}-1H-benzimidazol-2-yl)-1H-indazole-5-carboxylate | 416.5 |
| 224 | 3-(6-{[3-(1H-imidazol-1-yl)propyl]amino}-1H-benzimidazol-2-yl)-1H-indazole-5-carbonitrile | 383.4 |
| 225 | 2-[5-(benzyloxy)-1H-indazol-3-yl]-N-[3-(1H-imidazol-1-yl)propyl]-1H-benzimidazol-6-amine | 464.5 |
| 226 | N-[3-(1H-imidazol-1-yl)propyl]-2-(5-isopropoxy-1H-indazol-3-yl)-1H-benzimidazol-6-amine | 416.5 |
| 227 | 2-(6-fluoro-1H-indazol-3-yl)-N-[3-(1H-imidazol-1-yl)propyl]-1H-benzimidazol-6-amine | 376.4 |
| 228 | 2-(6-chloro-1H-indazol-3-yl)-N-[3-(1H-imidazol-1-yl)propyl]-1H-benzimidazol-6-amine | 392.9 |
| 229 | 2-(5-ethoxy-1H-indazol-3-yl)-N-[3-(1H-imidazol-1-yl)propyl]-1H-benzimidazol-6-amine | 402.5 |

-continued

| Example | Name | LC/MS (m/z) (MH+) |
|---|---|---|
| 230 | N-[3-(1H-imidazol-1-yl)propyl]-2-(6-nitro-1H-indazol-3-yl)-1H-benzimidazol-6-amine | 403.4 |
| 231 | 2-(1H-indazol-3-yl)-N-(2-morpholm-4-ylethyl)-1H-benzimidazol-6-amine | 363.4 |
| 232 | 2-(5-chloro-1H-indazol-3-yl)-N-(2-morpholin-4-ylethyl)-1H-benzimidazol-6-amine | 397.9 |
| 233 | 2-(5-methoxy-1H-indazol-3-yl)-N-(2-morpholin-4-ylethyl)-1H-benzimidazol-6-amine | 393.5 |
| 234 | 2-[5-(benzyloxy)-1H-indazol-3-yl]-N-(2-morpholin-4-ylethyl)-1H-benzimidazol-6-amine | 469.6 |
| 235 | 2-(6-fluoro-1H-indazol-3-yl)-N-(2-morpholin-4-ylethyl)-1H-benzimidazol-6-amine | 381.4 |
| 236 | 2-(6-chloro-1H-indazol-3-yl)-N-(2-morpholin-4-ylethyl)-1H-benzimidazol-6-amine | 397.9 |
| 237 | 2-(5-ethoxy-1H-indazol-3-yl)-N-(2-morpholin-4-ylethyl)-1H-benzimidazol-6-amine | 407.5 |
| 238 | N-(2-morpholin-4-ylethyl)-2-(6-nitro-1H-indazol-3-yl)-1H-benzimidazol-6-amine | 408.4 |
| 239 | 5-chloro-3-[6-(4-isopropylpiperazin-1-yl)-1H-benzimidazol-2-yl]-1H-indazole | 395.9 |
| 240 | 5-bromo-3-[6-(4-isopropylpiperazin-1-yl)-1H-benzimidazol-2-yl]-1H-indazole | 440.4 |
| 241 | 3-[6-(4-isopropylpiperazin-1-yl)-1H-benzimidazol-2-yl]-5-methoxy-1H-indazole | 391.5 |
| 242 | 3-[6-(4-isopropylpiperazin-1-yl)-1H-benzimidazol-2-yl]-5-nitro-1H-indazole | 406.5 |
| 243 | methyl 3-[6-(4-isopropylpiperazin-1-yl)-1H-benzimidazol-2-yl]-1H-indazole-5-carboxylate | 419.5 |
| 244 | 5-(benzyloxy)-3-[6-(4-isopropylpiperazin-1-yl)-1H-benzimidazol-2-yl]-1H-indazole | 467.6 |
| 245 | 6-chloro-3-[6-(4-isopropylpiperazin-1-yl)-1H-benzimidazol-2-yl]-1H-indazole | 395.9 |
| 246 | 3-[6-(4-isopropylpiperazin-1-yl)-1H-benzimidazol-2-yl]-6-methoxy-1H-indazole | 391.5 |
| 247 | 5-ethoxy-3-[6-(4-isopropylpiperazin-1-yl)-1H-benzimidazol-2-yl]-1H-indazole | 405.5 |
| 248 | 3-[6-(4-isopropylpiperazin-1-yl)-1H-benzimidazol-2-yl]-6-nitro-1H-indazole | 406.5 |
| 249 | 5-[(3R,5S)-3,5-dimethylpiperazin-1-yl]-2-(5-fluoro-1H-indazol-3-yl)-3H-imidazo[4,5-b]pyridine | 366.4 |
| 250 | 2-(5-chloro-1H-indazol-3-yl)-5-[(3R,5S)-3,5-dimethylpiperazin-1-yl]-3H-imidazo[4,5-b]pyridine | 382.9 |
| 251 | 5-[(3R,5S)-3,5-dimethylpiperazin-1-yl]-2-(5-nitro-1H-indazol-3-yl)-3H-imidazo[4,5-b]pyridine | 393.4 |
| 252 | 2-(6-chloro-1H-indazol-3-yl)-5-[(3R,5S)-3,5-dimethylpiperazin-1-yl]-3H-imidazo[4,5-b]pyridine | 382.9 |
| 253 | 5-[(3R,5S)-3,5-dimethylpiperazin-1-yl]-2-(6-nitro-1H-indazol-3-yl)-3H-imidazo[4,5-b]pyridine | 393.4 |
| 254 | 2-(5-fluoro-1H-indazol-3-yl)-N-[3-(4-methylpiperazin-1-yl)propyl]-1H-benzimidazol-6-amine | 408.5 |
| 255 | 2-(5-chloro-1H-indazol-3-yl)-N-[3-(4-methylpiperazin-1-yl)propyl]-1H-benzimidazol-6-amine | 424.9 |
| 256 | 2-(5-bromo-1H-indazol-3-yl)-N-[3-(4-methylpiperazin-1-yl)propyl]-1H-benzimidazol-6-amine | 469.4 |
| 257 | 2-(5-methoxy-1H-indazol-3-yl)-N-[3-(4-methylpiperazin-1-yl)propyl]-1H-benzimidazol-6-amine | 420.5 |
| 258 | N-[3-(4-methylpiperazin-1-yl)propyl]-2-(5-nitro-1H-indazol-3-yl)-1H-benzimidazol-6-amine | 435.5 |
| 259 | methyl 3-(6-{[3-(4-methylpiperazin-1-yl)propyl]amino}-1H-benzimidazol-2-yl)-1H-indazole-5-carboxylate | 448.5 |
| 260 | 2-[5-(benzyloxy)-1H-indazol-3-yl]-N-[3-(4-methylpiperazin-1-yl)propyl]-1H-benzimidazol-6-amine | 496.6 |
| 261 | 2-(6-fluoro-1H-indazol-3-yl)-N-[3-(4-methylpiperazin-1-yl)propyl]-1H-benzimidazol-6-amine | 408.5 |
| 262 | 2-(6-chloro-1H-indazol-3-yl)-N-[3-(4-methylpiperazin-1-yl)propyl]-1H-benzimidazol-6-amine | 424.9 |
| 263 | 2-(5-ethoxy-1H-indazol-3-yl)-N-[3-(4-methylpiperazin-1-yl)propyl]-1H-benzimidazol-6-amine | 434.6 |
| 264 | N-[3-(4-methylpiperazin-1-yl)propyl]-2-(6-nitro-1H-indazol-3-yl)-1H-benzimidazol-6-amine | 435.5 |
| 265 | 2-(5-methoxy-1H-indazol-3-yl)-N-(pyridin-2-ylmethyl)-1H-benzimidazol-6-amine | 359.4 |
| 266 | 2-(5-chloro-1H-indazol-3-yl)-N-(pyridin-2-ylmethyl)-1H-benzimidazol-6-amine | 375.8 |

-continued

| Example | Name | LC/MS (m/z) (MH+) |
|---|---|---|
| 267 | 2-(5-methoxy-1H-indazol-3-yl)-N-(pyridin-2-ylmethyl)-1H-benzimidazol-6-amine | 371.4 |
| 268 | 2-(5-nitro-1H-indazol-3-yl)-N-(pyridin-2-ylmethyl)-1H-benzimidazol-6-amine | 386.4 |
| 269 | methyl 3-{6-[(pyridin-2-ylmethyl)amino]-1H-benzimidazol-2-yl}-1H-indazole-5-carboxylate | 399.4 |
| 270 | 2-(6-fluoro-1H-indazol-3-yl)-N-(pyridin-2-ylmethyl)-1H-benzimidazol-6-amine | 359.4 |
| 271 | 2-(5-ethoxy-1H-indazol-3-yl)-N-(pyridin-2-ylmethyl)-1H-benzimidazol-6-amine | 385.4 |
| 272 | 2-(6-nitro-1H-indazol-3-yl)-N-(pyridin-2-ylmethyl)-1H-benzimidazol-6-amine | 386.4 |
| 273 | 2-(5-fluoro-1H-indazol-3-yl)-N-piperidin-3-yl-1H-benzimidazol-5-amine | 351.4 |
| 274 | methyl 3-[5-(piperidin-3-ylamino)-1H-benzimidazol-2-yl]-1H-indazole-5-carboxylate | 391.4 |
| 275 | 2-(5,6-difluoro-1H-indazol-3-yl)-N-piperidin-3-yl-1H-benzimidazol-5-amine | 369.4 |
| 276 | 3-[5-(piperidin-3-ylamino)-1H-benzimidazol-2-yl]-1H-indazole-6-carbonitrile | 358.4 |
| 277 | 2-(6-fluoro-1H-indazol-3-yl)-N-piperidin-3-yl-1H-benzimidazol-5-amine | 351.4 |
| 278 | 2-(5-chloro-1H-indazol-3-yl)-1H-benzimidazole-6-carboxylic acid | 313.7 |
| 279 | 2-[5-(benzyloxy)-1H-indazol-3-yl]-1H-benzimidazole-6-carboxylic acid | 385.4 |
| 280 | 3-(6-piperazin-1-yl-1H-benzimidazol-2-yl)-1H-indazole | 319.4 |
| 281 | 5-chloro-3-(6-piperazin-1-yl-1H-benzimidazol-2-yl)-1H-indazole | 353.8 |
| 282 | 5-bromo-3-(6-piperazin-1-yl-1H-benzimidazol-2-yl)-1H-indazole | 398.3 |
| 283 | 5-methoxy-3-(6-piperazin-1-yl-1H-benzimidazol-2-yl)-1H-indazole | 349.4 |
| 284 | 5-nitro-3-(6-piperazin-1-yl-1H-benzimidazol-2-yl)-1H-indazole | 364.4 |
| 285 | methyl 3-(6-piperazin-1-yl-1H-benzimidazol-2-yl)-1H-indazole-5-carboxylate | 377.4 |
| 286 | 5-(benzyloxy)-3-(6-piperazin-1-yl-1H-benzimidazol-2-yl)-1H-indazole | 425.5 |
| 287 | 5-isopropoxy-3-(6-piperazin-1-yl-1H-benzimidazol-2-yl)-1H-indazole | 377.5 |
| 288 | 6-fluoro-3-(6-piperazin-1-yl-1H-benzimidazol-2-yl)-1H-indazole | 337.4 |
| 289 | 6-chloro-3-(6-piperazin-1-yl-1H-benzimidazol-2-yl)-1H-indazole | 353.8 |
| 290 | 6-methoxy-3-(6-piperazin-1-yl-1H-benzimidazol-2-yl)-1H-indazole | 349.4 |
| 291 | 5-ethoxy-3-(6-piperazin-1-yl-1H-benzimidazol-2-yl)-1H-indazole | 363.4 |
| 292 | 6-nitro-3-(6-piperazin-1-yl-1H-benzimidazol-2-yl)-1H-indazole | 364.4 |
| 293 | 2-(5-methyl-1H-indazol-3-yl)-N-piperidin-3-yl-1H-benzimidazol-5-amine | 347.4 |
| 294 | 1-[2-(5-fluoro-1H-indazol-3-yl)-1H-benzimidazol-6-yl]piperidin-4-ol | 352.4 |
| 295 | 1-[2-(5-chloro-1H-indazol-3-yl)-1H-benzimidazol-6-yl]piperidin-4-ol | 368.8 |
| 296 | 1-[2-(5-bromo-1H-indazol-3-yl)-1H-benzimidazol-6-yl]piperidin-4-ol | 413.3 |
| 297 | 1-[2-(5-methoxy-1H-indazol-3-yl)-1H-benzimidazol-6-yl]piperidin-4-ol | 364.4 |
| 298 | 1-[2-(5-nitro-1H-indazol-3-yl)-1H-benzimidazol-6-yl]piperidin-4-ol | 379.4 |
| 299 | methyl 3-[6-(4-hydroxypiperidin-1-yl)-1H-benzimidazol-2-yl]-1H-indazole-5-carboxylate | 392.4 |
| 300 | 1-{2-[5-(benzyloxy)-1H-indazol-3-yl]-1H-benzimidazol-6-yl}piperidin-4-ol | 440.5 |
| 301 | 1-[2-(6-fluoro-1H-indazol-3-yl)-1H-benzimidazol-6-yl]piperidin-4-ol | 352.4 |
| 302 | 1-[2-(6-chloro-1H-indazol-3-yl)-1H-benzimidazol-6-yl]piperidin-4-ol | 368.8 |
| 303 | 1-[2-(6-nitro-1H-indazol-3-yl)-1H-benzimidazol-6-yl]piperidin-4-ol | 379.4 |
| 304 | 2-(5-fluoro-1H-indazol-3-yl)-N-(2-piperidin-1-ylethyl)-1H-benzimidazol-6-amine | 379.5 |

-continued

| Example | Name | LC/MS (m/z) (MH+) |
|---|---|---|
| 305 | 2-(1H-indazol-3-yl)-N-methyl-N-(2-pyridin-2-ylethyl)-1H-benzimidazol-6-amine | 369.4 |
| 306 | 2-(5-fluoro-1H-indazol-3-yl)-N-methyl-N-(2-pyridin-2-ylethyl)-1H-benzimidazol-6-amine | 387.4 |
| 307 | 2-(5-chloro-1H-indazol-3-yl)-N-methyl-N-(2-pyridin-2-ylethyl)-1H-benzimidazol-6-amine | 403.9 |
| 308 | 2-(5-methoxy-1H-indazol-3-yl)-N-methyl-N-(2-pyridin-2-ylethyl)-1H-benzimidazol-6-amine | 399.5 |
| 309 | 2-(6-fluoro-1H-indazol-3-yl)-N-methyl-N-(2-pyridin-2-ylethyl)-1H-benzimidazol-6-amine | 387.4 |
| 310 | 2-(6-chloro-1H-indazol-3-yl)-N-methyl-N-(2-pyridin-2-ylethyl)-1H-benzimidazol-6-amine | 403.9 |
| 311 | 2-(6-methoxy-1H-indazol-3-yl)-N-methyl-N-(2-pyridin-2-ylethyl)-1H-benzimidazol-6-amine | 399.5 |
| 312 | 2-(5-ethoxy-1H-indazol-3-yl)-N-methyl-N-(2-pyridin-2-ylethyl)-1H-benzimidazol-6-amine | 413.5 |
| 313 | N-methyl-2-(6-nitro-1H-indazol-3-yl)-N-(2-pyridin-2-ylethyl)-1H-benzimidazol-6-amine | 414.4 |
| 314 | N-{3-[6-(1,4'-bipiperidin-1'-yl)-1H-benzimidazol-2-yl]-1H-indazol-5-yl}-N'-(2,4-dimethoxyphenyl)urea | 595.7 |
| 315 | 2-(5-chloro-1H-indazol-3-yl)-N-methyl-N-(1-methylpiperidin-4-yl)-1H-benzimidazol-6-amine | 395.9 |
| 316 | 2-(5-bromo-1H-indazol-3-yl)-N-methyl-N-(1-methylpiperidin-4-yl)-1H-benzimidazol-6-amine | 440.4 |
| 317 | 2-(5-methoxy-1H-indazol-3-yl)-N-methyl-N-(1-methylpiperidin-4-yl)-1H-benzimidazol-6-amine | 391.5 |
| 318 | N-methyl-N-(1-methylpiperidin-4-yl)-2-(5-nitro-1H-indazol-3-yl)-1H-benzimidazol-6-amine | 406.5 |
| 319 | methyl 3-{6-[methyl(1-methylpiperidin-4-yl)amino]-1H-benzimidazol-2-yl}-1H-indazole-5-carboxylate | 419.5 |
| 320 | N-methyl-2-(5-methyl-1H-indazol-3-yl)-N-(1-methylpiperidin-4-yl)-1H-benzimidazol-6-amine | 375.5 |
| 321 | 2-[5-(benzyloxy)-1H-indazol-3-yl]-N-methyl-N-(1-methylpiperidin-4-yl)-1H-benzimidazol-6-amine | 467.6 |
| 322 | 2-(6-chloro-1H-indazol-3-yl)-N-methyl-N-(1-methylpiperidin-4-yl)-1H-benzimidazol-6-amine | 395.9 |
| 323 | 2-(6-methoxy-1H-indazol-3-yl)-N-methyl-N-(1-methylpiperidin-4-yl)-1H-benzimidazol-6-amine | 391.5 |
| 324 | 2-(5-ethoxy-1H-indazol-3-yl)-N-methyl-N-(1-methylpiperidin-4-yl)-1H-benzimidazol-6-amine | 405.5 |
| 325 | N-methyl-N-(1-methylpiperidin-4-yl)-2-(6-nitro-1H-indazol-3-yl)-1H-benzimidazol-6-amine | 406.5 |
| 326 | 2-(1H-[1,3]dioxolo[4,5-f]indazol-3-yl)-N-methyl-N-(1-methylpiperidin-4-yl)-1H-benzimidazol-6-amine | 405.5 |
| 327 | N-methyl-2-(7-methyl-1H-indazol-3-yl)-N-(1-methylpiperidin-4-yl)-1H-benzimidazol-6-amine | 375.5 |
| 328 | N-(1-benzylpiperidin-4-yl)-2-(5-methoxy-1H-indazol-3-yl)-1H-benzimidazol-6-amine | 453.6 |
| 329 | N-(1-benzylpiperidin-4-yl)-2-(6-fluoro-1H-indazol-3-yl)-1H-benzimidazol-6-amine | 441.5 |
| 330 | 2-(6-chloro-1H-indazol-3-yl)-N-(2-pyridin-4-ylethyl)-1H-benzimidazol-5-amine | 389.9 |
| 331 | 1-[2-(1H-indazol-3-yl)-1H-benzimidazol-6-yl]piperidin-3-ol | 334.4 |
| 332 | 1-[2-(5-fluoro-1H-indazol-3-yl)-1H-benzimidazol-6-yl]piperidin-3-ol | 352.4 |
| 333 | 1-[2-(5-chloro-1H-indazol-3-yl)-1H-benzimidazol-6-yl]piperidin-3-ol | 368.8 |
| 334 | 1-[2-(5-bromo-1H-indazol-3-yl)-1H-benzimidazol-6-yl]piperidin-3-ol | 413.3 |
| 335 | 1-[2-(5-methoxy-1H-indazol-3-yl)-1H-benzimidazol-6-yl]piperidin-3-ol | 364.4 |
| 336 | 1-[2-(5-nitro-1H-indazol-3-yl)-1H-benzimidazol-6-yl]piperidin-3-ol | 379.4 |
| 337 | methyl 3-[6-(3-hydroxypiperidin-1-yl)-1H-benzimidazol-2-yl]-1H-indazole-5-carboxylate | 392.4 |
| 338 | 1-[2-(5-methyl-1H-indazol-3-yl)-1H-benzimidazol-6-yl]piperidin-3-ol | 348.4 |
| 339 | 1-{2-[5-(benzyloxy)-1H-indazol-3-yl]-1H-benzimidazol-6-yl}piperidin-3-ol | 440.5 |
| 340 | 1-[2-(6-fluoro-1H-indazol-3-yl)-1H-benzimidazol-6-yl]piperidin-3-ol | 352.4 |
| 341 | 1-[2-(6-chloro-1H-indazol-3-yl)-1H-benzimidazol-6-yl]piperidin-3-ol | 368.8 |

-continued

| Example | Name | LC/MS (m/z) (MH+) |
|---|---|---|
| 342 | 1-[2-(6-methoxy-1H-indazol-3-yl)-1H-benzimidazol-6-yl]piperidin-3-ol | 364.4 |
| 343 | 1-[2-(5-ethoxy-1H-indazol-3-yl)-1H-benzimidazol-6-yl]piperidin-3-ol | 378.4 |
| 344 | 1-[2-(6-nitro-1H-indazol-3-yl)-1H-benzimidazol-6-yl]piperidin-3-ol | 379.4 |
| 345 | 1-[2-(1H-[1,3]dioxolo[4,5-f]indazol-3-yl)-1H-benzimidazol-6-yl]piperidin-3-ol | 378.4 |
| 346 | 1-[2-(7-methyl-1H-indazol-3-yl)-1H-benzimidazol-6-yl]piperidin-3-ol | 348.4 |
| 347 | (3R)-1-[2-(5-fluoro-1H-indazol-3-yl)-1H-benzimidazol-6-yl]pyrrolidin-3-ol | 338.4 |
| 348 | (3R)-1-[2-(5-chloro-1H-indazol-3-yl)-1H-benzimidazol-6-yl]pyrrolidin-3-ol | 354.8 |
| 349 | (3R)-1-[2-(5-bromo-1H-indazol-3-yl)-1H-benzimidazol-6-yl]pyrrolidin-3-ol | 399.3 |
| 350 | (3R)-1-[2-(5-methoxy-1H-indazol-3-yl)-1H-benzimidazol-6-yl]pyrrolidin-3-ol | 350.4 |
| 351 | (3R)-1-[2-(5-nitro-1H-indazol-3-yl)-1H-benzimidazol-6-yl]pyrrolidin-3-ol | 365.4 |
| 352 | (3R)-1-[2-(6-fluoro-1H-indazol-3-yl)-1H-benzimidazol-6-yl]pyrrolidin-3-ol | 378.4 |
| 353 | (3R)-1-[2-(5-methyl-1H-indazol-3-yl)-1H-benzimidazol-6-yl]pyrrolidin-3-ol | 334.4 |
| 354 | (3R)-1-{2-[5-(benzyloxy)-1H-indazol-3-yl]-1H-benzimidazol-6-yl}pyrrolidin-3-ol | 426.5 |
| 355 | (3R)-1-[2-(6-fluoro-1H-indazol-3-yl)-1H-benzimidazol-6-yl]pyrrolidin-3-ol | 338.4 |
| 356 | (3R)-1-[2-(6-chloro-1H-indazol-3-yl)-1H-benzimidazol-6-yl]pyrrolidin-3-ol | 354.8 |
| 357 | (3R)-1-[2-(6-methoxy-1H-indazol-3-yl)-1H-benzimidazol-6-yl]pyrrolidin-3-ol | 350.4 |
| 358 | (3R)-1-[2-(5-ethoxy-1H-indazol-3-yl)-1H-benzimidazol-6-yl]pyrrolidin-3-ol | 364.4 |
| 359 | (3R)-1-[2-(6-nitro-1H-indazol-3-yl)-1H-benzimidazol-6-yl]pyrrolidin-3-ol | 365.4 |
| 360 | (3R)-1-[2-(1H-[1,3]dioxolo[4,5-f]indazol-3-yl)-1H-benzimidazol-6-yl]pyrrolidin-3-ol | 364.4 |
| 361 | (3R)-1-[2-(7-methyl-1H-indazol-3-yl)-1H-benzimidazol-6-yl]pyrrolidin-3-ol | 334.4 |
| 362 | 6-fluoro-3-{6-[(4-methylpiperazin-1-yl)carbonyl]-1H-benzimidazol-2-yl}-1H-indazole | 379.4 |
| 363 | 1'-{[2-(6-fluoro-1H-indazol-3-yl)-1H-benzimidazol-6-yl]carbonyl}-1,4'-bipiperidine | 447.5 |
| 364 | 6-fluoro-3-[6-(morpholin-4-ylcarbonyl)-1H-benzimidazol-2-yl]-1H-indazole | 366.4 |
| 365 | 2-(6-fluoro-1H-indazol-3-yl)-N-methyl-N-(1-methylpiperidin-4-yl)-1H-benzimidazole-6-carboxamide | 407.5 |
| 366 | 3-(6-{[(2R,6S)-2,6-dimethylmorpholin-4-yl]carbonyl}-1H-benzimidazol-2-yl)-6-fluoro-1H-indazole | 394.4 |
| 367 | 2-(6-fluoro-1H-indazol-3-yl)-N-methyl-N-(1-methylpyrrolidin-3-yl)-1H-benzimidazole-6-carboxamide | 393.4 |
| 368 | (3S,5S)-1-[2-(6-fluoro-1H-indazol-3-yl)-1H-benzimidazol-5-yl]-N,N,5-trimethylpyrrolidin-3-amine | 379.5 |
| 369 | 1-[2-(1H-indazol-3-yl)-1H-benzimidazol-6-yl]-4-phenylpiperidin-4-ol | 410.5 |
| 370 | 1-[2-(5-fluoro-1H-indazol-3-yl)-1H-benzimidazol-6-yl]-4-phenylpiperidin-4-ol | 428.5 |
| 371 | 1-[2-(5-chloro-1H-indazol-3-yl)-1H-benzimidazol-6-yl]-4-phenylpiperidin-4-ol | 444.9 |
| 372 | 1-[2-(5-bromo-1H-indazol-3-yl)-1H-benzimidazol-6-yl]-4-phenylpiperidin-4-ol | 489.4 |
| 373 | 1-[2-(5-methoxy-1H-indazol-3-yl)-1H-benzimidazol-6-yl]-4-phenylpiperidin-4-ol | 440.5 |
| 374 | 1-[2-(5-nitro-1H-indazol-3-yl)-1H-benzimidazol-6-yl]-4-phenylpiperidin-4-ol | 455.5 |
| 375 | methyl 3-[6-(4-hydroxy-4-phenylpiperidin-1-yl)-1H-benzimidazol-2-yl]-1H-indazole-5-carboxylate | 468.5 |
| 376 | 1-[2-(5-methyl-1H-indazol-3-yl)-1H-benzimidazol-6-yl]-4-phenylpiperidin-4-ol | 424.5 |
| 377 | 1-{2-[5-(benzyloxy)-1H-indazol-3-yl]-1H-benzimidazol-6-yl}-4-phenylpiperidin-4-ol | 516.6 |
| 378 | 1-[2-(6-fluoro-1H-indazol-3-yl)-1H-benzimidazol-6-yl]-4-phenylpiperidin-4-ol | 428.5 |

-continued

| Example | Name | LC/MS (m/z) (MH+) |
|---|---|---|
| 379 | 1-[2-(6-chloro-1H-indazol-3-yl)-1H-benzimidazol-6-yl]-4-phenylpiperidin-4-ol | 444.9 |
| 380 | 1-[2-(6-methoxy-1H-indazol-3-yl)-1H-benzimidazol-6-yl]-4-phenylpiperidin-4-ol | 440.5 |
| 381 | 1-[2-(5-ethoxy-1H-indazol-3-yl)-1H-benzimidazol-6-yl]-4-phenylpiperidin-4-ol | 454.5 |
| 382 | 1-[2-(6-nitro-1H-indazol-3-yl)-1H-benzimidazol-6-yl]-4-phenylpiperidin-4-ol | 455.5 |
| 383 | 1-[2-(1H-[1,3]dioxolo[4,5-f]indazol-3-yl)-1H-benzimidazol-6-yl]-4-phenylpiperidin-4-ol | 454.5 |
| 384 | 1-[2-(7-methyl-1H-indazol-3-yl)-1H-benzimidazol-6-yl]-4-phenylpiperidin-4-ol | 424.5 |
| 385 | 1-[2-(7-chloro-1H-indazol-3-yl)-1H-benzimidazol-6-yl]-4-phenylpiperidin-4-ol | 444.9 |
| 386 | 1-[2-(1H-indazol-3-yl)-1H-benzimidazol-6-yl]-N,N-dimethylpyrrolidin-3-amine | 347.4 |
| 387 | 1-[2-(5-fluoro-1H-indazol-3-yl)-1H-benzimidazol-6-yl]-N,N-dimethylpyrrolidin-3-amine | 365.4 |
| 388 | 1-[2-(5-chloro-1H-indazol-3-yl)-1H-benzimidazol-6-yl]-N,N-dimethylpyrrolidin-3-amine | 381.9 |
| 389 | 1-[2-(5-bromo-1H-indazol-3-yl)-1H-benzimidazol-6-yl]-N,N-dimethylpyrrolidin-3-amine | 426.3 |
| 390 | 1-[2-(5-methoxy-1H-indazol-3-yl)-1H-benzimidazol-6-yl]-N,N-dimethylpyrrolidin-3-amine | 377.5 |
| 391 | N,N-dimethyl-1-[2-(5-nitro-1H-indazol-3-yl)-1H-benzimidazol-6-yl]pyrrolidin-3-amine | 392.4 |
| 392 | methyl 3-{6-[3-(dimethylamino)pyrrolidin-1-yl]-1H-benzimidazol-2-yl}-1H-indazole-5-carboxylate | 405.5 |
| 393 | 1-{2-[5-(benzyloxy)-1H-indazol-3-yl]-1H-benzimidazol-6-yl}-N,N-dimethylpyrrolidin-3-amine | 453.6 |
| 394 | 1-[2-(6-fluoro-1H-indazol-3-yl)-1H-benzimidazol-6-yl]-N,N-dimethylpyrrolidin-3-amine | 365.4 |
| 395 | 1-[2-(6-chloro-1H-indazol-3-yl)-1H-benzimidazol-6-yl]-N,N-dimethylpyrrolidin-3-amine | 381.9 |
| 396 | 1-[2-(6-methoxy-1H-indazol-3-yl)-1H-benzimidazol-6-yl]-N,N-dimethylpyrrolidin-3-amine | 377.5 |
| 397 | 1-[2-(5-ethoxy-1H-indazol-3-yl)-1H-benzimidazol-6-yl]-N,N-dimethylpyrrolidin-3-amine | 391.5 |
| 398 | N,N-dimethyl-1-[2-(6-nitro-1H-indazol-3-yl)-1H-benzimidazol-6-yl]pyrrolidin-3-amine | 392.4 |
| 399 | N,N-dimethyl-1-[2-(7-methyl-1H-indazol-3-yl)-1H-benzimidazol-6-yl]pyrrolidin-3-amine | 361.5 |
| 400 | 1-[2-(7-chloro-1H-indazol-3-yl)-1H-benzimidazol-6-yl]-N,N-dimethylpyrrolidin-3-amine | 381.9 |
| 401 | 5-fluoro-3-(6-morpholin-4-yl-1H-benzimidazol-2-yl)-1H-indazole | 338.4 |
| 402 | 5-chloro-3-(6-morpholin-4-yl-1H-benzimidazol-2-yl)-1H-indazole | 354.8 |
| 403 | 5-bromo-3-(6-morpholin-4-yl-1H-benzimidazol-2-yl)-1H-indazole | 399.3 |
| 404 | 5-methoxy-3-(6-morpholin-4-yl-1H-benzimidazol-2-yl)-1H-indazole | 350.4 |
| 405 | 3-(6-morpholin-4-yl-1H-benzimidazol-2-yl)-5-nitro-1H-indazole | 365.4 |
| 406 | methyl 3-(6-morpholin-4-yl-1H-benzimidazol-2-yl)-1H-indazole-5-carboxylate | 378.4 |
| 407 | 5-methyl-3-(6-morpholin-4-yl-1H-benzimidazol-2-yl)-1H-indazole | 334.4 |
| 408 | 5-(benzyloxy)-3-(6-morpholin-4-yl-1H-benzimidazol-2-yl)-1H-indazole | 426.5 |
| 409 | 6-fluoro-3-(6-morpholin-4-yl-1H-benzimidazol-2-yl)-1H-indazole | 338.4 |
| 410 | 6-chloro-3-(6-morpholin-4-yl-1H-benzimidazol-2-yl)-1H-indazole | 354.8 |
| 411 | 6-methoxy-3-(6-morpholin-4-yl-1H-benzimidazol-2-yl)-1H-indazole | 350.4 |
| 412 | 5-ethoxy-3-(6-morpholin-4-yl-1H-benzimidazol-2-yl)-1H-indazole | 364.4 |
| 413 | 3-(6-morpholin-4-yl-1H-benzimidazol-2-yl)-6-nitro-1H-indazole | 365.4 |
| 414 | 3-(6-morpholin-4-yl-1H-benzimidazol-2-yl)-1H-[1,3]dioxolo[4,5-f]indazole | 364.4 |
| 415 | 7-methyl-3-(6-morpholin-4-yl-1H-benzimidazol-2-yl)-1H-indazole | 334.4 |

-continued

| Example | Name | LC/MS (m/z) (MH+) |
|---|---|---|
| 416 | 7-chloro-3-(6-morpholin-4-yl-1H-benzimidazol-2-yl)-1H-indazole | 354.8 |
| 417 | N-({(2R,5S)-4-[2-(6-chloro-1H-indazol-3-yl)-1H-benzimidazol-5-yl]-5-methylmorpholin-2-yl}methyl)-N,N-dimethylamine | 425.9 |
| 418 | N-(3,4-dimethoxybenzyl)-3-[6-(4-methylpiperazin-1-yl)-1H-benzimidazol-2-yl]-1H-indazol-5-amine | 498.6 |
| 419 | N-[4-(benzyloxy)-3-methoxybenzyl]-3-[6-(4-methylpiperazin-1-yl)-1H-benzimidazol-2-yl]-1H-indazol-5-amine | 574.7 |
| 420 | 3-[6-(4-methylpiperazin-1-yl)-1H-benzimidazol-2-yl]-N-(4-phenoxybenzyl)-1H-indazol-5-amine | 530.6 |
| 421 | 3-[6-(4-acetylpiperazin-1-yl)-1H-benzimidazol-2-yl]-5-fluoro-1H-indazole | 379.4 |
| 422 | 3-[6-(4-acetylpiperazin-1-yl)-1H-benzimidazol-2-yl]-5-chloro-1H-indazole | 395.9 |
| 423 | 3-[6-(4-acetylpiperazin-1-yl)-1H-benzimidazol-2-yl]-5-bromo-1H-indazole | 440.3 |
| 424 | 3-[6-(4-acetylpiperazin-1-yl)-1H-benzimidazol-2-yl]-5-nitro-1H-indazole | 406.4 |
| 425 | methyl 3-[6-(4-acetylpiperazin-1-yl)-1H-benzimidazol-2-yl]-1H-indazole-5-carboxylate | 419.5 |
| 426 | 3-[6-(4-acetylpiperazin-1-yl)-1H-benzimidazol-2-yl]-5-methyl-1H-indazole | 375.4 |
| 427 | 3-[6-(4-acetylpiperazin-1-yl)-1H-benzimidazol-2-yl]-5-(benzyloxy)-1H-indazole | 467.5 |
| 428 | 3-[6-(4-acetylpiperazin-1-yl)-1H-benzimidazol-2-yl]-6-chloro-1H-indazole | 395.9 |
| 429 | 3-[6-(4-acetylpiperazin-1-yl)-1H-benzimidazol-2-yl]-6-methoxy-1H-indazole | 391.4 |
| 430 | 3-[6-(4-acetylpiperazin-1-yl)-1H-benzimidazol-2-yl]-5-ethoxy-1H-indazole | 405.5 |
| 431 | 3-[6-(4-acetylpiperazin-1-yl)-1H-benzimidazol-2-yl]-6-nitro-1H-indazole | 406.4 |
| 432 | 3-[6-(4-acetylpiperazin-1-yl)-1H-benzimidazol-2-yl]-1H-[1,3]dioxolo[4,5-f]indazole | 405.4 |
| 433 | 3-[6-(4-acetylpiperazin-1-yl)-1H-benzimidazol-2-yl]-7-methyl-1H-indazole | 375.4 |
| 434 | 3-[6-(4-acetylpiperazin-1-yl)-1H-benzimidazol-2-yl]-7-chloro-1H-indazole | 395.9 |
| 435 | 3-[6-(1,4'-bipiperidin-1'-yl)-1H-benzimidazol-2-yl]-N-[(2-chloropyridin-3-yl)methyl]-1H-indazol-5-amine | 542.1 |
| 436 | 2-(5-fluoro-1H-indazol-3-yl)-N-(2-pyridin-4-ylethyl)-1H-benzimidazol-6-amine | 373.4 |
| 437 | 2-(5-chloro-1H-indazol-3-yl)-N-(2-pyridin-4-ylethyl)-1H-benzimidazol-6-amine | 389.9 |
| 438 | 2-(5-methoxy-1H-indazol-3-yl)-N-(2-pyridin-4-ylethyl)-1H-benzimidazol-6-amine | 385.4 |
| 439 | 2-(5-nitro-1H-indazol-3-yl)-N-(2-pyridin-4-ylethyl)-1H-benzimidazol-6-amine | 400.4 |
| 440 | methyl 3-{6-[(2-pyridin-4-ylethyl)amino]-1H-benzimidazol-2-yl}-1H-indazole-5-carboxylate | 413.5 |
| 441 | 2-(6-fluoro-1H-indazol-3-yl)-N-(2-pyridin-4-ylethyl)-1H-benzimidazol-6-amine | 373.4 |
| 442 | 2-(6-chloro-1H-indazol-3-yl)-N-(2-pyridin-4-ylethyl)-1H-benzimidazol-6-amine | 389.9 |
| 443 | 2-(6-methoxy-1H-indazol-3-yl)-N-(2-pyridin-4-ylethyl)-1H-benzimidazol-6-amine | 385.4 |
| 444 | 2-(5-ethoxy-1H-indazol-3-yl)-N-(2-pyridin-4-ylethyl)-1H-benzimidazol-6-amine | 399.5 |
| 445 | 2-(6-nitro-1H-indazol-3-yl)-N-(2-pyridin-4-ylethyl)-1H-benzimidazol-6-amine | 400.4 |
| 446 | 2-(5-methyl-1H-indazol-3-yl)-N-(2-pyridin-4-ylethyl)-1H-benzimidazol-6-amine | 369.4 |
| 447 | 2-(1H-[1,3]dioxolo[4,5-f]indazol-3-yl)-N-(2-pyridin-4-ylethyl)-1H-benzimidazol-6-amine | 399.4 |
| 448 | 2-(5-methyl-1H-indazol-3-yl)-N-(3-morpholin-4-ylpropyl)-1H-benzimidazol-6-amine | 389.9 |
| 449 | 2-(1H-indazol-3-yl)-N-(3-morpholin-4-ylpropyl)-1H-benzimidazol-6-amine | 377.5 |
| 450 | 2-(5-fluoro-1H-indazol-3-yl)-N-(3-morpholin-4-ylpropyl)-1H-benzimidazol-6-amine | 395.5 |
| 451 | 2-(5-chloro-1H-indazol-3-yl)-N-(3-morpholin-4-ylpropyl)-1H-benzimidazol-6-amine | 411.9 |

-continued

| Example | Name | LC/MS (m/z) (MH+) |
|---|---|---|
| 452 | 2-(5-bromo-1H-indazol-3-yl)-N-(3-morpholin-4-ylpropyl)-1H-benzimidazol-6-amine | 456.4 |
| 453 | 2-(5-methoxy-1H-indazol-3-yl)-N-(3-morpholin-4-ylpropyl)-1H-benzimidazol-6-amine | 407.5 |
| 454 | N-(3-morpholin-4-ylpropyl)-2-(5-nitro-1H-indazol-3-yl)-1H-benzimidazol-6-amine | 422.5 |
| 455 | methyl 3-{6-[(3-morpholin-4-ylpropyl)amino]-1H-benzimidazol-2-yl}-1H-indazole-5-carboxylate | 435.5 |
| 456 | 2-(5-methyl-1H-indazol-3-yl)-N-(3-morpholin-4-ylpropyl)-1H-benzimidazol-6-amine | 391.5 |
| 457 | 2-[5-(benzyloxy)-1H-indazol-3-yl]-N-(3-morpholin-4-ylpropyl)-1H-benzimidazol-6-amine | 483.6 |
| 458 | 2-(6-fluoro-1H-indazol-3-yl)-N-(3-morpholin-4-ylpropyl)-1H-benzimidazol-6-amine | 395.5 |
| 459 | 2-(6-chloro-1H-indazol-3-yl)-N-(3-morpholin-4-ylpropyl)-1H-benzimidazol-6-amine | 411.9 |
| 460 | 2-(6-methoxy-1H-indazol-3-yl)-N-(3-morpholin-4-ylpropyl)-1H-benzimidazol-6-amine | 407.5 |
| 461 | 2-(5-ethoxy-1H-indazol-3-yl)-N-(3-morpholin-4-ylpropyl)-1H-benzimidazol-6-amine | 421.5 |
| 462 | N-(3-morpholin-4-ylpropyl)-2-(6-nitro-1H-indazol-3-yl)-1H-benzimidazol-6-amine | 422.5 |
| 463 | 2-(1H-[1,3]dioxolo[4,5-f]indazol-3-yl)-N-(3-morpholin-4-ylpropyl)-1H-benzimidazol-6-amine | 421.5 |
| 464 | 2-(7-chloro-1H-indazol-3-yl)-N-(3-morpholin-4-ylpropyl)-1H-benzimidazol-6-amine | 411.9 |
| 465 | N-(3-morpholin-4-ylpropyl)-2-[6-(trifluoromethyl)-1H-indazol-3-yl]-1H-benzimidazol-6-amine | 445.5 |
| 466 | 3,5-bis(1H-benzimidazol-2-yl)-1H-indazole | 351.4 |
| 467 | {1-[2-(1H-indazol-3-yl)-1H-benzimidazol-6-yl]piperidin-4-yl}methanol | 348.4 |
| 468 | {1-[2-(5-fluoro-1H-indazol-3-yl)-1H-benzimidazol-6-yl]piperidin-4-yl}methanol | 366.4 |
| 469 | {1-[2-(5-chloro-1H-indazol-3-yl)-1H-benzimidazol-6-yl]piperidin-4-yl}methanol | 382.9 |
| 470 | {1-[2-(5-bromo-1H-indazol-3-yl)-1H-benzimidazol-6-yl]piperidin-4-yl}methanol | 427.3 |
| 471 | {1-[2-(5-methoxy-1H-indazol-3-yl)-1H-benzimidazol-6-yl]piperidin-4-yl}methanol | 378.4 |
| 472 | {1-[2-(5-nitro-1H-indazol-3-yl)-1H-benzimidazol-6-yl]piperidin-4-yl}methanol | 393.4 |
| 473 | methyl 3-{6-[4-(hydroxymethyl)piperidin-1-yl]-1H-benzimidazol-2-yl}-1H-indazole-5-carboxylate | 406.5 |
| 474 | {1-[2-(5-methyl-1H-indazol-3-yl)-1H-benzimidazol-6-yl]piperidin-4-yl}methanol | 362.4 |
| 475 | (1-{2-[5-(benzyloxy)-1H-indazol-3-yl]-1H-benzimidazol-6-yl}piperidin-4-yl)methanol | 454.5 |
| 476 | {1-[2-(6-fluoro-1H-indazol-3-yl)-1H-benzimidazol-6-yl]piperidin-4-yl}methanol | 366.4 |
| 477 | {1-[2-(6-chloro-1H-indazol-3-yl)-1H-benzimidazol-6-yl]piperidin-4-yl}methanol | 382.9 |
| 478 | {1-[2-(6-methoxy-1H-indazol-3-yl)-1H-benzimidazol-6-yl]piperidin-4-yl}methanol | 378.4 |
| 479 | {1-[2-(5-ethoxy-1H-indazol-3-yl)-1H-benzimidazol-6-yl]piperidin-4-yl}methanol | 392.5 |
| 480 | {1-[2-(6-nitro-1H-indazol-3-yl)-1H-benzimidazol-6-yl]piperidin-4-yl}methanol | 393.4 |
| 481 | {1-[2-(1H-[1,3]dioxolo[4,5-f]indazol-3-yl)-1H-benzimidazol-6-yl]piperidin-4-yl}methanol | 392.4 |
| 482 | {1-[2-(7-chloro-1H-indazol-3-yl)-1H-benzimidazol-6-yl]piperidin-4-yl}methanol | 382.9 |
| 483 | (1-{2-[6-(trifluoromethyl)-1H-indazol-3-yl]-1H-benzimidazol-6-yl}piperidin-4-yl)methanol | 416.4 |
| 484 | 3-(1H-benzimidazol-2-yl)-5-(benzyloxy)-1H-indazole | 341.4 |
| 485 | 5-(1H-benzimidazol-2-yl)-3-[5-(4-methylpiperazin-1-yl)-1H-benzimidazol-2-yl]-1H-indazole | 449.5 |
| 486 | N-({1-[2-(6-fluoro-1H-indazol-3-yl)-1H-benzimidazol-6-yl]pyrrolidin-3-yl}methyl)-N,N-dimethylamine | 379.5 |
| 487 | 3-(1H-benzimidazol-2-yl)-1H-[1,3]dioxolo[4,5-f]indazole | 279.3 |
| 488 | 3-(1H-benzimidazol-2-yl)-6-chloro-1H-indazole | 269.7 |
| 489 | 3-(1H-benzimidazol-2-yl)-6-fluoro-1H-indazole | 253.3 |
| 490 | 3-(1H-benzimidazol-2-yl)-1H-indazole-6-carbonitrile | 260.3 |
| 491 | 3-(1H-benzimidazol-2-yl)-6-nitro-1H-indazole | 280.3 |
| 492 | 3-(1H-benzimidazol-2-yl)-N-(2-morpholin-4-ylethyl)-1H-indazole-6-carboxamide | 391.4 |

-continued

| Example | Name | LC/MS (m/z) (MH+) |
|---|---|---|
| 493 | 6-fluoro-3-{6-[(8aS)-hexahydropyrrolo[1,2-a]pyrazin-2(1H)-yl]-1H-benzimidazol-2-yl}-1H-indazole | 377.4 |
| 494 | 5-chloro-3-{5-[(3R,5S)-3,5-dimethylpiperazin-1-yl]-1H-benzimidazol-2-yl}-1H-indazole | 381.9 |
| 495 | 5-bromo-3-{5-[(3R,5S)-3,5-dimethylpiperazin-1-yl]-1H-benzimidazol-2-yl}-1H-indazole | 426.3 |
| 496 | 3-{5-[(3R,5S)-3,5-dimethylpiperazin-1-yl]-1H-benzimidazol-2-yl}-5-methoxy-1H-indazole | 377.5 |
| 497 | 3-{5-[(3R,5S)-3,5-dimethylpiperazin-1-yl]-1H-benzimidazol-2-yl}-5-nitro-1H-indazole | 392.4 |
| 498 | methyl 3-{5-[(3R,5S)-3,5-dimethylpiperazin-1-yl]-1H-benzimidazol-2-yl}-1H-indazole-5-carboxylate | 405.5 |
| 499 | 3-{5-[(3R,SS)-3,5-dimethylpiperazin-1-yl]-1H-benzimidazol-2-yl}-5-methyl-1H-indazole | 361.5 |
| 500 | 5-(benzyloxy)-3-{5-[(3R,5S)-3,5-dimethylpiperazin-1-yl]-1H-benzimidazol-2-yl}-1H-indazole | 453.6 |
| 501 | 3-{5-[(3R,5S)-3,5-dimethylpiperazin-1-yl]-1H-benzimidazol-2-yl}-6-fluoro-1H-indazole | 365.4 |
| 502 | 3-{5-[(3R,5S)-3,5-dimethylpiperazin-1-yl]-1H-benzimidazol-2-yl}-6-nitro-1H-indazole | 381.9 |
| 503 | 3-{5-[(3R,5S)-3,5-dimethylpiperazin-1-yl]-1H-benzimidazol-2-yl}-6-methoxy-1H-indazole | 377.5 |
| 504 | 5-[(3R,5S)-3,5-dimethylpiperazin-1-yl]-2-(1H-pyrazol-3-yl)-1H-benzimidazole | 297.4 |
| 505 | 3-{5-[(3R,5S)-3,5-dimethylpiperazin-1-yl]-1H-benzimidazol-2-yl}-5-ethoxy-1H-indazole | 391.5 |
| 506 | 3-{5-[(3R,5S)-3,5-dimethylpiperazin-1-yl]-1H-benzimidazol-2-yl}-6-nitro-1H-indazole | 392.4 |
| 507 | 3-{5-[(3R,5S)-3,5-dimethylpiperazin-1-yl]-1H-benzimidazol-2-yl}-1H-[1,3]dioxolo[4,5-f]indazole | 391.4 |
| 508 | 7-chloro-3-{5-[(3R,5S)-3,5-dimethylpiperazin-1-yl]-1H-benzimidazol-2-yl}-1H-indazole | 381.9 |
| 509 | 3-{5-[(3R,5S)-3,5-dimethylpiperazin-1-yl]-1H-benzimidazol-2-yl}-5-methoxy-4-methyl-1H-indazole | 391.5 |
| 510 | 3-{5-[(3R,5S)-3,5-dimethylpiperazin-1-yl]-1H-benzimidazol-2-yl}-1H-indazole-6-carbonitrile | 372.4 |
| 511 | 5-fluoro-3-(5-methyl-1H-benzimidazol-2-yl)-1H-indazole | 267.3 |
| 512 | 5-methoxy-3-(5-methyl-1H-benzimidazol-2-yl)-1H-indazole | 279.3 |
| 513 | methyl 3-(5-methyl-1H-benzimidazol-2-yl)-1H-indazole-5-carboxylate | 307.3 |
| 514 | 3-(5-methyl-1H-benzimidazol-2-yl)-1H-indazole-5-carbonitrile | 274.3 |
| 515 | 3-[6-(4-methyl-1,4-diazepan-1-yl)-1H-benzimidazol-2-yl]-1H-indazole | 347.4 |
| 516 | 5-fluoro-3-[6-(4-methyl-1,4-diazepan-1-yl)-1H-benzimidazol-2-yl]-1H-indazole | 365.4 |
| 517 | 5-chloro-3-[6-(4-methyl-1,4-diazepan-1-yl)-1H-benzimidazol-2-yl]-1H-indazole | 381.9 |
| 518 | 5-bromo-3-[6-(4-methyl-1,4-diazepan-1-yl)-1H-benzimidazol-2-yl]-1H-indazole | 426.3 |
| 519 | 5-methoxy-3-[6-(4-methyl-1,4-diazepan-1-yl)-1H-benzimidazol-2-yl]-1H-indazole | 377.5 |
| 520 | 3-[6-(4-methyl-1,4-diazepan-1-yl)-1H-benzimidazol-2-yl]-5-nitro-1H-indazole | 392.4 |
| 521 | methyl 3-[6-(4-methyl-1,4-diazepan-1-yl)-1H-benzimidazol-2-yl]-1H-indazole-5-carboxylate | 405.5 |
| 522 | 5-methyl-3-[6-(4-methyl-1,4-diazepan-1-yl)-1H-benzimidazol-2-yl]-1H-indazole | 361.5 |
| 523 | 5-(benzyloxy)-3-[6-(4-methyl-1,4-diazepan-1-yl)-1H-benzimidazol-2-yl]-1H-indazole | 453.6 |
| 524 | 6-fluoro-3-[6-(4-methyl-1,4-diazepan-1-yl)-1H-benzimidazol-2-yl]-1H-indazole | 365.4 |
| 525 | 6-chloro-3-[6-(4-methyl-1,4-diazepan-1-yl)-1H-benzimidazol-2-yl]-1H-indazole | 381.9 |
| 526 | 6-methoxy-3-[6-(4-methyl-1,4-diazepan-1-yl)-1H-benzimidazol-2-yl]-1H-indazole | 377.5 |
| 527 | 5-ethoxy-3-[6-(4-methyl-1,4-diazepan-1-yl)-1H-benzimidazol-2-yl]-1H-indazole | 391.5 |
| 528 | 3-[6-(4-methyl-1,4-diazepan-1-yl)-1H-benzimidazol-2-yl]-6-nitro-1H-indazole | 392.4 |
| 529 | 3-[6-(4-methyl-1,4-diazepan-1-yl)-1H-benzimidazol-2-yl]-1H-[1,3]dioxolo[4,5-f]indazole | 391.4 |
| 530 | 7-chloro-3-[6-(4-methyl-1,4-diazepan-1-yl)-1H-benzimidazol-2-yl]-1H-indazole | 381.9 |

-continued

| Example | Name | LC/MS (m/z) (MH+) |
|---|---|---|
| 531 | 3-[6-(4-methyl-1,4-diazepan-1-yl)-1H-benzimidazol-2-yl]-1H-indazole-6-carbonitrile | 372.4 |
| 532 | 5-(benzyloxy)-3-[6-(4-methylpiperazin-1-yl)-1H-benzimidazol-2-yl]-1H-indazole | 439.5 |
| 533 | 5-isopropoxy-3-[6-(4-methylpiperazin-1-yl)-1H-benzimidazol-2-yl]-1H-indazole | 391.5 |
| 534 | 3-[6-(4-methylpiperazin-1-yl)-1H-benzimidazol-2-yl]-5-[(5-nitropyridin-2-yl)oxy]-1H-indazole | 471.5 |
| 535 | 5-methyl-3-[6-(4-methylpiperazin-1-yl)-1H-benzimidazol-2-yl]-1H-indazole | 347.4 |
| 536 | 5-ethoxy-3-[6-(4-methylpiperazin-1-yl)-1H-benzimidazol-2-yl]-1H-indazole | 377.5 |
| 537 | 5-isobutoxy-3-[6-(4-methylpiperazin-1-yl)-1H-benzimidazol-2-yl]-1H-indazole | 405.5 |
| 538 | 3-[6-(4-methylpiperazin-1-yl)-1H-benzimidazol-2-yl]-6-nitro-1H-indazole | 378.4 |
| 539 | N-isopropyl-3-[6-(4-methylpiperazin-1-yl)-1H-benzimidazol-2-yl]-1H-indazol-6-amine | 390.5 |
| 540 | 5-bromo-3-(5-methyl-1H-benzimidazol-2-yl)-1H-indazole | 328.2 |
| 541 | 3-(1H-benzimidazol-2-yl)-5-nitro-1H-indazole | 280.3 |
| 542 | methyl 3-(1H-benzimidazol-2-yl)-1H-indazole-5-carboxylate | 293.3 |
| 543 | 6-chloro-3-[5-(4-methylpiperazin-1-yl)-1H-benzimidazol-2-yl]-1H-indazole | 367.9 |
| 544 | 3-[5-(4-methylpiperazin-1-yl)-1H-benzimidazol-2-yl]-6-nitro-1H-indazole | 378.4 |
| 545 | 3-[5-(4-methylpiperazin-1-yl)-1H-benzimidazol-2-yl]-1H-indazole-6-carbonitrile | 358.4 |
| 546 | 3-[5-(4-methylpiperazin-1-yl)-1H-benzimidazol-2-yl]-1H-indazole-6-carboxylic acid | 377.4 |
| 547 | 3-(1H-benzimidazol-2-yl)-6-methyl-1H-indazole | 249.3 |
| 548 | 5-methyl-3-[5-(4-methylpiperazin-1-yl)-1H-benzimidazol-2-yl]-1H-indazole | 347.4 |
| 549 | 3-[5-(4-methylpiperazin-1-yl)-1H-benzimidazol-2-yl]-1H-[1,3]dioxolo[4,5-f]indazole | 377.4 |
| 550 | 3-(1H-benzimidazol-2-yl)-1H-indazol-6-amine | 250.3 |
| 551 | 3-(1H-benzimidazol-2-yl)-1H-indazole-6-carboxylic acid | 279.3 |
| 552 | 3-(1H-benzimidazol-2-yl)-6-methoxy-1H-indazole | 265.3 |
| 553 | 3-(1H-benzimidazol-2-yl)-1H-indazole-5-carboxylic acid | 279.3 |
| 554 | 3-(1H-benzimidazol-2-yl)-5-chloro-1H-indazole | 269.7 |
| 555 | 3-(5-chloro-1H-benzimidazol-2-yl)-5-fluoro-1H-indazole | 287.7 |
| 556 | 3-(5-chloro-1H-benzimidazol-2-yl)-5-methoxy-1H-indazole | 299.7 |
| 557 | 3-(1H-benzimidazol-2-yl)-5-bromo-1H-indazole | 314.2 |
| 558 | 3-(1H-benzimidazol-2-yl)-5-fluoro-1H-indazole | 253.3 |
| 559 | 3-(1H-benzimidazol-2-yl)-1H-indazole-5-carbonitrile | 260.3 |
| 560 | 6-bromo-3-[5-(4-methylpiperazin-1-yl)-1H-benzimidazol-2-yl]-1H-indazole | 412.3 |
| 561 | 5-bromo-3-[5-(4-methylpiperazin-1-yl)-1H-benzimidazol-2-yl]-1H-indazole | 412.3 |
| 562 | 3-[6-(4-ethylpiperazin-1-yl)-1H-benzimidazol-2-yl]-1H-indazole | 347.4 |
| 563 | 3-[6-(4-ethylpiperazin-1-yl)-1H-benzimidazol-2-yl]-5-fluoro-1H-indazole | 365.4 |
| 564 | 5-chloro-3-[6-(4-ethylpiperazin-1-yl)-1H-benzimidazol-2-yl]-1H-indazole | 381.9 |
| 565 | 5-bromo-3-[6-(4-ethylpiperazin-1-yl)-1H-benzimidazol-2-yl]-1H-indazole | 426.3 |
| 566 | 3-[6-(4-ethylpiperazin-1-yl)-1H-benzimidazol-2-yl]-5-methoxy-1H-indazole | 377.5 |
| 567 | 3-[6-(4-ethylpiperazin-1-yl)-1H-benzimidazol-2-yl]-5-nitro-1H-indazole | 392.4 |
| 568 | methyl 3-[6-(4-ethylpiperazin-1-yl)-1H-benzimidazol-2-yl]-1H-indazole-5-carboxylate | 405.5 |
| 569 | 3-[6-(4-ethylpiperazin-1-yl)-1H-benzimidazol-2-yl]-5-methyl-1H-indazole | 361.5 |
| 570 | 5-(benzyloxy)-3-[6-(4-ethylpiperazin-1-yl)-1H-benzimidazol-2-yl]-1H-indazole | 453.6 |
| 571 | 3-[6-(4-ethylpiperazin-1-yl)-1H-benzimidazol-2-yl]-6-fluoro-1H-indazole | 365.4 |
| 572 | 6-chloro-3-[6-(4-ethylpiperazin-1-yl)-1H-benzimidazol-2-yl]-1H-indazole | 381.9 |
| 573 | 3-[6-(4-ethylpiperazin-1-yl)-1H-benzimidazol-2-yl]-6-methoxy-1H-indazole | 377.5 |

-continued

| Example | Name | LC/MS (m/z) (MH+) |
|---|---|---|
| 574 | 5-ethoxy-3-[6-(4-ethylpiperazin-1-yl)-1H-benzimidazol-2-yl]-1H-indazole | 391.5 |
| 575 | 3-[6-(4-ethylpiperazin-1-yl)-1H-benzimidazol-2-yl]-6-nitro-1H-indazole | 392.4 |
| 576 | 3-[6-(4-ethylpiperazin-1-yl)-1H-benzimidazol-2-yl]-1H-[1,3]dioxolo[4,5-f]indazole | 391.4 |
| 577 | 7-chloro-3-[6-(4-ethylpiperazin-1-yl)-1H-benzimidazol-2-yl]-1H-indazole | 381.9 |
| 578 | 3-[6-(4-ethylpiperazin-1-yl)-1H-benzimidazol-2-yl]-5-methoxy-4-methyl-1H-indazole | 391.5 |
| 579 | 3-[6-(4-ethylpiperazin-1-yl)-1H-benzimidazol-2-yl]-1H-indazole-6-carbontrile | 372.4 |
| 580 | 3-[6-(4-cyclohexylpiperazin-1-yl)-1H-benzimidazol-2-yl]-5-fluoro-1H-indazole | 419.5 |
| 581 | 5-chloro-3-[6-(4-cyclohexylpiperazin-1-yl)-1H-benzimidazol-2-yl]-1H-indazole | 436.0 |
| 582 | 5-bromo-3-[6-(4-cyclohexylpiperazin-1-yl)-1H-benzimidazol-2-yl]-1H-indazole | 480.4 |
| 583 | 3-[6-(4-cyclohexylpiperazin-1-yl)-1H-benzimidazol-2-yl]-5-methoxy-1H-indazole | 431.6 |
| 584 | 3-[6-(4-cyclohexylpiperazin-1-yl)-1H-benzimidazol-2-yl]-5-nitro-1H-indazole | 446.5 |
| 585 | methyl 3-[6-(4-cyclohexylpiperazin-1-yl)-1H-benzimidazol-2-yl]-1H-indazole-5-carboxylate | 459.6 |
| 586 | 3-[6-(4-cyclohexylpiperazin-1-yl)-1H-benzimidazol-2-yl]-5-methyl-1H-indazole | 415.6 |
| 587 | 5-(benzyloxy)-3-[6-(4-cyclohexylpiperazin-1-yl)-1H-benzimidazol-2-yl]-1H-indazole | 507.7 |
| 588 | 6-chloro-3-[6-(4-cyclohexylpiperazin-1-yl)-1H-benzimidazol-2-yl]-1H-indazole | 436.0 |
| 589 | 3-[6-(4-cyclohexylpiperazin-1-yl)-1H-benzimidazol-2-yl]-6-methoxy-1H-indazole | 431.6 |
| 590 | 3-[6-(4-cyclohexylpiperazin-1-yl)-1H-benzimidazol-2-yl]-5-ethoxy-1H-indazole | 445.6 |
| 591 | 3-[6-(4-cyclohexylpiperazin-1-yl)-1H-benzimidazol-2-yl]-6-nitro-1H-indazole | 446.5 |
| 592 | 3-[6-(4-cyclohexylpiperazin-1-yl)-1H-benzimidazol-2-yl]-1H-[1,3]dioxolo[4,5-f]indazole | 445.5 |
| 593 | 7-chloro-3-[6-(4-cyclohexylpiperazin-1-yl)-1H-benzimidazol-2-yl]-1H-indazole | 436.0 |
| 594 | 3-[6-(4-cyclohexylpiperazin-1-yl)-1H-benzimidazol-2-yl]-5-methoxy-4-methyl-1H-indazole | 445.6 |
| 595 | 3-[6-(4-cyclohexylpiperazin-1-yl)-1H-benzimidazol-2-yl]-1H-indazole-6-carbontrile | 426.5 |
| 596 | 3-(5-chloro-1H-benzimidazol-2-yl)-5-nitro-1H-indazole | 314.7 |
| 597 | 3-[5-(4-methylpiperazin-1-yl)-1H-benzimidazol-2-yl]-1H-indazole-5-carboxylic acid | 377.4 |
| 598 | 3-[5-(4-methylpiperazin-1-yl)-1H-benzimidazol-2-yl]-4-nitro-1H-indazole | 378.4 |
| 599 | 3-[6-(4-pyridin-2-ylpiperazin-1-yl)-1H-benzimidazol-2-yl]-1H-indazole | 396.5 |
| 600 | 5-fluoro-3-[6-(4-pyridin-2-ylpiperazin-1-yl)-1H-benzimidazol-2-yl]-1H-indazole | 414.5 |
| 601 | 5-chloro-3-[6-(4-pyridin-2-ylpiperazin-1-yl)-1H-benzimidazol-2-yl]-1H-indazole | 430.9 |
| 602 | 5-bromo-3-[6-(4-pyridin-2-ylpiperazin-1-yl)-1H-benzimidazol-2-yl]-1H-indazole | 475.4 |
| 603 | 5-methoxy-3-[6-(4-pyridin-2-ylpiperazin-1-yl)-1H-benzimidazol-2-yl]-1H-indazole | 426.5 |
| 604 | 5-nitro-3-[6-(4-pyridin-2-ylpiperazin-1-yl)-1H-benzimidazol-2-yl]-1H-indazole | 441.5 |
| 605 | methyl 3-[6-(4-pyridin-2-ylpiperazin-1-yl)-1H-benzimidazol-2-yl]-1H-indazole-5-carboxylate | 454.5 |
| 606 | 5-methyl-3-[6-(4-pyridin-2-ylpiperazin-1-yl)-1H-benzimidazol-2-yl]-1H-indazole | 410.5 |
| 607 | 5-(benzyloxy)-3-[6-(4-pyridin-2-ylpiperazin-1-yl)-1H-benzimidazol-2-yl]-1H-indazole | 502.6 |
| 608 | 6-fluoro-3-[6-(4-pyridin-2-ylpiperazin-1-yl)-1H-benzimidazol-2-yl]-1H-indazole | 414.5 |
| 609 | 6-chloro-3-[6-(4-pyridin-2-ylpiperazin-1-yl)-1H-benzimidazol-2-yl]-1H-indazole | 430.9 |
| 610 | 5-ethoxy-3-[6-(4-pyridin-2-ylpiperazin-1-yl)-1H-benzimidazol-2-yl]-1H-indazole | 440.5 |
| 611 | 3-[6-(4-pyridin-2-ylpiperazin-1-yl)-1H-benzimidazol-2-yl]-1H-[1,3]dioxolo[4,5-f]indazole | 440.5 |

-continued

| Example | Name | LC/MS (m/z) (MH+) |
|---|---|---|
| 612 | 7-chloro-3-[6-(4-pyridin-2-ylpiperazin-1-yl)-1H-benzimidazol-2-yl]-1H-indazole | 430.9 |
| 613 | 3-[6-(4-pyridin-2-ylpiperazin-1-yl)-1H-benzimidazol-2-yl]-1H-indazole-6-carbonitrile | 421.5 |
| 614 | 3-[5-(4-methylpiperazin-1-yl)-1H-benzimidazol-2-yl]-N-[(2S)-pyrrolidin-2-ylmethyl]-1H-indazol-4-amine | 431.6 |
| 615 | 3-(6-chloro-1H-benzimidazol-2-yl)-1H-indazole-5-carbonitrile | 294.7 |
| 616 | methyl 3-(6-chloro-1H-benzimidazol-2-yl)-1H-indazole-5-carboxylate | 327.7 |
| 617 | N'-[3-(1H-benzimidazol-2-yl)-1H-indazol-5-yl]-N,N-dimethylpropane-1,3-diamine | 335.4 |
| 618 | 5-chloro-3-(6-chloro-1H-benzimidazol-2-yl)-1H-indazole | 304.2 |
| 619 | 5-bromo-3-(5-chloro-1H-benzimidazol-2-yl)-1H-indazole | 348.6 |
| 620 | N-({4-[2-(5-chloro-1H-indazol-3-yl)-1H-benzimidazol-6-yl]morpholin-2-yl}methyl)-N,N-dimethylamine | 411.9 |
| 621 | N-({4-[2-(5-bromo-1H-indazol-3-yl)-1H-benzimidazol-6-yl]morpholin-2-yl}methyl)-N,N-dimethylamine | 456.4 |
| 622 | N,N-dimethyl-N-({4-[2-(5-nitro-1H-indazol-3-yl)-1H-benzimidazol-6-yl]morpholin-2-yl}methyl)amine | 422.5 |
| 623 | methyl 3-(6-{2-[(dimethylamino)methyl]morpholin-4-yl}-1H-benzimidazol-2-yl)-1H-indazole-5-carboxylate | 435.5 |
| 624 | N-[(4-{2-[5-(benzyloxy)-1H-indazol-3-yl]-1H-benzimidazol-6-yl}morpholin-2-yl)methyl]-N,N-dimethylamine | 483.6 |
| 625 | N-({4-[2-(6-fluoro-1H-indazol-3-yl)-1H-benzimidazol-6-yl]morpholin-2-yl}methyl)-N,N-dimethylamine | 395.5 |
| 626 | N-({4-[2-(6-chloro-1H-indazol-3-yl)-1H-benzimidazol-6-yl]morpholin-2-yl}methyl)-N,N-dimethylamine | 411.9 |
| 627 | 3-(6-{2-[(dimethylamino)methyl]morpholin-4-yl}-1H-benzimidazol-2-yl)-1H-indazole-6-carbonitrile | 402.5 |
| 628 | 2-(5-chloro-1H-indazol-3-yl)-N-(pyridin-4-ylmethyl)-1H-benzimidazol-6-amine | 375.8 |
| 629 | 2-(5-bromo-1H-indazol-3-yl)-N-(pyridin-4-ylmethyl)-1H-benzimidazol-6-amine | MW! |
| 630 | 2-(5-nitro-1H-indazol-3-yl)-N-(pyridin-4-ylmethyl)-1H-benzimidazol-6-amine | 386.4 |
| 631 | 2-(5-methyl-1H-indazol-3-yl)-N-(pyridin-4-ylmethyl)-1H-benzimidazol-6-amine | 355.4 |
| 632 | 2-[5-(benzyloxy)-1H-indazol-3-yl]-N-(pyridin-4-ylmethyl)-1H-benzimidazol-6-amine | 447.5 |
| 633 | 2-(6-fluoro-1H-indazol-3-yl)-N-(pyridin-4-ylmethyl)-1H-benzimidazol-6-amine | 359.4 |
| 634 | 2-(7-chloro-1H-indazol-3-yl)-N-(pyridin-4-ylmethyl)-1H-benzimidazol-6-amine | 375.8 |
| 635 | 3-{6-[(pyridin-4-ylmethyl)amino]-1H-benzimidazol-2-yl}-1H-indazole-6-carbonitrile | 366.4 |
| 636 | 3-[6-(4-methylpiperazin-1-yl)-1H-benzimidazol-2-yl]-1H-indazol-4-amine | 348.4 |
| 637 | N-({(2S,5S)-4-[2-(6-fluoro-1H-indazol-3-yl)-1H-benzimidazol-6-yl]-5-methylmorpholin-2-yl}methyl)-N,N-dimethylamine | 409.5 |
| 638 | N-({(2S,5S)-4-[2-(6-chloro-1H-indazol-3-yl)-1H-benzimidazol-6-yl]-5-methylmorpholin-2-yl}methyl)-N,N-dimethylamine | 425.9 |
| 639 | 3-[6-(1H-imidazol-1-yl)-1H-benzimidazol-2-yl]-1H-indazole | 301.3 |
| 640 | 5-fluoro-3-(6-(1H-imidazol-1-yl)-1H-benzimidazol-2-yl]-1H-indazole | 319.3 |
| 641 | 5-chloro-3-[6-(1H-imidazol-1-yl)-1H-benzimidazol-2-yl]-1H-indazole | 335.8 |
| 642 | 5-bromo-3-[6-(1H-imidazol-1-yl)-1H-benzimidazol-2-yl]-1H-indazole | 380.2 |
| 643 | 3-[6-(1H-imidazol-1-yl)-1H-benzimidazol-2-yl]-5-methoxy-1H-indazole | 331.4 |
| 644 | 3-[6-(1H-imidazol-1-yl)-1H-benzimidazol-2-yl]-5-nitro-1H-indazole | 346.3 |
| 645 | methyl 3-[6-(1H-imidazol-1-yl)-1H-benzimidazol-2-yl]-1H-indazole-5-carboxylate | 359.4 |
| 646 | 3-[6-(1H-imidazol-1-yl)-1H-benzimidazol-2-yl]-5-methyl-1H-indazole | 315.4 |
| 647 | 5-(benzyloxy)-3-[6-(1H-imidazol-1-yl)-1H-benzimidazol-2-yl]-1H-indazole | 407.4 |
| 648 | 6-fluoro-3-[6-(1H-imidazol-1-yl)-1H-benzimidazol-2-yl]-1H-indazole | 319.3 |

-continued

| Example | Name | LC/MS (m/z) (MH+) |
|---|---|---|
| 649 | 6-chloro-3-[6-(1H-imidazol-1-yl)-1H-benzimidazol-2-yl]-1H-indazole | 335.8 |
| 650 | 5-ethoxy-3-[6-(1H-imidazol-1-yl)-1H-benzimidazol-2-yl]-1H-indazole | 345.4 |
| 651 | 3-[6-(1H-imidazol-1-yl)-1H-benzimidazol-2-yl]-1H-[1,3]dioxolo[4,5-f]indazole | 345.3 |
| 652 | 7-chloro-3-[6-(1H-imidazol-1-yl)-1H-benzimidazol-2-yl]-1H-indazole | 335.8 |
| 653 | 3-[6-(1H-imidazol-1-yl)-1H-benzimidazol-2-yl]-1H-indazole-6-carbonitrile | 326.3 |
| 654 | 2-(5-fluoro-1H-indazol-3-yl)-N-(3-pyrrolidin-1-ylpropyl)-1H-benzimidazol-6-amine | 379.5 |
| 655 | 2-(5-chloro-1H-indazol-3-yl)-N-(3-pyrrolidin-1-ylpropyl)-1H-benzimidazol-6-amine | 395.9 |
| 656 | 2-(5-methoxy-1H-indazol-3-yl)-N-(3-pyrrolidin-1-ylpropyl)-1H-benzimidazol-6-amine | 391.5 |
| 657 | 2-(5-nitro-1H-indazol-3-yl)-N-(3-pyrrolidin-1-ylpropyl)-1H-benzimidazol-6-amine | 406.5 |
| 658 | 2-(5-methyl-1H-indazol-3-yl)-N-(3-pyrrolidin-1-ylpropyl)-1H-benzimidazol-6-amine | 375.5 |
| 659 | 2-[5-(benzyloxy)-1H-indazol-3-yl]-N-(3-pyrrolidin-1-ylpropyl)-1H-benzimidazol-6-amine | 467.6 |
| 660 | 2-(6-fluoro-1H-indazol-3-yl)-N-(3-pyrrolidin-1-ylpropyl)-1H-benzimidazol-6-amine | 379.5 |
| 661 | 2-(6-chloro-1H-indazol-3-yl)-N-(3-pyrrolidin-1-ylpropyl)-1H-benzimidazol-6-amine | 395.9 |
| 662 | 2-(5-ethoxy-1H-indazol-3-yl)-N-(3-pyrrolidin-1-ylpropyl)-1H-benzimidazol-6-amine | 405.5 |
| 663 | 2-(1H-[1,3]dioxolo[4,5-f]indazol-3-yl)-N-(3-pyrrolidin-1-ylpropyl)-1H-benzimidazol-6-amine | 405.5 |
| 664 | 2-(7-chloro-1H-indazol-3-yl)-N-(3-pyrrolidin-1-ylpropyl)-1H-benzimidazol-6-amine | 395.9 |
| 665 | N,N-diethyl-N'-[2-(5-fluoro-1H-indazol-3-yl)-1H-benzimidazol-6-yl]-N'-methylpropane-1,3-diamine | 395.5 |
| 666 | N-[2-(5-chloro-1H-indazol-3-yl)-1H-benzimidazol-6-yl]-N',N'-diethyl-N-methylpropane-1,3-diamine | 412.0 |
| 667 | N,N-diethyl-N'methyl-N'[2-(5-nitro-1H-indazol-3-yl)-1H-benzimidazol-6-yl]propane-1,3-diamine | 422.5 |
| 668 | N-{2-[5-(benzyloxy)-1H-indazol-3-yl]-1H-benzimidazol-6-yl}-N',N'-diethyl-N-methylpropane-1,3-diamine | 483.6 |
| 669 | N,N-diethyl-N'-[2-(6-fluoro-1H-indazol-3-yl)-1H-benzimidazol-6-yl]-N'-methylpropane-1,3-diamine | 395.5 |
| 670 | N-[2-(7-chloro-1H-indazol-3-yl)-1H-benzimidazol-6-yl]-N',N'-diethyl-N-methylpropane-1,3-diamine | 412.0 |

Example 671

3-[6-(1,4'-Bipiperidin-1'-yl)-1H-benzimidazol-2-yl]-1H-indazol-5-amine

To a solution of the product produced in Example 110 (1.0 eq) in ethanol:ethyl acetate (1:1) was added 10% Pd/C (0.5 eq). The reaction vessel was repeatedly purged with nitrogen and then stirred under a hydrogen atmosphere (1 atm) for 48 hours. The product was filtered through Celite with ethanol. The solvent was removed to provide a brown solid which was used without purification. LC/MS (m/z) 416.1 (MH+), $R_t$ 1.30 minutes.

Examples 672-684

Examples 672-684 were synthesized from amino substituted indazole benzimidzoles and isocyanates, using the procedure set forth below for the of various compounds which include a urea substituent.

Example 672

N-{3-[6-(1,4'-Bipiperidin-1'-yl)-1H-benzimidazol-2-yl]-1H-indazol-5-yl}-N'-phenylurea Benzimidazol-2-yl-1H-indazole-5-ylamine was dissolved in THF and phenylisocyanate (1.1 equivalents) was added. The mixture was shaken overnight, the solution was concentrated, and the resulting residue was purified by preparatory HPLC. LC/MS (m/z) 535.6 (MH+), $R_t$ 1.93 minutes.

| Example | Name | LC/MS (m/z) (MH+) |
|---|---|---|
| 673 | 1'-[2-(6-chloro-1H-indazol-3-yl)-3H-imidazo[4,5-bipyridin-5-yl]-1,4'-b]piperidine | 437.0 |
| 674 | N-{3-[6-(1,4'-b]piperidin-1'-yl)-1H-benzimidazol-2-yl]-1H-indazol-5-yl}-N'-isopropylurea | 501.6 |
| 675 | N-benzyl-N'-{3-[6-(1,4'-bipiperidin-1'-yl)-1H-benzimidazol-2-yl]-1H-indazol-5-yl}urea | 549.7 |
| 676 | N-{3-[6-(1,4'-bipiperidin-1'-yl)-1H-benzimidazol-2-yl]-1H-indazol-5-yl}-N'-(2,4-dimethoxyphenyl)urea | 595.7 |

-continued

| Example | Name | LC/MS (m/z) (MH+) |
|---|---|---|
| 677 | N-{3-[6-(1,4'-bipiperidin-1'-yl)-1H-benzimidazol-2-yl]-1H-indazol-5-yl}-N'-(tert-butyl)urea | 515.7 |
| 678 | N-[3-(1H-benzimidazol-2-yl)-1H-indazol-5-yl]-N'-(tert-butyl)urea | 349.4 |
| 679 | N-(tert-butyl)-N'-{3-[6-(4-methylpiperazin-1-yl)-1H-benzimidazol-2-yl]-1H-indazol-5-yl}urea | 447.6 |
| 680 | N-isopropyl-N'-{3-[6-(4-methylpiperazin-1-yl)-1H-benzimidazol-2-yl]-1H-indazol-6-yl}urea | 433.5 |
| 681 | N-(tert-butyl)-N'-{3-[6-(4-methylpiperazin-1-yl)-1H-benzimidazol-2-yl]-1H-indazol-6-yl}urea | 447.6 |
| 682 | N-ethyl-N'-{3-[6-(4-methylpiperazin-1-yl)-1H-benzimidazol-2-yl]-1H-indazol-6-yl}urea | 419.5 |
| 683 | N-(2-methoxyphenyl)-N'-{3-[6-(4-methylpiperazin-1-yl)-1H-benzimidazol-2-yl]-1H-indazol-6-yl}urea | 497.6 |
| 684 | N-{3-[6-(4-methylpiperazin-1-yl)-1H-benzimidazol-2-yl]-1H-indazol-6-yl}-N'-[3-(trifluoromethyl)phenyl]urea | 535.5 |

Examples 685-689

Examples 685-689 were synthesized from amino substituted indazole-benzimidazoles and acyl halides or sulfonyl halides, using the coupling procedures set forth below for the synthesis of various compounds that include the —N(H)—C(=O)—R or the —N(H)—(SO₂)—R' group.

Example 685

N-{3-[6-(1,4'-Bipiperidin-1'-yl)-1H-benzimidazol-2-yl]-1H-indazol-5-yl}benzamide Benzimidazol-2-yl-1H-indazole-5-ylamine was dissolved in CH₂Cl₂ and benzoyl chloride (1.1 equivalent) was added followed by diisopropylethylamine (1.1 equivalent). The resulting mixture was allowed to stir overnight. The solution was then concentrated and the resulting residue was purified by preparatory HPLC. LC/MS (m/z) 520.6 (MH⁺), R$_t$ 1.86 minutes Example 688

N-{3-[6-(1,4'-Bipiperidin-1'-yl)-1H-benzimidazol-2-yl]-1H-indazol-5-yl}methanesulfonamide 3-Benzimidazol-2-yl-1H-indazole-5-ylamine (1 equivalent), methanesulfonyl chloride (1.1 equivalent), and diisopropylethylamine (2 equivalents) in CH₂Cl₂ were stirred for 18 hours. The solvent was evaporated, and the resulting residue was purified by preparatory HPLC. LC/MS (m/z) 494.6 (MH⁺), R$_t$ 2.35 minutes.

| Example | Name | LC/MS (m/z) (MH+) |
|---|---|---|
| 686 | N-{3-[6-(1,4'-bipiperidin-1'-yl)-1H-benzimidazol-2-yl]-1H-indazol-5-yl}acetamide | 458.6 |
| 687 | N-{3-[6-(1,4'-bipiperidin-1'-yl)-1H-benzimidazol-2-yl]-1H-indazol-5-yl}-2-furamide | 510.6 |
| 689 | N-{3-[6-(4-methylpiperazin-1-yl)-1H-benzimidazol-2-yl]-1H-indazol-6-yl}ethanesulfonamide | 440.2 |

Examples 690-726

Examples 690-726 were synthesized from amino substituted indazole-benzimidazoles and carbonyl compounds, using the procedure set forth below for Example 710.

Example 710

3-(1H-Benzimidazol-2-yl)-N-(1,3-thiazol-2-ylmethyl)-1H-indazol-5-amine

3-Benzimidazol-2-yl-1H-indazole-5-ylamine (1 equivalent), 2-thiazolecaboxaldehyde (1.1 equivalent), BH₃:pyridine (10 equivalents, 8 M in pyridine) in AcOH:MeOH:CH₂Cl₂ (1:2:2) were stirred for 18 hours at room temperature. The solvent was removed, and the residue was purified by preparatory HPLC. LC/MS (m/z) 347.1 (MH⁺), R$_t$ 1.93 minutes.

| Example | Name | LC/MS (m/z) (MH+) |
|---|---|---|
| 690 | 3-[6-(1,4'-bipiperidin-1'-yl)-1H-benzimidazol-2-yl]-N-[(3-methyl-1H-pyrazol-4-yl)methyl]-1H-indazol-5-amine | 509.7 |
| 691 | 3-[6-(1,4'-bipiperidin-1'-yl)-1H-benzimidazol-2-yl]-N-(2-furylmethyl)-1H-indazol-5-amine | 495.6 |
| 692 | 3-[6-(1,4'-bipiperidin-1'-yl)-1H-benzimidazol-2-yl]-N-(2,3-dihydro-1-benzofuran-5-ylmethyl)-1H-indazol-5-amine | 547.7 |
| 693 | 3-[6-(1,4'-bipiperidin-1'-yl)-1H-benzimidazol-2-yl]-N-(1H-imidazol-2-ylmethyl)-1H-indazol-5-amine | 495.6 |
| 694 | 3-[6-(1,4'-bipiperidin-1'-yl)-1H-benzimidazol-2-yl]-N-(1,3-thiazol-2-ylmetbyl)-1H-indazol-5-amine | 512.7 |
| 695 | 3-[6-(1,4'-bipiperidin-1'-yl)-1H-benzimidazol-2-yl]-N-(3-methoxybenzyl)-1H-indazol-5-amine | 535.7 |
| 696 | 3-[6-(1,4'-bipiperidin-1'-yl)-1H-benzimidazol-2-yl]-N-[(2S)-pyrrolidin-2-ylmethyl]-1H-indazol-5-amine | 498.7 |
| 697 | 3-[6-(1,4'-bipiperidin-1'-yl)-1H-benzimidazol-2-yl]-N-({5-[(dimethylamino)methyl]-2-furyl}methyl)-1H-indazol-5-amine | 552.7 |

| Example | Name | LC/MS (m/z) (MH+) |
|---|---|---|
| 698 | 3-[6-(1,4'-bipiperidin-1'-yl)-1H-benzimidazol-2-yl]-N-[(3,5-dimethylisoxazol-4-yl)methyl]-1H-indazol-5-amine | 524.7 |
| 699 | N-(1H-1,2,3-benzotriazol-5-ylmethyl)-3-[6-(1,4'-bipiperidin-1'-yl)-1H-benzimidazol-2-yl]-1H-indazol-5-amine | 546.7 |
| 700 | N-(1H-benzimidazol-5-ylmethyl)-3-[6-(1,4'-bipiperidin-1'-yl)-1H-benzimidazol-2-yl]-1H-indazol-5-amine | 545.7 |
| 701 | 3-[6-(1,4'-bipiperidin-1'-yl)-1H-benzimidazol-2-yl]-N-[(5-chloro-1,3-dimethyl-1H-pyrazol-4-yl)methyl]-1H-indazol-5-amine | 558.1 |
| 702 | 3-[6-(1,4'-bipiperidin-1'-yl)-1H-benzimidazol-2-yl]-N-[(4-chloro-1-methyl-1H-pyrazol-3-yl)methyl]-1H-indazol-5-amine | 544.1 |
| 703 | 3-[6-(1,4'-bipiperidin-1'-yl)-1H-benzimidazol-2-yl]-N-[(2-ethyl-4-methyl-1H-imidazol-5-yl)methyl]-1H-indazol-5-amine | 537.7 |
| 704 | N-(1-(N-hydroxycarbamoyl)(1S,2R)-2-hydroxypropyl){4-[4-(N-ethylcarbamoyl)phenyl]phenyl}carboxamide | 385.4 |
| 705 | N-{4-[(4-fluorobenzyl)oxy]benzyl}-3-[6-(4-methylpiperazin-1-yl)-1H-benzimidazol-2-yl]-1H-indazol-6-amine | 561.7 |
| 706 | N-(1H-benzimidazol-2-ylmethyl)-3-[6-(1,4'-bipiperidin-1'-yl)-1H-benzimidazol-2-yl]-1H-indazol-5-amine | 545.7 |
| 707 | N-benzyl-3-[6-(1,4'-bipiperidin-1'-yl)-1H-benzimidazol-2-yl]-1H-indazol-5-amine | 505.7 |
| 708 | 3-[6-(1,4'-bipiperidin-1'-yl)-1H-benzimidazol-2-yl]-N-(cyclohexylmethyl)-1H-indazol-5-amine | 511.7 |
| 709 | N-(1-benzylpiperidin-4-yl)-3-[6-(1,4'-bipiperidin-1'-yl)-1H-benzimidazol-2-yl]-1H-indazol-5-amine | 588.8 |
| 711 | 3-(1H-benzimidazol-2-yl)-N-[(2S)-pyrrolidin-2-ylmethyl]-1H-indazol-5-amine | 332.4 |
| 712 | 3-[6-(4-methylpiperazin-1-yl)-1H-benzimidazol-2-yl]-N-(1,3-thiazol-2-ylmethyl)-1H-indazol-5-amine | 444.6 |
| 713 | 3-[6-(4-methylpiperazin-1-yl)-1H-benzimidazol-2-yl]-N-[(2S)-pyrrolidin-2-ylmethyl]-1H-indazol-5-amine | 430.6 |
| 714 | N-(2,5-dimethoxybenzyl)-3-[6-(4-methylpiperazin-1-yl)-1H-benzimidazol-2-yl]-1H-indazol-6-amine | 497.6 |
| 715 | 3-[6-(4-methylpiperazin-1-yl)-1H-benzimidazol-2-yl]-N-(1,3-thiazol-2-ylmethyl)-1H-indazol-6-amine | 444.6 |
| 716 | N-[(1-methyl-1H-benzimidazol-2-yl)methyl]-3-[6-(4-methylpiperazin-1-yl)-1H-benzimidazol-2-yl]-1H indazol-6-amine | 491.6 |
| 717 | 3-[6-(4-methylpiperazin-1-yl)-1H-benzimidazol-2-yl]-N-[(2-phenyl-1H-imidazol-4-yl)methyl]-1H-indazol-6-amine | 503.6 |
| 718 | N-benzyl-3-[6-(4-methylpiperazin-1-yl)-1H-benzimidazol-2-yl]-1H-indazol-6-amine | 437.5 |
| 719 | N-[(2-ethyl-4-methyl-1H-imidazol-5-yl)methyl]-3-[6-(4-methylpiperazin-1-yl)-1H-benzimidazol-2-yl]-1H-indazol-6-amine | 469.6 |
| 720 | N-(2-furylmethyl)-3-[6-(4-methylpiperazin-1-yl)-1H-benzimidazol-2-yl]-1H-indazol-6-amine | 427.5 |
| 721 | N-[(4-methoxyquinolin-2-yl)methyl]-3-[6-(4-methylpiperazin-1-yl)-1H-benzimidazol-2-yl]-1H-indazol-6-amine | 518.6 |
| 722 | 3-[6-(4-methylpiperazin-1-yl)-1H-benzimidazol-2-yl]-N-(1-methylpiperidin-4-yl)-1H-indazol-6-amine | 444.6 |
| 723 | N-(2-fluoro-5-methoxybenzyl)-3-[6-(4-methylpiperazin-1-yl)-1H-benzimidazol-2-yl]-1H-indazol-6-amine | 485.6 |
| 724 | N-{3-[6-(4-methylpiperazin-1-yl)-1H-benzimidazol-2-yl]-1H-indazol-6-yl}-2-furamide | 441.5 |
| 725 | N-{3-[6-(4-methylpiperazin-1-yl)-1H-benzimidazol-2-yl]-1H-indazol-6-yl}-1,3-oxazole-5-carboxamide | 442.5 |
| 726 | N-{3-[6-(4-methylpiperazin-1-yl)-1H-benzimidazol-2-yl]-1H-indazol-6-yl}acetamide | 389.5 |

Example 727

Synthesis of [(1Z)-2-aza-1-(4-methylpiperazinyl)-2-phenylvinyl]{3-[6-(4-piperidylpiperidyl)benzimidazol-2-yl](1H-indazol-5-yl)}amine*

3-[6-(4-piperidylpiperidyl)benzimidazol-2-yl]-1H-indazole-5-ylamine was dissolved in THF and shaken with benzenisothiocyanate (1.1 equivalents) for 18 hours. EDC—HCl (1.1 equivalents) and N-methylpiperazine (3 equivalents) were then added. The resulting solution was shaken for 18 hours. The solvent was then evaporated, and the residue was purified by preparatory HPLC to give [(1Z)-2-aza-1-(4-menthyl-piperazinyl)-2-phenylvinyl]{3-[6-(4-piperidylpiperidyl)benzimidazol-2-yl](1H-indazol-5-yl)}amine. LC/MS (m/z) 617.5 (MH+), $R_t$ 2.65 minutes.

*piperidyl and piperidinyl are the same groups and are both used in this application.

Example 728

Synthesis of N'-[3-(1H-Benzoimidazol-2-yl)-1H-indazol-5-yl]-N,N-dimethyl-propane-1,3-diamine Synthesis of 5-Bromo-1-(2-trimethylsilyl-ethoxymethyl)-3-[1-(2-trimethylsilanyl-ethoxymethyl)-1H-benzimidazol-2-yl]-1H-indazole A reaction mixture of 3-benzimidazol-2-yl-5-bromo-1H-indazole in $CH_2Cl_2$ and aqueous 50% NaOH solution was cooled to 0° C. and charged with SEMCl (2.2 equivalents). The reaction was stirred overnight and the cooling bath was gradually allowed to warm to room temperature. The reaction was partitioned between water and methylene chloride and the layers separated. The aqueous phase was extracted with $CH_2Cl_2$ (3×) and the organic extracts were combined and washed with brine. The resulting crude residue was purified by flash chromatography to give 5-bromo-1-(2-trimethylsilanyl-ethoxymethyl)-3-[1-(2-trimethylsilanyl-ethoxymethyl)-1H-benzimidazol-2-yl]-1H-indazole. LC/MS (m/z) 573.1 (MH+), $R_t$ 4.29 minutes.

Synthesis of N,N-Dinethyl-N'-{1-(2-trimethylsilanyl-ethoxymethyl)-3-[1-(2-trimethylsilanyl-ethoxymethyl)-1H-benzimidazol-2-yl]-1H-indazol-5-yl}-propane-1,3-diamine To a solution of 5-bromo-1-(2-trimethylsilanyl-ethoxymethyl)-3-[1-(2-trimethylsilanyl-ethoxymethyl)-1H-benzimidazol-2-yl]-1H-indazole in dry toluene was added $Pd_2(dba)_3$ (0.02 equivalents), (R)-BINAP (0.06 equivalents), N,N dimethyl propyldiamine (1.6 equivalents), and sodium t-butoxide (1.2 equivalents). The resulting reaction mixture was subjected to microwave irradiation (≈300 watts, 120° C., 10 minutes). The crude reaction product was purified by chromatography to furnish N,N-Dimethyl-N'-{1-(2-trimethylsilanyl-ethoxymethyl)-3-[1-(2-trimethylsilanyl-ethoxymethyl)-1H-benzimidazol-2-yl]-1H-indazol-5-yl}-propane-1,3-diamine. LC/MS (m/z) 595.3 (MH+), $R_t$ 2.95 minutes.

Synthesis of N'-[3-(1H-Benzoimidazol-2-yl)-1H-indazol-5-yl]-N,N-dimethyl-propane-1,3-diamine A solution of N,N-dimethyl-N'-{1-(2-trimethylsilanyl-ethoxymethyl)-3-[1-(2-trimethylsilanyl-ethoxymethyl)-1H-benzimidazol-2-yl]-1H-indazol-5-yl}-propane-1,3-diamine in THF was treated with ethylene diamine (20 equivalents) and tetrabutylammonium fluoride (20 equivalents) and heated at 70° C. overnight. The resulting crude residue was purified by reverse phase HPLC to N'-[3-(1H-Benzoimidazol-2-yl)-1H-indazol-5-yl]-N,N-dimethyl-propane-1,3-diamine. LC/MS (m/z) 335.1 (MH+), $R_t$ 1.30 minutes.

Example 729

2-{4-[2-(5-Ethoxy-1H-indazol-3-yl)-3H-benzimidazol-5-yl]-piperazin-1-yl}-ethanol Synthesis of 5-Ethoxyindole

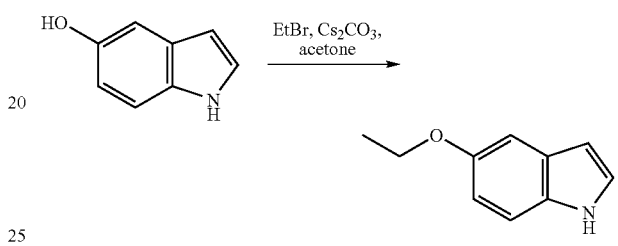

5-Hydroxyindole (1.0 equivalents) was dissolved in dry, degassed acetone. EtBr (5.0 equivalents) and $CS_2CO_3$ (2.5 equivalents) were added, and the resulting solution was stirred for 18 hours. The reaction mixture was filtered through a Celite plug. The solvent was evaporated and the product purified by flash chromatography (MeOH:$CH_2Cl_2$, 5:95) to yield the desired indole ether title compound. LC/MS (m/z) 162.1 (MH+), $R_t$ 2.45 minutes.

Synthesis of 5-Ethoxy-1H-indazole-3carbaldehyde

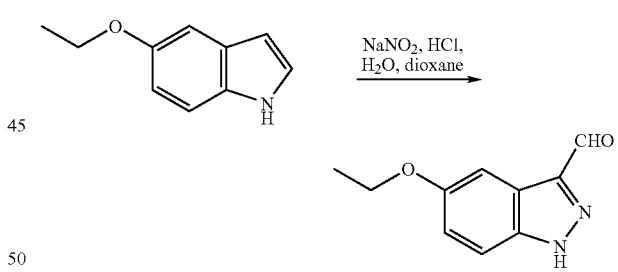

The formation of 5-ethoxy-1H-indazole-3-carbaldehyde from 5-ethoxyindole was carried out using the procedures described above in Example 4. LC/MS (m/z) 191.1 (MH+), $R_t$ 2.14 minutes.

Synthesis of 2-{4-[2-(5-Ethoxy-1H-indazol-3-yl)-3H-benzimidazol-5-yl]-piperazin-1-yl}-ethanol The formation of 2-{4-[2-(5-ethoxy-1H-indazol-3-yl)-3H-benzimidazol-5-yl]-piperazin-1-yl}-ethanol was carried out using 5-ethoxy-1H-indazole-3-carbaldehyde and 2-[4-(3,4-diaminophenyl)-piperazin-1-yl]-ethanol using the method described above in Example 4. LC/MS (m/z) 407.3, (MH+), $R_t$ 2.65 minutes.

Example 730

3-[6-(4-Methyl-piperazin-1-yl)-1H-benzimidazol-2-yl]-5-(5-nitro-pyridin-2-yloxy)-1H-indazole Synthesis of 5-(5-Nitro-pyridin-2-yloxy)-1H-indole

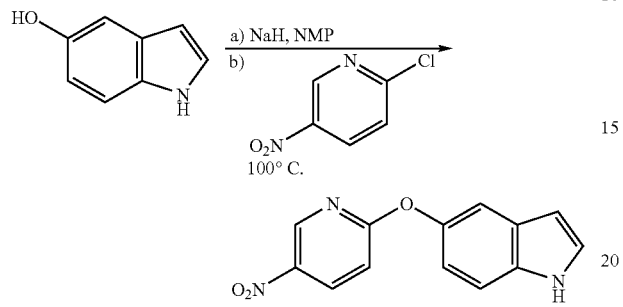

NaH (1.1 equivalents) was added to a solution of 5-hydroxyindole (1.0 equivalent) in NMP. The resulting mixture stirred for 2 hours at room temperature. 2-Chloro-5-nitropyridine (1.1 equivalents) was added and the solution was heated to 100° C. for 2 hours. The solution was cooled and poured into water. The aqueous layer was extracted with EtOAc three times. The organic layers were then combined and concentrated to yield the desired indole heteroaryl ether 5-(5-nitro-pyridin-2-yloxy)-1H-indole.

Synthesis of 5-(5-Nitro-pyridin-2-yloxy)-1H-indazole-3-carbaldehyde

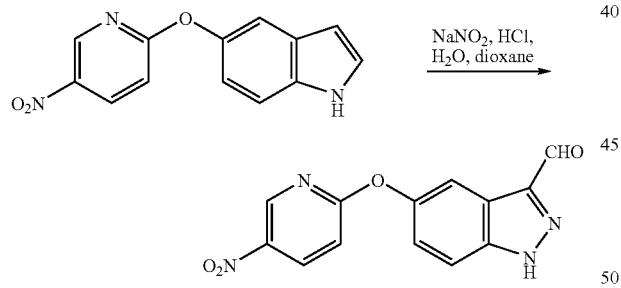

The formation of 5-(5-nitro-pyridin-2-yloxy)-1H-indazole-3-carbaldehyde from 5-(5-nitro-pyridin-2-yloxy)-1H-indole was carried using the method described above in Example 4. LC/MS (m/z) 285.2 (MH+), $R_t$ 2.43 minutes.

Synthesis of 3-[6-(4-Methyl-piperazin-1-yl)-1H-benzimidazol-2-yl]-5-(5-nitro-pyridin-2-yloxy)-1H-indazole The tide compound was synthesized from 5-(5-nitro-pyridin-2-yloxy)-1H-indazole-3-carbaldehyde and 4-(4-methyl-piperazin-1-yl)-benzene-1,2-diamine using the method described above in Example 4. LC/MS (m/z) 471.3 (MH+), $R_t$ 2.94 minutes.

Example 731

3-(1H-Benzoimidazol-2-yl)-1H-indazol-5-ol

A solution of 5-hydroxyindole (1.0 equivalent), benzyl chloroformate (1.1 equivalents), and diisopropylethylamine (2.0 equivalents) in CH$_2$Cl$_2$ was stirred for 18 hours. The solution is concentrated to yield the desired CBz protected indole ether. The product is then reacted with NaNO$_2$ in HCl and dioxane as previously described, followed by reaction with phenylenediamine in EtOH and toluene using the methods described above to yield the Cbz protected indazole benzimidazole. The Cbz-protected product is deprotected using 10% Pd/C and H$_2$ to provide the desired 5-hydroxyindole benzimidazole.

Example 732

4-[2-(5-Fluoro-1H-indazol-3-yl)-1-methyl-1H-benzimidazol-5-yloxy]-pyridine-2-carboxylic acid methylamide Synthesis of 4-(4-Amino-3-nitro-phenoxy)-pyridine-2-carboxylic acid methylamide

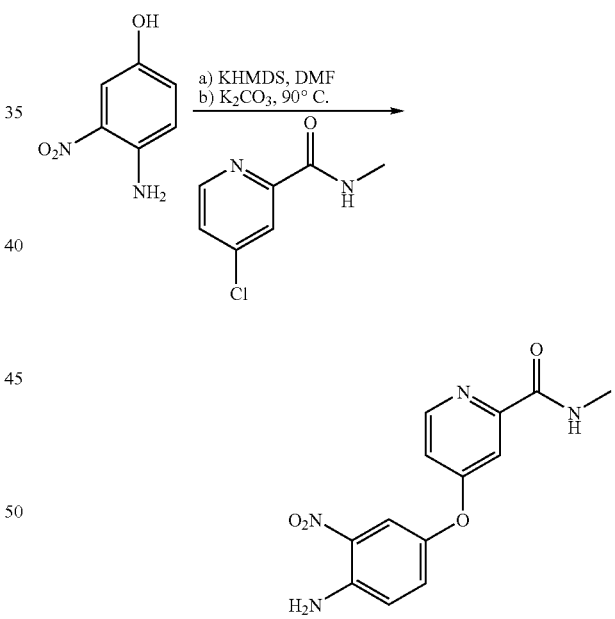

A mixture containing 4-amino-3-nitrophenol (1 equivalent) and potassium bis(trimethylsilyl)amide (2 equivalents) was stirred in dimethylformamide for 2 hours at room temperature. [4-chloro-(2-pyridiyl)]-N-methylcarboxamide (1 equivalent) and potassium carbonate (1.5 equivalents) were added to the mixture, and the reaction was stirred at 90° C. for 3 days. The reaction mixture was then concentrated and partitioned between ethyl acetate and water. The organic layer was separated, washed with brine (2×), dried, filtered, and concentrated to give brown solid. LC/MS (m/z) 289.2 (MH+), $R_t$ 2.18 minutes.

Synthesis of 4-(4-Methylamino-3-nitro-phenoxy)-pyridine-2-carboxylic acid methylamide

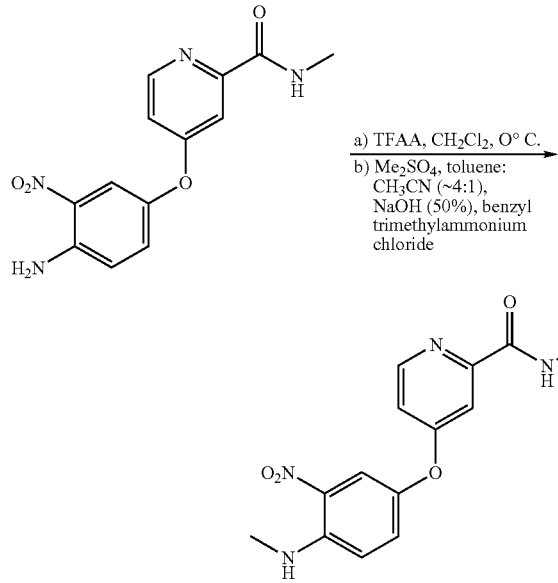

A solution of 4-(4-amino-3-nitro-phenoxy)-pyridine-2-carboxylic acid methylamide (1 equivalent) in CH$_2$Cl$_2$ was treated with trifluoroacetic anhydride (1 equivalent) and stirred for 10 minutes at 0° C. The mixture was quenched with a saturated NaHCO$_3$ solution. The organic layer was separated and washed with water and brine, dried, and evaporated to yield the trifluoroacetamide.

To the solution of the trifluoroacetamide (1 equivalent) in a mixture of toluene:acetonitrile (approximately 4:1) and sodium hydroxide solution (50%) was added benzyltrimethylammonium chloride (1 equivalent) and dimethyl sulfate (1.5 equivalents). The biphasic mixture was stirred overnight at room temperature. The mixture was evaporated and then taken up in ethyl acetate, washed with water (2×) and brine (2×), dried, and evaporated to yield the title compound as a reddish orange solid. LC/MS (m/z) 303.3 (MH+), R$_t$ 2.42 minutes.

Synthesis of 4-(3-Amino-4-methylamino-phenoxy)-pyridine-2-carboxylic acid methylamide

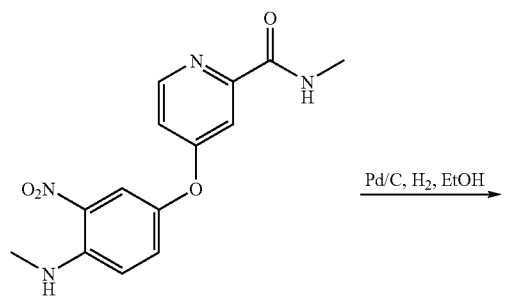

4-(4-Methylamino-3-nitro-phenoxy)-pyridine-2-carboxylic acid methylamide was reduced using the hydrogenation procedure described in Method 1. LC/MS (m/z) 273.3 (MH+), R$_t$ 1.63 minutes.

Synthesis of 4-[2-(5-Fluoro-1H-indazol-3-yl)-1-methyl-1H-benzimidazol-5-yloxy]-pyridine-2-carboxylic acid methylamide The title compound was synthesized from 5-fluoro-1H-indazole-3-carbaldehyde and 4-(3-amino-4-methylamino-phenoxy)-pyridine-2-carboxylic acid methylamide as described above in Example 4. LC/MS (m/z) 417.4 (MH+), R$_t$ 3.62 minutes.

Example 733

4-[2-(5-Fluoro-1H-indazol-3-yl)-1H-benzoimidazol-5-yloxy]-pyridine-2-carboxylic acid methylamide

Synthesis of 4-(3,4-Diamino-phenoxy)-pyridine-2-carboxylic acid methylamide

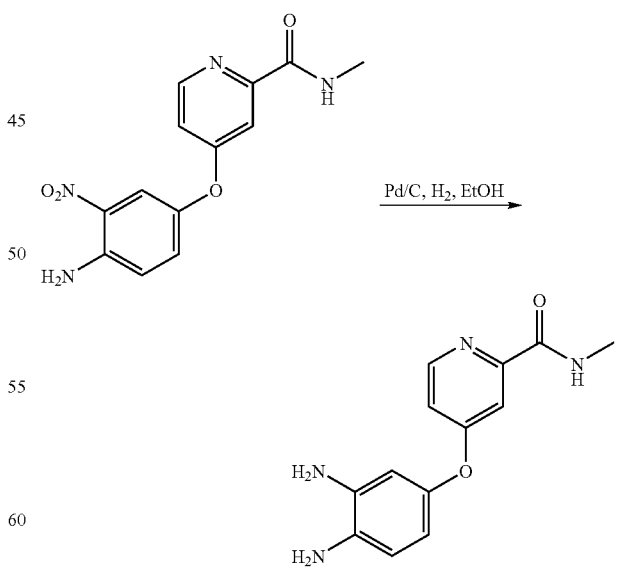

4-(4-Amino-3-nitro-phenoxy)-pyridine-2-carboxylic acid methylamide was reduced using the hydrogenation procedure described in Method 1. LC/MS (m/z) 259.2 (MH+), R$_t$ 1.32 minutes.

Synthesis of 4-[2-(5-Fluoro-1H-indazol-3-yl)-1H-benzoimidazol-5-yloxy]-pyridine-2-carboxylic acid methylamide The title compound was synthesized from 5-fluoro-1H-indazole-3-carbaldehyde and 4-(3,4-diamino-phenoxy)-pyridine-2-carboxylic acid methylamide using the method described above in Example 4. LC/MS (m/z) 403.1 (MH+), $R_t$ 2.26 minutes.

Examples 734-741

The compounds in the following table are synthesized using the procedures described above.

| Example | Name |
|---|---|
| 734 | {4-[2-(5-methoxy-1H-indazol-3-yl)-3H-benzoimidazol-5-yl]-5-methyl-morpholin-2-ylmethyl}-dimethyl-amine |
| 735 | {4-[2-(5-isopropoxy-1H-indazol-3-yl)-3H-benzoimidazol-5-yl]-5-methyl-morpholin-2-ylmethyl}-dimethyl-amine |
| 736 | {4-[2-(5-benzyloxy-1H-indazol-3-yl)-3H-benzoimidazol-5-yl]-5-methyl-morpholin-2-ylmethyl}-dimethyl-amine |
| 737 | dimethyl-(5-methyl-4-{2-[5-(1-methyl-piperidin-3-yloxy)-1H-indazol-3-yl]-3H-benzoimidazol-5-yl}-morpholin-2-ylmethyl)-amine |
| 738 | 1'-[2-(5-methoxy-1H-indazol-3-yl)-3H-benzoimidazol-5-yl]-[1,4']bipiperidinyl |
| 739 | 1'-[2-(5-isopropoxy-1H-indazol-3-yl)-3H-benzoimidazol-5-yl]-[1,4']bipiperidinyl |
| 740 | 3-[6-(4-methyl-piperazin-1-yl)-1H-benzoimidazol-2-yl]-5-(1-methyl-piperidin-3-yloxy)-1H-indazole |
| 741 | 1'-{2-[5-(1-methyl-piperidin-3-yloxy)-1H-indazol-3-yl]-3H-benzoimidazol-5-yl}-[1,4']bipiperidinyl |

Example 742

1'-[2-(4-Ethoxy-1H-indazol-3-yl)-3H-benzoimidazol-5-yl]-[1,4']bipiperidinyl

Synthesis of 4-Ethoxy-1H-indole

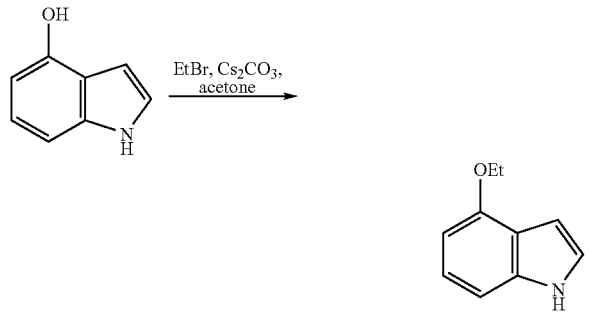

4-Hydroxyindole (1.0 equivalents) is dissolved in dry, degassed acetone. EtBr (5.0 equivalents) and $Cs_2CO_3$ (2.5 equivalents) are added, and the resulting solution is stirred for 18 hours. The reaction mixture is filtered through a Celite plug. The solvent is evaporated, and the product is purified by flash chromatography ($MeOH:CH_2Cl_2$, 5:95) to yield the title compound.

Synthesis of 4-Ethoxy-1H-indazole-3-carbaldehyde

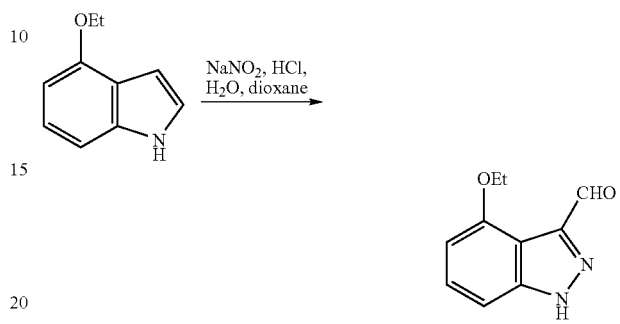

The formation of the title compound from 4-ethoxy-1H-indole is carried out using the procedure described above in Example 4.

Synthesis of 1'-[2-(4-Ethoxy-1H-indazol-3-yl)-3H-benzoimidazol-5-yl]-[1,4']bipiperidinyl The formation of the title compound is carried out using 4-ethoxy-1H-indazole-3-carbaldehyde and 4-[1,4']bipiperidinyl-1'-yl-benzene-1,2-diamine using the method described above in Example 4.

Examples 743-754

The compounds in the following table are synthesized using the procedures described above.

| Example | Name |
|---|---|
| 743 | {4-[2-(4-methoxy-1H-indazol-3-yl)-3H-benzoimidazol-5-yl]-5-methyl-morpholin-2-ylmethyl}-dimethyl-amine |
| 744 | {4-[2-(4-isopropoxy-1H-indazol-3-yl)-3H-benzoimidazol-5-yl]-5-methyl-morpholin-2-ylmethyl}-dimethyl-amine |
| 745 | {4-[2-(4-benzyloxy-1H-indazol-3-yl)-3H-benzoimidazol-5-yl]-5-methyl-morpholin-2-ylmethyl}-dimethyl-amine |
| 746 | (4-{2-[4-(1-ethyl-piperidin-3-yloxy)-1H-indazol-3-yl]-3H-benzoimidazol-5-yl}-5-methyl-morpholin-2-ylmethyl)-dimethyl-amine |
| 747 | 4-methoxy-3-[6-(4-methyl-piperazin-1-yl)-1H-benzoimidazol-2-yl]-1H-indazole |
| 748 | 4-isopropoxy-3-[6-(4-methyl-piperazin-1-yl)-1H-benzoimidazol-2-yl]-1H-indazole |
| 749 | 4-benzyloxy-3-[6-(4-methyl-piperazin-1-yl)-1H-benzoimidazol-2-yl]-1H-indazole |
| 750 | 4-(1-ethyl-piperidin-3-yloxy)-3-[6-(4-methyl-piperazin-1-yl)-1H-benzoimidazol-2-yl]-1H-indazole |
| 751 | 1'-[2-(4-methoxy-1H-indazol-3-yl)-3H-benzoimidazol-5-yl]-[1,4']bipiperidinyl |
| 752 | 1'-[2-(4-isopropoxy-1H-indazol-3-yl)-3H-benzoimidazol-5-yl]-[1,4']bipiperidinyl |
| 753 | 1'-[2-(4-benzyloxy-1H-indazol-3-yl)-3H-benzoimidazol-5-yl]-[1,4']bipiperidinyl |
| 754 | 1'-{2-[4-(1-ethyl-piperidin-3-yloxy)-1H-indazol-3-yl]-3H-benzoimidazol-5-yl}-[1,4']bipiperidinyl |

Example 755

1'-[2-(6-Ethoxy-1H-indazol-3-yl)-3H-benzoimidazol-5-yl]-[1,4']bipiperidinyl

Synthesis of 6-Ethoxy-1H-indole

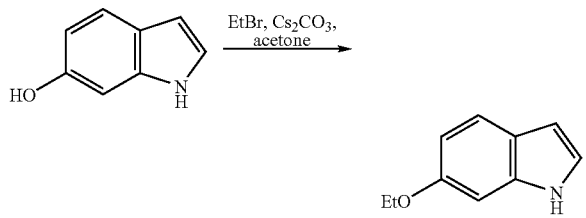

6-Hydroxyindole (1.0 equivalents) is dissolved in dry, degassed acetone. EtBr (5.0 equivalents) and $Cs_2CO_3$ (2.5 equivalents) are added, and the resulting solution is stirred for 18 hours. The reaction mixture is filtered through a Celite plug. The solvent is evaporated, and the product is purified by flash chromatography ($MeOH:CH_2Cl_2$, 5:95) to yield the title compound.

Synthesis of 6-Ethoxy-1H-indazole-3-carbaldehyde

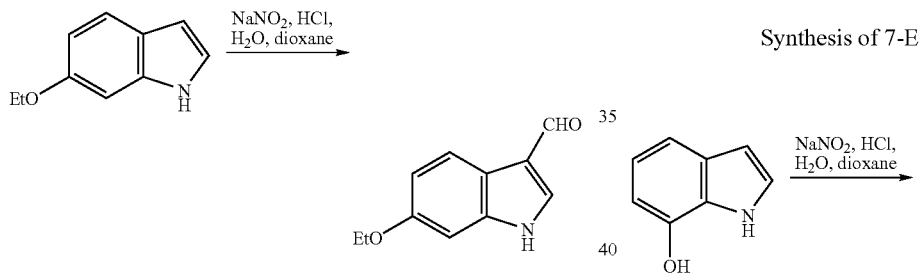

The formation of the title compound from 6-ethoxy-1H-indole is carried out using the procedure described above in Example 4.

Synthesis of 1'-[2-(6-Ethoxy-1H-indazol-3-yl)-3H-benzoimidazol-5-yl]-[1,4']bipiperidinyl The formation of the title compound is carried out using 6-ethoxy-1H-indazole-3-carbaldehyde and 4-[1,4']bipiperidinyl-1'-yl-benzene-1,2-diamine using the method described above in Example 4.

Examples 756-767

The compounds in the following table are synthesized using the procedures described above.

| Example | Name |
|---|---|
| 756 | {4-[2-(6-methoxy-1H-indazol-3-yl)-3H-benzoimidazol-5-yl]-5-methyl-morpholin-2-ylmethyl}-dimethyl-amine |
| 757 | {4-[2-(6-isopropoxy-1H-indazol-3-yl)-3H-benzoimidazol-5-yl]-5-methyl-morpholin-2-ylmethyl}-dimethyl-amine |
| 758 | {4-[2-(6-benzyloxy-1H-indazol-3-yl)-3H-benzoimidazol-5-yl]-5-methyl-morpholin-2-ylmethyl}-dimethyl-amine |
| 759 | (4-{2-[6-(1-ethyl-piperidin-3-yloxy)-1H-indazol-3-yl}-3H-benzoimidazol-5-yl}-5-methyl-morpholin-2-ylmethyl)-dimethyl-amine |
| 760 | 6-methoxy-3-[6-(4-methyl-piperazin-1-yl)-1H-benzoimidazol-2-yl]-1H-indazole |
| 761 | 6-isopropoxy-3-[6-(4-methyl-piperazin-1-yl)-1H-benzoimidazol-2-yl]-1H-indazole |
| 762 | 6-benzyloxy-3-[6-(4-methyl-piperazin-1-yl)-1H-benzoimidazol-2-yl]-1H-indazole |
| 763 | 6-(1-ethyl-piperidin-3-yloxy)-3-[6-(4-methyl-piperazin-1-yl)-1H-benzoimidazol-2-yl]-1H-indazole |
| 764 | 1'-[2-(6-methoxy-1H-indazol-3-yl)-3H-benzoimidazol-5-yl]-[1,4']bipiperidinyl |
| 765 | 1'-[2-(6-isopropoxy-1H-indazol-3-yl)-3H-benzoimidazol-5-yl]-[1,4']bipiperidinyl |
| 766 | 1'-[2-(6-benzyloxy-1H-indazol-3-yl)-3H-benzoimidazol-5-yl]-[1,4']bipiperidinyl |
| 767 | 1'-{2-[6-(1-ethyl-piperidin-3-yloxy)-1H-indazol-3-yl]-3H-benzoimidazol-5-yl}-[1,4']bipiperidinyl |

Example 768

1'-[2-(7-Ethoxy-1H-indazol-3-yl)-3H-benzoimidazol-5-yl]

Synthesis of 7-Ethoxy-1H-indole

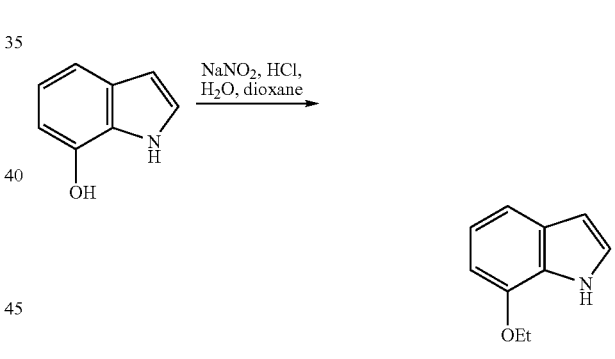

7-Hydroxyindole (1.0 equivalents) is dissolved in dry, degassed acetone. EtBr (5.0 equivalents) and $Cs_2CO_3$ (2.5 equivalents) are added, and the resulting solution is stirred for 18 hours. The reaction mixture is filtered through a Celite plug. The solvent is evaporated, and the product is purified by flash chromatography ($MeOH:CH_2Cl_2$, 5:95) to yield the title compound.

Synthesis of 7-Ethoxy-1H-indazole-3-carbaldehyde

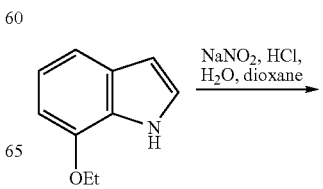

The formation of the title compound from 7-ethoxy-1H-indole is carried out using the procedure described above in Example 4.

Synthesis of 1'-[2-(7-Ethoxy-1H-indazol-3-yl)-3H-benzoimidazol-5-yl]-[1,4']bipiperidinyl The formation of the title compound is carried out using 7-ethoxy-1H-indazole-3-carbaldehyde and 4-[1,4']bipiperidinyl-1'-yl-benzene-1,2-diamine using the method described above in Example 4.

Examples 769-780

The compounds in the following table are synthesized using the procedures described above.

| Example | Name |
|---|---|
| 769 | {4-[2-(7-methoxy-1H-indazol-3-yl)-3H-benzoimidazol-5-yl]-5-methyl-morpholin-2-ylmethyl}-dimethyl-amine |
| 770 | {4-[2-(7-isopropoxy-1H-indazol-3-yl)-3H-benzoimidazol-5-yl]-5-methyl-morpholin-2-ylmethyl}-dimethyl-amine |
| 771 | {4-[2-(7-benzyloxy-1H-indazol-3-yl)-3H-benzoimidazol-5-yl]-5-methyl-morpholin-2-ylmethyl}-dimethyl-amine |
| 772 | (4-{2-[7-(1-ethyl-piperidin-3-yloxy)-1H-indazol-3-yl]-3H-benzoimidazol-5-yl}-5-methyl-morpholin-2-ylmethyl)-dimethyl-amine |
| 773 | 7-methoxy-3-[6-(4-methyl-piperazin-1-yl)-1H-benzoimidazol-2-yl]-1H-indazole |
| 774 | 7-isopropoxy-3-[6-(4-methyl-piperazin-1-yl)-1H-benzoimidazol-2-yl]-1H-indazole |
| 775 | 7-benzyloxy-3-[6-(4-methyl-piperazin-1-yl)-1H-benzoimidazol-2-yl]-1H-indazole |
| 776 | 7-(1-ethyl-piperidin-3-yloxy)-3-[6-(4-methyl-piperazin-1-yl)-1H-benzoimidazol-2-yl]-1H-indazole |
| 777 | 1'-[2-(7-methoxy-1H-indazol-3-yl)-3H-benzoimidazol-5-yl]-[1,4']bipiperidinyl |
| 778 | 1'-[2-(7-isopropoxy-1H-indazol-3-yl)-3H-benzoimidazol-5-yl]-[1,4']bipiperidinyl |
| 779 | 1'-[2-(7-benzyloxy-1H-indazol-3-yl)-3H-benzoimidazol-5-yl]-[1,4']bipiperidinyl |
| 780 | 1'-{2-[7-(1-ethyl-piperidin-3-yloxy)-1H-indazol-3-yl]-3H-benzoimidazol-5-yl}-[1,4']bipiperidinyl |

Examples 781-792

The compounds in the following table are synthesized using the procedures described in Example 730

| Example | Name |
|---|---|
| 781 | dimethyl-(5-methyl-4-{2-[5-(pyridin-2-yloxy)-1H-indazol-3-yl]-3H-benzoimidazol-5-yl}-morpholin-2-ylmethyl)-amine |
| 782 | (4-{2-[5-(3-methoxy-pyridin-2-yloxy)-1H-indazol-3-yl]-3H-benzoimidazol-5-yl}-5-methyl-morpholin-2-ylmethyl)-dimethyl-amine |
| 783 | 2-{3-[6-(2-dimethylaminomethyl-5-methyl-morpholin-4-yl)-1H-benzoimidazol-2-yl]-1H-indazol-5-yloxy}-nicotinonitrile |
| 784 | dimethyl-(5-methyl-4-{2-[5-(4-methyl-pyridin-2-yloxy)-1H-indazol-3-yl]-3H-benzoimidazol-5-yl}-morpholin-2-ylmethyl)-amine |
| 785 | 3-[6-(4-methyl-piperazin-1-yl)-1H-benzoimidazol-2-yl]-5-(pyridin-2-yloxy)-1H-indazole |
| 786 | 5-(3-methoxy-pyridin-2-yloxy)-3-[6-(4-methyl-piperazin-1-yl)-1H-benzoimidazol-2-yl]-1H-indazole |
| 787 | 2-{3-[6-(4-methyl-piperazin-1-yl)-1H-benzoimidazol-2-yl]-1H-indazol-5-yloxy}-nicotinonitrile |
| 788 | 3-[6-(4-methyl-piperazin-1-yl)-1H-benzoimidazol-2-yl]-5-(4-methyl-pyridin-2-yloxy)-1H-indazole |
| 789 | 1'-{2-[5-(pyridin-2-yloxy)-1H-indazol-3-yl]-3H-benzoimidazol-5-yl}-[1,4']bipiperidinyl |
| 790 | 1'-{2-[5-(3-methoxy-pyridin-2-yloxy)-1H-indazol-3-yl]-3H-benzoimidazol-5-yl}-[1,4']bipiperidinyl |
| 791 | 2-[3-(6-[1,4']bipiperidinyl-1'-yl-1H-benzoimidazol-2-yl)-1H-indazol-5-yloxy]-nicotinonitrile |
| 792 | 1'-{2-[5-(4-methyl-pyridin-2-yloxy)-1H-indazol-3-yl]-3H-benzoimidazol-5-yl}-[1,4']bipiperidinyl |

Example 793

3-[6-(4-Methyl-piperazin-1-yl)-1H-benzoimidazol-2-yl]-4-(5-nitro-pyridin-2-yloxy)-1H-indazole Synthesis of 4-(5-Nitropyridin-2-yloxy)-1H-indole

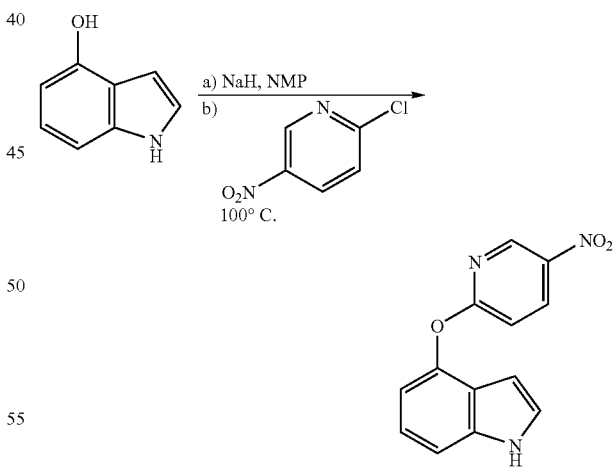

NaH (1.1 equivalents) is added to a solution of 4-hydroxyindole (1.0 equivalent) in NMP. The resulting mixture is stirred for 2 hours at room temperature. 2-Chloro-5-nitropyridine (1.1 equivalents) is added and the solution is heated to 100° C. for 2 hours. The solution is cooled and poured into water. The aqueous layer is extracted with EtOAc three times. The organic layers are combined and concentrated to yield the title compound.

Synthesis of 4-(5-Nitro-pyridin-2-yloxy)-1H-indazole-3-carbaldehyde

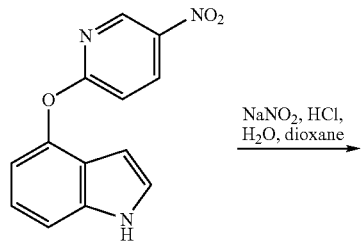

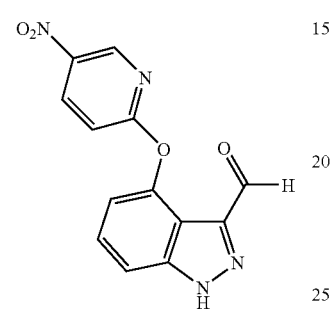

The formation of the title compound from 4-(5-nitropyridin-2-yloxy)-1H-indole is carried out using the procedure described above in Example 4.

Synthesis of 3-[6-(4-Methyl-piperazin-1-yl)-1H-benzoimidazol-2-yl]-4-(5-nitro-pyridin-2-yloxy)-1H-indazole The formation of the tide compound is carried out using 4-(5-nitropyridin-2-yloxy)-1H-indazole-3-carbaldehyde and 4-(4-methylpiperazin-1-yl)-benzene-1,2-diamine using the method described above in Example 4.

Examples 794-805

The compounds in the following table are synthesized using the procedures described above.

| Example | Name |
|---|---|
| 794 | dimethyl-(5-methyl-4-{2-[4-(pyridin-2-yloxy)-1H-indazol-3-yl]-3H-benzoimidazol-5-yl}-morpholin-2-ylmethyl)-amine |
| 795 | (4-{2-[4-(3-methoxy-pyridin-2-yloxy)-1H-indazol-3-yl]-3H-benzoimidazol-5-yl}-5-methyl-morpholin-2-ylmethyl)-dimethyl-amine |
| 796 | 2-{3-[6-(2-dimethylaminomethyl-5-methyl-morpholin-4-yl)-1H-benzoimidazol-2-yl]-1H-indazol-4-yloxy}-nicotinonitrile |
| 797 | dimethyl-(5-methyl-4-{2-[4-(4-methyl-pyridin-2-yloxy)-1H-indazol-3-yl]-3H-benzoimidazol-5-yl}-morpholin-2-ylmethyl)-amine |
| 798 | 3-[6-(4-methyl-piperazin-1-yl)-1H-benzoimidazol-2-yl]-4-(pyridin-2-yloxy)-1H-indazole |
| 799 | 4-(3-methoxy-pyridin-2-yloxy)-3-[6-(4-methyl-piperazin-1-yl)-1H-benzoimidazol-2-yl]-1H-indazole |
| 800 | 2-{3-[6-(4-methyl-piperazin-1-yl)-1H-benzoimidazol-2-yl]-1H-indazol-4-yloxy}-nicotinonitrile |
| 801 | 3-[6-(4-methyl-piperazin-1-yl)-1H-benzoimidazol-2-yl]-4-(4-methyl-pyridin-2-yloxy)-1H-indazole |
| 802 | 1'-{2-[4-(pyridin-2-yloxy)-1H-indazol-3-yl]-3H-benzoimidazol-5-yl}-[1,4']bipiperidinyl |
| 803 | 1'-{2-[4-(3-methoxy-pyridin-2-yloxy)-1H-indazol-3-yl]-3H-benzoimidazol-5-yl}-[1,4']bipiperidinyl |
| 804 | 2-[3-(6-[1,4']Bipiperidinyl-1'-yl-1H-benzoimidazol-2-yl)-1H-indazol-4-yloxy]-nicotinonitrile |
| 805 | 1'-{2-[4-(4-Methyl-pyridin-2-yloxy)-1H-indazol-3-yl]-3H-benzoimidazol-5-yl}-[1,4']bipiperidinyl |

Example 806

3-[6-(4Methyl-piperazin-1-yl)-1H-benzoimidazol-2-yl]-6-(5-nitro-pyridin-2-yloxy)-1H-indazole Synthesis of 6-(5-Nitropyridin-2-yloxy)-1H-indole

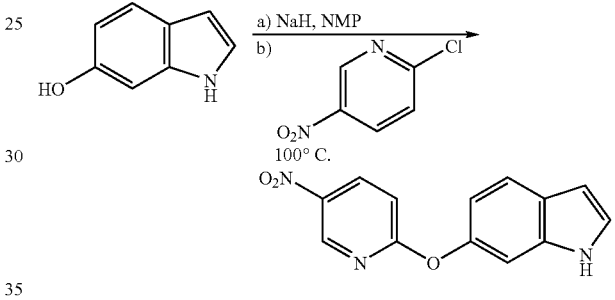

NaH (1.1 equivalents) is added to a solution of 6-hydroxyindole (1.0 equivalent) in NMP. The resulting mixture is stirred for 2 hours at room temperature. 2-Chloro-5-nitropyridine (1.1 equivalents) is added and the solution is heated to 100° C. for 2 hours. The solution is cooled and poured into water. The aqueous layer is extracted with EtOAc three times. The organic layers are combined and concentrated to yield the titled compound.

Synthesis of 6-(5-Nitropyridin-2-yloxy)-1H-indazole-3-carbaldehyde

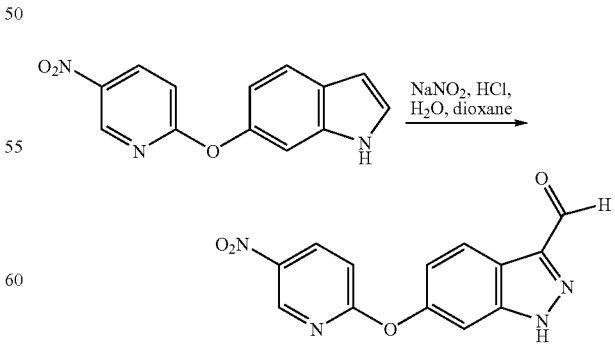

The formation of the title compound from 6-(5-nitropyridin-2-yloxy)-1H-indole is carried out using the procedure described in Example 4.

Synthesis of 3-[6-(4-Methyl-piperazin-1-yl)-1H-benzoimidazol-2-yl]-6-(5-nitro-pyridin-2-yloxy)-1H-indazole The formation of the title compound is carried out using 6-(5-nitropyridin-2-yloxy)-1H-indazole-3-carbaldehyde and 4-(4-methylpiperazin-1-yl)-benzene-1,2-diamine using the method described above in Example 4.

Examples 807-818

The compounds in the following table are synthesized using the procedures described above.

| Example | Name |
| --- | --- |
| 807 | dimethyl-(5-methyl-4-{2-[6-(pyridin-2-yloxy)-1H-indazol-3-yl]-3H-benzoimidazol-5-yl}-morpholin-2-ylmethyl)-amine |
| 808 | (4-{2-[6-(3-methoxy-pyridin-2-yloxy)-1H-indazol-3-yl]-3H-benzoimidazol-5-yl}-5-methyl-morpholin-2-ylmethyl)-dimethyl-amine |
| 809 | 2-{3-[6-(2-dimethylaminomethyl-5-methyl-morpholin-4-yl)-1H-benzoimidazol-2-yl]-1H-indazol-6-yloxy}-nicotinonitrile |
| 810 | dimethyl-(5-methyl-4-{2-[6-(4-methyl-pyridin-2-yloxy)-1H-indazol-3-yl]-3H-benzoimidazol-5-yl}-morpholin-2-ylmethyl)-amine |
| 811 | 3-[6-(4-methyl-piperazin-1-yl)-1H-benzoimidazol-2-yl]-6-(pyridin-2-yloxy)-1H-indazole |
| 812 | 6-(3-methoxy-pyridin-2-yloxy)-3-[6-(4-methyl-piperazin-1-yl)-1H-benzoimidazol-2-yl]-1H-indazole |
| 813 | 2-{3-[6-(4-methyl-piperazin-1-yl)-1H-benzoimidazol-2-yl]-1H-indazol-6-yloxy}-nicotinonitrile |
| 814 | 3-[6-(4-methyl-piperazin-1-yl)-1H-benzoimidazol-2-yl]-6-(4-methyl-pyridin-2-yloxy)-1H-indazole |
| 815 | 1'-{2-[6-(pyridin-2-yloxy)-1H-indazol-3-yl]-3H-benzoimidazol-5-yl}-[1,4']bipiperidinyl |
| 816 | 1'-{2-[6-(3-methoxy-pyridin-2-yloxy)-1H-indazol-3-yl]-3H-benzoimidazol-5-yl}-[1,4']bipiperidinyl |
| 817 | 2-[3-(6-[1,4']bipiperidinyl-1'-yl-1H-benzoimidazol-2-yl)-1H-indazol-6-yloxy]-nicotinonitrile |
| 818 | 1'-{2-[6-(4-methyl-pyridin-2-yloxy)-1H-indazol-3-yl]-3H-benzoimidazol-5-yl}-[1,4']bipiperidinyl |

Example 819

3-[6-(4-Methylpiperazin-1-yl)-1H-benzoimidazol-2-yl]-7-(5-nitro-pyridin-2-yloxy)-1H-indazole Synthesis of 7-(5-Nitropyridin-2-yloxy)-1H-indole

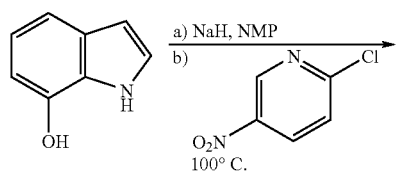

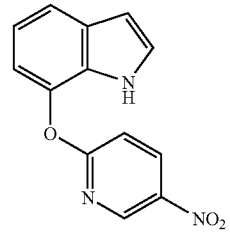

NaH (1.1 equivalents) is added to a solution of 7-hydroxy-indole (1.0 equivalent) in NMP. The resulting mixture is stirred for 2 hours at room temperature. 2-Chloro-5-nitropyridine (1.1 equivalents) is added and the solution is heated to 100° C. for 2 hours. The solution is cooled and poured into water. The aqueous layer is extracted with EtOAc three times. The organic layers are combined and concentrated to yield the desired indole heteroaryl ether.

Synthesis of 7-(5-Nitropyridin-2-yloxy)-1H-indazole-3-carbaldehyde

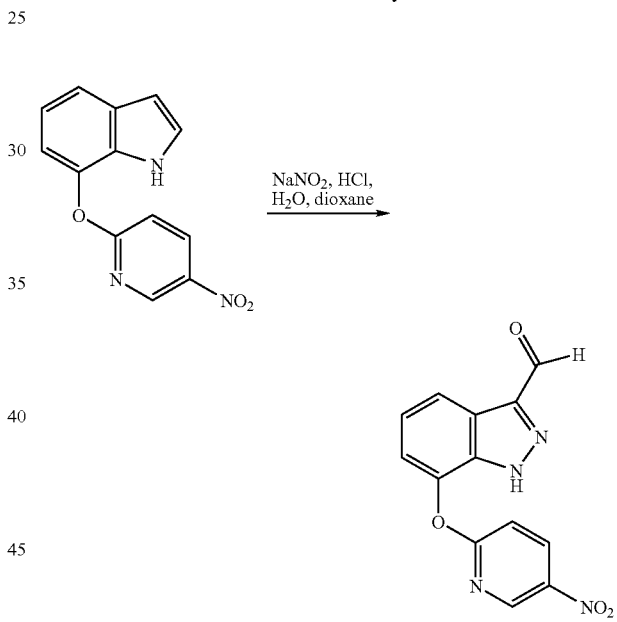

The formation of the title compound from 7-(5-nitropyridin-2-yloxy)-1H-indole is carried out using the procedure described above in Example 4.

Synthesis of 3-[6-(4-Methylpiperazin-1-yl)-1H-benzoimidazol-2-yl]-7-(5-nitro-pyridin-2-yloxy)-1H-indazole The formation of the title compound is carried out using 7-(5-nitropyridin-2-yloxy)-1H-indazole-3-carbaldehyde and 4-(4-methylpiperazin-1-yl)-benzene-1,2-diamine using the method described above in Example 4.

Examples 820-831

The compounds in the following table are synthesized using the procedures described above.

| Example | Name |
|---|---|
| 820 | dimethyl-(5-methyl-4-{2-[7-(pyridin-2-yloxy)-1H-indazol-3-yl]-3H-benzoimidazol-5-yl}-morpholin-2-ylmethyl)-amine |
| 821 | (4-{2-[7-(3-methoxy-pyridin-2-yloxy)-1H-indazol-3-yl]-3H-benzoimidazol-5-yl}-5-methyl-morpholin-2-ylmethyl)-dimethyl-amine |
| 822 | 2-{3-[6-(2-dimethylaminomethyl-5-methyl-morpholin-4-yl)-1H-benzoimidazol-2-yl]-1H-indazol-7-yloxy}-nicotinonitrile |
| 823 | dimethyl-(5-methyl-4-{2-[7-(4-methyl-pyridin-2-yloxy)-1H-indazol-3-yl]-3H-benzoimidazol-5-yl}-morpholin-2-ylmethyl)-amine |
| 824 | 3-[6-(4-methyl-piperazin-1-yl)-1H-benzoimidazol-2-yl]-7-(pyridin-2-yloxy)-1H-indazole |
| 825 | 7-(3-methoxy-pyridin-2-yloxy)-3-[6-(4-methyl-piperazin-1-yl)-1H-benzoimidazol-2-yl]-1H-indazole |
| 826 | 2-{3-[6-(4-methyl-piperazin-1-yl)-1H-benzoimidazol-2-yl]-1H-indazol-7-yloxy}-nicotinonitrile |
| 827 | 3-[6-(4-methyl-piperazin-1-yl)-1H-benzoimidazol-2-yl]-7-(4-methyl-pyridin-2-yloxy)-1H-indazole |
| 828 | 1'-{2-[7-(pyridin-2-yloxy)-1H-indazol-3-yl]-3H-benzoimidazol-5-yl}-[1,4']bipiperidinyl |
| 829 | 1'-{2-[7-(3-methoxy-pyridin-2-yloxy)-1H-indazol-3-yl]-3H-benzoimidazol-5-yl}-[1,4']bipiperidinyl |
| 830 | 2-[3-(6-[1,4']bipiperidinyl-1'-yl-1H-benzoimidazol-2-yl)-1H-indazol-7-yloxy]-nicotinonitrile |
| 831 | 1'-{2-[7-(4-methyl-pyridin-2-yloxy)-1H-indazol-3-yl]-3H-benzoimidazol-5-yl}-[1,4']bipiperidinyl |

Examples 832-842

The compounds in the following table are synthesized using the procedures described in Example 685.

| Example | Name |
|---|---|
| 832 | N-{3-[6-(2-dimethylaminomethyl-5-methyl-morpholin-4-yl)-1H-benzoimidazol-2-yl]-1H-indazol-5-yl}-acetamide |
| 833 | N-{3-[6-(2-dimethylaminomethyl-5-methyl-morpholin-4-yl)-1H-benzoimidazol-2-yl]-1H-indazol-5-yl}-2,2-dimethyl-propionamide |
| 834 | N-{3-[6-(2-dimethylaminomethyl-5-methyl-morpholin-4-yl)-1H-benzoimidazol-2-yl]-1H-indazol-5-yl}-2,4-difluoro-benzamide |
| 835 | N-{3-[6-(2-dimethylaminomethyl-5-methyl-morpholin-4-yl)-1H-benzoimidazol-2-yl]-1H-indazol-5-yl}-2-methoxy-benzamide |
| 836 | N-{3-[6-(4-methyl-piperazin-1-yl)-1H-benzoimidazol-2-yl]-1H-indazol-5-yl}-acetamide |
| 837 | 2,2-dimethyl-N-{3-[6-(4-methyl-piperazin-1-yl)-1H-benzoimidazol-2-yl]-1H-indazol-5-yl}-propionamide |
| 838 | 2,4-difluoro-N-{3-[6-(4-methyl-piperazin-1-yl)-1H-benzoimidazol-2-yl]-1H-indazol-5-yl}-benzamide |
| 839 | 2-methoxy-N-{3-[6-(4-methyl-piperazin-1-yl)-1H-benzoimidazol-2-yl]-1H-indazol-5-yl}-benzamide |
| 840 | N-[3-(6-[1,4']bipiperidinyl-1'-yl-1H-benzoimidazol-2-yl)-1H-indazol-5-yl]-2,2-dimethyl-propionamide |
| 841 | N-[3-(6-[1,4']bipiperidinyl-1'-yl-1H-benzoimidazol-2-yl)-1H-indazol-5-yl]-2,4-difluoro-benzamide |
| 842 | N-[3-(6-[1,4']bipiperidinyl-1'-yl-1H-benzoimidazol-2-yl)-1H-indazol-5-yl]-2-methoxy-benzamide |

Examples 843-854

The compounds in the following table are synthesized using the procedures described in Example 688.

| Example | Name |
|---|---|
| 843 | N-{3-[6-(2-dimethylaminomethyl-5-methyl-morpholin-4-yl)-1H-benzoimidazol-2-yl]-1H-indazol-5-yl}-C,C,C-trifluoro-methanesulfonamide |
| 844 | thiophene-2-sulfonic acid {3-[6-(2-dimethylaminomethyl-5-methyl-morpholin-4-yl)-1H-benzoimidazol-2-yl]-1H-indazol-5-yl}-amide |
| 845 | N-{3-[6-(2-dimethylaminomethyl-5-methyl-morpholin-4-yl)-1H-benzoimidazol-2-yl]-1H-indazol-5-yl}-benzenesulfonamide |
| 846 | N-{3-[6-(2-dimethylaminomethyl-5-methyl-morpholin-4-yl)-1H-benzoimidazol-2-yl]-1H-indazol-5-yl}-4-methoxy-benzenesulfonamide |
| 847 | C,C,C-trifluoro-N-{3-[6-(4-methyl-piperazin-1-yl)-1H-benzoimidazol-2-yl]-1H-indazol-5-yl}-methanesulfonamide |
| 848 | thiophene-2-sulfonic acid {3-[6-(4-methyl-piperazin-1-yl)-1H-benzoimidazol-2-yl]-1H-indazol-5-yl}-amide |
| 849 | N-{3-[6-(4-methyl-piperazin-1-yl)-1H-benzoimidazol-2-yl]-1H-indazol-5-yl}-benzenesulfonamide |
| 850 | 4-methoxy-N-{3-[6-(4-methyl-piperazin-1-yl)-1H-benzoimidazol-2-yl]-1H-indazol-5-yl}-benzenesulfonamide |
| 851 | N-[3-(6-[1,4']bipiperidinyl-1'-yl-1H-benzoimidazol-2-yl)-1H-indazol-5-yl]-C,C,C-trifluoro-methanesulfonamide |
| 852 | thiophene-2-sulfonic acid [3-(6-[1,4']bipiperidinyl-1'-yl-1H-benzoimidazol-2-yl)-1H-indazol-5-yl]-amide |
| 853 | N-[3-(6-[1,4']bipiperidinyl-1'-yl-1H-benzoimidazol-2-yl)-1H-indazol-5-yl]-benzenesulfonamide |
| 854 | N-[3-(6-[1,4']bipiperidinyl-1'-yl-1H-benzoimidazol-2-yl)-1H-indazol-5-yl]-4-methoxy-benzenesulfonamide |

Examples 855-865

The compounds in the following table are synthesized using the procedures described in Example 685 using 3-benzimidazol-2-yl-1H-indazol-6-ylamine as the starting material.

| Example | Name |
|---|---|
| 855 | N-{3-[6-(2-dimethylaminomethyl-5-methyl-morpholin-4-yl)-1H-benzoimidazol-2-yl]-1H-indazol-6-yl}-acetamide |
| 856 | N-{3-[6-(2-dimethylaminomethyl-5-methyl-morpholin-4-yl)-1H-benzoimidazol-2-yl]-1H-indazol-6-yl}-2,2-dimethyl-propionamide |
| 857 | N-{3-[6-(2-dimethylaminomethyl-5-methyl-morpholin-4-yl)-1H-benzoimidazol-2-yl]-1H-indazol-6-yl}-2,4-difluoro-benzamide |
| 858 | N-{3-[6-(2-dimethylaminomethyl-5-methyl-morpholin-4-yl)-1H-benzoimidazol-2-yl]-1H-indazol-6-yl}-2-methoxy-benzamide |
| 859 | 2,2-dimethyl-N-{3-[6-(4-methyl-piperazin-1-yl)-1H-benzoimidazol-2-yl]-1H-indazol-6-yl}-propionamide |
| 860 | 2,4-difluoro-N-{3-[6-(4-methyl-piperazin-1-yl)-1H-benzoimidazol-2-yl]-1H-indazol-6-yl}-benzamide |
| 861 | 2-methoxy-N-{3-[6-(4-methyl-piperazin-1-yl)-1H-benzoimidazol-2-yl]-1H-indazol-6-yl}-benzamide |
| 862 | N-[3-(6-[1,4']bipiperidinyl-1'-yl-1H-benzoimidazol-2-yl)-1H-indazol-6-yl]-acetamide |
| 863 | N-[3-(6-[1,4']bipiperidinyl-1'-yl-1H-benzoimidazol-2-yl)-1H-indazol-6-yl]-2,2-dimethyl-propionamide |
| 864 | N-[3-(6-[1,4']bipiperidinyl-1'-yl-1H-benzoimidazol-2-yl)-1H-indazol-6-yl]-2,4-difluoro-benzamide |
| 865 | N-[3-(6-[1,4']bipiperidinyl-1'-yl-1H-benzoimidazol-2-yl)-1H-indazol-6-yl]-2-methoxy-benzamide |

Examples 866-877

The compounds in the following table are synthesized using the procedures described in Example 688 using 3-benzimidazol-2-yl-1H-indazol-6-ylamine as the starting material.

| Example | Name |
|---|---|
| 866 | N-{3-[6-(2-dimethylaminomethyl-5-methyl-morpholin-4-yl)-1H-benzoimidazol-2-yl]-1H-indazol-6-yl}-C,C,C-trifluoro-methanesulfonamide |
| 867 | thiophene-2-sulfonic acid {3-[6-(2-dimethylaminomethyl-5-methyl-morpholin-4-yl)-1H-benzoimidazol-2-yl]-1H-indazol-6-yl}-amide |
| 868 | N-{3-[6-(2-dimethylaminomethyl-5-methyl-morpholin-4-yl)-1H-benzoimidazol-2-yl]-1H-indazol-6-yl}-benzenesulfonamide |
| 869 | N-{3-[6-(2-dimethylaminomethyl-5-methyl-morpholin-4-yl)-1H-benzoimidazol-2-yl]-1H-indazol-6-yl}-4-methoxy-benzenesulfonamide |
| 870 | C,C,C-trifluoro-N-{3-[6-(4-methyl-piperazin-1-yl)-1H-benzoimidazol-2-yl]-1H-indazol-6-yl}-methanesulfonamide |
| 871 | thiophene-2-sulfonic acid {3-[6-(4-methyl-piperazin-1-yl)-1H-benzoimidazol-2-yl]-1H-indazol-6-yl}-amide |
| 872 | N-{3-[6-(4-methyl-piperazin-1-yl)-1H-benzoimidazol-2-yl]-1H-indazol-6-yl}-benzenesulfonamide |
| 873 | 4-methoxy-N-{3-[6-(4-methyl-piperazin-1-yl)-1H-benzoimidazol-2-yl]-1H-indazol-6-yl)-beuzenesulfonamide |
| 874 | N-[3-(6-[1,4']bipiperidinyl-1'-yl-1H-benzoimidazol-2-yl)-1H-indazol-6-yl]-C,C,C-trifluoro-methanesulfonamide |
| 875 | Thiophene-2-sulfonic acid [3-(6-[1,4']bipiperidinyl-1'-yl-1H-benzoimidazol-2-yl)-1H-indazol-6-yl]-amide |
| 876 | N-[3-(6-[1,4']bipiperidinyl-1'-yl-1H-benzoimidazol-2-yl)-1H-indazol-6-yl]-benzenesulfonamide |
| 877 | N-[3-(6-[1,4']bipiperidinyl-1'-yl-1H-benzoimidazol-2-yl)-1H-indazol-6-yl]-4-methoxy-benzenesulfonamide |

Example 878

N-{3-[6-(4Methylpiperazin-1-yl)-1H-benzoimidazol-2-yl]-1H-indazol-4-yl}-benzamide 3-[6-(4-Methylpiperazin-1-yl)-1H-benzoimidazol-2-yl]-1H-indazol-4-ylamine as dissolved in CH$_2$C$_2$ and benzoyl chloride (1.1 equivalent) is added followed by diisopropyl-ethylamine (1.1 equivalent). The resulting mixture is stirred overnight. The solution is then concentrated and the resulting residue is purified by preparatory HPLC to provide the title compound.

Examples 879-890

The compounds in the following table are synthesized using the procedures described above.

| Example | Name |
|---|---|
| 879 | N-{3-[6-(2-dimethylaminomethyl-5-methyl-morpholin-4-yl)-1H benzoimidazol-2-yl]-1H-indazol-4-yl}-acetamide |
| 880 | N-{3-[6-(2-dimethylaminomethyl-5-methyl-morpholin-4-yl)-1H-benzoimidazol-2-yl]-1H-indazol-4-yl}-2,2-dimethyl-propionamide |
| 881 | N-{3-[6-(2-dimethylaminomethyl-5-methyl-morpholin-4-yl)-1H-benzoimidazol-2-yl]-1H-indazol-4-yl}-2,4-difluoro-benzamide |
| 882 | N-{3-[6-(2-dimethylaminomethyl-5-methyl-morpholin-4-yl)-1H-benzoimidazol-2-yl]-1H-indazol-4-yl}-2-methoxy-benzamide |
| 883 | N-{3-[6-(4-methyl-piperazin-1-yl)-1H-benzoimidazol-2-yl]-1H-indazol-4-yl}-acetamide |
| 884 | 2,2-dimethyl-N-{3-[6-(4-methyl-piperazin-1-yl)-1H-benzoimidazol-2-yl]-1H-indazol-4-yl}-propionamide |
| 885 | 2,4-difluoro-N-{3-[6-(4-methyl-piperazin-1-yl)-1H-benzoimidazol-2-yl]-1H-indazol-4-yl}-benzamide |
| 886 | 2-methoxy-N-{3-[6-(4-methyl-piperazin-1-yl)-1H-benzoimidazol-2-yl]-1H-indazol-4-yl}-benzamide |
| 887 | N-[3-(6-[1,4']bipiperidinyl-1'-yl-1H-benzoimidazol-2-yl)-1H-indazol-4-yl]-acetamide |
| 888 | N-[3-(6-[1,4']bipiperidinyl-1'-yl-1H-benzoimidazol-2-yl)-1H-indazol-4-yl]-2,2-dimethyl-propionamide |
| 889 | N-[3-(6-[1,4']bipiperidinyl-1'-yl-1H-benzoimidazol-2-yl)-1H-indazol-4-yl]-2,4-difluoro-benzamide |
| 890 | N-[3-(6-[1,4']Bipiperidinyl-1'-yl-1H-benzoimidazol-2-yl)-1H-indazol-4-yl]-2-methoxy-benzamide |

Example 891

N-{3-[6-(4Methylpiperazin-1-yl)-1H-benzoimidazol-2-yl]-1H-indazol-4-yl}-methanesulfonamide 3-[6-(4-Methylpiperazin-1-yl)-1H-benzoimidazol-2-yl]-1H-indazol-4-ylamine (1 equivalent), methanesulfonyl chloride (1.1 equivalent), and diisopropylethylamine (2 equivalents) in CH$_2$Cl$_2$ are stirred for 18 hours. The solvent is evaporated, and the resulting residue is purified by preparatory HPLC to provide the title compound.

Examples 892-903

The compounds in the following table are synthesized using the procedures described above.

| Example | Name |
|---|---|
| 892 | N-{3-[6-(2-dimethylaminomethyl-5-methyl-morpholin-4-yl)-1H-benzoimidazol-2-yl]-1H-indazol-4-yl}-C,C,C-trifluoro-methanesulfonamide |
| 893 | thiophene-2-sulfonic acid {3-[6-(2-dimethylaminomethyl-5-methyl-morpholin-4-yl)-1H-benzoimidazol-2-yl]-1H-indazol-4-yl)-amide |
| 894 | N-{3-[6-(2-dimethylaminomethyl-5-methyl-morpholin-4-yl)-1H-benzoimidazol-2-yl]-1H-indazol-4-yl}-benzenesulfonamide |
| 895 | N-{3-[6-(2-dimethylaminomethyl-5-methyl-morpholin-4-yl)-1H-benzoimidazol-2-yl]-1H-indazol-4-yl}-4-methoxy-benzenesulfonamide |
| 896 | C,C,C-trifluoro-N-{3-[6-(4-methyl-piperazin-1-yl)-1H-benzoimidazol-2-yl]-1H-indazol-4-yl}-methanesulfonamide |
| 897 | thiophene-2-sulfonic acid {3-[6-(4-methyl-piperazin-1-yl)-1H-benzoimidazol-2-yl]-1H-indazol-4-yl}-amide |
| 898 | N-{3-[6-(4-methyl-piperazin-1-yl)-1H-benzoimidazol-2-yl]-1H-indazol-4-yl}-benzenesulfonamide |
| 899 | 4-methoxy-N-{3-[6-(4-methyl-piperazin-1-yl)-1H-benzoimidazol-2-yl]-1H-indazol-4-yl}-benzenesulfonamide |
| 900 | N-[3-(6-[1,4']bipiperidinyl-1'-yl-1H-benzoimidazol-2-yl)-1H-indazol-4-yl]-C,C,C-trifluoro-methanesulfonamide |
| 901 | thiophene-2-sulfonic acid [3-(6-[1,4']bipiperidinyl-1'-yl-1H-benzoimidazol-2-yl)-1H-indazol-4-yl]-amide |
| 902 | N-[3-(6-[1,4']bipiperidinyl-1'-yl-1H-benzoimidazol-2-yl)-1H-indazol-4-yl]-benzenesulfonamide |
| 903 | N-[3-(6-[1,4']bipiperidinyl-1'-yl-1H-benzoimidazol-2-yl)-1H-indazol-4-yl]-4-methoxy-benzenesulfonamide |

Example 904

3-[6-(4-Methylpiperazin-1-yl)-1H-benzoimidazol-2-yl]-7-nitro-1H-indazole

Synthesis of 7-Nitro-1H-indazole-3-carbaldehyde

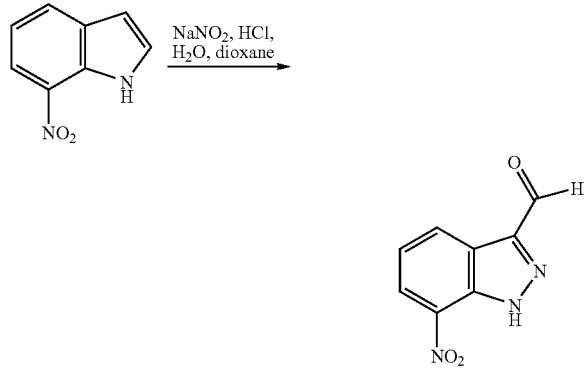

The formation of 7-nitro-1H-indazole-3-carbaldehyde is carried out from the commercially available 7-nitroindole using the method described above in Example 4.

Synthesis of 3-[6-(4-Methylpiperazin-1-yl)-1H-benzoimidazol-2-yl]-7-nitro-1H-indazole The formation of the title compound from 7-nitro-1H-indazole-3-carbaldehyde and 4-(4-methylpiperazin-1-yl)benzene-1,2-diamine is carried out using the procedure described above in Example 4.

Example 905

3-[6-(4-Methylpiperazin-1-yl)-1H-benzoimidazol-2-yl]-1H-indazol-7-ylamine

The title compound is obtained by reducing the nitro group of 3-[6-(4-methylpiperazin-1-yl)-1H-benzoimidazol-2-yl]-7-nitro-1H-indazole of Example 742 using the method described in Method 1.

Example 906

N-{3-[6-(4Methylpiperazin-1-yl)-1H-benzoimidazol-2-yl]-1H-indazol-7-yl}-benzamide The 3-[6-(4-methylpiperazin-1-yl)-1H-benzoimidazol-2-yl]-1H-indazol-7-ylamine of Example 743 is dissolved in $CH_2Cl_2$ and benzoyl chloride (1.1 equivalent) is added followed by diisopropylethylamine (1.1 equivalent). The resulting mixture is stirred overnight. The solution is then concentrated and the resulting residue is purified by preparatory HPLC to provide the title compound.

Examples 907-918

The compounds in the following table are synthesized using the procedures described above.

| Example | Name |
|---|---|
| 907 | N-{3-[6-(2-dimethylaminomethyl-5-methyl-morpholin-4-yl)-1H-benzoimidazol-2-yl]-1H-indazol-7-yl}-acetamide |
| 908 | N-{3-[6-(2-dimethylaminomethyl-5-methyl-morpholin-4-yl)-1H-benzoimidazol-2-yl]-1H-indazol-7-yl}-2,2-dimethyl-propionamide |
| 909 | N-{3-[6-(2-dimethylaminomethyl-5-methyl-morpholin-4-yl)-1H-benzoimidazol-2-yl]-1H-indazol-7-yl}-2,4-difluoro-benzamide |
| 910 | N-{3-[6-(2-dimethylaminomethyl-5-methyl-morpholin-4-yl)-1H-benzoimidazol-2-yl]-1H-indazol-7-yl}-2-methoxy-benzamide |
| 911 | N-{3-[6-(4-methyl-piperazin-1-yl)-1H-benzoimidazol-2-yl]-1H-indazol-7-yl}-acetamide |
| 912 | 2,2-dimethyl-N-{3-[6-(4-methyl-piperazin-1-yl)-1H-benzoimidazol-2-yl]-1H-indazol-7-yl}-propionamide |
| 913 | 2,4-difluoro-N-{3-[6-(4-methyl-piperazin-1-yl)-1H-benzoimidazol-2-yl]-1H-indazol-7-yl}-benzamide |
| 914 | 2-methoxy-N-{3-[6-(4-methyl-piperazin-1-yl)-1H-benzoimidazol-2-yl]-1H-indazol-7-yl}-benzamide |
| 915 | N-[3-(6-[1,4']bipiperidinyl-1'-yl-1H-benzoimidazol-2-yl)-1H-indazol-7-yl]-acetamide |
| 916 | N-[3-(6-[1,4']bipiperidinyl-1'-yl-1H-benzoimidazol-2-yl)-1H-indazol-7-yl]-2,2-dimethyl-propionamide |
| 917 | N-[3-(6-[1,4']bipiperidinyl-1'-yl-1H-benzoimidazol-2-yl)-1H-indazol-7-yl]-2,4-difluoro-benzamide |
| 918 | N-[3-(6-[1,4']bipiperidinyl-1'-yl-1H-benzoimidazol-2-yl)-1H-indazol-7-yl]-2-methoxy-benzamide |

Example 919

N-{3-[6-(4Methyl-piperazin-1-yl)-1H-benzoimidazol-2-yl]-1H-indazol-7-yl}-methanesulfonamide 3-[6-(4-methylpiperazin-1-yl)-1H-benzoimidazol-2-yl]-1H-indazol-7-ylamine (1 equivalent), methanesulfonyl chloride (1.1 equivalent), and diisopropylethylamine (2 equivalents) in $CH_2Cl_2$ are stirred for 18 hours. The solvent is evaporated, and the resulting residue is purified by preparatory HPLC to provide the title compound.

Examples 920-931

The compounds in the following table are synthesized using the procedures described above.

| Example | Name |
|---|---|
| 920 | N-{3-[6-(2-dimethylaminomethyl-5-methyl-morpholin-4-yl)-1H-benzoimidazol-2-yl]-1H-indazol-7-yl}-C,C,C-trifluoro-methanesulfonamide |
| 921 | thiophene-2-sulfonic acid {3-[6-(2-dimethylaminomethyl-5-methyl-morpholin-4-yl)-1H-benzoimidazol-2-yl]-1H-indazol-7-yl}-amide |
| 922 | N-{3-[6-(2-dimethylaminomethyl-5-methyl-morpholin-4-yl)-1H-benzoimidazol-2-yl]-1H-indazol-7-yl}-benzenesulfonamide |
| 923 | N-{3-[6-(2-dimethylaminomethyl-5-methyl-morpholin-4-yl)-1H-benzoimidazol-2-yl]-1H-indazol-7-yl}-4-methoxy-benzenesulfonamide |
| 924 | C,C,C-trifluoro-N-{3-[6-(4-methyl-piperazin-1-yl)-1H-benzoimidazol-2-yl]-1H-indazol-7-yl}-methanesulfonamide |
| 925 | thiophene-2-sulfonic acid {3-[6-(4-methyl-piperazin-1-yl)-1H-benzoimidazol-2-yl]-1H-indazol-7-yl}-amide |
| 926 | N-{3-[6-(4-methyl-piperazin-1-yl)-1H-benzoimidazol-2-yl]-1H-indazol-7-yl}-benzenesulfonamide |
| 927 | 4-methoxy-N-{3-[6-(4-methyl-piperazin-1-yl)-1H-benzoimidazol-2-yl]-1H-indazol-7-yl}-benzenesulfonamide |
| 928 | N-[3-(6-[1,4']bipiperidinyl-1'-yl-1H-benzoimidazol-2-yl)-1H-indazol-7-yl]-C,C,C-trifluoro-methanesulfonamide |

-continued

| Example | Name |
|---|---|
| 929 | thiophene-2-sulfonic acid [3-(6-[1,4']bipiperidinyl-1'-yl-1H-benzoimidazol-2-yl)-1H-indazol-7-yl]-amide |
| 930 | N-[3-(6-[1,4']bipiperidinyl-1'-yl-1H-benzoimidazol-2-yl)-1H-indazol-7-yl]-benzenesulfonamide |
| 931 | N-[3-(6-[1,4']bipiperidinyl-1'-yl-1H-benzoimidazol-2-yl)-1H-indazol-7-yl]-4-methoxy-benzenesulfonamide |

Example 932

({(2R,5S)-4-[2-(6-Fluoro(1H-indazol-3-yl))benzimidazol-6-yl]-5-methylmorpholin-2-yl}methyl)diethylamine Synthesis of {[(2R,5S)-5-Methyl-4-benzylmorpholin-2-yl]methyl}diethylamine

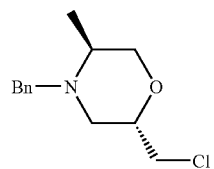

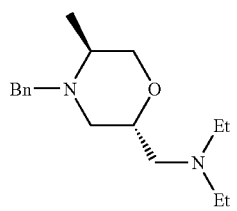

The title compound is obtained from (2S,5S)-2-(chloromethyl)-5-methyl-4-benzylmorpholine (see Method 8 Steps 1 and 2) displacing the chloride with diethylamine under the same reaction conditions used in Method 8 Step 3.

Synthesis of [((2S,5S)-5-Methylmorpholin-2-yl)methyl]diethylamine

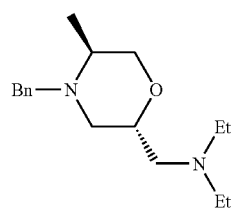

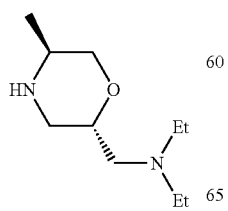

The formation of the title compound is carried out using the same procedure described in Method 8 Step 4 from {[(5S,2R)-5-methyl-4-benzylmorpholin-2-yl]methyl}diethylamine.

Synthesis of {[(2R,5S)-4-(3-Amino-4-nitrophenyl)-5-methylmorpholin-2-yl]methyl}diethylamine

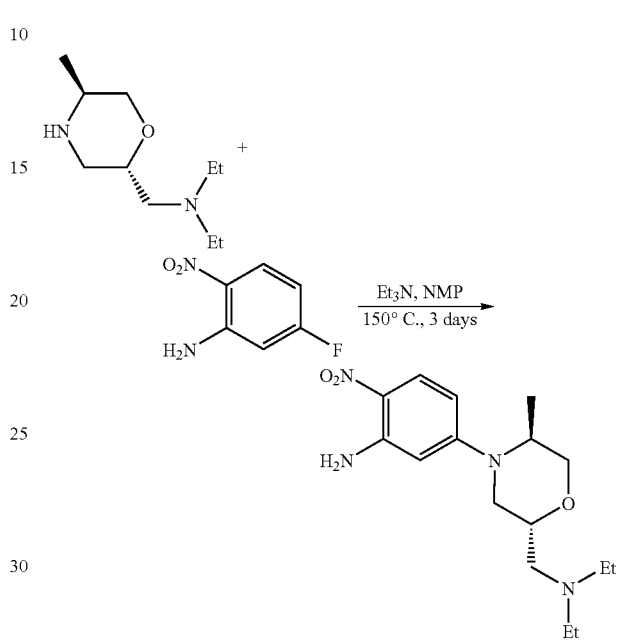

The formation of the title compound is carried out using the same procedure described in Method 8 Step 5 using [((2S,5S)-5-methylmorpholin-2-yl)methyl]diethylamine and 5-fluoro-2-nitro-phenylamine.

Synthesis of {[(2R,5S)-4-(3,4-Diaminophenyl)-5-methylmorpholin-2-yl]methyl}diethylamine

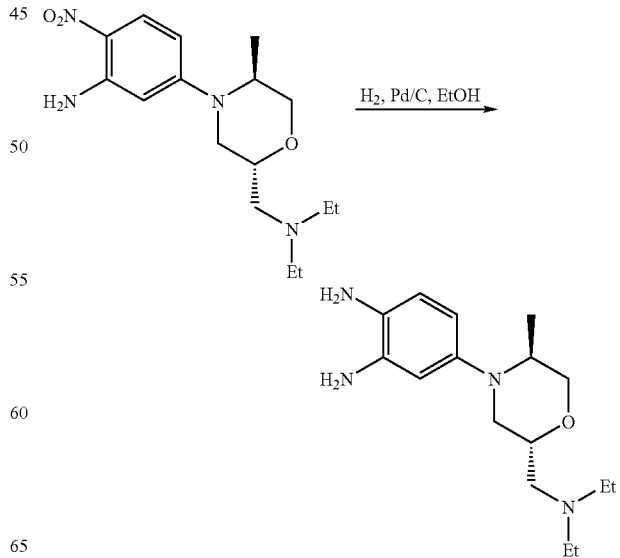

The formation of the title compound is carried out using the same procedure described in Method 8 Step 6 {[(2R,5S)-4-(3-amino-4-nitrophenyl)-5-methylmorpholin-2-yl]methyl}diethylamine.

Synthesis of ({(2R,5S)-4-[2-(6-Fluoro(1H-indazol-3-yl))benzimidazol-6-yl]-5-methylmorpholin-2-yl}methyl)diethylamine The title compund is synthesized according to the general procedure described in Example 4 with {[(2R,5S)-4-(3,4-diaminophenyl)-5-methylmorpholin-2-yl]methyl}diethylamine and 6-fluoro-1H-indazole-3-carbaldehyde.

Examples 933-940

The compounds in the following table are synthesized using the procedures described above in Example 932.

| Example | Name |
|---|---|
| 933 | (2R,5S)-diethyl-{4-[2-(6-fluoro-1H-indazol-3-yl)-3H-benzoimidazol-5-yl]-5-methyl-morpholin-2-ylmethyl}-amine |
| 934 | (2R,5S)-{4-[2-(6-fluoro-1H-indazol-3-yl)-3H-benzoimidazol-5-yl]-5-methyl-morpholin-2-ylmethyl}-isopropyl-methyl-amine |
| 935 | (2R,5S)-{4-[2-(6-chloro-1H-indazol-3-yl)-3H-benzoimidazol-5-yl]-5-methyl-morpholin-2-ylmethyl}-diethyl-amine |
| 936 | (2R,5S)-{4-[2-(6-chloro-1H-indazol-3-yl)-3H-benzoimidazol-5-yl]-5-methyl-morpholin-2-ylmethyl}-isopropyl-methyl-amine |
| 937 | (2R,5S)-diethyl-{4-[2-(5-methoxy-1H-indazol-3-yl)-3H-benzoimidazol-5-yl]-5-methyl-morpholin-2-ylmethyl}-amine |
| 938 | (2R,5S)-isopropyl-{4-[2-(5-methoxy-1H-indazol-3-yl)-3H-benzoimidazol-5-yl]-5-methyl-morpholin-2-ylmethyl}-methyl-amine |
| 939 | (2R,5S)-3-[6-(2-azetidin-1-ylmethyl-5-methyl-morpholin-4-yl)-1H-benzoimidazol-2-yl]-6-fluoro-1H-indazole |
| 940 | (2R,5S)-6-fluoro-3-[6-(5-methyl-2-pyrrolidin-1-ylmethyl-morpholin-4-yl)-1H-benzoimidazol-2-yl]-1H-indazole |

Examples 941-964

The compounds in the following table are synthesized using the procedures described above in Example 932 starting from the appropriate (2S,5R)-2-(chloromethyl)-5-methyl-4-benzylmorpholine, (2R,5S)-2-(chloromethyl)-5-methyl-4-benzylmorpholine, or (2R,5R)-2-(chloromethyl)-5-methyl-4-benzylmorpholine.

| Example | Name |
|---|---|
| 941 | (2S,5S)-diethyl-{4-[2-(6-fluoro-1H-indazol-3-yl)-3H-benzoimidazol-5-yl]-5-methyl-morpholin-2-ylmethyl}-amine |
| 942 | (2S,5S)-{4-[2-(6-fluoro-1H-indazol-3-yl)-3H-benzoimidazol-5-yl]-5-methyl-morpholin-2-ylmethyl}-isopropyl-methyl-amine |
| 943 | (2S,5S)-{4-[2-(6-chloro-1H-indazol-3-yl)-3H-benzoimidazol-5-yl]-5-methyl-morpholin-2-ylmethyl}-diethyl-amine |
| 944 | (2S,5S)-{4-[2-(6-chloro-1H-indazol-3-yl)-3H-benzoimidazol-5-yl]-5-methyl-morpholin-2-ylmethyl}-isopropyl-methyl-amine |
| 945 | (2S,5S)-diethyl-{4-[2-(5-methoxy-1H-indazol-3-yl)-3H-benzoimidazol-5-yl]-5-methyl-morpholin-2-ylmethyl}-amine |
| 946 | (2S,5S)-isopropyl-{4-[2-(5-methoxy-1H-indazol-3-yl)-3H-benzoimidazol-5-yl]-5-methyl-morpholin-2-ylmethyl}-methyl-amine |
| 947 | (2S,5S)-3-[6-(2-azetidin-1-ylmethyl-5-methyl-morpholin-4-yl)-1H-benzoimidazol-2-yl]-6-fluoro-1H-indazole |
| 948 | (2S,5S)-6-fluoro-3-[6-(5-methyl-2-pyrrolidin-1-ylmethyl-morpholin-4-yl)-1H-benzoimidazol-2-yl]-1H-indazole |
| 949 | (2S,5R)-diethyl-{4-[2-(6-fluoro-1H-indazol-3-yl)-3H-benzoimidazol-5-yl]-5-methyl-morpholin-2-ylmethyl}-amine |
| 950 | (2S,5R)-{4-[2-(6-fluoro-1H-indazol-3-yl)-3H-benzoimidazol-5-yl]-5-methyl-morpholin-2-ylmethyl}-isopropyl-methyl-amine |
| 951 | (2S,5R)-{4-[2-(6-chloro-1H-indazol-3-yl)-3H-benzoimidazol-5-yl]-5-methyl-morpholin-2-ylmethyl}-diethyl-amine |
| 952 | (2S,5R)-{4-[2-(6-chloro-1H-indazol-3-yl)-3H-benzoimidazol-5-yl]-5-methyl-morpholin-2-ylmethyl}-isopropyl-methyl-amine |
| 953 | (2S,5R)-diethyl-{4-[2-(5-methoxy-1H-indazol-3-yl)-3H-benzoimidazol-5-yl]-5-methyl-morpholin-2-ylmethyl}-amine |
| 954 | (2S,5R)-isopropyl-{4-[2-(5-methoxy-1H-indazol-3-yl)-3H-benzoimidazol-5-yl]-5-methyl-morpholin-2-ylmethyl}-methyl-amine |
| 955 | (2S,5R)-3-[6-(2-azetidin-1-ylmethyl-5-methyl-morpholin-4-yl)-1H-benzoimidazol-2-yl]-6-fluoro-1H-indazole |
| 956 | (2S,5R)-6-fluoro-3-[6-(5-methyl-2-pyrrolidin-1-ylmethyl-morpholin-4-yl)-1H-benzoimidazol-2-yl]-1H-indazole |
| 957 | (2R,5R)-diethyl-{4-[2-(6-fluoro-1H-indazol-3-yl)-3H-benzoimidazol-5-yl]-5-methyl-morpholin-2-ylmethyl}-amine |
| 958 | (2R,5R)-{4-[2-(6-fluoro-1H-indazol-3-yl)-3H-benzoimidazol-5-yl]-5-methyl-morpholin-2-ylmethyl}-isopropyl-methyl-amine |
| 959 | (2R,5R)-{4-[2-(6-chloro-1H-indazol-3-yl)-3H-benzoimidazol-5-yl]-5-methyl-morpholin-2-ylmethyl}-diethyl-amine |
| 960 | (2R,5R)-{4-[2-(6-chloro-1H-indazol-3-yl)-3H-benzoimidazol-5-yl]-5-methyl-morpholin-2-ylmethyl}-isopropyl-methyl-amine |
| 961 | (2R,5R)-diethyl-{4-[2-(5-methoxy-1H-indazol-3-yl)-3H-benzoimidazol-5-yl]-5-methyl-morpholin-2-ylmethyl}-amine |
| 962 | (2R,5R)-isopropyl-{4-[2-(5-methoxy-1H-indazol-3-yl)-3H-benzoimidazol-5-yl]-5-methyl-morpholin-2-ylmethyl}-methyl-amine |
| 963 | (2R,5R)-3-[6-(2-azetidin-1-ylmethyl-5-methyl-morpholin-4-yl)-1H-benzoimidazol-2-yl]-6-fluoro-1H-indazole |
| 964 | (2R,5R)-6-fluoro-3-[6-(5-methyl-2-pyrrolidin-1-ylmethyl-morpholin-4-yl)-1H-benzoimidazol-2-yl]-1H-indazole |

Examples 965-972

The compounds in the following table are synthesized using the procedures described above in Example 932 using (S)-(+)-2-amino-1-butanol or (R)-(−)-2-amino-1-butanol and performing the displacement on the chloromethyl intermediate with dimethylamine or diethylamine.

| Example | Name |
|---|---|
| 965 | (2R,5S)-{5-ethyl-4-[2-(6-fluoro-1H-indazol-3-yl)-3H-benzoimidazol-5-yl]-morpholin-2-ylmethyl}-dimethyl-amine |
| 966 | (2R,5S)-diethyl-{5-ethyl-4-[2-(6-fluoro-1H-indazol-3-yl)-3H-benzoimidazol-5-yl]-morpholin-2-ylmethyl}-amine |
| 967 | (2R,5R)-{5-ethyl-4-[2-(6-fluoro-1H-indazol-3-yl)-3H-benzoimidazol-5-yl]-morpholin-2-ylmethyl}-dimethyl-amine |
| 968 | (2R-5R)-diethyl-{5-ethyl-4-[2-(6-fluoro-1H-indazol-3-yl)-3H-benzoimidazol-5-yl]-morpholin-2-ylmethyl}-amine |
| 969 | (2S,5S)-{5-ethyl-4-[2-(6-fluoro-1H-indazol-3-yl)-3H-benzoimidazol-5-yl]-morpholin-2-ylmethyl}-dimethyl-amine |
| 970 | (2S-5S)-diethyl-{5-ethyl-4-[2-(6-fluoro-1H-indazol-3-yl)-3H-benzoimidazol-5-yl]-morpholin-2-ylmethyl}-amine |
| 971 | (2S,5R)-{5-ethyl-4-[2-(6-fluoro-1H-indazol-3-yl)-3H-benzoimidazol-5-yl]-morpholin-2-ylmethyl}-dimethyl-amine |
| 972 | (2S-5R)-diethyl-{5-ethyl-4-[2-(6-fluoro-1H-indazol-3-yl)-3H-benzoimidazol-5-yl]-morpholin-2-ylmethyl}-amine |

Examples 973-983

The following compounds are synthesized as previously described using 4-amino-1-propanol as a starting material

| Example | Name |
|---|---|
| 973 | {4-[2-(6-fluoro-1H-indazol-3-yl)-3H-benzoimidazol-5-yl]-[1,4]oxazepan-2-ylmethyl}-dimethyl-amine |
| 974 | diethyl-{4-[2-(6-fluoro-1H-indazol-3-yl)-3H-benzoimidazol-5-yl]-[1,4]oxazepan-2-ylmethyl}-amine |
| 975 | {4-[2-(6-chloro-1H-indazol-3-yl)-3H-benzoimidazol-5-yl]-[1,4]oxazepan-2-ylmethyl}-dimethyl-amine |
| 976 | {4-[2-(6-chloro-1H-indazol-3-yl)-3H-benzoimidazol-5-yl]-[1,4]oxazepan-2-ylmethyl}-diethyl-amine |
| 977 | diethyl-{4-[2-(5-methoxy-1H-indazol-3-yl)-3H-benzoimidazol-5-yl]-[1,4]oxazepan-2-ylmethyl}-amine |
| 978 | {4-[2-(5-chloro-1H-indazol-3-yl)-3H-benzoimidazol-5-yl]-[1,4]oxazepan-2-ylmethyl}-diethyl-amine |
| 979 | diethyl-{4-[2-(5-fluoro-1H-indazol-3-yl)-3H-benzoimidazol-5-yl]-[1,4]oxazepan-2-ylmethyl}-amine |
| 980 | diethyl-{4-[2-(5-phenoxy-1H-indazol-3-yl)-3H-benzoimidazol-5-yl]-[1,4]oxazepan-2-ylmethyl}-amine |
| 981 | {4-[2-(6-fluoro-1H-indazol-3-yl)-3H-benzoimidazol-5-yl]-[1,4]oxazepan-2-ylmethyl}-isopropyl-methyl-amine |
| 982 | 3-[6-(2-azetidin-1-ylmethyl-[1,4]oxazepan-4-yl)-1H-benzoimidazol-2-yl]-6-fluoro-1H-indazole |
| 983 | 6-fluoro-3-[6-(2-pyrrolidin-1-ylmethyl-[1,4]oxazepan-4-yl)-1H-benzoimidazol-2-yl]-1H-indazole |

Example 984

3-[6-((3S)-3,4-Dimethylpiperazinyl)benzimidazol-2-yl]-6-fluoro-1H-indazole

Synthesis of (3S)-3-Methylpiperazine-1-carboxylic acid tert-butyl ester

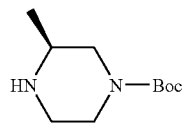

To a stirred solution of (2S)-2-methylpiperazine (2 equivalents) in dichloromethane at −10° C., di-tert-butyl dicarbonate (1 equivalent) was added. The mixture was stirred at −10° C. for two minutes, and subsequently quenched with saturated aqueous NaHCO₃. The two phases were separated, and the organic layer was extracted with methylene chloride. The organic extracts were collected, dried over Na₂SO₄, and concentrated to give the desired product. LC/MS (m/z) 201.0 (MH +), R$_t$ 1.67 minutes.

Synthesis of (2S)-1,2-Dimethyl-piperazine

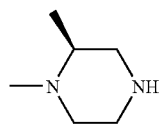

(3S)-3-Methylpiperazine-1-carboxylic acid tert-butyl ester (1 equivalent) and paraformaldehyde (5 equivalents) were dissolved in a mixture of MeOH and AcOH (5:1) on molecular sieves. NaCNBH₃ (4 equivalents) was added to the suspension at 25° C. The slurry was subsequently heated to 80° C. After 10 hours, the mixture was cooled, filtered, and concentrated. The residue was dissolved in dichloromethane and washed with saturated aqueous NaHCO₃. The organic solution was dried (Na₂SO₄), and concentrated. The tert-butoxycarbonyl group was removed by treating the crude amine with saturated HCl in MeOH at room temperature for 30 minutes. The mixture was then concentrated and excess HCl was removed in-vacuo. The desired (2S)-1,2-dimethylpiperazine was thus obtained as the bis HCl salt. LC/MS (m/z) 115.0 (MH+), R$_t$ 0.33 minutes.

Synthesis of 5-(3S)-(3,4-Dimethyl-piperazin-1-yl)-2-nitro-phenylamine

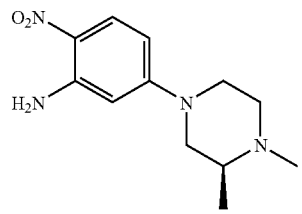

The title compound was prepared from (2S)-1,2-dimethylpiperazine using the procedure described in Method 8 Step 5. LC/MS (m/z) 251.3 (MH+), R$_t$ 1.48 minutes.

Synthesis of 4-(3S)-(3,4-Dimethyl-piperazin-1-yl)-benzene-1,2-diamine

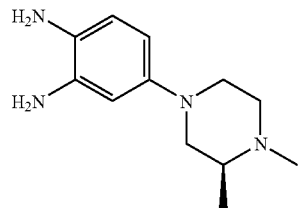

The title compound was prepared by reducing 5-(3S)-(3,4-dimethyl-piperazin-1-yl)-2-nitro-phenylamine using the procedure described in Method 8 Step 6.

Synthesis of 3-[6-(3S)-(3,4-Dimethyl-piperazin-1-yl)-1H-benzoimidazol-2-yl]-fluoro-1H-indazole The title compound is synthesized from 4-(3S)-(3,4-dimethyl-piperazin-1-yl)-benzene-1,2-diamine using the procedure described in Example 4.

Examples 985-988

The following compounds are synthesized as previously described using of 4-(3S)-(3,4-dimethyl-piperazin-1-yl)-benzene-1,2-diamine.

| Example | Name |
|---|---|
| 985 | 5-chloro-3-[6-(3S)-(3,4-dimethyl-piperazin-1-yl)-1H-benzoimidazol-2-yl]-1H-indazole |
| 986 | 6-chloro-3-[6-(3S)-(3,4-dimethyl-piperazin-1-yl)-1H-benzoimidazol-2-yl]-1H-indazole |
| 987 | 3-[6-(3S)-(3,4-dimethyl-piperazin-1-yl)-1H-benzoimidazol-2-yl]-5-methoxy-1H-indazole |

-continued

| Example | Name |
|---|---|
| 988 | 3-[6-(3S)-(3,4-Dimethyl-piperazin-1-yl)-1H-benzoimidazol-2-yl]-5-fluoro-1H-indazole |

Examples 989-993

The following compounds are synthesized as previously described in Example 984 starting from (2R)-2-methylpiperazine.

| Example | Name |
|---|---|
| 989 | 5-chloro-3-[6-(3R)-(3,4-dimethyl-piperazin-1-yl)-1H-benzoimidazol-2-yl]-1H-indazole |
| 990 | 6-chloro-3-[6-(3R)-(3,4-dimethyl-piperazin-1-yl)-1H-benzoimidazol-2-yl]-1H-indazole |
| 991 | 3-[6-(3R)-(3,4-dimethyl-piperazin-1-yl)-1H-benzoimidazol-2-yl]-6-fluoro-1H-indazole |
| 992 | 3-[6-(3R)-(3,4-dimethyl-piperazin-1-yl)-1H-benzoimidazol-2-yl]-5-fluoro-1H-indazole |
| 993 | 3-[6-(3R)-(3,4-dimethhyl-piperazin-1-yl)-1H-benzoimidazol-2-yl]-5-methoxy-1H-indazole |

Example 994

6-Chloro-3-[6-((2S)-2-methylpiperazin-1-yl)-1H-benzoimidazol-2-yl]-1H-indazole

Synthesis of tert-Butyl (3S)-4-(3-amino-4-nitrophenyl)-3-methylpiperazinecarboxylate

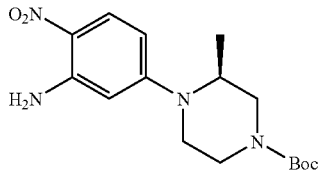

The title compound was synthesized as described in Method 8 Step 5 from tert-butyl (3S)-3-methylpiperazine carboxylate (see Example 984). LC/MS (m/z) 281.3 (MH+), $R_t$ 2.90 minutes.

Synthesis of tert-butyl (3S)-4-(3,4-diaminophenyl)-3-methylpiperazinecarboxylate

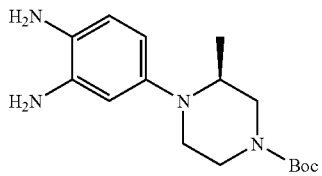

The title compound is synthesized as described in Method 8 Step 6 using tert-butyl (3S)-4-(3-amino-4-nitrophenyl)-3-methylpiperazinecarboxylate.

Synthesis of 6-Chloro-3-[6-((2S)-2-methylpiperazin-1-yl)-1H-benzoimidazol-2-yl]-1H-indazole The title compound is synthesized from (3S)-4-(3,4-diaminophenyl)-3-methylpiperazinecarboxylate using the procedure described in Example 4. The tert-butoxycarbonyl protecting groups is removed by treatment with saturated HCl in MeOH.

Example 995

3-[6-((2S)-2,4-dimethylpiperazinyl)benzimidazol-2-yl]-6-chloro-1H-indazole

Synthesis of 3-[6-((2S)-2,4-dimethylpiperazinyl)benzimidazol-2-yl]-6chloro-1H-indazole 3-[6-((2S)-2-methylpiperazinyl)benzimidazol-2-yl]-6-chloro-1H-indazole (1 equivalent) is dissolved in a mixture of MeOH and acetic acid (10:1), on molecular sieves. Paraformaldehyde (10 equivalents) is added in one portion. The reaction mixture is stirred at room temperature overnight then solid NaCNBH$_3$ is added in small portions. The reaction mixture is refluxed for 5 hours, cooled to room temperature, filtered, and concentrated under reduced pressure. The residue is dissolved in dichloromethane and washed with saturated aqueous NaHCO$_3$. The organic solution is dried over Na$_2$SO$_4$, and the solvent removed under reduced afford the desired product.

Examples 996-1005

The following compounds are synthesized from: 3-[6-((2S)-2-methylpiperazinyl)benzimidazol-2-yl]-6-chloro-1H-indazole and 3-[6-((2R)-2-methylpiperazinyl)benzimidazol-2-yl]-6-chloro-1H-indazole according to the described above in examples 994 and 995.

| Example | Name |
|---|---|
| 996 | 6-chloro-3-[6-((2S)-4-ethyl-2-methyl-piperazin-1-yl)-1H-benzoimidazol-2-yl]-1H-indazole |
| 997 | 6-chloro-3-[6-((2S)-4-isopropyl-2-methyl-piperazin-1-yl)-1H-benzoimidazol-2-yl]-1H-indazole |
| 998 | 6-chloro-3-[6-((2S)-4-cyclobutyl-2-methyl-piperazin-1-yl)-1H-benzoimidazol-2-yl]-1H-indazole |
| 999 | 6-chloro-3-[6-((2R)-2,4-dimethyl-piperazin-1-yl)-1H-benzoimidazol-2-yl]-1H-indazole |
| 1000 | 6-chloro-3-[6-((2R)-4-ethyl-2-methyl-piperazin-1-yl)-1H-benzoimidazol-2-yl]-1H-indazole |
| 1001 | 6-chloro-3-[6-((2R)-4-isopropyl-2-methyl-piperazin-1-yl)-1H-benzoimidazol-2-yl]-1H-indazole |
| 1002 | 6-chloro-3-[6-((2R)-4-cyclobutyl-2-methyl-piperazin-1-yl)-1H-benzoimidazol-2-yl]-1H-indazole |
| 1003 | 6-fluoro-3-[6-((2S)-4-isopropyl-2-methyl-piperazin-1-yl)-1H-benzoimidazol-2-yl]-1H-indazole |
| 1004 | 5-chloro-3-[6-((2S)-4-isopropyl-2-methyl-piperazin-1-yl)-1H-benzoimidazol-2-yl]-1H-indazole |
| 1005 | 3-[6-((2S)-4-isopropyl-2-methyl-piperazin-1-yl)-1H-benzoimidazol-2-yl]-5-methoxy-1H-indazole |

Example 1006

({4-[2-(6-Fluoro(1H-indazol-3-yl))benzimidazol-6-yl]-1-methylpiperazin-2-yl}methyl)dimethylamine Synthesis of 1,4-Bisbenzyl-2-(chloromethyl)piperazine

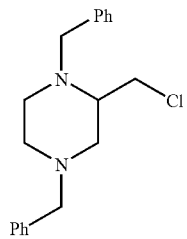

The title compound was synthesized as previously described in U.S. Pat. No. 4,940,710 incorporated herein by reference.

Synthesis of {[1,4-Bisbenzylpiperazin-2-yl]methyl}dimethylamine

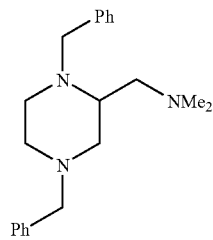

A mixture of 1,4-bisbenzyl-2-(chloromethyl)piperazine (1 equivalent) and dimethylamine (5 equivalents) in ethanol, was heated at 150° C. for 36 hours in a sealed high pressure vessel. The reaction mixture was cooled to room temperature and concentrated under reduced pressure. The residue was taken up in 1 N HCl, and the solution was washed with $CH_2Cl_2$. The water phase was made basic with a 30% aqueous NaOH solution (pH=12) and extracted with $CH_2Cl_2$. The organic extracts were collected and dried over $Na_2SO_4$. Evaporation of the solvent under reduced pressure afforded {[1,4-bisbenzylpiperazin-2-yl]methyl}dimethylamine. LC/MS (m/z): 324.3 (MH+), $R_t$ 1.76 minutes.

Synthesis of Dimethyl(piperazin-2-ylmethyl)amine

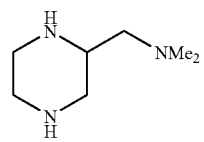

{[1,4-bisbenzylpiperazin-2-yl]methyl}dimethylamine (1 equivalent), was dissolved in EtOH and the solution was transferred to a stainless steel high pressure vessel equipped with a pressure gauge. 10% Pd/C was added (10 wt. %), and the vessel charged with $H_2$. The reaction mixture was stirred at 130° C. and 200 psi of $H_2$ overnight. The reaction mixture was cooled to room temperature, filtered over a pad of Celite, and then evaporated. The desired amine was obtained in quantitative yield as a pale yellow oil. GC/MS: 143 (10%, M+), $R_t$=14.3 minutes.

Synthesis of tert-butyl 3-[(dimethylamino)methyl]piperazine-carboxylate

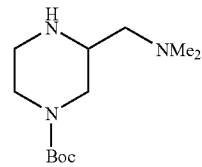

The title compound was synthesized from dimethyl(piperazin-2-ylmethyl)amine using the procedure described in example 984. GC/MS: 170 (20%, M±tBuO), $R_t$=13.5 minutes.

Synthesis of Dimethyl[(1-methylpiperazin-2-yl)methyl]amine

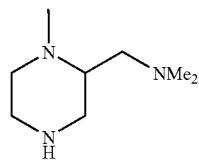

The title compound was synthesized from tert-butyl 3-[(dimethylamino)methyl]piperazinecarboxylate using the procedure described in example 984. Purification by column chromatography on silica gel afforded the Boc protected amine which was treated with HCl in MeOH to afford the desired product. LC/MS (m/z): 158.1 (MH+), $R_t$ 0.27 minutes.

Synthesis of {[4-(3-amino-4-nitrophenyl)-1-methylpiperazin-2-yl]methyl}dimethylamine

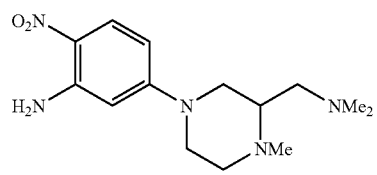

The title compound was synthesized from dimethyl[(1-methylpiperazin-2-yl)methyl]amine using the procedure described in Method 8 Step 5. LC/MS (m/z): 294.1 (MH+), $R_t$ 1.11 minutes.

Synthesis of {[4-(3,4-diaminophenyl)-1-methylpiperazin-2-yl]methyl}dimethylamine

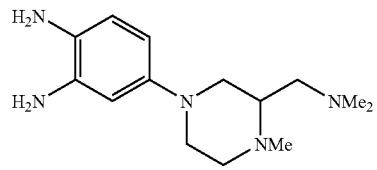

The title compound is synthesized from {[4-(3-amino-4-nitrophenyl)-1-methylpiperazin-2-yl]methyl}dimethylamine using the procedure described in Method 8 Step 6.

Synthesis of ({4-[2-(6-fluoro(1H-indazol-3-yl))benzimidazol-6-yl]-1-methylpiperazin-2-yl}methyl)dimethylamine The title compound is synthesized from {[4-(3,4-diaminophenyl)-1-methylpiperazin-2-yl]methyl}dimethylamine using the procedure described in Example 4.

Examples 1007-1012

The following compounds are synthesized according to the procedure above in Example 1006.

| Example | Name |
|---|---|
| 1007 | {4-[2-(6-chloro-1H-indazol-3-yl)-3H-benzoimidazol-5-yl]-1-methyl-piperazin-2-ylmethyl}-dimethyl-amine |
| 1008 | {4-[2-(5-methoxy-1H-indazol-3-yl)-3H-benzoimidazol-5-yl]-1-methyl-piperazin-2-ylmethyl}-dimethyl-amine |
| 1009 | {4-[2-(5-benzyloxy-1H-indazol-3-yl)-3H-benzoimidazol-5-yl]-1-methyl-piperazin-2-ylmethyl)-dimethyl-amine |
| 1010 | {4-[2-(6-chloro-1H-indazol-3-yl)-3H-benzoimidazol-5-yl]-1-ethyl-piperazin-2-ylmethyl}-dimethyl-amine |
| 1011 | Diethyl-{4-[2-(6-fluoro-1H-indazol-3-yl)-3H-benzoimidazol-5-yl]-1-methyl-piperazin-2-ylmethyl}-amine |
| 1012 | Diethyl-{1-ethyl-4-[2-(6-fluoro-1H-indazol-3-yl)-3H-benzoimidazol-5-yl]-piperazin-2-ylmethyl}-amine |

Example 1013

3-(6-(1,4-Diazaperhydroepinyl)benzimidazol-2-yl)-6-fluoro-1H-indazole

Synthesis of tert-Butyl 4-(3-amino-4-nitrophenyl)-1,4-diazaperhydroepinecarboxylate

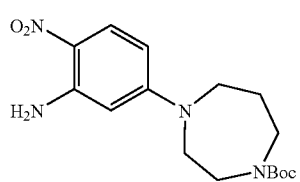

The title compound is synthesized from commercially available Boc-homopiperazine according to the procedure described in Method 1.

Synthesis of 3-(6-(1,4-Diazaperhydroepinyl)benzimidazol-2-yl)-4-fluoro-1H-indazole The title compound is synthesized from tert-butyl 4-(3-amino-4-nitrophenyl)-1,4-diazaperhydroepinecarboxylate after the nitro group has been reduced according to the procedure described in Example 4. The tert-butoxycarbonyl is removed treating with saturated HCl in MeOH.

Example 1014

6-Fluoro-3-[6-(4-methyl(1,4-diazaperhydroepinyl))benzimidazol-2-yl]-1H-indazole

Synthesis of 6-Fluoro-3-[6-(4-methyl(1,4-diazaperhydroepinyl))-benzimidazol-2-yl]-1H-indazole The title compound is synthesized from 3-(6-(1,4-diazaperhydro-epinyl)benzimidazol-2-yl)-6-fluoro-1H-indazole according to the procedure in Examples 984 and 985.

Examples 1015-1018

The following compounds are synthesized according to the procedure described above in Example 1014 using an appropriate carbonyl compound.

| Example | Name |
|---|---|
| 1015 | 6-Fluoro-3-[6-(4-ethyl(1,4-diazaperhydroepinyl))-benzimidazol-2-yl]-1H-indazole |
| 1016 | 6-Fluoro-3-[6-(4-isopropyl(1,4-diazaperhydroepinyl))-benzimidazol-2-yl]-1H-indazole |
| 1017 | 6-Fluoro-3-[6-(4-cyclobutyl(1,4-diazaperhydroepinyl))-benzimidazol-2-yl]-1H-indazole |

Example 1019

2-(6-Fluoro(1H-indazol-3-yl))-6-(1-methyl(3-piperidyloxy))-benzimidazole

Synthesis of 4-(1-Methyl-3-piperidyloxy)phenylamine

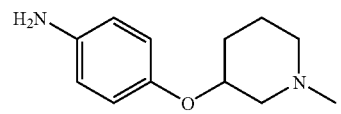

KHMDS (1.1 equivalent) was added to a THF solution of 1-methylpiperidin-3-ol (1 equivalent) at 0° C. and stirred until $H_2$ evolution ceased. 1-fluoro-4-nitrobenzene (1 equivalent) was then added and the solution was allowed to warm to room temperature. After 2 hours, water was added and the mixture was extracted with EtOAc (3×). The combined organic extracts were dried over $Na_2SO_4$, and concentrated in vacuo to give a bright yellow oil which was directly used in the reduction step. The oil (1 equivalent) and a catalytic amount of 10% Pd/C were suspended in anhydrous EtOH at room temperature. The reaction flask was evacuated and subsequently filled with $H_2$. After stirring for 18 hours, the mixture was filtered through Celite, and the solvent was concen-

Synthesis of N-[4-(1-Methyl-3-piperidyloxy)phenyl]acetamide

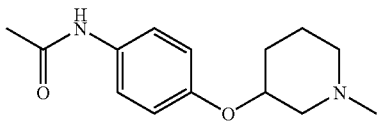

4-(1-methyl-3-piperidyloxy)phenylamine (1 equivalent) was dissolved in $CH_2Cl_2$ and a catalytic amount of DMAP was added. Acetic anhydride (1.3 equivalents) was added slowly, and the solution was stirred at room temperature overnight. The reaction was then quenched with water and the aqueous layer was extracted with $CH_2Cl_2$ (3×). The combined organic extracts were dried over $Na_2SO_4$ and concentrated in vacuo, to yield N-[4-(1-methyl-3-piperidyloxy)phenyl]acetamide as a yellow oil. LC/MS (m/z) 249.3 (MH+), $R_t$ 1.24 minutes.

Synthesis of N-[4-(1-Methyl(3-piperidyloxy))-2-nitrophenyl]-acetamide

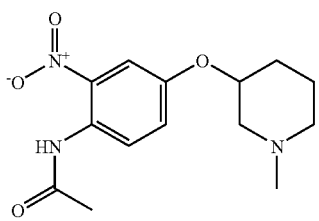

A mixture of $HNO_3/H_2SO_4$ (1:1, 60% $HNO_3$:concentrated $H_2SO_4$) cooled to 0° C. was added dropwise to N-[4-(1-methyl-3-piperidyloxy)phenyl]-acetamide to form a 0.16 M solution. The solution was stirred at 0° C. for 10 minutes and then at room temperature for 30 minutes. The solution was then diluted with water and made basic (pH=10) with 6 N NaOH. The mixture was then extracted with $CH_2Cl_2$ (5×), dried over $Na_2SO_4$, and concentrated in vacuo to yield N-[4-(1-methyl(3-piperidyloxy))-2-nitrophenyl]acetamide. LC/MS (m/z) 294.0 (MH+), $R_t$ 1.24 minutes.

Synthesis of 4-(1-Methyl(3-piperidyloxy))-2-nitrophenylamine

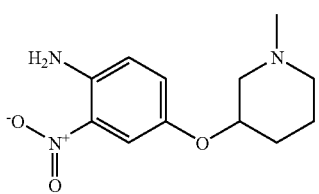

N-[4-(1-methyl(3-piperidyloxy))-2-nitrophenyl]acetamide was dissolved in 1:1 MeOH:6N NaOH (aq) solution (0.03 M). After stirring at room temperature for 2 hours, MeOH was removed in vacuo. The remaining solution was extracted with EtOAc (3×). The combined organic extracts were then dried over $Na_2SO_4$ and concentrated in vacuo to give 4-(1-methyl(3-piperidyloxy))-2-nitrophenylamine.

Synthesis of 4-(1-Methyl-3-piperidyloxy)benzene-1,2-diamine

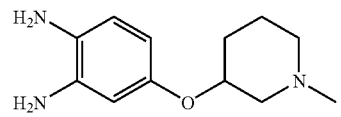

The title compound is synthesized from 4-(1-methyl(3-piperidyloxy))-2-nitrophenylamine using the procedure described in Method 1.

Synthesis of 2-(6-fluoro(1H-indazol-3-yl))-6-(1-methyl(3-piperidyloxy))benzimidazole The title compound is synthesized from 4-(1-Methyl-3-piperidyloxy)benzene-1,2-diamine using the procedure described in Example 4.

Examples 1020-1023

The following compounds are synthesized according to the procedure described above in Example 1019.

| Example | Name |
|---|---|
| 1020 | 6-chloro-3-[6-(1-methyl-piperidin-3-yloxy)-1H-benzoimidazol-2-yl]-1H-indazole |
| 1021 | 5-methoxy-3-[6-(1-methyl-piperidin-3-yloxy)-1H-benzoimidazol-2-yl]-1H-indazole |
| 1022 | 5-benzyloxy-3-[6-(1-methyl-piperidin-3-yloxy)-1H-benzoimidazol-2-yl]-1H-indazole |
| 1023 | 3-[6-(1-methyl-piperidin-3-yloxy)-1H-benzoimidazol-2-yl]-1H-5,7-dioxa-1,2-diaza-s-indacene |

Example 1024

[2-(1H-Indazol-3-yl)-3H-benzoimidazol-5-yl]-methyl-amine

Synthesis of $N^1$-Methyl-4-nitro-benzene-1,3-diamine

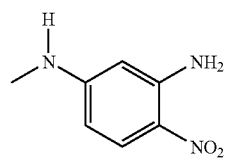

The title compound was synthesized according to the procedure described in Method 1. LC/MS (m/z) 168.3 (MH+), $R_t$ 1.78 minutes.

Synthesis of $N^4$-Methylbenzene-1,2,4-triamine

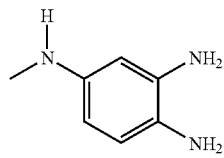

The title compound is synthesized by reducing $N^1$-methyl-4-nitro-benzene-1,3-diamine using the procedure described above in Method 8 Step 6.

Synthesis of [2-(1H-Indazol-3-yl)-3H-benzoimidazol-5-yl]-methyl-amine

The title compound is synthesized from $N^4$-methylbenzene-1,2,4-triamine using the procedure described above in Example 4.

Examples 1025-1033

The following nitroaniline compounds were synthesized according to the procedure described above in Example 1024 starting from the appropriate commercially available amine. The spirocyclic materials used to prepare some of the examples in the following table were synthesized using the procedure following the table.

| Example | Name | LC/MS (m/z) (MH+) | $R_t$ (minutes) |
|---|---|---|---|
| 1025 | $N^1$-(2-dimethylamino-1-methyl-ethyl)-4-nitro-benzene-1,3-diamine | 239.4 | 1.53 |
| 1026 | 4-nitro-$N^1$-(2-piperidin-1-yl-ethyl)-benzene-1,3-diamine | 265.1 | 1.45 |
| 1027 | $N^1$-(1-benzyl-piperidin-4-yl)-4-nitro-benzene-1,3-diamine | 294.5 | 1.71 |
| 1028 | $N^1$-(1-ethyl-pyrrolidin-3-ylmethyl)-4-nitro-benzene-1,3-diamine | 265.1 | 1.39 |
| 1029 | $N^1$-[3-(4-methyl-piperazin-1-yl)-propyl]-4-nitro-benzene-1,3-diamine | 294.5 | 1.38 |
| 1030 | $N^1$-methyl-$N^1$-(1-methyl-piperidin-4-yl)-4-nitro-benzene-1,3-diamine | 265.1 | 1.40 |
| 1031 | $N^1$-(2-dimethylamino-ethyl)-$N^1$-methyl-4-nitro-benzene-1,3-diamine | 239.2 | 1.48 |
| 1032 | 5-(9-isopropyl-1-oxa-4,9-diaza-spiro[5.5]undec-4-yl)-2-nitro-phenylamine | 335.3 | 1.87 |
| 1033 | 5-(2-isopropyl-5-oxa-2,8-diaza-spiro[3.5]non-8-yl)-2-nitro-phenylamine | 309.1 | 1.60 |

Preparation of Spirocycle Nitroanilines

The spirocyclic nitroanilines of Examples 1032 and 1033 were synthesized according to the following procedure. The synthesis of Example 1033 is provided below. The synthesis of Example 1032 was carried out in an analogous manner starting from 5-oxa-2,8-diaza-spiro[3.5]nonan-7-one.

Synthesis of 9-Isopropyl-1-oxa-4,9-diaza-spiro[5.5]undecan-3-one

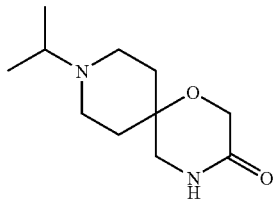

1-Oxa-4,9-diaza-spiro[5.5]undecan-3-one was dissolved in MeOH and treated with acetone (6 equivalents) and NaCNBH$_3$ (4 equivalents). To the reaction mixture was added acetic acid (3 equivalents). The reaction was heated at 50° C. for 6 hours and then cooled to room temperature. The reaction was then poured into an aqueous NaHCO$_3$ solution and extracted with EtOAc (3×). The fractions were dried over MgSO$_4$ and concentrated to provide the title compound as a yellow oil that was purified by chromatography (10% MeOH/CH$_2$Cl$_2$). LC/MS (m/z) 213.1 (MH+), $R_t$=1.38 minutes.

Synthesis of 9-Isopropyl-1-oxa-4,9-diaza-spiro[5.5]undecane

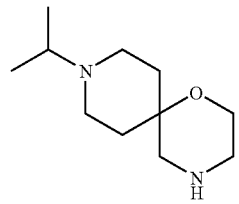

9-Isopropyl-1-oxa-4,9-diaza-spiro[5.5]undecan-3-one was dissolved in THF and LiAlH$_4$ (5 equivalents) was added. The reaction was heated at reflux for 4 hours and then cooled to room temperature. NaF (20 equivalents) and water (5 equivalents) were added and the reaction was stirred vigorously for 1 hour. The resulting precipitate was filtered away and the filtrate was concentrated to provide the title compound as a colorless oil. GC/MS (m/z) 198, $R_t$=12.57 minutes.

Synthesis of 5-(9-Isopropyl-1-oxa-4,9-diaza-spiro[5.5]undec-4-yl)-2-nitro-phenylamine

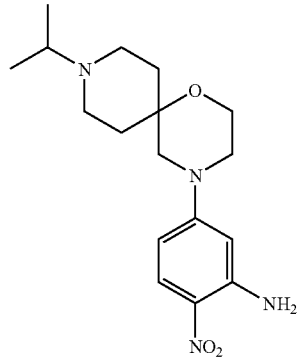

The title compound was synthesized from 9-isopropyl-1-oxa-4,9-diaza-spiro[5.5]undecane using the procedure described above in Method 2.

Various indazole benzimidazoles are synthesized following the procedure of Example 4 using the nitroanilines of Examples 1024-1033 in combination with a indazole-3-carbaldehyde of formula XVI where $R^1$, $R^2$, $R^3$, and $R^4$ Have any of the values described above. For example, various indazole benzimidazoles are synthesized by reacting the nitroanilines of Examples 1024-1033 with 5-fluoroindazole, 5-chloroindazole, 6-fluoroindazole, 6-chloroindazole, 5-methoxyindazole, 6-methoxyindazole, 5-ethoxyindazole, and 6-ethoxyindazole 3-carbaldehydes.

Indazole benzimidazole compounds prepared from the nitroanilines of Examples 1024-1029 are reacted with an acyl halide such as acetyl chloride to provide benzimidazole indazoles with an amide group. In an acetylation procedure, a DMA solution of an indazole benzimidazole (1 equivalent) prepared from a nitroaniline of Examples 1024-1029 is added to a room temperature solution of acetyl chloride (1.5 equivalents) in THF over 15 minutes. After this time, triethylamine (4 equivalents) is added dropwise and the reaction mixture is stirred for 2 hours at room temperature. The reaction is then partitioned between EtOAc and water. Aqueous layers are extracted with EtOAc (2×) and the combined extractions are washed with water once. Drying over anhydrous MgSO₄ and concentration provides an oil that is purified by reverse phase HPLC to provide the desired product.

Indazole benzimidazole compounds prepared from the nitroanilines of Examples 1024-1029 are reacted with an acyl halide such as bromoacetyl chloride to provide benzimidazole indazoles with an amide group that includes a bromide for further reaction. In such an acetylation procedure, a DMA solution of an indazole benzimidazole (1 equivalent) prepared from a nitroaniline of Examples 1024-1029 is added to a room temperature solution of bromoacetyl chloride (1.5 equivalents) in THF over 15 minutes. After this time, triethylamine (4 equivalents) is added dropwise and the reaction mixture is stirred for 2 hours at room temperature. The reaction is then partitioned between EtOAc and water. Aqueous layers are extracted with EtOAc (2×) and the combined extractions are washed with water once. Drying over anhydrous MgSO₄ and concentration provides an oil that is purified by reverse phase HPLC to provide the desired product.

An indazole benzimidazole compound that has been reacted with a bromoacetyl chloride such as described in the preceding paragraph is further functionalized by reaction with an amine. In such a reaction, the bromoacetylated product resulting from the reaction of the bromoacetyl chloride with an indazole benzimidazole prepared from the nitroanilines of Examples 1024-1029 is suspended in a desired amine such as, but not limited to, N-methylpiperazine, morpholine, and piperidine and the reaction is heated at reflux for 1 hour. The reaction is concentrated and the residue is purified via reverse phase HPLC to provide the desired product in which the bromide has been displaced by the amine.

Example 1034

5-Fluoro-3-[5-fluoro-6-(4-isopropyl-piperazin-1-yl)-1H-benzoimidazol-2-yl]-1H-indazole Synthesis of 4-Fluoro-5-(4-isopropyl-piperazin-1-yl)-2-nitro-phenylamine

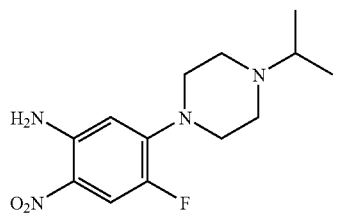

4,5-Difluoro-2-nitrophenylamine (1.0 equivalent) and N-isopropyl piperazine were heated at 100° C. for 3 hours. The solution was then cooled to room temperature and diluted with water. The resulting precipitate was filtered and dried under vacuum to provide title compound product. LC/MS (m/z) 283.2 (MH+), R$_t$ 1.56 minutes.

Synthesis of 4-Fluoro-5-(4-isopropyl-piperazin-1-yl)-benzene-1,2-diamine

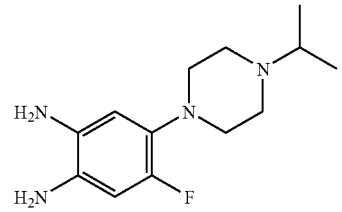

Reduction of 4-fluoro-5-(4-isopropyl-piperazin-1-yl)-2-nitro-phenylamine is carried out using the procedures described in Method 1 to afford the title product.

Synthesis of 5-Fluoro-3-[5-fluoro-4-(4-isopropyl-piperazin-1-yl)-1H-benzoimidazol-2-yl]-1H-indazole The title compound was synthesized as described in Example 4 from 4-fluoro-5-(4-isopropyl-piperazin-1-yl)-benzene-1,2-diamine and 5-fluoro-1H-indazole-3-carbaldehyde. LC/MS (m/z) 397.5 (MH+), R$_t$ 2.78 minutes.

Example 1035

3,5-Bis-(1H-benzoimidazol-2-yl)-1H-indazole

Synthesis of 1H-Indazole-3,5-dicarbaldehyde

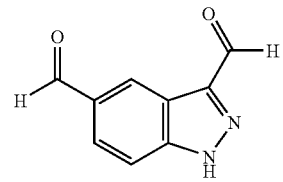

The title compound was synthesized as described in Example 4 from the commercially available 5-formylindole. LC/MS (m/z) 175.3 (MH+), R$_t$ 1.80 min.

Synthesis of 3,5-Bis-(1H-benzoimidazol-2-yl)-1H-indazole

The title compound was synthesized from 1H-Indazole-3,5-dicarbaldehyde and 1,2-diaminobenzene using the methods described in Example 4 except that an excess of 1,2-diaminobenzene was used. LC/MS m/z 351.2 (MH+), R$_t$ 2.03 minutes.

Example 1036

5-(1H-Benzoimidazol-2-yl)-3-[6-(4-methyl-piperazin-1-yl)-1H-benzoimidazol-2-yl]-1H-indazole Synthesis of 5-(1H-Benzoimidazol-2-yl)-3-[6-(4-methyl-piperazin-1-yl)-1H-benzoimidazol-2-yl]-1H-indazole The title compound was synthesized as described in Example 4 in three steps. First, 1H-indole-5-carbaldehyde is reacted with 1,2-diaminobenzene in toluene and ethanol. The product of the first reaction is then reacted with NaNO₂ in dioxane with aqueous HCl. The 5-benzimidazole 3-carbaldehyde thus obtained is then reacted with 4-(4-methyl-piperazin-1-yl)-benzene-1,2-diamine to produce the title compound. LC/MS m/z 449.3 (MH+), $R_t$ 1.71 minutes.

Example 1037

1'-[2-(4-Ethoxymethyl-1H-indazol-3-yl)-3H-benzoimidazol-5-yl]-[1,4']bipiperidinyl Synthesis of 4-Ethoxymethyl-1H-indole

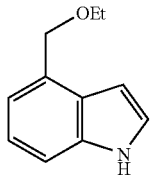

Indole-4-methanol (1.0 equivalent) in THF is added to NaH (1.2 equivalents) in THF at 0° C. EtBr (5.0 equivalents) is added, and the resulting solution is warmed to room temperature and then heated at 50° C. for 9 hours. The reaction mixture is quenched with $H_2O$, extracted with EtOAc. The organic layer is dried over $Na_2SO_4$, filtered and concentrated. The organic layer is dried over $Na_2SO_4$, filtered, and concentrated. The product is purified by flash chromatography (MeOH:$CH_2Cl_2$, 5:95) to yield the desired indole ether title compound.

Synthesis of 4-Ethoxymethyl-1H-indazole-3-carbaldehyde

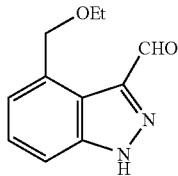

The formation of 4-ethoxymethyl-1H-indazole-3-carbaldehyde from 4-ethoxymethyl-1H-indole is carried out as described in Example 4.

Synthesis of 1'-[2-(4-Ethoxymethyl-1H-indazol-3-yl)-3H-benzoimidazol-5-yl]-[1,4']bipiperidinyl The title compound is formed by reaction of 4-ethoxymethyl-1H-indazole-3-carbaldehyde with 4-[1,4']bipiperidinyl-1'-yl-benzene-1,2-diamine and is carried out as described in Example 4.

Examples 1038-1046

The following compounds are synthesized according to the procedure described above in Example 1037 using the appropriate starting materials.

| Example | Name |
|---|---|
| 1038 | {4-[2-(4-methoxymethyl-1H-indazol-3-yl)-3H-benzoimidazol-5-yl]-5-methyl-morpholin-2-ylmethyl}-dimethyl-amine |
| 1039 | {4-[2-(4-benzyloxymethyl-1H-indazol-3-yl)-3H-benzoimidazol-5-yl]-5-methyl-morpholin-2-ylmethyl}-dimethyl-amine |
| 1040 | {4-[2-(4-isopropoxymethyl-1H-indazol-3-yl)-3H-benzoimidazol-5-yl]-5-methyl-morpholin-2-ylmethyl}-dimethyl-amine |
| 1041 | 4-methoxymethyl-3-[6-(4-methyl-piperazin-1-yl)-1H-benzoimidazol-2-yl]-1H-indazole |
| 1042 | 4-benzyloxymethyl-3-[6-(4-methyl-piperazin-1-yl)-1H-benzoimidazol-2-yl]-1H-indazole |
| 1043 | 4-isopropoxymethyl-3-[6-(4-methyl-piperazin-1-yl)-1H-benzoimidazol-2-yl]-1H-indazole |
| 1044 | 1'-[2-(4-methoxymethyl-1H-indazol-3-yl)-3H-benzoimidazol-5-yl]-[1,4']bipiperidinyl |
| 1045 | 1'-[2-(4-benzyloxymethyl-1H-indazol-3-yl)-3H-benzoimidazol-5-yl]-[1,4']bipiperidinyl |
| 1046 | 1'-[2-(4-isopropoxymethyl-1H-indazol-3-yl)-3H-benzoimidazol-5-yl]-[1,4']bipiperidinyl |

Example 1047

1'-[2-(5-Ethoxymethyl-1H-indazol-3-yl)-3H-benzoimidazol-5-yl]-[1,4']bipiperidinyl Synthesis of 5-Ethoxymethyl-1H-indole

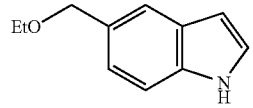

Indole-5-methanol (1.0 equivalent) in THF is added to NaH (1.2 equivalent) in THF at 0° C. EtBr (5.0 equivalents) is added, and the resulting solution is warmed to room temperature and then heated at 50° C. for 9 hours. The reaction mixture is then quenched with $H_2O$, extracted with EtOAc. The organic layer is dried over $Na_2SO_4$, filtered and concentrated. The product is purified by flash chromatography (MeOH:$CH_2Cl_2$, 5:95) to yield the desired indole ether title compound.

Synthesis of 5-Ethoxymethyl-1H-indazole-3-carbaldehyde

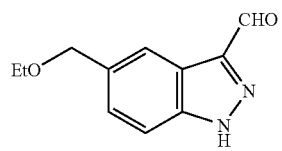

The formation of 5-ethoxymethyl-1H-indazole-3-carbaldehyde from 5-ethoxymethyl-1H-indole is carried out as described in Example 4.

Synthesis of 1'-[2-(5-Ethoxymethyl-1H-indazol-3-yl)-3H-benzoimidazol-5-yl]-[1,4']bipiperidinyl The title compound is formed by reaction of 5-ethoxymethyl-1H-indazole-3-carbaldehyde with 4-[1,4']bipiperidinyl-1'-yl-benzene-1,2-diamine and is carried out as described in Example 4.

Examples 1048-1056

The following compounds are synthesized according to the procedure described above in Example 1047 using the appropriate starting materials.

| Example | Name |
|---|---|
| 1048 | {4-[2-(5-methoxymethyl-1H-indazol-3-yl)-3H-benzoimidazol-5-yl]-5-methyl-morpholin-2-ylmethyl}-dimethyl-amine |
| 1049 | {4-[2-(5-benzyloxymethyl-1H-indazol-3-yl)-3H-benzoimidazol-5-yl]-5-methyl-morpholin-2-ylmethyl}-dimethyl-amine |
| 1050 | {4-[2-(5-isopropoxymethyl-1H-indazol-3-yl)-3H-benzoimidazol-5-yl]-5-methyl-morpholin-2-ylmethyl}-dimethyl-amine |
| 1051 | 5-methoxymethyl-3-[6-(4-methyl-piperazin-1-yl)-1H-benzoimidazol-2-yl]-1H-indazole |
| 1052 | 5-benzyloxymethyl-3-[6-(4-methyl-piperazin-1-yl)-1H-benzoimidazol-2-yl]-1H-indazole |
| 1053 | 5-isopropoxymethyl-3-[6-(4-methyl-piperazin-1-yl)-1H-benzoimidazol-2-yl]-1H-indazole |
| 1054 | 1'-[2-(5-methoxymethyl-1H-indazol-3-yl)-3H-benzoimidazol-5-yl]-[1,4']bipiperidinyl |
| 1055 | 1'-[2-(5-benzyloxymethyl-1H-indazol-3-yl)-3H-benzoimidazol-5-yl]-[1,4']bipiperidinyl |
| 1056 | 1'-[2-(5-isopropoxymethyl-1H-indazol-3-yl)-3H-benzoimidazol-5-yl]-[1,4']bipiperidinyl |

Example 1057

1'-[2-(6-Ethoxymethyl-1H-indazol-3-yl)-3H-benzoimidazol-5-yl]-[1,4']bipiperidinyl Synthesis of 6-Ethoxymethyl-1H-indole

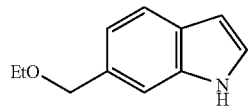

Indole-6-methanol (1.0 equivalent) in THF is added to NaH (1.2 equivalents) in THF at 0° C. EtBr (5.0 equivalents) is added, and the resulting solution is warmed to room temperature and then heated at 50° C. for 9 hours. The reaction mixture is then quenched with $H_2O$, extracted with EtOAc. The organic layer is dried over $Na_2SO_4$, filtered and concentrated. The product is purified by flash chromatography (MeOH:$CH_2Cl_2$, 5:95) to yield the desired indole ether title compound.

Synthesis of 6-Ethoxymethyl-1H-indazole-3-carbaldehyde

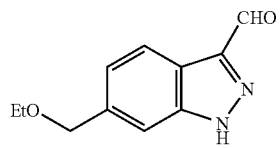

The formation of 6-ethoxymethyl-1H-indazole-3-carbaldehyde from 6-ethoxymethyl-1H-indole is carried out as described in Example 4.

Synthesis of 1'-[2-(6-Ethoxymethyl-1H-indazol-3-yl)-3H-benzoimidazol-5-yl]-[1,4']bipiperidinyl The title compound is formed by reaction of 6-ethoxymethyl-1H-indazole-3-carbaldehyde with 4-[1,4']bipiperidinyl-1'-yl-benzene-1,2-diamine and is carried out as described in Example 4.

Examples 1058-1066

The following compounds are synthesized according to the procedure described above in Example 1057 using the appropriate starting materials.

| Example | Name |
|---|---|
| 1058 | {4-[2-(6-methoxymethyl-1H-indazol-3-yl)-3H-benzoimidazol-5-yl]-5-methyl-morpholin-2-ylmethyl}-dimethyl-amine |
| 1059 | {4-[2-(6-benzyloxymethyl-1H-indazol-3-yl)-3H-benzoimidazol-5-yl]-5-methyl-morpholin-2-ylmethyl}-dimethyl-amine |
| 1060 | {4-[2-(6-isopropoxymethyl-1H-indazol-3-yl)-3H-benzoimidazol-5-yl]-5-methyl-morpholin-2-ylmethyl}-dimethyl-amine |
| 1061 | 6-methoxymethyl-3-[6-(4-methyl-piperazin-1-yl)-1H-benzoimidazol-2-yl]-1H-indazole |
| 1062 | 6-benzyloxymethyl-3-[6-(4-methyl-piperazin-1-yl)-1H-benzoimidazol-2-yl]-1H-indazole |
| 1063 | 6-isopropoxymethyl-3-[6-(4-methyl-piperazin-1-yl)-1H-benzoimidazol-2-yl]-1H-indazole |
| 1064 | 1'-[2-(6-methoxymethyl-1H-indazol-3-yl)-3H-benzoimidazol-5-yl]-[1,4']bipiperidinyl |
| 1065 | 1'-[2-(6-benzyloxymethyl-1H-indazol-3-yl)-3H-benzoimidazol-5-yl]-[1,4']bipiperidinyl |
| 1066 | 1'-[2-(6-isopropoxymethyl-1H-indazol-3-yl)-3H-benzoimidazol-5-yl]-[1,4']bipiperidinyl |

Example 1067

1'-[2-(7-Ethoxymethyl-1H-indazol-3-yl)-3H-benzoimidazol-5-yl]-[1,4']bipiperidinyl Synthesis of 7-Ethoxymethyl-1H-indole

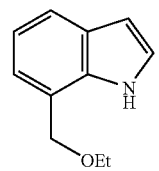

Indole-7-methanol (1.0 equivalent) in THF is added to NaH (1.2 equivalents) in THF at 0° C. EtBr (5.0 equivalents) is added, and the resulting solution is warmed to room temperature and then heated at 50° C. for 9 hours. The reaction mixture is then quenched with $H_2O$, extracted with EtOAc. The organic layer is dried over $Na_2SO_4$, filtered and concentrated. The product is purified by flash chromatography (MeOH:$CH_2Cl_2$, 5:95) to yield the desired indole ether title compound.

Synthesis of 7-Ethoxymethyl-1H-indazole-3-carbaldehyde

The formation of 7-ethoxymethyl-1H-indazole-3-carbaldehyde from 7-ethoxymethyl-1H-indole is carried out as described in Example 4.

Synthesis of 1'-[2-(7-Ethoxymethyl-1H-indazol-3-yl)-3H-benzoimidazol-5-yl]-[1,4']bipiperidinyl The title compound is formed by reaction of 7-ethoxymethyl-1H-indazole-3-carbaldehyde with 4-[1,4']bipiperidinyl-1'-yl-benzene-1,2-diamine and is carried out as described in Example 4.

Examples 1068-1076

The following compounds are synthesized according to the procedure described above in Example 1067 using the appropriate starting materials.

| Example | Name |
|---|---|
| 1068 | {4-[2-(7-methoxymethyl-1H-indazol-3-yl)-3H-benzoimidazol-5-yl]-5-methyl-morpholin-2-ylmethyl}-dimethyl-amine |
| 1069 | {4-[2-(7-benzyloxymethyl-1H-indazol-3-yl)-3H-benzoimidazol-5-yl]-5-methyl-morpholin-2-ylmethyl}-dimethyl-amine |
| 1070 | {4-[2-(7-isopropoxymethyl-1H-indazol-3-yl)-3H-benzoimidazol-5-yl]-5-methyl-morpholin-2-ylmethyl}-dimethyl-amine |
| 1071 | 7-methoxymethyl-3-[6-(4-methyl-piperazin-1-yl)-1H-benzoimidazol-2-yl]-1H-indazole |
| 1072 | 7-benzyloxymethyl-3-[6-(4-methyl-piperazin-1-yl)-1H-benzoimidazol-2-yl]-1H-indazole |
| 1073 | 7-isopropoxymethyl-3-[6-(4-methyl-piperazin-1-yl)-1H-benzoimidazol-2-yl]-1H-indazole |
| 1074 | 1'-[2-(7-methoxymethyl-1H-indazol-3-yl)-3H-benzoimidazol-5-yl]-[1,4']bipiperidinyl |
| 1075 | 1'-[2-(7-benzyloxymethyl-1H-indazol-3-yl)-3H-benzoimidazol-5-yl]-[1,4']bipiperidinyl |
| 1076 | 1'-[2-(7-isopropoxymethyl-1H-indazol-3-yl)-3H-benzoimidazol-5-yl]-[1,4']bipiperidinyl |

Example 1077

3-(1H-Benzoimidazol-2-yl)-1H-indazol-4-ol

A solution of 4-hydroxyindole (1.0 equivalent), benzyl chloroformate (1.1 equivalents), and diisopropylethylamine (2.0 equivalents) in $CH_2Cl_2$ is stirred for 18 hours. The solution is concentrated to yield the desired CBz protected indole ether. The product is then reacted with $NaNO_2$ in HCl and dioxane as described in Example 4, followed by reaction with phenylenediamine in EtOH and toluene using the methods described above to yield the Cbz protected indazole benzimidazole. The Cbz-protected product is deprotected using 10% Pd/C and $H_2$ to provide the desired 4-hydroxyindole benzimidazole.

Example 1078

3-(1H-Benzoimidazol-2-yl)-1H-indazol-6-ol

A solution of 6-hydroxyindole (1.0 equivalent), benzyl chloroformate (1.1 equivalents), and diisopropylethylamine (2.0 equivalents) in $CH_2Cl_2$ is stirred for 18 hours. The solution is concentrated to yield the desired CBz protected indole ether. The product is then reacted with $NaNO_2$ in HCl and dioxane as described in Example 4, followed by reaction with phenylenediamine in EtOH and toluene using the methods described above to yield the Cbz protected indazole benzimidazole. The Cbz-protected product is deprotected using 10% Pd/C and $H_2$ to provide the desired 6-hydroxyindole benzimidazole.

Example 1079

3-(1H-Benzoimidazol-2-yl)-1H-indazol-7-ol

A solution of 7-hydroxyindole (1.0 equivalent), benzyl chloroformate (1.1 equivalents), and diisopropylethylamine (2.0 equivalents) in $CH_2Cl_2$ is stirred for 18 hours. The solution is concentrated to yield the desired CBz protected indole ether. The product is then reacted with $NaNO_2$ in HCl and dioxane as described in Example 4, followed by reaction with phenylenediamine in EtOH and toluene using the methods described above to yield the Cbz protected indazole benzimidazole. The Cbz-protected product is deprotected using 10% Pd/C and $H_2$ to provide the desired 7-hydroxyindole benzimidazole.

Examples 1080-1095

The following compounds are synthesized according to the procedures described above using the appropriate starting materials.

| Example | Name |
|---|---|
| 1080 | 3-[5-(4-methyl-piperazin-1-yl)-1H-benzoimidazol-2-yl]-1H-indazol-4-ol |
| 1081 | 3-[5-(4-isopropyl-piperazin-1-yl)-1H-benzoimidazol-2-yl]-1H-indazol-4-ol |
| 1082 | 3-[5-(2,4-dimethyl-piperazin-1-yl)-1H-benzoimidazol-2-yl]-1H-indazol-4-ol |
| 1083 | 3-[5-(2-dimethylaminomethyl-5-methyl-morpholin-4-yl)-1H-benzoimidazol-2-yl]-1H-indazol-4-ol |
| 1084 | 3-[5-(4-methyl-piperazin-1-yl)-1H-benzoimidazol-2-yl]-1H-indazol-5-ol |
| 1085 | 3-[5-(4-isopropyl-piperazin-1-yl)-1H-benzoimidazol-2-yl]-1H-indazol-5-ol |
| 1086 | 3-[5-(2,4-dimethyl-piperazin-1-yl)-1H-benzoimidazol-2-yl]-1H-indazol-5-ol |
| 1087 | 3-[5-(2-dimethylaminomethyl-5-methyl-morpholin-4-yl)-1H-benzoimidazol-2-yl]-1H-indazol-5-ol |
| 1088 | 3-[5-(4-methyl-piperazin-1-yl)-1H-benzoimidazol-2-yl]-1H-indazol-6-ol |
| 1089 | 3-[5-(4-isopropyl-piperazin-1-yl)-1H-benzoimidazol-2-yl]-1H-indazol-6-ol |
| 1090 | 3-[5-(2,4-dimethyl-piperazin-1-yl)-1H-benzoimidazol-2-yl]-1H-indazol-6-ol |
| 1091 | 3-[5-(2-dimethylaminomethyl-5-methyl-morpholin-4-yl)-1H-benzoimidazol-2-yl]-1H-indazol-6-ol |
| 1092 | 3-[5-(4-methyl-piperazin-1-yl)-1H-benzoimidazol-2-yl]-1H-indazol-7-ol |

-continued

| Example | Name |
|---|---|
| 1093 | 3-[5-(4-isopropyl-piperazin-1-yl)-1H-benzoimidazol-2-yl]-1H-indazol-7-ol |
| 1094 | 3-[5-(2,4-dimethyl-piperazin-1-yl)-1H-benzoimidazol-2-yl]-1H-indazol-7-ol |
| 1095 | 3-[5-(2-dimethylaminomethyl-5-methyl-morpholin-4-yl)-1H-benzoimidazol-2-yl]-1H-indazol-7-ol |

Example 1096

5-[5-(4-Methyl-piperazin-1-yl)-1H-benzoimidazol-2-yl]-3-[6-(4-methyl-piperazin-1-yl)-1H-benzoimidazol-2-yl]-1H-indazole The synthesis of the title compound is carried out using 1H-indazole-3,5-dicarbaldehyde and 4-(4-methylpiperazin-1-yl)-benzene-1,2-diamine and the methods described in Example 4 except that an excess of the 4-(4-methylpiperazin-1-yl)-benzene-1,2-diamine is used.

Example 1097

5-(1H-Benzoimidazol-2-yl)-3-[6-(4-isopropyl-piperazin-1-yl)-1H-benzoimidazol-2-yl]-1H-indazole Synthesis of 5-(1H-Benzoimidazol-2-yl)-3-[6-(4-isopropyl-piperazin-1-yl)-1H-benzoimidazol-2-yl]-1H-indazole The synthesis of the title compound is carried out as described in Example 1036 from 4-(4-isopropyl-piperazin-1-yl)-benzene-1,2-diamine to produce the title compound.

Examples 1098-1106

The following compounds are synthesized according to the procedures described above using the appropriate starting materials.

| Example | Name |
|---|---|
| 1098 | [4-(2-{3-[6-(2-dimethylaminomethyl-5-methyl-morpholin-4-yl)-1H-benzoimidazol-2-yl]-1H-indazol-5-yl}-1H-benzoimidazol-5-yl)-5-methyl-morpholin-2-ylmethyl]-dimethyl-amine |
| 1099 | 5-[5-(2,4-dimethyl-piperazin-1-yl)-1H-benzoimidazol-2-yl]-3-[6-(2,4-dimethyl-piperazin-1-yl)-1H-benzoimidazol-2-yl]-1H-indazole |
| 1100 | 3-(1H-benzoimidazol-2-yl)-5-[5-(2,4-dimethyl-piperazin-1-yl)-1H-benzoimidazol-2-yl]-1H-indazole |
| 1101 | 5-[5-(4-isopropyl-2-methyl-piperazin-1-yl)-1H-benzoimidazol-2-yl]-3-[6-(4-isopropyl-2-methyl-piperazin-1-yl)-1H-benzoimidazol-2-yl]-1H-indazole |
| 1102 | (4-{2-[5-(1H-benzoimidazol-2-yl)-1H-indazol-3-yl]-3H-benzoimidazol-5-yl}-5-methyl-morpholin-2-ylmethyl)-dimethyl-amine |
| 1103 | 3-(1H-benzoimidazol-2-yl)-5-[5-(4-methyl-piperazin-1-yl)-1H-benzoimidazol-2-yl]-1H-indazole |
| 1104 | 5-(1H-benzoimidazol-2-yl)-3-[6-(2,4-dimethyl-piperazin-1-yl)-1H-benzoimidazol-2-yl]-1H-indazole |
| 1105 | 5-(1H-benzoimidazol-2-yl)-3-[6-(4-isopropyl-2-methyl-piperazin-1-yl)-1H-benzoimidazol-2-yl]-1H-indazole |
| 1106 | (4-{2-[3-(1H-benzoimidazol-2-yl)-1H-indazol-5-yl]-1H-benzoimidazol-5-yl}-5-methyl-morpholin-2-ylmethyl)-dimethyl-amine |

Example 1107

3,4-Bis-(1H-benzoimidazol-2-yl)-1H-indazole

Synthesis of 1H-Indazole-3,4-dicarbaldehyde

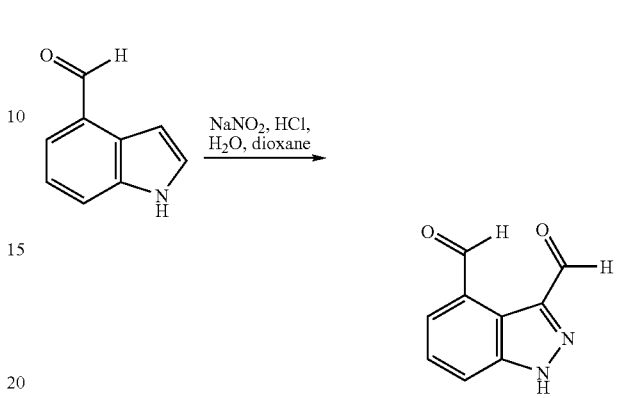

The commercially available 1H-indole-4-carbaldehyde is reacted with NaNO$_2$ in the presence of HCl and H$_2$O in dioxane to produce the title compound.

Synthesis of 3,4-Bis-(1H-benzoimidazol-2-yl)-1H-indazole

The title compound is prepared using the procedure described in Example 4 from 1H-indazole-3,4-dicarbaldehyde and an excess of 1,2-diaminobenzene.

Example 1108

4-(1H-Benzoimidazol-2-yl)-3-[6-(4-methyl-piperazin-1-yl)-1H-benzoimidazol-2-yl]-1H-indazole Synthesis of 4-(1H-Benzoimidazol-2-yl)-3-[6-(4-methyl-piperazin-1-yl)-1H-benzoimidazol-2-yl]-1H-indazole The synthesis of the title compound is carried out as described in 1036 from 4-benzimidazole-3-indazole carbaldehyde and 4-(4-methylpiperazin-1-yl)-benzene-1,2-diamine to produce the title compound.

Examples 1109-1115

The following compounds are synthesized according to the procedures described above in Example 1108 using the appropriate starting materials.

Example 1116

3,6-Bis-(1H-benzoimidazol-2-yl)-1H-indazole

Synthesis of 1H-Indazole-3,6-dicarbaldehyde

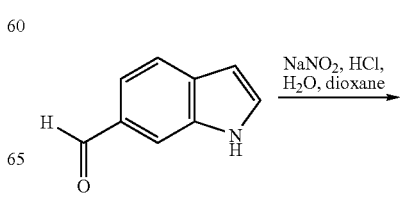

-continued

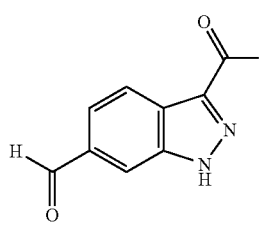

The synthesis of the title compound is carried out from 1H-indole-6-carbaldehyde by reacting it with NaNO$_2$ in dioxane with aqueous HCl using the method described in Example 4.

Synthesis of 3,6-Bis-(1H-benzoimidazol-2-yl)-1H-indazole

The synthesis of the title compound is carried out from 1H-Indazole-3,6-dicarbaldehyde by reacting it with an excess of 1,2-diaminobenzene using the method described in Example 4.

Example 1117

6-(1H-Benzoimidazol-2-yl)-3-[6-(4-methyl-piperazin-1-yl)-1H-benzoimidazol-2-yl]-1H-indazole Synthesis of 6-(1H-Benzoimidazol-2-yl)-3-[6-(4-methyl-piperazin-1-yl)-1H-benzoimidazol-2-yl]-1H-indazole The synthesis of the title compound is carried out as described in 1036 from 6-benzimidazole-3-indazole carbaldehyde and 4-(4-methylpiperazin-1-yl)-benzene-1,2-diamine to produce the title compound.

Examples 1118-1124

The following compounds are synthesized according to the procedures described above in Example 1108 using the appropriate starting materials.

| Example | Name |
| --- | --- |
| 1118 | 6-(1H-benzoimidazol-2-yl)-3-[6-(4-isopropyl-piperazin-1-yl)-1H benzoimidazol-2-yl]-1H-indazole |
| 1119 | 6-(1H-benzoimidazol-2-yl)-3-[6-(2,4-dimethyl-piperazin-1-yl)-1H-benzoimidazol-2-yl]-1H-indazole |
| 1120 | (4-{2-[6-(1H-benzoimidazol-2-yl)-1H-indazol-3-yl]-3H-benzoimidazol-5-yl}-5-methyl-morpholin-2-ylmethyl)-dimethyl-amine |
| 1121 | 3-(1H-benzoimidazol-2-yl)-6-[5-(4-methyl-piperazin-1-yl)-1H-benzoimidazol-2-yl]-1H-indazole |
| 1122 | 3-(1H-benzoimidazol-2-yl)-6-[5-(4-isopropyl-piperazin-1-yl)-1H-benzoimidazol-2-yl]-1H-indazole |
| 1123 | 3-(1H-benzoimidazol-2-yl)-6-[5-(2,4-dimethyl-piperazin-1-yl)-1H-benzoimidazol-2-yl]-1H-indazole |
| 1124 | 3-(1H-benzoimidazol-2-yl)-6-[5-(2-isobutyl-5-methyl-morpholin-4-yl)-1H-benzoimidazol-2-yl]-1H-indazole |

Example 1125

3,7-Bis-(1H-benzoimidazol-2-yl)-1H-indazole

Synthesis of 1H-Indazole-3,7-dicarbaldehyde

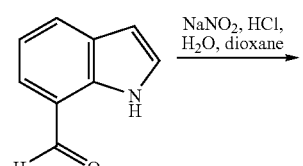

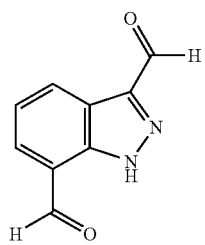

The synthesis of the title compound is carried out from 1H-indole-7-carbaldehyde by reacting it with NaNO$_2$ in dioxane with aqueous HCl using the method described in Example 4.

Synthesis of 3,7-Bis-(1H-benzoimidazol-2-yl)-1H-indazole

The synthesis of the title compound is carried out from 1H-indazole-3,7-dicarbaldehyde by reacting it with an excess of 1,2-diaminobenzene using the method described in Example 4.

Example 1126

7-(1H-Benzoimidazol-2-yl)-3-[6-(4-methyl-piperazin-1-yl)-1H-benzoimidazol-2-yl]-1H-indazole Synthesis of 7-(1H-Benzoimidazol-2-yl)-3-[6-(4-methyl-piperazin-1-yl)-1H-benzoimidazol-2-yl]-1H-indazole The synthesis of the title compound is carried out as described 1036 from 7-benzimidazole-3 indazolecarbaldehyde and 4-(4-methylpiperazin-1-yl)-benzene-1,2-diamine to produce the title compound.

Examples 1127-1133

The following compounds are synthesized according to the procedures described above in Example 1108 using the appropriate starting materials.

| Example | Name |
| --- | --- |
| 1127 | 7-(1H-benzoimidazol-2-yl)-3-[6-(4-isopropyl-piperazin-1-yl)-1H benzoimidazol-2-yl]-1H-indazole |
| 1128 | 7-(1H-benzoimidazol-2-yl)-3-[6-(2,4-dimethyl-piperazin-1-yl)-1H-benzoimidazol-2-yl]-1H-indazole |

-continued

| Example | Name | |
|---|---|---|
| 1129 | (4-{2-[7-(1H-benzoimidazol-2-yl)-1H-indazol-3-yl]-3H-benzoimidazol-5-yl}-5-methyl-morpholin-2-ylmethyl)-dimethyl-amine | |
| 1130 | 3-(1H-benzoimidazol-2-yl)-7-[5-(4-methyl-piperazin-1-yl)-1H-benzoimidazol-2-yl]-1H-indazole | |
| 1131 | 3-(1H-benzoimidazol-2-yl)-7-[5-(4-isopropyl-piperazin-1-yl)-1H-benzoimidazol-2-yl]-1H-indazole | |
| 1132 | 3-(1H-benzoimidazol-2-yl)-7-[5-(2,4-dimethyl-piperazin-1-yl)-1H-benzoimidazol-2-yl]-1H-indazole | |
| 1133 | 3-(1H-benzoimidazol-2-yl)-7-[5-(2-isobutyl-5-methyl-morpholin-4-yl)-1H-benzoimidazol-2-yl]-1H-indazole | |

Examples 1134-1160

Examples 1134-1160 were using the procedure set forth above in Example 732 for the synthesis of indazole benzimidazoles.

| Example | Name | LC/MS m/z (MH+) |
|---|---|---|
| 1134 | 4-{[2-(5-fluoro-1H-indazol-3-yl)-1-methyl-1H-benzimidazol-5-yl]oxy}-N-methylpyridine-2-carboxamide | 417.4 |
| 1135 | 4-{[2-(5-methoxy-1H-indazol-3-yl)-1-methyl-1H-benzimidazol-5-yl]oxy}-N-methylpyridine-2-carboxamide | 429.4 |
| 1136 | Methyl 3-[1-methyl-5-({2-[(methylamino)carbonyl]pyridin-4-yl}oxy)-1H-benzimidazol-2-yl]-1H-indazole-5-carboxylate | 457.5 |
| 1137 | N-methyl-4-{[1-methyl-2-(5-methyl-1H-indazol-3-yl)-1H-benzimidazol-5-yl]oxy}pyridine-2-carboxamide | 413.5 |
| 1138 | 4-({2-[5-(benzyloxy)-1H-indazol-3-yl]-1-methyl-1H-benzimidazol-5-yl}oxy)-N-methylpyridine-2-carboxamide | 505.5 |
| 1139 | 4-{[2-(6-fluoro-1H-indazol-3-yl)-1-methyl-1H-benzimidazol-5-yl]oxy}-N-methylpyridine-2-carboxamide | 417.4 |
| 1140 | 4-{[2-(6-chloro-1H-indazol-3-yl)-1-methyl-1H-benzimidazol-5-yl]oxy}-N-methylpyridine-2-carboxamide | 433.9 |
| 1141 | 4-{[2-(5,6-difluoro-1H-indazol-3-yl)-1-methyl-1H-benzimidazol-5-yl]oxy}-N-methylpyridine-2-carboxamide | 435.4 |
| 1142 | 4-{[2-(6-chloro-5-fluoro-1H-indazol-3-yl)-1-methyl-1H-benzinidazol-5-yl]oxy}-N-methylpyridine-2-carboxamide | 451.9 |
| 1143 | 4-{[2-(1H-[1,3]dioxolo[4,5-f]indazol-3-yl)-1-methyl-1H-benzimidazol-5-yl]oxy}-N-methylpyridine-2-carboxamide | 443.4 |
| 1144 | 4-{[2-(5-chloro-1H-indazol-3-yl)-1H-benzimidazol-6-yl]oxy}-N-methylpyridine-2-carboxamide | 419.8 |
| 1145 | 4-{[2-(5-bromo-1H-indazol-3-yl)-1H-benzimidazol-6-yl]oxy}-N-methylpyridine-2-carboxamide | 464.3 |
| 1146 | Methyl 3-[6-({2-[(methylamino)carbonyl]pyridin-4-yl}oxy)-1H-benzimidazol-2-yl]-1H-indazole-5-carboxylate | 443.4 |
| 1147 | N-methyl-4-{[2-(5-methyl-1H-indazol-3-yl)-1H-benzimidazol-6-yl]oxy}pyridine-2-carboxamide | 399.4 |
| 1148 | 4-({2-[5-(benzyloxy)-1H-indazol-3-yl]-1H-benzimidazol-6-yl}oxy)-N-methylpyridine-2-carboxamide | 491.5 |
| 1149 | 4-{[2-(6-fluoro-1H-indazol-3-yl)-1H-benzimidazol-6-yl]oxy}-N-methylpyridine-2-carboxamide | 403.4 |
| 1150 | 4-{[2-(5,6-difluoro-1H-indazol-3-yl)-1H-benzimidazol-6-yl]oxy}-N-methylpyridine-2-carboxamide | 421.4 |
| 1151 | 4-{[2-(1H-[1,3]dioxolo[4,5-f]indazol-3-yl)-1H-benzimidazol-6-yl]oxy}-N-methylpyridine-2-carboxamide | 429.4 |
| 1152 | 4-{[2-(7-chloro-1H-indazol-3-yl)-1H-benzimidazol-6-yl]oxy}-N-methylpyridine-2-carboxamide | 419.8 |
| 1153 | 4-{[2-(6-cyano-1H-indazol-3-yl)-1H-benzimidazol-6-yl]oxy}-N-methylpyridine-2-carboxamide | 410.4 |
| 1154 | 4-{[2-(5-isobutoxy-1H-indazol-3-yl)-1H-benzimidazol-6-yl]oxy}-N-methylpyridine-2-carboxamide | 457.5 |
| 1155 | 5-fluoro-3-[5-fluoro-6-(4-isopropylpiperazin-1-yl)-1H-benzimidazol-2-yl]-1H-indazole | 397.4 |
| 1156 | 3-[5-fluoro-6-(4-isopropylpiperazin-1-yl)-1H-benzimidazol-2-yl]-5-methyl-1H-indazole | 393.5 |
| 1157 | 5-(benzyloxy)-3-[5-fluoro-6-(4-isopropyl-piperazin-1-yl)-1H-benzimidazol-2-yl]-1H-indazole | 485.6 |
| 1158 | 6-fluoro-3-[5-fluoro-6-(4-isopropyl-piperazin-1-yl)-1H-benzimidazol-2-yl]-1H-indazole | 397.4 |
| 1159 | 6-chloro-3-[5-fluoro-6-(4-isopropyl-piperazin-1-yl)-1H-benzimidazol-2-yl]-1H-indazole | 413.9 |
| 1160 | 3-[5-fluoro-6-(4-isopropyl-piperazin-1-yl)-1H-benzimidazol-2-yl]-1H-[1,3]dioxolo[4,5-f]indazole | 423.5 |

Example 1161

8-[2-(1H-Indazol-3-yl)-1H-benzoimidazol-5-yl]-1,4-dioxa-8-aza-spiro[4.5]decane

Synthesis of 5-(1,4-Dioxa-8-aza-spiro[4.5]dec-8-yl)-2-nitro-phenylamine

The title compound was synthesized as described in Method 10, Step 2 from 1,4-dioxa-8-aza-spiro[4.5]decane and 5-fluoro-2-nitrophenylamine. LC/MS (m/z) 280.3 (MH+), $R_t$ 2.41 minutes.

Synthesis of 8-[2-(1H-Indazol-3-yl)-1H-benzoimidazol-5-yl]-1,4-dioxa-8-aza-spiro[4.5]decane 5-(1,4-Dioxa-8-aza-spiro[4.5]dec-8-yl)-2-nitro-phenylamine was reduced to produce 4-(1,4-dioxa-8-aza-spiro[4.5]dec-8-yl)-benzene-1,2-diamine using the procedures described above. The reduced 1,2-diaminobenzene product is heated in toluene and EtOH at 100° C. overnight with indazole-3-carbaldehyde (1.0 equivalent) to give the title compound.

Example 1162

{1-[2-(1H-Indazol-3-yl)-1H-benzoimidazol-5-yl]-piperidin-4-yl}-dimethyl-amine

Synthesis of {1-[2-(1H-Indazol-3-yl)-1H-benzoimidazol-5-yl]-piperidin-4-yl}-dimethyl-amine The dioxolane protecting group of 8-[2-(1H-indazol-3-yl)-1H-benzoimidazol-5-yl]-1,4-dioxa-8-aza-spiro[4.5]decane is removed with PPTS (1.15 equivalents) in acetone in the microwave (~300 watts, 150° C., 11 minutes) to give the ketone. The ketone is reacted with dimethylamine and $BH_3$:pyridine (10 equivalents) in $AcOH:MeOH:CH_2Cl_2$ as described in Example 710 to yield the title compound.

Examples 1163-1199

The following compounds are synthesized according to the procedures described in Examples 1161 and 1162 using the appropriate starting materials.

| Example | Name |
|---|---|
| 1163 | {1-[2-(5-chloro(1H-indazol-3-yl))benzimidazol-5-yl](4-piperidyl)}dimethylamine |
| 1164 | {1-[2-(5-fluoro(1H-indazol-3-yl))benzimidazol-5-yl](4-piperidyl)}dimethylamine |
| 1165 | {1-{2-(5-methoxy(1H-indazol-3-yl))benzimidazol-5-yl](4-piperidyl)}dimethylamine |
| 1166 | 5-chloro-3-[5-(4-pyrrolidinylpiperidyl)benzimidazol-2-yl]-1H-indazole |
| 1167 | 5-fluoro-3-[5-(4-pyrrolidinylpiperidyl)benzimidazol-2-yl]-1H-indazole |
| 1168 | 5-methoxy-3-[5-(4-pyrrolidinylpiperidyl)benzimidazol-2-yl]-1H-indazole |
| 1169 | {1-[2-(6-chloro(1H-indazol-3-yl))benzimidazol-5-yl](4-piperidyl)}dimethylamine |
| 1170 | {1-[2-(6-fluoro(1H-indazol-3-yl))benzimidazol-5-yl](4-piperidyl)}dimethylamine |
| 1171 | {1-[2-(6-methoxy(1H-indazol-3-yl))benzimidazol-5-yl](4-piperidyl)}dimethylamine |
| 1172 | 6-chloro-3-[5-(4-pyrrolidinylpiperidyl)benzimidazol-2-yl]-1H-indazole |
| 1173 | 6-fluoro-3-[5-(4-pyrrolidinylpiperidyl)benzimidazol-2-yl]-1H-indazole |
| 1174 | 6-methoxy-3-[5-(4-pyrrolidinylpiperidyl)benzimidazol-2-yl]-1H-indazole |
| 1175 | 5-chloro-3-{5-[4-(4-methylpiperazinyl)piperidyl]benzimidazol-2-yl}-1H-indazole |
| 1176 | 5-fluoro-3-{5-[4-(4-methylpiperazinyl)piperidyl]benzimidazol-2-yl}-1H-indazole |
| 1177 | 5-methoxy-3-{5-[4-(4-methylpiperazinyl)piperidyl]benzimidazol-2-yl}-1H-indazole |
| 1178 | 4-{1-[2-(5-chloro-1H-indazol-3-yl)benzimidazol-5-yl]-4-piperidyl}morpholine |
| 1179 | 4-{1-[2-(5-fluoro-1H-indazol-3-yl)benzimidazol-5-yl]-4-piperidyl}morpholine |
| 1180 | 5-methoxy-3-[5-(4-morpholin-4-ylpiperidyl)benzimidazol-2-yl]-1H-indazole |
| 1181 | 6-chloro-3-{5-[4-(4-methylpiperazinyl)piperidyl]benzimidazol-2-yl}-1H-indazole |
| 1182 | 6-fluoro-3-{5-[4-(4-methylpiperazinyl)piperidyl]benzimidazol-2-yl}-1H-indazole |
| 1183 | 6-methoxy-3-{5-[4-(4-methylpiperazinyl)piperidyl]benzimidazol-2-yl}-1H-indazole |
| 1184 | 4-{1-[2-(6-chloro-1H-indazol-3-yl)benzimidazol-5-yl]-4-piperidyl}morpholine |
| 1185 | 4-{1-[2-(6-fluoro-1H-indazol-3-yl)benzimidazol-5-yl]-4-piperidyl}morpholine |
| 1186 | 6-methoxy-3-[5-(4-morpholin-4-ylpiperidyl)benzimidazol-2-yl]-1H-indazole |
| 1187 | {1'-[2-(1H-Indazol-3-yl)-1H-benzoimidazol-5-yl]-[1,4']bipiperidinyl-4-yl}-dimethyl-amine |
| 1188 | {1'-[2-(5-chloro-1H-indazol-3-yl)-1H-benzoimidazol-5-yl]-[1,4']bipiperidinyl-4-yl}-dimethyl-amine |
| 1189 | {1'-[2-(5-fluoro-1H-indazol-3-yl)-1H-benzoimidazol-5-yl]-[1,4']bipiperidinyl-4-yl}-dimethyl-amine |
| 1190 | {1'-[2-(5-methoxy-1H-indazol-3-yl)-1H-benzoimidazol-5-yl]-[1,4']bipiperidinyl-4-yl}-dimethyl-amine |
| 1191 | 1'-[2-(5-chloro-1H-indazol-3-yl)-1H-benzoimidazol-5-yl]-4-pyrrolidin-1-yl-[1,4']bipiperidinyl |
| 1192 | 1'-[2-(5-fluoro-1H-indazol-3-yl)-1H-benzoimidazol-5-yl]-4-pyrrolidin-1-yl-[1,4']bipiperidinyl |
| 1193 | 1'-[2-(5-methoxy-1H-indazol-3-yl)-1H-benzoimidazol-5-yl]-4-pyrrolidin-1-yl-[1,4']bipiperidinyl |
| 1194 | {1'-[2-(6-chloro-1H-indazol-3-yl)-1H-benzoimidazol-5-yl]-[1,4']bipiperidinyl-4-yl}-dimethyl-amine |
| 1195 | {1'-[2-(6-fluoro-1H-indazol-3-yl)-1H-benzoimidazol-5-yl]-[1,4']bipiperidinyl-4-yl}-dimethyl-amine |
| 1196 | {1'-[2-(6-methoxy-1H-indazol-3-yl)-1H-benzoimidazol-5-yl]-[1,4']bipiperidinyl-4-yl}-dimethyl-amine |
| 1197 | 1'-[2-(6-chloro-1H-indazol-3-yl)-1H-benzoimidazol-5-yl]-4-pyrrolidin-1-yl-[1,4']bipiperidinyl |
| 1198 | 1'-[2-(6-fluoro-1H-indazol-3-yl)-1H-benzoimidazol-5-yl]-4-pyrrolidin-1-yl-[1,4']bipiperidinyl |
| 1199 | 1'-[2-(6-methoxy-1H-indazol-3-yl)-1H-benzoimidazol-5-yl]-4-pyrrolidin-1-yl-[1,4']bipiperidinyl |

The following Example compounds were synthesized following the indole modification and coupling procedure of Example 4. The aryl diamine and the indole precursors are readily recognizable by one skilled in the art and are commercially available from Aldrich (Milwaukee, Wis.) or Acros Organics (Pittsburgh, Pa.). 5,6-Dibenzyloxyindole, 5-benzyloxy-6-methoxyindole, 6-benzyloxyindole and 7-benzyloxyindole may be obtained from Sigma (St. Louis, Mo.) 7-Fluoroindole, 6-cyanoindole and 6-(trifluoromethyl)indole may be obtained from Biosynth International (Naperville, Ill.). 5,6-Methylenedioxyindole may be obtained from Maybridge Chemical Company Ltd. (Cornwall, UK). 5-Phenoxyindole was prepared by the method described in Anderson, W. K.; Gopalsamy, A.; Reddy, P. S. *Journal of Medicinal Chemistry* 1994, 37, 1955-1963. The preparation for some of the compounds employed is described in the various methods disclosed herein including the procedures described after the following table.

| Example | STRUCTURE | Name |
|---|---|---|
| 1200 | 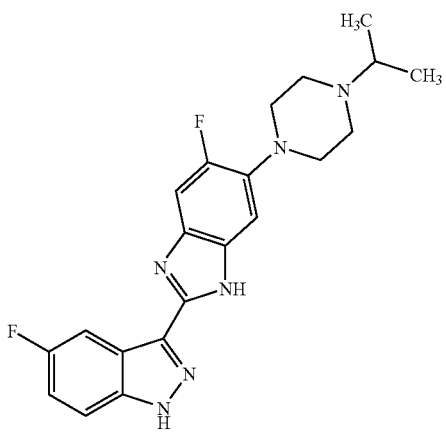 | 5-fluoro-3-[5-fluoro-6-(4-isopropylpiperazin-1-yl)-1H-benzimidazol-2-yl]-1H-indazole |
| 1201 | 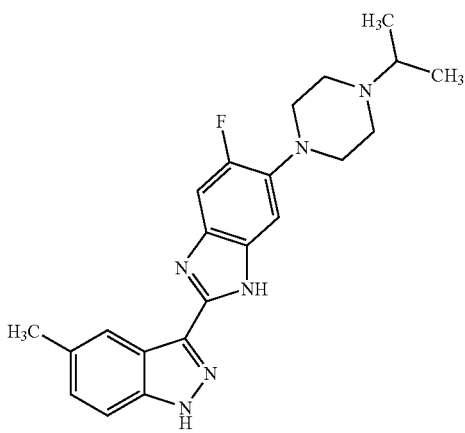 | 3-[5-fluoro-6-(4-isopropylpiperazin-1-yl)-1H-benzimidazol-2-yl]-5-methyl-1H-indazole |
| 1202 | 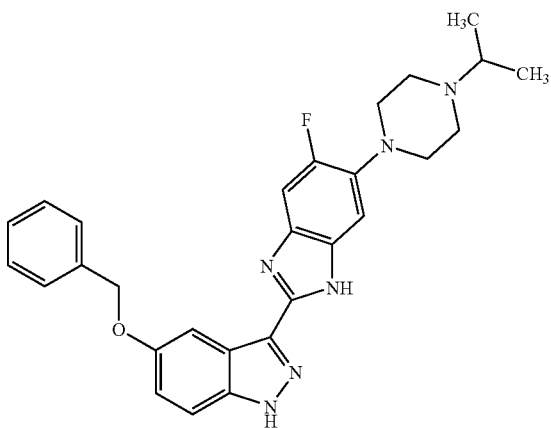 | 5-(benzyloxy)-3-[5-fluoro-6-(4-isopropylpiperazin-1-yl)-1H-benzimidazol-2-yl]-1H-indazole |

| Example | STRUCTURE | Name |
|---|---|---|
| 1203 | 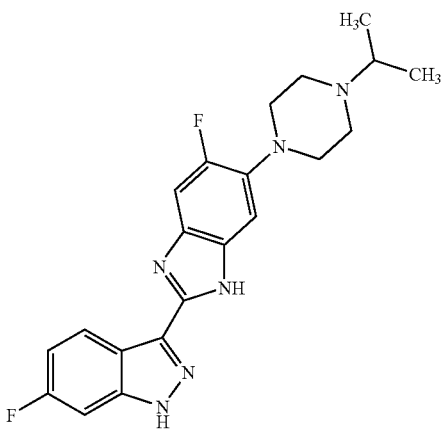 | 6-fluoro-3-[5-fluoro-6-(4-isopropylpiperazin-1-yl)-1H-benzimidazol-2-yl]-1H-indazole |
| 1204 | 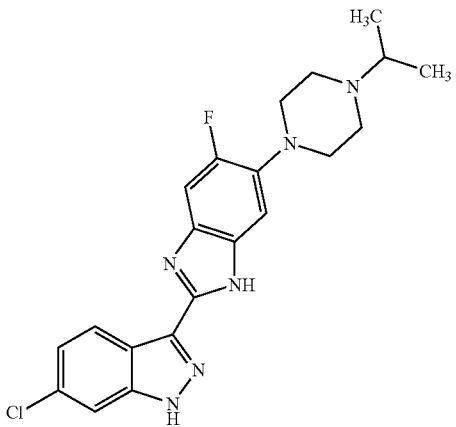 | 6-chloro-3-[5-fluoro-6-(4-isopropylpiperazin-1-yl)-1H-benzimidazol-2-yl]-1H-indazole |
| 1205 | 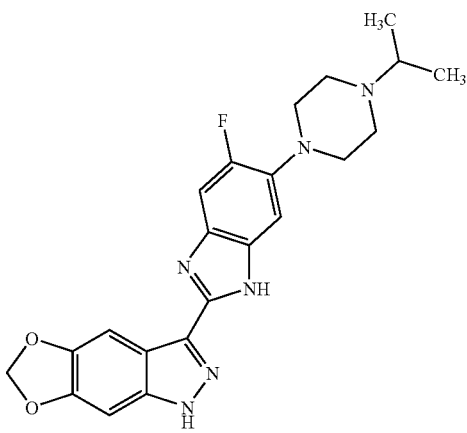 | 3-[5-fluoro-6-(4-isopropylpiperazin-1-yl)-1H-benzimidazol-2-yl]-1H-[1,3]dioxolo[4,5-f]indazole |
| 1206 | 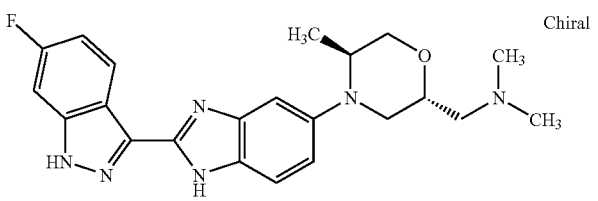 Chiral | N-({(2R,5S)-4-[2-(6-fluoro-1H-indazol-3-yl)-1H-benzimidazol-5-yl]-5-methylmorpholin-2-yl}methyl)-N,N-dimethylamine |

-continued
| Example | STRUCTURE | Name |
|---|---|---|
| 1207 | 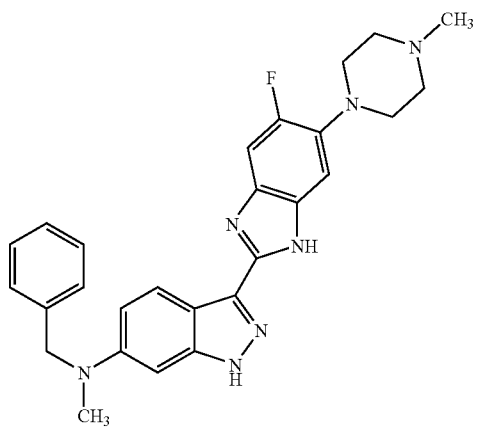 | N-benzyl-N-methyl-3-[6-(4-methylpiperazin-1-yl)-1H-benzimidazol-2-yl]-1H-indazol-6-amine |
| 1208 | 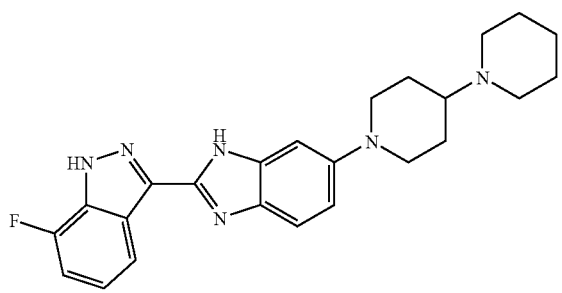 | 1'-[2-(7-fluoro-1H-indazol-3-yl)-1H-benzimidazol-6-yl]-1,4'-bipiperidine |
| 1209 | 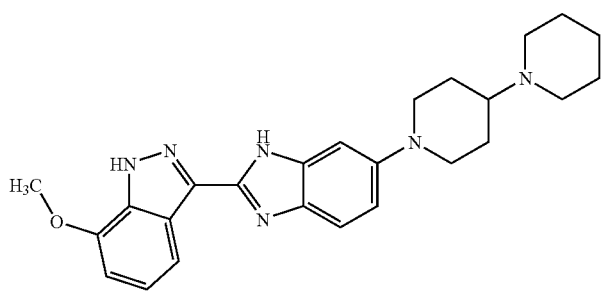 | 1'-[2-(7-methoxy-1H-indazol-3-yl)-1H-benzimidazol-6-yl]-1,4'-bipiperidine |
| 1210 | 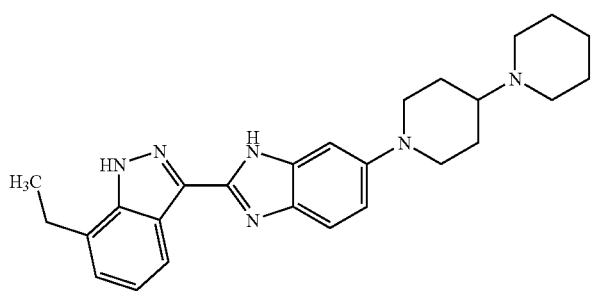 | 1'-[2-(7-ethyl-1H-indazol-3-yl)-1H-benzimidazol-6-yl]-1,4'-bipiperidine |
| 1211 | 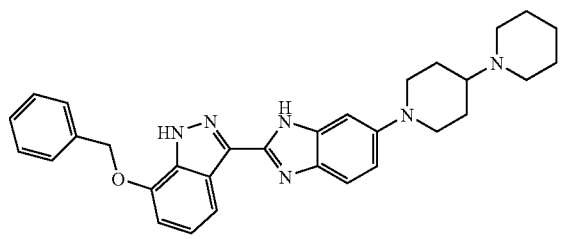 | 1'-{2-[7-(benzyloxy)-1H-indazol-3-yl]-1H-benzimidazol-6-yl}-1,4'-bipiperidine |

-continued
| Example | STRUCTURE | Name |
|---|---|---|
| 1212 | 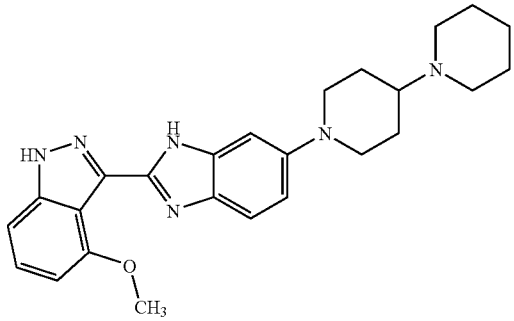 | 1'-[2-(4-methoxy-1H-indazoi-3-yl)-1H-benzimidazol-6-yl]-1,4'-bipiperidine |
| 1213 | 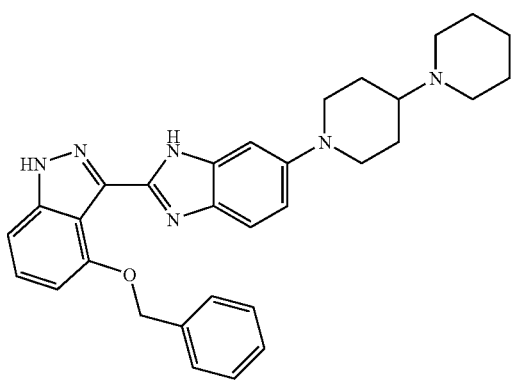 | 1'-{2-[4-(benzyloxy)-1H-indazol-3-yl]-1H-benzimidazol-6-yl}-1,4'-bipiperidine |
| 1214 | 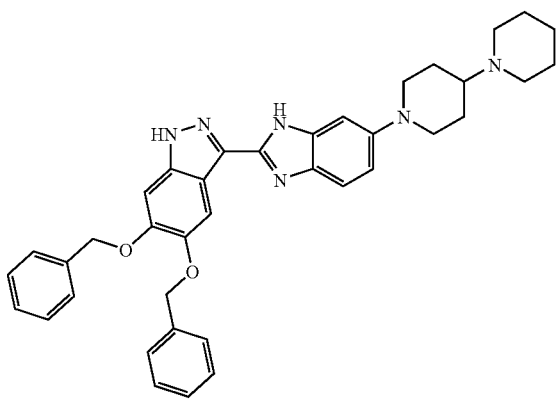 | 1'-{2-[5,6-bis(benzyloxy)-1H-indazol-3-yl]-1H-benzimidazol-6-yl}-1,4-bipiperidine |
| 1215 | 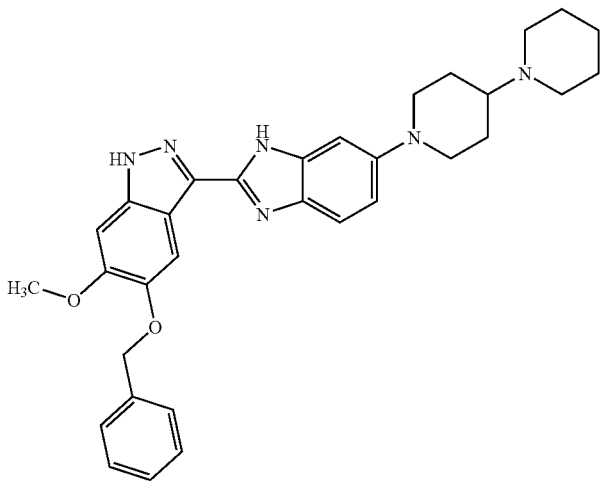 | 1'-{2-[5-(benzyloxy)-6-methoxy-1H-indazol-3-yl]-1H-benzimidazol-6-yl}-1,4'-bipiperidine |

-continued
| Example | STRUCTURE | Name |
|---|---|---|
| 1216 | 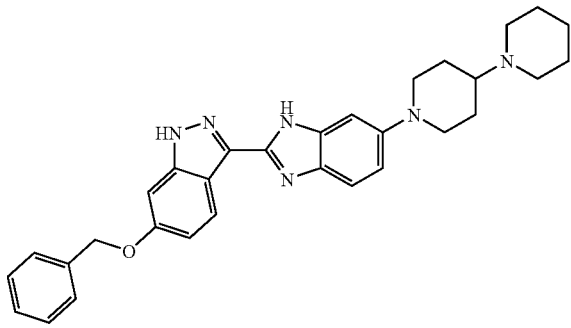 | 1'-{2-[6-(benzyloxy)-1H-indazol-3-yl]-1H-benzimidazol-6-yl}-1,4-bipiperidine |
| 1217 | 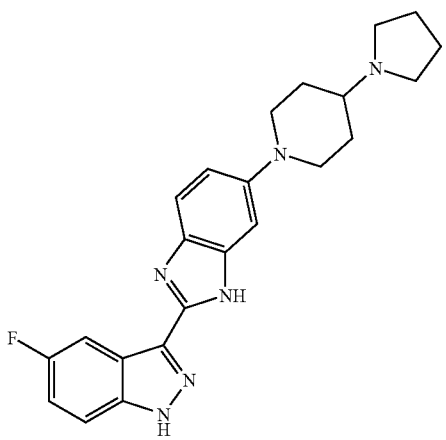 | 5-fluoro-3-[6-(4-pyrrolidin-1-ylpiperidin-1-yl)-1H-benzimidazol-2-yl]-1H-indazole |
| 1218 | 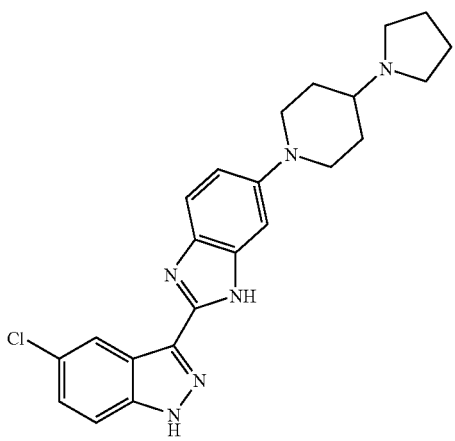 | 5-chloro-3-[6-(4-pyrrolidin-1-ylpiperidin-1-yl)-1H-benzimidazol-2-yl]-1H-indazole |

| Example | STRUCTURE | Name |
|---|---|---|
| 1219 | 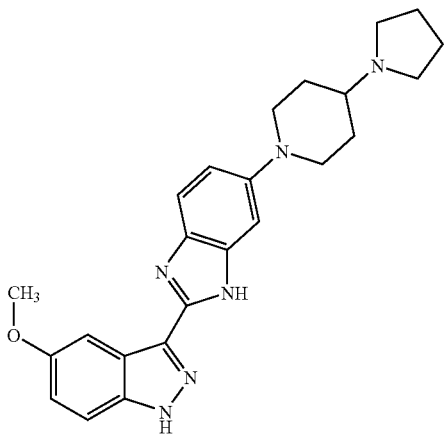 | 5-methoxy-3-[6-(4-pyrrolidin-1-ylpiperidin-1-yl)-1H-benzimidazol-2-yl]-1H-indazole |
| 1220 | 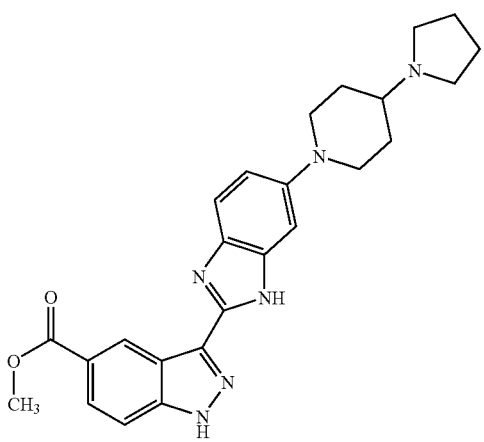 | methyl 3-[6-(4-pyrrolidin-1-ylpiperidin-1-yl)-1H-benzimidazol-2-yl]-1H-indazole-5-carboxylate |
| 1221 | 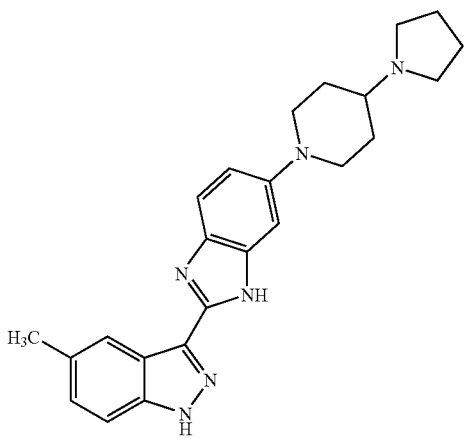 | 5-methyl-3-[6-(4-pyrrolidin-1-ylpiperidin-1-yl)-1H-benzimidazol-2-yl]-1H-indazole |

-continued
| Example | STRUCTURE | Name |
|---|---|---|
| 1222 | 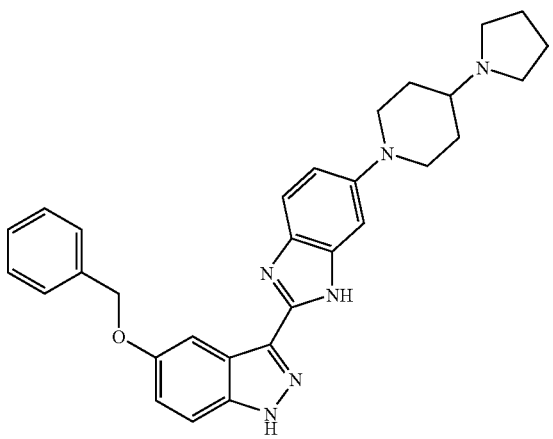 | 5-(benzyloxy)-3-[6-(4-pyrrolidin-1-ylpiperidin-1-yl)-1H-benzimidazol-2-yl]-1H-indazole |
| 1223 | 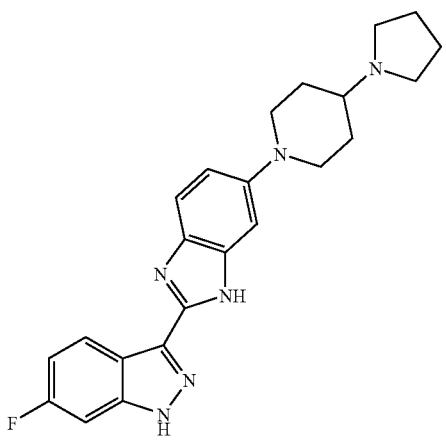 | 6-fluoro-3-[6-(4-pyrrolidin-1-ylpiperidin-1-yl)-1H-benzimidazol-2-yl]-1H-indazole |
| 1224 | 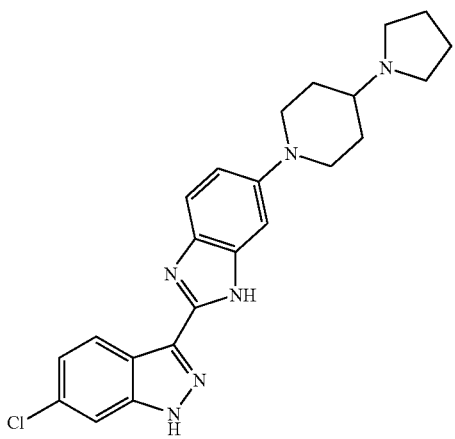 | 6-chloro-3-[6-(4-pyrrolidin-1-ylpiperidin-1-yl)-1H-benzimidazol-2-yl]-1H-indazole |

-continued
| Example | STRUCTURE | Name |
|---|---|---|
| 1225 | 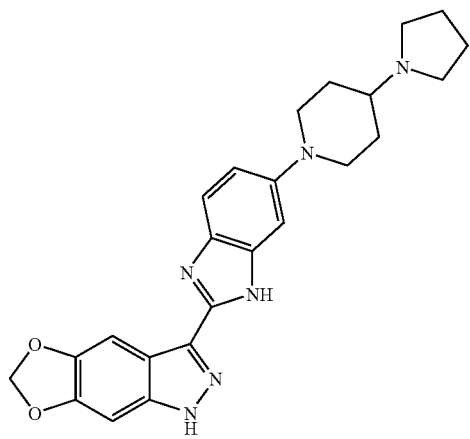 | 3-[6-(4-pyrrolidin-1-ylpiperidin-1-yl)-1H-benzimidazol-2-yl]-1H-[1,3]dioxolo[4,5-f]indazole |
| 1226 | 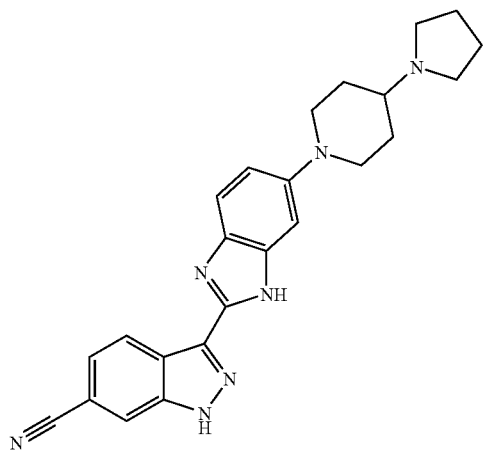 | 3-[6-(4-pyrrolidin-1-ylpiperidin-1-yl)-1H-benzimidazol-2-yl]-1H-indazole-6-carbonitrile |
| 1227 | 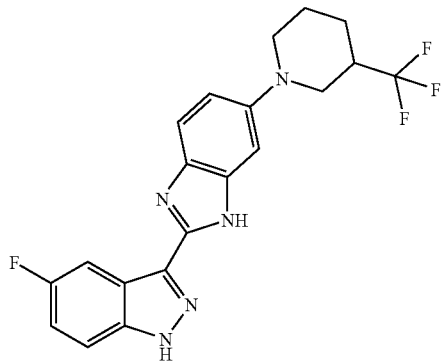 | 5-fluoro-3-{6-[3-(trifluoromethyl)piperidin-1-yl]-1H-benzimidazol-2-yl}-1H-indazole |

-continued
| Example | STRUCTURE | Name |
|---|---|---|
| 1228 | 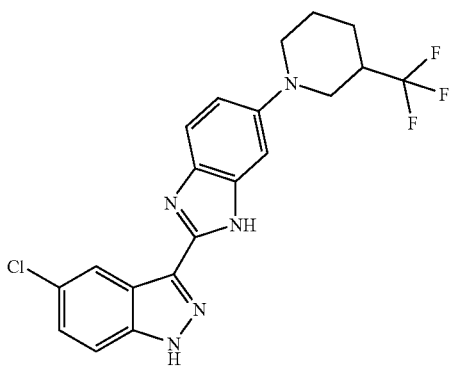 | 5-chloro-3-{6-[3-(trifluoromethyl)piperidin-1-yl]-1H-benzimidazol-2-yl}-1H-indazole |
| 1229 | 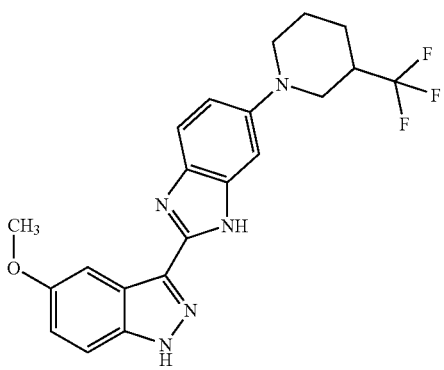 | 5-methoxy-3-{6-[3-(trifluoromethyl)piperidin-1-yl]-1H-benzimidazol-2-yl}-1H-indazole |
| 1230 | 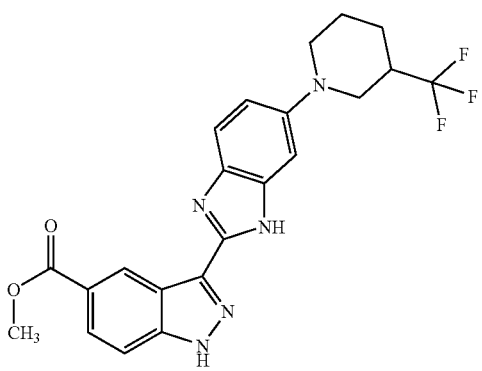 | methyl 3-{6-[3-(trifluoromethyl)piperidin-1-yl]-1H-benzimidazol-2-yl}-1H-indazole-5-carboxylate |
| 1231 | 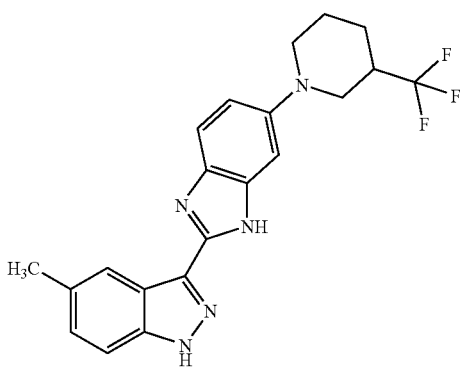 | 5-methyl-3-{6-[3-(trifluoromethyl)piperidin-1-yl]-1H-benzimidazol-2-yl}-1H-indazole |

-continued
| Example | STRUCTURE | Name |
|---|---|---|
| 1232 | 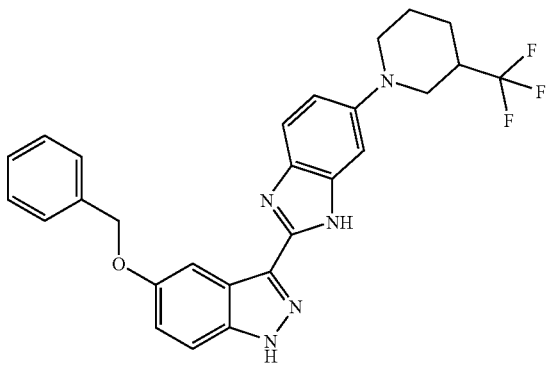 | 5-(benzyloxy)-3-{6-[3-(trifluoromethyl)-piperidin-1-yl]-1H-benzimidazol-2-yl}-1H-indazole |
| 1233 | 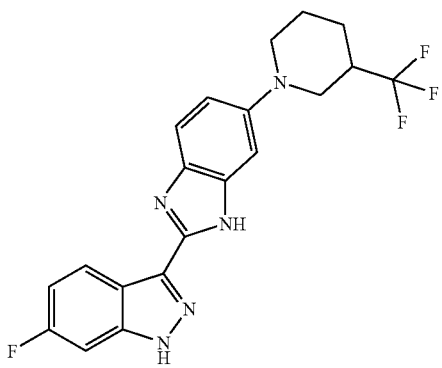 | 6-fluoro-3-{6-[3-(trifluoromethyl)piperidin-1-yl]-1H-benzimidazol-2-yl}-1H-indazole |
| 1234 | 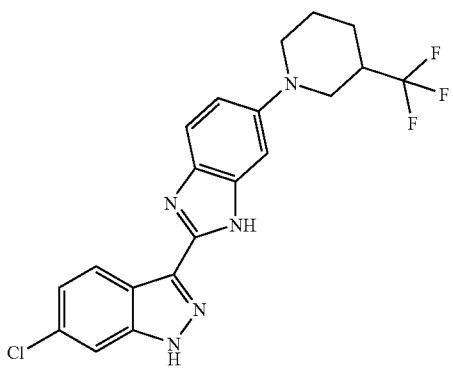 | 6-chloro-3-(6-[3-(trifluorometbyl)piperidin-1-yl]-1H-benzimidazol-2-yl}-1H-indazole |
| 1235 | 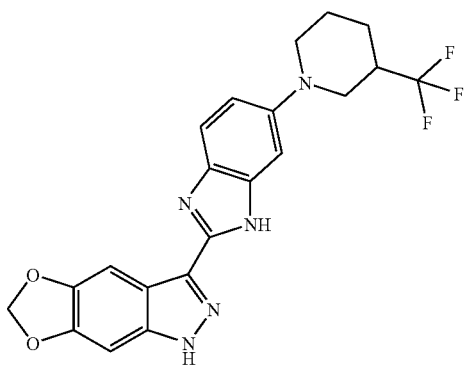 | 3-{6-[3-(trifluoromethyl)piperidin-1-yl]-1H-benzimidazol-2-yl}-1H-[1,3]dioxolo[4,5-f]indazole |

| Example | STRUCTURE | Name |
|---|---|---|
| 1236 | 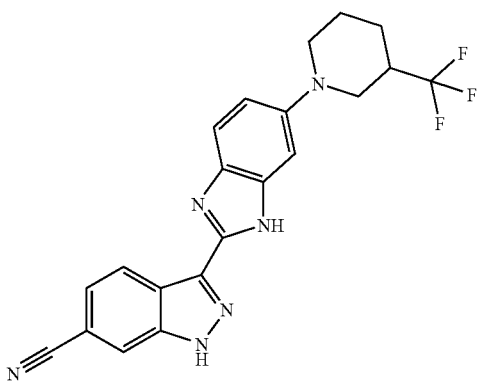 | 3-{6-[3-(trifluoromethyl)piperidin-1-yl]-1H-benzimidazol-2-yl}-1H-indazole-6-carbonitrile |
| 1237 | 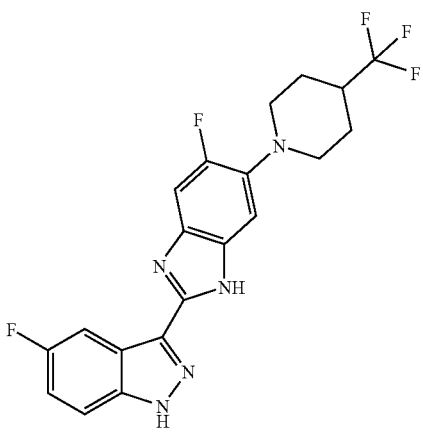 | 5-fluoro-3-{6-[4-(trifluoromethyl)piperidin-1-yl]-1H-benzimidazol-2-yl}-1H-indazole |
| 1238 | 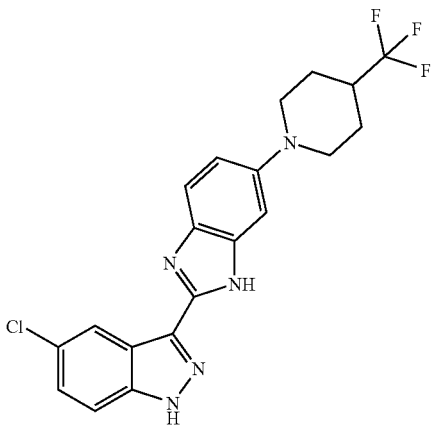 | 5-chloro-3-{6-[4-(trifluoromethyl)piperidin-1-yl]-1H-benzimidazol-2-yl}-1H-indazole |

-continued
| Example | STRUCTURE | Name |
|---|---|---|
| 1239 | 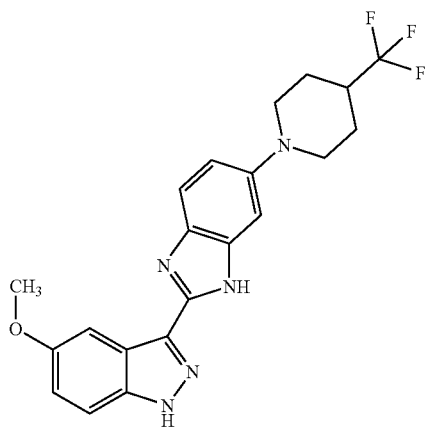 | 5-methoxy-3-{6-[4-(trifluoromethyl)piperidin-1-yl]-1H-benzimidazol-2-yl}-1H-indazole |
| 1240 | 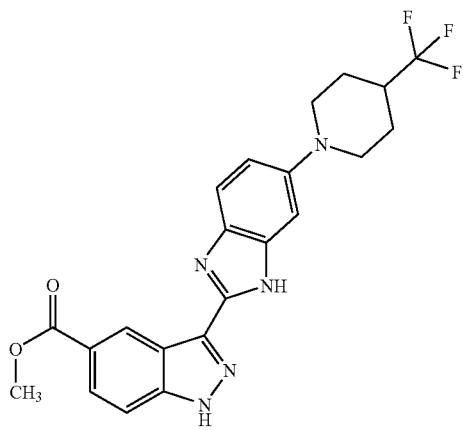 | methyl 3-{6-[4-(trifluoromethyl)piperidin-1-yl]-1H-benzimidazol-2-yl}-1H-indazole-5-carboxylate |
| 1241 | 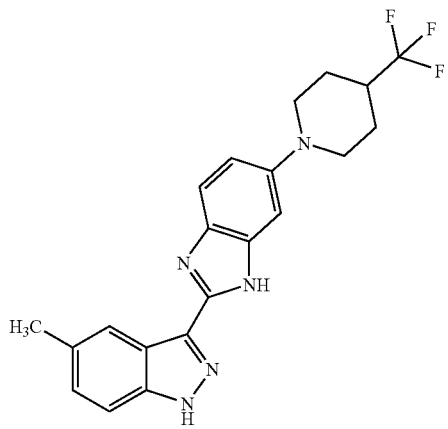 | 5-methyl-3-{6-[4-(trifluoromethyl)piperidin-1-yl]-1H-benzimidazol-2-yl}-1H-indazole |

-continued
| Example | STRUCTURE | Name |
|---|---|---|
| 1242 | 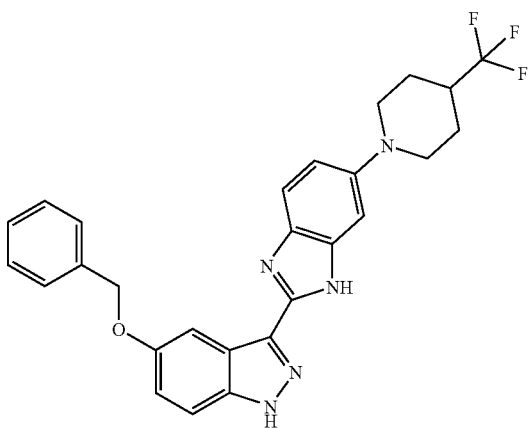 | 5-(benzyloxy)-3-{6-[4-(trifluoromethyl)piperidin-1-yl]-1H-benzimidazol-2-yl}-1H-indazole |
| 1243 | 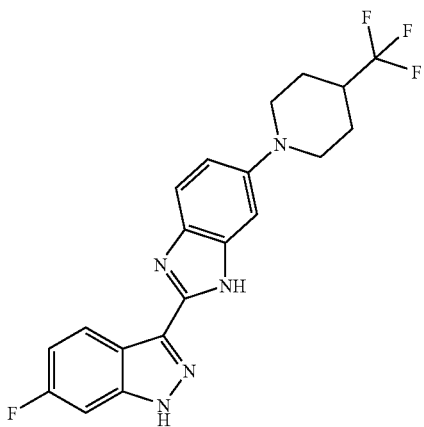 | 6-fluoro-3-{6-[4-(trifluoromethyl)piperidin-1-yl]-1H-benzimidazol-2-yl}-1H-indazole |
| 1244 | 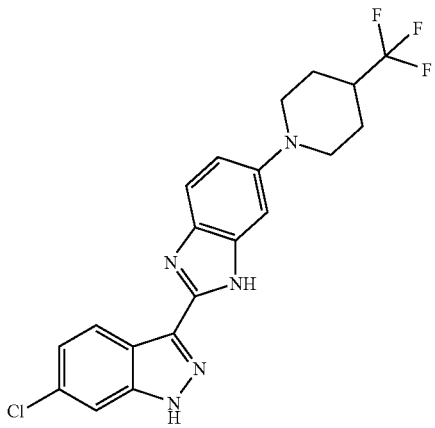 | 6-chloro-3-{6-[4-(trifluoromethyl)piperidin-1-yl]-1H-benzimidazol-2-yl}-1H-indazole |

-continued
| Example | STRUCTURE | Name |
|---|---|---|
| 1245 | 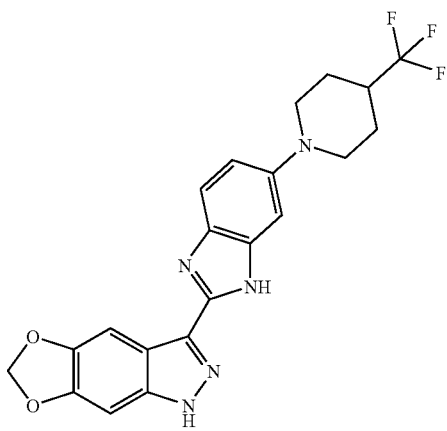 | 3-{6-[4-(trifluoromethyl)piperidin-1-yl]-1H-benzimidazol-2-yl}-1H-[1,3]dioxolo[4,5-f]indazole |
| 1246 | 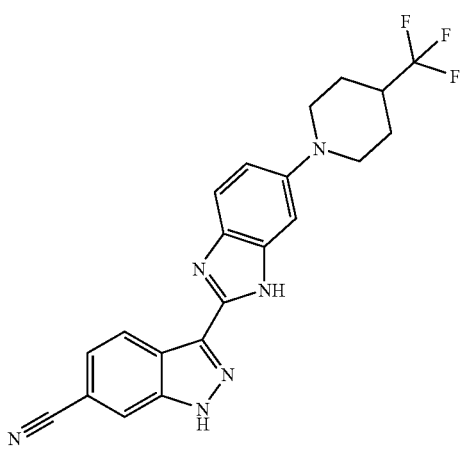 | 3-{6-[4-(trifluorometbyl)piperidin-1-yl]-1H-benzimidazol-2-yl}-1H-indazole-6-carbonitrile |
| 1247 | 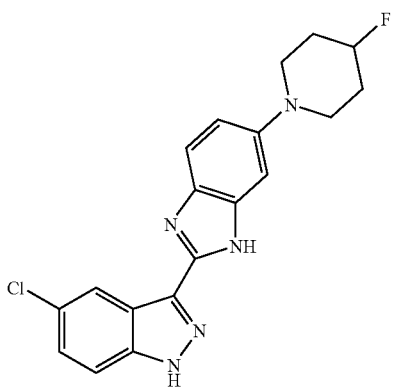 | 5-chloro-3-[6-(4-fluoropiperidin-1-yl)-1H-benzimidazol-2-yl]-1H-indazole |

-continued
| Example | STRUCTURE | Name |
|---|---|---|
| 1248 | 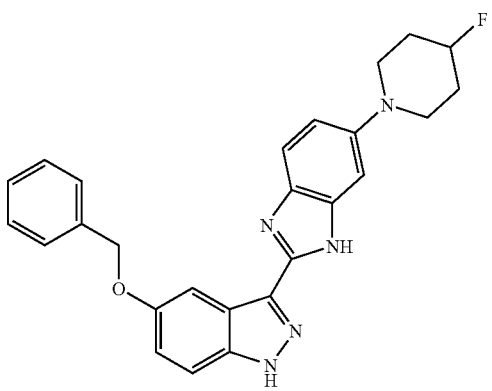 | 5-(benzyloxy)-3-[6-(4-fluoropiperidin-1-yl)-1H-benzimidazol-2-yl]-1H-indazole |
| 1249 | 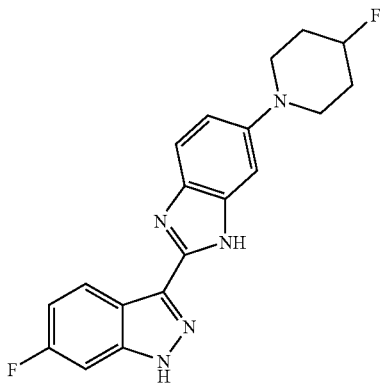 | 6-fluoro-3-[6-(4-fluoropiperidin-1-yl)-1H-benzimidazol-2-yl]-1H-indazole |
| 1250 | 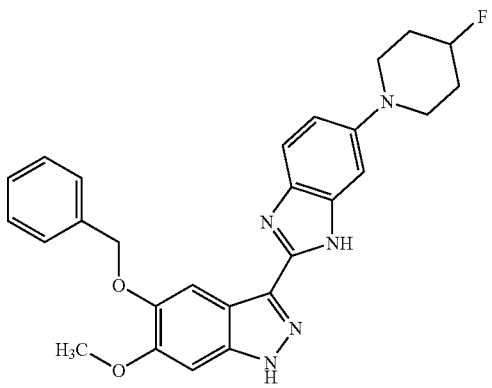 | 5-(benzyloxy)-3-[6-(4-fluoropiperidin-1-yl)-1H-benzimidazol-2-yl]-6-metboxy-1H-indazole |

-continued
| Example | STRUCTURE | Name |
|---|---|---|
| 1251 | 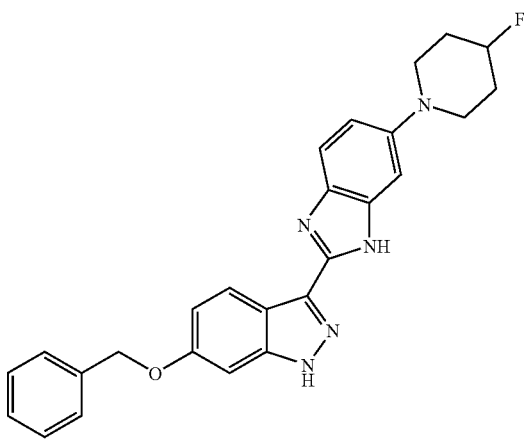 | 6-(benzyloxy)-3-[6-(4-fluoropiperidin-1-yl)-1H-benzimidazol-2-yl]-1H-indazole |
| 1252 | 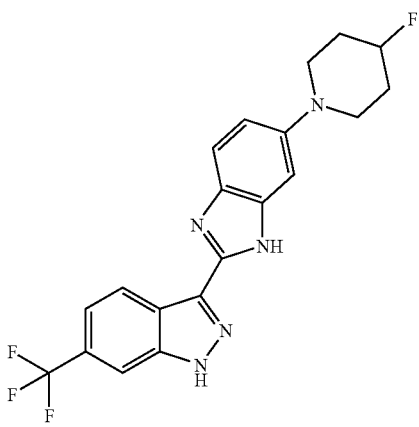 | 3-[6-(4-fluoropiperidin-1-yl)-1H-benzimidazol-2-yl]-6-{trifluoromethyl)-1H-indazole |
| 1253 | 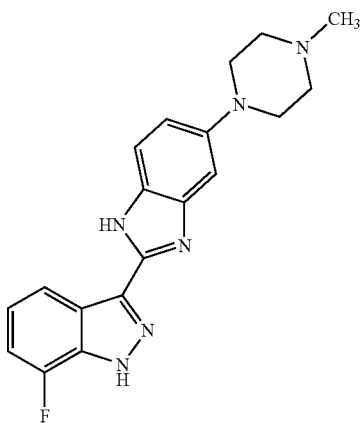 | 7-fluoro-3-[5-(4-methylpiperazin-1-yl)-1H-benzimidazol-2-yl]-1H-indazole |

-continued
| Example | STRUCTURE | Name |
|---|---|---|
| 1254 | 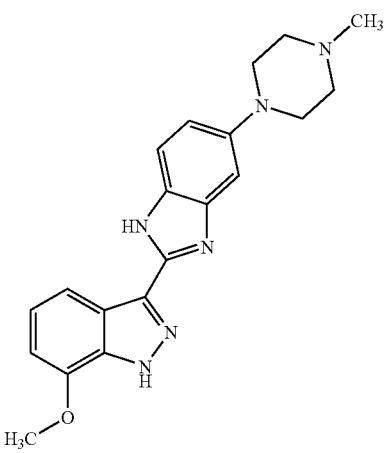 | 7-methoxy-3-[5-(4-methylpiperazin-1-yl)-1H-benzimidazol-2-yl]-1H-indazole |
| 1255 | 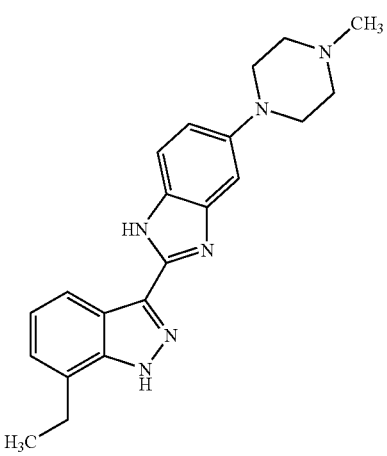 | 7-ethyl-3-[5-(4-methylpiperazin-1-yl)-1H-benzimidazol-2-yl]-1H-indazole |
| 1256 | 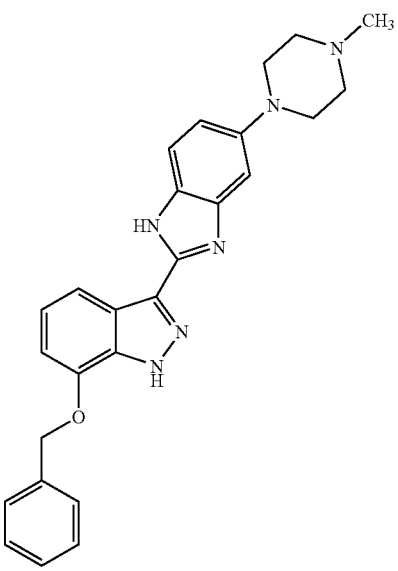 | 7-(benzyloxy)-3-[5-(4-methylpiperazin-1-yl)-1H-benzimidazol-2-yl]-1H-indazole |

| Example | STRUCTURE | Name |
|---|---|---|
| 1257 | 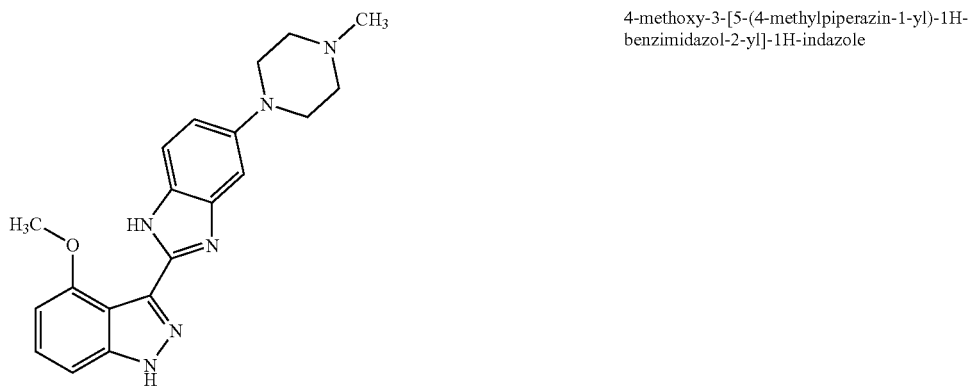 | 4-methoxy-3-[5-(4-methylpiperazin-1-yl)-1H-benzimidazol-2-yl]-1H-indazole |
| 1258 | 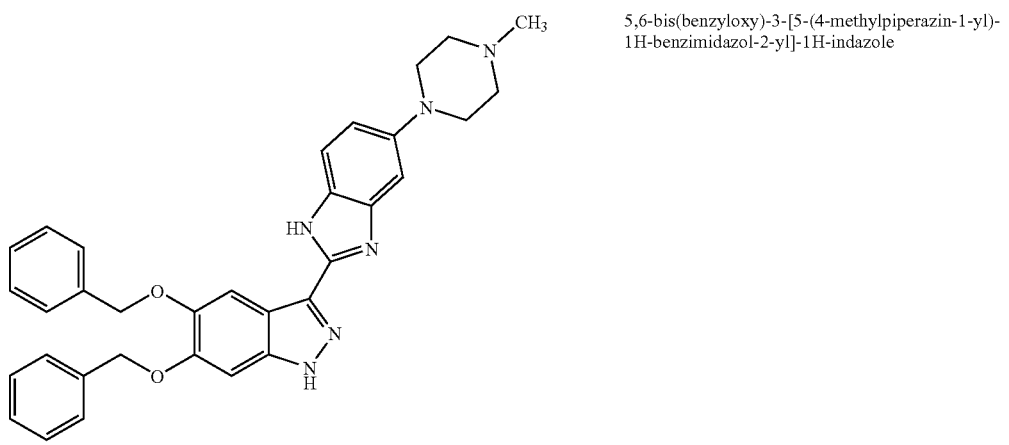 | 5,6-bis(benzyloxy)-3-[5-(4-methylpiperazin-1-yl)-1H-benzimidazol-2-yl]-1H-indazole |
| 1259 | 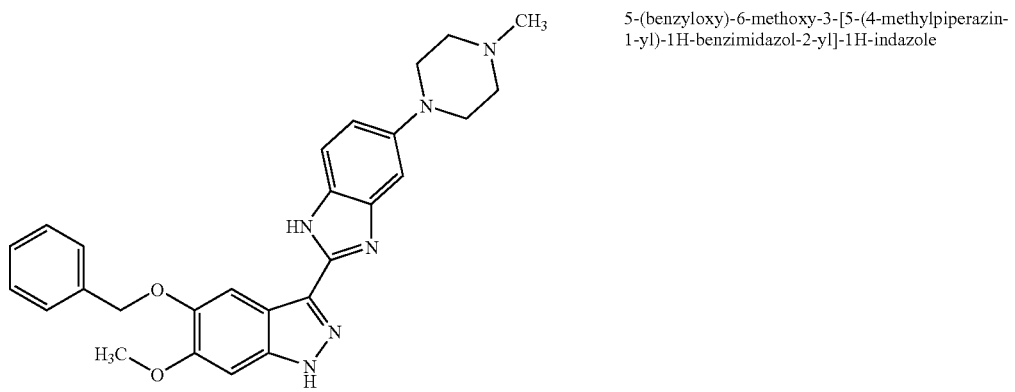 | 5-(benzyloxy)-6-methoxy-3-[5-(4-methylpiperazin-1-yl)-1H-benzimidazol-2-yl]-1H-indazole |

-continued
| Example | STRUCTURE | Name |
|---------|-----------|------|
| 1260 | 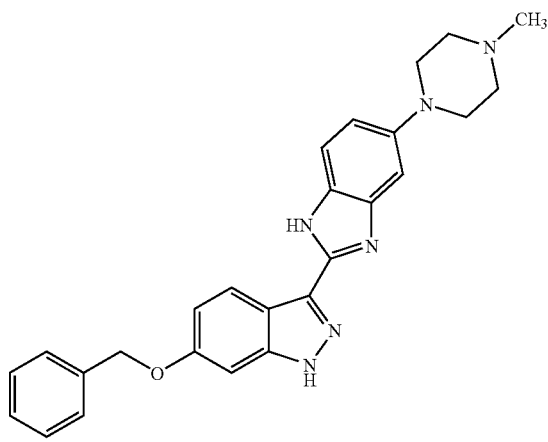 | 6-(benzyloxy)-3-[5-(4-methylpiperazin-1-yl)-1H-benzimidazol-2-yl]-1H-indazole |
| 1261 | 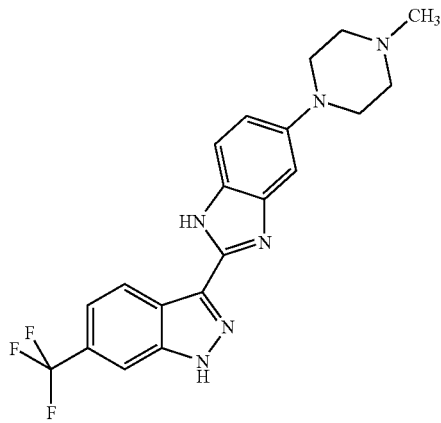 | 3-[5-(4-methylpiperazin-1-yl)-1H-benzimidazol-2-yl]-6-(trifluoromethyl)-1H-indazole |
| 1262 | 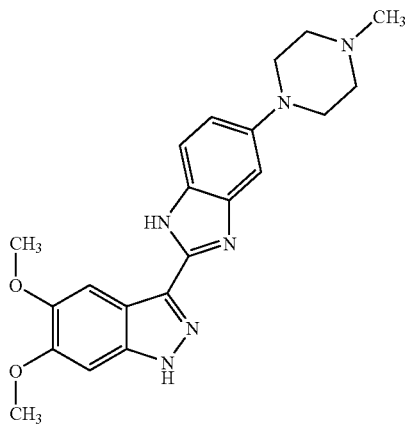 | 5,6-dimethoxy-3-[5-(4-methylpiperazin-1-yl)-1H-benzimidazol-2-yl]-1H-indazole |

-continued
| Example | STRUCTURE | Name |
|---|---|---|
| 1263 | 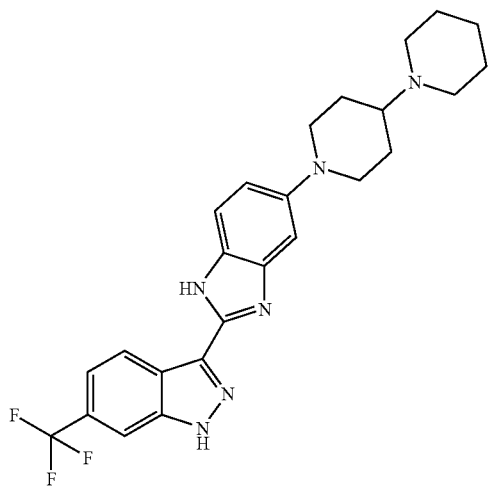 | 1'-{2-[6-(trifluorometbyl)-1H-indazol-3-yl]-1H-benzimidazol-5-yl}-1,4'-bipiperidine |
| 1264 | 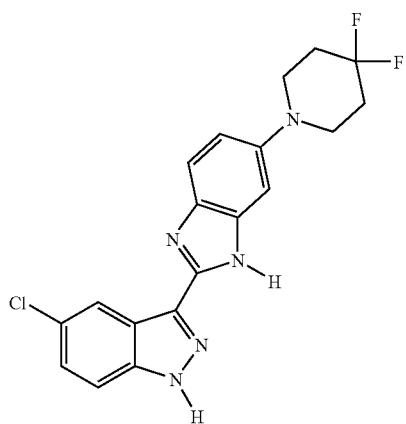 | 5-chloro-3-[6-(4,4-difluoropiperidin-1-yl)-1H-benzimidazol-2-yl]-1H-indazole |
| 1265 | 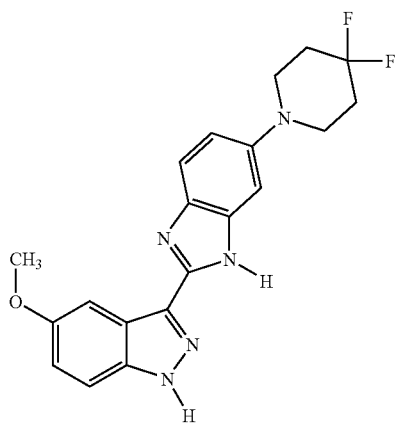 | 3-[6-(4,4-difluoropiperidin-1-yl)-1H-benzimidazol-2-yl]-5-methoxy-1H-indazole |

| Example | STRUCTURE | Name |
|---|---|---|
| 1266 | 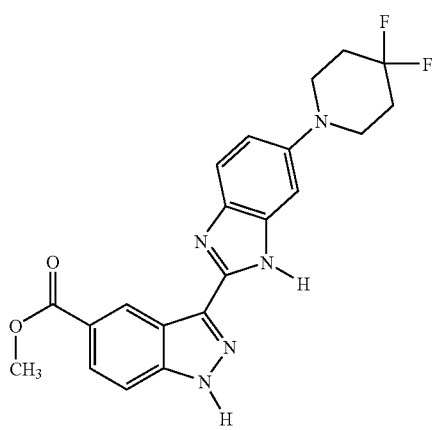 | methyl 3-[6-(4,4-difluoropiperidin-1-yl)-1H-benzimidazol-2-yl]-1H-indazole-5-carboxylate |
| 1267 | 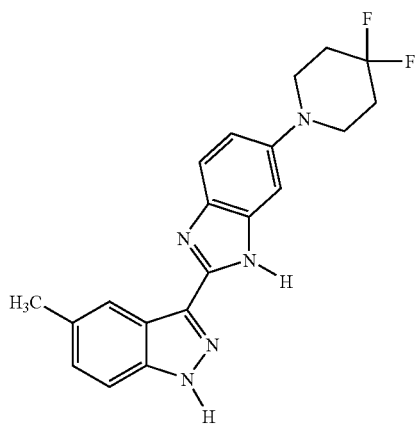 | 3-[6-(4,4-difluoropiperidin-1-yl)-1H-benzimidazol-2-yl]-5-methyl-1H-indazole |
| 1268 | 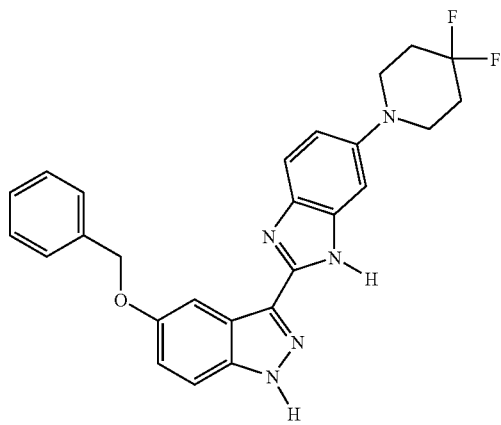 | 5-(benzyloxy)-3-(6-(4,4-difluoropiperidin-1-yl)-1H-benzimidazol-2-yl)-1H-indazole |

-continued
| Example | STRUCTURE | Name |
|---|---|---|
| 1269 | 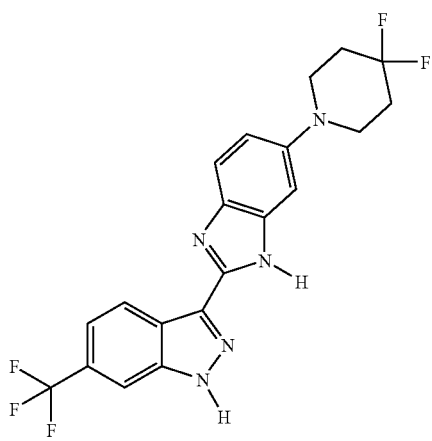 | 3-[6-(4,4-difluoropiperidin-1-yl)-1H-benzimidazol-2-yl]-6-(trifluoromethyl)-1H-indazole |
| 1270 | 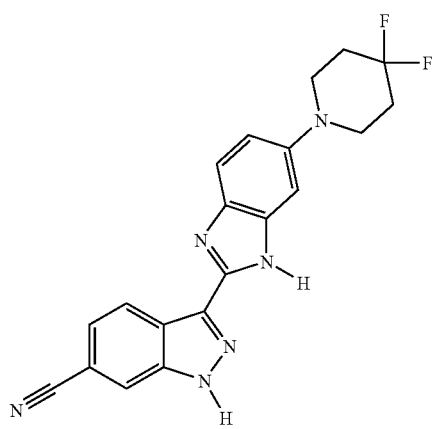 | 3-[6-(4,4-difluoropiperidin-1-yl)-1H-benzimidazol-2-yl]-1H-indazole-6-carbonitrile |
| 1271 | 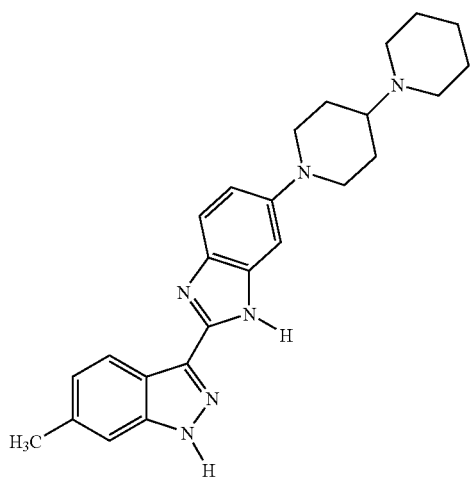 | 1'-[2-(6-methyl-1H-indazol-3-yl)-1H-benzimidazol-6-yl]-1,4'-bipiperidine |

| Example | STRUCTURE | Name |
|---|---|---|
| 1272 | 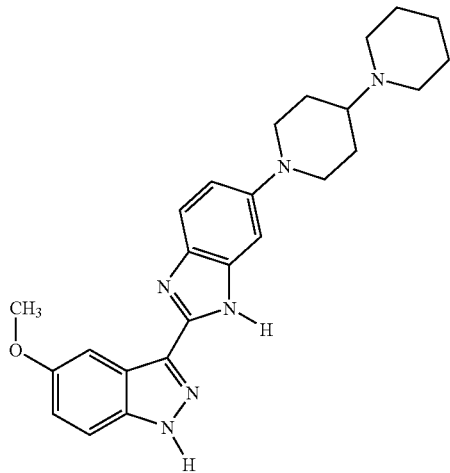 | 1'-[2-(5-methoxy-1H-indazol-3-yl)-1H-benzimidazol-6-yl]-1,4'-bipiperidine |
| 1273 | 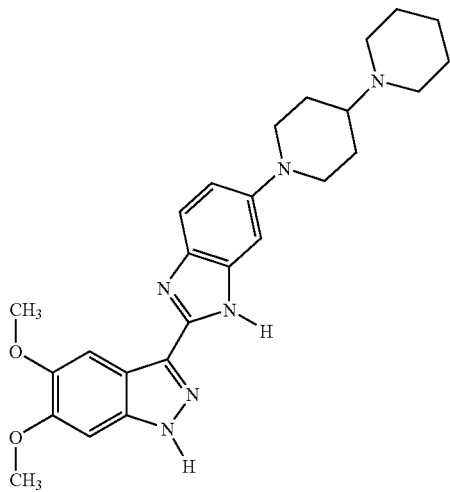 | 1'-[2-(5,6-dimethoxy-1H-indazol-3-yl)-1H-benzimidazol-6-yl]-1,4'-bipiperidine |
| 1274 | 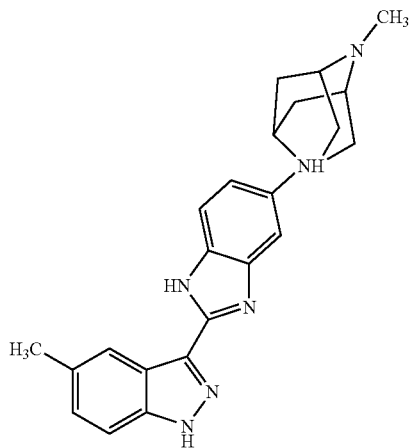 | N-(9-methyl-9-azabicyclo[3.3.1]non-3-yl)-2-(5-methyl-1H-indazol-3-yl)-1H-benzimidazol-5-amine |

-continued
| Example | STRUCTURE | Name |
|---|---|---|
| 1275 | 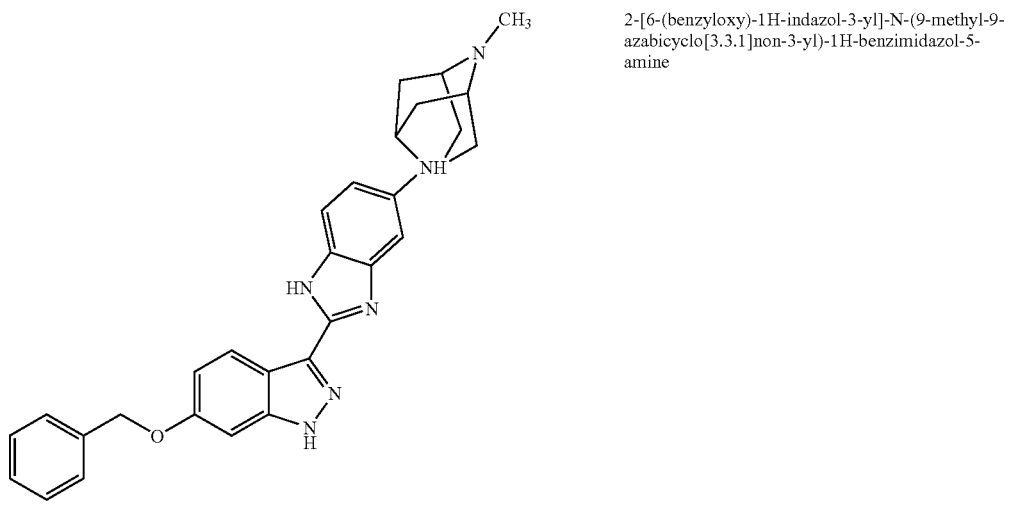 | 2-[6-(benzyloxy)-1H-indazol-3-yl]-N-(9-methyl-9-azabicyclo[3.3.1]non-3-yl)-1H-benzimidazol-5-amine |
| 1276 | 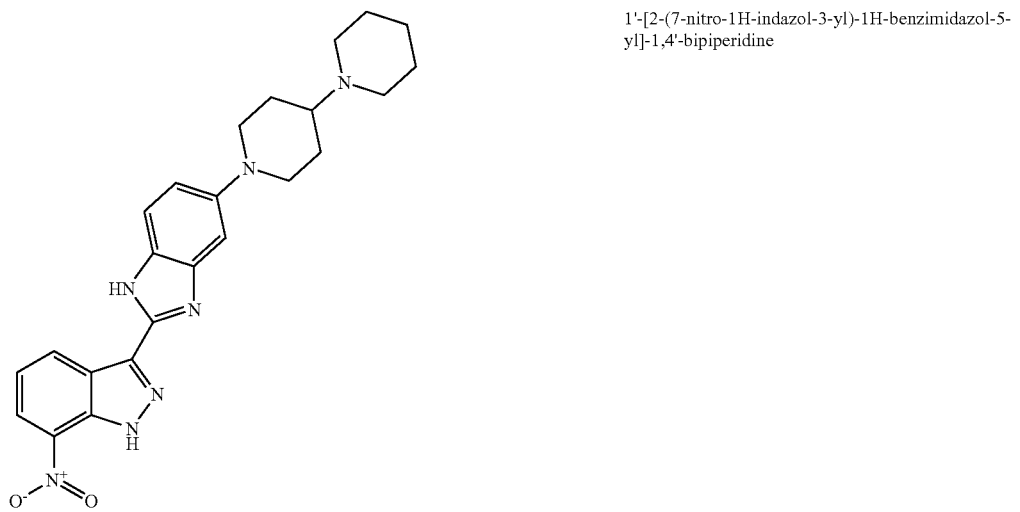 | 1'-[2-(7-nitro-1H-indazol-3-yl)-1H-benzimidazol-5-yl]-1,4'-bipiperidine |
| 1277 | 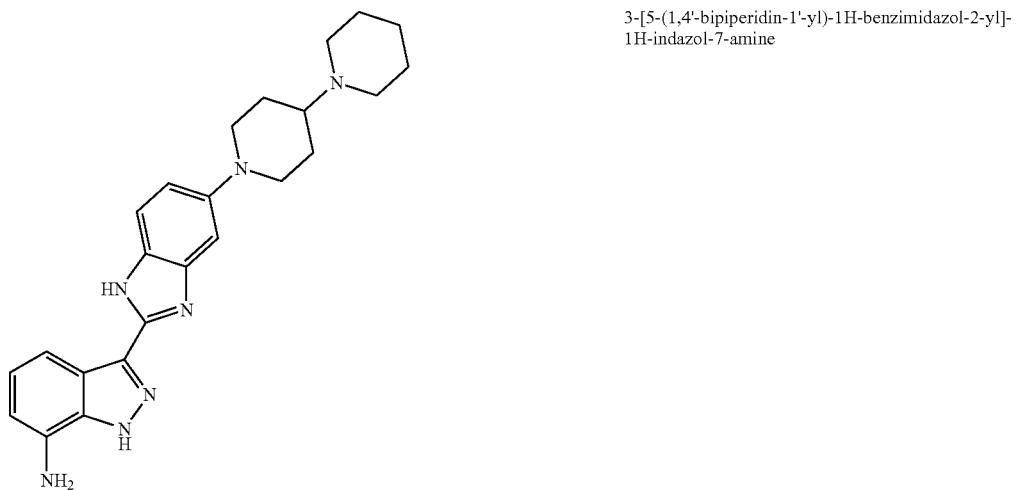 | 3-[5-(1,4'-bipiperidin-1'-yl)-1H-benzimidazol-2-yl]-1H-indazol-7-amine |

| Example | STRUCTURE | Name |
|---|---|---|
| 1278 | 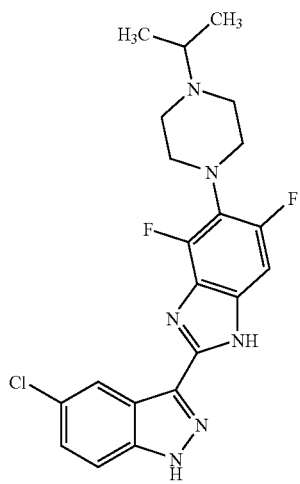 | 5-chloro-3-[4,6-difluoro-5-(4-isopropylpiperazin-1-yl)-1H-benzimidazol-2-yl]-1H-indazole |
| 1279 | 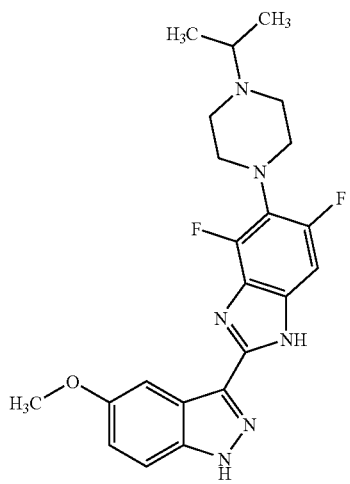 | 3-[4,6-difluoro-5-(4-isopropylpiperazin-1-yl)-1H-benzimidazol-2-yl]-5-methoxy-1H-indazole |
| 1280 | 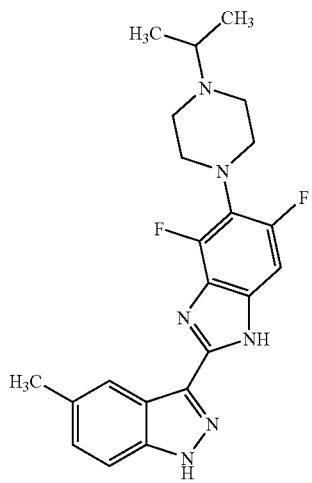 | 3-[4,6-difluoro-5-(4-isopropylpiperazin-1-yl)-1H-benzimidazol-2-yl]-5-methyl-1H-indazole |

| Example | STRUCTURE | Name |
|---|---|---|
| 1281 | 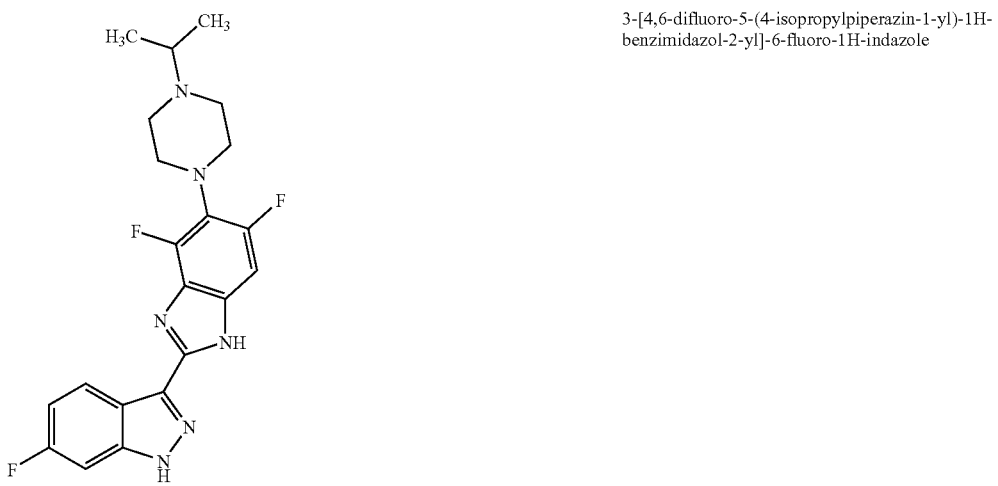 | 3-[4,6-difluoro-5-(4-isopropylpiperazin-1-yl)-1H-benzimidazol-2-yl]-6-fluoro-1H-indazole |
| 1282 | 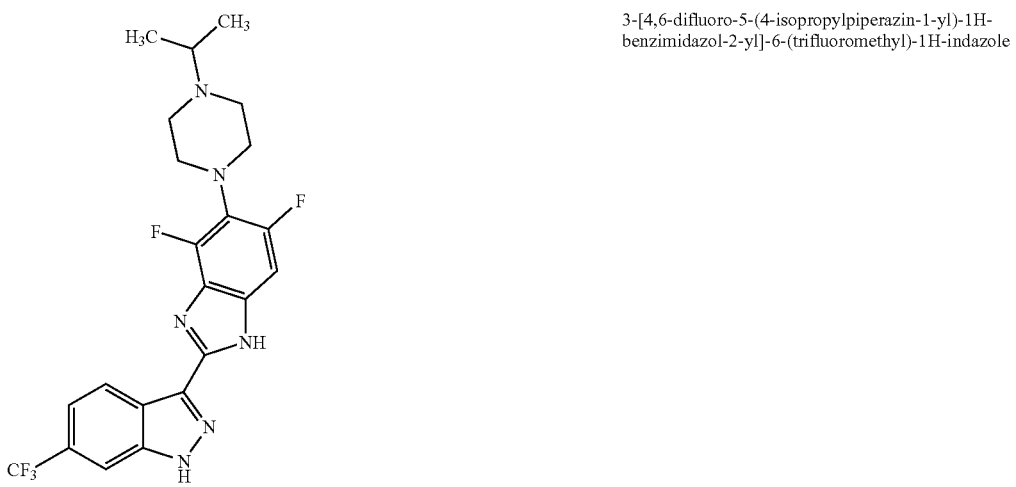 | 3-[4,6-difluoro-5-(4-isopropylpiperazin-1-yl)-1H-benzimidazol-2-yl]-6-(trifluoromethyl)-1H-indazole |
| 1283 | 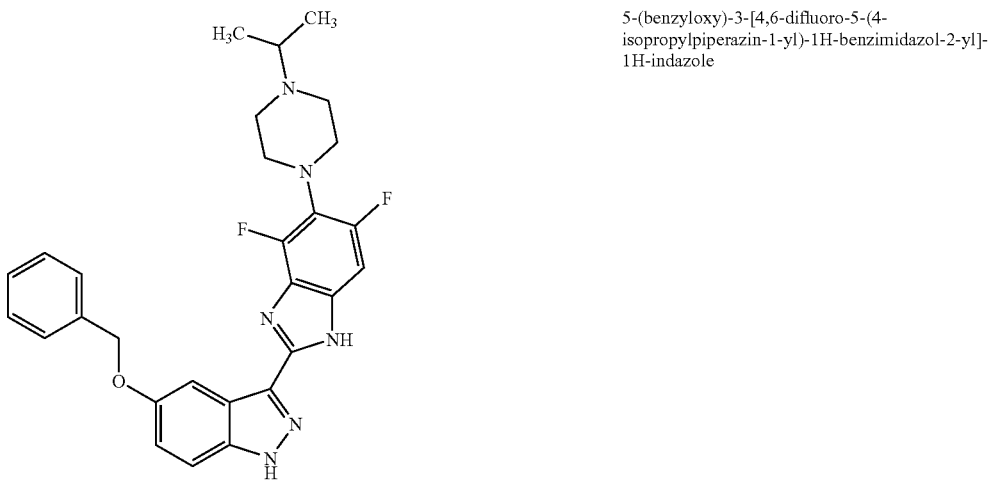 | 5-(benzyloxy)-3-[4,6-difluoro-5-(4-isopropylpiperazin-1-yl)-1H-benzimidazol-2-yl]-1H-indazole |

-continued
| Example | STRUCTURE | Name |
|---------|-----------|------|
| 1284 | 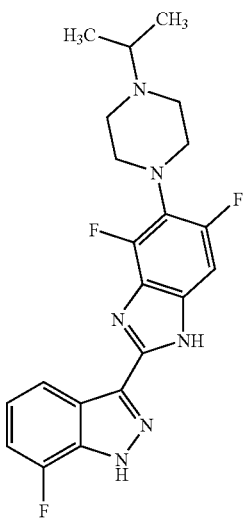 | 3-[4,6-difluoro-5-(4-isopropylpiperazin-1-yl)-1H-benzimidazol-2-yl]-7-fluoro-1H-indazole |
| 1285 | 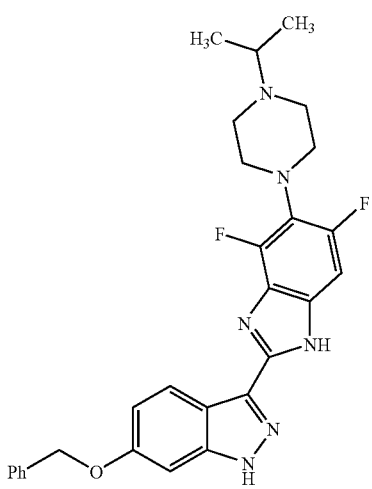 | 6-(benzyloxy)-3-[4,6-difluoro-5-(4-isopropylpiperazin-1-yl)-1H-benzimidazol-2-yl]-1H-indazole |
| 1286 | 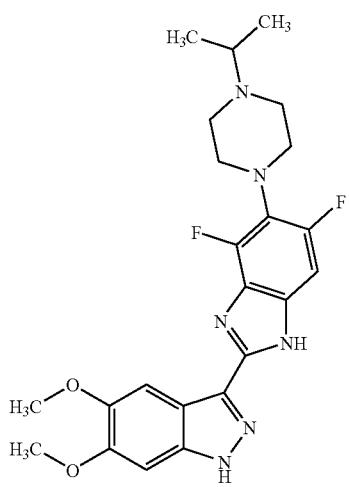 | 3-[4,6-difluoro-5-(4-isopropylpiperazin-1-yl)-1H-benzimidazol-2-yl]-5,6-dimethoxy-1H-indazole |

-continued
| Example | STRUCTURE | Name |
|---|---|---|
| 1287 | 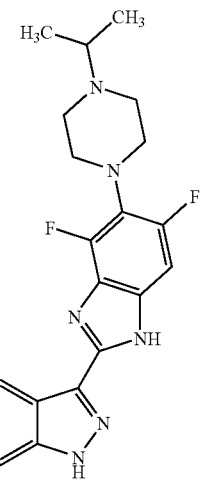 | 3-[4,6-difluoro-5-(4-isopropylpiperazin-1-yl)-1H-benzimidazol-2-yl]-6-methyl-1H-indazole |
| 1288 | 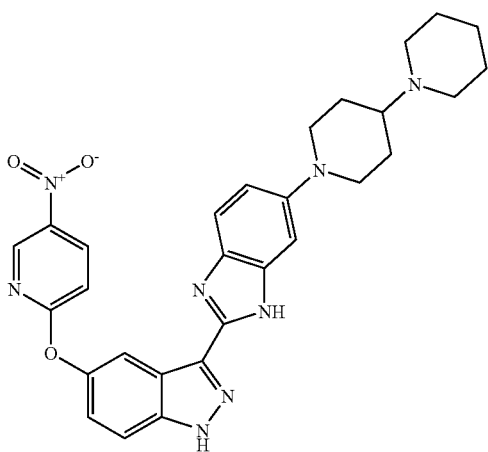 | 1'-(2-{5-[(5-nitropyridin-2-yl)oxy]-1H-indazol-3-yl}-1H-benzimidazol-6-yl)-1,4'-bipiperidine |
| 1289 | 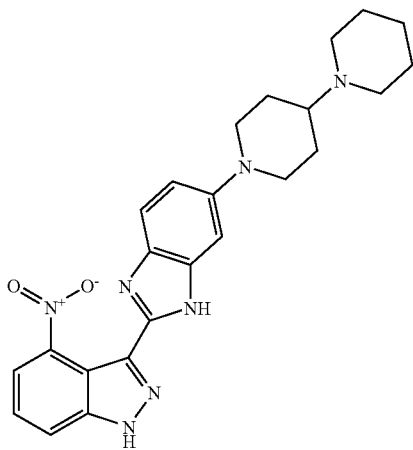 | 1'-[2-(4-nitro-1H-indazol-3-yl)-1H-benzimidazol-6-yl]-1,4'-bipiperidine |

-continued
| Example | STRUCTURE | Name |
|---|---|---|
| 1290 | 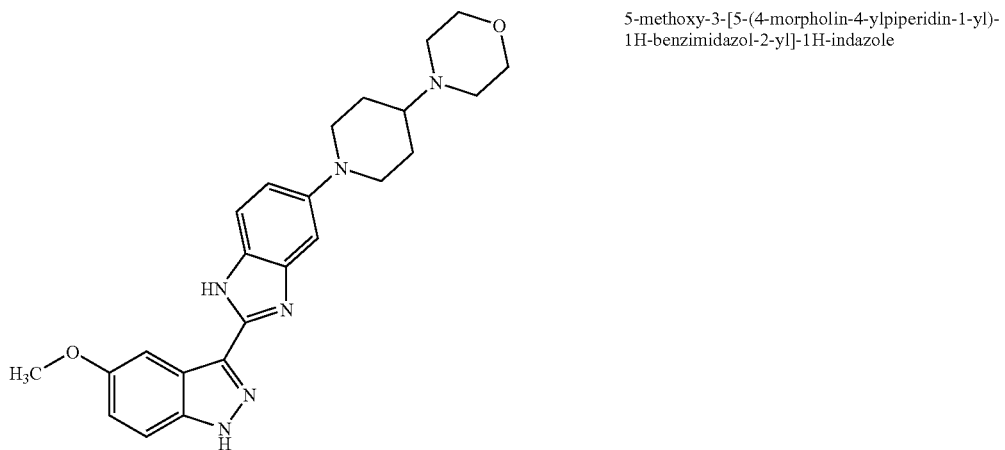 | 5-methoxy-3-[5-(4-morpholin-4-ylpiperidin-1-yl)-1H-benzimidazol-2-yl]-1H-indazole |
| 1291 | 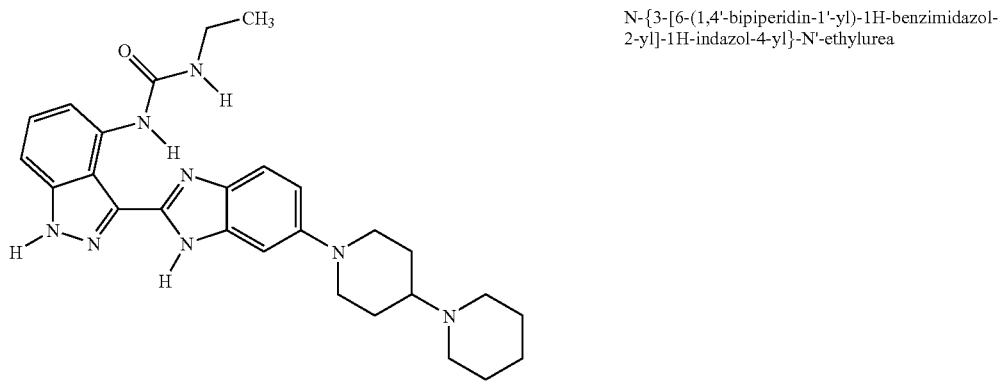 | N-{3-[6-(1,4'-bipiperidin-1'-yl)-1H-benzimidazol-2-yl]-1H-indazol-4-yl}-N'-ethylurea |
| 1292 | 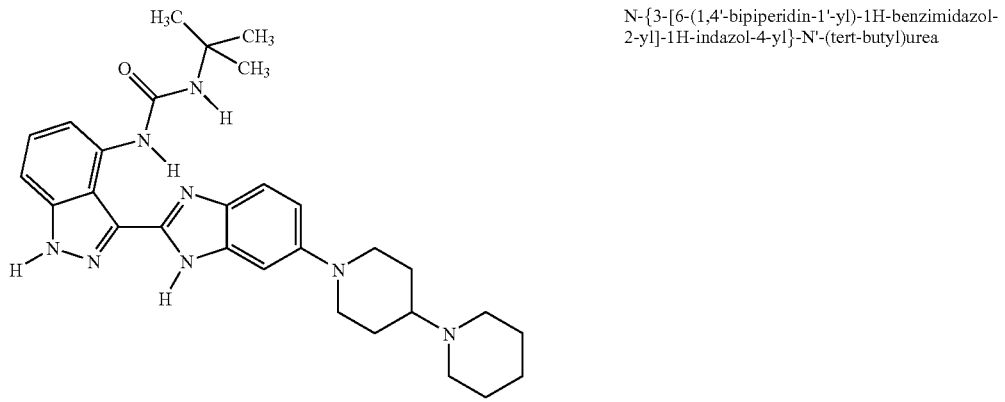 | N-{3-[6-(1,4'-bipiperidin-1'-yl)-1H-benzimidazol-2-yl]-1H-indazol-4-yl}-N'-(tert-butyl)urea |

-continued
| Example | STRUCTURE | Name |
|---|---|---|
| 1293 | 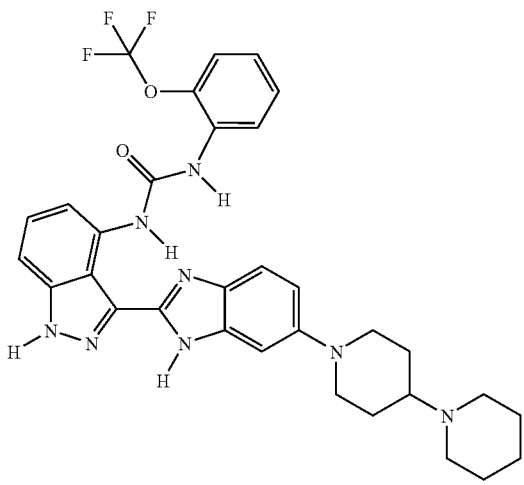 | N-{3-[6-(1,4'-bipiperidin-1'-yl)-1H-benzimidazol-2-yl]-1H-indazol-4-yl}-N'-[2-(trifluoromethoxy)phenyl]urea |
| 1294 | 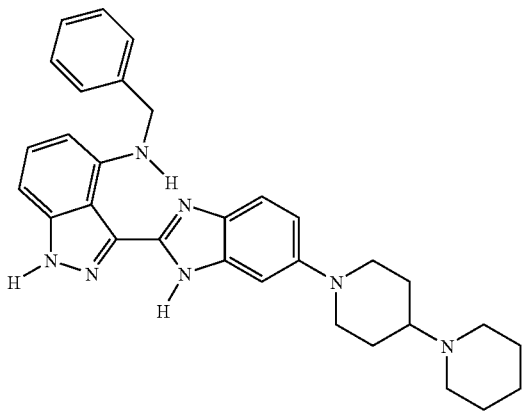 | N-benzyl-3-[6-(1,4-bipiperidin-1-yl)-1H-benzimidazol-2-yl]-1H-indazol-4-amine |
| 1295 | 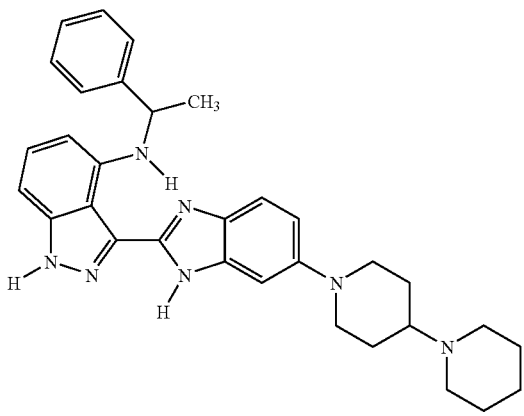 | 3-[6-(1,4'-bipiperidin-1'-yl)-1H-benzimidazol-2-yl]-N-(1-phenylethyl)-1H-indazol-4-amine |

-continued
| Example | STRUCTURE | Name |
|---|---|---|
| 1296 | 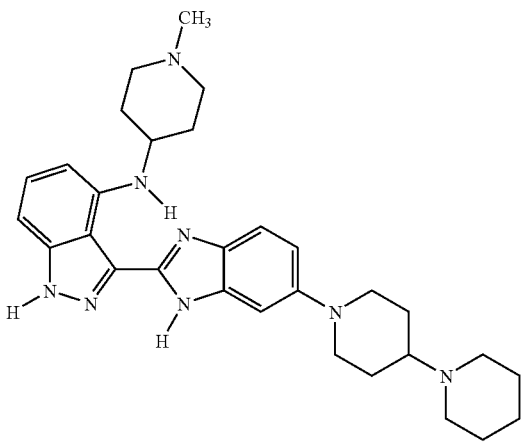 | 3-[6-(1,4'-bipiperidin-1'-yl)-1H-benzimidazol-2-yl]-N-(1-methylpiperidin-4-yl)-1H-indazol-4-amine |
| 1297 | 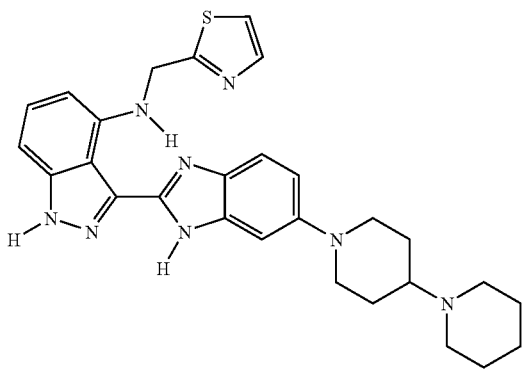 | 3-[6-(1,4'-bipiperidin-1'-yl)-1H-benzimidazol-2-yl]-N-(1,3-thiazol-2-ylmethyl)-1H-indazol-4-amine |
| 1298 | 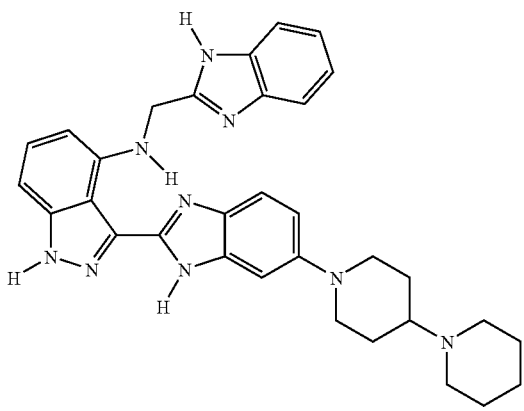 | N-(1H-benzimidazol-2-ylmethyl)-3-[6-(1,4'-bipiperidin-1'-yl)-1H-benzimidazol-2-yl]-1H-indazol-4-amine |

-continued
| Example | STRUCTURE | Name |
|---|---|---|
| 1299 | 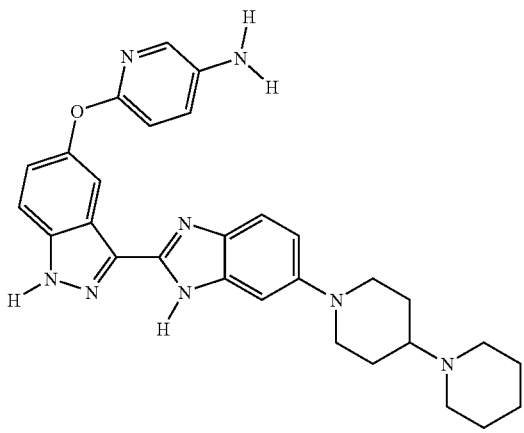 | 6-({3-[6-(1,4'-bipiperidin-1'-yl)-1H-benzimidazol-2-yl]-1H-indazol-5-yl}oxy)pyridin-3-amine |
| 1300 | 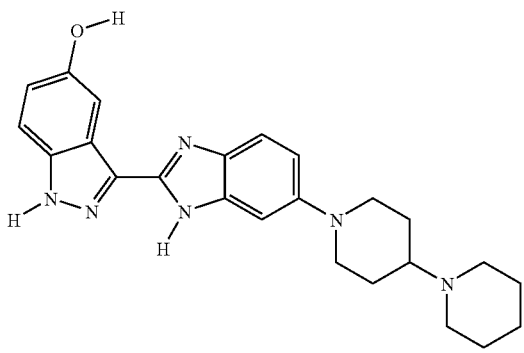 | 3-[6-(1,4'-bipiperidin-1'-yl)-1H-benzimidazol-2-yl]-1H-indazol-5-ol |
| 1301 | 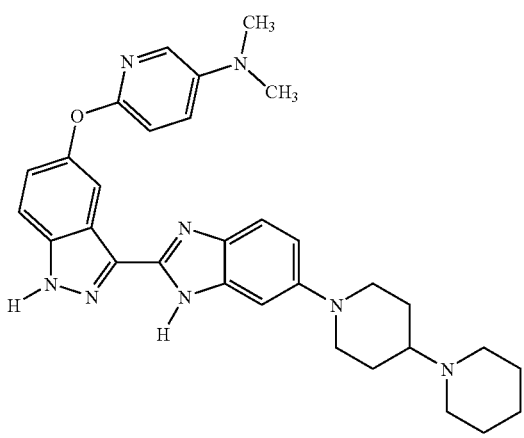 | 6-({3-[6-(1,4'-bipiperidin-1'-yl)-1H-benzimidazol-2-yl]-1H-indazol-5-yl}oxy)-N,N-dimethylpyridin-3-amine |

-continued
| Example | STRUCTURE | Name |
|---|---|---|
| 1302 | 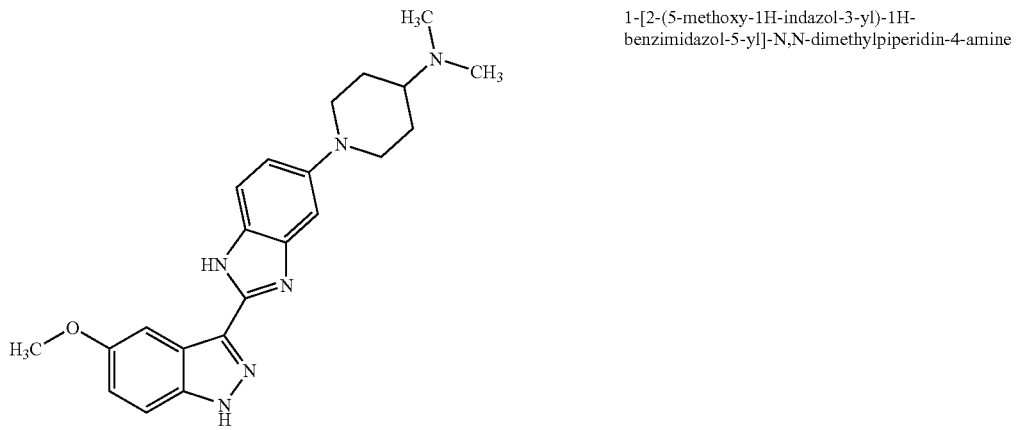 | 1-[2-(5-methoxy-1H-indazol-3-yl)-1H-benzimidazol-5-yl]-N,N-dimethylpiperidin-4-amine |
| 1303 | 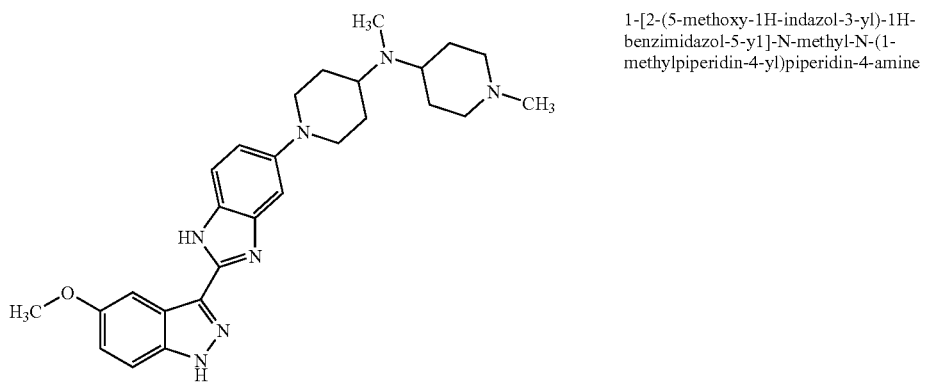 | 1-[2-(5-methoxy-1H-indazol-3-yl)-1H-benzimidazol-5-yl]-N-methyl-N-(1-methylpiperidin-4-yl)piperidin-4-amine |
| 1304 | 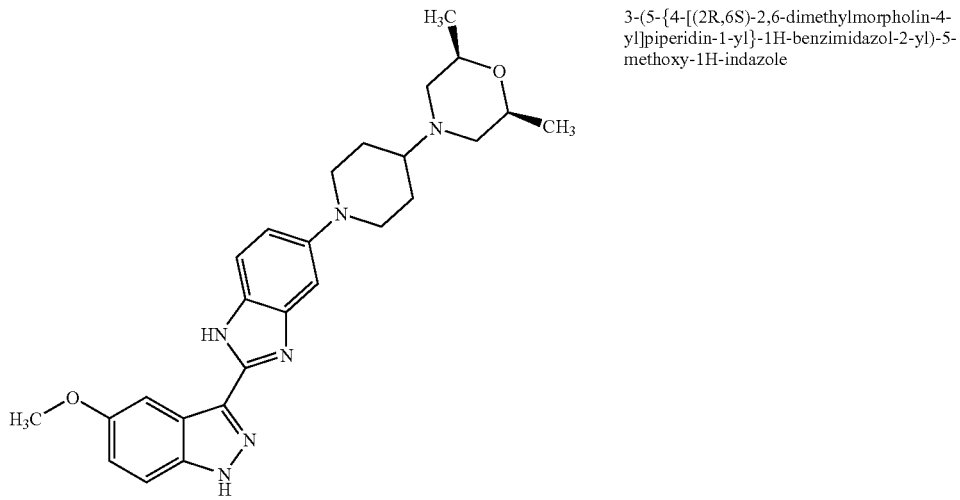 | 3-(5-{4-[(2R,6S)-2,6-dimethylmorpholin-4-yl]piperidin-1-yl}-1H-benzimidazol-2-yl)-5-methoxy-1H-indazole |

-continued
| Example | STRUCTURE | Name |
|---|---|---|
| 1305 | 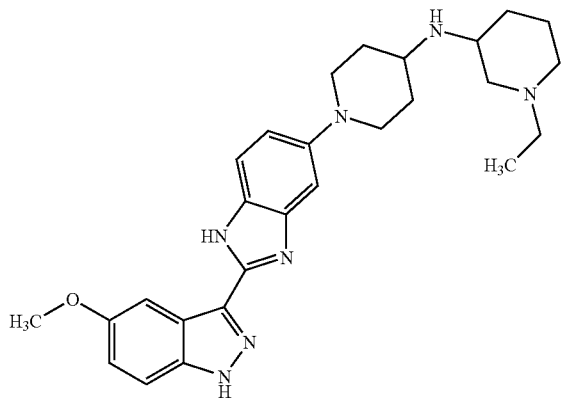 | 1-ethyl-N-{1-[2-(5-methoxy-1H-indazol-3-yl)-1H-benzimidazol-5-yl]piperidin-4-yl}piperidin-3-amine |
| 1306 | 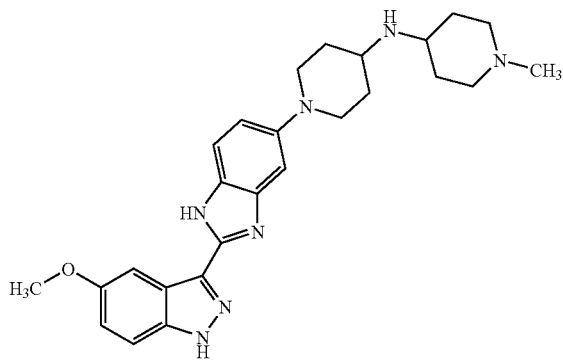 | 1-[2-(5-methoxy-1H-indazol-3-yl)-1H-benzimidazol-5-yl]-N-(1-methylpiperidin-4-yl)piperidin-4-amine |
| 1307 | 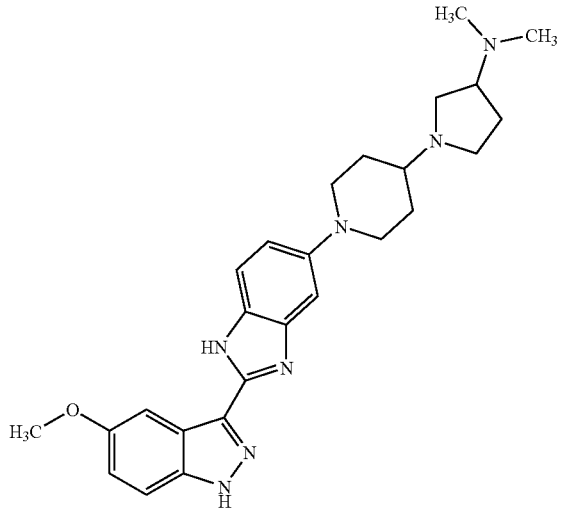 | 1-{1-[2-(5-methoxy-1H-indazol-3-yl)-1H-benzimidazol-5-yl]piperidin-4-yl}-N,N-dimethylpyrrolidin-3-amine |

| Example | STRUCTURE | Name |
|---|---|---|
| 1308 | 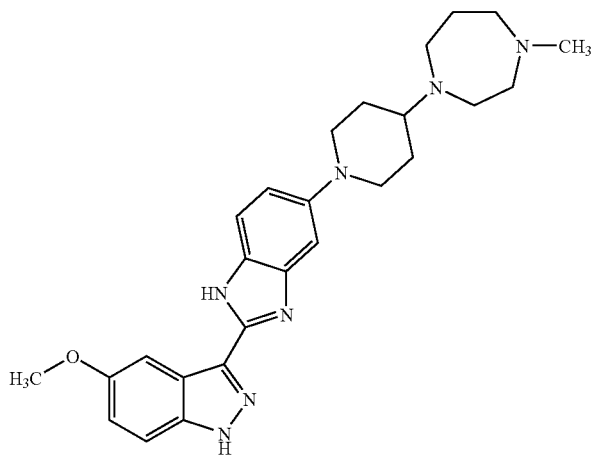 | 5-methoxy-3-{5-[4-(4-methyl-1,4-diazepan-1-yl)piperidin-1-yl]-1H-benzimidazol-2-yl}-1H-indazole |
| 1309 | 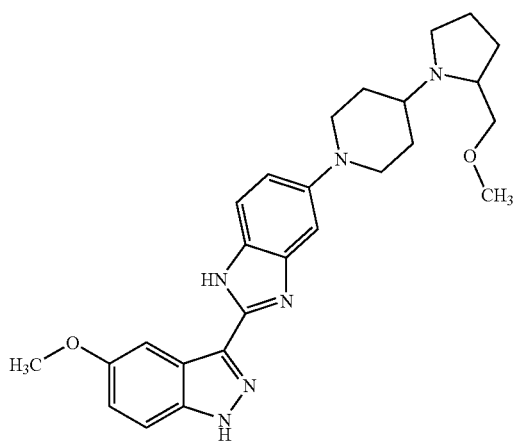 | 5-methoxy-3-(5-{4-[2-(methoxymethyl)pyrrolidin-1-yl]piperidin-1-yl}-1H-benzimidazol-2-yl)-1H-indazole |
| 1310 | 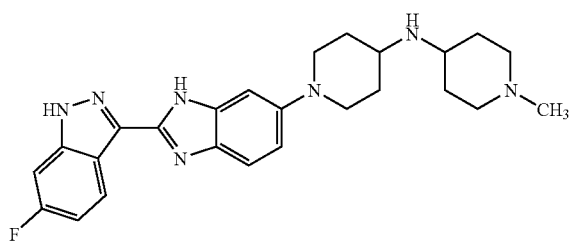 | 1-[2-(6-fluoro-1H-indazol-3-yl)-1H-benzimidazol-6-yl]-N-(1-methylpiperidin-4-yl)piperidin-4-amine |
| 1311 | 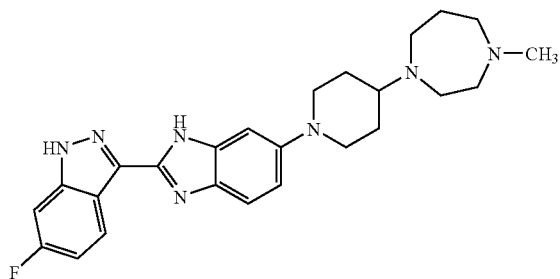 | 6-fluoro-3-{6-[4-(4-methyl-1,4-diazepan-1-yl)piperidin-1-yl]-1H-benzimidazol-2-yl}-1H-indazole |

| Example | STRUCTURE | Name |
|---|---|---|
| 1312 | 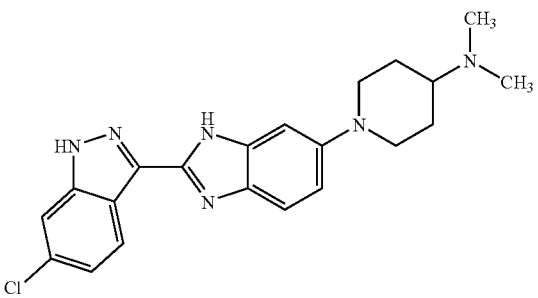 | 1-[2-(6-chloro-1H-indazol-3-yl)-1H-benzimidazol-6-yl]-N,N-dimethylpiperidin-4-amine |
| 1313 | 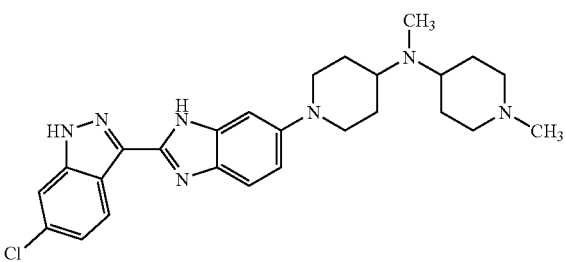 | 1-[2-(6-chloro-1H-indazol-3-yl)-1H-benzimidazol-6-yl]-N-methyl-N-(1-methylpiperidin-4-yl)piperidin-4-amine |
| 1314 | 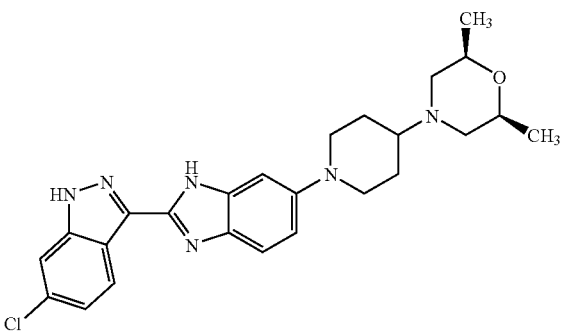 | 6-chloro-3-(6-{4-[(2R,6S)-2,6-dimethylmorpholin-4-yl]piperidin-1-yl}-1H-benzimidazol-2-yl)-1H-indazole |
| 1315 | 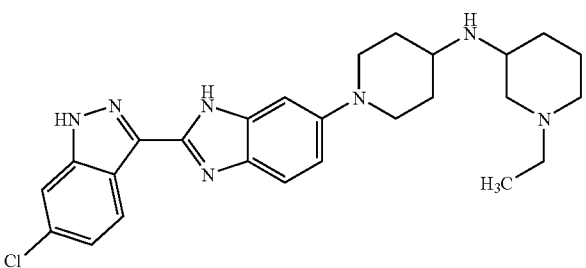 | N-{1-[2-(6-chloro-1H-indazol-3-yl)-1H-benzimidazol-6-yl]piperidin-4-yl}-1-ethylpiperidin-3-amine |
| 1316 | 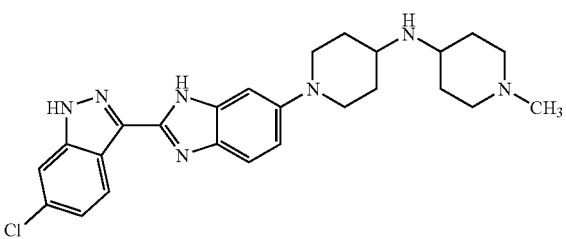 | 1-[2-(6-chloro-1H-indazol-3-yl)-1H-benzimidazol-6-yl]-N-(1-methylpiperidin-4-yl)piperidin-4-amine |

-continued

| Example | STRUCTURE | Name |
|---|---|---|
| 1317 | 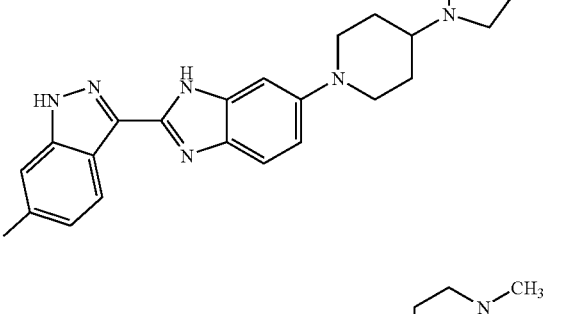 | 1-{1-[2-(6-chloro-1H-indazol-3-yl)-1H-benzimidazol-6-yl]piperidin-4-yl}-N,N-dimethylpyrrolidin-3-amine |
| 1318 | 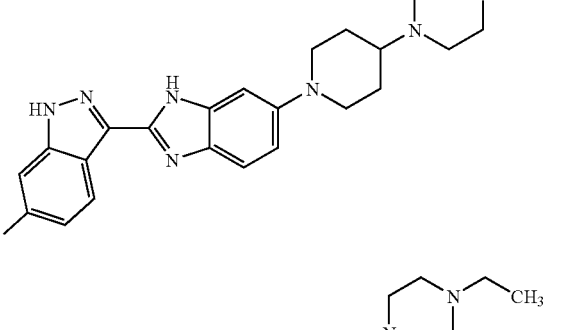 | 6-chloro-3-{6-[4-(4-methylpiperazin-1-yl)piperidin-1-yl]-1H-benzimidazol-2-yl}-1H-indazole |
| 1319 | 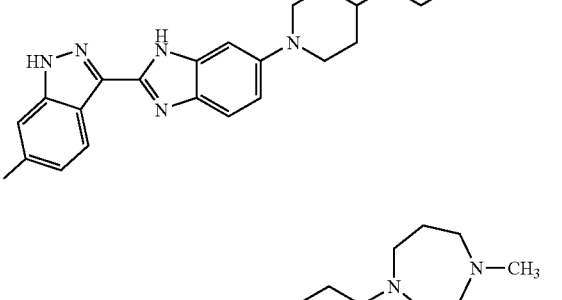 | 6-chloro-3-{6-[4-(4-ethylpiperazin-1-yl)piperidin-1-yl]-1H-benzimidazol-2-yl}-1H-indazole |
| 1320 | 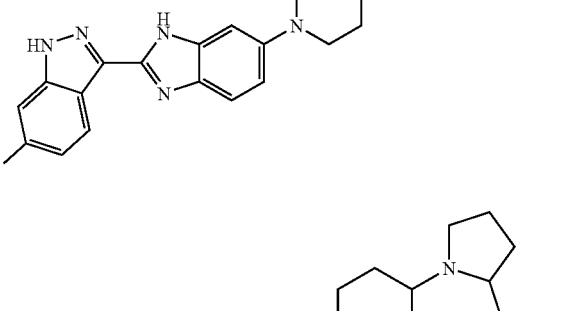 | 6-chloro-3-{6-[4-(4-methyl-1,4-diazepan-1-yl)piperidin-1-yl]-1H-benzimidazol-2-yl}-1H-indazole |
| 1321 | 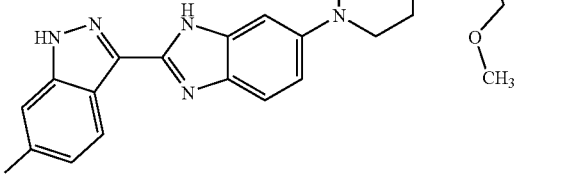 | 6-chloro-3-(6-{4-[2-(methoxymethyl)pyrrolidin-1-yl]piperidin-1-yl}-1H-benzimidazol-2-yl)-1H-indazole |

-continued

| Example | STRUCTURE | Name |
|---------|-----------|------|
| 1322 | 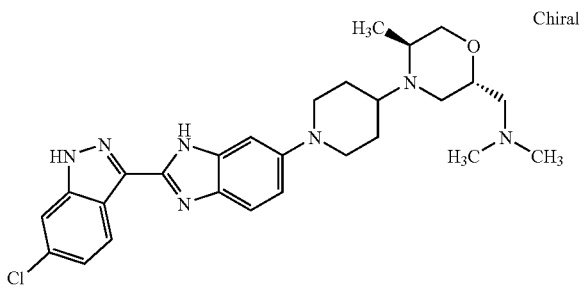 Chiral | N-[((2R,5S)-4-{1-[2-(6-chloro-1H-indazol-3-yl)-1H-bezimidazol-6-yl]piperidin-4-yl}-5-methylmorpholin-2-yl)methyl]-N,N-dimethylamine |
| 1323 | 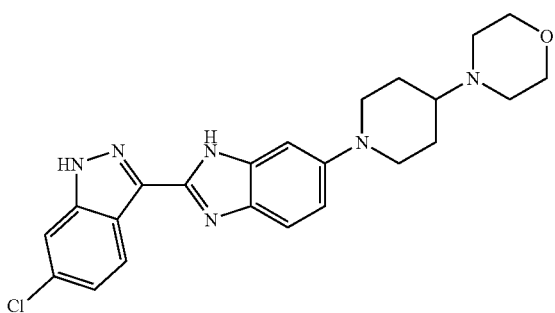 | 6-chloro-3-[6-(4-morpholin-4-ylpiperidin-1-yl)-1H-benzimidazol-2-yl]-1H-indazole |
| 1324 | 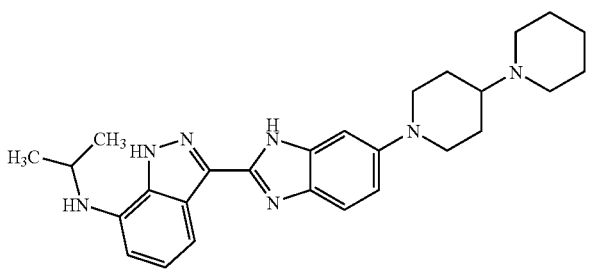 | 3-[6-(1,4'-bipiperidin-1'-yl)-1H-benzimidazol-2-yl]-N-isopropyl-1H-indazol-7-amine |
| 1325 | 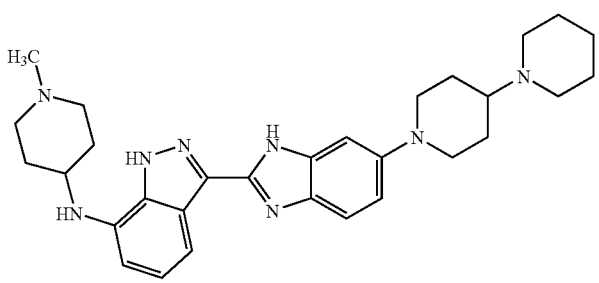 | 3-[6-(1,4'-bipiperidin-1'-yl)-1H-benzimidazol-2-yl]-N-(1-methylpiperidin-4-yl)-1H-indazol-7-amine |
| 1326 | 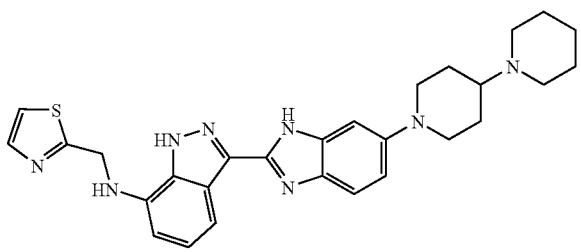 | 3-[6-(1,4'-bipiperidin-1'-yl)-1H-benzimidazol-2-yl]-N-(1,3-thiazol-2-ylmethyl)-1H-indazol-7-amine |

-continued

| Example | STRUCTURE | Name |
|---|---|---|
| 1327 | 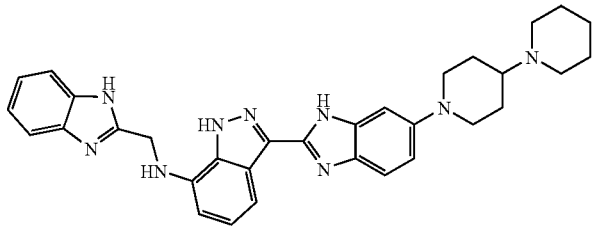 | N-(1H-benzimidazol-2-ylmethyl)-3-[6-(1,4'-bipiperidin-1'-yl)-1H-benzimidazol-2-yl]-1H-indazol-7-amine |
| 1328 | 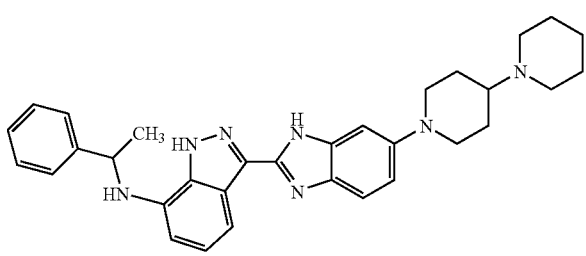 | 3-[6-(1,4'-bipiperidin-1'-yl)-1H-benzimidazol-2-yl]-N-(1-phenylethyl)-1H-indazol-7-amine |
| 1329 | 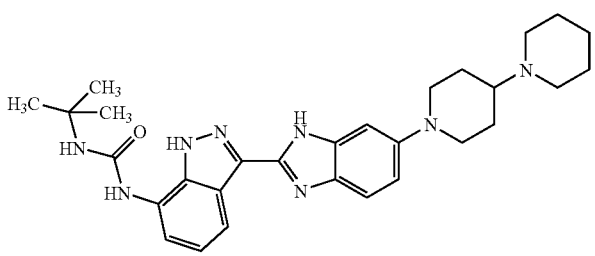 | N-{3-[6-(1,4-bipiperidin-1-yl)-1H-benzimidazol-2-yl]-1H-indazol-7-yl}-N'-(tert-butyl)urea |
| 1330 | 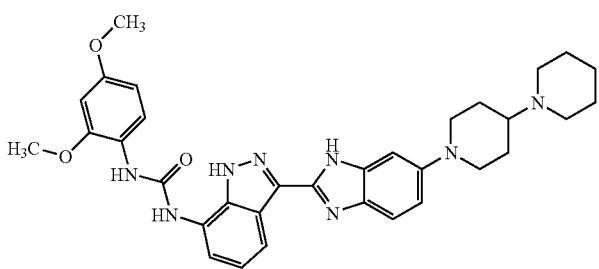 | N-{3-[6-(1,4'-bipiperidin-1'-yl)-1H-benzimidazol-2-yl]-1H-indazol-7-yl}-N'-(2,4-dimethoxyphenyl)urea |
| 1331 | 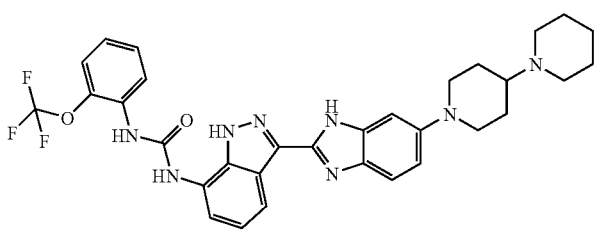 | N-{3-[6-(1,4'-bipiperidin-1'-yl)-1H-benzimidazol-2-yl]-1H-indazol-7-yl}-N'-[2-(trifluoromethoxy)phenyl]urea |

-continued
| Example | STRUCTURE | Name |
|---------|-----------|------|
| 1332 | 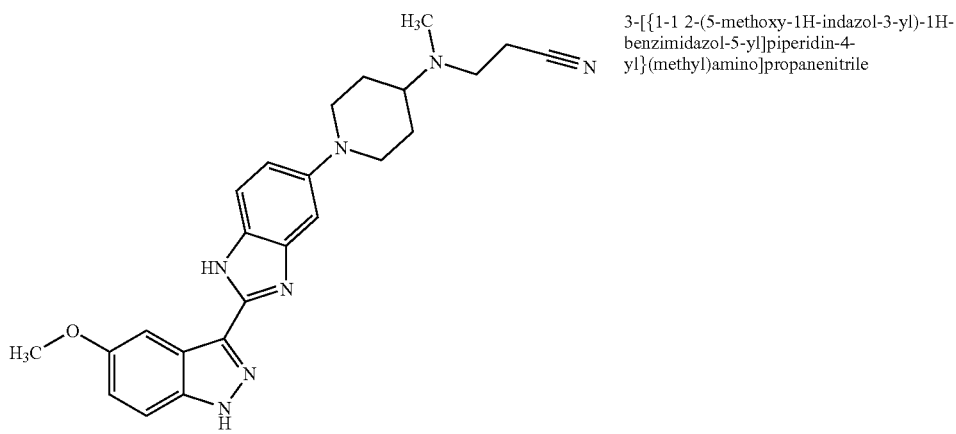 | 3-[{1-1 2-(5-methoxy-1H-indazol-3-yl)-1H-benzimidazol-5-yl]piperidin-4-yl}(methyl)amino]propanenitrile |
| 1333 | 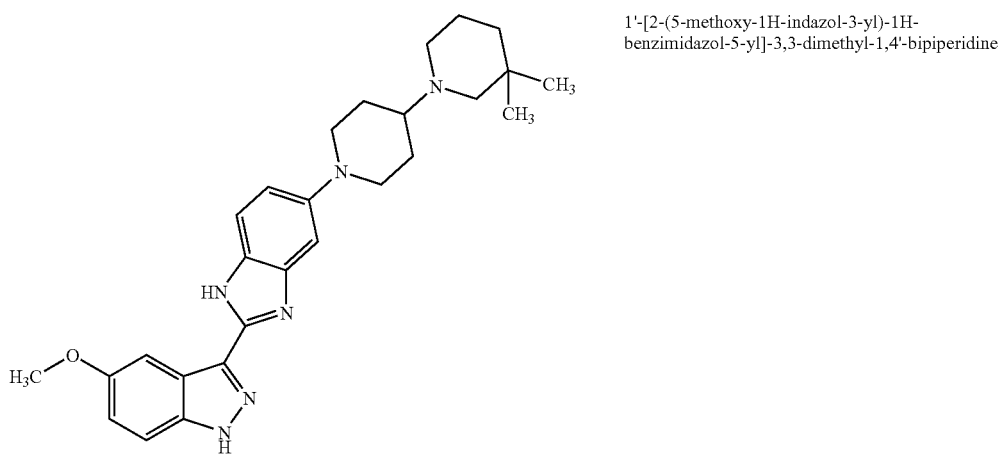 | 1'-[2-(5-methoxy-1H-indazol-3-yl)-1H-benzimidazol-5-yl]-3,3-dimethyl-1,4'-bipiperidine |
| 1334 | 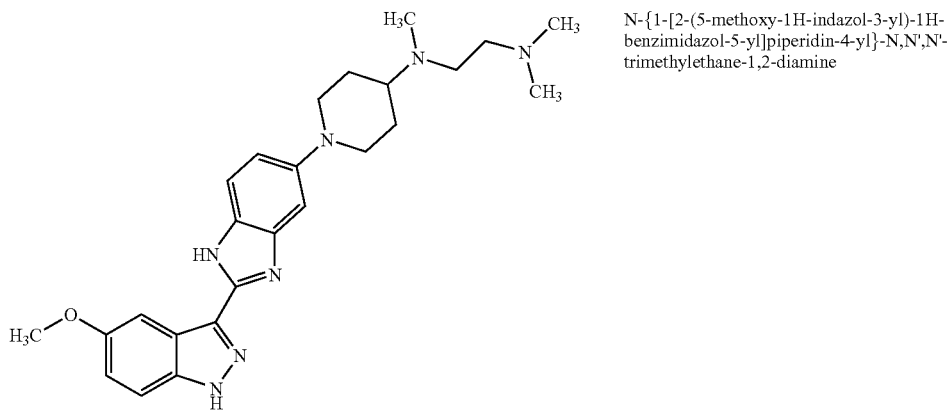 | N-{1-[2-(5-methoxy-1H-indazol-3-yl)-1H-benzimidazol-5-yl]piperidin-4-yl}-N,N',N'-trimethylethane-1,2-diamine |

-continued
| Example | STRUCTURE | Name |
|---|---|---|
| 1335 | 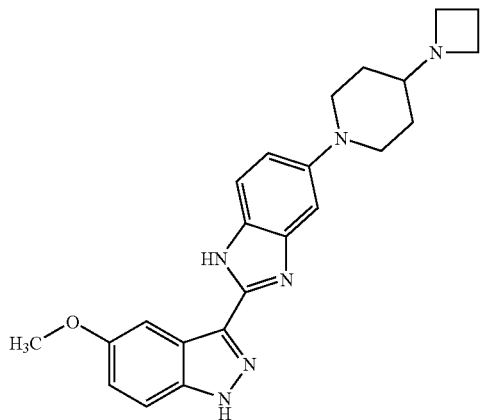 | 3-[5-(4-azetidin-1-ylpiperidin-1-yl)-1H-benzimidazol-2-yl]-5-methoxy-1H-indazole |
| 1336 | 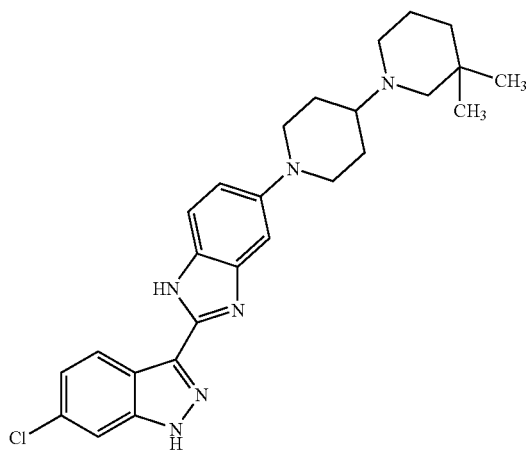 | 1'-[2-(6-chloro-1H-indazol-3-yl)-1H-benzimidazol-5-yl]-3,3-dimethyl-1,4'-bipiperidine |
| 1337 | 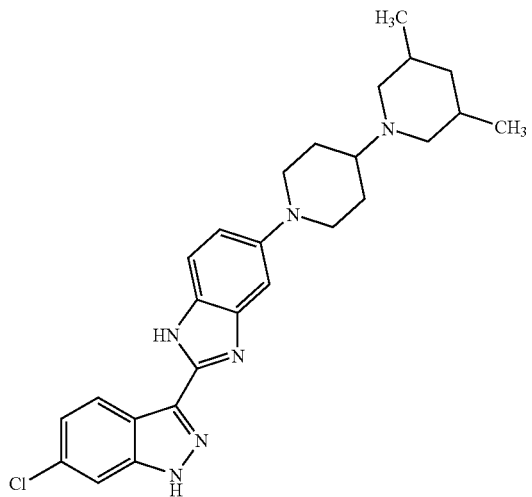 | 1'-12-(6-chloro-1H-indazol-3-yl)-1H-benzimidazol-5-yl]-3,5-dimethyl-1,4'-bipiperidine |

-continued
| Example | STRUCTURE | Name |
|---|---|---|
| 1338 | 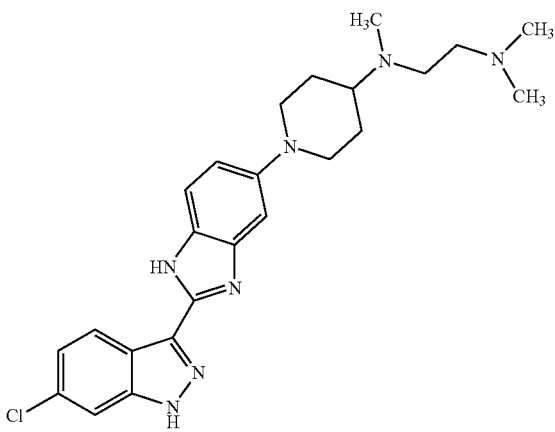 | N-{1-[2-(6-chloro-1H-indazol-3-yl)-1H-benzimidazol-5-yl]piperidin-4-yl}-N,N',N'-trimethylethane-1,2-diamine |
| 1339 | 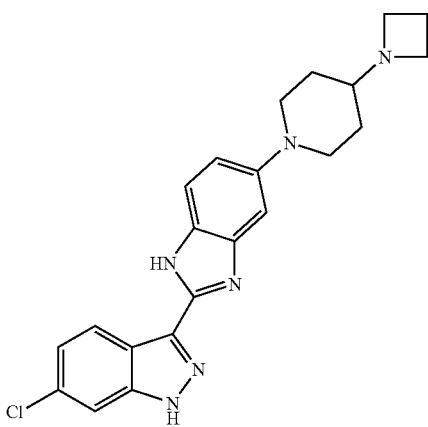 | 3-[5-(4-azetidin-1-ylpiperidin-1-yl)-1H-benzimidazol-2-yl]-6-chloro-1H-indazole |
| 1340 | 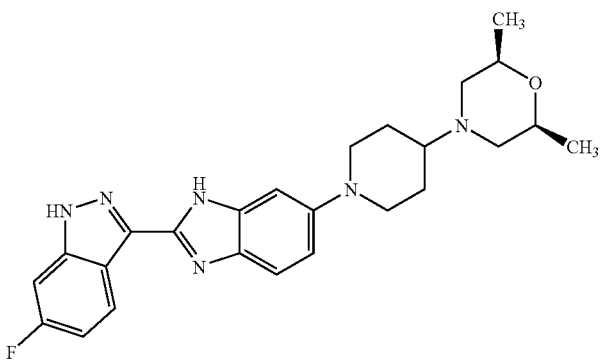 | 3-(6-{4-[(2R,6S)-2,6-dimethylmorpholin-4-yl]piperidin-1-yl}-1H-benzimidazol-2-yl)-6-fluoro-1H-indazole |
| 1341 | 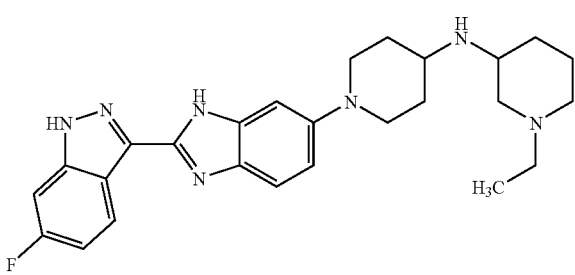 | 1-ethyl-N-{1-[2-(6-fluoro-1H-indazol-3-yl)-1H-benzimidazol-6-yl]piperidin-4-yl}piperidin-3-amine |

-continued
| Example | STRUCTURE | Name |
|---------|-----------|------|
| 1342 | 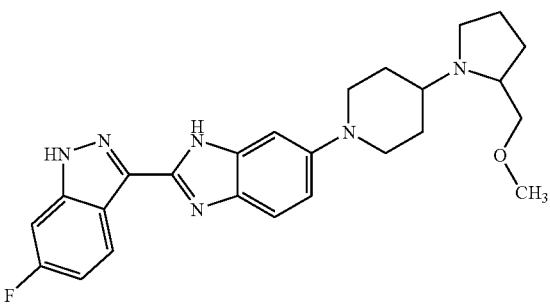 | 6-fluoro-3-(6-{4-[2-(methoxymethyl)pyrrolidin-1-yl]piperidin-1-yl}-1H-benzimidazol-2-yl)-1H-indazole |
| 1343 | 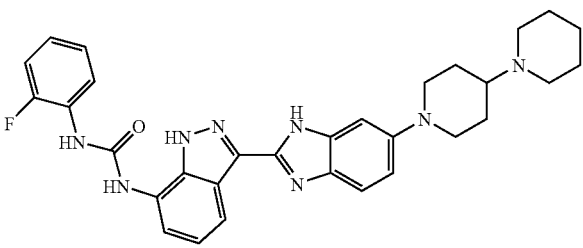 | N-{3-[6-{1,4'-bipiperidin-1'-yl}-1H-benzimidazol-2-yl]-1H-indazol-7-yl}-N'-(2-fluorophenyl)urea |
| 1344 | 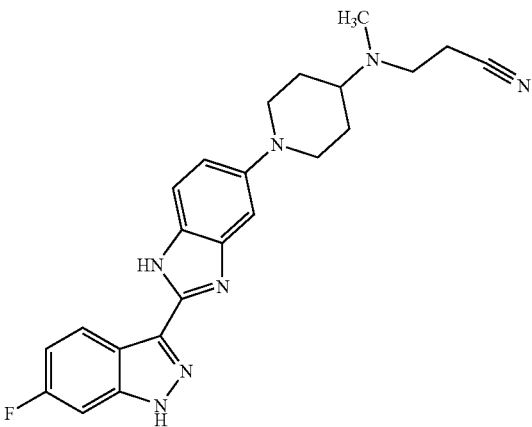 | 3-[{1-[2-(6-fluoro-1H-indazol-3-yl)-1H-benzimidazol-5-yl]piperidin-4-yl}(methyl)amino]propanenitrile |
| 1345 | 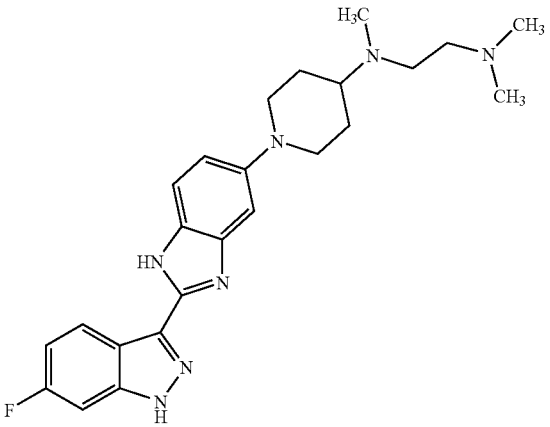 | N-{1-[2-(6-fluoro-1H-indazol-3-yl)-1H-benzimidazol-5-yl]piperidin-4-yl}-N,N',N'-trimethylethane-1,2-diamine |

-continued
| Example | STRUCTURE | Name |
|---|---|---|
| 1346 | 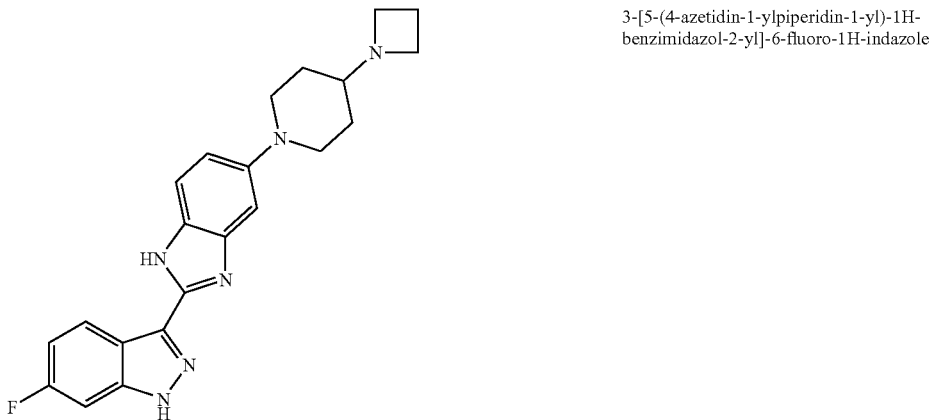 | 3-[5-(4-azetidin-1-ylpiperidin-1-yl)-1H-benzimidazol-2-yl]-6-fluoro-1H-indazole |
| 1347 | 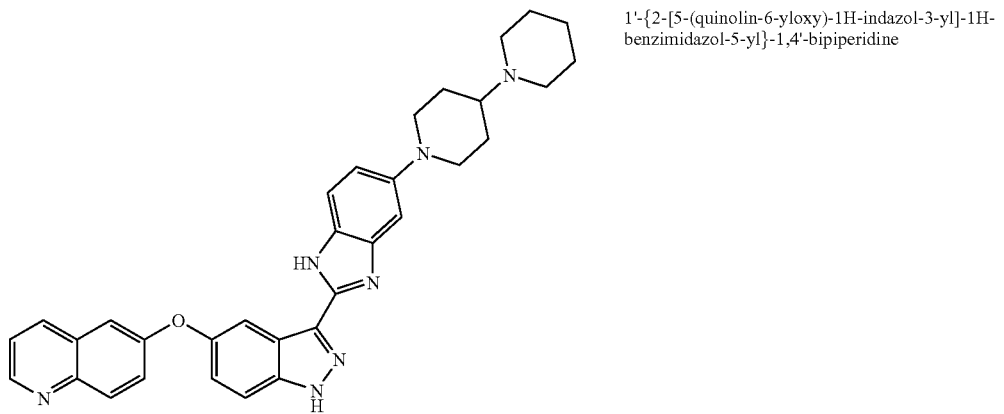 | 1'-{2-[5-(quinolin-6-yloxy)-1H-indazol-3-yl]-1H-benzimidazol-5-yl}-1,4'-bipiperidine |
| 1348 | 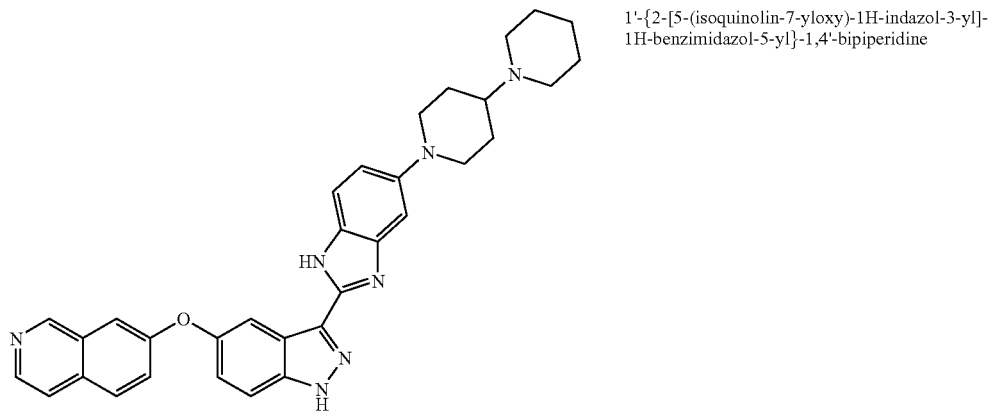 | 1'-{2-[5-(isoquinolin-7-yloxy)-1H-indazol-3-yl]-1H-benzimidazol-5-yl}-1,4'-bipiperidine |

-continued
| Example | STRUCTURE | Name |
|---|---|---|
| 1349 | 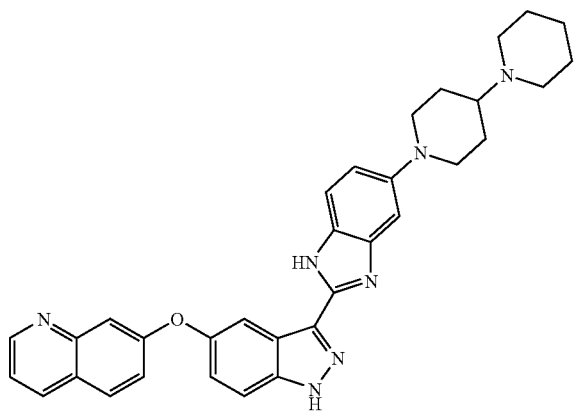 | 1'-{2-[5-(quinolin-7-yloxy)-1H-indazol-3-yl]-1H-benzimidazol-5-yl}-1,4'-bipiperidine |
| 1350 | 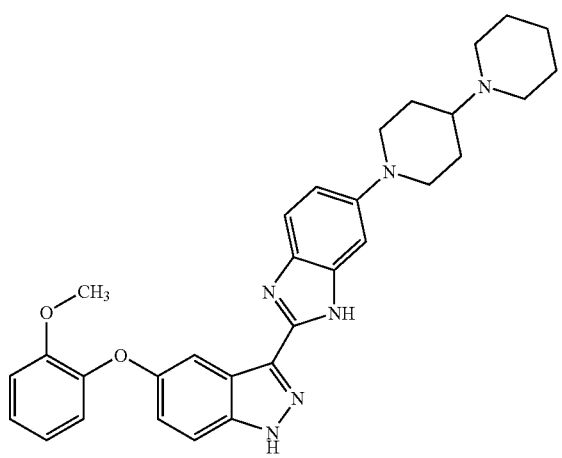 | 1-{2-[5-(2-methoxyphenoxy)-1H-indazol-3-yl]-1H-benzimidazol-6-yl}-1,4'-bipiperidine |
| 1351 | 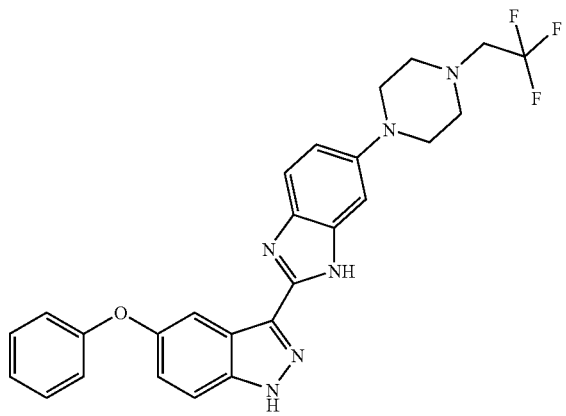 | 5-phenoxy-3-{6-[4-(2,2,2-trifluoroethyl)piperazin-1-yl]-1H-benzimidazol-2-yl}-1H-indazole |

| Example | STRUCTURE | Name |
|---|---|---|
| 1352 | 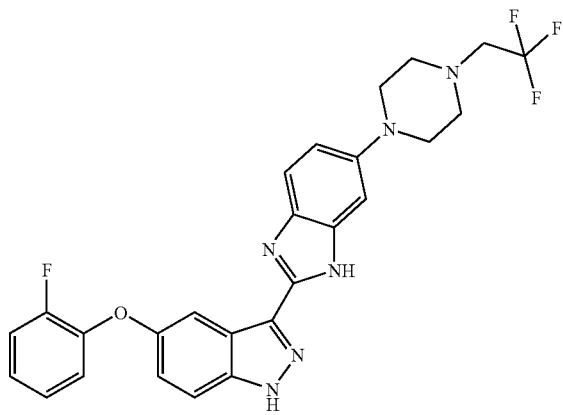 | 5-(2-fluorophenoxy)-3-{6-[4-(2,2,2-trifluoroethyl)piperazin-1-yl]-1H-benzimidazol-2-yl}-1H-indazole |
| 1353 | 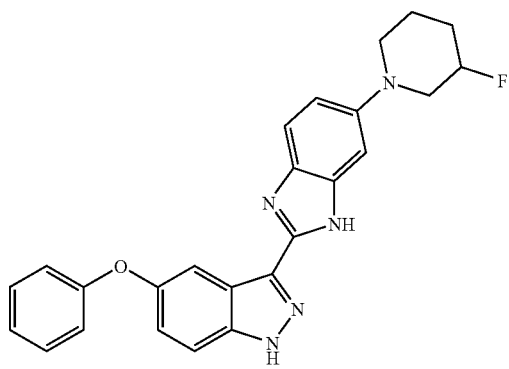 | 3-[6-(3-fluoropiperidin-1-yl)-1H-benzimidazol-2-yl]-5-phenoxy-1H-indazole |
| 1354 | 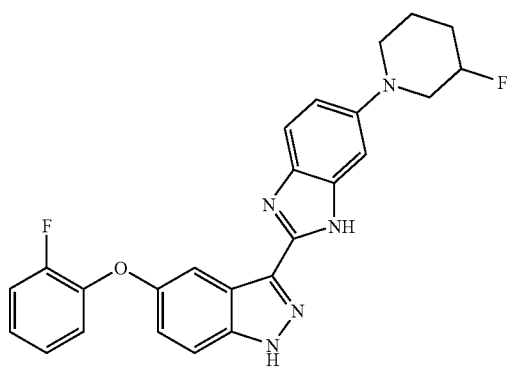 | 5-(2-fluorophenoxy)-3-[6-(3-fluoropiperidin-1-yl)-1H-benzimidazol-2-yl]-1H-indazole |
| 1355 | 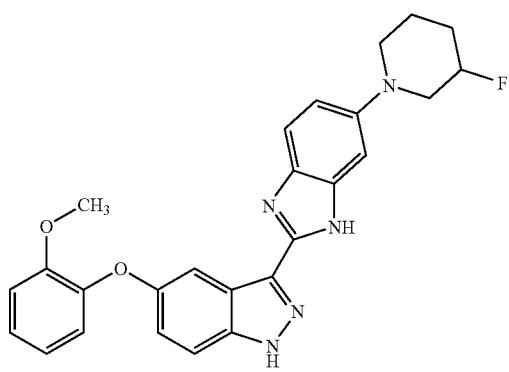 | 3-[6-(3-fluoropiperidin-1-yl)-1H-benzimidazol-2-yl]-5-(2-methoxyphenoxy)-1H-indazole |

-continued
| Example | STRUCTURE | Name |
|---|---|---|
| 1356 | 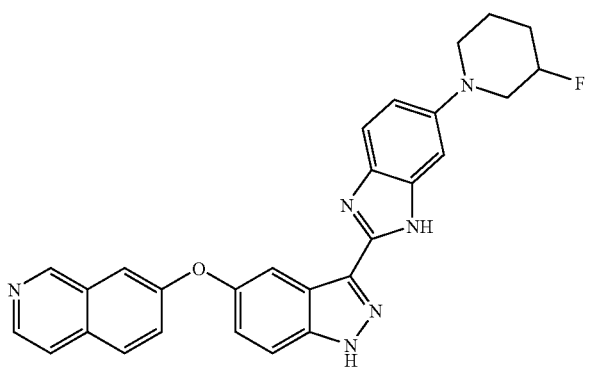 | 7-({3-[6-(3-fluoropiperidin-1-yl)-1H-benzimidazol-2-yl]-1H-indazol-5-yl}oxy)isoquinoline |
| 1357 | 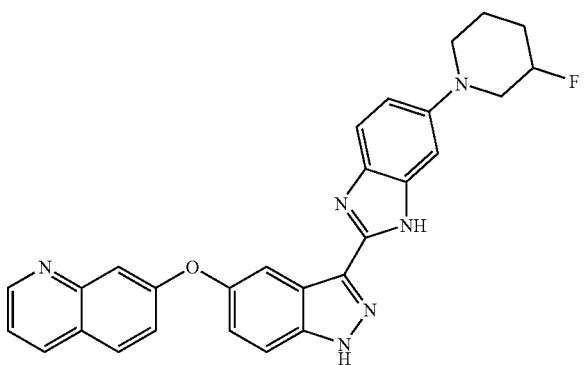 | 7-({3-[6-(3-fluoropiperidin-1-yl)-1H-benzimidazol-2-yl]-1H-indazol-5-yl}oxy)quinoline |
| 1358 | 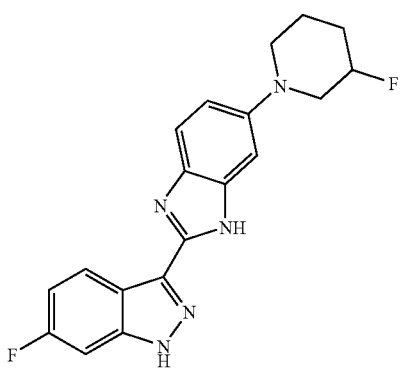 | 6-fluoro-3-[6-(3-fluoropiperidin-1-yl)-1H-benzimidazol-2-yl]-1H-indazole |
| 1359 | 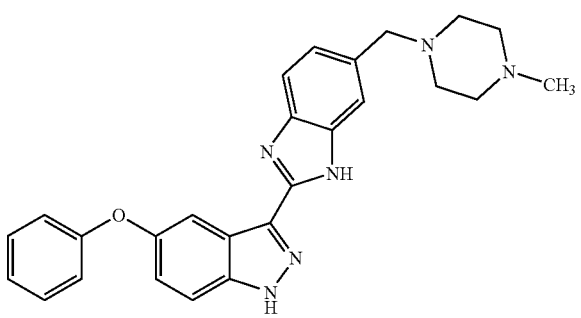 | 3-{6-[(4-methylpiperazin-1-yl)methyl]-1H-benzimidazol-2-yl}-5-phenoxy-1H-indazole |

-continued

| Example | STRUCTURE | Name |
|---|---|---|
| 1360 | 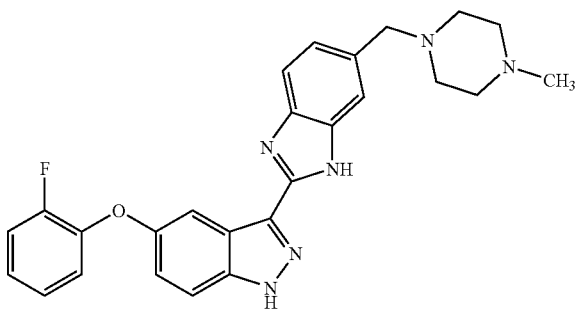 | 5-(2-fluorophenoxy)-3-{6-[(4-methylpiperazin-1-yl)methyl]-1H-benzimidazol-2-yl}-1H-indazole |
| 1361 | 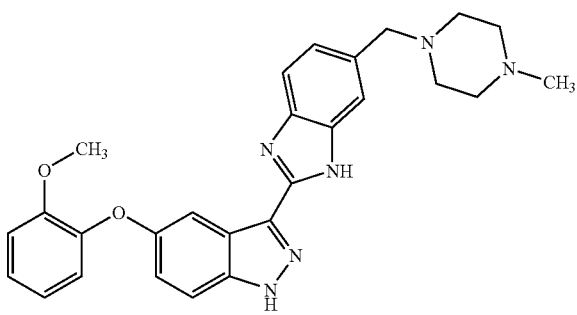 | 5-(2-methoxyphenoxy)-3-{6-[(4-methylpiperazin-1-yl)methyl]-1H-benzimidazol-2-yl}-1H-indazole |
| 1362 | 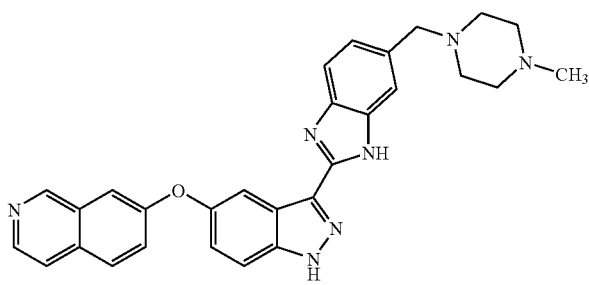 | 7-[(3-{6-[(4-methylpiperazin-1-yl)methyl]-1H-benzimidazol-2-yl}-1H-indazol-5-yl)oxy]isoquinoline |
| 1363 | 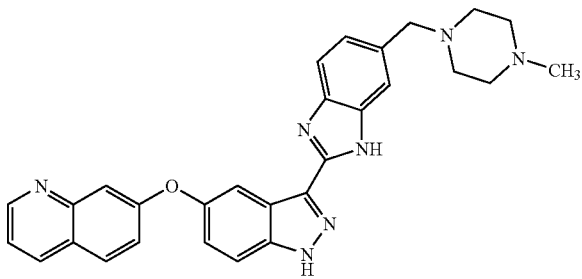 | 7-[(3-{6-[(4-methylpiperazin-1-yl)methyl]-1H-benzimidazol-2-yl}-1H-indazol-5-yl)oxy]quinoline |
| 1364 | 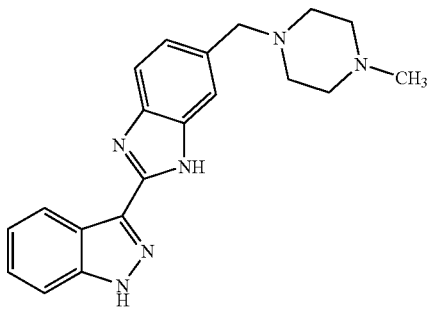 | 3-{6-[(4-methylpiperazin-1-yl)methyl]-1H-benzimidazol-2-yl}-1H-indazole |

-continued

| Example | STRUCTURE | Name |
|---|---|---|
| 1365 | 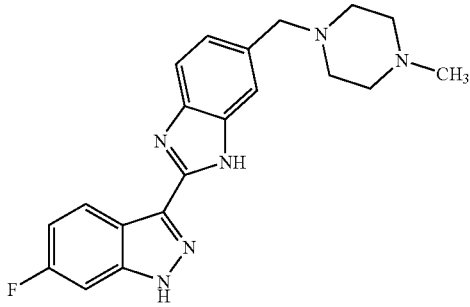 | 6-fluoro-3-{6-[(4-methylpiperazin-1-yl)methyl]-1H-benzimidazol-2-yl}-1H-indazole |
| 1366 | 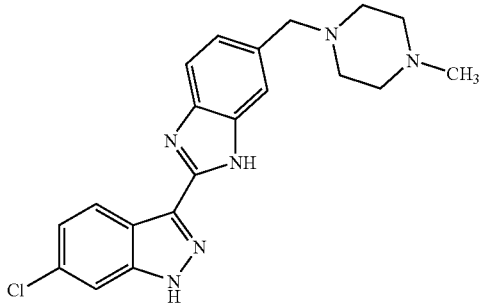 | 6-chloro-3-{6-[(4-methylpiperazin-1-yl)methyl]-1H-benzimidazol-2-yl}-1H-indazole |
| 1367 | 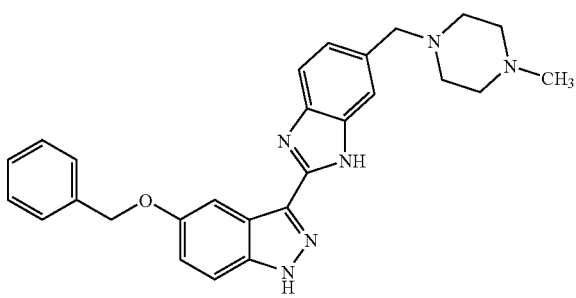 | 5-(benzyloxy)-3-{6-[(4-methylpiperazin-1-yl)methyl]-1H-benzimidazol-2-yl}-1H-indazole |
| 1368 | 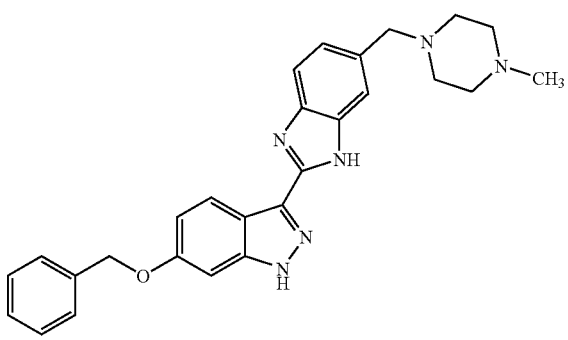 | 6-(benzyloxy)-3-{6-[(4-methylpiperazin-1-yl)methyl]-1H-benzimidazol-2-yl}-1H-indazole |
| 1369 | 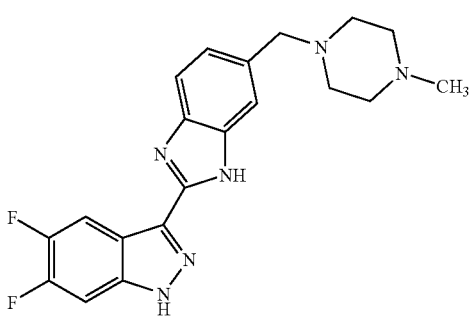 | 5,6-difluoro-3-{6-[(4-methylpiperazin-1-yl)methyl]-1H-benzimidazol-2-yl}-1H-indazole |

-continued

| Example | STRUCTURE | Name |
|---|---|---|
| 1370 | 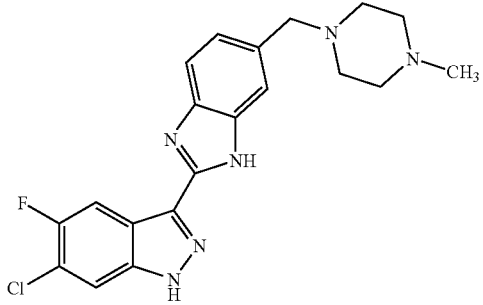 | 6-chloro-5-fluoro-3-{6-[(4-methylpiperazin-1-yl)methyl]-1H-benzimidazol-2-yl}-1H-indazole |
| 1371 | 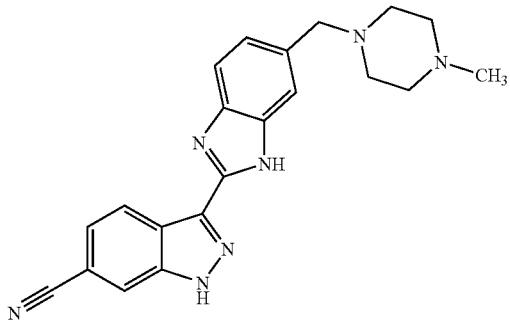 | 3-{6-[(4-methylpiperazin-1-yl)methyl]-1H-benzimidazol-2-yl}-1H-indazole-6-carbonitrile |
| 1372 | 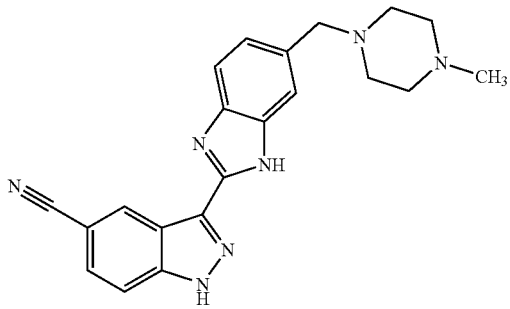 | 3-{6-[(4-methylpiperazin-1-yl)methyl]-1H-benzimidazol-2-yl}-1H-indazole-5-carbonitrile |
| 1373 | 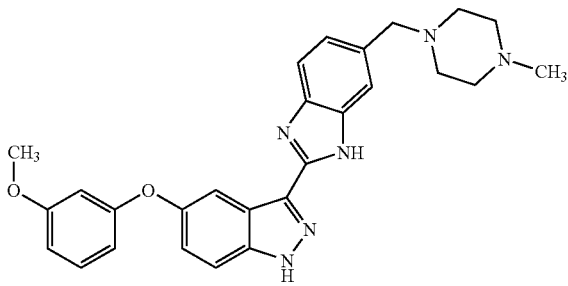 | 5-(3-methoxyphenoxy)-3-{6-[(4-methylpiperazin-1-yl)methyl]-1H-benzimidazol-2-yl}-1H-indazole |
| 1374 | 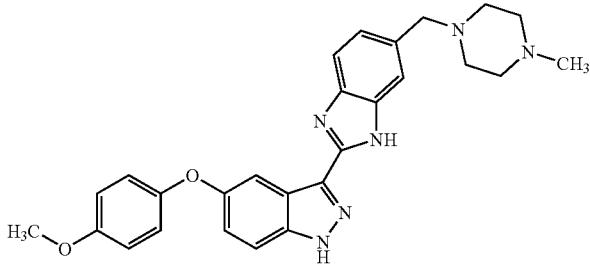 | 5-(4-methoxyphenoxy)-3-{6-[(4-methylpiperazin-1-yl)methyl]-1H-benzimidazol-2-yl}-1H-indazole |

-continued
| Example | STRUCTURE | Name |
|---|---|---|
| 1375 | 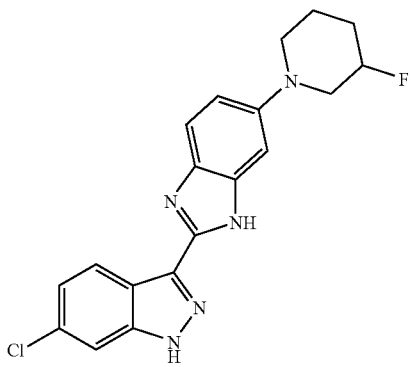 | 6-chloro-3-[6-(3-fluoropiperidin-1-yl)-1H-benzimidazol-2-yl]-1H-indazole |
| 1376 | 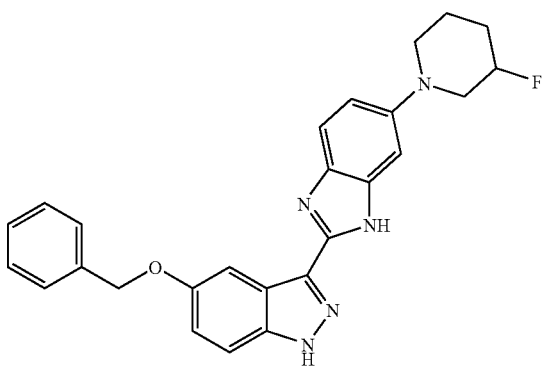 | 5-(benzyloxy)-3-[6-(3-fluoropiperidin-1-yl)-1H-benzimidazol-2-yl]-1H-indazole |
| 1377 | 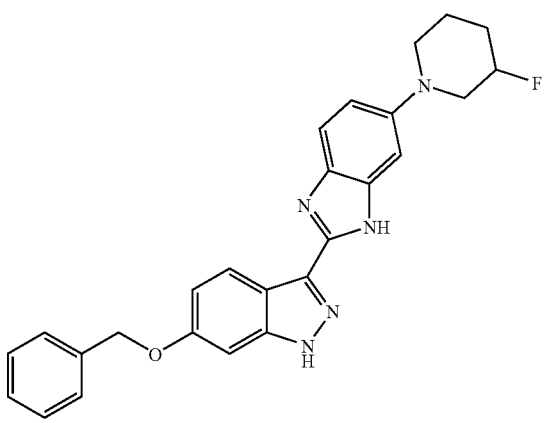 | 6-(benzyloxy)-3-[6-(3-fluoropiperidin-1-yl)-1H-benzimidazol-2-yl]-1H-indazole |
| 1378 | 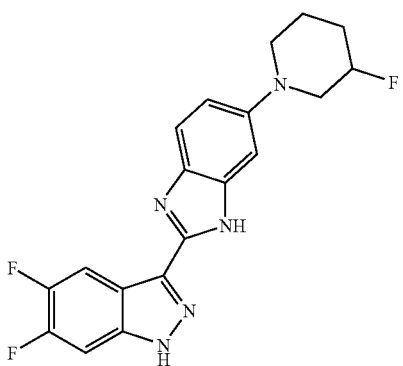 | 5,6-difluoro-3-[6-(3-fluoropiperidin-1-yl)-1H-benzimidazol-2-yl]-1H-indazole |

-continued
| Example | STRUCTURE | Name |
|---|---|---|
| 1379 | 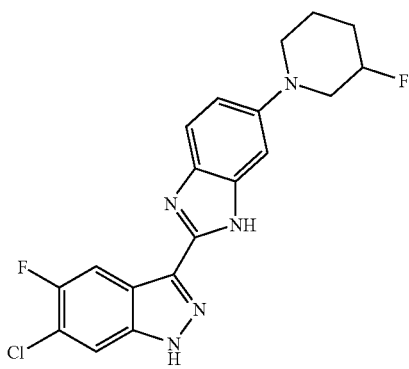 | 6-chloro-5-fluoro-3-[6-(3-fluoropiperidin-1-yl)-1H-benzimidazol-2-yl]-1H-indazole |
| 1380 | 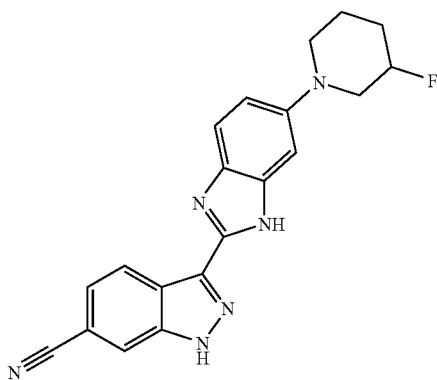 | 3-[6-(3-fluoropiperidin-1-yl)-1H-benzimidazol-2-yl]-1H-indazole-6-carbonitrile |
| 1381 | 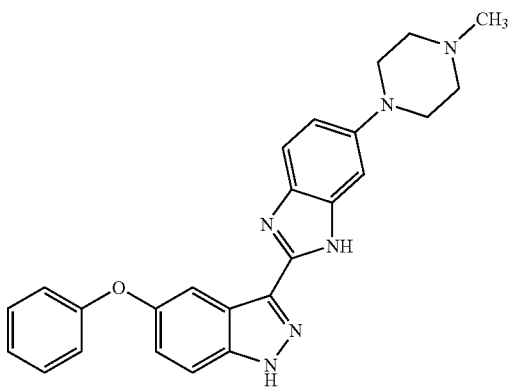 | 3-[6-(4-methylpiperazin-1-yl)-1H-benzimidazol-2-yl]-5-phenoxy-1H-indazole |
| 1382 | 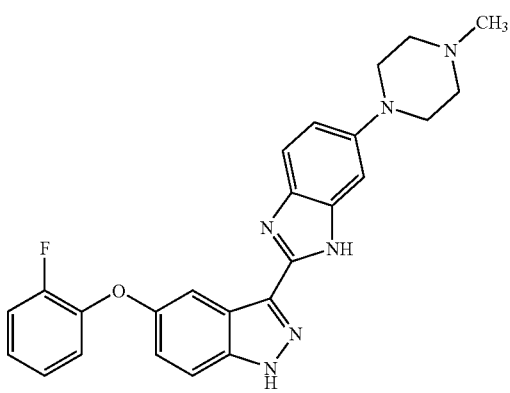 | 5-(2-fluorophenoxy)-3-[6-(4-methylpiperazin-1-yl)-1H-benzimidazol-2-yl]-1H-indazole |

-continued
| Example | STRUCTURE | Name |
|---|---|---|
| 1383 | 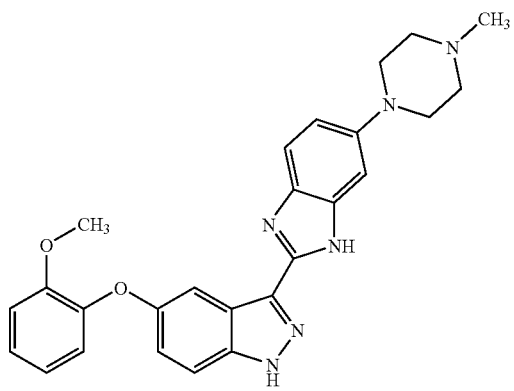 | 5-(2-methoxyphenoxy)-3-[6-(4-methylpiperazin-1-yl)-1H-benzimidazol-2-yl]-1H-indazole |
| 1384 | 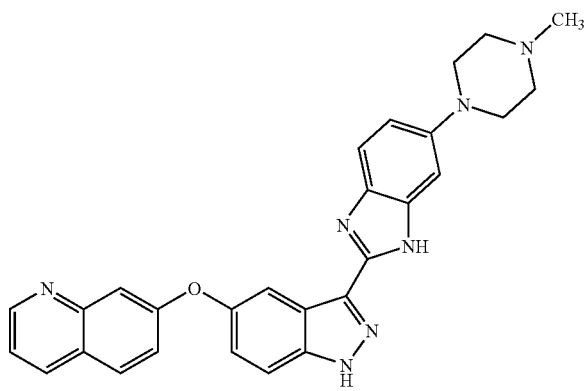 | 7-({3-[6-(4-methylpiperazin-1-yl)-1H-benzimidazol-2-yl]-1H-indazol-5-yl}oxy)quinoline |
| 1385 | 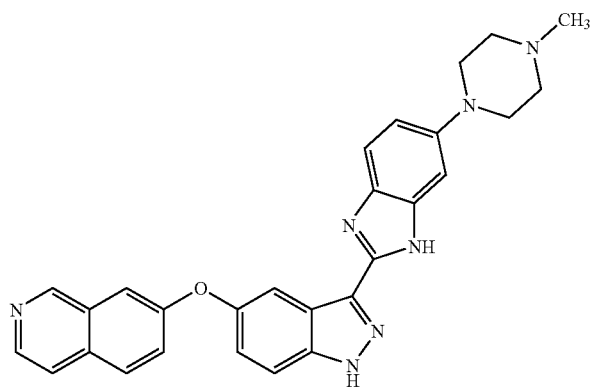 | 7-({3-{6-(4-methylpiperazin-1-yl)-1H-benzimidazol-2-yl]-1H-indazol-5-yl}oxy)isoquinoline |
| 1386 | 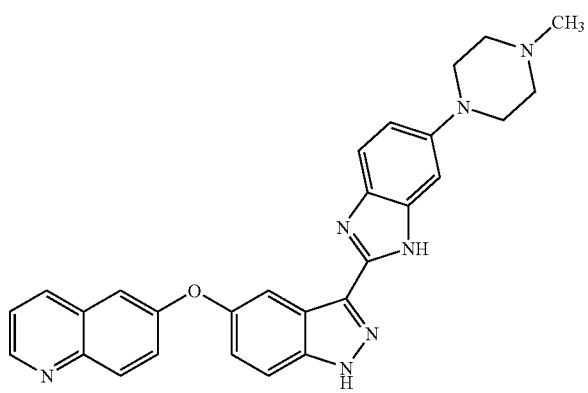 | 6-({3-[6-(4-methylpiperazin-1-yl)-1H-benzimidazol-2-yl]-1H-indazol-5-yl}oxy)quinoline |

| Example | STRUCTURE | Name |
|---|---|---|
| 1387 | 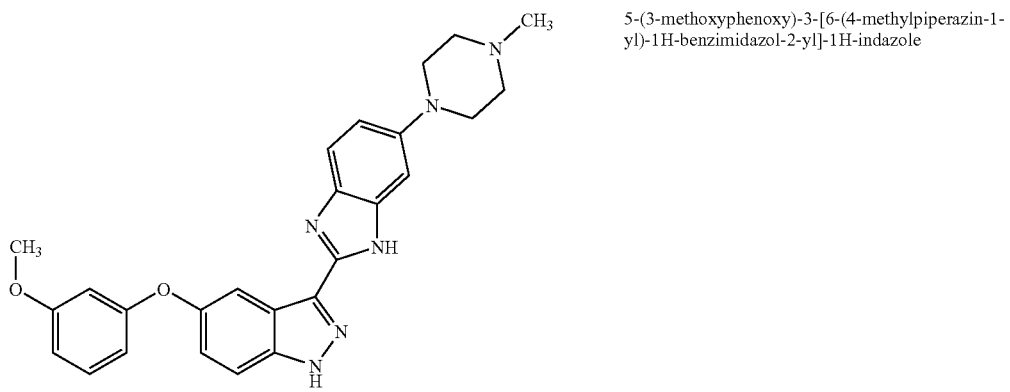 | 5-(3-methoxyphenoxy)-3-[6-(4-methylpiperazin-1-yl)-1H-benzimidazol-2-yl]-1H-indazole |
| 1388 | 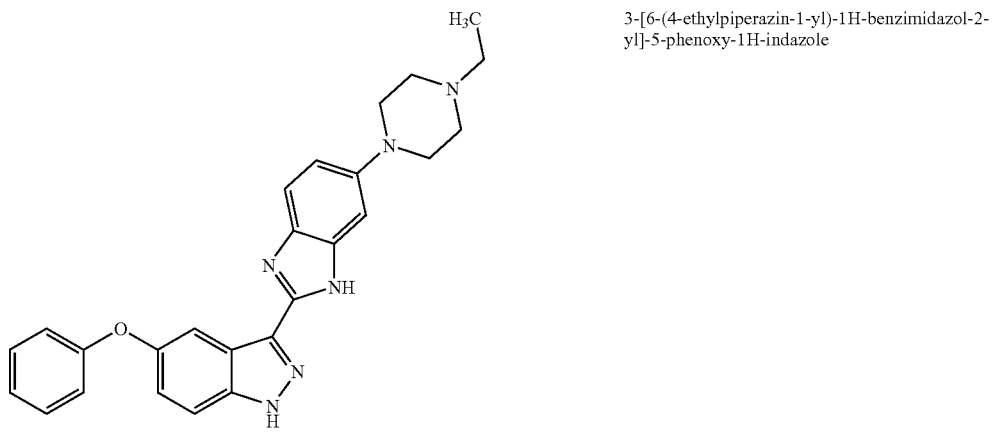 | 3-[6-(4-ethylpiperazin-1-yl)-1H-benzimidazol-2-yl]-5-phenoxy-1H-indazole |
| 1389 | 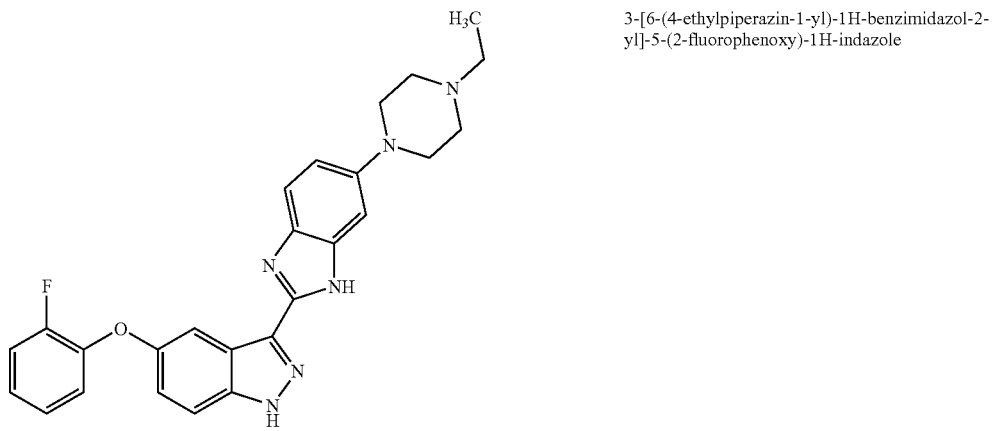 | 3-[6-(4-ethylpiperazin-1-yl)-1H-benzimidazol-2-yl]-5-(2-fluorophenoxy)-1H-indazole |

-continued
| Example | STRUCTURE | Name |
|---|---|---|
| 1390 | 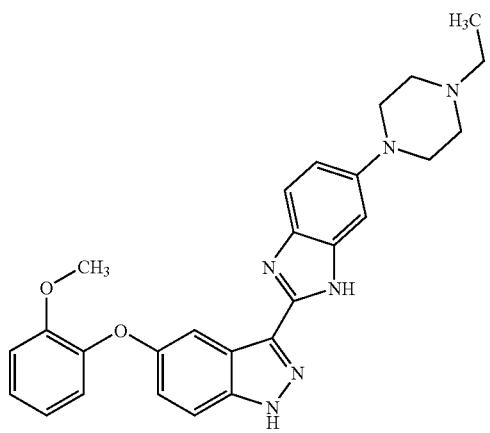 | 3-[6-(4-ethylpiperazin-1-yl)-1H-benzimidazol-2-yl]-5-(2-methoxyphenoxy)-1H-indazole |
| 1391 | 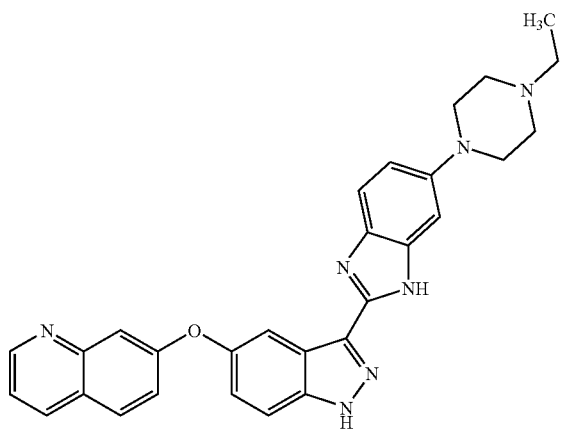 | 7-({3-[6-(4-ethylpiperazin-1-yl)-1H-benzimidazol-2-yl]-1H-indazol-5-yl}oxy)quinoline |
| 1392 | 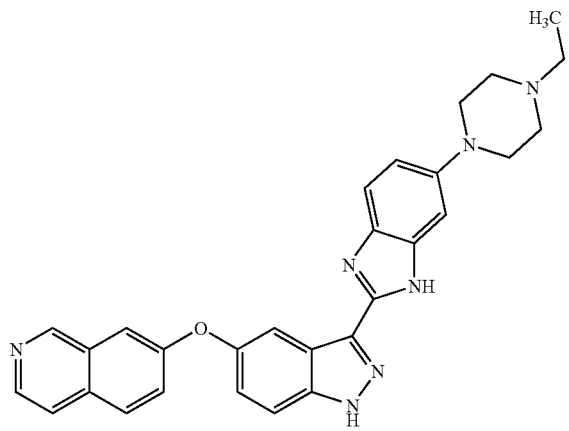 | 7-({3-[6-(4-ehtylpiperazin-1-yl)-1H-benzimidazol-2-yl]-1H-indazol-5-yl}oxy)isoquinoline |

-continued
| Example | STRUCTURE | Name |
|---|---|---|
| 1393 | 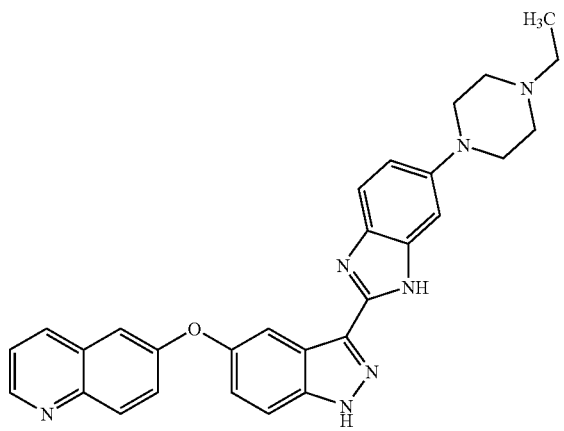 | 6-({3-[6-(4-ethylpiperazin-1-yl)-1H-benzimidazol-2-yl]-1H-indazol-5-yl}oxy)quinoline |
| 1394 | 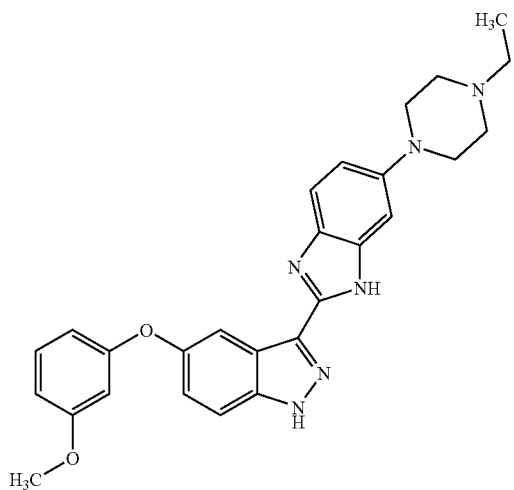 | 3-[6-(4-ethylpiperazin-1-yl)-1H-benzimidazol-2-yl]-5-(3-methoxyphenoxy)-1H-indazole |
| 1395 | 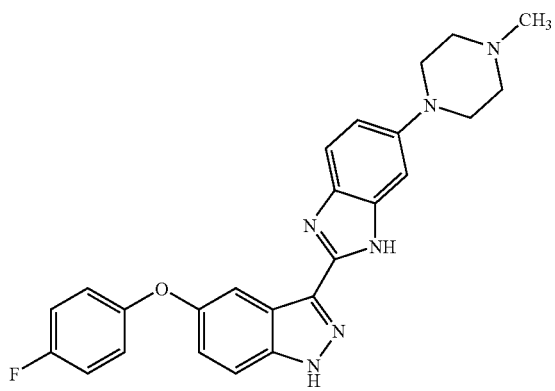 | 5-(4-fluorophenoxy)-3-[6-(4-methylpiperazin-1-yl)-1H-benzimidazol-2-yl]-1H-indazole |

-continued
| Example | STRUCTURE | Name |
|---|---|---|
| 1396 | 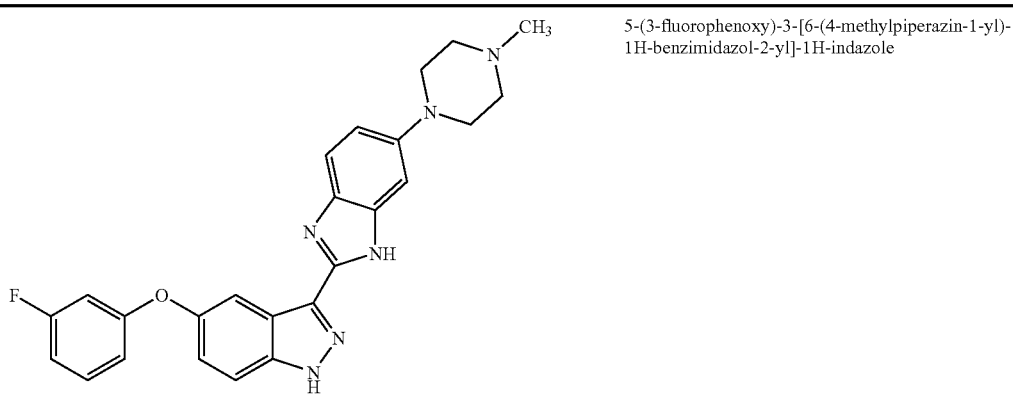 | 5-(3-fluorophenoxy)-3-[6-(4-methylpiperazin-1-yl)-1H-benzimidazol-2-yl]-1H-indazole |
| 1397 | 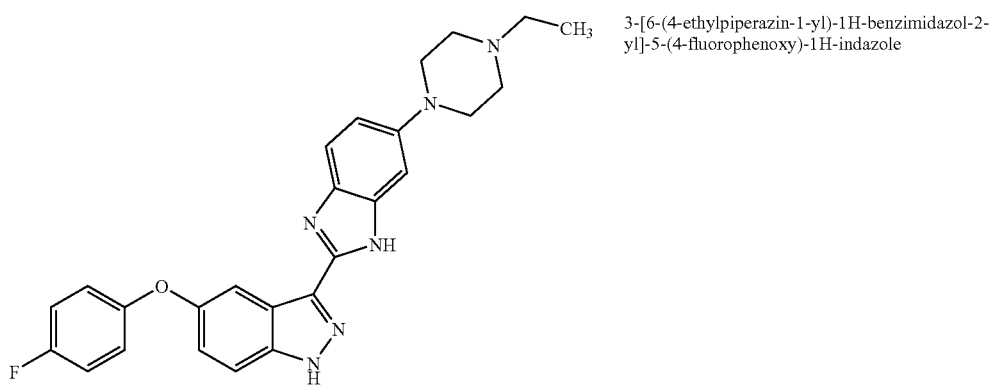 | 3-[6-(4-ethylpiperazin-1-yl)-1H-benzimidazol-2-yl]-5-(4-fluorophenoxy)-1H-indazole |
| 1398 | 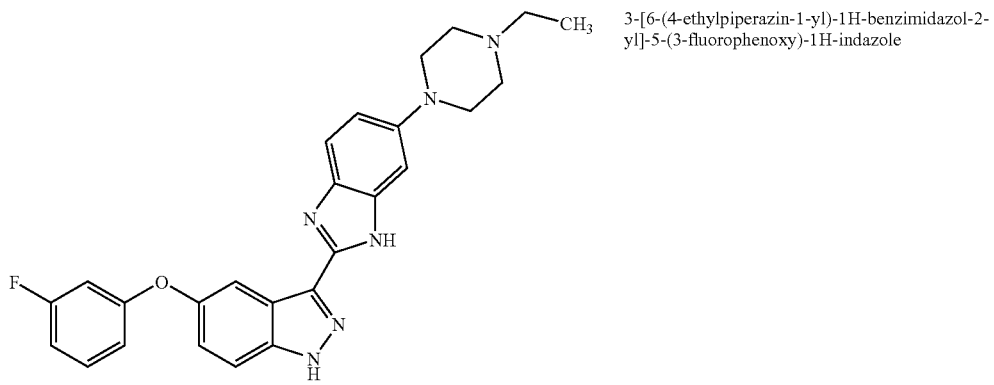 | 3-[6-(4-ethylpiperazin-1-yl)-1H-benzimidazol-2-yl]-5-(3-fluorophenoxy)-1H-indazole |
| 1399 | 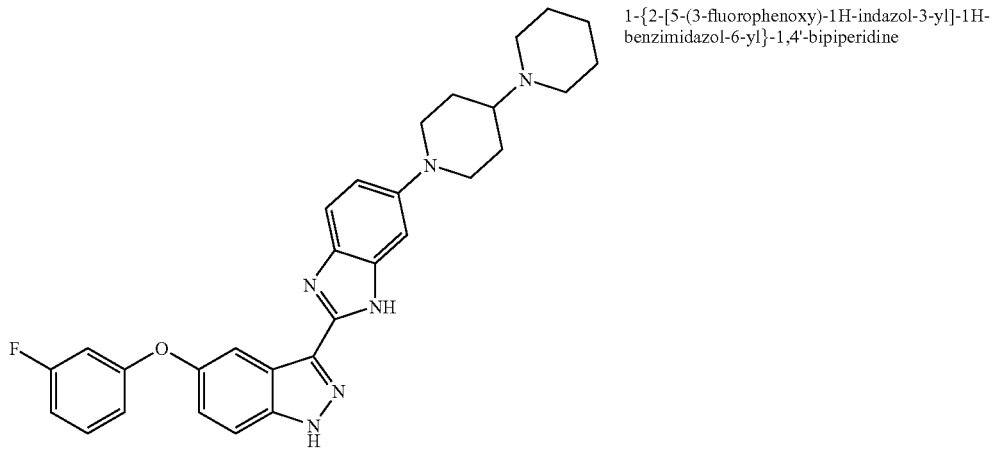 | 1-{2-[5-(3-fluorophenoxy)-1H-indazol-3-yl]-1H-benzimidazol-6-yl}-1,4'-bipiperidine |

-continued
| Example | STRUCTURE | Name |
|---|---|---|
| 1400 | 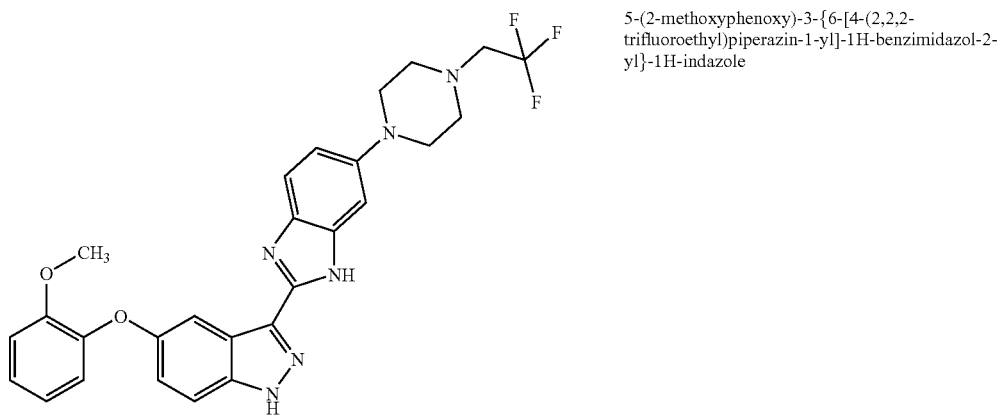 | 5-(2-methoxyphenoxy)-3-{6-[4-(2,2,2-trifluoroethyl)piperazin-1-yl]-1H-benzimidazol-2-yl}-1H-indazole |
| 1401 | 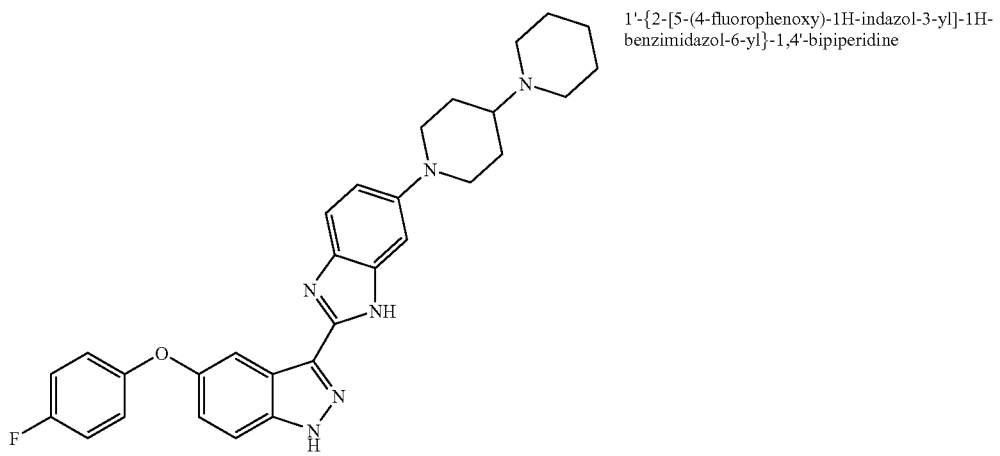 | 1'-{2-[5-(4-fluorophenoxy)-1H-indazol-3-yl]-1H-benzimidazol-6-yl}-1,4'-bipiperidine |
| 1402 | 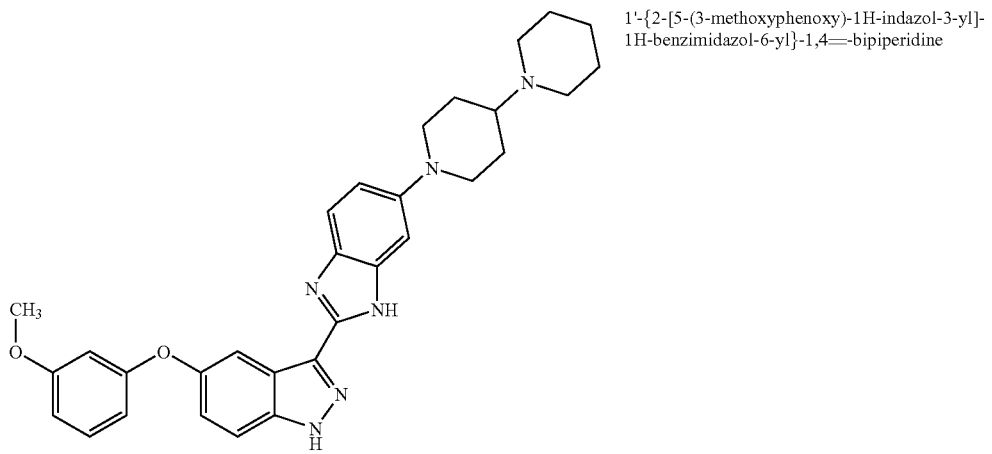 | 1'-{2-[5-(3-methoxyphenoxy)-1H-indazol-3-yl]-1H-benzimidazol-6-yl}-1,4=-bipiperidine |

-continued
| Example | STRUCTURE | Name |
|---|---|---|
| 1403 | 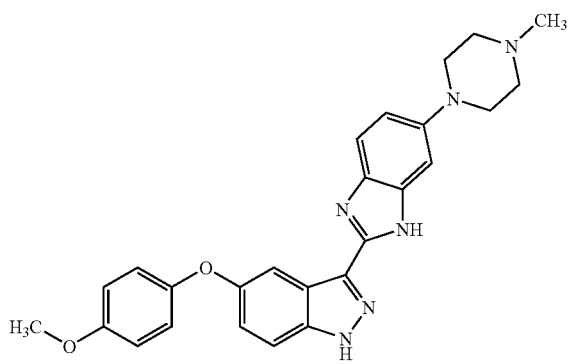 | 5-(4-methoxyphenoxy)-3-[6-(4-methylpiperazin-1-yl)-1H-benzimidazol-2-yl]-1H-indazole |
| 1404 | 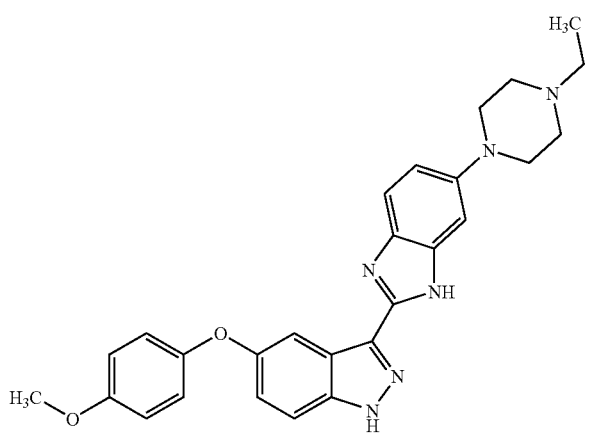 | 3-[6-(4-ethylpiperazin-1-yl)-1H-benzimidazol-2-yl]-5-(4-methoxyphenoxy)-1H-indazole |
| 1405 | 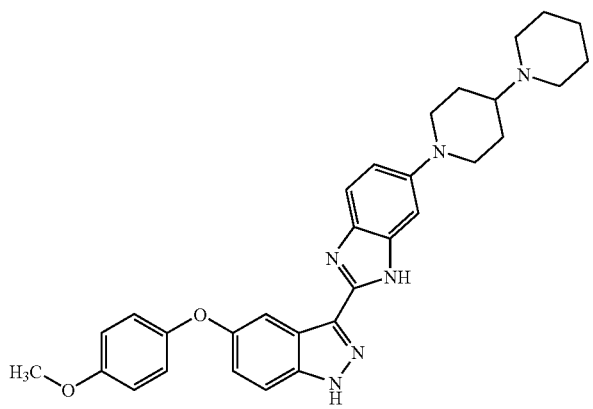 | 1'-{2-[5-(4-methoxyphenoxy)-1H-indazol-3-yl]-1H-benzimidazol-6-yl}-1,4'-bipiperidine |
| 1406 | 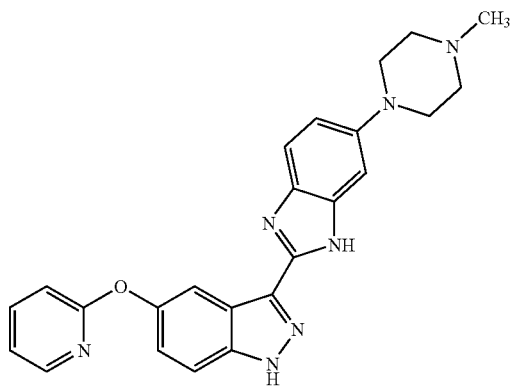 | 3-{6-(4-methylpiperazin-1-yl)-1H-benzimidazol-2-yl]-5-(pyridin-2-yloxy)-1H-indazole |

-continued
| Example | STRUCTURE | Name |
|---|---|---|
| 1407 | 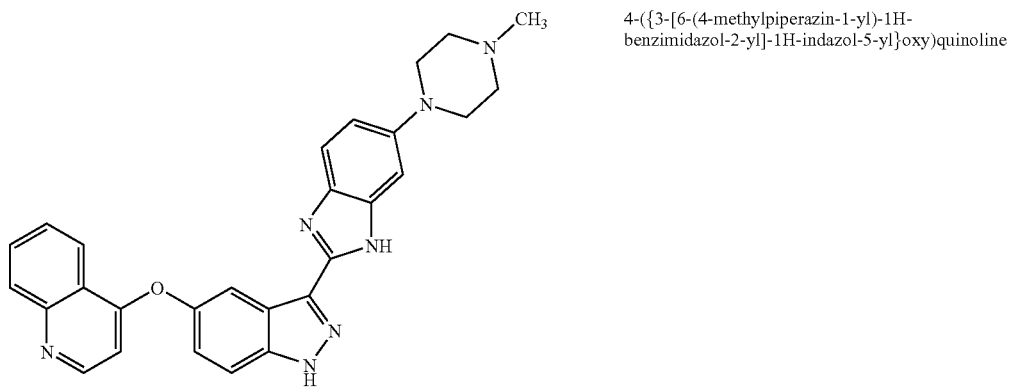 | 4-({3-[6-(4-methylpiperazin-1-yl)-1H-benzimidazol-2-yl]-1H-indazol-5-yl}oxy)quinoline |
| 1408 | 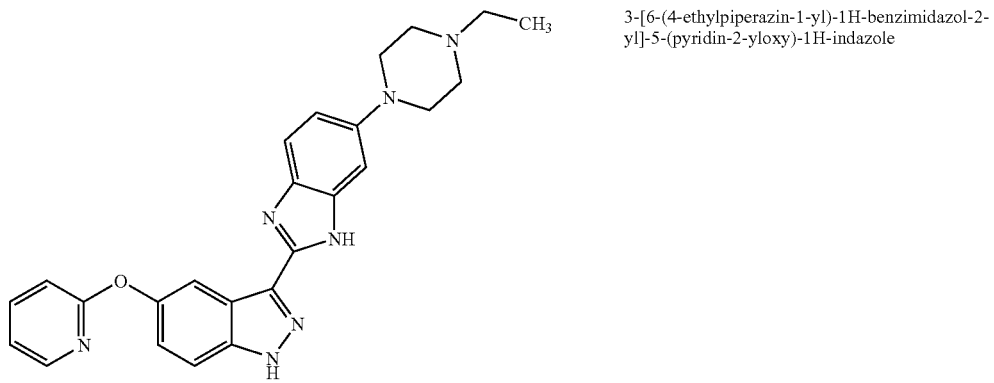 | 3-[6-(4-ethylpiperazin-1-yl)-1H-benzimidazol-2-yl]-5-(pyridin-2-yloxy)-1H-indazole |
| 1409 | 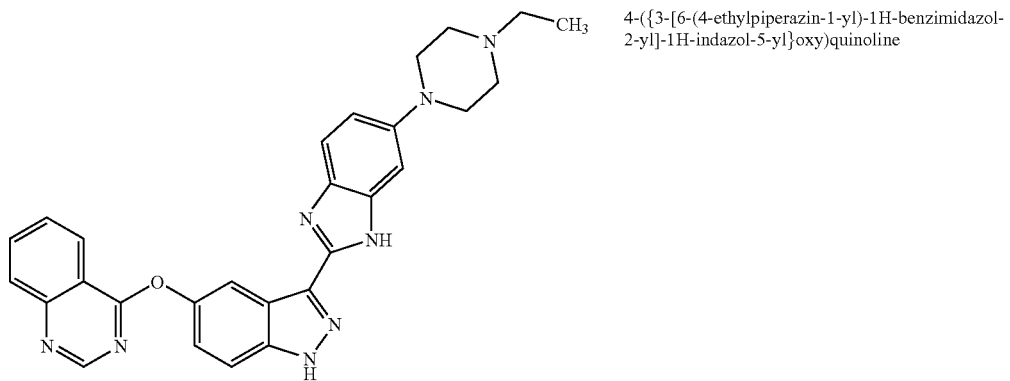 | 4-({3-[6-(4-ethylpiperazin-1-yl)-1H-benzimidazol-2-yl]-1H-indazol-5-yl}oxy)quinoline |

-continued
| Example | STRUCTURE | Name |
|---------|-----------|------|
| 1410 | 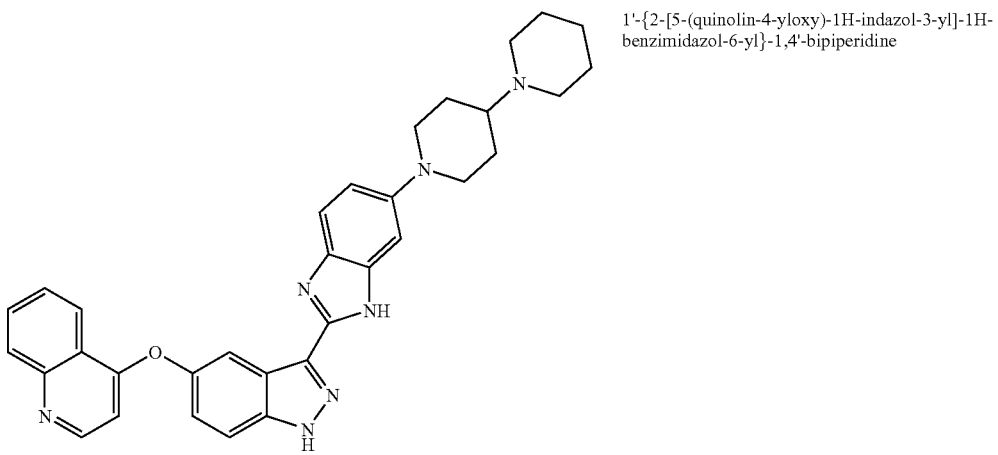 | 1'-{2-[5-(quinolin-4-yloxy)-1H-indazol-3-yl]-1H-benzimidazol-6-yl}-1,4'-bipiperidine |
| 1411 | 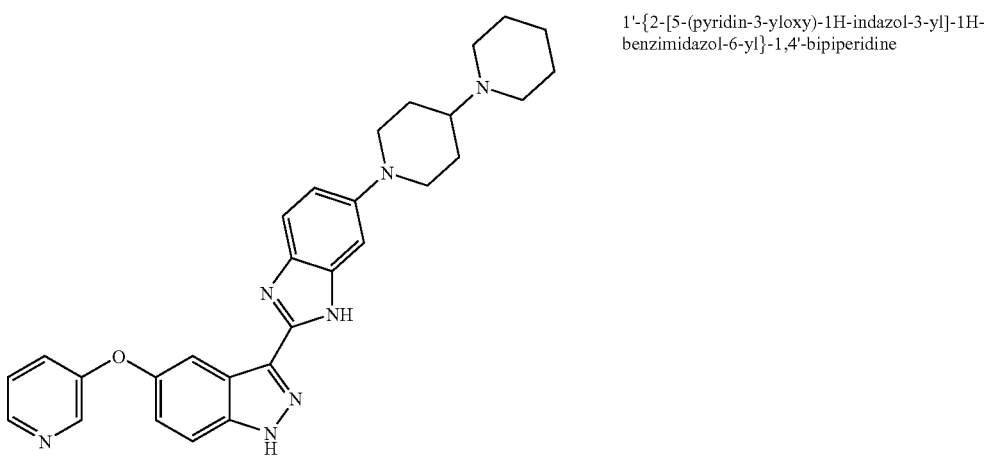 | 1'-{2-[5-(pyridin-3-yloxy)-1H-indazol-3-yl]-1H-benzimidazol-6-yl}-1,4'-bipiperidine |
| 1412 | 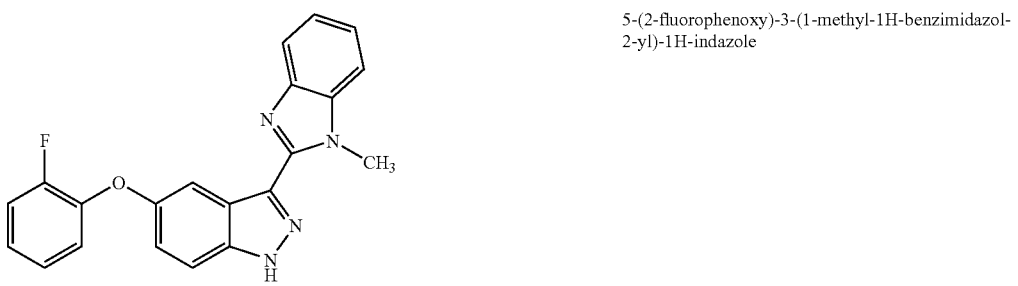 | 5-(2-fluorophenoxy)-3-(1-methyl-1H-benzimidazol-2-yl)-1H-indazole |
| 1413 | 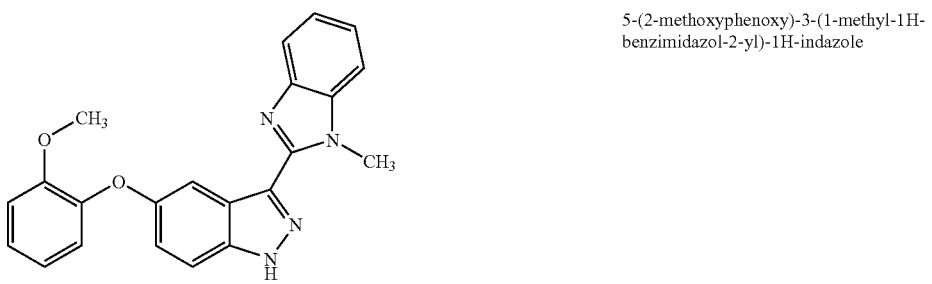 | 5-(2-methoxyphenoxy)-3-(1-methyl-1H-benzimidazol-2-yl)-1H-indazole |

-continued
| Example | STRUCTURE | Name |
|---|---|---|
| 1414 | 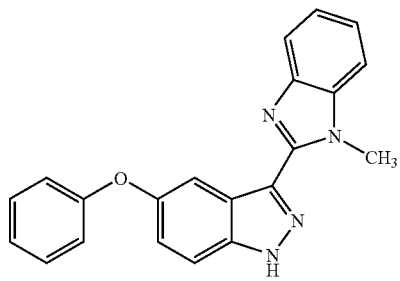 | 3-(1-methyl-1H-benzimidazol-2-yl)-5-phenoxy-1H-indazole |
| 1415 | 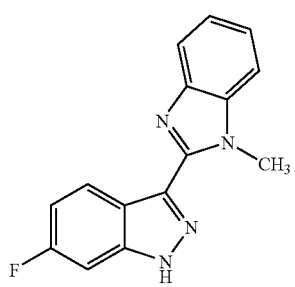 | 6-fluoro-3-(1-methyl-1H-benzimidazol-2-yl)-1H-indazole |
| 1416 | 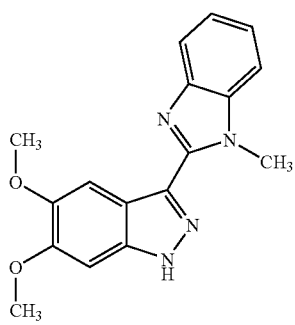 | 5,6-dimethoxy-3-(1-methyl-1H-benzimidazol-2-yl)-1H-indazole |
| 1417 | 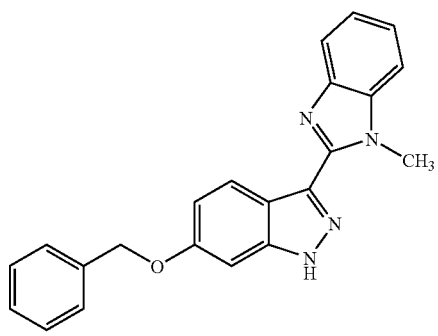 | 6-(benzyloxy)-3-(1-methyl-1H-benzimidazol-2-yl)-1H-indazole |
| 1418 | 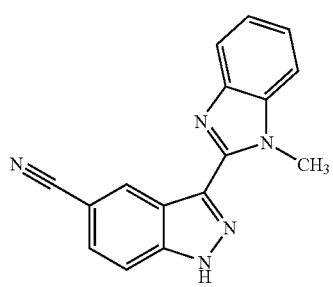 | 3-(1-methyl-1H-benzimidazol-2-yl)-1H-indazole-5-carbonitrile |

-continued
| Example | STRUCTURE | Name |
|---|---|---|
| 1419 | 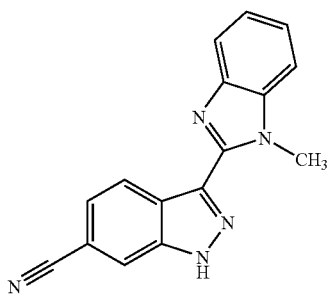 | 3-(1-methyl-1H-benzimidazol-2-yl)-1H-indazole-6-carbonitrile |
| 1420 | 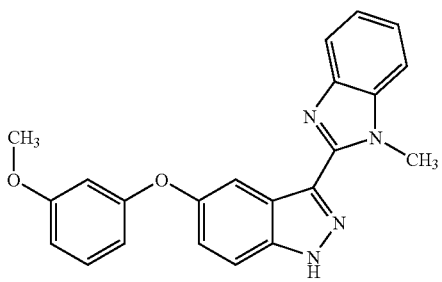 | 5-(3-methoxyphenoxy)-3-(1-methyl-1H-benzimidazol-2-yl)-1H-indazole |
| 1421 | 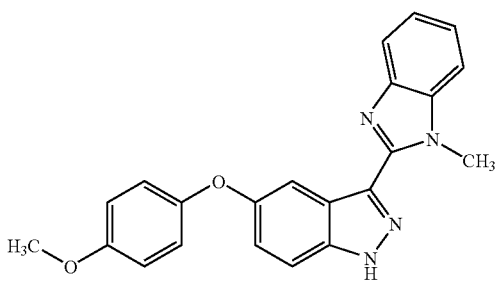 | 5-(4-methoxyphenoxy)-3-(1-methyl-1H-benzimidazol-2-yl)-1H-indazole |
| 1422 | 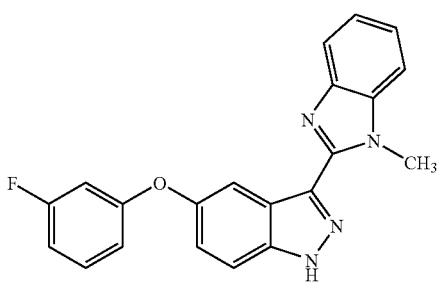 | 5-(3-fluorophenoxy)-3-(1-methyl-1H-benzimidazol-2-yl)-1H-indazole |
| 1423 | 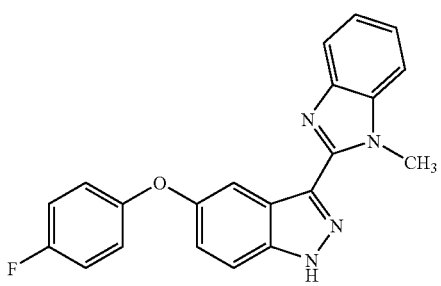 | 5-(4-fluorophenoxy)-3-(1-methyl-1H-benzimidazol-2-yl)-1H-indazole |

-continued
| Example | STRUCTURE | Name |
|---|---|---|
| 1424 | 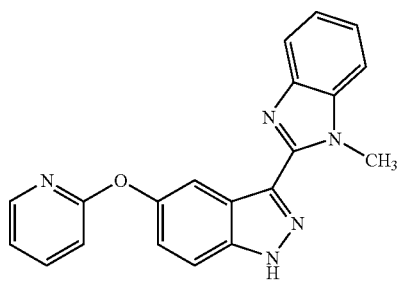 | 3-(1-methyl-1H-benzimidazol-2-yl)-5-(pyridin-2-yloxy)-1H-indazole |
| 1425 | 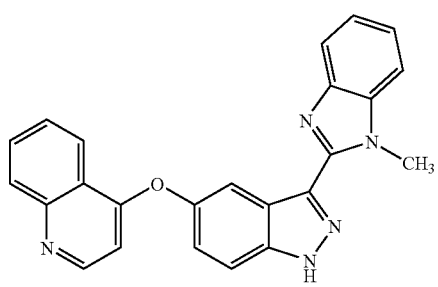 | 4-{[3-(1-methyl-1H-benzimidazol-2-yl)-1H-indazol-5-yl]oxy}quinoline |
| 1426 | 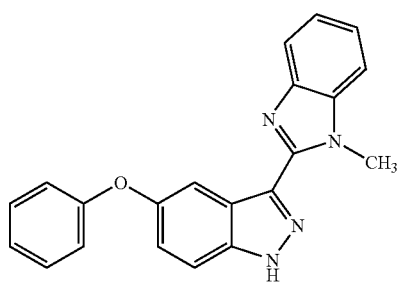 | 3-(1-methyl-1H-benzimidazol-2-yl)-5-(pyridin-3-yloxy)-1H-indazole |
| 1427 | 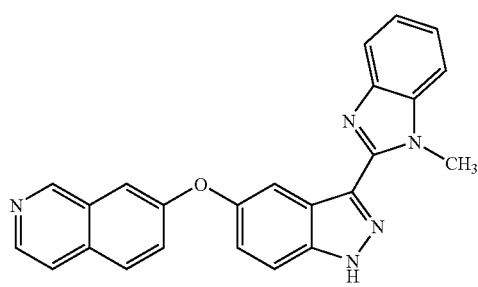 | 7-{(3-(1-methyl-1H-benzimidazol-2-yl)-1H-indazol-5-yl]oxy}isoquinoline |
| 1428 | 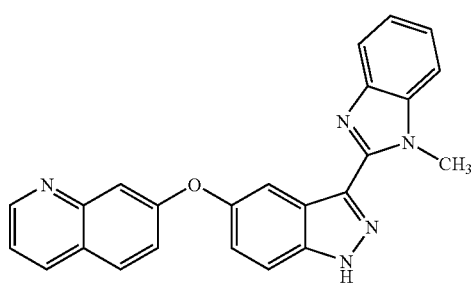 | 7-{[3-(1-methyl-1H-benzimidazol-2-yl)-1H-indazol-5-yl]oxy}quinoline |

-continued

| Example | STRUCTURE | Name |
|---|---|---|
| 1429 | 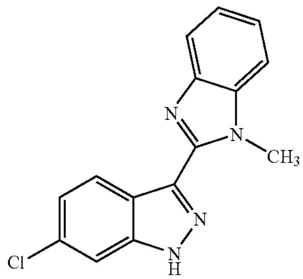 | 6-chloro-3-(1-methyl-1H-benzimidazol-2-yl)-1H-indazole |
| 1430 | 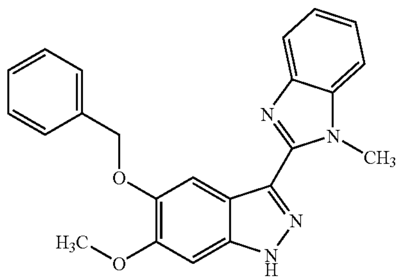 | 5-(benzyloxy)-6-methoxy-3-(1-methyl-1H-benzimidazol-2-yl)-1H-indazole |
| 1431 | 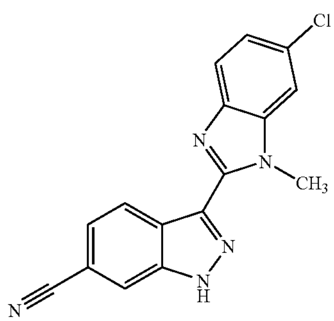 | 3-(6-chloro-1-methyl-1H-benzimidazol-2-yl)-1H-indazole-6-carbonitrile |
| 1432 | 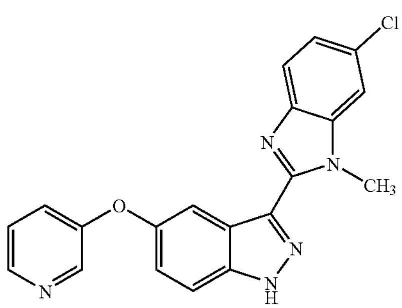 | 3-(6-chloro-1-methyl-1H-benzimidazol-2-yl)-5-(pyridin-3-yloxy)-1H-indazole |
| 1433 | 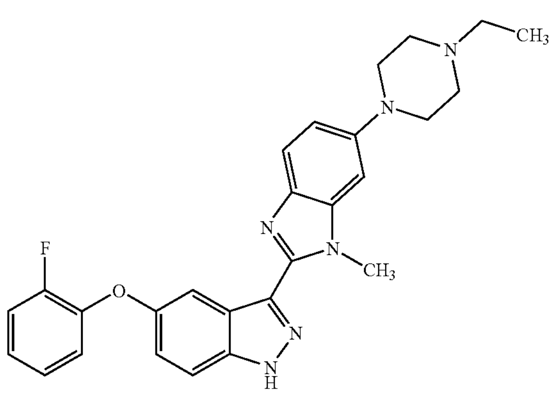 | 3-[6-(4-ethylpiperazin-1-yl)-1-methyl-1H-benzimidazol-2-yl]-5-(2-fluorophenoxy)-1H-indazole |

-continued
| Example | STRUCTURE | Name |
|---|---|---|
| 1434 | 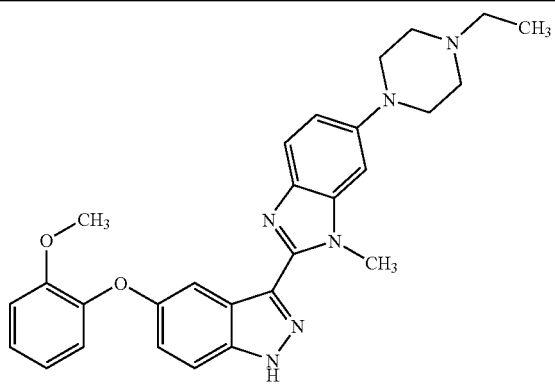 | 3-[6-(4-ethylpiperazin-1-yl)-1-methyl-1H-benzimidazol-2-yl]-5-(2-methoxyphenoxy)-1H-indazole |
| 1435 | 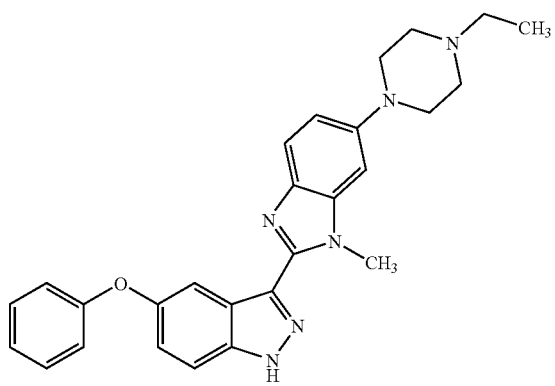 | 3-[6-(4-ethylpiperazin-1-yl)-1-methyl-1H-benzimidazol-2-yl]-5-phenoxy-1H-indazole |
| 1436 | 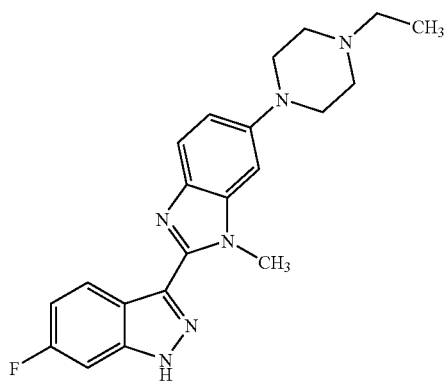 | 3-[6-(4-ethylpiperazin-1-yl)-1-methyl-1H-benzimidazol-2-yl]-6-fluoro-1H-indazole |
| 1437 | 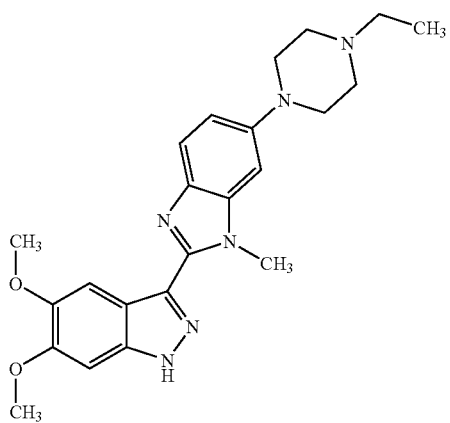 | 3-[6-(4-ethylpiperazin-1-yl)-1-methyl-1H-benzimidazol-2-yl]-5,6-dimethoxy-1H-indazole |

-continued
| Example | STRUCTURE | Name |
|---|---|---|
| 1438 | 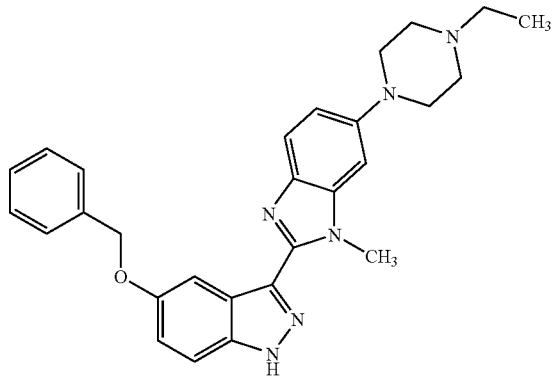 | 5-(benzyloxy)-3-[6-(4-ethylpiperazin-1-yl)-1-methyl-1H-benzimidazol-2-yl]-1H-indazole |
| 1439 | 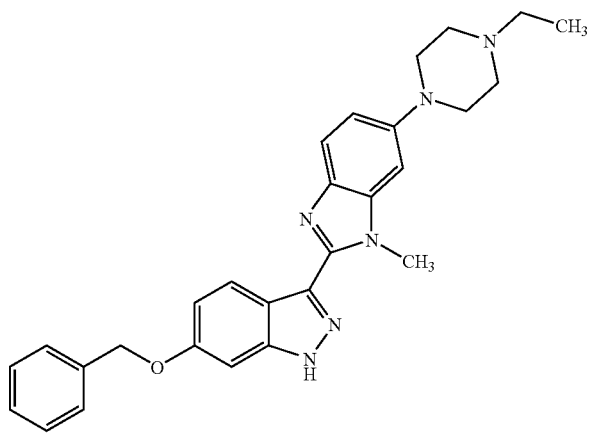 | 6-(benzyloxy)-3-[6-(4-ethylpiperazin-1-yl)-1-methyl-1H-benzimidazol-2-yl]-1H-indazole |
| 1440 | 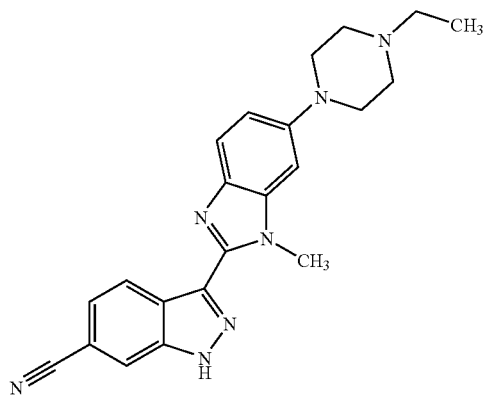 | 3-[6-(4-ethylpiperazin-1-yl)-1-methyl-1H-benzimidazol-2-yl]-1H-indazole-6-carbonitrile |
| 1441 | 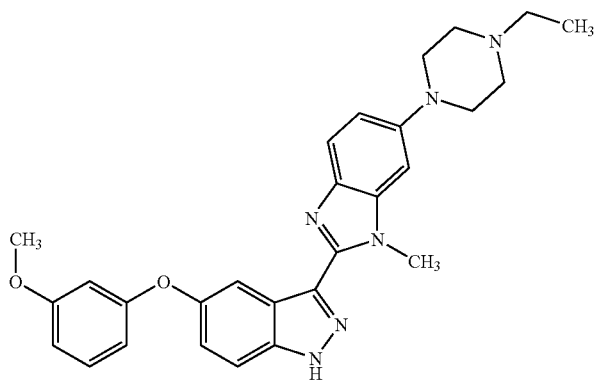 | 3-[6-(4-ethylpiperazin-1-yl)-1-methyl-1H-benzimidazol-2-yl]-5-(3-methoxyphenoxy)-1H-indazole |

-continued
| Example | STRUCTURE | Name |
|---|---|---|
| 1442 | 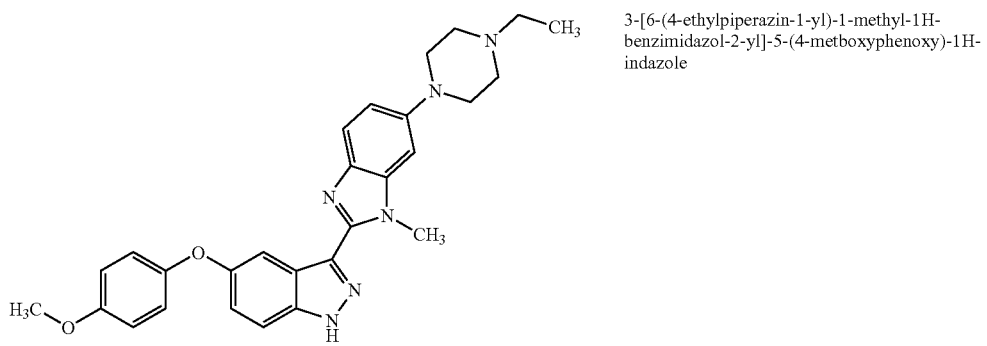 | 3-[6-(4-ethylpiperazin-1-yl)-1-methyl-1H-benzimidazol-2-yl]-5-(4-metboxyphenoxy)-1H-indazole |
| 1443 | 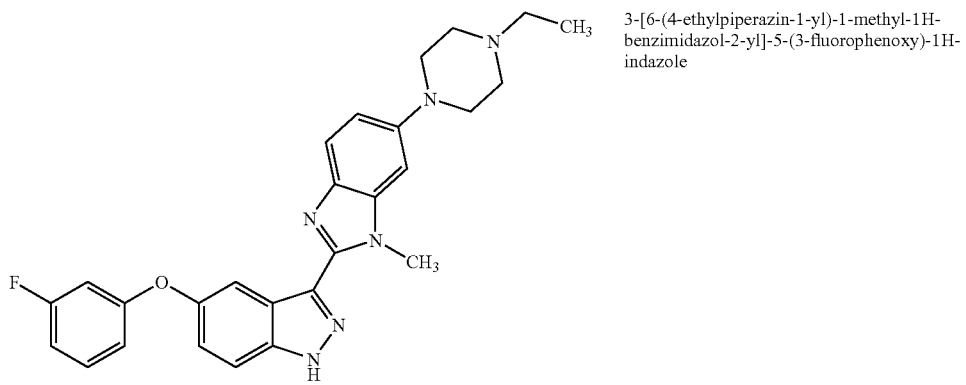 | 3-[6-(4-ethylpiperazin-1-yl)-1-methyl-1H-benzimidazol-2-yl]-5-(3-fluorophenoxy)-1H-indazole |
| 1444 | 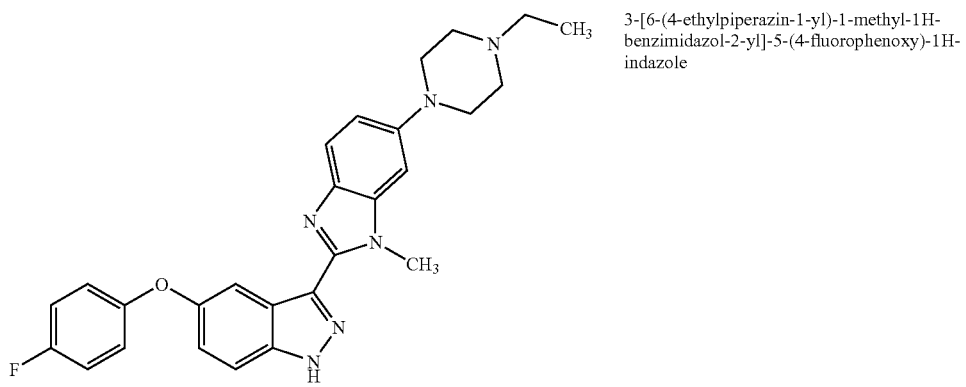 | 3-[6-(4-ethylpiperazin-1-yl)-1-methyl-1H-benzimidazol-2-yl]-5-(4-fluorophenoxy)-1H-indazole |
| 1445 | 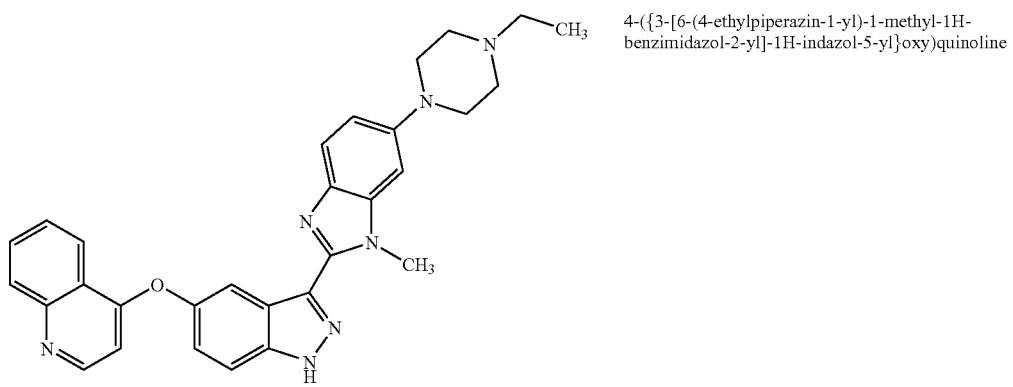 | 4-({3-[6-(4-ethylpiperazin-1-yl)-1-methyl-1H-benzimidazol-2-yl]-1H-indazol-5-yl}oxy)quinoline |

-continued
| Example | STRUCTURE | Name |
|---------|-----------|------|
| 1446 | 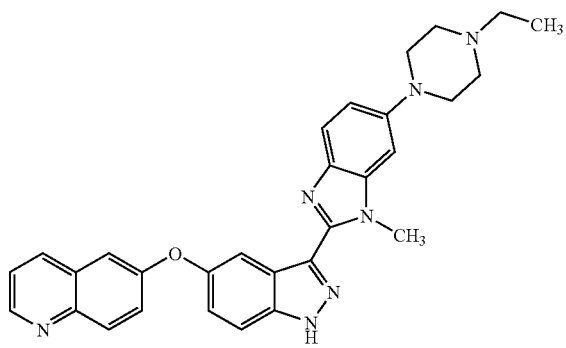 | 6-({3-[6-(4-ethylpiperazin-1-yl)-1-methyl-1H-benzimidazol-2-yl]-1H-indazol-5-yl}oxy)quinoline |
| 1447 | 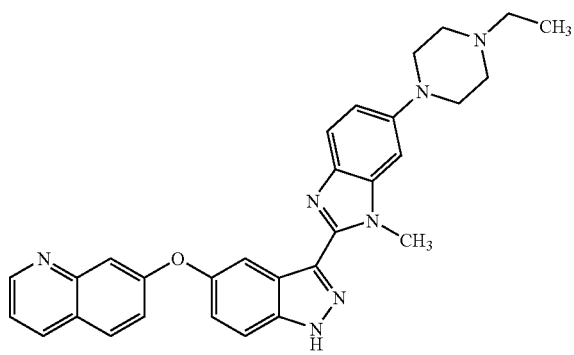 | 7-({3-[6-(4-ethylpiperazin-1-yl)-1-methyl-1H-benzimidazol-2-yl]-1H-indazol-5-yl}oxy)quinoline |
| 1448 | 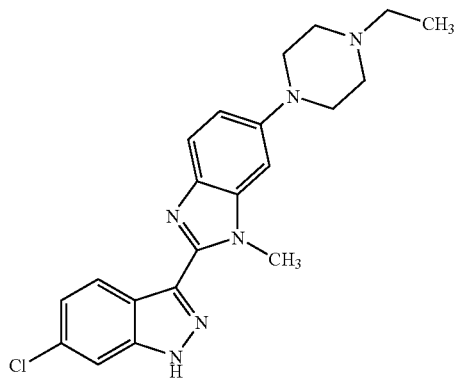 | 6-chloro-3-[6-(4-ethylpiperazin-1-yl)-1-methyl-1H-benzimidazol-2-yl]-1H-indazole |
| 1449 | 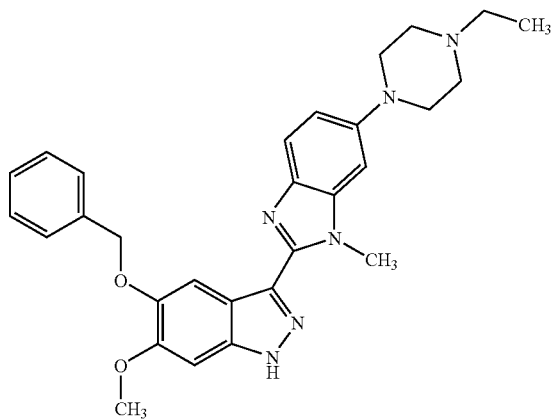 | 5-(benzyloxy)-3-[6-(4-ethylpiperazin-1-yl)-1-methyl-1H-benzimidazol-2-yl]-6-methoxy-1H-indazole |

| Example | STRUCTURE | Name |
|---|---|---|
| 1450 | 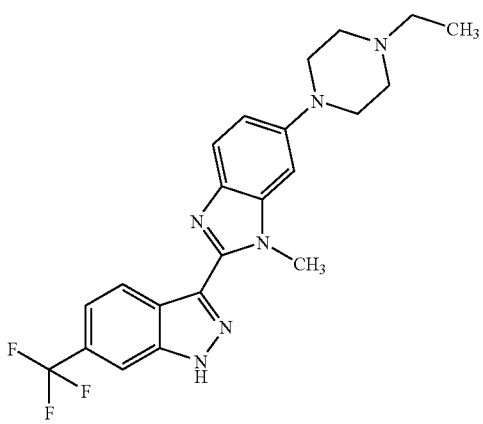 | 3-[6-(4-ethylpiperazin-1-yl)-1-methyl-1H-benzimidazol-2-yl]-6-(trifluoromethyl)-1H-indazole |
| 1451 | 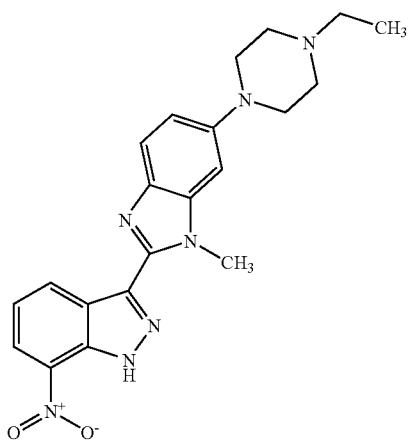 | 3-[6-(4-ethylpiperazin-1-yl)-1-methyl-1H-benzimidazol-2-yl]-7-nitro-1H-indazole |
| 1452 | 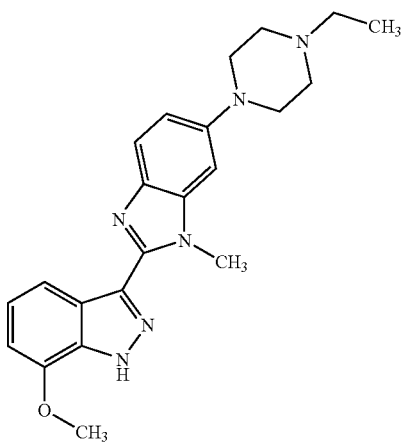 | 3-[6-(4-ethylpiperazin-1-yl)-1-methyl-1H-benzimidazol-2-yl]-7-methoxy-1H-indazole |

| Example | STRUCTURE | Name |
|---|---|---|
| 1453 | 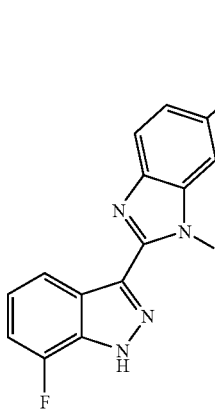 | 3-[6-(4-ethylpiperazin-1-yl)-1-methyl-1H-benzimidazol-2-yl]-7-fluoro-1H-indazole |
| 1454 | 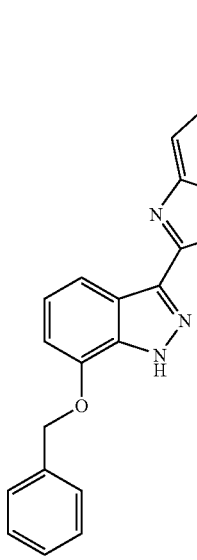 | 7-(benzyloxy)-3-[6-(4-ethylpiperazin-1-yl)-1-methyl-1H-benzimidazol-2-yl]-1H-indazole |
| 1455 | 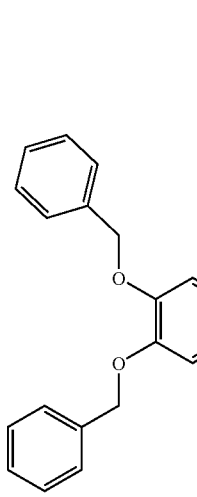 | 5,6-bis(benzyloxy)-3-[6-(4-ethylpiperazin-1-yl)-1-methyl-1H-benzimidazol-2-yl]-1H-indazole |

| Example | STRUCTURE | Name |
|---|---|---|
| 1456 | 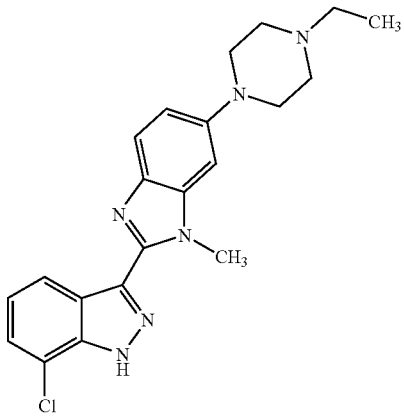 | 7-chloro-3-{6-(4-ethylpiperazin-1-yl}-1-methyl-1H-benzimidazol-2-yl]-1H-indazole |
| 1457 | 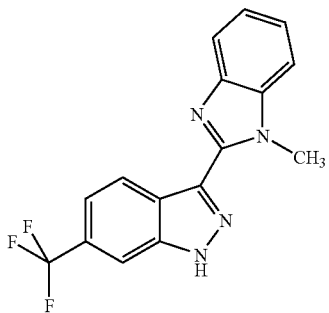 | 3-(1-methyl-1H-benzimidazol-2-yl)-6-(trifluoromethyl)-1H-indazole |
| 1458 | 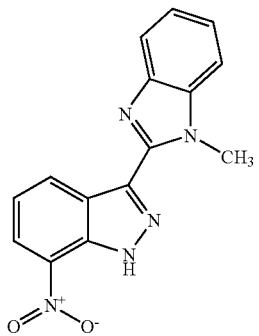 | 3-(1-methyl-1H-benzimidazol-2-yl)-7-nitro-1H-indazole |
| 1459 | 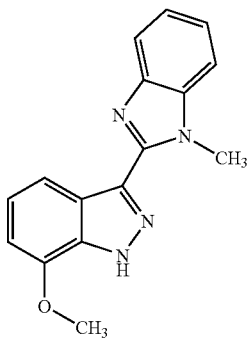 | 7-methoxy-3-(1-methyl-1H-benzimidazol-2-yl)-1H-indazole |

-continued
| Example | STRUCTURE | Name |
|---|---|---|
| 1460 | 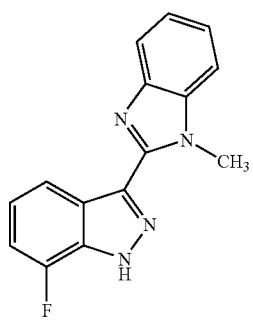 | 7-fluoro-3-(1-methyl-1H-benzimidazol-2-yl)-1H-indazole |
| 1461 | 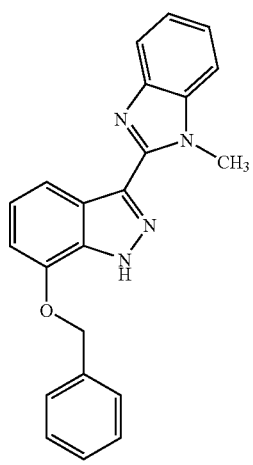 | 7-(benzyloxy)-3-(1-methyl-1H-benzimidazol-2-yl)-1H-indazole |
| 1462 | 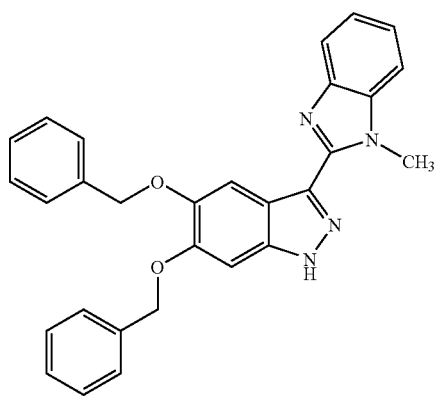 | 5,6-bis(benzyloxy)-3-(1-methyl-1H-benzimidazol-2-yl)-1H-indazole |
| 1463 | 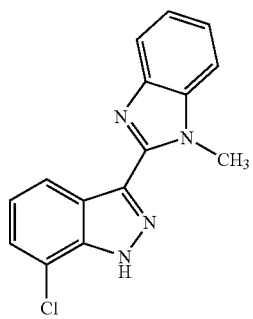 | 7-chloro-3-(1-methyl-1H-benzimidazol-2-yl)-1H-indazole |

| Example | STRUCTURE | Name |
|---|---|---|
| 1464 | 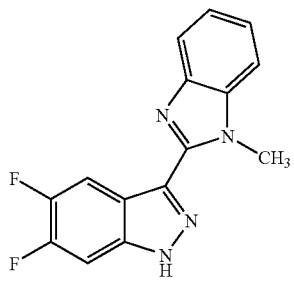 | 5,6-difluoro-3-(1-methyl-1H-benzimidazol-2-yl)-1H-indazole |
| 1465 | 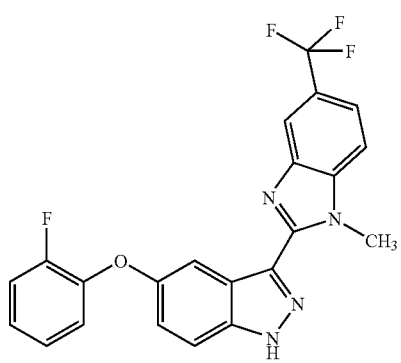 | 5-(2-fluorophenoxy)-3-[1-methyl-5-(trifluoromethyl)-1H-benzimidazol-2-yl]-1H-indazole |
| 1466 | 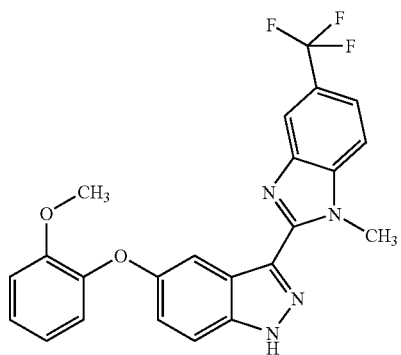 | 5-(2-methoxyphenoxy)-3-[1-methyl-5-(trifluoromethyl)-1H-benzimidazol-2-yl]-1H-indazole |
| 1467 | 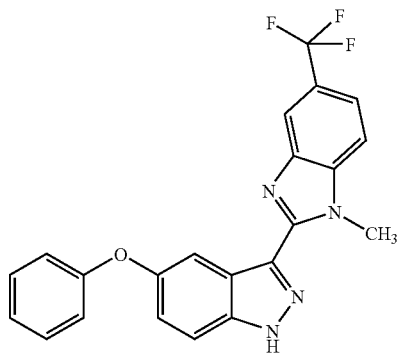 | 3-[1-methyl-5-(trifluoromethyl)-1H-benzimidazol-2-yl]-5-phenoxy-1H-indazole |

-continued
| Example | STRUCTURE | Name |
|---|---|---|
| 1468 | 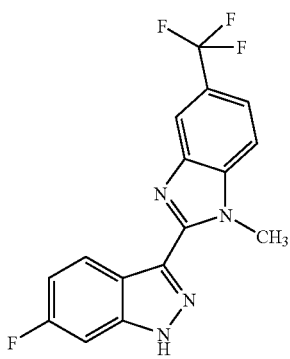 | 6-fluoro-3-[1-methyl-5-(trifluoromethyl)-1H-benzimidazol-2-yl]-1H-indazole |
| 1469 | 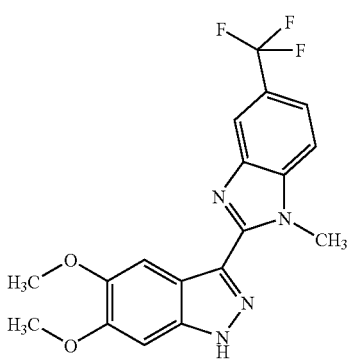 | 5,6-dimetboxy-3-{1-methyl-5-(trifluoromethyl)-1H-benzimidazol-2-yl]-1H-indazole |
| 1470 | 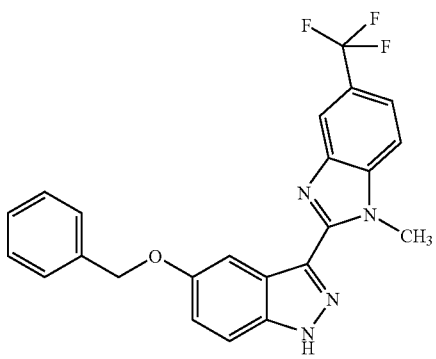 | 5-(benzyloxy)-3-[1-methyl-5-(trifluoromethyl)-1H-benzimidazol-2-yl]-1H-indazole |
| 1471 | 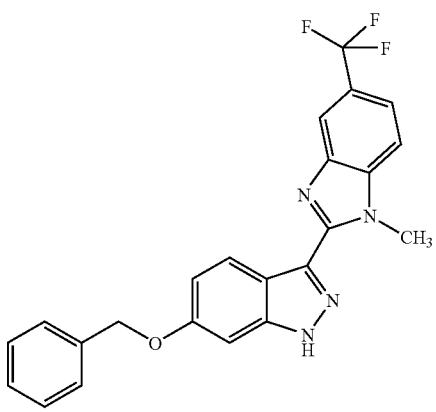 | 6-(benzyloxy)-3-[1-methyl-5-(trifluoromethyl)-1H-benzimidazol-2-yl]-1H-indazole |

| Example | STRUCTURE | Name |
|---|---|---|
| 1472 | 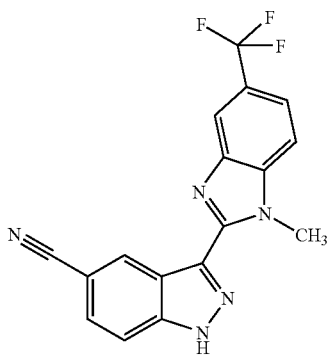 | 3-[1-methyl-5-(trifluoromethyl)-1H-benzimidazol-2-yl]-1H-indazole-5-carbonitrile |
| 1473 | 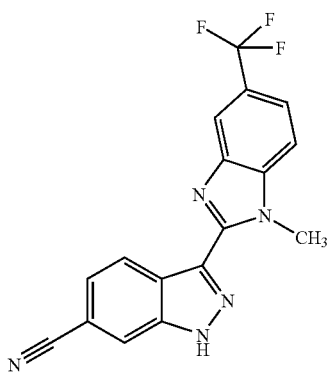 | 3-[1-methyl-5-(trifluoromethyl)-1H-benzimidazol-2-yl]-1H-indazole-6-carbonitrile |
| 1474 | 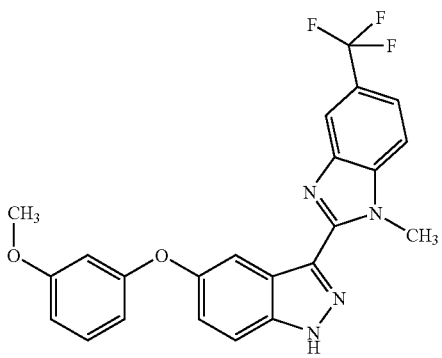 | 5-(3-methoxyphenoxy)-3-[1-methyl-5-(trifluoromethyl)-1H-benzimidazol-2-yl]-1H-indazole |
| 1475 | 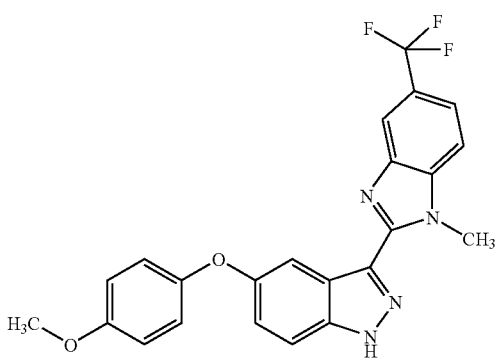 | 5-(4-methoxyphenoxy)-3-[1-methyl-5-(trifluoromethyl)-1H-benzimidazol-2-yl]-1H-indazole |

-continued
| Example | STRUCTURE | Name |
|---|---|---|
| 1476 | 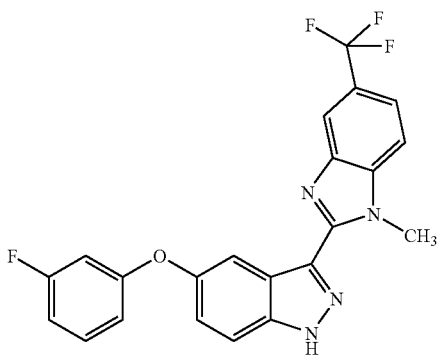 | 5-(3-fluorophenoxy)-3-[1-methyl-5-(trifluoromethyl)-1H-benzimidazol-2-yl]-1H-indazole |
| 1477 | 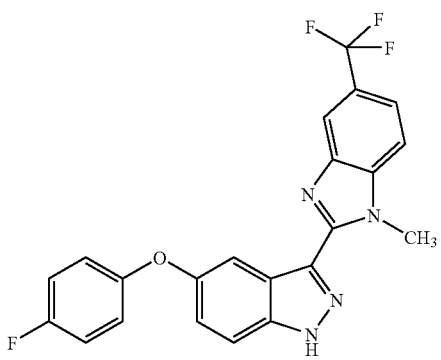 | 5-(4-fluorophenoxy)-3-[1-methyl-5-(trifluoromethyl)-1H-benzimidazol-2-yl]-1H-indazole |
| 1478 | 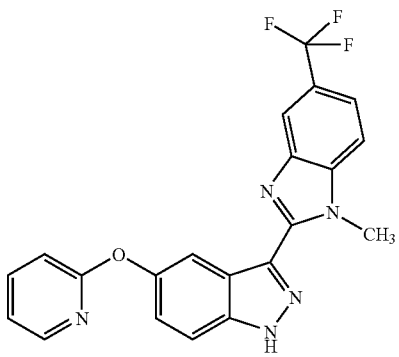 | 3-[1-methyl-5-(trifluoromethyl)-1H-benzimidazol-2-yl]-5-(pyridin-2-yloxy)-1H-indazole |
| 1479 | 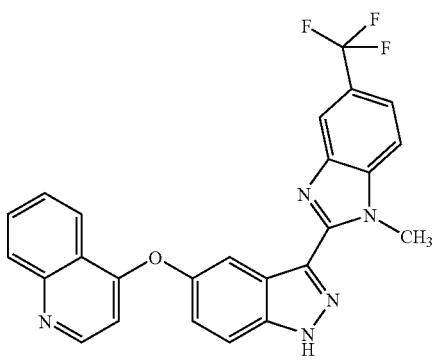 | 4-({3-[1-methyl-5-(trifluoromethyl)-1H-benzimidazol-2-yl]-1H-indazol-5-yl}oxy)quinoline |

-continued
| Example | STRUCTURE | Name |
|---|---|---|
| 1480 | 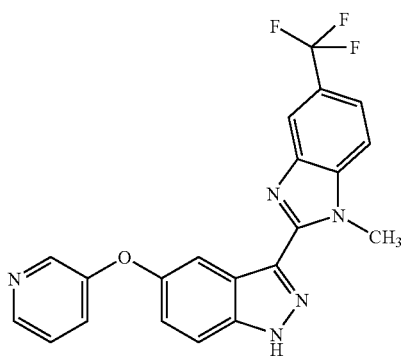 | 3-[1-methyl-5-(trifluoromethyl)-1H-benzimidazol-2-yl]-5-(pyridin-3-yloxy)-1H-indazole |
| 1481 | 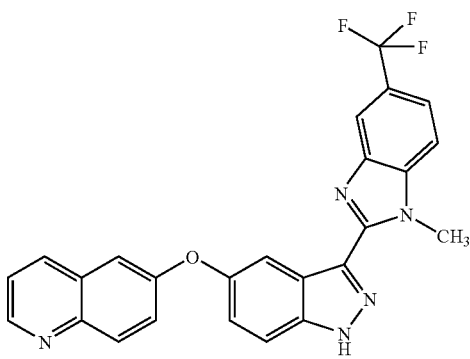 | 6-({3-[1-methyl-5-(trifluoromethyl)-1H-benzimidazol-2-yl]-1H-indazol-5-yl}oxy)quinoline |
| 1482 | 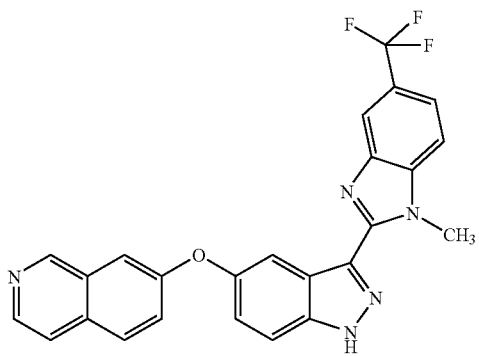 | 7-({3-[1-methyl-5-(trifluoromethyl)-1H-benzimidazol-2-yl]-1H-indazol-5-yl}oxy)isoquinoline |
| 1483 | 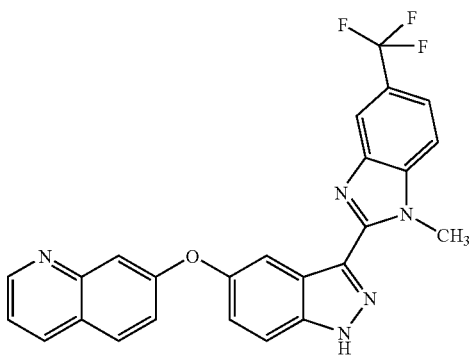 | 7-({3-[1-methyl-5-(trifluoromethyl)-1H-benzimidazol-2-yl]-1H-indazol-5-yl}oxy)quinoline |

| Example | STRUCTURE | Name |
|---|---|---|
| 1484 | (structure) | 6-chloro-3-[1-metbyl-5-(trifluoromethyl)-1H-benzimidazol-2-yl]-1H-indazole |
| 1485 | (structure) | 5-(benzyloxy)-6-methoxy-3-[1-methyl-5-(trifluoromethyl)-1H-benzimidazol-2-yl]-1H-indazole |

In one aspect, the invention provides any of the Example compounds in the above tables. In some embodiments, the invention provides any of the compounds corresponding to Examples 1200 to 1485 as set forth in the above table.

Example 1277

To a solution of 7-nitro-3-[5-(4-piperidylpiperidyl)benzimidazol-2-yl]-1H-indazole (1.0 equivalent) in ethanol:ethyl acetate (1:1), was added 10% Pd/C. The reaction vessel was repeatedly purged with nitrogen and then stirred under a hydrogen atmosphere (1 atm) for 48 hours. The product was filtered through Celite with ethanol. The solvent was removed to provide a brown solid which was used without purification. LCMS m/z 416.5 (MH$^+$), R$_t$ 2.15 min.

Example 1324

A mixture of 3-[5-(4-piperidylpiperidyl)benzimidazol-2-yl]-1H-indazole-7-ylamine (1 equivalent), acetone (1.1 equivalent), and BH$_3$:pyridine (10 equivalents, 8 M in pyridine) in AcOH:MeOH:CH$_2$Cl$_2$ (1:2:2) were stirred for 18 hours at room temperature. The solvent was removed, and the residue was purified by preparatory HPLC. LCMS m/z 458.4 (MH$^+$), R$_t$ 2.09 min. An analogous method was used to prepare the following Example compounds: Example 1325 (LCMS m/z 513.4 (MH$^+$), R$_t$ 1.70 min), Example 1326 (LCMS m/z 513.4 (MH$^+$), R$_t$ 1.94 min), Example 1327 (LCMS m/z 546.4 (MH$^+$), R$_t$ 1.84 min), and Example 1328 (LCMS m/z 513.4 (MH$^+$), R$_t$ 1.70 min).

Example 1329

3-[5-(4-Piperidylpiperidyl)benzimidazol-2-yl]-1H-indazole-7-ylamine was dissolved in THF and t-butylisocyanate (1.1 equivalents) was added. The mixture was shaken overnight, the solution was concentrated, and the resulting residue was purified by preparatory HPLC. LCMS m/z 515.5 (MH$^+$), R$_t$ 2.02 min. An analogous method was used to prepare the following Example compounds: Example 1330 (LCMS m/z 595.5 (MH$^+$), R$_t$ 2.10 min), Example 1331 (LCMS m/z 619.4 (MH$^+$), R$_t$ 2.31 min), and Example 1343 (LCMS m/z 553.4 (MH$^+$), R$_t$ 2.12 min).

Example 1291

To a solution containing Example 1289 in MeOH was added a catalytic amount of 10% Pd/C. The atmosphere was purged with nitrogen, and the solution was left to stir overnight under a hydrogen atmosphere. At this time, the reaction mixture was filtered through a pad of Celite and concentrated. The crude amino indazole benzimidazole was then solubilized in THF and MeOH (1:1), and ethyl isocyanate (1.2 equivalents) was added. The resulting mixture was heated overnight at 70° C. The solution was then cooled, the solvent evaporated, and the residue purified by preparatory LC. LCMS m/z 487.4 (MH$^+$), R$_t$ 1.62 min. An analogous method was used to prepare Example 1292 (LCMS m/z 515.3 (MH$^+$), R$_t$ 1.82 min) and Example 1293 (LCMS m/z 619.4 (MH$^+$), R$_t$ 2.04 min).

Example 1294

To a solution containing Example 1289 in MeOH was added a catalytic amount of 10% Pd/C. The atmosphere was purged with nitrogen, and the solution was left to stir overnight under a hydrogen atmosphere. At this time, the reaction mixture was filtered through a pad of Celite and concentrated. The crude amino indazole was then solubilized in DCM:MeOH:AcOH (2:2:1). Benzaldehyde (2 equivalents) and borane-pyridine were then added (8M, 10 equivalents). The mixture was left to shake overnight loosely capped. At this time, the solvent was evaporated, and the residue was purified by prep LC. LCMS m/z 506.3 (MH$^+$), R$_t$ 2.07 min. An analogous method was used to prepare Example 1295 (LCMS m/z 520.3 (MH$^+$), R$_t$ 2.11 min), Example 1296 (LCMS m/z 513.4 (MH$^+$), R$_t$ 1.85 min), Example 1297 (LCMS m/z 513.6 (MH$^+$), R$_t$ 1.93 min), and Example 1298 (LCMS m/z 546.3 (MH$^+$), R$_t$ 2.01 min).

Example 1288

5-Hydroxy-3-indazole carboxaldehyde (1 equivalent), 2-chloro-5-nitropyridine (1 equivalent), and potassium carbonate (2 equivalents) were heated overnight in DMF at 100° C. The reaction mixture was then cooled and poured into water. The aqueous phase was extracted with ethyl acetate three times, the organic layers combined, washed with brine, dried, and concentrated. This indazole ether was then reacted with the dianiline as described in Example 4 to afford the desired product. LCMS m/z 538.3 (MH$^+$), R$_t$ 1.86 min.

Example 1299

Example 1288 was solubilized in ethanol. To the solubilized compound was added a catalytic amount of 10% Pd/C. The atmosphere was purged with nitrogen, and the solution was left to stir overnight under a hydrogen atmosphere. At this time, the reaction mixture was filtered through a pad of Celite and concentrated. The residue was triturated with dichloromethane, sonicated, and filtered to provide the desired product. LCMS m/z 509.4 (MH$^+$), R$_t$ 1.62 min.

Example 1301

To a solution of Example 1299 in DCM:MeOH:AcOH (2:2:1), was added paraformaldehyde (10 equivalents) and borane-pyridine (8M, 10 equivalents). The mixture was left to shake overnight at 60° C. At this time, the solvent was evaporated, and the residue was purified by preparatory LC. LCMS m/z 537.5 (MH$^+$), R$_t$ 1.83 min.

Method A

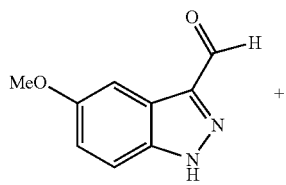

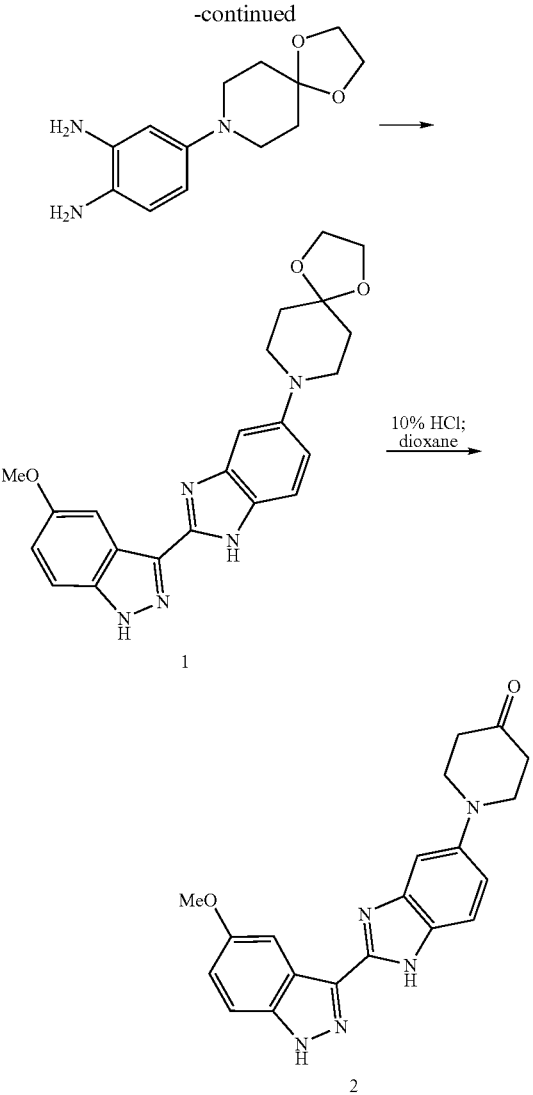

Compound 1 of Method A was synthesized as described in Example 4 and shown above. LCMS m/z 406.3 (MH$^+$), R$_t$ 2.09 min. Subsequently, compound 1 was combined with 10% HCl and dioxane and heated to 65° C. overnight. The reaction mixture was poured into NaHCO$_3$ (aq, satd) and extracted with EtOAc. The organic layer was washed twice with H$_2$O, once with brine, dried over Na$_2$SO$_4$, filtered, and concentrated to provide a brown foam (2). LCMS m/z 362.2 (MH$^+$), R$_t$ 1.96 min.

Example 1290

NaCNBH$_3$ (excess) was added to compound 2 in DMA, MeOH and AcOH. When the reaction was complete, it was quenched with H$_2$O and NaHCO$_3$ (aq, satd) and extracted with EtOAc. The organic layer was washed twice with H$_2$O, once with brine, dried over Na$_2$SO$_4$, filtered, and concentrated to provide a yellow solid. LCMS m/z 433.4 (MH$^+$), R$_t$ 1.74 min. An analogous method was used to prepare Example 1302 (LCMS m/z 391.4 (MH$^+$), R$_t$ 1.73 min), Example 1303 (LCMS m/z 474.5 (MH$^+$), R$_t$ 1.61 min), Example 1304 (LCMS m/z 461.5 (MH$^+$), R$_t$ 1.83 min), Example 1305 (LCMS m/z 474.5 (MH$^+$), R$_t$ 1.64 min), Example 1306

(LCMS m/z 460.4 (MH⁺), R_t 1.66 min), Example 1307
(LCMS m/z 460.4 (MH⁺), R_t 2.15 min), Example 1308
(LCMS m/z 460.4 (MH⁺), R_t 1.85 min), Example 1309
(LCMS m/z 461.4 (MH⁺), R_t 1.91 min), Example 1332
(LCMS m/z 430.2 (MH⁺), R_t 1.87 min), Example 1332
(LCMS m/z 430.2 (MH⁺), R_t 1.87 min), Example 1333
(LCMS m/z 459.3 (MH⁺), R_t 2.08 min), Example 1334
(LCMS m/z 448.3 (MH⁺), R_t 1.81 min), and Example 1335
(LCMS m/z 430.3 (MH⁺), R_t 1.82 min).

Method B

Step 1

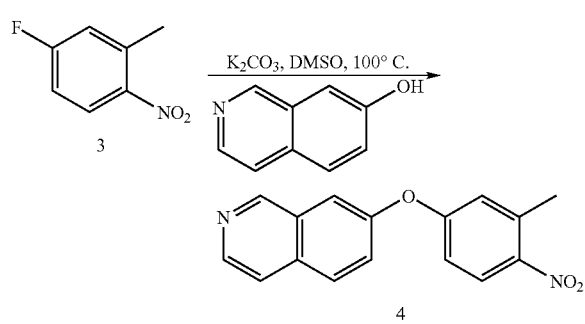

Powdered, flame-dried K₂CO₃ (1.2 equivalents) was added to 7-hydroxyisoquinoline (1.1 equivalents) in DMSO. After 2 hours, 5-fluoro-2-nitrotoluene (1.0 eq) was added. The reaction was heated to 100° C. for 2 hours at which time the reaction was complete. The reaction mixture was poured into MTBE, and was washed with H₂O four times and then was washed with brine. The organic layer was dried over Na₂SO₄, filtered, and concentrated to provide a yellow solid. LCMS m/z 281.2 (MH⁺), R_t 2.28 min.

Step 2

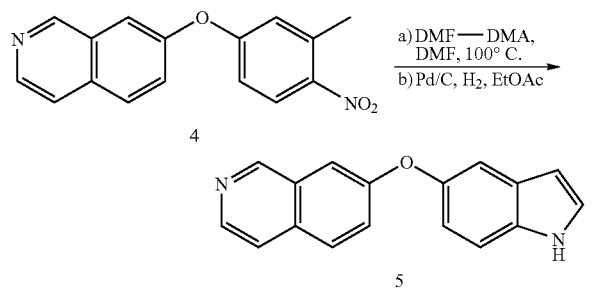

Compound 4 was heated in 1:1 DMF-DMA and DMF at 100° C. overnight. The reaction mixture was then concentrated, and the red gum was dissolved in EtOH. The reaction mixture was purged with N₂ and then Pd/C (10%, wet) was added. After purging for several more minutes with N₂, the reaction vessel was evacuated and then purged with H₂. This was repeated twice more. After 24 hours, the reaction was filtered through Celite and concentrated. The crude material was purified by column chromatography (20% EtOAc/Hex) to give the product 5 as a brown gum. LCMS m/z 261.2 (MH⁺), R_t 2.15 min.

Step 3

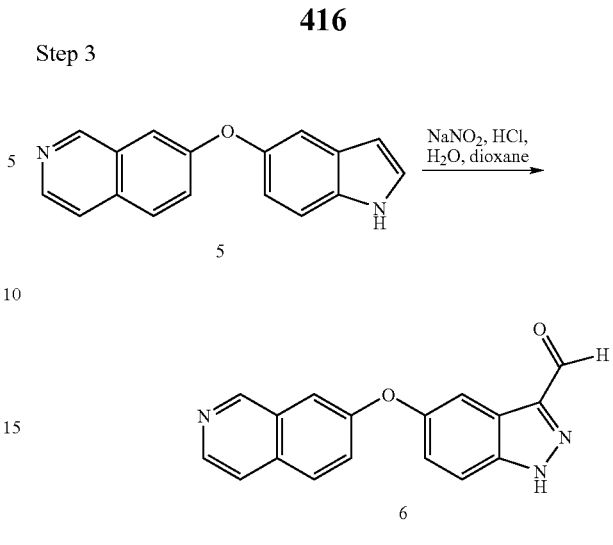

Compound 5 in dioxane was added to NaNO₂ (5.1 equivalents) in HCl and H₂O. The reaction stirred for 4 hours at room temperature. The reaction mixture was extracted twice with EtOAc, and then the aqueous layer was made basic to pH 8 with NaHCO₃ (aq, satd) which caused a precipitate to form. The resulting solid was filtered and washed with H₂O. The brown solid was then purified by column chromatography (5-10% MeOH/CH₂Cl₂) to give compound 6. LCMS m/z 290.3 (MH⁺), R_t 1.93 min.

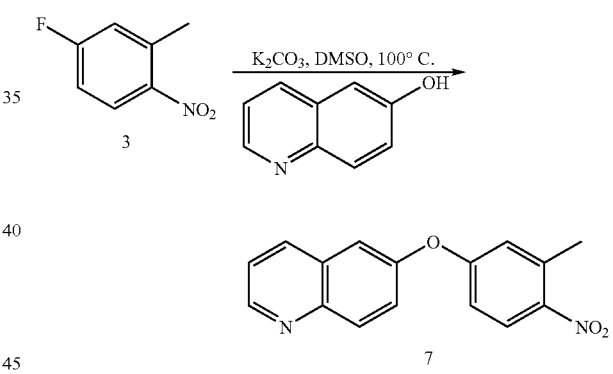

Compound 7 was synthesized using the procedure set forth in Method B, Step 1. LCMS m/z 281.2 (MH⁺), R_t 2.34 min.

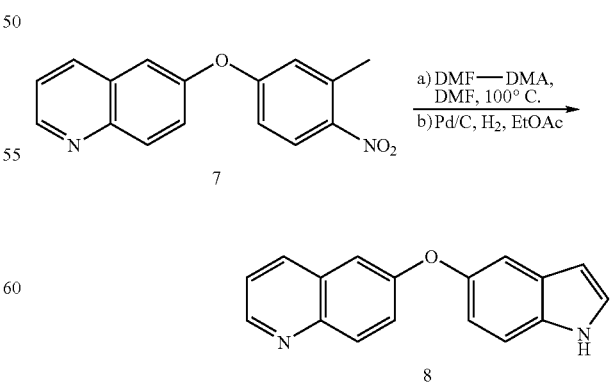

Compound 8 was synthesized using the procedure set forth in Method B, Step 2. LCMS m/z 261.2 (MH⁺), R_t 2.13 min.

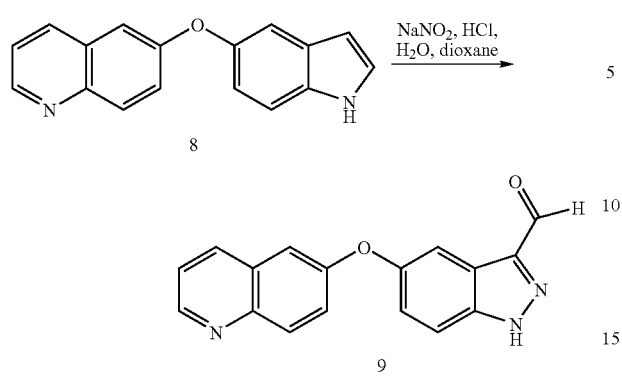

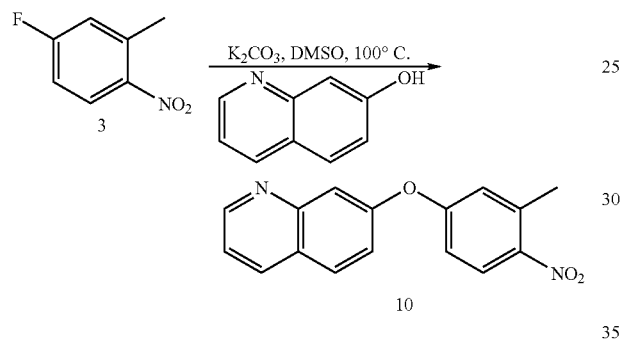

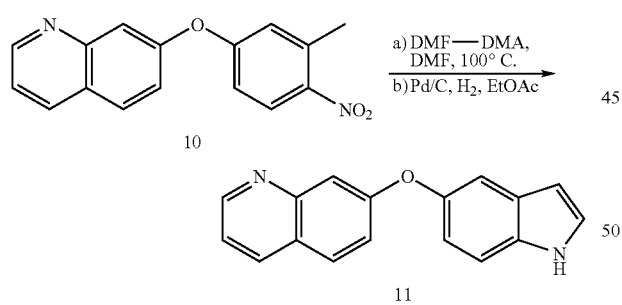

Compound 9 was synthesized using the procedure set forth in Method B, Step 3. LCMS m/z 290.2 (MH+), R$_t$ 1.88 min.

Compound 10 was synthesized using the procedure set forth in Method B, Step 1. LCMS m/z 281.2 (MH+), R$_t$ 2.24 min.

Compound 11 was synthesized using the procedure set forth in Method B, Step 2. LCMS m/z 261.2 (MH+), R$_t$ 2.12 min.

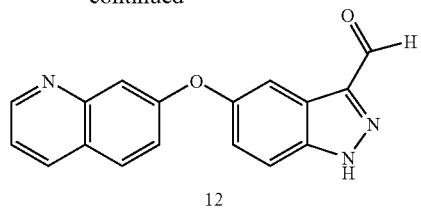

Compound 12 was synthesized using the procedure set forth in Method B, Step 3. LCMS m/z 290.3 (MH+), R$_t$ 1.95 min.

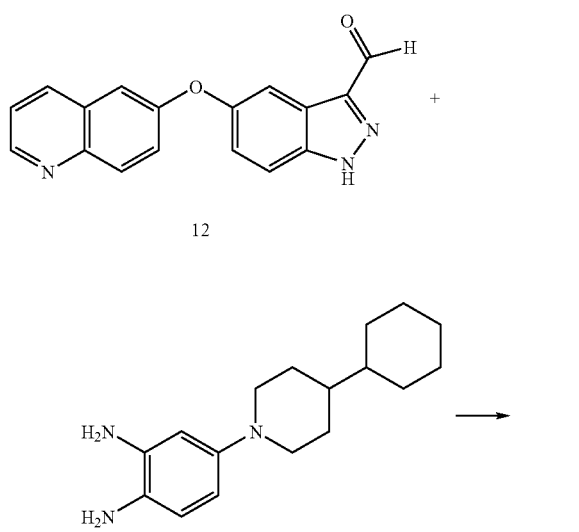

Example 1347

Example 1347 was synthesized from compound 12 and 4-(4-(piperidin-1-yl)piperidin-1-yl)benzene-1,2-diamine, as described in Example 4. LCMS m/z 544.4 (MH+), R$_t$ 2.53 min. The analogous compounds of Example 1348 (LCMS m/z 544.4 (MH+), R$_t$ 2.54 min) and Example 1349 (LCMS m/z 544.4 (MH+), R$_t$ 1.86 min) were prepared using the same procedure.

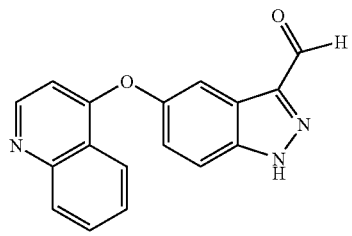

The compound shown above was synthesized using the procedure of Method B, Steps 1-3. LCMS m/z 290.0 (MH$^+$), R$_t$ 1.94 min.

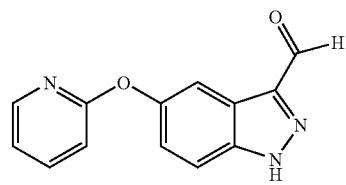

The compound shown above was synthesized using the procedure of Method B, Steps 1-3. LCMS m/z 240.0 (MH$^+$), R$_t$ 1.72 min.

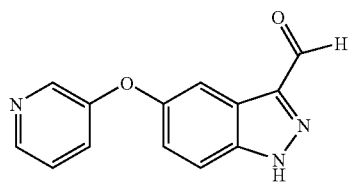

The compound shown above was synthesized using the procedure of Method B, Steps 1-3. LCMS m/z 240.0 (MH$^+$), R$_t$ 1.57 min.

Method C

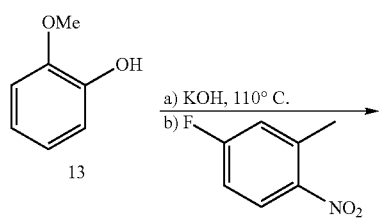

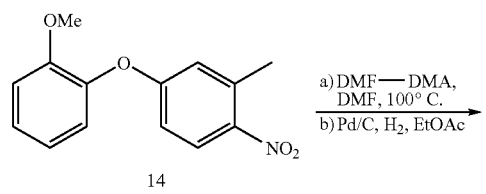

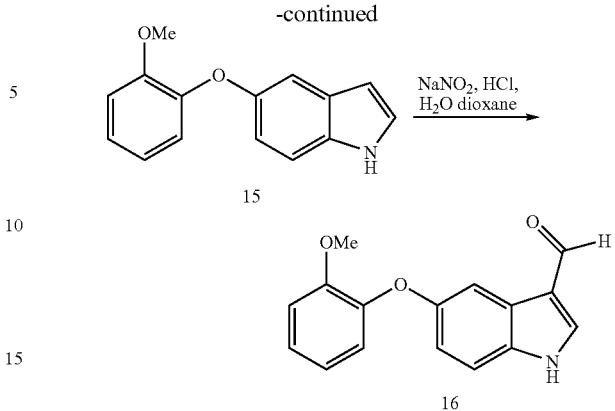

KOH (1.0 equivalent) was added to molten 2-methoxyphenol (3.0 equivalents), and the mixture was heated to 110° C. The reaction became homogeneous during this period. The reaction was cooled to 50° C. and 5-fluoro-2-nitrotoluene (1.0 equivalent) was then added. The reaction was heated to 130° C. for 1 hour after which the reaction was complete. The reaction mixture was cooled, poured into 10% NaOH, and extracted twice with Et$_2$O. The organic later was washed twice with H$_2$O and then dried over Na$_2$SO$_4$, filtered, and concentrated. The crude material was purified by column chromatography (20% CH$_2$Cl$_2$/Hex) to give 14. Compound 14 was heated in 1:1 DMF-DMA and DMF at 100° C. overnight. The reaction mixture was concentrated, and the red gum was dissolved in EtOH. The reaction mixture was purged with N$_2$ and then Pd/C (10%, wet) was added. After purging for several more minutes with N$_2$, the reaction vessel was evacuated and then purged with H$_2$. This procedure was repeated two more times. After 24 hours, the reaction was filtered through Celite and concentrated. The crude material was purified using column chromatography (20% CH$_2$Cl$_2$/Hex) to give the product 15. A mixture of compound 15 in dioxane was added to NaNO$_2$ (5.1 equivalents) in HCl and H$_2$O. The reaction was then stirred for 4 hours at room temperature. The reaction mixture was extracted twice with EtOAc, and then the aqueous layer was made basic to pH 8 with NaHCO$_3$ (aq, satd) which caused a precipitate to form. The resulting solid was filtered and washed with H$_2$O. The brown solid was then purified by column chromatography (15-20% EtOAc/Hex) to give compound 16. LCMS m/z 269.1 (MH$^+$), R$_t$ 2.63 min.

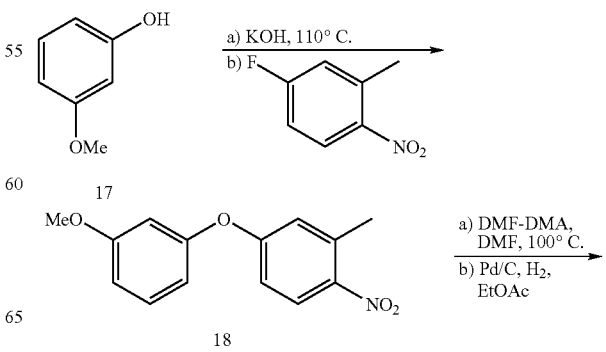

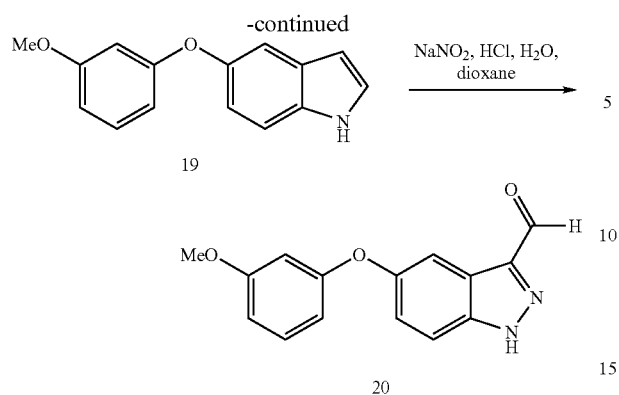
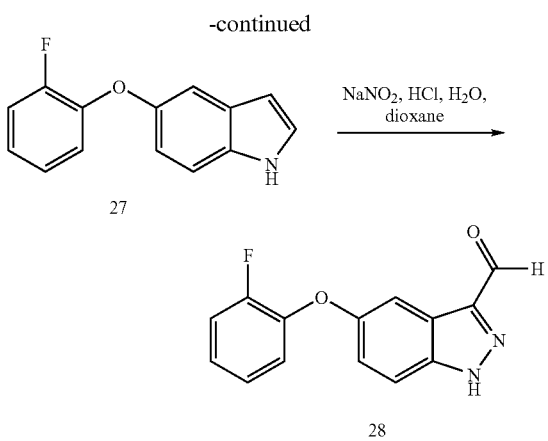
Compound 20 was synthesized using Method C (see above scheme). LCMS m/z 269.0 (MH$^+$), $R_t$ 2.77 min.
Compound 28 was synthesized using Method C (see above scheme). LCMS m/z 257.0 (MH$^+$), $R_t$ 2.74 min.
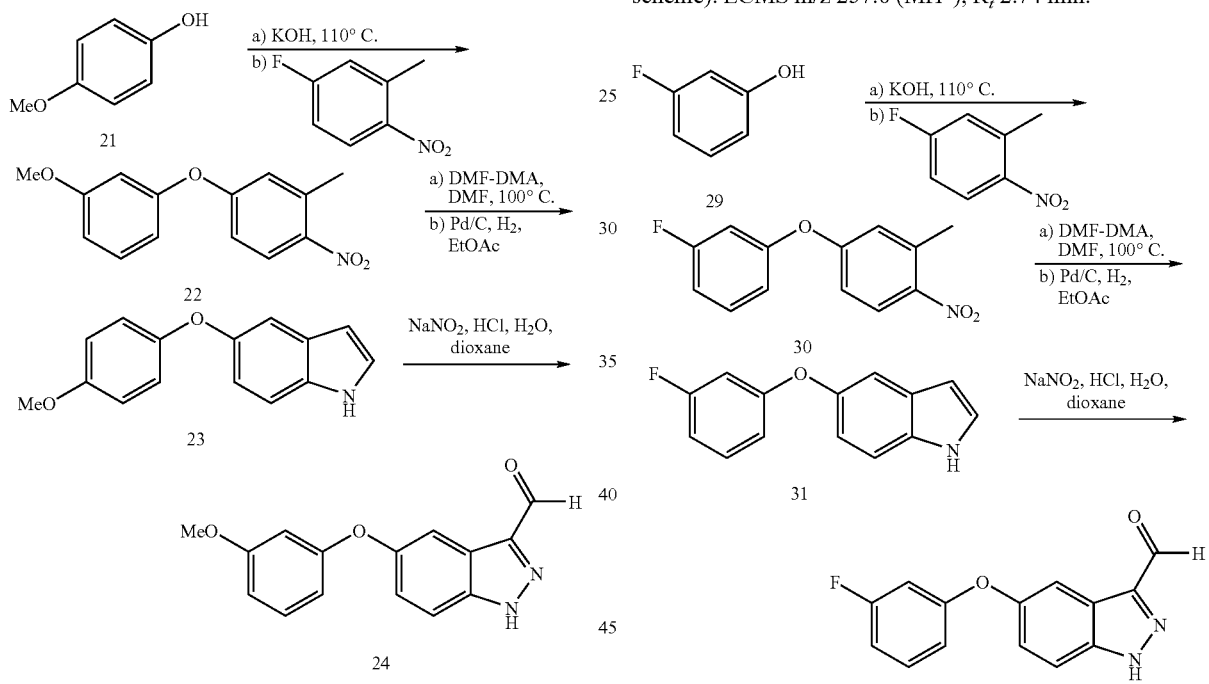
Compound 24 was synthesized using Method C (see above scheme). LCMS m/z 269.0 (MH$^+$), $R_t$ 2.65 min.
Compound 32 was synthesized using Method C (see above scheme). LCMS m/z 257.0 (MH$^+$), $R_t$ 2.83 min.
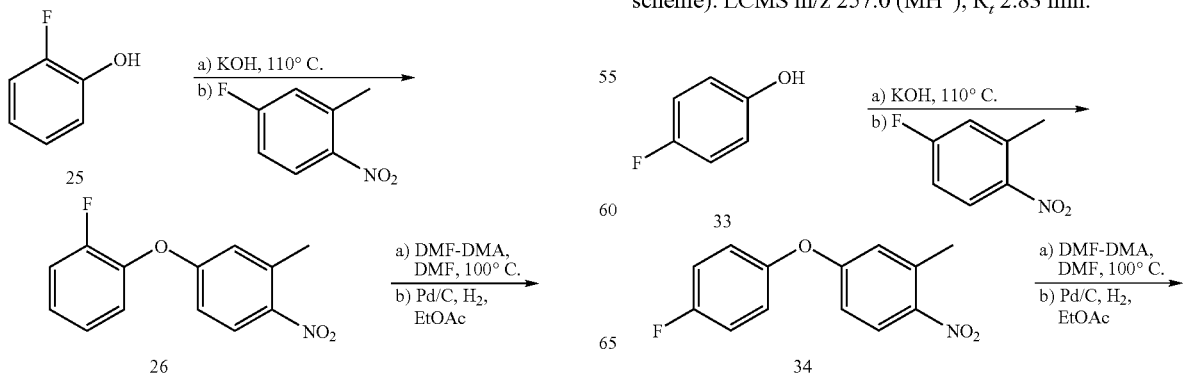

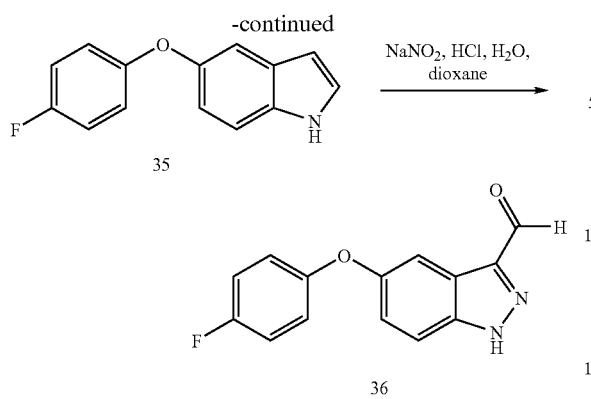

Compound 36 synthesized using Method C (see above scheme). LCMS m/z 257.0 (MH+), $R_t$ 2.81 min.

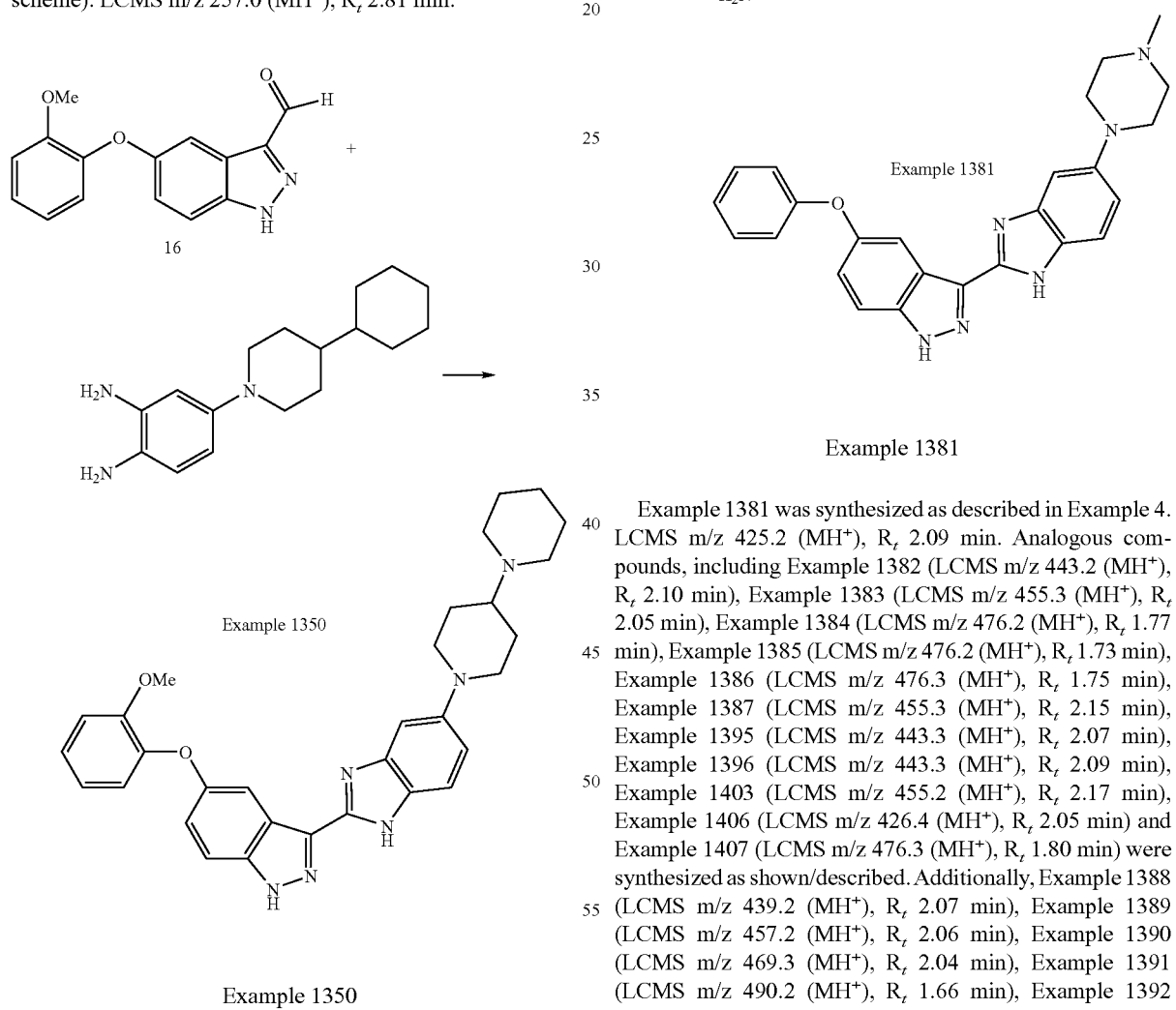

Example 1350

Utilizing the intermediate compound 16, Example 1350 was synthesized as described in Example 4. LCMS m/z 523.3 (MH+), $R_t$ 2.21 min. An analogous procedure was used to prepare Example 1399 (LCMS m/z 511.2 (MH+), $R_t$ 2.05 min), Example 1401 (LCMS m/z 511.2(MH+), $R_t$ 2.04 min), Example 1402 (LCMS m/z 523.2 (MH+), $R_t$ 2.03 min), Example 1405 (LCMS m/z 523.3 (MH+), $R_t$ 2.28 min), Example 1410 (LCMS m/z 544.4 (MH+), $R_t$ 1.89 min), and Example 1411 (LCMS m/z 494.4 (MH+), $R_t$ 1.67 min).

Example 1381

Example 1381 was synthesized as described in Example 4. LCMS m/z 425.2 (MH+), $R_t$ 2.09 min. Analogous compounds, including Example 1382 (LCMS m/z 443.2 (MH+), $R_t$ 2.10 min), Example 1383 (LCMS m/z 455.3 (MH+), $R_t$ 2.05 min), Example 1384 (LCMS m/z 476.2 (MH+), $R_t$ 1.77 min), Example 1385 (LCMS m/z 476.2 (MH+), $R_t$ 1.73 min), Example 1386 (LCMS m/z 476.3 (MH+), $R_t$ 1.75 min), Example 1387 (LCMS m/z 455.3 (MH+), $R_t$ 2.15 min), Example 1395 (LCMS m/z 443.3 (MH+), $R_t$ 2.07 min), Example 1396 (LCMS m/z 443.3 (MH+), $R_t$ 2.09 min), Example 1403 (LCMS m/z 455.2 (MH+), $R_t$ 2.17 min), Example 1406 (LCMS m/z 426.4 (MH+), $R_t$ 2.05 min) and Example 1407 (LCMS m/z 476.3 (MH+), $R_t$ 1.80 min) were synthesized as shown/described. Additionally, Example 1388 (LCMS m/z 439.2 (MH+), $R_t$ 2.07 min), Example 1389 (LCMS m/z 457.2 (MH+), $R_t$ 2.06 min), Example 1390 (LCMS m/z 469.3 (MH+), $R_t$ 2.04 min), Example 1391 (LCMS m/z 490.2 (MH+), $R_t$ 1.66 min), Example 1392 (LCMS m/z 490.3 (MH+), $R_t$ 1.67 min), Example 1393 (LCMS m/z 490.3 (MH+), $R_t$ 1.64 min), Example 1394 (LCMS m/z 469.3 (MH+), $R_t$ 2.12 min), Example 1397 (LCMS m/z 457.3 (MH+), $R_t$ 2.10 min), Example 1398 (LCMS m/z 457.3 (MH+), $R_t$ 2.12 min), Example 1404 (LCMS m/z 469.2 (MH+), $R_t$ 2.20 min), Example 1408 (LCMS m/z 440.3 (MH+), $R_t$ 1.07 min), and Example 1409 (LCMS m/z 490.3 (MH+), $R_t$ 1.76 min) were prepared.

Method D

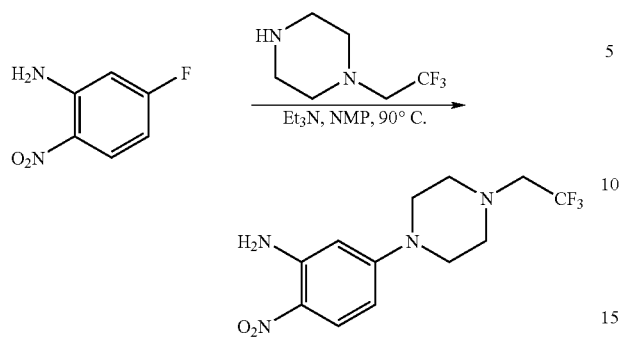

1-Trifluoroethylpiperazine (W. V. Curran, R. B. Angier *J. Org. Chem.*, 1966, 31, 3867-8), 1 equivalent), 5-fluoro-2-nitroaniline (1 equivalent), and triethylamine (2 equivalents) were taken up in NMP. The reaction was heated to 90° C. and stirred for 16 hours. The reaction mixture was then cooled to room temperature and poured into water. The resulting orange precipitate was collected by filtration and washed with diethyl ether affording the desired compound. LCMS m/z 305.1 (MH$^+$), R$_t$ 2.45 min.

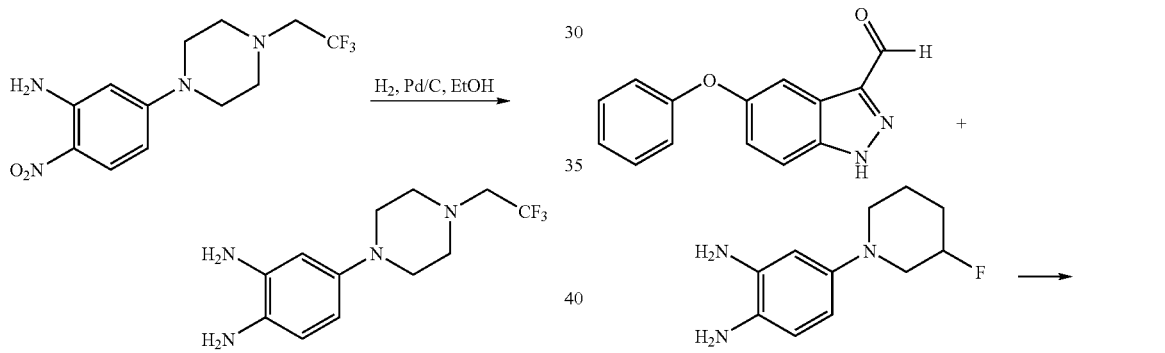

To a solution of 2-nitro-5-[4-(2,2,2-trifluoroethyl)piperazinyl]-phenylamine (1.0 equivalent) in ethanol was added 10% Pd/C. The reaction vessel was repeatedly purged with nitrogen and then stirred under a hydrogen atmosphere (1 atm) for 48 hours. The product was filtered through Celite with ethanol. The solvent was removed to provide the product which was used without purification.

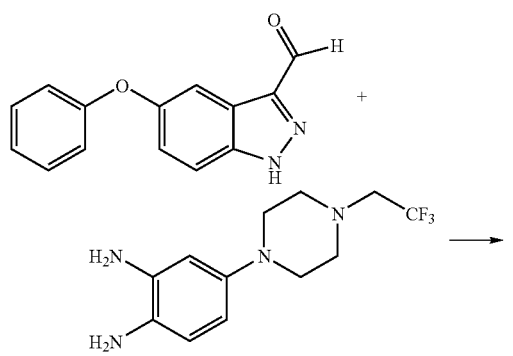

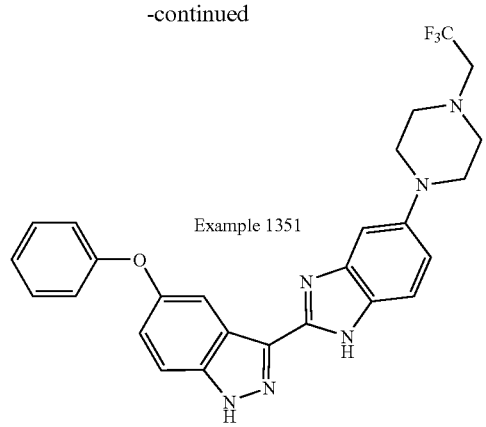

Example 1351

Example 1351 was synthesized as described in Example 4. LCMS m/z 493.2 (MH$^+$), R$_t$ 2.68 min. Analogous Example 1352 (LCMS m/z 511.2 (MH$^+$), R$_t$ 2.65 min) and Example 1400 (LCMS m/z 523.3 (MH$^+$), R$_t$ 2.61 min) were also synthesized according to the procedure described for Example 4.

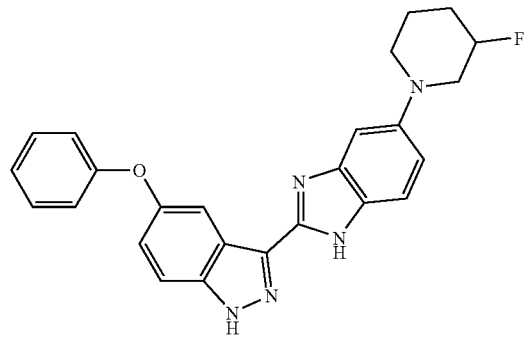

Example 1353

Example 1353 was synthesized using the procedure described in Example 4 (LCMS m/z 428.2 (MH$^+$), R$_t$ 2.67 min). Example 1354 (LCMS m/z 446.2 (MH$^+$), R$_t$ 2.66 min), Example 1355 (LCMS m/z 458.2 (MH$^+$), R$_t$ 2.58 min), Example 1356 (LCMS m/z 479.2 (MH$^+$), R$_t$ 2.07 min), Example 1357 (LCMS m/z 479.2 (MH$^+$), R$_t$ 2.00 min), Example 1358 (LCMS m/z 354.2 (MH$^+$), R$_t$ 2.16 min), Example 1376 (LCMS m/z 442.2 (MH⁺), $R_t$ 2.66 min), Example 1375 (LCMS m/z 370.2 (MH⁺), $R_t$ 2.26 min), Example 1377 (LCMS m/z 442.2 (MH⁺), $R_t$ 2.70 min), Example 1378 (LCMS m/z 372.2 (MH⁺), $R_t$ 2.33 min), Example 1379 (LCMS m/z 388.2 (MH⁺), $R_t$ 2.42 min) and Example 1380 (LCMS m/z 361.2 (MH⁺), $R_t$ 2.20 min) were also synthesized using the procedure described in Example 4.

Method E

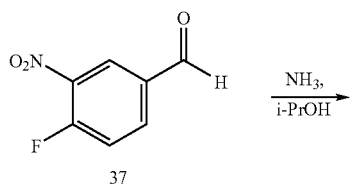

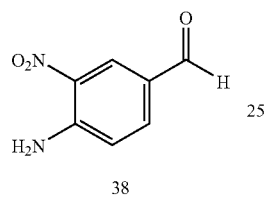

Ammonia gas was bubbled through a room temperature solution of 37 (1.0 equivalent) in isopropyl alcohol for 10 minutes. The reaction was sealed and stirred at room temperature for 24 hrs. The reaction was then concentrated and triturated with water. The resulting solid was collected and dried to give nitro-aniline 38. $R_t$=2.24 min, m/z (MH⁺)=167.2.

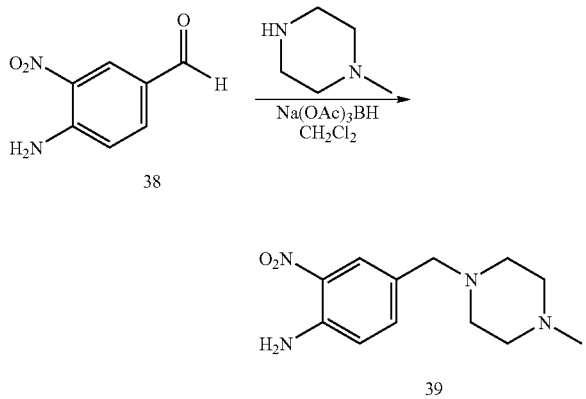

Nitro-aniline 38 (1.0 equivalent) was dissolved in CH₂Cl₂ and treated with N-methyl piperizine (2.0 equivalents) at room temperature. To this solution was added sodium triacetoxyborohydride (2.5 equivalents). The reaction was stirred at room temperature for 12 hours and then quenched with aqueous 1N NaOH. The organic layer was separated and aqueous extracted twice with CH₂Cl₂. The combined organic layers were washed with water and dried (MgSO₄). Concentration followed by silica gel chromatography (10% MeOH/ CH₂Cl₂) provided compound 39 as an amorphous yellow solid. $R_t$=1.32 min, m/z (MH⁺)=251.1.

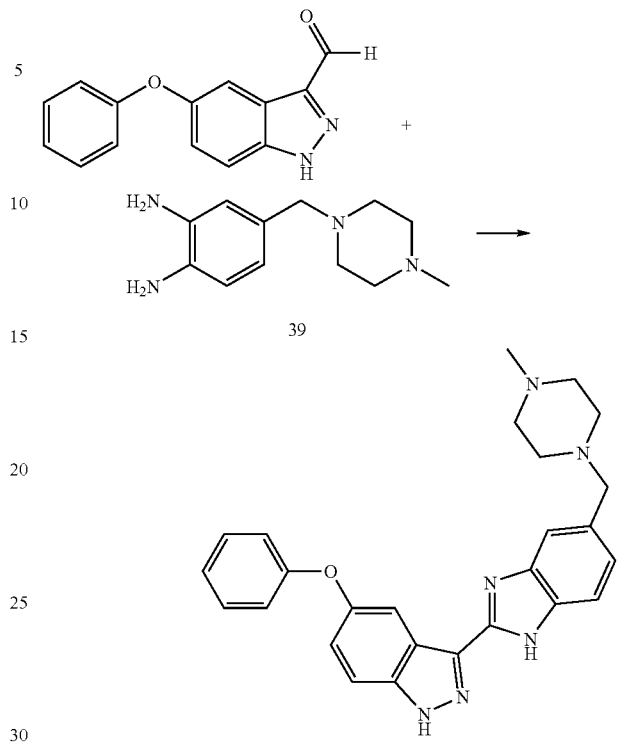

Example 1359

Example 1359 was synthesized using the procedure described in Example 4 and shown above. LCMS m/z 439.2 (MH⁺), $R_t$ 2.08 min. Example 1360 (LCMS m/z 457.2 (MH⁺), $R_t$ 2.14 min), Example 1361 (LCMS m/z 469.3 (MH⁺), $R_t$ 2.16 min), Example 1362 (LCMS m/z 490.3 (MH⁺), $R_t$ 1.77 min), Example 1363 (LCMS m/z 490.3 (MH⁺), $R_t$ 1.72 min), Example 1367 (LCMS m/z 453.3 (MH⁺), $R_t$ 2.19 min), Example 1368 (LCMS m/z 453.3 (MH⁺), $R_t$ 2.20 min), Example 1373 (LCMS m/z 469.3 (MH⁺), $R_t$ 2.08 min), Example 1374 (LCMS m/z 469.3 (MH⁺), $R_t$ 2.10 min), Example 1364 (LCMS m/z 347.3 (MH⁺), $R_t$ 1.03 min), Example 1365 (LCMS m/z 365.3 (MH⁺), $R_t$ 1.77 min), Example 1366 (LCMS m/z 381.2 (MH⁺), $R_t$ 1.85 min), Example 1369 (LCMS m/z 383.2 (MH⁺), $R_t$ 1.81 min), Example 1370 (LCMS m/z 399.2 (MH⁺), $R_t$ 1.98 min), Example 1371 (LCMS m/z 372.3 (MH⁺), $R_t$ 1.76 min), and Example 1372 (LCMS m/z 372.3 (MH⁺), $R_t$ 1.76 min) were also synthesized using the procedure described in Example 4.

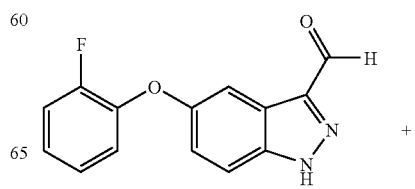

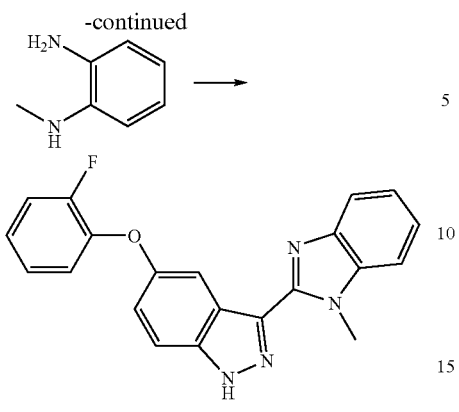

Example 1412

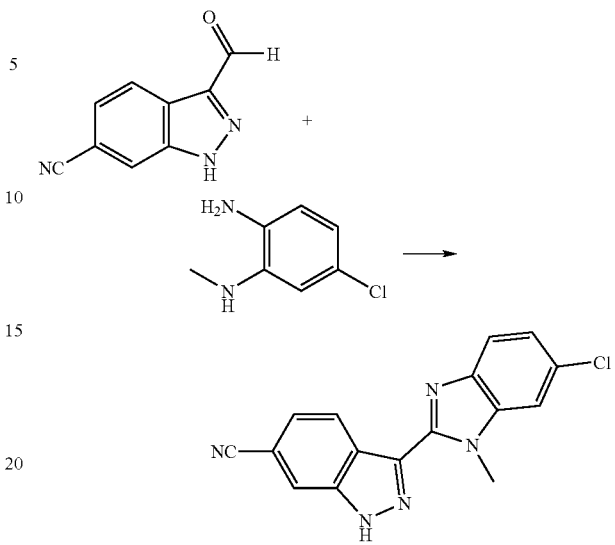

Example 1431

Example 1412 synthesized using the procedure described in Example 4 as shown above. LCMS m/z 359.3 (MH$^+$), R$_t$ 2.59 min. Example 1413 (LCMS m/z 371.3 (MH$^+$), R$_t$ 2.50 min), Example 1414 (LCMS m/z 341.3 (MH$^+$), R$_t$ 2.61 min), Example 1415 (LCMS m/z 267.3 (MH$^+$), R$_t$ 2.06 min), Example 1416 (LCMS m/z 309.3 (MH$^+$), R$_t$ 1.95 min), Example 1417 (LCMS m/z 355.3 (MH$^+$), R$_t$ 2.51 min), Example 1418 (LCMS m/z 274.2 (MH$^+$), R$_t$ 2.01 min), Example 1419 (LCMS m/z 274.3 (MH$^+$), R$_t$ 2.09 min), Example 1420 (LCMS m/z 371.3 (MH$^+$), R$_t$ 2.57 min), Example 1421 (LCMS m/z 371.3 (MH$^+$), R$_t$ 2.55 min), Example 1422 (LCMS m/z 359.3 (MH$^+$), R$_t$ 2.64 min), Example 1423 (LCMS m/z 359.2 (MH$^+$), R$_t$ 2.51 min), Example 1424 (LCMS m/z 342.2 (MH$^+$), R$_t$ 1.85 min), Example 1425 (LCMS m/z 392.2 (MH$^+$), R$_t$ 2.02 min), Example 1426 (LCMS m/z 342.2 (MH$^+$), R$_t$ 1.74 min), Example 1427 (LCMS m/z 392.2 (MH$^+$), R$_t$ 1.89 min), Example 1428 (LCMS m/z 392.3 (MH$^+$), R$_t$ 2.02 min), Example 1429 (LCMS m/z 283.2 (MH$^+$), R$_t$ 2.22 min), Example 1430 (LCMS m/z 385.3 (MH$^+$), R$_t$ 2.44 min), Example 1457 (LCMS m/z 317.2 (MH$^+$), R$_t$ 2.48 min), Example 1458 (LCMS m/z 294.2 (MH$^+$), R$_t$ 2.27 min), Example 1459 (LCMS m/z 279.2 (MH$^+$), R$_t$ 2.11 min), Example 1460 (LCMS m/z 267.2 (MH$^+$), R$_t$ 2.07 min), Example 1461 (LCMS m/z 355.2 (MH$^+$), R$_t$ 2.60 min), Example 1462 (LCMS m/z 461.2 (MH$^+$), R$_t$ 3.01 min), Example 1463 (LCMS m/z 283.2 (MH$^+$), R$_t$ 2.20 min) and Example 1464 (LCMS m/z 285.2 (MH$^+$), R$_t$ 2.16 min) were also synthesized using the procedure described in Example 4.

Example 1431 was synthesized using the procedure described in Example 4. LCMS m/z 308.2 (MH$^+$), R$_t$ 2.74 min. Example 1432 (LCMS m/z 376.2 (MH$^+$), R$_t$ 2.20 min was also synthesized using the procedure.

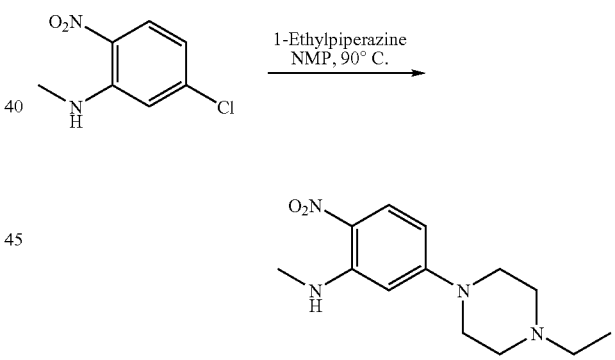

5-Chloro-N-methyl-2-nitrobenzamine (1.0 equivalent) and 1-ethylpiperazine (6.1 equivalent) in NMP were heated overnight at 90° C. A precipitate formed when the reaction mixture was poured into H$_2$O. The solid was filtered and dried to give the product as a dark yellow solid. LCMS m/z 265.3 (MH$^+$), R$_t$ 1.61 min.

5-Chloro-N-methyl-2-nitrobenzamine was reduced using the procedure as described in Method D. LCMS m/z 157.2 (MH$^+$), R$_t$ 1.73 min.

-continued

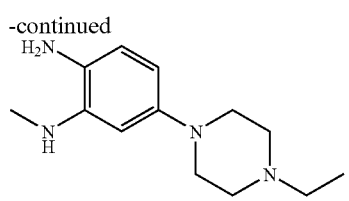

[5-(4-Ethylpiperazinyl)-2-nitrophenyl]methylamine was reduced as described in Method D. LCMS m/z 235.2 (MH⁺), $R_t$ 0.77 min.

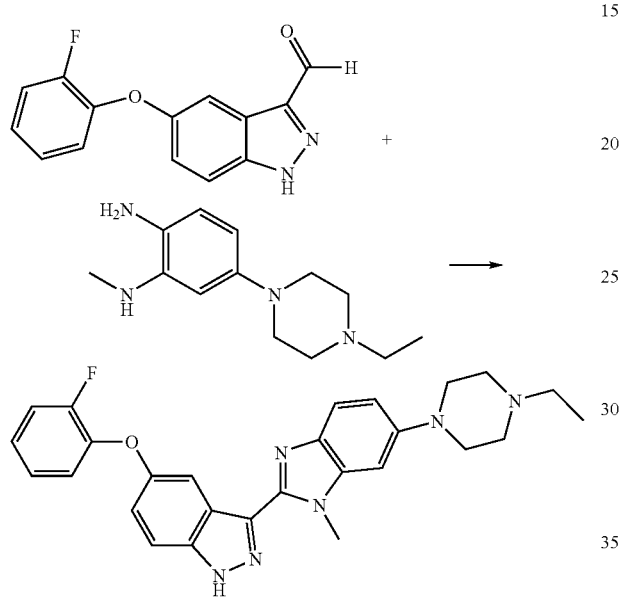

Example 1433

Example 1433

Example 1433 was synthesized using the procedure described in Example 4 as shown above. LCMS m/z 471.2 (MH⁺), $R_t$ 2.18 min. Example 1434 (LCMS m/z 483.3 (MH⁺), $R_t$ 2.18 min), Example 1435 (LCMS m/z 453.3 (MH⁺), $R_t$ 2.19 min), Example 1436 (LCMS m/z 379.3 (MH⁺), $R_t$ 1.84 min), Example 1437 (LCMS m/z 421.3 (MH⁺), $R_t$ 1.68 min), Example 1438 (LCMS m/z 467.3 (MH⁺), $R_t$ 2.14 min), Example 1439 (LCMS m/z 467.3 (MH⁺), $R_t$ 2.17 min), Example 1440 (LCMS m/z 386.3 (MH⁺), $R_t$ 1.79 min), Example 1441 (LCMS m/z 483.3 (MH⁺), $R_t$ 2.20 min), Example 1442 (LCMS m/z 483.3 (MH⁺), $R_t$ 2.19 min), Example 1443 (LCMS m/z 471.3 (MH⁺), $R_t$ 2.13 min), Example 1444 (LCMS m/z 471.3 (MH⁺), $R_t$ 2.13 min), Example 1445 (LCMS m/z 504.4 (MH⁺), $R_t$ 1.84 min), Example 1446 (LCMS m/z 504.3 (MH⁺), $R_t$ 1.72 min), Example 1447 (LCMS m/z 504.4 (MH⁺), $R_t$ 1.75 min), Example 1448 (LCMS m/z 395.3 (MH⁺), $R_t$ 1.86 min), Example 1449 (LCMS m/z 497.3 (MH⁺), $R_t$ 2.13 min), Example 1450 (LCMS m/z 429.3 (MH⁺), $R_t$ 2.05 min), Example 1451 (LCMS m/z 406.3 (MH⁺), $R_t$ 1.89 min), Example 1452 (LCMS m/z 391.4 (MH⁺), $R_t$ 1.80 min), Example 1453 (LCMS m/z 379.3 (MH⁺), $R_t$ 1.77 min), Example 1454 (LCMS m/z 467.3 (MH⁺), $R_t$ 2.22 min), Example 1455 (LCMS m/z 573.2 (MH⁺), $R_t$ 2.55 min), and Example 1456 (LCMS m/z 395.3 (MH⁺), $R_t$ 1.85 min) were also synthesized using the procedure described in Example 4.

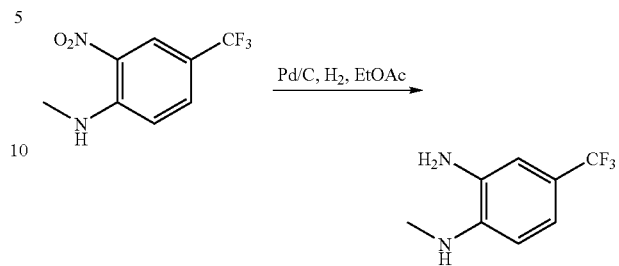

N-Methyl-2-nitro-4-(trifluoromethyl)aniline (1.0 equivalent) was reduced as described in Method D. LCMS m/z 191.2 (MH⁺), $R_t$ 2.20 min.

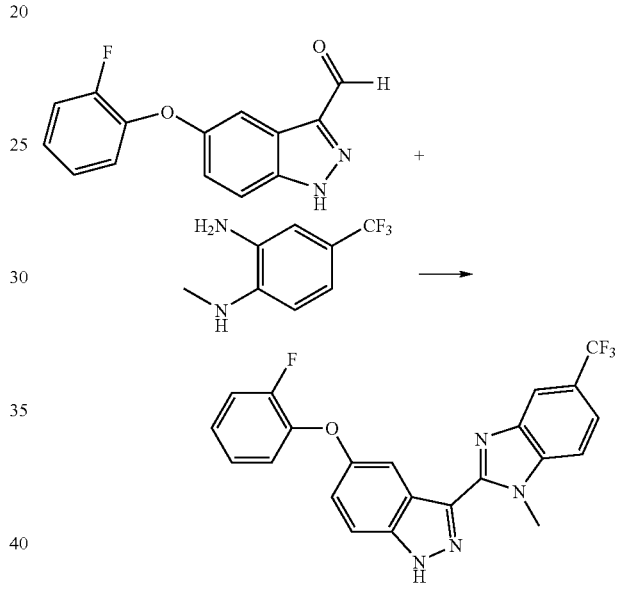

Example 1465

Example 1465

Example 1465 was synthesized using the procedure described in Example 4 as shown above. LCMS m/z 427.2 (MH⁺), $R_t$ 3.52 min. Example 1466 (LCMS m/z 439.3 (MH⁺), $R_t$ 3.35 min), Example 1467 (LCMS m/z 409.3 (MH⁺), $R_t$ 3.55 min), Example 1468 (LCMS m/z 335.3 (MH⁺), $R_t$ 3.20 min), Example 1469 (LCMS m/z 377.3 (MH⁺), $R_t$ 2.75 min), Example 1470 (LCMS m/z 423.3 (MH⁺), $R_t$ 3.46 min), Example 1471 (LCMS m/z 423.3 (MH⁺), $R_t$ 3.50 min), Example 1472 (LCMS m/z 342.3 (MH⁺), $R_t$ 3.17 min), Example 1473 (LCMS m/z 342.3 (MH⁺), $R_t$ 3.21 min), Example 1474 (LCMS m/z 439.3 (MH⁺), $R_t$ 3.44 min), Example 1475 (LCMS m/z 439.3 (MH⁺), $R_t$ 3.38 min), Example 1476 (LCMS m/z 427.3 (MH⁺), $R_t$ 3.56 min), Example 1477 (LCMS m/z 427.3 (MH⁺), $R_t$ 3.48 min), Example 1478 (LCMS m/z 410.3 (MH⁺), $R_t$ 2.64 min), Example 1479 (LCMS m/z 460.3 (MH⁺), $R_t$ 2.87 min), Example 1480 (LCMS m/z 410.3 (MH⁺), $R_t$ 2.52 min), Example 1481 (LCMS m/z 460.3 (MH⁺), $R_t$ 2.65 min), Example 1482 (LCMS m/z 460.3 (MH⁺), $R_t$ 2.67 min), Example 1483 (LCMS m/z 460.3

(MH+), R$_t$ 2.72 min), Example 1484 (LCMS m/z 351.3 (MH+), R$_t$ 3.40 min) and Example 1485 (LCMS m/z 453.3 (MH+), R$_t$ 3.32 min) were also synthesized using the procedure described in Example 4.

ASSAY PROCEDURES

In vitro Kinase Assays for Receptor Tyrosine Kinases

The kinase activity of various protein tyrosine kinases can be measured by providing ATP and a suitable peptide or protein tyrosine-containing substrate, and assaying the transfer of phosphate moiety to the tyrosine residue. Recombinant proteins corresponding to the cytoplasmic domains of the flt-1 (VEGFR1), flt-3, Flk-1, Tie-2, PDGF, and bFGF receptors were expressed in Sf9 insect cells using a Baculovirus expression system (InVitrogen) and purified via Glu antibody interaction (for Glu-epitope tagged constructs) or by Metal Ion Chromatography (for His$_6$ (SEQ ID NO: 1) tagged constructs). For each assay, test compounds were serially diluted in DMSO then mixed with an appropriate kinase reaction buffer plus ATP. Kinase protein and an appropriate biotinylated peptide substrate were added to give a final volume of 50-100 µL, reactions were incubated for 1-3 hours at room temperature and stopped by the addition of 25-50 µL of 45 mM EDTA, 50 mM Hepes pH 7.5. Stopped reaction mix (75 µL) was transferred to a streptavidin coated microtiter plate (Boehringer Mannheim) and incubated for 1 hour. Phosphorylated peptide product was measured with the DELFIA time-resolved fluorescence system (Wallac or PE Biosciences), using a Eu-labeled anti-phosphotyrosine antibody PT66 with the modification that the DELFIA assay buffer was supplemented with 1 mM MgCl$_2$ for the antibody dilution. Time resolved fluorescence was read on a Wallac 1232 DELFIA fluorometer or a PE Victor II multiple signal reader. The concentration of each compound for 50% inhibition (IC$_{50}$) was calculated by non-linear regression using XL Fit data analysis software.

Flt-1, Flk-1, Tie-2, and bFGFR kinases were assayed in 50 mM Hepes pH 7.0, 2 mM MgCl$_2$, 10 mM MnCl$_2$, 1 mM NaF, 1 mM DTT, 1 mg/ml BSA, 2 µM ATP, and 0.20-0.50 µM corresponding biotinylated peptide substrate. Flt-1, Flk-1, Tie-2, and bFGFR kinases were added at 0.1 µg/mL, 0.05 µg/mL, or 0.1 µg/mL respectively. For the PDGFR kinase assay, 120 µg/mL enzyme with the same buffer conditions as above was used except for changing ATP and peptide substrate concentrations to 1.4 µM ATP, and 0.25 µM biotin -GGLFDDPSYVNVQNL-NH$_2$ (SEQ ID NO: 2) peptide substrate.

In-vitro Assay for c-ABL Kinase

The kinase activity of various protein tyrosine kinases can be measured by providing ATP and a suitable peptide or protein tyrosine-containing substrate, and assaying the transfer of phosphate moiety to the tyrosine residue. Recombinant protein corresponding to c-ABL was expressed in Sf9 insect cells using a Baculovirus expression system (InVitrogen) and purified via Glu antibody interaction (for Glu-epitope tagged construct). For each assay, test compounds were serially diluted in DMSO and then mixed with kinase reaction buffer plus $^{33}$P-ATP. Kinase protein and a biotinylated peptide substrate were added to give a final volume of 250 µL, reactions were incubated for 34 hours at room temperature and stopped by the addition of 100 µL of 0.2 M EDTA, 50 µM ATP, and PBS. Stopped reaction mix (100 µL) was transferred to a streptavidin-coated microtiter plate (Boehringer Mannheim) and incubated for 30 to 45 minutes. The plates were washed with PBS, Microscint scintillation fluid (200 µL) was added to the wells, and the plates were shaken for 20 minutes. Phosphorylated peptide product was measured on Top Count.

C-ABL was assayed in 50 mM Tris-HCl pH7.5, 10 mM MgCl$_2$, 30 mM MnCl$_2$, 2 mM DTT, 1 mM EDTA, 25 mM beta-glycerol phosphate, 0.01% BSA/PBS, 0.5 uM peptide substrate (biotin-GGGGEAIYAAPFAKKK—NH$_2$ (SEQ ID NO: 3)), and 1 nM c-ABL.

In-vitro Assay for c-Kit and FLT-3 Kinase

The kinase activity of c-Kit and FLT-3 were measured by providing ATP and a peptide or protein containing a tyrosine amino acid residue for phosphorylation, and assaying for the transfer of phosphate moiety to the tyrosine residue. Recombinant proteins corresponding to the cytoplasmic domains of the c-Kit and FLT-3 receptors were purchased (Proquinase). For testing, an exemplary compound, for example 4-amino-5-fluoro-3-[5-(4-methylpiperazin-1-yl)-1H -benzimidazol-2-yl]quinolin-2(1H)-one, was diluted in DMSO and then mixed with the kinase reaction buffer described below plus ATP. The kinase protein (c-Kit or FLT-3) and the biotinylated peptide substrate (biotin-GGLFDDPSYVNVQNL-NH2 (SEQ ID NO: 2)) were added to give a final volume of 100 µL. These reactions were incubated for 2 hours at room temperature and then stopped by addition of 50 µL of 45 mM EDTA, 50 mM HEPES, pH 7.5. The stopped reaction mixture (75 µL) was transferred to a streptavidin-coated microtiter plate (Boehringer Mannheim) and incubated for 1 hour. Phosphorylated peptide product was measured with the DELPHIA time-resolved fluorescence system (Wallac or PE Biosciences), using a Europium-labeled anti-phosphotyrosine antibody, PT66, with the modification that the DELFIA assay buffer was supplemented with 1 mM MgCl$_2$ for the antibody dilution. Time resolved fluorescence values were determined on a Wallac 1232 DELFIA fluorometer or a PE Victor II multiple signal reader. The concentration of each compound for 50% inhibition (IC$_{50}$) was calculated employing non-linear regression using XL Fit data analysis software.

FLT-3 and c-Kit kinases were assayed in 50 mM Hepes pH 7.5, 1 mM NaF, 2 mM MgCl$_2$, 10 mM MnCl$_2$ and 1 mg/mL BSA, 8 µM ATP and 1 µM of corresponding biotinylated peptide substrate (biotin-GGLFDDPSYVNVQNL-NH2 (SEQ ID NO: 2)). The concentration of FLT-3 and c-Kit kinases were assayed at 2 nM.

The kinase activity of various protein serine/threonine kinases can be measured by providing ATP and a suitable peptide or protein serine/threonine containing substrate, and assaying the transfer of phosphate moiety to the serine or threonine residue. Recombinant proteins containing the kinase domains of GSK-3, NEK-2, and CHK 1 enzymes were expressed in Sf9 insect cells using a Baculovirus expression system (InVitrogen) and purified via Glu antibody interaction (for Glu-epitope tagged constructs) or by Metal Ion Chromatography (for His$_6$ (SEQ ID NO: 1) tagged constructs). The purified cdc 2 enzyme used in the assay is commercially available and was purchased from New England Bio Labs. For each assay, test compounds were serially diluted in DMSO then mixed with an appropriate kinase reaction buffer plus $^{32}$P g-labeled ATP. Kinase protein and an appropriate biotinylated peptide substrate were added to give a final volume of 100 µL. Reactions were incubated for 1-2 hours at room temperature and stopped by the addition of 50 µL of a solution of 45 mM EDTA, 50 mM Hepes pH 7.5, 50 µL unlabelled ATP. Stopped reaction mix (75 µL) was transferred to a streptavidin coated microtiter plate (Boehringer Mannheim) and incubated for 1 hour. Streptavidin plates were washed with PBS, diluted with 200 µL Microscint 20 scintillation fluid, sealed, and counted using TopCount. The concentration of each compound for 50% inhibition ($IC_{50}$) was calculated by non-linear regression using XL Fit data analysis software.

Each of the compounds produced in Examples 1-728 were synthesized and assayed using the procedures described above. The majority of the exemplary compounds displayed an $IC_{50}$ value of less than 10 μM with respect to VEGFR1, Flk-1, bFGF, Tie-2, CHK-1, cdc2, GSK-3, NEK-2, c-ABL, and/or PDGF. In addition, many of the exemplary compounds exhibited $IC_{50}$ values in the nM range and showed potent activity with respect to VEGFR1, Flk-1, bFGF, Tie-2, CHK-1, cdc2, GSK-3, NEK-2, and PDGF with $IC_{50}$ values of less than 1 μM. The other examples also exhibited such activity with respect to VEGFR1, Flk-1, bFGF, Tie-2, CHK-1, cdc2, GSK-3, NEK-2, and PDGF or will be shown to exhibit such activity. The exemplary compounds also exhibit inhibition activity with respect to KDR.

Many of Example compounds 729-1485 were tested and found to exhibit significant activity with an $IC_{50}$ of less than 10 μM with respect to inhibition of c-ABL. Many of Example compounds 729 to 1199 also exhibited significant activity with an $IC_{50}$ of less than 10 μM with respect to one or more of VEGFR1, Flk-1, bFGF, Tie-2, CHK-1, cdc2, GSK-3, NEK-2, and PDGF. Many of the other exemplary compounds have been shown or will be shown to exhibit activity when tested with the c-ABL assay described above.

Many of the Examples 1-1485 also exhibited inhibitory activity at less than 10 uM against other kinases such as CDC7, CSF1R and c-KIT. Many of the Examples 1-1485 also exhibited inhibitory activity at less than 1 uM against at least one of the kinases selected from VEGFR1, Flk-1, bFGF, Tie-2, CHK-1, cdc2, GSK-3, NEK-2, PDGF, CDC7, CSF1R, cABL, and c-KIT. Many of the Examples 1-1485 also exhibited inhibitory activity at less than 0.1 uM against at least one of the kinases selected from VEGFR1, Flk1, bFGF, Tie-2, CHK-1, cdc2, GSK-3, NEK-2, PDGF, CDC7, CSF1R, cABL, and c-KIT.

Each of Examples 1-728 and many of the other examples exhibited activity in one or more important assays. Many of the other exemplary compounds will be shown to exhibit activity in these assays. Many of Examples 729-1485 also exhibited activity in one or more of the assays described above. For this reason, each of the Exemplary compounds is both individually preferred and is preferred as a group. One, two, or more compounds of the invention may be used in combination in pharmaceutical formulations, medicaments, and in methods of treating subjects. Furthermore, each of the $R^1$-$R^{10}$ groups of the exemplary compounds is preferred individually and as a member of a group.

In one embodiment, the invention provides a method of inhibiting flt-1 (VEGFR1). The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting flt-3. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting KDR (VEGFR2). The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting Flk-1. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting bFGFR. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting GSK-3. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting NEK-2. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting CHK-1. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting cdc 2. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting Tie-2. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting c-ABL. The method includes administering an effective amount of a compound, a tautomer of the compound, a pharmaceutically acceptable salt of the compound, or a pharmaceutically acceptable salt of the tautomer of any of the embodiments of the compounds set forth herein to a subject, such as a human, in need thereof. In some embodiments, the compound, tautomer, pharmaceutically acceptable salt of the compound, or pharmaceutically acceptable salt of the tautomer has an $IC_{50}$ of less than 10 micromolar, and in some embodiments less than 1 micromolar, with respect to c-ABL. In some embodiments, the invention provides a method of treating a cancer such as chronic myelogeneous leukemia, acute lymphoblastic leukemia, or acute myeloblastic leukemia. In such methods, an effective amount of a compound according to any of the embodiments described herein is administered to a subject, such as a human cancer patient. In some embodiments the patient has a reciprocal translocation between chromosome 9 and 22.

In one embodiment, the invention provides a method of inhibiting PDGF. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting bFGF. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting a serine/threonine kinase. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting a tyrosine kinase. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting a cdc7. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting cKit. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

In one embodiment, the invention provides a method of inhibiting CSF1R. The method includes administering an effective amount of a compound, or a pharmaceutically acceptable salt thereof, of any of the embodiments of the first, second, third, fourth, fifth, sixth, seventh, eighth, and/or ninth groups of compounds of formula I to a subject, such as a human, in need thereof.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the following claims.

What is claimed is:

1. A method for inhibiting c-ABL in a patient in need of c-ABL inhibitors, comprising: administering an effective amount of a compound having the structure I, a tautomer of the compound, a pharmaceutically-acceptable salt of the compound, or a pharmaceutically-acceptable salt of the tautomer to a cancer patient, wherein the cancer is selected from chronic myelogenous leukemia, acute lymphoblastic leukemia, or acute myeloblastic leukemia, the $IC_{50}$ value of the compound, the tautomer, the pharmaceutically-acceptable salt of the compound, or the pharmaceutically-acceptable salt of the tautomer is less than 10 micromolar with respect to c-ABL and the compound having the structure I has the following structure:

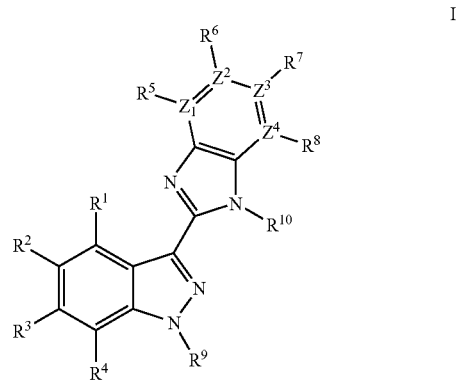

wherein, $Z^1$, $Z^2$, $Z^3$, and $Z^4$ are C;

$R^1$ is selected from the group consisting of —H, —F, —Cl, —Br, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted —N(H)—C(=O)-aryl groups, substituted and unsubstituted —N(H)—C(=O)-alkyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted alkyl groups, substituted and unsubstituted alkoxy groups, substituted and unsubstituted amino groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

$R^2$ is selected from the group consisting of —H, —F, —Cl, —Br —C≡N —NO$_2$, —CO$_2$H, —OH, substituted and unsubstituted guanidinyl groups, substituted and unsubstituted amino groups, substituted and unsubstituted alkyl groups, substituted and unsubstituted —C(=O)O-alkyl groups, substituted and unsubstituted —C(=O)O-aryl groups, substituted and unsubstituted —C(=O)O-heteroaryl groups, substituted and unsubstituted —C(=O)N(H)-alkyl groups, substituted and unsubstituted —C(=O)—N(H)-alkyl-heterocyclyl groups, substituted and unsubstituted —C(=O)N(H)-aryl groups, substituted and unsubstituted —C(=O)N(H)-heterocyclyl groups, substituted and unsubstituted —N(H)C(=O)-alkyl groups, substituted and unsubstituted —N(H)C(=O)-aryl groups, substituted and unsubstituted —N(H)C(=O)-heterocyclyl groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted —N(H)—(SO$_2$)-alkyl groups, substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)-heterocyclyl groups, substituted and unsubstituted heterocyclylalkylamino groups, substituted and unsubstituted arylalkylamino groups, substituted and unsubstituted heterocyclyl groups, substituted and unsubstituted alkoxy groups, substituted and unsubstituted arylalkoxy groups, substituted and unsubstituted aryloxy groups, substituted and unsubstituted alkoxyalkyl groups, substituted and unsubstituted arylalkoxyalkyl groups, substituted and unsubstituted heterocyclyloxy, substituted and unsubstituted heterocyclylalkoxy groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups; or $R^2$ and $R^3$ are a group of formula —OCH$_2$O— such that $R^2$ and $R^3$ define a fused 5-membered ring that includes 2 oxygen atoms;

$R^3$ is selected from the group consisting of —H, —F, —Cl, —Br, —CF$_3$, —C≡N, —NO$_2$, —CO$_2$H, substituted and unsubstituted amino groups, substituted and unsubstituted alkyl groups, substituted and unsubstituted alkoxy groups, substituted and unsubstituted —C(=O)—O-alkyl groups, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy group, substituted and unsubstituted heterocycyl groups, substituted and unsubstituted —N(H)—C(=O)-alkyl groups, substituted and unsubstituted —N(H)—C(=O)-aryl groups, substituted and unsubstituted —N(H)—(SO$_2$)-alkyl groups substituted and unsubstituted —N(H)—(SO$_2$)-aryl groups, —N(H)—(SO$_2$)—CF$_3$ groups, substituted and unsubstituted —N(H)—(SO$_2$)-heterocyclyl groups, substituted and unsubstituted —N(H)C(=O)N(H)-alkyl groups, substituted and unsubstituted —N(H)C(=O)N(H)-aryl groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, and substituted and unsubstituted -alkyl-N(H)—C(=O)-alkyl-aryl groups, and substituted and unsubstituted -alkyl-N(H)—C(=O)-alkyl-heterocyclyl groups;

$R^4$ is selected from the group consisting of —H, —F, —Br, —Cl, —NO$_2$, —C≡N, —C(=O)—O-alkyl groups, —OH, substituted and unsubstituted arylalkoxy groups, substituted and unsubstituted heterocyclyloxy groups, substituted and unsubstituted alkoxyalkyl groups, substituted and unsubstituted arylalkoxyalkyl groups, substituted and unsubstituted aryloxy groups, substituted and unsubstituted N(H)—C(=O)-aryl groups, substituted and unsubstituted —N(H)—C(=O)-alkyl groups, substituted and unsubstituted —N(H)—SO$_2$-alkyl groups, substituted and unsubstituted —N(H)—SO$_2$-aryl groups, —N(H)—SO$_2$—CF$_3$ groups, substituted and unsubstituted —N(H)—SO$_2$-heterocyclyl groups, substituted and unsubstituted heterocyclyl groups, substituted and unsubstituted amino groups, substituted and unsubstituted alkyl groups, substituted and unsubstituted alkoxy groups, substituted and unsubstituted —C(=O)—N(H)-alkyl groups, substituted and unsubstituted —C(=O)—N(H)-alkyl-heterocyclyl groups, substituted and unsubstituted (alkyl)(alkyl)aminoalkyl groups, substituted and unsubstituted (alkyl)(aryl)aminoalkyl groups, substituted and unsubstituted (alkyl)(heterocyclyl)aminoalkyl groups substituted and unsubstituted (alkyl)(arylalkyl)aminoalkyl groups, substituted and unsubstituted (alkyl)(heterocyclylalkyl)aminoalkyl groups, substituted and unsubstituted -alkyl-N(alkyl)-C(=O)-alkyl groups, substituted and unsubstituted -alkyl-N(alkyl)-C(=O)-aryl groups, substituted and unsubstituted -alkyl-N(alkyl)-C(=O)-heterocyclyl groups, substituted and unsubstituted -alkyl-N(alkyl)-C(=O)-alkyl-aryl groups, substituted and unsubstituted -alkyl-N(alkyl)-C(=O)-alkyl-heterocyclyl groups, substituted and unsubstituted alkylaminoalkyl groups, substituted and unsubstituted arylaminoalkyl groups, substituted and unsubstituted heterocyclylaminoalkyl groups substituted and unsubstituted arylalkylaminoalkyl groups, substituted and unsubstituted heterocyclylalkylaminoalkyl groups, substituted and unsubstituted -alkyl-N(H)—C(=O)-alkyl groups, substituted and unsubstituted -alkyl-N(H)—C(=O)-aryl groups, substituted and unsubstituted -alkyl-N(H)—C(=O)-heterocyclyl groups, substituted and unsubstituted -alkyl-N(H)—C(=O)-alkyl-aryl groups, and substituted and unsubstituted -alkyl-N(H)—C(=O)-alkyl-heterocyclyl groups;

R$^5$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups;

R$^6$ is selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups;

R$^7$ selected from the group consisting of —H, —F, —Cl, —Br, —CF$_3$, —CO$_2$H, substituted and unsubstituted alkyl groups, substituted and unsubstituted alkoxy groups including substituted and unsubstituted heterocyclylalkoxy groups, substituted and unsubstituted arylalkoxy groups, and substituted and unsubstituted alkoxyalkoxy groups; substituted and unsubstituted heterocyclyl groups including substituted and unsubstituted heterocyclylheterocyclyl groups, substituted and unsubstituted arylheterocyclyl groups, substituted and unsubstituted alkylheterocyclyl groups, and substituted and unsubstituted cycloalkylheterocyclyl groups; substituted and unsubstituted heterocyclyloxy groups, substituted and unsubstituted aryloxy groups, substituted and unsubstituted amino groups including substituted and unsubstituted dialkylamino groups, substituted and unsubstituted (alkyl)(heterocyclyl)amino groups, substituted and unsubstituted heterocyclylalkylamino groups, substituted and unsubstituted arylalkylamino groups, and substituted and unsubstituted heterocyclylamino groups; substituted and unsubstituted —C(=O)N(H)-alkyl groups, substituted and unsubstituted —C(=O)N(H)-aryl groups, substituted and unsubstituted —C(=O)N(H)-heterocyclyl groups, substituted and unsubstituted —C(=O)N(alkyl)(heterocyclyl) groups, and substituted and unsubstituted —C(=O)-heterocyclyl groups;

R$^8$ is selected from the group consisting of —H, —F, —Cl, substituted and unsubstituted alkyl groups, substituted and unsubstituted alkoxy groups, substituted and unsubstituted amino groups, substituted and unsubstituted alkylamino groups, substituted and unsubstituted dialkylamino groups, and substituted and unsubstituted heterocyclyl groups;

R$^9$ —H; and

R$^{10}$ is selected from the group consisting of —H, and substituted and unsubstituted alkyl groups.

2. The method of claim 1, wherein R$^{10}$ is H.

3. The method of claim 2, wherein R$^2$ is selected from the group consisting of substituted and unsubstituted arylalkoxy groups, substituted and unsubstituted aryloxy groups, substituted and unsubstituted —N(H)C(=O)N(H)-alkyl groups, substituted and unsubstituted —N(H)C(=O)N(H)-aryl groups, substituted and unsubstituted —N(H)C(=O)N(H)-heterocyclyl groups, substituted and unsubstituted heterocyclylalkylamino groups, substituted and unsubstituted arylalkylamino groups; substituted and unsubstituted —N(H)-heterocyclyl groups, substituted and unsubstituted alkoxy groups, and substituted and unsubstituted heterocyclyloxy groups.

4. The method of claim 3, wherein R$^2$ is selected from the group consisting of:

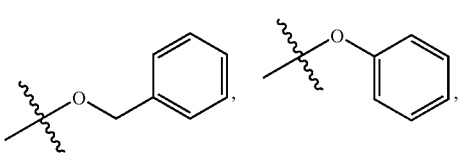

-continued

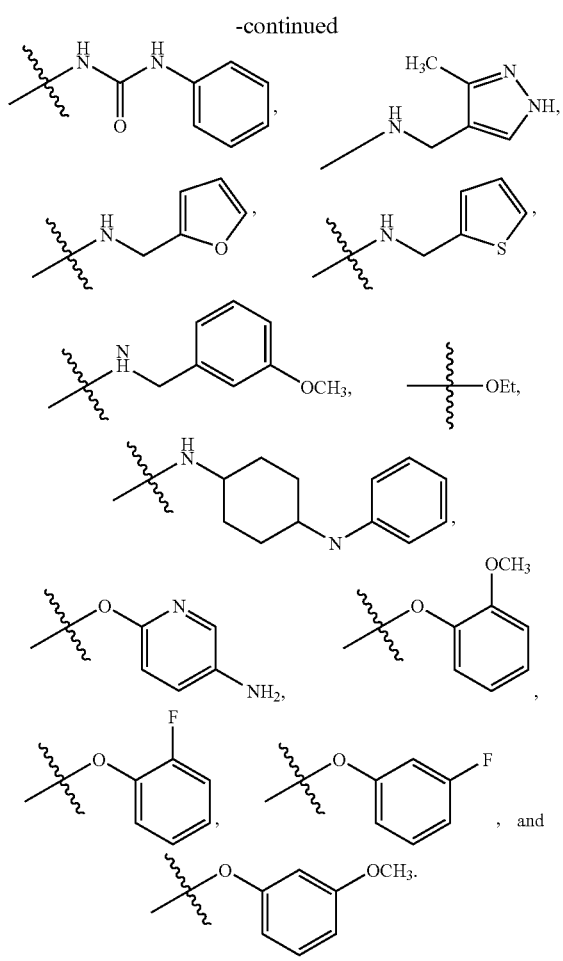

5. The method of claim 3, wherein at least one of $R^6$ or $R^7$ is selected from the group consisting of substituted and unsubstituted heterocyclyl groups, substituted and unsubstituted heterocyclylalkyl groups, and substituted and unsubstituted amino groups.

6. The method of claim 5, wherein at least one of $R^6$ or $R^7$ is selected from the group consisting of substituted and unsubstituted heterocyclylheterocyclyl groups, substituted and unsubstituted alkylheterocyclyl groups, substituted and unsubstituted (alkyl)(heterocyclyl)amino groups, and substituted and unsubstituted heterocyclylalkyl groups.

7. The method of claim 3, wherein at least one of $R^6$ or $R^7$ is selected from the group consisting of substituted and unsubstituted heterocyclyl groups, substituted and unsubstituted heterocyclylalkyl groups, and substituted and unsubstituted amino groups, and further wherein the other of $R^6$ or $R^7$ is selected from H or F.

8. The method of claim 3, wherein $R^1$, $R^4$, $R^5$, and $R^8$ are all H.

9. The method of claim 3, wherein $R^3$ is selected from H or a substituted or unsubstituted alkoxy group.

10. The method of claim 2, wherein at least one of $R^6$ or R is selected from the group consisting of substituted and unsubstituted heterocyclyl groups, substituted and unsubstituted heterocyclylalkyl groups, and substituted and unsubstituted amino groups.

11. The method of claim 10, wherein at least one of $R^6$ or $R^7$ is selected from the group consisting of substituted and unsubstituted heterocyclylheterocyclyl groups, substituted and unsubstituted alkylheterocyclyl groups, substituted and unsubstituted (alkyl)(heterocyclyl)amino groups, and substituted and unsubstituted heterocyclylalkyl groups.

12. The method of claim 10, wherein at least one of $R^6$ or $R^7$ is selected from the group consisting of:

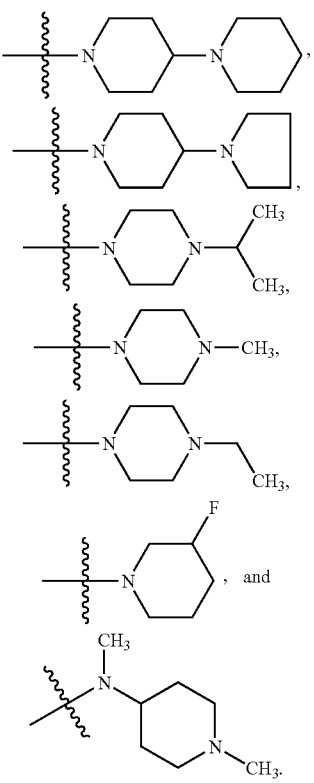

* * * * *

UNITED STATES PATENT AND TRADEMARK OFFICE
CERTIFICATE OF CORRECTION

PATENT NO. : 7,642,278 B2
APPLICATION NO. : 11/261995
DATED : January 5, 2010
INVENTOR(S) : Jansen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 940 days.

Signed and Sealed this

Twenty-first Day of December, 2010

David J. Kappos
*Director of the United States Patent and Trademark Office*